US011851715B2

(12) United States Patent
Mayhew et al.

(10) Patent No.: US 11,851,715 B2
(45) **Date of Patent: *Dec. 26, 2023**

(54) DETECTING CANCER CELL OF ORIGIN

(71) Applicants: GeneCentric Therapeutics, Inc., Durham, NC (US); The University of North Carolina at Chapel Hill, Chapel Hill, NC (US)

(72) Inventors: Greg Mayhew, Durham, NC (US); Hawazin Faruki, Durham, NC (US); Myla Lai-Goldman, Durham, NC (US); Charles M. Perou, Carrboro, NC (US); Joel S. Parker, Apex, NC (US)

(73) Assignees: GeneCentric Therapeutics, Inc., Durham, NC (US); The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/820,546

(22) Filed: Aug. 17, 2022

(65) Prior Publication Data

US 2023/0037765 A1 Feb. 9, 2023

Related U.S. Application Data

(63) Continuation of application No. 17/284,310, filed as application No. PCT/US2019/055318 on Oct. 9, 2019.

(60) Provisional application No. 62/819,893, filed on Mar. 18, 2019, provisional application No. 62/743,256, filed on Oct. 9, 2018.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/158* (2013.01)

(58) Field of Classification Search
CPC ............ C12Q 1/6886; C12Q 2600/112; C12Q 2600/158
See application file for complete search history.

(56) References Cited

U.S. PATENT DOCUMENTS

| | | | |
|---|---|---|---|
| 4,683,202 | A | 7/1987 | Mullis |
| 4,843,155 | A | 6/1989 | Chomczynski |
| 5,384,261 | A | 1/1995 | Winkler et al. |
| 5,445,934 | A | 8/1995 | Fodor et al. |
| 5,593,839 | A | 1/1997 | Hubbell et al. |
| 5,677,195 | A | 10/1997 | Winkler et al. |
| 5,708,153 | A | 1/1998 | Dower et al. |
| 5,733,729 | A | 3/1998 | Lipshutz et al. |
| 5,744,305 | A | 4/1998 | Fodor et al. |
| 5,770,358 | A | 6/1998 | Dower et al. |
| 5,770,722 | A | 6/1998 | Lockhart et al. |
| 5,789,162 | A | 8/1998 | Dower et al. |
| 5,795,716 | A | 8/1998 | Chee |
| 5,800,992 | A | 9/1998 | Fodor et al. |
| 5,854,033 | A | 12/1998 | Lizardi |
| 5,856,174 | A | 1/1999 | Lipshutz et al. |
| 5,874,219 | A | 2/1999 | Rava et al. |
| 5,922,591 | A | 7/1999 | Anderson et al. |
| 5,974,164 | A | 10/1999 | Chee |
| 6,020,135 | A | 2/2000 | Levine et al. |
| 6,033,860 | A | 3/2000 | Lockhart et al. |
| 6,040,138 | A | 3/2000 | Lockhart et al. |
| 6,040,193 | A | 3/2000 | Winkler et al. |
| 6,066,454 | A | 5/2000 | Lipshutz et al. |
| 6,090,555 | A | 7/2000 | Fiekowsky et al. |
| 6,185,561 | B1 | 2/2001 | Balaban et al. |
| 6,188,783 | B1 | 2/2001 | Balaban et al. |
| 6,223,127 | B1 | 4/2001 | Berno |
| 6,229,911 | B1 | 5/2001 | Balaban et al. |
| 6,308,170 | B1 | 10/2001 | Balaban |
| 6,344,316 | B1 | 2/2002 | Lockhart et al. |
| 6,420,108 | B2 | 7/2002 | Mack et al. |
| 6,524,581 | B1 | 2/2003 | Adamis |
| 7,473,767 | B2 | 1/2009 | Dimitrov |
| 8,822,153 | B2 | 9/2014 | Hayes et al. |
| 2002/0183936 | A1 | 12/2002 | Kulp et al. |
| 2003/0097222 | A1 | 5/2003 | Craford et al. |
| 2003/0100995 | A1 | 5/2003 | Loraine et al. |
| 2003/0120432 | A1 | 6/2003 | Zhou et al. |
| 2004/0002818 | A1 | 1/2004 | Kulp et al. |
| 2004/0049354 | A1 | 3/2004 | Loraine et al. |
| 2004/0126840 | A1 | 7/2004 | Cheng et al. |
| 2005/0042654 | A1 | 2/2005 | Mei et al. |
| 2005/0079536 | A1 | 4/2005 | Su |
| 2005/0108197 | A1 | 5/2005 | Jevons et al. |
| 2005/0244883 | A1 | 11/2005 | Williams et al. |
| 2005/0250151 | A1 | 11/2005 | Mei et al. |
| 2016/0019337 | A1 | 1/2016 | Roberts et al. |
| 2016/0115551 | A1 | 4/2016 | Cowens |
| 2017/0114416 | A1 | 4/2017 | Faruki et al. |
| 2021/0388449 | A1 | 12/2021 | Mayhew et al. |

FOREIGN PATENT DOCUMENTS

| | | | |
|---|---|---|---|
| WO | WO-2014028884 | A2 | 2/2014 |
| WO | WO-2017201164 | A1 | 11/2017 |
| WO | WO-2017201165 | A1 | 11/2017 |
| WO | WO-2019032525 | A1 | 2/2019 |
| WO | WO-2019046585 | A1 | 3/2019 |

OTHER PUBLICATIONS

Ma et al., “Molecular Classification of Human Cancers Using A 92-Gene Real-Time Quantitative Polymerase Chain Reaction Assay,” Archives of pathology & laboratory medicine, 1 Arch Pathol Lab Med, 130(4):465-731; Apr. 2006 (Jan. 4, 2006).

(Continued)

*Primary Examiner* — Sarae L Bausch
(74) *Attorney, Agent, or Firm* — COOLEY LLP

(57) ABSTRACT

Methods and compositions are provided for determining a pan-cancer clustering of cluster assignment (COCA) subtype of a cancer in an individual by detecting the expression level of at least one classifier biomarker selected from a group of classifier biomarkers for COCA subtypes. Also provided herein are methods and compositions for determining the response of an individual with a COCA subtype to a therapy such as immunotherapy.

7 Claims, 15 Drawing Sheets

Specification includes a Sequence Listing.

(56) References Cited

OTHER PUBLICATIONS

Marisa L et al "Gene Expression Classification of Colon Cancer Into Molecular Subtypes: Characterization, Validation, and Prognostic Value", Plos Medicine 10(5):e1001453, pp. 1-13; May 21, 2013 (May 21, 2013).
Banerjee et al., "JAK-STAT Signaling as a Target for Inflammatory and Autoimmune Diseases: Current and Future Prospects," Drugs 77(5):521-546 (2017).
Barany, "Cloning, overexpression and nucleotide sequence of a thermostable DNA ligase-encoding gene," Proc. Natl. Acad. Sci. USA 88:189-193 (1991).
Bibikova et al., "Quantitative gene expression profiling in formalin-fixed, paraffin-embedded tissues using universal bead arrays," Am J. Pathol 165:1799-1807 (2004).
Bindea et al., "Spatiotemporal dynamics of intratumoral immune cells reveal the immune landscape in human cancer," Immunity 39(4):782-795 (2013).
Brenner et al., "Gene expression analysis by massively parallel signature sequencing (MPSS) on microbead arrays," Nat. Biotech. 18:630-634 (2000).
Cancer Genome Atlas Research Network. "Comprehensive genomic characterization of squamous cell lung cancers." Nature 489.7417 (2012): 519-525.
Charoentong et al., "Pan-cancer Immunogenomic Analyses Reveal Genotype-Immunophenotype Relationships and Predictors of Response to Checkpoint Blockade," Cell Reports 18(1): 248-262 (2017).
Clark et al., "Suppression of nonspecific binding of avidin-biotin complex (ABC) to proteins electroblotted to nitrocellulose paper," J Histochem Cytochem 34:1509-1512 (1986).
Cronin et al., "Measurement of gene expression in archival paraffin-embedded tissues: development and performance of a 92-gene reverse transcriptase-polymerase chain reaction assay" Am. J Pathol. 164(1):35-42 (2004).
Dabney, "ClaNC: Point-and-click software for classifying microarrays to nearest centroids," Bioinformatics. 22: 122-123 (2006).
Dabney, "Classification of microarrays to nearest centroids," Bioinformatics 21(22):4148-4154 (2005).
De Andres et al., "Improved method for mRNA extraction from paraffin-embedded tissues," BioTechniques 18:42-44 (1995).
Fan et al., "A Versatile Assay for High-Throughput Gene Expression Profiling on Universal Array Matrices," Genome Res. 14:878-885 (2004).
Faruki et al., "Lung Adenocarcinoma and Squamous Cell Carcinoma Gene Expression Subtypes Demonstrate Significant Differences in Tumor Immune Landscape," Journal of Thoracic Oncology 12(6):943-953 (2017).
Fishel and Kaufman et al., "Meta-analysis of gene expression data: a predictor-based approach," Bioinformatics 23(13): 1599-606 ( 2007).
Fox et al., "Formaldehyde Fixation," J Histochem Cytochem 33:845-853 (1985).
Friedman et al., "Regularization Paths for Generalized Linear Models via Coordinate Descent" Journal of statistical software 33(1): 1-22 (2010).
Geiss et al., "Direct multiplexed measurement of gene expression with color-coded probe pairs," Nat. Biotechnol. 26:317-325 (2008).
Guatelli et al., "Isothermal, in vitro amplification of nucleic acids by a multienzyme reaction modeled after retroviral replication," Proc Natl Acad Sci U S A. 87(5):1874-1878 (1990).
Hoadley et al. "Multiplatform analysis of 12 cancer types reveals molecular classification within and across tissues of origin." Cell 158(4):929-944.
Hoadley, K.A. et al. (2018) "Cell-of-Origin Patterns Dominate the Molecular Classification of 10,000 Tumors from 33 Types of Cancer" Cell, 173(2):291-304. HHS Public Access Author Manuscript; available in PMC Apr. 5, 2019, 40 pages.
International Search Report and Written Opinion issued by the International Searching Authority for Application No. PCT/US19/55318, dated Mar. 9, 2020, 17 pages.
Invitation to Pay Additional Search Fees issued by the International Searching Authority for Application No. PCT/US19/55318, dated Jan. 8, 2020, 24 pages.
Irizarry et al., "Exploration, normalization, and summaries of high density oligonucleotide array probe level data," Biostatistics April 4(2): 249-64 (2003).
Kwoh et al., "Transcription-based amplification system and detection of amplified human immunodeficiency virus type 1 with a bead-based sandwich hybridization format (TI RNA polymerase/in vitro nucleic acid amplification)," Proc. Natl. Acad. Sci. USA, 86:1173-1177 (1989).
Liu et al., "Integrative Proteomics and Tissue Microarray Profiling Indicate the Association between Overexpressed Serum Proteins and Non-Small Cell Lung Cancer," PLoS ONE 7(12):1-13 (2012).
Martin et al., "PAM50 proliferation score as a predictor of weekly paclitaxel benefit in breast cancer," Breast Cancer Res Treat 138:457-466 (2013).
McGhee and Von Hippel, "Formaldehyde as a probe of DNA structure. II. Reaction with endocyclic amino groups of DNA bases," Biochemistry 14:1281-1296 (1975).
Mullins et al., "Agreement in breast cancer classification between microarray and quantitative reverse transcription PCR from fresh-frozen and formalin-fixed, paraffin-embedded tissues," Clin Chem. 53(7):1273-1279 (2007).
Paolillo et al., "Small molecule integrin antagonists in cancer therapy," Mini Rev Med Chem 12:1439-1446 (2009).
Parker et al., (2009) Supervised risk predictor of breast cancer based on intrinsic subtypes. J Clin Oncol 27:1160-1167.
Robertson et al., "Comprehensive molecular characterization of muscle invasive bladder cancer," Cell, 171(3): 540-556 (2017).
Robin et al., "pROC: an open source package for R and S+ to analyze and compare ROC curves," BMC bioinformatic 12:77 (2011), 8 pages.
Rouskin et al., "Genome-wide probing of RNA structure reveals active unfolding of mRNA structures in vivo," Nature 505, pp. 701-705 (2014).
Rupp G and Locker J., University of Pittsburgh School of Medicine, "Purification and analysis of RNA from paraffin embedded tissues," BioTechniques 6(1):56-60 (1988).
Seiler et al., Gene Expression Omnibus (GEO) dataset: GSE87304, Eur Urol, 72(4):544-554 (2017).
Sjodah et al., "A Molecular Taxonomy for Urothelial Carcinoma," Clin Cancer Res, 18(12):3377-3386 (2012).
Smyth, G. K., Limma: linear models for microarray data. In: Bioinformatics and Computational Biology Solutions using Rand Bioconductor, R. Gentleman, V. Carey, S. Dudoit, R.Irizarry, W. Huber (eds.), Springer, New York, pp. 397-420 (2005).
Smyth, G. K., "Linear Models and Empirical Bayes Methods for Assessing Differential Expression in Microarray Experiments," Stat. Appi. Genet. Mol. Biol. 3: Article 3 (2004), 28 pages.
Suykens Jak, Vandewalle J., "Least Squares Support Vector Machine Classifiers," Neural Processing Letters 9(3): 293-300 (1999).
Szumilas, "Explaining odds ratios," J. Can. Acad. Child Adolesc. Psychiatry 19(3): 227-229 (2010).
The Cancer Genome Atlas Network. Comprehensive genomic characterization defines human glioblastoma genes and core pathways. Nature. 2008;455:1061-1068.
The Cancer Genome Atlas Network. Comprehensive molecular characterization of clear cell renal cell carcinoma. Nature. 2013a;499:43-49.
The Cancer Genome Atlas Network. Comprehensive molecular characterization of human colon and rectal cancer. Nature. 2012b;487:330-337.
The Cancer Genome Atlas Network. Comprehensive molecular portraits of human breast tumours. Nature. 2012c;490:61-70.
The Cancer Genome Atlas Network. Genomic and epigenomic landscapes of adult de novo acute myeloid leukemia. The New England journal of medicine. 2013b;368:2059-2074.
The Cancer Genome Atlas Network. Integrated genomic analyses of ovarian carcinoma. Nature 2011;474:609-615.

(56) References Cited

OTHER PUBLICATIONS

The Cancer Genome Atlas Research Network, "Comprehensive molecular characterization of urothelial bladder carcinoma," Nature, 507(492): 315-322 (2014).
Thorsson, V. et al., "The immune landscape of cancer," Immunity, 48(4), pp. 812-830 (2018).
Tibshirani et al., "Diagnosis of multiple cancer types by shrunken centroids of gene expression," Proc. Natl. Acad. Sci. USA 99(10):6576-6572 (2002).
Trapnell et al., "TopHat: discovering splice junctions with RNA-Seq.," Bioinformatics 25(9):1105-11 (2009).
Velculescu et al., "Characterization of the yeast transcriptome," Cell 88(2):243-251 (1997).
Wu and Wallace, "The ligation amplification reaction (LAR)—amplification of specific DNA sequences using sequential rounds of template dependent ligation.," Genomics, 4(4):560-569 (1989).

| | C1 | C2 | C3 | C4 | C5 | C6 | C8 | C9 | C10 | C12 | C14 | C15 |
|---|---|---|---|---|---|---|---|---|---|---|---|---|
| ACC | 74 | | | 1 | | | | | | | | |
| BLCA | 5 | | | 66 | 7 | | 1 | 3 | 10 | 2 | | |
| BRCA | 3 | | | 5 | 5 | 1 | | | 141 | 9 | | |
| CESC | 1 | | | 212 | 2 | | | 2 | 1 | 10 | | 53 |
| CHOL | | | | | | | 30 | | | | | |
| COAD | | | | | | | 3 | | | | | |
| DLBC | | | | | | | | | | | | |
| ESCA | | | | 85 | 1 | | 5 | | 4 | | | |
| GBM | 6 | 113 | | | | | | | 1 | | | |
| HNSC | | | | 493 | 4 | | | | 4 | | | |
| KICH | | | | | | | | | | | | |
| KIRC | | | | | | 1 | | | | 1 | | 1 |
| KIRP | | | | | | | 1 | | | 1 | | |
| LGG | 5 | 502 | | | | | | | | | | |
| LIHC | 1 | | | | | | 10 | | 1 | | | |
| LUAD | 2 | | | 48 | 15 | 388 | 4 | | 6 | 2 | | 1 |
| LUSC | 1 | | | 361 | 28 | 34 | | | 17 | 6 | | |
| MESO | 2 | | | 1 | | 5 | | | | | | |
| OV | | | 246 | | | | | 3 | 1 | 8 | | |
| PAAD | | | | | | | 147 | | 1 | | | |
| PCPG | 161 | | | | | | | | | | | |
| PRAD | | | | | | | 1 | | | | 482 | |
| READ | | | | | | | 1 | | | | | |
| SARC | 35 | | | 3 | | 1 | | 3 | | | | |
| SKCM | | | | | | | | | | | | |
| STAD | | | | 1 | 4 | 1 | 84 | 1 | 1 | 1 | | 1 |
| TGCT | | | | | | | | 3 | | | | |
| THCA | | | | | | | | | | | | |
| THYM | | | | 2 | | | | | | | | |
| UCEC | 4 | | 1 | | | | | 2 | 3 | 161 | | 2 |
| UCS | 1 | | | | 1 | | | 36 | 2 | 14 | | |
| UVM | | | | | | | | | | | | |
| Sum | 301 | 615 | 247 | 1278 | 67 | 431 | 287 | 53 | 193 | 215 | 482 | 58 |

FIG. 1

| C16 | C17 | C19 | C20 | C21 | C22 | C24 | C25 | C26 | C28 | Sum |
|---|---|---|---|---|---|---|---|---|---|---|
| | | | 1 | | | | | | | 76 |
| 273 | | | 6 | | | | 1 | | 8 | 382 |
| | | | 1 | | | 843 | | | 5 | 1013 |
| | | 2 | | | | 1 | | | 2 | 286 |
| | | 2 | 1 | | 1 | | 1 | | | 35 |
| | | 266 | | | | | | | | 269 |
| | | | | | | | 47 | | | 47 |
| 1 | | 75 | | | | | | | | 171 |
| | | | | | | | | | | 120 |
| 1 | 1 | | 1 | | | 1 | | | | 505 |
| | | | 2 | 63 | | | | | | 65 |
| | | | 2 | 482 | | | | | | 487 |
| 3 | | | | 266 | | | | | 1 | 272 |
| | | | | | | | | | | 507 |
| | | | 1 | | 337 | | | | 1 | 351 |
| | 1 | | 5 | | 1 | | | | | 473 |
| 1 | | | 1 | | | | 1 | | 1 | 451 |
| | | | 78 | | | | | | | 86 |
| | | | | | | | | | 1 | 259 |
| | | 4 | 1 | | | | 1 | | 1 | 155 |
| | | | | | | | | | | 161 |
| | | | | | | | | | | 483 |
| | | 87 | | | | | | | | 88 |
| | 1 | | 202 | | | | | 2 | | 247 |
| | | | | | | | | 96 | | 96 |
| | 1 | 297 | | | | | 1 | | | 393 |
| | 145 | | | | | | | | | 148 |
| | | | | | | | | | 494 | 494 |
| | | | | | | | 115 | | 1 | 118 |
| | | | | | | | | | | 173 |
| | | | | | | | | | | 54 |
| | | | | | | | | 80 | | 80 |
| 279 | 149 | 733 | 302 | 811 | 339 | 845 | 167 | 178 | 515 | 8545 |

FIG. 1 (Continued)

| | |
|---|---|
| C1 | C1 ACC/PCPG |
| C2 | C2 GBM/LGG |
| C3 | C3 OV |
| C4 | C4 Squamous-like |
| C5 | |
| C6 | C6 LUAD-Enriched |
| C8 | C8 PAAD/some STAD |
| C9 | C9 UCS |
| C10 | C10 BRCA/Basal |
| C12 | C12 UCEC |
| C14 | C14 PRAD |
| C15 | C15 CESC (subset of cervical) |
| C16 | C16 BLCA |
| C17 | C17 TGCT |
| C19 | C19 COAD/READ<br>(column, rectum, esophogous, stomach aka GI tract) |
| C20 | C20 SARC/MESO |
| C21 | C21 KIRC/KICH/KIRP (kidney) |
| C22 | C22 liver |
| C24 | C24 BRCA/Luminal |
| C25 | C25 THYM |
| C26 | C26 SKCM/UVM |
| C28 | C28 THCA |

FIG. 1 (Continued)

| | train | test | Sum |
|---|---|---|---|
| ACC | 51 | 25 | 76 |
| BLCA | 255 | 127 | 382 |
| BRCA | 675 | 338 | 1013 |
| CESC | 191 | 95 | 286 |
| CHOL | 23 | 12 | 35 |
| COAD | 179 | 90 | 269 |
| DLBC | 31 | 16 | 47 |
| ESCA | 114 | 57 | 171 |
| GBM | 80 | 40 | 120 |
| HNSC | 337 | 168 | 505 |
| KICH | 43 | 22 | 65 |
| KIRC | 325 | 162 | 487 |
| KIRP | 181 | 91 | 272 |
| LGG | 338 | 169 | 507 |
| LIHC | 234 | 117 | 351 |
| LUAD | 315 | 158 | 473 |
| LUSC | 301 | 150 | 451 |
| MESO | 57 | 29 | 86 |
| OV | 173 | 86 | 259 |
| PAAD | 103 | 52 | 155 |
| PCPG | 107 | 54 | 161 |
| PRAD | 322 | 161 | 483 |
| READ | 59 | 29 | 88 |
| SARC | 165 | 82 | 247 |
| SKCM | 64 | 32 | 96 |
| STAD | 262 | 131 | 393 |
| TGCT | 99 | 49 | 148 |
| THCA | 329 | 165 | 494 |
| THYM | 79 | 39 | 118 |
| UCEC | 115 | 58 | 173 |
| UCS | 36 | 18 | 54 |
| UVM | 53 | 27 | 80 |
| Sum | 5696 | 2849 | 8545 |

FIG. 2

| | | | | | | | | | | | |
|---|---|---|---|---|---|---|---|---|---|---|---|
| [1] ====== test fit ====== | | | | | | | | | | | |
| [1] | | | | | | | | | | | |
| [1] Gold standard subtype (rows) vs clanc (84) subtype (columns) | | | | | | | | | | | |
| [1] Agreement: 0.9 | | | | | | | | | | | |
| [1] | | | | | | | | | | | |
| | | | | | | | | | | | |
| | C1 | C2 | C3 | C4 | C5 | C6 | C8 | C9 | C10 | C12 | C14 |
| C1 | 74 | 1 | | | | 3 | | 6 | 1 | 1 | |
| C2 | | 206 | | | | | | | | | |
| C3 | | | 78 | | | | | 1 | | 1 | |
| C4 | | | | 385 | | 18 | 1 | | 2 | | |
| C5 | | | | 15 | | 5 | 2 | 2 | 1 | | |
| C6 | | | | 4 | | 131 | 4 | | | | |
| C8 | 1 | | | 2 | | | 81 | | | | 1 |
| C9 | | | | | | | | 16 | | 4 | |
| C10 | | | | 7 | | | | 3 | 54 | | |
| C12 | | | 10 | 1 | | 2 | | 5 | 1 | 48 | |
| C14 | | | | | | | | | | | 160 |
| C15 | | | | | | | | | | | |
| C16 | | | | 13 | | | | | 2 | | |
| C17 | 2 | 1 | | | | | 4 | 1 | | | |
| C19 | | | | | | | 50 | | | | |
| C20 | 1 | | | 3 | | 1 | 1 | 1 | | | |
| C21 | | | | | | | | | | | |
| C22 | | | | | | | | | | | |
| C24 | | | | 4 | | | | | 8 | | 1 |
| C25 | | 1 | | 1 | | | 2 | | | | |
| C26 | | | | 3 | | | | | | | |
| C28 | | | | | | | 1 | | 4 | | |
| Sum | 78 | 209 | 88 | 438 | | 160 | 146 | 35 | 73 | 54 | 162 |

FIG. 4

Train agreement with COCA was 0.91
Test set agreement 0.9

| C15 | C16 | C17 | C19 | C20 | C21 | C22 | C24 | C25 | C26 | C28 | Sum |
|---|---|---|---|---|---|---|---|---|---|---|---|
| | 1 | | | 16 | 1 | | | | | | 104 |
| | | | | 1 | | | | | | | 207 |
| | | 1 | | | | | | | | | 81 |
| 4 | 8 | | | 3 | | | 1 | 3 | | | 425 |
| 1 | | | | | | | | | | | 26 |
| 2 | | | 2 | 3 | | | | | | | 146 |
| | | | 6 | | | 12 | | | | | 103 |
| | | | | | | 1 | | | 1 | | 22 |
| | 1 | | 2 | | | 1 | 1 | | | | 69 |
| | | | | | | | | | 1 | | 68 |
| | | | | | | | | | | | 160 |
| 16 | | | 1 | | | | | | | | 17 |
| 1 | 73 | | | 2 | | | | | | | 91 |
| | | 41 | | | | | | | | | 49 |
| 1 | | | 189 | | | | | | | | 240 |
| | | | | 92 | | | | | | | 99 |
| | | | | 1 | 270 | 1 | | | | 2 | 274 |
| | | | | | | 110 | | | | | 110 |
| | | | | | | | 259 | | | | 272 |
| 1 | | | | 3 | | | | 46 | | | 54 |
| | | | | | | | | | 56 | | 59 |
| | 2 | | | 1 | | | | | | 165 | 173 |
| 26 | 85 | 42 | 200 | 122 | 271 | 125 | 261 | 49 | 58 | 167 | 2849 |

FIG. 4 (Continued)

| COCA | Agreement |
|---|---|
| C1 | 0.71 |
| C2 | 1 |
| C3 | 0.96 |
| C4 | 0.91 |
| C5 | 0 |
| C6 | 0.9 |
| C8 | 0.79 |
| C9 | 0.73 |
| C10 | 0.78 |
| C12 | 0.71 |
| C14 | 1 |
| C15 | 0.94 |
| C16 | 0.8 |
| C17 | 0.84 |
| C19 | 0.79 |
| C20 | 0.93 |
| C21 | 0.99 |
| C22 | 1 |
| C24 | 0.95 |
| C25 | 0.85 |
| C26 | 0.95 |
| C28 | 0.95 |

FIG. 4 (Continued)

Test set proportion called correctly by 84-typer

| | C1 | C2 | C3 | C4 | C5 | C6 | C8 |
|---|---|---|---|---|---|---|---|
| ACC | 18/24 | | | 0/1 | | | |
| BLCA | 0/2 | | | 16/27 | 0/2 | | |
| BRCA | 0/1 | | | 0/3 | 0/2 | | |
| CESC | | | | 67/69 | 0/2 | | |
| CHOL | | | | | | | 3/11 |
| COAD | | | | | | | |
| DLBC | | | | | | | |
| ESCA | | | | 25/25 | 0/1 | | 1/3 |
| GBM | 0/1 | 38/39 | | | | | |
| HNSC | | | | 167/167 | | | |
| KICH | | | | | | | |
| KIRC | | | | | | | |
| KIRP | | | | | | | |
| LGG | 0/1 | 168/168 | | | | | |
| LIHC | | | | | | | 1/5 |
| LUAD | 0/2 | | | 4/17 | 0/4 | 123/130 | 1/1 |
| LUSC | 0/1 | | | 106/112 | 0/12 | 8/13 | |
| MESO | 0/1 | | | 0/1 | | 0/1 | |
| OV | | | 78/81 | | | | |
| PAAD | | | | | | | 49/49 |
| PCPG | 54/54 | | | | | | |
| PRAD | | | | | | | 0/1 |
| READ | | | | | | | |
| SARC | 2/14 | | | 0/1 | | 0/1 | |
| SKCM | | | | | | | |
| STAD | | | | | 0/3 | 0/1 | 26/33 |
| TGCT | | | | | | | |
| THCA | | | | | | | |
| THYM | | | | 0/2 | | | |
| UCEC | 0/2 | | | | | | |
| UCS | 0/1 | | | | | | |
| UVM | | | | | | | |

FIG. 5

| C9 | C10 | C12 | C14 | C15 | C16 | C17 | C19 |
|---|---|---|---|---|---|---|---|
| | | | | | | | |
| | 0/1 | | | | 73/90 | | |
| | 53/57 | 0/1 | | | | | |
| 1/2 | | 1/3 | | 16/17 | | | 1/1 |
| | | | | | | | |
| | | | | | | | 89/90 |
| | | | | | | | |
| | 0/1 | | | | | | 17/27 |
| | | | | | | | |
| | | | | | | | |
| | | | | | | | |
| | | | | | | | |
| | | | | | | | |
| | | | | | | | |
| | 0/1 | | | | | | |
| | 1/1 | | | | | | |
| | 0/7 | 0/2 | | | 0/1 | | |
| | | | | | | | |
| 1/1 | | 0/4 | | | | | |
| | | | | | | | 0/2 |
| | | | | | | | |
| | | | 160/160 | | | | |
| | | | | | | | 29/29 |
| 1/2 | | | | | | | |
| | | | | | | | |
| 0/1 | 0/1 | 0/1 | | | | | 53/91 |
| | | | | | | 41/49 | |
| | | | | | | | |
| | | | | | | | |
| 1/2 | | 45/54 | | | | | |
| 12/14 | | 2/3 | | | | | |
| | | | | | | | |

FIG. 5 (Continued)

| C20 | C21 | C22 | C24 | C25 | C26 | C28 | Sum |
|---|---|---|---|---|---|---|---|
| | | | | | | | 18/25 |
| 2/2 | | | | | | 0/3 | 91/127 |
| | | | 259/271 | | | 0/3 | 312/338 |
| | | | 0/1 | | | | 86/95 |
| 0/1 | | | | | | | 3/12 |
| | | | | | | | 89/90 |
| | | | | 11/16 | | | 11/16 |
| | | | | | | | 43/57 |
| | | | | | | | 38/40 |
| 0/1 | | | | | | | 167/168 |
| 1/1 | 19/21 | | | | | | 20/22 |
| | 160/162 | | | | | | 160/162 |
| | 91/91 | | | | | | 91/91 |
| | | | | | | | 168/169 |
| | | 110/110 | | | | 0/1 | 111/117 |
| 1/3 | | | | | | | 130/158 |
| 0/1 | | | | | | 0/1 | 114/150 |
| 25/26 | | | | | | | 25/29 |
| | | | | | | | 79/86 |
| | | | | 0/1 | | | 49/52 |
| | | | | | | | 54/54 |
| | | | | | | | 160/161 |
| | | | | | | | 29/29 |
| 63/64 | | | | | | | 66/82 |
| | | | | | 29/32 | | 29/32 |
| | | | | | | | 79/131 |
| | | | | | | | 41/49 |
| | | | | | | 165/165 | 165/165 |
| | | | | 35/37 | | | 35/39 |
| | | | | | | | 46/58 |
| | | | | | | | 14/18 |
| | | | | | 27/27 | | 27/27 |

FIG. 5 (Continued)

Within-cancer type survival analysis

```
[1] "====== BLCA ======"

C10   C15  C16   C20   C25  C4   C8   C9  Sum
  5     2  252     8     4  93    5    6  375
[1] "C16" "C4"
Call:
coxph(formula = y~age + stage + cianc, data = dat)

           coef   exp(coef)  se(coef)   z      p
age       0.0270  1.0274     0.0087    3.10   0.0019
stageIII  0.4437  1.5586     0.2505    1.77   0.0765
stageIV   1.0369  2.8204     0.2330    4.45   8.6e-06
ciancC4   0.4226  1.5260     0.1822    2.32   0.0204

Likelihood ratio test=40.3 on 4 df, p=3.71e-08
n= 345, number of events = 133
```

FIG. 6

Within-cancer type survival analysis

```
[1] "====== BRCA ======"

C10    C14  C15   C16   C20   C24   C4   C9   Sum
163      2    4     3     3   795   13    3   986
[1] "C10" "C24"
Call:
coxph(formula = y~age + stage + clanc, data = dat)

              coef    exp(coef)   se(coef)      z         p
age        0.04135      1.04221    0.00848   4.87   1.1e-06
stageII    0.70550      2.02485    0.41651   1.69   0.09030
stageIII   1.79395      6.01316    0.41819   4.29   1.8e-05
stageIV    3.07669     21.68653    0.48515   6.34   2.3e-10
clancC24  -0.98790      0.37236    0.25755  -3.84   0.00013

Likelihood ratio test=82.6 on 5 df, p=2.22e-16
n= 958, number of events = 85
```

Within-cancer type survival analysis

[1] "====== STAD ======"

| C1 | C15 | C19 | C20 | C22 | C4 | C8 | Sum |
|---|---|---|---|---|---|---|---|
| 1 | 3 | 184 | 2 | 2 | 7 | 162 | 361 |

[1] "C10" "C24"

Call:

coxph(formula = y~age + stage + clanc, data = dat)

| | coef | exp(coef) | se(coef) | z | p |
|---|---|---|---|---|---|
| age | 0.0405 | 1.0414 | 0.0099 | 4.10 | 4.2e-05 |
| stageII | 0.9046 | 2.4709 | 0.4538 | 1.99 | 0.04623 |
| stageIII | 1.4369 | 4.2076 | 0.4310 | 3.33 | 0.00086 |
| stageIV | 2.2202 | 9.2095 | 0.4832 | 4.60 | 4.3e-06 |
| clancC8 | 0.5121 | 1.6689 | 0.1895 | 2.70 | 0.00689 |

Likelihood ratio test=50 on 5 df, p=1.36e-09
n= 346, number of events = 119

SEQUENCE LISTING

```
Sequence total quantity: 84
SEQ ID NO: 1          moltype = DNA  length = 1766
FEATURE               Location/Qualifiers
source                1..1766
                      mol_type = other DNA
                      organism = Homo sapiens
```

-continued

```
SEQUENCE: 1
gggcctcatt gctgcagacg ctcaccccag acactcactg caccggagtg agcgcgacca  60
tcatgtccat gctcgtggtc tttctcttgc tgtggggtgt cacctggggc ccagtgacag  120
aagcagccat attttatgag acgcagccca gcctgtgggc agagtccgaa tcactgctga  180
aacccttggc caatgtgacg ctgacgtgcc aggcccacct ggagactcca gacttccagc  240
tgttcaagaa tggggtggcc caggagcctg tgcaccttga ctcacctgcc atcaagcacc  300
agttcctgct gacgggtgac acccagggcc gctaccgctg ccgctcgggc ttgtccacag  360
gatggaccca gctgagcaag ctcctggagc tgacagggcc aaagtccttg cctgctccct  420
ggctctcgat ggcgccagtg tcctggatca cccccggcct gaaaacaaca gcagtgtgcc  480
gaggtgtgct gcggggtgtg acttttctgc tgaggcggga gggcgaccat gagtttctgg  540
aggtgcctga ggcccaggag gatgtggagg ccacctttcc agtccatcag cctggcaact  600
acagctgcag ctaccggacc gatggggaag gcgccctctc tgagcccagc gctactgtga  660
ccattgagga gctcgctgca ccaccaccgc ctgtgctgat gcaccatgga gagtcctccc  720
aggtcctgca ccctggcaac aaggtgaccc tcacctgcgt ggctcccctg agtggagtgg  780
acttccagct acggcgcggg gagaaagagc tgctggtacc caggagcagc accagcccag  840
atcgcatctt ctttcacctg aacgcggtgg ccctgggggga tggaggtcac tacacctgcc  900
gctaccggct gcatgacaac caaaacggct ggtccgggga cagcgcgccg gtcgagctga  960
ttctgagcga tgagacgctg cccgcgccgg agttctcccc ggagccggag tccggcaggg  1020
ccttgcggct gcggtgcctg gcgcccctgg agggcgcgcg cttcgccctg gtgcgcgagg  1080
acaggggcgg gcgccgcgtg caccgtttcc agagccccgc tgggaccgag gcgctcttcg  1140
agctgcacaa catttccgtg gctgactccg ccaactacag ctgcgtctac gtggacctga  1200
agccgccttt cgggggctcc gcgcccagcg agcgcttgga gctgcacgtg gacggacccc  1260
ctcccaggcc tcagctccgg gcgacgtgga gtggggcggt cctggcgggc cgagatgccg  1320
tcctgcgctg cgagggaccc atccccgacg tcaccttcga gctgctgcgc gagggcgaga  1380
cgaaggccgt gaagacggtc cgcacccccg gggccgcggc gaacctcgag ctgatcttcg  1440
tggggcccca gcacgccggc aactacaggt gccgctaccg ctcctgggtg ccccacacct  1500
tcgaatcgga gctcagcgac cctgtggagc tcctggtggc agaaagctga tgcagccgcg  1560
ggcccagggt gctgttggtg tcctcagaag tgccggggat tctggactgg ctccctcccc  1620
tcctgttgca gcacaaggcc ggggtctctg gggggctgga gaagcctccc tcattcctcc  1680
caggaattaa taaatgtgaa gagaggctct gtttaaaatg tctttggact cccagggctg  1740
agtgggctgg gatctcgtgt cctcaa                                      1766

SEQ ID NO: 2           moltype = DNA  length = 3174
FEATURE                Location/Qualifiers
source                 1..3174
                       mol_type = other DNA
                       organism = Homo sapiens
SEQUENCE: 2
gaagtggtag cagttcctcc taactcctgc cagaaacagc tctcctcaac atgagagctg  60
cacccctcct cctggccagg gcagcaagcc ttagccttgg cttcttgttt ctgcttttt  120
tctggctaga ccgaagtgta ctagccaagg agttgaagtt tgtgactttg gtgtttcggc  180
atggagaccg aagtcccatt gacaccttc ccactgaccc cataaaggaa tcctcatggc  240
cacaaggatt tggccaactc acccagctgg gcatggagca gcattatgaa cttggagagt  300
atataagaaa gagatataga aaattcttga atgagtccta taaacatgaa caggtttata  360
ttcgaagcac agacgttgac cggactttga tgagtgctat gacaaacctg gcagccctgt  420
ttcccccaga aggtgtcagc atctggaatc ctatcctact ctggcagccc atcccggtgc  480
acacagttcc tctttctgaa gatcagttgc tatacctgcc tttcaggaac tgccctcgtt  540
ttcaagaact tgagagtgag actttgaaat cagaggaatt ccagaagagg ctgcacccctt  600
ataaggattt tatagctacc ttgggaaaac tttcaggatt acatggccag gaccttttg  660
gaatttggag taaagtctac gaccctttat attgtgagag tgttcacaat ttcactttac  720
cctcctgggc cactgaggac accatgacta agttgagaga attgtcagaa ttgtccctcc  780
tgtccctcta tggaattcac aagcagaaag agaaatctag gctccaaggg ggtgtcctgg  840
tcaatgaaat cctcaatcac atgaagagag caactcagat accaagctac aaaaaactca  900
tcatgtattc tgcgcatgac actactgtga gtggcctaca gatggcgcta gatgtttaca  960
acggactcct tcctccctat gcttcttgcc acttgacgga attgtacttt gagaaggggg  1020
agtactttgt ggagatgtac tatcggaatg agacgcagca cgagccgtat cccctcatgc  1080
tacctggctg cagccccagc tgtcctctgg agaggtttgc tgagctggtt ggccctgtga  1140
tccctcaaga ctggtccacg gagtgtatga cccacaaacag ccatcaaggt actgaagaca  1200
gtacagatta gtgtgcacag agatctctgt agaaggagta gctgcccttt ctcagggcag  1260
atgatgcttt gagaacatac tttggccatt acccccagct ttgaggaaaa tgggctttgg  1320
atgattattt tatgttttag ggacccccaa cctcaggcaa ttcctacctc ttcacctgac  1380
cctgccccca cttgccataa aacttagcta agttttgttt tgtttttcag cgttaatgta  1440
aaggggcagc agtgccaaaa tataatcaga gataaagctt aggtcaaagt tcatagagtt  1500
cccatgaact atatgactgg ccacacagga tcttttgtat ttaaggattc tgagattttg  1560
cttgagcagg attagataag gctgttcttt aaatgtctga aatggaacag atttcaaaaa  1620
aaaaccccac aatctaggat gggaacaagg aaggaaagat gtgaataggc tgatgggcaa  1680
aaaaccaatt tacccatcag ttccagcctt ctctcaagga gaggcaaaga aaggagatac  1740
agtggagaca tctggaaagt tttctccact ggaaaactgc tactatctgt ttttatattt  1800
ctgttaaaat atatgaggct acagaactaa aaattaaaac ctctttgtgt cccttggtcc  1860
tggaacattt atgttccttt taaagaaaca aaaatcaaac tttacagaaa gatttgatgt  1920
atgtaataca tatagcagct cttgaagtat atatatcata gcaaataagt catctgatga  1980
gaacaagcta tttgggcaca acacatcagg aaagagagca ccacgtgatg gagtttctct  2040
agaagctcca gtgataagag atgttgactc taaagttgat ttaaggccag gcatggtggt  2100
ttacgcctat aatcccagca ttttgggagt ccgaggtggg cagatcactt gagctcagga  2160
ggtcaagatc agcctgggca acatggtgaa acctggtctc tacataaaat acaaaaactt  2220
agatgggcat ggtggtgtgt gcctatagtc ccactacttg tggggctaag gcaggaggat  2280
cacttgagcc ccggaggtcg aggctacagt gagccaagag tgcactactg tactccagcc  2340
agggcaagag agcgagaccc tgtctcaata aataaataaa taaataaata aataaataaa  2400
taaataaata aaaacaaagt tgattaagaa aggaagtata ggccaggcac agtggctcac  2460
```

```
acctgtaatc cttgcatttt ggaaggctga ggcaggagga tcactttagg cctggtgtgt  2520
tcaagaccag cctggtcaac atagtgagac actgtctcta ccaaaaaaag gaaggaaggg  2580
acacatatca aactgaaaca aaattagaaa tgtaattatg ttctaagtgc ctccaagttc  2640
aaaacttatt ggaatgttga gagtgtggtt acgaaatacg ttaggaggac aaaaggaatg  2700
tgtaagtctt taatgccgat atcttcagaa aacctaagca aacttacagg tcctgctgaa  2760
actgcccact ctgcaagaag aaatcatgat atagctttgc catgtggcag atctacatgt  2820
ctagagaaca ctgtgctcta ttaccattat ggataaagat gagatggttt ctagagatgg  2880
tttctactgg ctgccagaat ctagagcaaa gccatccccg ctcctggttg gtcacagaat  2940
gactgacaaa gacatcgatt gatatgcttc tttgtgttat ttccctccca agtaaatgtt  3000
tgtccttggg tccattttct atgcttgtaa ctgtcttcta gcagtgagcc aaatgtaaaa  3060
tagtgaataa agtcattatt aggaagttca aaagcattgc ttttataatg aacttagaaa  3120
aacgtatgtg tgtgtgttta attagaataa aattcctcta ggcagatttc agga        3174

SEQ ID NO: 3           moltype = DNA  length = 9958
FEATURE                Location/Qualifiers
source                 1..9958
                       mol_type = other DNA
                       organism = Homo sapiens
SEQUENCE: 3
acgctgcagg agctgaagat ggcgagctcc gtggcgccct acgagcagct ggtgaggcag  60
gtggaggcct tgaaggctga gaacagccac ctgaggcagg agctaaggga caactccagc  120
cacctgtcca agctggagac agagacgtcg ggcatgaagg aggtcctgaa gcacctacag  180
ggaaaactgg agcaggaggc ccgagtgctg gtgtcctcgg ggcagacgga ggtgctggag  240
cagctgaagg ccctacagat ggacatcacc agcctgtaca acctcaagtt ccagccgccc  300
accctgggcc cggagcctgc cgcccggacc cccgagggca gcccagtaca cggctccggg  360
ccctccaagg acagctttgg ggagctgagc cgggccacca tccggctgct ggaggaactg  420
gaccgggaac ggtgtttcct gctgaatgag attgagaagg aggagaagga gaagctctgg  480
tactactctc agctgcaggg cctgtccaag cgcctggacg agctgccgca cgtggagacg  540
ttctcgatgc agatggacct gatccggcag cagcttgagt tcgaggccca gcacatccgc  600
tcgctgatgg aggagcgctt cggcacctcg gacgagatgg tgcagcgggc acagatccgc  660
gcctcgcgcc tggagcagat tgacaaggag ctgctggagg cgcaggaccg agtgcagcag  720
acggagcccc aggccttgct ggcggtgaag tcggtgccgg tggacgagga ccccgagaca  780
gaggtcccca cacaccctga ggatggcacc cctcagccgg gcaacagcaa ggtggaggtg  840
gtcttctggc tgttgtccat gttggcgacg cgcgaccagg aggatacagc gcgcacgctg  900
ctggccatgt ccagctcgcc cgagagctgc gtggccatgc gccgctcggg ctgtctgcct  960
ctgctgctgc aaatcctcca cggcaccgag gccgcggccg ggggtcgcgc cggggcccca  1020
ggggcaccgg gcgccaagga cgcacgcatg cgcgccaacg cggcgctgca caacatcgtc  1080
ttctcgcagc cggaccaggg cctggcgcgc aaggagatgc gcgtcctgca cgtgctggag  1140
cagatccggg cctactgcga gacctgctgg gactggctgc aggcccgaga cggcgggccc  1200
gagggaggtg gcgccggcag cgccccgatc cccatcgagc cgcagatctg ccaggccacc  1260
tgtgctgtta tgaagctgtc ctttgatgag gagtaccgcc gtgccatgaa cgagctaggt  1320
gggctgcagg ccgtggcaga gctgctgcag gttgactatg agatgcacaa gatgacccgg  1380
gacccgctga acctggcgct gcgccgctac gcgggcatga ccctcaccaa cctcaccttt  1440
ggggacgttg ccaacaaggc caccctgtgt gcgcgcccgcg gctgcatgga ggccatcgtg  1500
gcccagctgg cctccgacag tgaggagctc caccaggtgg tgtccagcat ccttcggaac  1560
ttgtcctgga gggccgacat caacagcaag aaggtgctga gggaggcggg cagcgtgact  1620
gccctggtgc agtgtgtcct gcgggccacc aaggagtcca ccctgaagag cgtgctgagc  1680
gccctgtgga atctgtctgc acacagcaca gagaacaagg cggccatctg ccaggtggat  1740
ggcgccctgg gcttcctggt gagcaccctg acctacaagt gtcagagcaa ctcgctggcc  1800
atcatcgaga gcggcggcgg catcctccgc aatgtgtcca gcctcgtcgc cacccgtgag  1860
gactacaggc aggtgctccg ggatcacaac tgtctgcaga cgctgctgca gcatctgact  1920
tcgcacagcc tgaccatcgt gagcaacgcg tgcggcacgc tctggaacct gtcggcccgc  1980
agcgcccgtg accaggagct gctgtgggac ctgggcgccg tgggcatgct gcgtaatctg  2040
gtgcactcca agcacaagat gatcgccatg ggcagcgccg ccgccctgcg caacctgctg  2100
gcccatcggc ccgccaagca ccaggcggcc gccaccgccg tgtccccagg cagctgcgtg  2160
cccagcctgt acgtgcgcaa gcagcgggcg ctggaggccg agctggacgc acggcacctc  2220
gcgcaggcgc tggagcacct ggagaagcag ggcccgccgg cagccgaggc cgccactaag  2280
aagccgctgc cgcccctgcg acacctggac ggcctggccc aagactatgc ttccgattcg  2340
ggctgctttg acgacgacga tgcaccgtca tccctggctg cggccgcggc caccggggag  2400
ccagccagcc ctgccgcgct gtccctcttc ctgggcagcc ccttcctgca ggggcaggcg  2460
ctggctcgca ccccgcccac ccgccgaggc ggcaaggagg cagagaagga caccagtggg  2520
gaggcagccg tggcggccaa ggccaaggcc aagctggcgc ttgcagtggc gcgcatcgac  2580
cagctggtgg aggacatctc cgccctgcac acctcgtccg acgatagctt cagcctcagc  2640
tctggagacc cgggacagga ggcgccacgg gagggccgcg cccagtcctg ctcgccatgc  2700
cgcggcccgg agggcgggcg gcgagaggca ggaagccggg cgcacccgct gctgcggctc  2760
aaggcggccc acgccagcct ctccaacgac agcctcaaca gcggcagtgc cagcgacggg  2820
tactgcccac gcgaacatat gctgccctgc ccgctggccg cactggcttc gcgccgcgag  2880
gaccccaggt gtgggcagcc tcggcccagc cggcttgacc ttgacctgcc cggctgccag  2940
gccgagcccc cggcccgcga ggcacctcc gccgacgccc gcgtgcgcac catcaagctg  3000
tcgcctacct atcagcacgt gccactgctt gagggtgcct caagggcggg tgcagagccc  3060
ctcgcggggc ctggaatctc tccaggggcc cggaagcagg cctggctgcc ggcagaccac  3120
ctgagcaagg ttcccgagaa gctggcggct gccccgctgt ctgtggccag caaggcactg  3180
cagaaactgg cggcgcaaga ggggccactc tcgctgtccc gatgcagctc cctttcctcg  3240
ctgtcctcgg ccggccgccc aggccccagc gagggtggtg acctggatga cagtgactcc  3300
tccctggagg ggctggagga ggccggcccc agcgaggctg agctggacag cacgtggcgg  3360
gcgcccgggg ccacctcgct gcccgtagcc attccggctc cccggcgtaa ccgaggccgg  3420
ggcctggggg tggaagacgc cacgccgtcc agctcgtcgg agaactacgt gcaggagaca  3480
ccgcttgtgc tgagccgctg cagctctgtg agctcgctgg gcagcttcga gagcccgtcc  3540
atcgccagct ccatccccag tgaaccttgc agcgggcagg gcagcggcac catcagccct  3600
```

-continued

```
agcgagctgc ccgacagccc cggacagacc atgcctccca gccggagcaa gacgccaccg  3660
ctggcgcccg cgcccacaggg tccccccgag gccacccagt tcagcctgca gtgggagagc  3720
tacgtgaagc gcttcctgga catcgccgac tgccgggagc gctgccggct gccatctgag  3780
ctggacgcag gcagcgtgcg ctttaccgtg gagaagccag acgagaactt ctcgtgcgcc  3840
tccagcctca gcgcgctggc cttgcacgag cactacgtgc agcaggacgt ggagctgcgg  3900
ctgctgccct cggcctgccc cgagcgcggc gggggcgccg ggggcgccgg cctccacttt  3960
gcagggcacc ggcggcggga ggagggggcc gcgcccacgg gttctcgccc tcgcggcgcc  4020
gcggaccagg agctggaact gctgcgggag tgcctgggag ccgccgtgcc tgcccggctg  4080
cgcaaggtgg cctccgcgct ggtgccaggt cgccgcgcac tccccgtgcc cgtctacatg  4140
ttggtgcccg ccccggcccc ggcccaggag gacgactcct gcactgactc cgcggagggc  4200
acgccggtca acttctctag cgccgcctcg ctcagcgacg agacgctgca gggacccccc  4260
agggaccagc ccgggggacc agcgggcagg caaagaccca ccggccgccc cacctctgcc  4320
agacaggcca tggggcaccg gcacaaggcg ggaggcgccg gccgcagcgc ggagcagtct  4380
cggggcgcgg gcaagaacag agcagggctg gagctgcccc tgggccggcc cccgagcgcc  4440
cccgcagaca aggacggctc aaagcccggc cggacccgcg gggacggggc gctccagtcg  4500
ctgtgcctca cgacgcccac tgaggaggcc gtgtactgct tctacggcaa cgactcggac  4560
gaggagcccc cggcggccgc gcccacgcca acccaccggc gcacatcggc catccctcgc  4620
gcttttacgc gggagcgtcc gcagggccgg aaggaggccc ctgccccgtc caaggctgca  4680
ccagctgccc cgccgcccgc ccggacccag cccagcctca ttgctgacga gaccccgccc  4740
tgctactccc tgagctcctc cgccagctcc ctcagcgagc ccgagccctc ggagccgccg  4800
gccgtccatc cacgaggccg ggagcccgcg gtcaccaagg acccgggccc aggaggcgga  4860
cgcgacagct cgcccagccc gcgggccgcg gaggagcttc tgcagcggtg catcagctcg  4920
gccctgccca ggcgccggcc ccccgtgtct ggcctgcggc gccgcaagcc ccgagccacc  4980
cggctggatg agcggcccgc agaggggtcc cgggaacgcg gcgaggaggc agcgggctcg  5040
gaccgggcct ccgacctgga tagcgtggag tggcgcgcca tccaggaggg cgccaattca  5100
attgtcacgt ggctgcacca ggcagcagct gccacgcggg aggcctcgtc cgagtccgac  5160
tccatcctgt ccttcgtatc cgggctgtca gtgggatcca ccctacagcc ccccaagcac  5220
aggaagggac gacaggcgga gggagaaatg ggcagtgccc ggcggccaga gaaaaggggc  5280
gcagcctcag tcaagaccag cgggagcccc cgttcccctg caggccccga gaagccacgt  5340
ggcacacaga agaccacgcc cggggtgcca gctgtgctcc ggggacgaac agtgatctac  5400
gtccccagcc cggcaccccg tgcccagccc aaagggaccc ccggcccccg cgccacaccg  5460
cggaaggtgg cgcccccttg cctggcacag cccgcggctc cagccaaagt cccgagcccc  5520
gggcagcagc ggtcgcggag cctacaccgg cctgccaaga cctcggagct ggcgacgctg  5580
agccagcccc ccagaagcgc cacaccgccc gcccgcctcg ccaagacccc ctcctccagc  5640
tcctcccaga cctcgcccgc ctcccagccc ctgcccagaa agcgcccccc ggtcacccag  5700
gctgctgggg ccctgcccgg ccccggagcc tccccggtgc ccaaaacgcc ggcgcgcacc  5760
cttctggcga agcagcacaa gacgcagaga tcgcccgtgc ggatcccgtt catgcagagg  5820
ccggcccggc gtgggccgcc accgctggct cgggcagtcc cggagccggg ccccaggggc  5880
cgggcgggga ccgaggcggg cccgggggcg cgcgggggcc gcctgggcct ggtgcgtgtg  5940
gcctcagccc tctccagcgg cagcgagtcc tccgaccgct cgggcttccg gcgacagcta  6000
accttcatca aggagtcgcc gggcttgcgg cgccgccgct ccgagctgtc ctcggccgag  6060
tccgcggcct ctgcccccca gggcgcctcg ccccgccgcg gccggcccgc gctgcccgcc  6120
gtcttcctct gctcctcgcg ctgcgaagag ctccgagcgg caccccggca gggcccggcc  6180
ccggcccggc agcggccccc cgcggcccga cccagccctg gcgagcgccc tgcccggcgc  6240
accacctccg agagcccgtc ccgcctgcct gtgcgcgcgc ccgccgcccg gccggagact  6300
gtcaagcgct acgcgtcgct gccgcacatc agcgtggccc gcaggcccga cggcgccgtc  6360
cccgcggccc ctgcctcagc cgacgccgcg cgccgcagca gcgacgggga gccccggccg  6420
ctccccaggg tggccgcgcc gggcacgacc tggcggcgca tccgagatga ggacgtgccc  6480
cacatcctgc gcagcacgct tcccgccacg gccctgccac tgcggggctc cacgcccgag  6540
gacgccccgg ccgggccccc gccgcgcaag accagcgacg ccgtggtcca gaccgaggag  6600
gtcgccgccc ccaagaccaa ctccagcacg tccccgagcc tggagaccag ggagcccccc  6660
ggggcccccg ccggcggcca gctctccctc ctcggcagcg acgtggacgg tcccagcctc  6720
gccaaggctc ccatctccgc acccttcgtg cacgagggcc tgggggtcgc cgtgggggc   6780
ttccccgcca gccggcacgg ctcccccagc cgctcggccc gagtaccccc cttcaactat  6840
gtgcccagcc ccatggtggt cgcagccacc accgactcgg ccgcggagaa agcccccggcc  6900
actgcctccg ccaccctcct ggaatagtgg cctaggccgg ccttctggaa cgttctctcc  6960
cggccctgcg gcgcggtctg gctgccccat gggcctgcgc tgtagacgtc cccccataggt  7020
cgccccaggg cctctgccca cccgagcccc accactctca gaaccccccgc ccagcgcacg  7080
gcgacctcgc gcctcaccgg aagaccttgc ctctgtgccg cggaggtcca ggaggaaacg  7140
gggcggccgc taggcctcaa gtcccgaccg tggagcgctg gcaagggcgt cctggcccag  7200
ccctgagcgc gcggcccttc ccctgtcgga agccgttgct tgaccccggg cgagggaggc  7260
ggtagcctcc gggtccgggt ctgggtctgg gtccgctgct tcgcagggac agcgctgggg  7320
aggtgacggc gcccgccgca ggtggggcga ggctgggggga gggcggcgcc gcggcgggcc  7380
tgccagctgg gggcctttgc ggcgcgcagg ggcgaagcct gtaatcactg cagccgccgg  7440
taattcgcta atgagggctt tgcagggatt gttttcattc tcagccccag ctgtgggagt  7500
gcgggtgggg gtgtggccga gccccggcag gaagccccgc ccagacggtg ttcagggaac  7560
ccggagccca agcgctccgg cggagcccaa aagggtgggg gtgggagggg cagaggccaa  7620
cggatccccc tgcctgtcgc accccttggc gggagacggg aaggcagcgg gctgcgtacg  7680
atgggaccct ggtgcagacg ccgggccggc tgacatttgg accccatccc agaggagatg  7740
ctggctacca gctggggcga ccccaagggt cgctggagtc agtatcggcc cggcgcagcc  7800
gcggcgggcg aggccaatgg aaaggagact gaggggagtc ccggcagtga gcccgaggcc  7860
ctgggacctg gagcccgcgc tggcctctcc ccagcggagc ctgcacgtta cggagaccat  7920
cacatgtggg cgtggtcagt gcccaggacc gcaccgctgc tcatcttgtc ccttttcaat  7980
tcccttctgg ttcatgatgc ataaagcgct aggccctaga actccagaaa cagcacagct  8040
ggggcgggga cccagccttg ccctccaccc gaggctctgg gacaaggcgg gaggttcggg  8100
ggccttccgg caggtgaacg cagggctgga gagtatttgg tgccagatga ggtgaaagct  8160
tatagaaggg cctgaggggc tcggctgcct catcccctgg cgggggaggc tgggagctgg  8220
gcctcctgcg tggggtggga ctcgcagggg ccgggtctcc gtgactgggg caacgcctcg  8280
tcctgcagag ggagccgacg acctcttttc tgcagaaaag ctccagcagg cgctgccttc  8340
```

-continued

```
acccacggat ctgcccaggc tgaaggcaca cgctcaatgc cccacgtgcc ttctccagga  8400
ggaacgaagc agggtttgag ggttgggtgg atggagctca gaaggaaacc ccagccccac  8460
cacggatgac accatccctc ccgtcccatc cccagcatgg gcaaggccag cctttctggc  8520
agaaggagct gtcctcaact cagggccgct gtgagcaaag ctgaccccag cccccacccc  8580
cagttaacac tgctgcttct ctgaatgcat gtcacgctgc accccatgct ccgggcccac  8640
accctgcagg acaaggagct ccagacagga cgtccataag tcaccgaggt gtgccaccca  8700
gcaggtgctg gaggtgccca atgctccctc ctaggacctc gcagccaggc aaggctgtca  8760
ggttgttttg ggggaagagg gggtcatgga tggctgagca gagagcgggg aaaatgcagg  8820
ctgagtgggg cgacctcctg cctgccagga gcccccttc aggacacagc gggggtctca  8880
cacttgctgt ccccatccat ggcccgaggg ggaacctggt ggtctcttct gagcttttgg  8940
acttggggat gccaaacacg tgctcaccct cacactcgcc ccggcccgct gcgcccctaa  9000
ttgccaaagg gtagggaaat ggcgaagcca gccaccaggt cgctggtgac agggccaggg  9060
ttatgcagga aggtggtgcg gcattgcctt ccacatatgt aagtctctgg gcggcgccct  9120
cccagctccc tgcctctgtt tccccatgtg ggccgtgggg aactcccaga gctacctctt  9180
gggggagcgt ggtggcagcg atgatgggga gacgcctgga agctcacaga acttgggtct  9240
ggctggctcc tgcccgtgac gccttgccca gcagcaaggt gcgcaacatg gctgccagcc  9300
ccgcctccca cccccacccc gagtcctgag ctcactttcg ccttctccat cccctgccgt  9360
gggggccaca gccacacctc accgcccagt ccagctgtct ccagaagggg acaggcagtc  9420
cgcggtctct ggacaatcaa ctcaaggtac gcccactgca aggcctccct cccaccgcgg  9480
cccctgcctg gccacctggc ctctctgcac cagggtgaca aggggtcctc gtctgccccc  9540
caatgctcca gggccagtcc taaggagctg agggtctgag gacgcaggga gggtggaggt  9600
gtcctgaggc tgatggacag tgaccgccac tggcccccaa catgaccaca cgtgggtgct  9660
gaactcgggg cgccgtgccc accggcatgg tcctcccgag ctccgacagc attacctcac  9720
ccggccccat ctgttgcccc ggtccagccc tgatggcgcg cgcctggtct gtctgattcc  9780
cctagccgcc accccacgtt tctgtaccgg gtctctgcag tgttaaacgg acgtgtaaat  9840
agtggtaaat agtgaaagcc tgtccttccc taaatgtaaa gccatctgtc cggcgtaagg  9900
acgacaccgt cagctgtccg actcgcacac atttaataaa ctgagctctt gcattgcc    9958

SEQ ID NO: 4           moltype = DNA  length = 1449
FEATURE                Location/Qualifiers
source                 1..1449
                       mol_type = other DNA
                       organism = Homo sapiens
SEQUENCE: 4
aggccgccag cctcggagtg ggcgcgggac agtgcgcggc gccccgcagc caggcccccg  60
cccccgccgc atccacctcc tccgccgcct gcgacccaac gggcgccccc cgccgcggca  120
gctgccgccg ggcccccgcg gccaccatga agaaggaggt gtgctccgtg gccttcctca  180
aggccgtgtt cgcagagttc ttggccaccc tcatcttcgt cttctttggc ctgggctcgg  240
ccctcaagtg gccgtcggcg ctgcctacca tcctgcagat cgcgctggcg tttggcctgg  300
ccataggcac gctggcccag gccctgggac ccgtgagcgg cggccacatc aaccccgcca  360
tcaccctggc cctcttggtg ggcaaccaga tctcgctgct ccgggctttc ttctacgtgg  420
cggcccagct ggtgggcgcc attgccgggg ctggcatcct ctacggtgtg gcaccgctca  480
atgcccgggg caatctggcc gtcaacgcgc tcaacaacaa cacaacgcag ggccaggcca  540
tggtggtgga gctgattctg accttccagc tggcactctg catcttcgcc tccactgact  600
cccgccgcac cagccctgtg ggctccccag ccctgtccat tggcctgtct gtcaccctgg  660
gccaccttgt cggaatctac ttcactggct gctccatgaa cccagcccgc tcttttggcc  720
ctgcggtggt catgaatcgg ttcagccccg ctcactgggt tttctgggta gggcccatcg  780
tgggggcggt cctggctgcc atcctttact tctacctgct cttccccaac tccctgagcc  840
tgagtgagcg tgtggccatc atcaaaggca cgtatgagcc tgacgaggac tgggaggagc  900
agcgggaaga gcggaagaag accatggagc tgaccacccg ctgaccagtg tcaggcaggg  960
gccagcccct cagcccctga gccaaggggg aaaagaagaa aaagtaccta acacaagctt  1020
cctttttgca caaccggtcc tcttggctga ggaggaggag ctggtcaccc tggctgcaca  1080
gttagagagg ggagaaggaa cccatgatgg gactcctggg gtaggggcca ggggctgggg  1140
tctgctgggg acaggtctct ctgggacaga cctcagagat tgtgaatgca gtgccaagct  1200
cacaggctgc aagggccagg ccagaaaagg gcgggcctgc agcctgcacc ccccaccttc  1260
cccaaccctt cctcaagagc tgaagggatc ccagccccta ggtgggcaga ggcagaccct  1320
ccccagagct ccttaggaag aagacagact ggttcattga atgccgcctt atttatttct  1380
ggtgaggatg catgcgtggg gctgctggtg tttagagtgg gggctaccca ataaatcact  1440
gatactcac                                                         1449

SEQ ID NO: 5           moltype = DNA  length = 1310
FEATURE                Location/Qualifiers
source                 1..1310
                       mol_type = other DNA
                       organism = Homo sapiens
SEQUENCE: 5
acacagacac gcagacacag agacaccggg gcccagggcc ctcctatgga ccctgcccgc  60
tcccctccca ttgtccacgg ctgtccgccc acccccattc tccaagcttc agccccctcc  120
ttagttcggc atctgcacag cactgaagaa cctgggaatc agaccctgag accctgagca  180
atcccaggtc cagcgccagc cctatcatga ccaaggagta tcaagacctt cagcatctgg  240
acaatgagga gagtgaccac catcagctca gaaaagggcc acctcctccc cagcccctcc  300
tgcagcgtct ctgctccgga cctcgcctcc tcctgctctc cctgggcctc agcctcctgc  360
tgcttgtggt tgtctgtgtg atcggatccc aaaactccca gctgcaggag gagctgcggg  420
gcctgagaga gacgttcagc aacttcacag cgagcacgga ggcccaggtc aagggcttga  480
gcacccaggg aggcaatgtg ggaagaaaga tgaagtcgct agagtcccag ctggagaaac  540
agcagaagga cctgagtgaa gatcactcca gcctgctgct ccacgtgaag cagttcgtgt  600
```

-continued

```
ctgacctgcg gagcctgagc tgtcagatgg cggcgctcca gggcaatggc tcagaaagga  660
cctgctgccc ggtcaactgg gtggagcacg agcgcagctg ctactggttc tctcgctccg  720
ggaaggcctg ggctgacgcc gacaactact gccggctgga ggacgcgcac ctggtggtgg  780
tcacgtcctg ggaggagcag aaatttgtcc agcaccacat aggccctgtg aacacctgga  840
tgggcctcca cgaccaaaac gggccctgga agtgggtgga cgggacggac tacgagacgg  900
gcttcaagaa ctggaggccg gagcagccgg acgactggta cggccacggg ctcggaggag  960
gcgaggactg tgcccacttc accgacgacg gccgctggaa cgacgacgtc tgccagaggc  1020
cctaccgctg ggtctgcgag acagagctgg acaaggccag ccaggagcca cctctccttt  1080
aatttatttc ttcaatgcct cgacctgccg caggggtccg ggattgggaa tccgcccatc  1140
tgggggcctc ttctgctttc tcgggaattt tcatctagga ttttaaggga aggggaagga  1200
tagggtgatg ttccgaaggt gaggagcttg aaacccgtgg cgctttctgc agtttgcagg  1260
ttatcattgt gaactttttt tttttaagag taaaaagaaa tatacctaaa            1310

SEQ ID NO: 6            moltype = DNA  length = 3297
FEATURE                 Location/Qualifiers
source                  1..3297
                        mol_type = other DNA
                        organism = Homo sapiens
SEQUENCE: 6
ctcttccgaa tgtcctgcgg ccccagcctc tcctcacgct cgcgcagtct ccgccgcagt  60
ctcagctgca gctgcaggac tgagccgtgc acccggagga gacccccgga ggaggcgaca  120
aacttcgcag tgccgcgacc caaccccagc cctgggtagc ctgcagcatg gcccagctgt  180
tcctgcccct gctggcagcc ctggtcctgg cccaggctcc tgcagcttta gcagatgttc  240
tggaaggaga cagctcagag gaccgcgctt ttcgcgtgcg catcgcgggc gacgcgccac  300
tgcagggcgt gctcggcggc gccctcacca tcccttgcca cgtccactac ctgcggccac  360
cgccgagccg ccgggctgtg ctgggctctc cgcgggtcaa gtggactttc ctgtcccggg  420
gccgggaggc agaggtgctg gtggcgcggg gagtgcgcgt caaggtgaac gaggcctacc  480
ggttccgcgt ggcactgcct gcgtacccag cgtcgctcac cgacgtctcc ctggcgctga  540
gcgagctgcg ccccaacgac tcaggtatct atcgctgtga ggtccagcac ggcatcgatg  600
acagcagcga cgctgtggag gtcaaggtca aaggggtcgt ctttctctac cgagagggct  660
ctgcccgcta tgctttctcc ttttctgggg cccaggaggc ctgtgcccgc attggagccc  720
acatcgccac cccggagcag ctctatgccg cctaccttgg gggctatgag caatgtgatg  780
ctggctggct gtcggatcag accgtgaggt atcccatcca gaccccacga gaggcctgtt  840
acggagacat ggatggcttc cccggggtcc ggaactatgg tgtggtggac ccggatgacc  900
tctatgatgt gtactgttat gctgaagacc taaatggaga actgttcctg ggtgaccctc  960
cagagaagct gacattggag gaagcacggg cgtactgcca ggagcggggt gcagagattg  1020
ccaccacggg ccaactgtat gcagcctggg atggtggcct ggaccactgc agcccagggt  1080
ggctagctga tggcagtgtg cgctacccca tcgtcacacc cagccagcgc tgtggtgggg  1140
gcttgcctgg tgtcaagact ctcttcctct tccccaacca gactggcttc cccaataagc  1200
acagccgctt caacgtctac tgcttccgag actcggccca gccttctgcc atccctgagg  1260
cctccaaccc agcctccaac ccagcctctg atggactaga ggctatcgtc acagtgacag  1320
agaccctgga ggaactgcag ctgcctcagg aagccacaga gagtgaatcc cgtggggcca  1380
tctactccat ccccatcatg gaggacggag gaggtggaag ctccactcca gaagacccag  1440
cagaggcccc taggacgctc ctagaatttg aaacacaatc catggtaccg cccacggggt  1500
tctcagaaga ggaaggtaag gcattggagg aagaagagaa atatgaagat gaagaagaga  1560
aagaggagga agaagaagag gaggaggtgg aggatgaggc tctgtgggca tggcccagcg  1620
agctcagcag cccgggccct gaggcctctc tccccactga gccagcagcc caggaggagt  1680
cactctccca ggcgccagca agggcagtcc tgcagcctgg tgcatcacca cttcctgatg  1740
gagagtcaga agcttccagg cctccaaggg tccatggacc acctactgag actctgccca  1800
ctcccaggga gaggaaccta gcatccccat caccttccac tctggttgag gcaagagagg  1860
tgggggaggc aactggtggt cctgagctat ctggggtccc tcgaggagag agcgaggaga  1920
caggaagctc cgagggtgcc ccttccctgc ttccagccac acgggcccct gagggtacca  1980
gggagctgga ggcccccctct gaagataatt ctggaagaac tgccccagca gggacctcag  2040
tgcaggccca gccagtgctg cccactgaca gcgccagccg aggtggagtg gccgtggtcc  2100
ccgcatcagg tgactgtgtc cccagcccct gccacaatgg tgggacatgc ttggaggagg  2160
aggaaggggt ccgctgccta tgtctgcctg gctatggggg ggacctgtgc gatgttggcc  2220
tccgcttctg caaccccggc tgggacgcct tccagggcgc ctgctacaag cacttttcca  2280
cacgaaggag ctgggaggag gcagagaccc agtgccggat gtacggcgcg catctggcca  2340
gcatcagcac acccgaggaa caggacttca tcaacaaccg gtaccgggag taccagtgga  2400
tcggactcaa cgacaggacc atcgaaggcg acttcttgtg gtcggatggc gtcccccctgc  2460
tctatgagaa ctggaaccct gggcagcctg acagctactt cctgtctgga gagaactgcg  2520
tggtcatggt gtggcatgat cagggacaat ggagtgacgt gccctgcaac taccacctgt  2580
cctacacctg caagatgggg ctggtgtcct gtgggccgcc accggagctg cccctggctc  2640
aagtgttcgg ccgcccacgg ctgcgctatg aggtggacac tgtgcttcgc taccggtgcc  2700
gggaaggact ggcccagcgc aatctgccgc tgatccgatg ccaagagaac ggtcgttggg  2760
aggcccccca gatctcctgt gtgcccagaa gacctgcccg agctctgcac ccagaggagg  2820
acccagaagg acgtcagggg aggctactgg gacgctggaa ggcgctgttg atccccccctt  2880
ccagccccat gccaggtccc tagggggcaa ggccttgaac actgccggcc acagcactgc  2940
cctgtcaccc aaattttccc tcacaccctg cgctcccgcc accacaggaa gtgacaacat  3000
gacgaggggt ggtactggag tccaggtgac agttcctgaa ggggcttctg ggaaatacct  3060
aggaggctcc agcccagccc aggccctctc cccctaccct gggcaccaga tcttccatca  3120
gggccggagt aaatccctaa gtgcctcaac tgccctctcc ctggcagcca tcttgtcccc  3180
tctattcctc tagggagcac tgtgcccact ctttctgggt tttccaaggg aatgggcttg  3240
caggatggag tgtctgtaaa atcaacagga aataaaactg tgtatgagcc caggcaa     3297
```

-continued

```
SEQ ID NO: 7            moltype = DNA  length = 5005
FEATURE                 Location/Qualifiers
source                  1..5005
                        mol_type = other DNA
                        organism = Homo sapiens
SEQUENCE: 7
agttccaagt aggtaatcct tctgagaagt cccacctttc tgagcagctg tgtttgaaga  60
aagctagtgg gaaaagttcc aggattacat gtcaggaaac tacaagaggt agaaacattt  120
gttgatttac cagtgttttt aacttcctgc tgggctgaaa actgcttgtt tcgtggaaaa  180
gcaaaacttg acagcaaaca tctaaaatga agagctccca aacttttgag gaacaaacgg  240
aatgcattgt gaacactcta ctcatggact tcttgagccc aacattgcag gttgccagcc  300
ggaacctatg ctgtgtagat gaagtagatt caggagagcc ttgttctttt gatgtggcta  360
tcattgctgg tcgccttcgg atgttgggtg accagttcaa cggagaattg gaagcttctg  420
ccaaaaacgt cattgcagaa accattaagg gacagacagg agctatactc caggacactg  480
tggaatctct cagcaagacc tggtgtgctc aggattccag cttagcttat gagagagctt  540
ttctggcagt gtcagtgaaa cttcttgagt acatggctca cattgctcct gaagtagtgg  600
gacaggtggc tatccccatg acgggtatga tcaatgggaa ccaagccatc cgggagttca  660
tccagggcca gggaggttgg gaaaatctgg agagctgaag agttggagct attcacgaga  720
ctgaacatca cttccttgtt gactgattgg gtgattgatt cctgggaatt caaacaaaca  780
aataaaaaag cactttttc attttatcag aactgaactt agctgaataa gttatttttt  840
actgattgtt aaagttggga gcagctgcca gaggcctgca gagttggttt ttgttttgtt  900
ttgttttgtc aacttaatgc aaaccacaga gattttctac tttctgtttt cacatgagtt  960
ttaatgaggt tctgttgaag caaagacccc tagacacaaa gtaatgactt gttagtagtg  1020
gaattataag caacagggca ggcctttgct ggaggtattt tgagagaaag ggagaacaat  1080
ggaaactatt tcttcagatg tagccctgtc ttttggtaag aattgtgcct actaattttg  1140
caatttaaag gatttcagga agctttttgg ttgaaaaatc ttgttttttt tttttagac  1200
gtagtctcac tctgtcaccc aggctggagt gcagtggtgc gatctcagct cactgcaagc  1260
tccacctccc ggtttcactc cattctcctg cctcagcctc ctgagtagct gggactacag  1320
gagcccgcca tcacgcccgg ctaatttttt gtatttttag tagagatgag gtttcgccgt  1380
gttagccagg atggtctgga tctcctgacc tcgtgattcg cccgccttgg cctcccaaag  1440
tgctgggatt acaggcgtga gccaccacgc ccggcctaaa atcttgttat tttaagttga  1500
gcattttcat tcaaaatcat ccctaaactt catgttaatt tcacctgaga aggactattt  1560
tatgcatttt agaggttgga agcaaaaaac aaacaaacaa acaaaaacag ttgtttctac  1620
taggaaggtc aaagaaaata aaagttactc catttttact gccacaggat gcaggaagtg  1680
ctggcccaca tctaggacag caaggccacc ccagcttaga tgaagctagc tgcataacac  1740
aaagctttaa aagtgtggtt cacacaccac ttgtggacct tattgaattg ctgattcgca  1800
ttcctagaga ttctgattct gtaggggtag gctggagcct aggaacctac cttttaaact  1860
agttccatag gtgattctga tgtacatata gagtgtgaca gccatcacta tagagaatag  1920
attgataaat tacaacccac gcgtcaaatc tggcttgctg tcttattttg taaataaagt  1980
tttattggaa tagagcaaca ttcacttgtt tacatattgt ccatggccgc ttttgtgcta  2040
caatggcaga gttgaatgat tatagaagac catatggctg gttaagtcca aaatatttac  2100
tagctggccc tttacagaaa aagttggctg accccttctc taaatcaaca tttctccttg  2160
gtaactgaaa ctctattaca gtcctgacaa ttccagcaaa cacagctgta gatagggttt  2220
aaactcaaag atatttaact cttctttggg aacttagtct ccatatgttt gttagttctt  2280
gcataatcca cagtttctct gggtcttcag ccaatcagag agctctgtag ctcctgagta  2340
gtccatttct ctggccctac aagtgagagt gattggaagc aaagcttatg atttgtatga  2400
tcttgtatct caaaatagtc cttaatgatc taatagatta gtaggcagtc atcaggtaga  2460
gactccaaaa accagactac tttcctaaat atcaagaaga aaggcattgc tacagtgatt  2520
catgaaaagc agcattaata actttggcta aagtttaaca aagctaacca cttcccctct  2580
atcagccagc catctatgta tctcctctaa atgcagagaa gtaaatatgt agtgctgtta  2640
atacattttt gctttttaaa gttatgcttt gtcctggcgc agtggctcat gcctgtaatc  2700
ccagcacttt gggaggccaa ggcgggtgga tcacctgagg ttaggagttt gagaccagcc  2760
tggccaacat ggtgaaaccc tgtctctgct aaaaatacaa aaaattagcc aggcttggtg  2820
gcacgtgcct gtaatgccag ctactcagga ggctgaggca ggagaatcac ttgaacctgg  2880
gaggcggagg ttgctgtgag ctgagttcgc gccattgcac tccagcctgg gctacaaaag  2940
cgaaactgtc taaaaaaaaa aaaagaaaat aaataaagtt atgctttttc ctctattcct  3000
agttaaatca caacaagtta gtaatccata aatgatgtgt cctgtttctc tttagtagaa  3060
attatatttt tggctaccag ttaagaaact tgtactcctt tgtcccttat gttactataa  3120
actcaagatg atgagttttg tggtatttga cttcataggc aaaatcaaaa tttttacttt  3180
gttgctattc tgttttatga aataaacttc tgtctatgca tttgaactaa gtttcagcaa  3240
attcaatcta aattgaataa ttccagctcc cagttttatc ctatgttgct cataaaacag  3300
ttccaagtat actgcattat cttgagattt gaagatatgg tgcccacggg gattatacta  3360
ggcaaatgcg ttaagcagct ctggcctagg tgttgtgtat tttaagagac tctatcttag  3420
gagagcttaa gtgattgggc tgcaggaaga agacattgta acccaggaat taaaaatgga  3480
ttcagattgc ctgattttaa cactttagtt tcaccatagg ctaattatgt gacattgggc  3540
aagagacata attcttctgt accttagttt ctacatttgt aaaatagaga tgatttggta  3600
acttattaat aagatttttg tgagagataa ataaaacaaa tacattttgt aaagggtgag  3660
tacttggaat attttaaaca ctgtgccatt agcaatttgg aattctgtgt tatgcagttc  3720
ataaggttct agcttgactt ttttctctct ccattaaccc tgtctctcac agatgcaaac  3780
cactcttaat ggctttactt tcacatcaat gtgagtgatt cctaaatatg atttatttcc  3840
cttctcaatt ccatacccac agatgcttat tatttattta tgtgtacctt tcttatcccc  3900
atactctccc tgtttgcgat acaactagct caaaacctca gtcattttta ccttgtctct  3960
ctctctccag tccaactcac ccaactagtt tttctcattt gttacttcat ttttgtcctg  4020
gttcttctac cagatttatt agcaactgcc tggactatta ataaagcctc ctacttaggc  4080
tttcaataga ttgttctgtt cctgctccat tccagtctgt cctatatact gccatcagat  4140
tgatcaaagc tgtggtttct ttgtctatta ttttgattca tttttagata tggtatcatt  4200
catttttaaa tttaacatac caatgaagat tacaagactt aaacatctta tcagaagggg  4260
gcatttattt tttaaatcaa gaaataactt tccaaaagca ttgctttgaa tgccattctc  4320
ttaaagtcct tcagtggaac ttttgagtgt gattagacat gttcattatc ttgattgtag  4380
```

-continued

```
tgattttatg ggtgatgatt tcacaccaac ttatcaaact gcatactttg aaatgtgtag  4440
tttattgtac atcagcacta ccttaataag gttgtttttt ttaaaaaaaa aaaaaaaacc  4500
ttcagctgct ccctactgtt catcaaataa cagtctgata ttcaaattcc cccagtatct  4560
ggccctaact gccctatata gccttaatca atcatgattc tcctctacaa tcccaatgct  4620
ctagtataac cgagccagtc actaaagctg ccctcctcct actgttccct atgtttcata  4680
ttcctttttc tgaggctcta cctgtagaca tcttcaagac ccaacccaac tgtcatgaag  4740
ccttctccat gaaggctatc catataacca gaataagaag tggtctttgc ctccttgaac  4800
ttttgtttgt accactttta tgtttcttat ccaaaaaatg gccttaagtt gtaattatct  4860
gtatagtcat cttccccact aggataaagg attgctgaat gatacaattt gttgtatact  4920
tctgtaacac ccctcctctt cattatctgg catgtacatc gatattaaaa atattcatta  4980
aatgaatgaa tagctgattg actca                                         5005

SEQ ID NO: 8           moltype = DNA  length = 1855
FEATURE                Location/Qualifiers
source                 1..1855
                       mol_type = other DNA
                       organism = Homo sapiens
SEQUENCE: 8
aagtgtgtcc ctagcggcgg cccgtgcagc gctcccgcga gacgctcacc tgcgccccag  60
gtgagcggcg agggggcggg ggagggggctg agccggaggc ggctcacctg gcgggacagg  120
tgcctggctg ctacaaacca tgcaatgagc catgccccgc cctggacacc cccgcccagc  180
atctgggcct ccacgcttgg gaccgtggga gcggccaaca gagctatgtc tggagacata  240
tgataaacca cctcagcccc caccaagccg ccgcacccgt agaccagacc ccaaggaccc  300
tggccaccat gggccagaga gcattacctt catctctggc tctgctgagc cggcccttga  360
gtcccccacc tgctgcctgc tctggcgacc ctgggtgtgg gagtggtgcc gggctgcctt  420
ctgcttccgc cgctgccggg attgcctcca gcgctgtgga gcctgtgtgc ggggatgcag  480
cccctgcctg tctactgagg actccactga ggggactgct gaagccaact gggccaagga  540
gcacaatgga gtgcccccca gccctgatcg tgcacccccc agccggcggg atggccagcg  600
gctcaagtca accatgggca gcagcttcag ctaccccgat gttaagctca aaggcatccc  660
tgtgtatccc tacccgaggg ccacctcccc agcccctgat gcggactcct gctgcaagga  720
gccactggcc gatcccccac ccatgcgaca cagcctgccc agcacctttg ccagtagtcc  780
tcgtggctcc gaggagtact attctttcca tgagtcggac ctggacctgc cggagatggg  840
cagtggctcc atgtcgagcc gagaaattga tgtgctcatc ttcaagaagc tgacagagct  900
gttcagcgta caccagatcg atgagctggc caagtgcaca tcagacactg tgttcctgga  960
gaagaccagt aagatctcgg accttatcag cagcatcacg caggactacc acctggatga  1020
gcaggatgct gagggcgcgc tggtacgcgg catcattcgc attagtaccc gaaagagccg  1080
tgctcgccca cagacctcgg agggtcgttc aactcgggct gctgccccaa ccgctgctgc  1140
ccctgacagt ggccatgaga ccatggtggg ctcaggtctc agccaggatg agctgacagt  1200
gcagatctcc caggagacga ctgcagatgc catcgcccgg aagctgaggc cttatggagc  1260
tccagggtac ccagcaagcc atgactcatc cttccagggc accgacacag actcgtcggg  1320
ggcacccttg ctccaggtgt actgctaacc cctgccaggc ccagctgcca cacccctttct  1380
gggagaagca tggcctacag aatgaagagg gggaccagga acccctgtgg gagaggctta  1440
gacctgaagc agtgcccact ctggctcctc ctgccttggc tgactgggtt cctggaccat  1500
gtgcatttca ctgggccatg ggatctacat ctccttgcat ccccagctgg tctgatccct  1560
gccagggccc cttccttcct gctcatggtc ttcaggtggc ctgatcatgg aaagtaagga  1620
gttaggcatt accttctggg agtgaaccct gactccatcc ccctattgcc accctaacca  1680
atcatgcaaa cttctccctc cctggggtaa ttcaacagtt aaaagaagct tatcttaaat  1740
gtattgtatt ggggggtggg cagggcccac tctatgttat gttaaggagt tggttctggt  1800
tcttggctga tgttctgtat cttaacatga ccacagtttg taagtacaaa ggtaa        1855

SEQ ID NO: 9           moltype = DNA  length = 1537
FEATURE                Location/Qualifiers
source                 1..1537
                       mol_type = other DNA
                       organism = Homo sapiens
SEQUENCE: 9
acaacacagc taacacaagg ccccgcaggc aggactctgg gacagacgca ggccagctgc  60
ccagagccca gaccaagcat ggacgccgtg gatgccacca tggagaaact ccgggcacag  120
tgcctgtccc gcggggcctc gggcatccag ggcctggcca ggtttttccg ccaactagac  180
cgggacggga gcagatccct ggacgctgat gagttccggc agggtctggc caaactcggg  240
ctggtgctgg accaggcgga ggcagagggt gtgtgcagga agtgggaccg caatggcagc  300
gggacgctgg atctggagga gttccttcgg gcgctgcggc cccccatgtc ccaggcccgg  360
gaggctgtca tcgcagctgc atttgccaag ctggaccgca gtggggacgg cgtcgtgacg  420
gtggacgacc tccgcggggt gtacagtggc cgtgcccacc ccaaggtgcg cagtggggag  480
tggaccgagg acgaggtgct gcgccgcttc ctggacaact tcgactcctc tgagaaggac  540
gggcaggtca cactggcgga attccaggac tactacagcg gcgtgagtgc ctccatgaac  600
acggatgagg agttcgtggc catgatgacc agtgcctggc agctgtgagc agctccggct  660
cagccctgct gccctggcct gtcactcccc acccctgccg gagacctccc ttccctgggc  720
cccttctctc ctgggcagcc acaccacaga gcggggaggg gcaggtgggg gaatggaggc  780
tgcaggactg gctagaccag gtccctgccg gtccaccagg cggaggtggg acaaaggtcc  840
taacaggagt cactggctca ggaccccagg gagaaacgct ctccccaccc acgccatgct  900
gaccagagat cttgcagccc ctgtggatgc ccccgccgag gtcccccgat ccccgcaccc  960
ggactgctgc tccctgcccc tcccttgcgg gtcccccagg aagccaggtg accccaggtg  1020
ggaggctgtg tgtggaggcc atcctggaag gaagtttaga cctgcccagg tgtggagcga  1080
ggggcacagg ggcatcctaa cctcagaaac tgaaataaag cctttgaaaa aaaaatctgt  1140
aaaacatcaa cccccaatca gaagatggca aatggggaat aaaaatagca ggtaacatgt  1200
ccagcgggcc cagtatctac attctggtga gcggcccgag gctgggagct ctgggcgggg  1260
gcagaccggc ggggccttgc agcaggggtg ggggtaaagt gcgggtggtg gtggagagaa  1320
cagggctgtg gctggacccc agcactggtg acacgctggg tgggagcatg aggccccagg  1380
```

-continued

```
ctgctggagg tcctcgcccg gggaggtgga ggccgttcct ggtcaggggc ttcctgaggc  1440
ccctggggca tgcagaggcc agggttttag ttaaaagttt aatgtagttc ccaaatacat  1500
ttcatatgac aatcttacat aaatgttcca aaacaca                            1537

SEQ ID NO: 10          moltype = DNA  length = 1576
FEATURE                Location/Qualifiers
source                 1..1576
                       mol_type = other DNA
                       organism = Homo sapiens
SEQUENCE: 10
atcccagccg caccggtcct tcccggcaca cgcgaggctc ccatggctct ggcggtggcc  60
ccgtgggggc gacagtggga agaggcccgc gccctgggcc gggcagtcag gatgctgcag  120
cgcctagaag agcaatgcgt cgacccccgg ctgtccgtga gtcccccttc gctgcgggac  180
ctgctgcccc gcacagcgca gctgcttcga gaggtggccc attctcggcg ggcggccggc  240
ggaggcggcc ccgggggtcc cggcggctct ggggactttc tactcatcta cctggccaat  300
ctggaggcca agagcaggca ggtggccgcg ctgctgcctc cccggggccg aaggagtgcc  360
aacgacgagc tcttccgggc gggctccaga ctcaggcgac agctggccaa gctggccatc  420
atcttcagcc acatgcacgc agagctgcac gcactcttcc ccgggggaaa gtactgtgga  480
cacatgtacc agctcaccaa ggcccccgcc cacaccttct ggagggaaag ttgcggagcc  540
cggtgtgtgc tgccctgggc tgagtttgag tccctcctgg gcacctgcca ccctgtggaa  600
ccaggctgca cagccctggc cttgcgcacc accattgacc tcacctgcag cgggcacgtg  660
tccatcttcg agttcgacgt cttcaccagg ctctttcagc catggccaac actcctcaag  720
aactggcagc tcctggcagt caaccaccca ggctacatgg ccttcctcac ctatgatgag  780
gtccaagagc gtctgcaggc ctgcagggac aagccaggca gttacatctt ccggcccagc  840
tgtactcgcc tggggcagtg ggccatcggc tatgtgagct cagatggcag catcctgcag  900
accatccctg ccaacaaacc cctgtcccag gtgctcctgg agggacagaa ggacggcttc  960
tacctctacc cagatggaaa gacccacaac ccagacctga ctgagctcgg ccaggcagaa  1020
ccccagcagc gcatccacgt gtcagaggag cagctgcagc tctactgggc catggactcc  1080
acatttgagc tctgcaagat ctgtgctgag agcaacaagg atgtgaagat tgagccgtgc  1140
gggcacctgc tctgcagctg ctgcctggct gcctggcagc actcggacag ccagacctgc  1200
cccttctgcc gctgcgagat caagggctgg gaggccgtga gtatctacca gttccacggt  1260
caggctactg ctgaggactc agggaacagc agtgaccagg aaggcaggga gttggagctg  1320
gggcaggtgc ccctttcggc tcctccattg cccccacggc cagatctgcc ccccaggaag  1380
cccagaaatg cccagccgaa agtgagactc ctaaagggga actcccctcc agctgcgctg  1440
ggaccccagg accctgcccc ggcctgaagg ccagggcacc cagatgtgct gctcaaggga  1500
gccccaaggg ctggaagggg gttgtgaaac cgaaataaac tgccaagcct ggtctgtcct  1560
ccagggtgca aaggaa                                                   1576

SEQ ID NO: 11          moltype = DNA  length = 4811
FEATURE                Location/Qualifiers
source                 1..4811
                       mol_type = other DNA
                       organism = Homo sapiens
SEQUENCE: 11
agtggcgtcg gaactgcaaa gcacctgtga gcttgcggaa gtcagttcag actccagccc  60
gctccagccc ggcccgaccc gaccgcaccc ggcgcctgcc ctcgctcggc gtccccggcc  120
agccatgggc ccttggagcc gcagcctctc ggcgctgctg ctgctgctgc aggtctcctc  180
ttggctctgc caggagccgg agccctgcca ccctggcttt gacgccgaga gctacacgtt  240
cacggtgccc cggcgccacc tggagagagg ccgcgtcctg ggcagagtga attttgaaga  300
ttgcaccggt cgacaaagga cagcctattt ttccctcgac acccgattca aagtgggcac  360
agatggtgtg attacagtca aaaggcctct acggtttcat aacccacaga tccatttctt  420
ggtctacgcc tgggactcca cctacagaaa gttttccacc aaagtcacgc tgaatacagt  480
ggggcaccac caccgccccc cgccccatca ggcctccgtt tctggaatcc aagcagaatt  540
gctcacattt cccaactcct ctcctggcct cagaagacag aagagagact gggttattcc  600
tcccatcagc tgcccagaaa atgaaaaagg cccatttcct aaaaacctgg ttcagatcaa  660
atccaacaaa gacaaagaag gcaaggtttt ctacagcatc actggccaag gagctgacac  720
accccctgtt ggtgtcttta ttattgaaag agaaacagga tggctgaagg tgacagagcc  780
tctggataga gaacgcattg ccacatacac tctcttctct cacgctgtgt catccaacgg  840
gaatgcagtt gaggatccaa tggagatttt gatcacggta accgatcaga atgacaacaa  900
gcccgaattc acccaggagg tctttaaggg gtctgtcatg gaaggtgctc ttccaggaac  960
ctctgtgatg gaggtcacag ccacagacgc ggacgatgat gtgaacacct acaatgccgc  1020
catcgcttac accatcctca gccaagatcc tgagctccct gacaaaaata tgttcaccat  1080
taacaggaac acaggagtca tcagtgtggt caccactggg ctggaccgag agagtttccc  1140
tacgtatacc ctggtggttc aagctgctga ccttcaaggt gaggggttaa gcacaacagc  1200
aacagctgtg atcacagtca ctgacaccaa cgataatcct ccgatcttca atcccaccac  1260
gtacaagggt caggtgcctg agaacgaggc taacgtcgta atcaccacac tgaaagtgac  1320
tgatgctgat gcccccaata ccccagcgtg ggaggctgta tacaccatat tgaatgatga  1380
tggtggacaa tttgtcgtca ccacaaatcc agtgaacaac gatggcattt tgaaaacagc  1440
aaagggcttg gattttgagg ccaagcagca gtacattcta cacgtagcag tgacgaatgt  1500
ggtacctttt gaggtctctc tcaccacctc cacagccacc gtcaccgtgg atgtgctgga  1560
tgtgaatgaa gcccccatct ttgtgcctcc tgaaaagaga gtggaagtgt ccgaggactt  1620
tggcgtgggc caggaaatca catcctacac tgcccaggag ccagacacat ttatggaaca  1680
gaaaataaca tatcggattt ggagagacac tgccaactgg ctggagatta atccggacac  1740
tggtgccatt tccactcggg ctgagctgga cagggaggat tttgagcacg tgaagaacag  1800
cacgtacaca gccctaatca tagctacaga caatggttct ccagttgcta ctggaacagg  1860
gacacttctg ctgatcctgt ctgatgtgaa tgacaacgcc cccataccag aacctcgaac  1920
tatattcttc tgtgagagga atccaaagcc tcaggtcata aacatcattg atgcagacct  1980
tcctcccaat acatctccct tcacagcaga actaacacac ggggcgagtg ccaactggac  2040
cattcagtac aacgacccaa cccaagaatc tatcattttg aagccaaaga tggccttaga  2100
```

```
ggtgggtgac tacaaaatca atctcaagct catggataac cagaataaag accaagtgac  2160
caccttagag gtcagcgtgt gtgactgtga aggggccgct ggcgtctgta ggaaggcaca  2220
gcctgtcgaa gcaggattgc aaattcctgc cattctgggg attcttggag gaattcttgc  2280
tttgctaatt ctgattctgc tgctcttgct gtttcttcgg aggagagcgg tggtcaaaga  2340
gcccttactg cccccagagg atgacacccg ggacaacgtt tattactatg atgaagaagg  2400
aggcggagaa gaggaccagg actttgactt gagccagctg cacaggggcc tggacgctcg  2460
gcctgaagtg actcgtaacg acgttgcacc aaccctcatg agtgtccccc ggtatcttcc  2520
ccgccctgcc aatcccgatg aaattggaaa ttttattgat gaaaatctga aagcggctga  2580
tactgacccc acagccccgc cttatgattc tctgctcgtg tttgactatg aaggaagcgg  2640
ttccgaagct gctagtctga gctccctgaa ctcctcagag tcagacaaag accaggacta  2700
tgactacttg aacgaatggg gcaatcgctt caagaagctg gctgacatgt acggaggcgg  2760
cgaggacgac taggggactc gagagaggcg ggccccagac ccatgtgctg ggaaatgcag  2820
aaatcacgtt gctggtggtt tttcagctcc cttcccttga gatgagtttc tggggaaaaa  2880
aaagagactg gttagtgatg cagttagtat agctttatac tctctccact ttatagctct  2940
aataagtttg tgttagaaaa gtttcgactt atttcttaaa gctttttttt ttttcccatc  3000
actctttaca tggtggtgat gtccaaaaga tacccaaatt ttaatattcc agaagaacaa  3060
ctttagcatc agaaggttca cccagcacct tgcagatttt cttaaggaat tttgtctcac  3120
ttttaaaaag aaggggagaa gtcagctact ctagttctgt tgttttgtgt atataatttt  3180
ttaaaaaaaa tttgtgtgct tctgctcatt actacactgg tgtgtccctc tgcctttttt  3240
tttttttaa gacagggtct cattctatcg gccaggctgg agtgcagtgg tgcaatcaca  3300
gctcactgca gccttgtcct cccaggctca agctatcctt gcacctcagc ctcccaagta  3360
gctgggacca caggcatgca ccactacgca tgactaattt tttaaatatt tgagacgggg  3420
tctccctgtg ttacccaggc tggtctcaaa ctcctgggct caagtgatcc tcccatcttg  3480
gcctcccaga gtattgggat tacagacatg agccactgca cctgcccagc tccccaactc  3540
cctgccattt tttaagagac agtttcgctc catcgcccag gcctgggatg cagtgatgtg  3600
atcatagctc actgtaacct caaactctgg ggctcaagca gttctcccac cagcctcctt  3660
tttattttt tgtacagatg gggtcttgct atgttgccca agctggtctt aaactcctgg  3720
cctcaagcaa tccttctgcc ttggcccccc aaagtgctgg gattgtgggc atgagctgct  3780
gtgcccagcc tccatgtttt aatatcaact ctcactcctg aattcagttg ctttgcccaa  3840
gataggagtt ctctgatgca gaaattattg ggctctttta gggtaagaag tttgtgtctt  3900
tgtctggcca catcttgact aggtattgtc tactctgaag acctttaatg gcttccctct  3960
ttcatctcct gagtatgtaa cttgcaatgg gcagctatcc agtgacttgt tctgagtaag  4020
tgtgttcatt aatgtttatt tagctctgaa gcaagagtga tatactccag gacttagaat  4080
agtgcctaaa gtgctgcagc caaagacaga gcggaactat gaaaagtggg cttggagatg  4140
gcaggagagc ttgtcattga gcctggcaat ttagcaaact gatgctgagg atgattgagg  4200
tgggtctacc tcatctctga aaattctgga aggaatggag gagtctcaac atgtgtttct  4260
gacacaagat ccgtggtttg tactcaaagc ccagaatccc caagtgcctg cttttgatga  4320
tgtctacaga aaatgctggc tgagctgaac acatttgccc aattccaggt gtgcacagaa  4380
aaccgagaat attcaaaatt ccaaattttt ttcttaggag caagaagaaa atgtggccct  4440
aaagggggtt agttgagggg taggggggtag tgaggatctt gatttggatc tctttttatt  4500
taaatgtgaa tttcaacttt tgacaatcaa agaaaagact tttgttgaaa tagctttact  4560
gtttctcaag tgttttggag aaaaaaatca accctgcaat cactttttgg aattgtcttg  4620
atttttcggc agttcaagct atatcgaata tagttctgtg tagagaatgt cactgtagtt  4680
ttgagtgtat acatgtgtgg gtgctgataa ttgtgtattt tctttggggg tggaaaagga  4740
aaacaattca agctgagaaa agtattctca aagatgcatt tttataaatt ttattaaaca  4800
attttgttaa a                                                       4811
```

```
SEQ ID NO: 12          moltype = DNA  length = 3542
FEATURE                Location/Qualifiers
source                 1..3542
                       mol_type = other DNA
                       organism = Homo sapiens
SEQUENCE: 12
gatgctgaga agtactcctg ccctaggaag agactcaggg cagagggagg aaggacagca  60
gaccagacag tcacagcagc cttgacaaaa cgttcctgga actcaagctc ttctccacag  120
aggaggacag agcagacagc agagaccatg gagtctccct cggcccctcc ccacagatgg  180
tgcatcccct ggcagaggct cctgctcaca gcctcacttc taaccttctg gaacccgccc  240
accactgcca agctcactat tgaatccacg ccgttcaatg tcgcagaggg gaaggaggtg  300
cttctacttg tccacaatct gccccagcat ctttttggct acagctggta caaaggtgaa  360
agagtggatg gcaaccgtca aattatagga tatgtaatag gaactcaaca agctacccca  420
gggcccgcat acagtggtcg agagataata taccccaatg catccctgct gatccagaac  480
atcatccaga atgacacagg attctacacc ctacacgtca taaagtcaga tcttgtgaat  540
gaagaagcaa ctggccagtt ccgggtatac ccggagctgc ccaagccctc catctccagc  600
aacaactcca aacccgtgga ggacaaggat gctgtggcct tcacctgtga acctgagact  660
caggacgcaa cctacctgtg gtgggtaaac aatcagagcc tcccggtcag tcccaggctg  720
cagctgtcca atggcaacag gaccctcact ctattcaatg tcacaagaaa tgacacagca  780
agctacaaat gtgaaaccca gaacccagtg agtgccaggc gcagtgattc agtcatcctg  840
aatgtcctct atggcccgga tgcccccacc atttcccctc taaacacatc ttacagatca  900
ggggaaaatc tgaacctctc ctgccacgca gcctctaacc cacctgcaca gtactcttgg  960
tttgtcaatg ggactttcca gcaatccacc caagagctct ttatccccaa catcactgtg  1020
aataatagtg gatcctatac gtgccaagcc cataactcag acactggcct caataggacc  1080
acagtcacga cgatcacagt ctatgcagag ccacccaaac ccttcatcac cagcaacaac  1140
tccaaccccg tggaggatga ggatgctgta gccttaacct gtgaacctga gattcagaac  1200
acaacctacc tgtggtgggt aaataatcag agcctcccgg tcagtcccag gctgcagctg  1260
tccaatgaca acaggaccct cactctactc agtgtcacaa ggaatgatgt aggaccctat  1320
gagtgtggaa tccagaacga attaagtgtt gaccacagcg acccagtcat cctgaatgtc  1380
ctctatggcc cagacgaccc caccatttcc ccctcataca cctattaccg tccaggggtg  1440
aacctcagcc tctcctgcca tgcagcctct aacccacctg cacagtattc ttggctgatt  1500
gatgggaaca tccagcaaca cacacaagag ctctttatct ccaacatcac tgagaagaac  1560
```

-continued

```
agcggactct atacctgcca ggccaataac tcagccagtg gccacagcag gactacagtc  1620
aagacaatca cagtctctgc ggagctgccc aagccctcca tctccagcaa caactccaaa  1680
cccgtggagg acaaggatgc tgtggccttc acctgtgaac ctgaggctca gaacacaacc  1740
tacctgtggt gggtaaatgg tcagagcctc ccagtcagtc ccaggctgca gctgtccaat  1800
ggcaacagga ccctcactct attcaatgtc acaagaaatg acgcaagagc ctatgtatgt  1860
ggaatccaga actcagtgag tgcaaaccgc agtgacccag tcaccctgga tgtcctctat  1920
gggccggaca cccccatcat ttccccccca gactcgtctt acctttcggg agcgaacctc  1980
aacctctcct gccactcggc ctctaaccca tccccgcagt attcttggcg tatcaatggg  2040
ataccgcagc aacacacaca agttctcttt atcgccaaaa tcacgccaaa taataacggg  2100
acctatgcct gttttgtctc taacttggct actggccgca ataattccat agtcaagagc  2160
atcacagtct ctgcatctgg aacttctcct ggtctctcag ctggggccac tgtcggcatc  2220
atgattggag tgctggttgg ggttgctctg atatagcagc cctggtgtag tttcttcatt  2280
tcaggaagac tgacagttgt tttgcttctt ccttaaagca tttgcaacag ctacagtcta  2340
aaattgcttc tttaccaagg atatttacag aaaagactct gaccagagat cgagaccatc  2400
ctagccaaca tcgtgaaacc ccatctctac taaaaataca aaaatgagct gggcttggtg  2460
gcgcacacct gtagtcccag ttactcggga ggctgaggca ggagaatcgc ttgaacccgg  2520
gaggtggaga ttgcagtgag cccagatcgc accactgcac tccagtctgg caacagagca  2580
agactccatc tcaaaaagaa aagaaaagaa gactctgacc tgtactcttg aatacaagtt  2640
tctgatacca ctgcactgtc tgagaatttc caaaacttta atgaactaac tgacagcttc  2700
atgaaactgt ccaccaagat caagcagaga aaataattaa tttcatggga ctaaatgaac  2760
taatgaggat aatattttca taatttttta tttgaaattt tgctgattct ttaaatgtct  2820
tgtttcccag atttcaggaa actttttttc ttttaagcta tccacagctt acagcaattt  2880
gataaaatat acttttgtga acaaaaaattg agacatttac attttctccc tatgtggtcg  2940
ctccagactt gggaaactat tcatgaatat ttatattgta tggtaatata gttattgcac  3000
aagttcaata aaaatctgct ctttgtatga cagaatacat ttgaaaacat tggttatatt  3060
accaagactt tgactagaat gtcgtatttg aggatataaa cccataggta ataaacccac  3120
aggtactaca aacaaagtct gaagtcagcc ttggtttggc ttcctagtgt caattaaact  3180
tctaaaagtt taatctgaga ttccttataa aaacttccag caaagcaact ttaaaaaagt  3240
ctgtgtgggc cgggcgcggt ggctcacgcc tgtaatccca gcactttgat ccgccgaggc  3300
gggcggatca cgaggtcagg agatccagac catcctggct aacacagtga aaccccgtct  3360
ctactaaaaa tacaaaaaaa gttagccggg cgtggtggtg ggggcctgta gtcccagcta  3420
ctcaggaggc tgaggcagga gaacggcatg aacccgggag gcagggcttg cagtgagcca  3480
agatcatgcc gctgcactcc agcctgggag acaaagtgag actccgtcaa aaaaaaaaaa  3540
aa                                                                 3542

SEQ ID NO: 13           moltype = DNA  length = 2594
FEATURE                 Location/Qualifiers
source                  1..2594
                        mol_type = other DNA
                        organism = Homo sapiens
SEQUENCE: 13
acagaaggag gaaggacagc agggccaaca gtcacagcag ccctgaccag agcattcctg  60
gagctcaagc tcctctacaa agaggtggac agagaagaca gcagagacca tgggaccccc  120
ctcagcccct ccctgcagat tgcatgtccc ctggaaggag gtcctgctca cagcctcact  180
tctaaccttc tggaacccac ccaccactgc caagctcact attgaatcca cgccgttcaa  240
tgtcgcagag gggaaggagg ttcttctact cgcccacaac ctgccccaga atcgtattgg  300
ttacagctgg tacaaaggcg aaagagtgga tggcaacagt ctaattgtag gatatgtaat  360
aggaactcaa caagctaccc cagggcccgc atacagtggt cgagagacaa tataccccaa  420
tgcatccctg ctgatccaga acgtcaccca gaatgacaca ggattctata ccctacaagt  480
cataaagtca gatcttgtga atgaagaagc aaccggacag ttccatgtat acccggagct  540
gcccaagccc tccatctcca gcaacaactc caaccccgtg gaggacaagg atgctgtggc  600
cttcacctgt gaacctgagg ttcagaacac aacctacctg tggtgggtaa atggtcagag  660
cctcccggtc agtcccaggc tgcagctgtc caatggcaac atgaccctca ctctactcag  720
cgtcaaaagg aacgatgcag gatcctatga atgtgaaata cagaacccag cgagtgccaa  780
ccgcagtgac ccagtcaccc tgaatgtcct ctatggccca gatgtcccca ccatttcccc  840
ctcaaaggcc aattaccgtc caggggaaaa tctgaacctc tcctgccacg cagcctctaa  900
cccacctgca cagtactctt ggtttatcaa tgggacgttc cagcaatcca cacaagagct  960
ctttatcccc aacatcactg tgaataatag cggatcctat atgtgccaag cccataactc  1020
agccactggc ctcaatagga ccacagtcac gatgatcaca gtctctggaa gtgctcctgt  1080
cctctcagct gtggccaccg tcggcatcac gattggagtg ctggccaggg tggctctgat  1140
atagcagccc tggtgtattt tcgatatttc aggaagactg gcagattgga ccagaccctg  1200
aattcttcta gctcctccaa tcccatttta tcccatggaa ccactaaaaa caaggtctgc  1260
tctgctcctg aagccctata tgctggagat ggacaactca atgaaaattt aaagggaaaa  1320
ccctcaggcc tgaggtgtgt gccactcaga gacttcacct aactagagac agtcaaactg  1380
caaaccatgg tgagaaattg acgacttcac actatggaca gcttttccca agatgtcaaa  1440
acaagactcc tcatcatgat aaggctctta ccccctttta atttgtcctt gcttatgcct  1500
gcctctttcg cttggcagga tgatgctgtc attagtattt cacaagaagt agcttcagag  1560
ggtaacttaa cagagtgtca gatctatctt gtcaatccca acgttttaca taaaataaga  1620
gatcctttag tgcacccagt gactgacatt agcagcatct ttaacacagc cgtgtgttca  1680
aatgtacagt ggtccttttc agagttggac ttctagactc acctgttctc actccctgtt  1740
ttaattcaac ccagccatgc aatgccaaat aatagaattg ctccctacca gctgaacagg  1800
gaggagtctg tgcagtttct gacacttgtt gttgaacatg gctaaataca atgggtatcg  1860
ctgagactaa gttgtagaaa ttaacaaatg tgctgcttgg ttaaaatggc tacactcatc  1920
tgactcattc tttattctat tttagttggt ttgtatcttg cctaaggtgc gtagtccaac  1980
tcttggtatt accctcctaa tagtcatact agtagtcata ctccctggtg tagtgtattc  2040
tctaaaagct ttaaatgtct gcatgcagcc agccatcaaa tagtgaatgg tctctctttg  2100
gctggaatta caaaactcag agaaatgtgt catcaggaga acatcataac ccatgaagga  2160
taaaagcccc aaatggtggt aactgataat agcactaatg ctttaagatt tggtcacact  2220
ctcacctagg tgagcgcatt gagccagtgg tgctaaatgc tacatactcc aactgaaatg  2280
```

```
ttaaggaaga agatagatcc aattaaaaaa aattaaaacc aatttaaaaa aaaaaagaac  2340
acaggagatt ccagtctact tgagttagca taatacagaa gtcccctcta ctttaacttt  2400
tacaaaaaag taacctgaac taatctgatg ttaaccaatg tatttatttc tgtggttctg  2460
tttccttgtt ccaatttgac aaaacccact gttcttgtat tgtattgccc agggggagct  2520
atcactgtac ttgtagagtg gtgctgcttt aattcataaa tcacaaataa aagccaatta  2580
gctctataac taaa                                                    2594

SEQ ID NO: 14          moltype = DNA  length = 1852
FEATURE                Location/Qualifiers
source                 1..1852
                       mol_type = other DNA
                       organism = Homo sapiens
SEQUENCE: 14
agccaggaaa tgccctggag tgtgtgtcac ctgtccagga cgacttgttg attcccagga  60
gggccgcctt tccggtctgg gtccccgaga ggactgcctt gctcacctgt cccctcggcg  120
cggccccggg gagctcccga gaggccccg ggatcgctgg ccctccgaac tccacagcaa  180
tgagcaagtt gggcaagttc tttaaagggg gcggctcttc taagagccga gccgctccca  240
gtccccagga ggccctggtc cgacttcggg agactgagga gatgctgggc aagaaacaag  300
agtacctgga aaatcgaatc cagagagaaa tcgccctggc caagaagcac ggcacgcaga  360
ataagcgagc tgcattacag gcactaaaga gaaagaagag gttcgagaaa cagctcactc  420
agattgatgg cacactttct accattgagt tccagagaga agccctggag aactcacaca  480
ccaacactga ggtgttgagg aacatgggct ttgcagcaaa agcgatgaaa tctgttcatg  540
aaaacatgga tctgaacaaa atagatgatt tgatgcaaga gatcacagag caacaggata  600
tcgcccaaga aatctcagaa gcattttctc aacgggttgg ctttggtgat gactttgatg  660
aggatgagtt gatggcagaa cttgaagaat tggaacagga ggaattaaat aagaagatga  720
caaatatccg ccttccaaat gtgccttcct cttctctccc agcacagcca aatagaaaac  780
caggcatgtc gtccactgca cgtcgatccc gagcagcatc ttcccagagg gcagaagaag  840
aggatgatga tatcaaacaa ttggcagctt gggctaccta aactaaaaca catttttgat  900
acctaaatta atgagctata gataaaatat aaaaaatgtt tttaccaagt tcagaagtta  960
acaaagactc tgctttataa ttatattgaa tgaataattg tgttttaagc ctcctaagta  1020
aaagtaaaaa aggagtcatg tgcatacata gaatcagtga tggaggccag gcacggtatc  1080
tcatgcctat aatcccagca ctttgggagg ctgaggcagt tgagaccagg agttcgagtc  1140
cagcctgacc aacatgaaga aaccctgtct gtactaaaaa tacaaaaatt agccggacat  1200
ggtggcaggc acctgtaatc ccagctactt gggaggctga gtcaggagaa tcgcttgagc  1260
ccaggagatg gaggttgcag tgagccaaga tcatgccact gcactccaga ctgggcaaca  1320
gagggagact ccgtctcaaa aactaaaaaa aaaaaataca tttagtatag cggggggtgg  1380
gggggagaaa taatgttatt tcctatgcga atgacgtgta tccctgtacc catggtaaat  1440
gtaaatatac tgtgtctctt ttgggagagc cttttagtag aggagtctta tatgagtctc  1500
tacataagta gtttcacttg agttttgcag tttgaaatct taaaggagct ttaattgaca  1560
tttattatac caattaagct tggaatgggg caatggatgc atttcccaaa acgtgtgaaa  1620
gcactaacag cttatattgc tgaatgagaa tctcctgggt gtaatttagc cacttaggga  1680
actgcgtgaa cactcccagg ccattatgat gctgttacag cttcagtgta taaatgcatg  1740
agtattcttt ctgttctgtt ttgtgctctc ttgtacattt atttaccctt tacagaatat  1800
ttcttgtaaa tacataaaaa tattggcaat taaaagtaca tcttgaataa aa          1852

SEQ ID NO: 15          moltype = DNA  length = 3935
FEATURE                Location/Qualifiers
source                 1..3935
                       mol_type = other DNA
                       organism = Homo sapiens
SEQUENCE: 15
atctgcatcc atattgaaaa cctgacacaa tgtatgcagc aggctcagtg tgagtgaact  60
ggaggcttct ctacaacatg acccaaagga gcattgcagg tcctatttgc aacctgaagt  120
ttgtgactct cctggttgcc ttaagttcag aactcccatt cctgggagct ggagtacagc  180
ttcaagacaa tgggtataat ggattgctca ttgcaattaa tcctcaggta cctgagaatc  240
agaacctcat ctcaaacatt aaggaaatga taactgaagc ttcattttac ctatttaatg  300
ctaccaagag aagagtattt ttcagaaata taaagatttt aatacctgcc acatggaaag  360
ctaataataa cagcaaaata aaacaagaat catatgaaaa ggcaaatgtc atagtgactg  420
actggtatgg ggcacatgga gatgatccat acaccctaca atacagaggg tgtggaaaag  480
agggaaaata cattcatttc acacctaatt tcctactgaa tgataactta acagctggct  540
acggatcacg aggccgagtg tttgtccatg aatgggccca cctccgttgg ggtgtgttcg  600
atgagtataa caatgacaaa cctttctaca taaatgggca aaatcaaatt aaagtgacaa  660
ggtgttcatc tgacatcaca ggcatttttg tgtgtgaaaa aggtccttgc ccccaagaaa  720
actgtattat tagtaagctt tttaaagaag gatgcacctt tatctacaat agcacccaaa  780
atgcaactgc atcaataatg ttcatgcaaa gtttatcttc tgtggttgaa ttttgtaatg  840
caagtaccca caaccaagaa gcaccaaacc tacagaacca gatgtgcagc ctcagaagtg  900
catgggatgt aatcacagac tctgctgact ttcaccacag ctttcccatg aatgggactg  960
agcttccacc tcctcccaca ttctcgcttg tacaggctgg tgacaaagtg gtctgtttag  1020
tgctggatgt gtccagcaag atggcagagg ctgacagact ccttcaacta caacaagccg  1080
cagaatttta tttgatgcag attgttgaaa ttcatacctt cgtgggcatt gccagtttcg  1140
acagcaaagg agagatcaga gcccagctac accaaattaa cagcaatgat gatcgaaagt  1200
tgctggtttc atatctgccc accactgtat cagctaaaac agacatcagc atttgttcag  1260
ggcttaagaa aggatttgag gtggttgaaa aactgaatgg aaaagcttat ggctctgtga  1320
tgatattagt gaccagcgga gatgataagc ttcttggcaa ttgcttaccc actgtgctca  1380
gcagtggttc aacaattcac tccattgccc tgggttcatc tgcagcccca aatctggagg  1440
aattatcacg tcttacagga ggtttaaagt tctttgttcc agatatatca aactccaata  1500
gcatgattga tgctttcagt agaatttcct ctggaactgg agacattttc cagcaacata  1560
ttcagcttga aagtacaggt gaaaatgtca aacctcacca tcaattgaaa aacacagtga  1620
ctgtggataa tactgtgggc aacgacacta tgtttctagt tacgtggcag gccagtggtc  1680
```

-continued

```
ctcctgagat tatattattt gatcctgatg gacgaaaata ctacacaaat aattttatca  1740
ccaatctaac ttttcggaca gctagtcttt ggattccagg aacagctaag cctgggcact  1800
ggacttacac cctgaacaat acccatcatt ctctgcaagc cctgaaagtg acagtgacct  1860
ctcgcgcctc caactcagct gtgcccccag ccactgtgga agcctttgtg gaaagagaca  1920
gcctccattt tcctcatcct gtgatgattt atgccaatgt gaaacaggga ttttatccca  1980
ttcttaatgc cactgtcact gccacagttg agccagagac tggagatcct gttacgctga  2040
gactccttga tgatggagca ggtgctgatg ttataaaaaa tgatggaatt tactcgaggt  2100
attttttctc ctttgctgca aatggtagat atagcttgaa agtgcatgtc aatcactctc  2160
ccagcataag caccccagcc cactctattc cagggagtca tgctatgtat gtaccaggtt  2220
acacagcaaa cggtaatatt cagatgaatg ctccaaggaa atcagtaggc agaaatgagg  2280
aggagcgaaa gtggggcttt agccgagtca gctcaggagg ctccttttca gtgctgggag  2340
ttccagctgg cccccaccct gatgtgtttc caccatgcaa aattattgac ctggaagctg  2400
taaaagtaga agaggaattg accctatctt ggacagcacc tggagaagac tttgatcagg  2460
gccaggctac aagctatgaa ataagaatga gtaaaagtct acagaatatc caagatgact  2520
ttaacaatgc tattttagta aatacatcaa agcgaaatcc tcagcaagct ggcatcaggg  2580
agatatttac gttctcaccc caaatttcca cgaatggacc tgaacatcag ccaaatggag  2640
aaacacatga aagccacaga atttatgttg caatacgagc aatggatagg aactccttac  2700
agtctgctgt atctaacatt gcccaggcgc ctctgtttat tccccccaat tctgatcctg  2760
tacctgccag agattatctt atattgaaag gagttttaac agcaatgggt ttgataggaa  2820
tcatttgcct tattatagtt gtgacacatc atactttaag caggaaaaag agagcagaca  2880
agaaagagaa tggaacaaaa ttattataaa taaatatcca aagtgtcttc cttcttagat  2940
ataagaccca tggccttcga ctacaaaaac atactaacaa agtcaaatta acatcaaaac  3000
tgtattaaaa tgcattgagt ttttgtacaa tacagataag atttttacat ggtagatcaa  3060
caaattcttt ttgggggtag attagaaaac ccttacactt tggctatgaa caaataataa  3120
aaattattct ttaaagtaat gtctttaaag gcaaagggaa gggtaaagtc ggaccagtgt  3180
caaggaaagt ttgttttatt gaggtggaaa aatagcccca agcagagaaa aggagggtag  3240
gtctgcatta taactgtctg tgtgaagcaa tcatttagtt actttgatta atttttcttt  3300
tctccttatc tgtgcagaac aggttgcttg tttacaactg aagatcatgc tatattttat  3360
atatgaagcc cctaatgcaa agctctttac ctcttgctat tttgttatat atattacaga  3420
tgaaatctca ctgctaatgc tcagagatct tttttcactg taagaggtaa cctttaacaa  3480
tatgggtatt acctttgtct cttcataccg gttttatgac aaaggtctat tgaatttatt  3540
tgtttgtaag tttctactcc catcaaagca gctttctaag ttattgcctt ggttattatg  3600
gatgatagtt atagccctta taatgcctta actaaggaag aaaagatgtt attctgagtt  3660
tgttttaata catatatgaa catatagttt tattcaatta aaccaaagaa gaggtcagca  3720
gggagatact aacctttgga aatgattagc tggctctgtt ttttggttaa ataagagtct  3780
ttaatccttt ctccatcaag agttacttac caagggcagg ggaaggggga tatagaggtc  3840
acaaggaaat aaaaatcatc tttcatcttt aattttactc cttcctctta tttttttaaa  3900
agattatcga acaataaaat catttgcctt tttaa                            3935
```

```
SEQ ID NO: 16          moltype = DNA  length = 1859
FEATURE                Location/Qualifiers
source                 1..1859
                       mol_type = other DNA
                       organism = Homo sapiens
SEQUENCE: 16
aaaagtgcct ttgttggcct gggctcagga atccagagaa actggtcagg aggaggcccc  60
agtgacaaaa accccctccct ctgcccccgc ccctctgcca gagccatata actgctcaac  120
ctgtccccga gagagagtgc cctggcagct gtcggctgga aggaactggt ctgctcacac  180
ttgctggctt gcgcatcagg actggcttta tctcctgact cacggtgcaa aggtgcactc  240
tgcgaacgtt aagtccgtcc ccagcgcttg gaatcctacg gcccccacag ccggatcccc  300
tcagccttcc aggtcctcaa ctcccgtgga cgctgaacaa tggcctccat ggggctacag  360
gtaatgggca tcgcgctggc cgtcctgggc tggctggccg tcatgctgtg ctgcgcgctg  420
cccatgtggc gcgtgacggc cttcatcggc agcaacattg tcacctcgca gaccatctgg  480
gagggcctat ggatgaactg cgtggtgcag agcaccggcc agatgcagtg caaggtgtac  540
gactcgctgc tggcactgcc gcaggacctg caggcggccc gcgccctcgt catcatcagc  600
atcatcgtgg ctgctctggg cgtgctgctg tccgtggtgg ggggcaagtg taccaactgc  660
ctggaggatg aaagcgccaa ggccaagacc atgatcgtgg cgggcgtggt gttcctgttg  720
gccggcctta tggtgatagt gccggtgtcc tggacggccc acaacatcat ccaagacttc  780
tacaatccgc tggtggcctc cgggcagaag cgggagatgg gtgcctcgct ctacgtcggc  840
tgggccgcct ccggcctgct gctccttggc ggggggctgc tttgctgcaa ctgtccaccc  900
cgcacagaca agccttactc cgccaagtat tctgctgccc gctctgctgc tgccagcaac  960
tacgtgtaag gtgccacggc tccactctgt tcctctctgc tttgttcttc cctggactga  1020
gctcagcgca ggctgtgacc ccaggagggc cctgccacgg gccactggct gctggggact  1080
ggggactggg cagagactga gccaggcagg aaggcagcag ccttcagcct ctctggccca  1140
ctcggacaac ttcccaaggc cgcctcctgc tagcaagaac agagtccacc ctcctctgga  1200
tattggggag ggacggaagt gacagggtgt ggtggtggag tggggagctg gcttctgctg  1260
gccaggatag cttaaccctg actttgggat ctgcctgcat cggcgttggc cactgtcccc  1320
atttacattt tccccactct gtctgcctgc atctcctctg ttccgggtag gccttgatat  1380
cacctctggg actgtgcctt gctcaccgaa acccgcgccc aggagtatgg ctgaggcctt  1440
gcccacccac ctgcctggga agtgcagagt ggatggacgg gtttagaggg gaggggcgaa  1500
ggtgctgtaa acaggtttgg gcagtggtgg gggagggggc cagagaggcg gctcaggttg  1560
cccagctctg tggcctcagg actctctgcc tcacccgctt cagcccaggg cccctggaga  1620
ctgatcccct ctgagtcctc tgccccttcc aaggacacta atgagcctgg gagggtggca  1680
gggaggaggg gacagcttca cccttggaag tcctggggtt tttcctcttc cttctttgtg  1740
gtttctgttt tgtaatttaa gaagagctat tcatcactgt aattattatt attttctaca  1800
ataaatggga cctgtgcaca ggaggaaatt taaaaaaaaa aaaaaaaaaa aaaaaaaaa   1859
```

-continued

```
SEQ ID NO: 17          moltype = DNA  length = 6425
FEATURE                Location/Qualifiers
source                 1..6425
                       mol_type = other DNA
                       organism = Homo sapiens
SEQUENCE: 17
cacacagaag cggcagccac cgaggaggga gcagtgccgg gagccccgac ggcgccttgc  60
tgcatggagc tgggccgctg acagctgtcg ctgcccgcag cctctgacct ccctgggacc  120
ccggcgtctg aggctcatag tctgctccct gtcttctgtc agcctcaggg catccagcgt  180
ctcaggccga cctgggtccc tgggacccgg cgtttcggct tctcagccat ggagcggtgc  240
agccgctgcc atcgcctcct cctcctccta cctctggtgc tggggctgag cgcggcccca  300
ggctgggcag gtgcaccccc tgtggatgtg ctccgggccc tgaggttccc ctccctccct  360
gatggtgtcc ggagagcgaa aggcatctgt ccagctgatg tggcctaccg agtggcacga  420
cctgcccagc tcagtgcacc cactcgccag cttttcccag gaggatttcc caaagatttc  480
tctctgctga ctgttgtccg gacccgccct ggtctccaag ctcccctcct gactctctac  540
agtgcccagg gtgtccgaca gctgggcctg gagctgggcc gacctgtccg cttcctgtat  600
gaagaccaga ctgggcggcc tcaacctccc tctcagccag tcttccgagg cctcagccta  660
gcagatggca agtggcaccg tgtggctgtg gctgtgaagg gccagtctgt caccctcatt  720
gttgactgca agaagcgagt cacccggcct ctcccccgaa gtgctcgtcc agtattggac  780
acccatggag tgatcatctt tggtgcccgt attctggatg aagaagtctt tgagggtgat  840
gtccaggagc tggccattgt cccaggggtc caggcagcct atgaatcatg tgaacagaag  900
gagctggaat gcgagggggg ccagagggaa agaccccaaa accaacagcc tcacagagcc  960
cagagatctc cacagcagca accatcaaga cttcacaggc cacaaaatca ggaaccccag  1020
agccagccca ctgagtctct ctactatgac tacgagcccc cctattatga tgtgatgact  1080
acggggacaa cccctgatta tcaggacccc accccaggtg aagaggaaga aatcctggag  1140
tcgagcctct tgccacccct tgaggaggag cagacagatc tccaggtccc ccccacagcc  1200
gacaggttcc aggcagagga atatggggag ggtggcacag acccccctga agggccctac  1260
gattacacct atggctatgg ggatgattat cgtgaggaga cagagcttgg ccctgccctc  1320
tctgcggaga cagcccactc aggagccgct gcccatggac cccgagggct gaagggagag  1380
aaaggagagc ctgcagtgtt ggaacctggt atgctcgtgg aggggccccc tggcccagaa  1440
ggccctgcgg gattgattgg tccccctggc atccagggga acccaggccc agttggagac  1500
cctggagaga ggggcccccc tggccgagca gggctccctg gatcagatgg ggctcctggt  1560
cctcctggca catctctcat gctcccattc cggtttggca gtggtggggg tgacaagggc  1620
cctgtggtgg cggcccagga ggctcaggcc caggcgatcc tgcagcaggc gaggctggcg  1680
ctccgtggac cccctggccc catgggatac acagggcgcc ctggaccctt gggccaacct  1740
gggagccctg gcctgaaagg agagtctgga gacttaggac ctcagggccc cagaggacct  1800
cagggcctca caggccctcc tggcaaggct gggcgaaggg gccgggcagg tgctgatgga  1860
gcccgaggga tgcctggaga tcctggagtg aagggtgacc gaggttttga tggactccca  1920
gggctccctg gagagaaggg ccataggggt gatactggtg cccagggcct tcctggtccc  1980
cctggtgagg atggagagag gggagatgac ggggagattg ggcctcgagg gctgcctgga  2040
gagtcgggac ctcgaggtct ccttggcccc aaaggcccac ctggtattcc tggaccccct  2100
ggcgtccgag gcatggatgg tccccagggc cccaaaggga gcttgggacc ccagggagag  2160
ccaggacctc ctggacaaca gggcacccct gggacccagg gtcttcccgg gccccagggt  2220
gccatcggcc ctcatggaga gaagggtcct caagggaagc cagggctccc cggcatgcct  2280
ggctcagacg gacccccggg tcacccaggg aaggaaggtc cccctggaac caaaggaaac  2340
cagggtccct ctggacctca gggacctcta ggatacccag gacctcgagg ggtcaagggt  2400
gtggacggaa ttcggggtct gaagggtcat aagggtgaga agggtgagga tggctttcct  2460
gggttcaaag gtgacatagg cgtgaaaggt gacagggggcg aagttggagt ccctggttcc  2520
aggggagagg atggtcctga ggggccaaag ggacgcactg gaccgactgg agaccctggg  2580
cccccagggc tcatgggcga gaagggcaag ctgggtgttc ctggtctgcc tggctatcct  2640
ggacgtcagg gacccaaggg gtccctagga tttcctggct ttcctggtgc cagtggagag  2700
aagggagccc ggggcctgtc ggggaagtca gggcctcggg gagaacgggg ccccacgggt  2760
ccacggggtc agcggggacc ccgaggtgcc actgggaagt ctggagctaa gggaacatct  2820
ggtggtgatg gcccccatgg gcccctgga gagaggggcc tccctggacc tcagggtccc  2880
aacgggtttc ctggaccgaa aggaccccg ggcccccctg ggaaggatgg gctgccggga  2940
cacccaggcc aaagaggaga agtgggtttc caagggaaga ccggcccccc tggtcctcca  3000
ggagtggtgg gacctcaggg agcagcagga gaaaccggcc ctatgggggga gagaggtcac  3060
ccaggccccc cggggccccc tggagagcag ggactacctg ggacagctgg aaaagaagga  3120
acaaagggtg accctggtcc ccctggggcc ccagggaagg atggtcctgc tggtctgagg  3180
ggattcccag gagagagagg cctcccaggc actgctggtg gacctggttt gaaggggaat  3240
gaaggtccgt ctggcccccc tggccctgca ggctcccctg ggaacgaggg tgcagcagga  3300
tcagggggac ccattggtcc gccagggcgc ccaggcccgc agggtccccc tggagcagca  3360
ggagagaaag gtgtcccagg tgagaagggc cccattggcc cgactggccg agatggagtg  3420
cagggtcctg tggggcttcc tggtcctgct gggcctccag gtgtggctgg agaggatgga  3480
gacaagggtg aggtggggga ccccggacag aagggcacca aagggaacaa gggtgaacat  3540
ggccctcctg gacccctgg acccattggt cctgtggggc agcctggagc agcgggagca  3600
gatggggagc ccggagctcg gggaccccag ggacactttg gagccaaagg tgatgaagga  3660
acaagaggat tcaatgggcc cccaggaccc attggcctac agggtttgcc aggcccctct  3720
ggggagaagg gagaaacagg agatgtgggt cctatgggac cacctggccc cccaggacct  3780
cgaggtccag ctggacccaa tggcgctgat ggcccacaag gtcccccagg aggtgttggg  3840
aacctgggtc cccctggaga gaagggggaa ccaggagagt caggatctcc agggatccag  3900
ggcgagccag gtgtcaaggg tccacgcggg gaacgtggag agaaaggaga gtcggggcag  3960
ccaggagagc cagggccacc agggcctaaa ggccccacag gcgatgatgg ccccaaaggg  4020
aaccctggtc ctgttggttt tcctggtgac cctggccccc ctggagaagg tggccctcgg  4080
ggccaggatg gtgctaaggg tgaccgaggc gaggatggtg agccaggaca gcctggatcc  4140
cctggtccca ccggggagaa tggaccccca gggccacttg gaaagcgagg tcctgctggc  4200
tcgcctggtt ccgaggggcg acaaggaggg aagggagcca agggagatcc tggcgctata  4260
ggtgccccgg ggaagacagg cccggtgggt cctgcaggcc cagcagggaa acctggccct  4320
gatggtctga gggggctccc aggctcagtg ggtcagcaag gccgacctgg agctacaggc  4380
```

```
caggctgggc ccccaggtcc tgtgggaccc ccagggctgc ctggtctccg gggcgatgct  4440
ggagccaagg gagagaaggg ccacccaggt ctcattggac tgattgggcc cccgggtgag  4500
cagggagaga agggagatcg gggacttcct gggcctcagg gctcccctgg gcagaagggt  4560
gagatgggta tcccaggagc atccggcccc attggtcctg gaggtccccc cggcctcccc  4620
ggacctgctg gccccaaagg agccaaagga gccacaggcc caggcggacc caagggagag  4680
aagggtgtgc agggccctcc aggacacccg ggtcccccag gcgaggtgat ccagccactg  4740
cccattcaga tgcccaagaa gactcggcgc tcggtggatg gaagccgtct gatgcaggaa  4800
gatgaggcca taccgaccgg gggagccccc ggcagtcctg gggggctgga ggagatcttt  4860
ggctcactcg actccctgcg ggaggagatc gagcagatga ggcggccaac agggacccag  4920
gacagccctg ctcgcacctg ccaggacctg aagctgtgcc acccagagct tcccgatgga  4980
gagtactggg tcgaccccaa ccagggctgt gctcgggatg ccttccgagt tttctgcaac  5040
ttcacagcag ggggtgagac ctgtgtgacg cctagggatg acgtcacgca gttctcttac  5100
gtggactcag agggctcccc agtgggtgtg gtccagctca ccttcctgcg gctgctcagc  5160
gtctcagccc accaggacgt ctcctacccc tgctctggag cagcccgtga cggtcccctg  5220
agactccgtg gggccaatga ggatgagctg agcccggaga ctagccccta tgtcaaagaa  5280
ttcagagatg gctgccagac acagcaaggc cggacggtgc tggaggtgcg aacgcctgtg  5340
ctggagcagc tgccagtgct ggatgcctcc ttctcagacc tgggagcccc accgaggcgg  5400
ggaggggtgc tgctggggcc tgtctgcttc atgggatagg accgtctctg tctgatcctg  5460
tccattcgga accaggccca cctggaatcc cacaacatca gctctgtgcc acctcccaag  5520
agggctcctc actatctagg gagccctggg ccagggcgtg gagagccctc agtcggggca  5580
ggccagggga ggggtgaagt ggttgcctgg acaccccacg ggaggagtgg catctggggc  5640
tcttggccct cccacctgga gcctgttacc cgttagagag ctgagaccct tatttaaaac  5700
tcacctccca atcaccccaa acaaatggaa gagaagagaa aggacatggc gtattttgta  5760
tttaaaagta attgtattaa ttatttaaag tgtggaaagc aaaataacaa aaaagagaaa  5820
cgccaacaaa aatcagcaga tgttgaagac aggggtctcg gggtgggct ccggcaccca  5880
catcctggag tcaggacttt cctcagtgac tgtgtgtagg ggggtttcag ggctgaaccc  5940
cacctccctc ccaccttcct cccacctcac ctgtcgcacc cactgtgaaa gttggaatat  6000
gtggtctccc tggcctcagg gctctgactc tgccagggtg gggctctcta acccacaggt  6060
gttggctgcc tggcccatgt gcccactgtc tcttccactt ggtctgggtt tggcaggcac  6120
tgcctgctac ttgagggcca ggatgctccc ccagggaaga aacggaatag tgtggggtgt  6180
gtgcagggct gcatcccgca gatggctgga atattaaaat tcttctatat tggctggtaa  6240
attgccatgg ccctgagcca ctgagtatgt tcattgccac ccctgtccct cccctgggca  6300
cccctcactt tccctgatcc tgcaattaaa gggttaatgt gtggcatatg gaagggactc  6360
ccaggaccct gtgcccagct tccatgctga ctgatggtta aataatgtga ttgtctcctc  6420
ccagg                                                              6425

SEQ ID NO: 18          moltype = DNA  length = 1086
FEATURE                Location/Qualifiers
source                 1..1086
                       mol_type = other DNA
                       organism = Homo sapiens
SEQUENCE: 18
acagaacgac cgacggaccg agggttcgag ggagggacac ggaccaggaa cctgagctag  60
gtcaaagacg cccgggccag gtgccccgtc gcaggtgccc ctggccggag atgcggtagg  120
aggggcgagc gcgagaagcc ccttcctcgg cgctgccaac ccgccaccca gcccatggcg  180
aaccccgggc tggggctgct tctggcgctg ggcctgccgt tcctgctggc ccgctggggc  240
cgagcctggg ggcaaataca gaccacttct gcaaatgaga atagcactgt tttgccttca  300
tccaccagct ccagctccga tggcaacctg cgtccagaag ccatcactgc tatcatcgtg  360
gtcttctccc tcttggctgc cttgctcctg gctgtggggc tggcactgtt ggtgcggaag  420
cttcgggaga agcggcagac ggagggcacc taccggccca gtagcgagga gcaggtgggt  480
gcccgcgtgc caccgacccc caacctcaag ttgccgccgg aagagcggct catctgaacg  540
ctggggcctg ctgcagccac caacactgcc caggactgcg ggttgctggc ttgtacaccg  600
cagctgccac cgagacacca gcctctgatg gctcaggagg acttgtgggg agaggctggg  660
ggcacccatg tggtgggctc tgtgcagcat gttgcctctg cttggctgtg cctgcagctc  720
agggtgctgg ggctcgggac ccaccccccct gcttgcggaa ccaactttc tctgtgtgtc  780
cagcaggccc cacaaccccc tctcctttct ttcagttctc ccatgcagcc gaggcccggg  840
cccctcagga ctccaaggag acggtgcagg gctgcctgcc catctaggtc ccctctcctg  900
catctgtctc ccttcattgc tgtgtgacct tggggaaagg cagtgccctc tctgggcagt  960
cagatccacc cagtgcttaa tagcagggaa gaaggtactt caaagactct gcccctgagg  1020
tcaagagagg atggggctat tcacttttat atatttatat aaaattagta gtgagatgta  1080
acaaaa                                                             1086

SEQ ID NO: 19          moltype = DNA  length = 2214
FEATURE                Location/Qualifiers
source                 1..2214
                       mol_type = other DNA
                       organism = Homo sapiens
SEQUENCE: 19
agactgggct gggcaggtct gagagttagg gaaagtccgt tcccactgcc ctcggggaga  60
gaagaaagga gggggcaagg gagaagctgc tggtcggact cacaatgaaa acgctccttc  120
ttttgctgct ggtgctcctg gagctgggag aggcccaagg atcccttcac agggtgcccc  180
tcaggaggca tccgtccctc aagaagaagc tgcgggcacg gagccagctc tctgagttct  240
ggaaatccca taatttggac atgatccagt tcaccgagtc ctgctcaatg gaccagagtg  300
ccaaggaacc cctcatcaac tacttggata tggaatactt cggcactatc tccattggct  360
ccccaccaca gaacttcact gtcatcttcg acactggctc ctccaacctc tgggtcccct  420
ctgtgtactg cactagccca gcctgcaaga cgcacagcag gttccagcct tcccagtcca  480
gcacatacag ccagccaggt caatctttct ccattcagta tggaaccggg agcttgtccg  540
ggatcattgg agccgaccaa gtctctgtgg aaggactaac cgtggttggc cagcagtttg  600
gagaaagtgt cacagagcca ggccagacct ttgtggatgc agagtttgat ggaattctgg  660
```

```
gcctgggata cccctccttg gctgtgggag gagtgactcc agtatttgac aacatgatgg  720
ctcagaacct ggtggacttg ccgatgtttt ctgtctacat gagcagtaac ccagaaggtg  780
gtgcggggag cgagctgatt tttggaggct acgaccactc ccatttctct gggagcctga  840
attgggtccc agtcaccaag caagcttact ggcagattgc actggataac atccaggtgg  900
gaggcactgt tatgttctgc tccgagggct gccaggccat tgtggacaca gggacttccc  960
tcatcactgg cccttccgac aagattaagc agctgcaaaa cgccattggg gcagcccccg  1020
tggatggaga atatgctgtg gagtgtgcca accttaacgt catgccggat gtcaccttca  1080
ccattaacgg agtcccctat accctcagcc caactgccta caccctactg gacttcgtgg  1140
atggaatgca gttctgcagc agtggctttc aaggacttga catccaccct ccagctgggc  1200
ccctctggat cctgggggat gtcttcattc gacagtttta ctcagtcttt gaccgtggga  1260
ataaccgtgt gggactggcc ccagcagtcc cctaaggagg ggccttgtgt ctgtgcctgc  1320
ctgtctgaca gaccttgaat atgttaggct ggggcattct ttacacctac aaaaagttat  1380
tttccagaga atgtagctgt ttccagggtt gcaacttgaa ttaagaccaa acagaacatg  1440
agaatacaca cacacacaca catatacaca cacacacact tcacacatac acaccactcc  1500
caccaccgtc atgatggagg aattacgtta tacattcata ttttgtattg atttttgatt  1560
atgaaaatca aaaatttttca catttgatta tgaaaatctc caaacatatg cacaagcaga  1620
gatcatggta taataaatcc ctttgcaact ccactcagcc ctgacaaccc atccacacac  1680
ggccaggcct gtttatctac actgctgccc actcctctct ccagctccac atgctgtacc  1740
tggatcattc tgaagcaaat tccgagcatt acatcatttt gtccataaat atttctaaca  1800
tccttaaata tacaatcgga attcaagcat ctcccattgt cccacaaatg tttggctgtt  1860
tttgtagttg gattgtttgt attaggattc aagcaaggcc catatattgc atttatttga  1920
aatgtctgta agtctctttc catctacaga gtttagcaca tttgaacgtt gctggttgaa  1980
atcccgaggt gtcatttgac atggttctct gaacttatct ttcctataaa atggtagtta  2040
gatctggagg tctgattttg tggcaaaaat acttcctagg tggtgctggg tacttcttgt  2100
tgcatcctgt caggaggcag ataatgctgg tgcctctcta ttggtaatgt taagactgct  2160
gggtgggttt ggagttcttg gctttaatca ttcattacaa agttcagcat ttta        2214
```

```
SEQ ID NO: 20          moltype = DNA  length = 11933
FEATURE                Location/Qualifiers
source                 1..11933
                       mol_type = other DNA
                       organism = Homo sapiens
SEQUENCE: 20
atgctcagtt ggttggagtg gcctcactct tacctgccaa cctgggaggt tgatgatgaa  60
catgtcttta ccttttcttt ggagtttgct taccttatta atatttgctg aagtaaatgg  120
cgaagctgga gaacttgagc tgcagagaca aaaaagaagc atcaatctcc aacagcctcg  180
aatggctaca gagagaggaa atttggtgtt tcttacgggg tctgctcaaa acattgagtt  240
tagaaccgga tccctgggaa aaattaaatt aaatgatgaa gatctcagtg agtgtttaca  300
tcagatccag aaaaacaaag aagatattat agagttaaaa gggagtgcaa ttggtctgcc  360
tcaaaatata tctagtcaaa tctatcagct taattccaag ctggtggatc ttgagagaaa  420
attccaaggc ttgcagcaga ctgttgacaa aaaggtttgc agcagcaatc cttgccagaa  480
tggtggaacc tgcctcaatc tgcatgattc ctttttttgt atctgtcccc cacagtggaa  540
gggtcctctc tgctcagctg atgttaacga atgtgagatt tactcaggaa cacccttgag  600
ctgccagaat ggaggcacat gtgttaatac aatgggaagt tacagttgtc actgcccacc  660
tgagacgtac ggaccccagt gtgcatccaa atatgacgac tgtgaagggg gttctgtggc  720
acgctgtgtc catggcatct gtgaggattt aatgcgagag caagctggag agcccaagta  780
cagctgcgtc tgtgatgctg ggtggatgtt ttcacccaac agccctgcct gcacgctgga  840
cagagacgag tgcagcttcc agcccgggcc ttgctcccaca cttgtgcagt gtttcaacac  900
tcaaggctct ttctactgtg ggcctgtcc aacaggctgg caaggcaatg gatatatttg  960
cgaagatatc aatgaatgtg agataaataa cggcggctgt tctgtggctc cacccgttga  1020
gtgtgtgaat acacctgggt cttcccactg ccaggcctgt ccaccagggt accagggtga  1080
cggaagagtg tgcacactca cagacatctg ctcagtcagt aatggaggct gccacccaga  1140
tgcctcatgc tcctcaactc taggttcctt acctctctgc acgtgtctcc cgggttatac  1200
tggaaatggt tatgggccaa atggatgtgt gcagctcagt aatatttgcc taagtcaccc  1260
ctgtctaaat ggacaatgca tcgacactgt ctctggttat ttttgtaagt gtgactcagg  1320
ttggacaggt gtcaactgta cagaaaacat caatgagtgt ttgagcaacc cctgtttgaa  1380
tggaggaact tgtgttgatg gcgttgattc tttcagttgt gaatgcacac gtctctggac  1440
tggagctctc tgtcaggttc ctcagcaagt ttgtggagag tcccctctcag gaataaatgg  1500
aagcttcagc tacaggagcc cggatgttgg ttatgttcat gatgttaact gcttctgggt  1560
tatcaaaact gaaatgggaa aggtcctgcg tatcactttc actttttttcc ggttagaatc  1620
catggacaac tgtccacacg agtttcttca ggtttatgat ggagattcct cttctgcttt  1680
tcaacttgga agattttgtg gctccagcct ccctcatgaa ctcctcagca gtgacaatgc  1740
tctctatttt catctctatt ctgaacattt aagaaatggg agaggcttta cagtaagatg  1800
ggaaacacag caaccagagt gtggaggtat cctgactggt ccttacggtt ctattaagtc  1860
tccggggtat cctggaaact atcccccagg aagagattgt gtctggattg ttgtaactag  1920
tcctgacctc ctggtaacat ttacttttgg gaccttgagc ctcgagcacc atgatgactg  1980
caacaaagat taccttgaga ttcgagatgg tcctttgtat caggaccccc ttcttgggaa  2040
gttctgcacc actttctctg tcccaccgct ccagactact ggccccttttg ccagaattca  2100
cttccattca gactcccaga ttagtgacca aggcttccat atcacctact taacatcacc  2160
ttcggatctg cgttgtggtg ggaactacac ggacccagag ggtgaactct tcttgcctga  2220
gttgtctggg cctttcactc acaccaggca atgcgtctat atgatgaagc agccccaggg  2280
agaacaaata caaatcaact tcacccacgt ggagctgcaa tgccagagtg acagttctca  2340
gaattacatt gaggttcgag atggtgaaac cttacttgga aaagtctgtg gcaacggaac  2400
catctctcac attaaatcca ttactaatag tgtctggatc aggtttaaaa tagatgcttc  2460
tgttgaaaaa gctagtttca gagctgttta tcaagtcgct tgcggggatg aattaactgg  2520
agaaggggtc attcgctcgc cttttttttcc taacgtgtat cctggagaaa gaacctgtag  2580
gtggaccatc caccagcccc aaagccaagt cattctcctc aacttcactg tctttgaaat  2640
tggaagttct gcccactgtg aaacagatta tgttgagatt ggtagcagtt ccattttggg  2700
ttctcctgaa aataaaaagt attgcggtac agacatacct tcatttataa catctgtgta  2760
```

-continued

```
caattttctt tatgtcacat tcgtgaaaag ttcttctact gaaaaccatg gtttcatggc  2820
taagttcagt gctgaggatt tggcatgtgg agaaattctt acagaatcaa cagggaccat  2880
tcaaagtcct ggccatccaa atgtctaccc ccacggtatc aactgtactt ggcatatatt  2940
agtccaacct aatcacctga ttcatttaat gttcgaaaca tttcatctgg agtttcatta  3000
caattgcaca aacgactact tggaagttta tgacaccgac tctgagacat cccttggaag  3060
atactgtgga aagtcgatcc cgccatctct cacaagcagt ggtaactcat tgatgctggt  3120
gtttgtgact gactccgacc tcgcttatga aggcttctta ataaactatg aagcaatcag  3180
tgcagcaaca gcatgtttgc aagactacac agatgatttg ggacattca cttctccaaa  3240
cttccccaat aattatccca acaactggga atgcatttat cggatcacag tgagaactgg  3300
ccaactgatt gcagtgcact tcacaaactt ctccttggag gaagccattg gaaactatta  3360
tacagatttt ctggaaatca gagatggagg ctatgaaaaa tcaccattgc tgggaatatt  3420
ctatggctca aatctacccc caacaatcat ctctcatagt aacaaactat ggttaaaatt  3480
taagagtgac caaatagaca caaggtctgg attctcagct tactgggatg ggtcatcaac  3540
aggttgcggg ggtaatctca ccacttcaag cggcacgttc atatctccca actacccgat  3600
gccctattac cacagctctg aatgctactg gtggttgaaa tctagccacg gcagcgcatt  3660
tgaactggaa ttcaaagact ttcacttgga gcatcatcca aactgcactt tagattacct  3720
ggctgtatat gatggcccaa gtagcaactc tcatctgcta actcagcttt gtggggatga  3780
gaaacccccct cttattcgtt ctagtggaga cagcatgttt ataaaactga ggacagatga  3840
aggtcagcaa ggacgtggct tcaaggctga ataccggcag acatgtgaga atgtggtaat  3900
agtcaatcaa acctatggca tcttagagag tatagggtat ccgaatcctt attctgaaaa  3960
tcagcattgc aactggacca tccgggcaac aacaggcaac actgtgaact acacattttt  4020
agcatttgac ttggaacatc acataaactg ctccacagat tatttagagc tctatgatgg  4080
accacggcag atgggacgct actgtggagt agacctgccc cctccaggga gtactacaag  4140
ctccaagctt caagtgctgc tccttacaga tggggttggc cgccgtgaga aaggatttca  4200
gatgcagtgg tttgtttacg gttgtggtgg agagctgtct ggggccacag gctccttcag  4260
cagccccggg ttccccaaca ggtatccacc aaacaaggag tgtatctggt acattaggac  4320
ggaccccggg agtagcattc agctcaccat ccatgacttc gatgtggagt atcattcaag  4380
gtgcaacttt gatgtcttgg agatctatgg aggccccgat ttccactctc ccagaatagc  4440
ccaactgtgt acccagagat cacctgagaa ccccatgcag gtctccagca ctggaaatga  4500
gctagcaatt cgattcaaga ccgacttgtc cataaatggg agaggcttca atgcgtcatg  4560
gcaagcagtc actggaggtt gtggtgggat tttccaggct cccagtggag agattcattc  4620
tccaaattac cccagtcctt ataggagcaa cacagactgt tcttgggtca ttcgggttga  4680
cagaaatcat cgtgttctct tgaacttcac tgactttgat cttgaaccac aagactcttg  4740
tattatggca tacgatggct taagctccac aatgtcccgc cttgccagga cgtgtggaag  4800
ggagcagctg gctaacccca tcgtctcctc aggaaacagc ctcttcttga gatttcagtc  4860
tggcccttcc agacagaaca gaggcttccg agctcaattc aggcaagcct gcggaggcca  4920
catcctcacc agctcatttg atactgtttc ctctccacgg ttccctgcca attatccaaa  4980
caatcagaac tgcagctgga tcattcaagc gcaacctcca ttaaatcata tcaccctctc  5040
ttttacccac tttgaacttg aaagaagcac aacgtgtgca cgtgactttg tagaaatttt  5100
ggatggcggc cacgaagacg cgcccctccg aggccgttac tgtggcaccg acatgcccca  5160
tcctatcaca tccttcagca gcgccctgac gctgagattc gtctctgatt ctagcatcag  5220
tgctggggt ttccacacca cggtcaccgc atcagtgtcg gcttgtggtg gaacgttcta  5280
catggctgaa ggcatcttca acagccctgg ctacccagac atttatcccc ctaatgtgga  5340
atgtgtctgg aacatcgtca gttcccctgg caaccggctc cagctgtctt ttatatcttt  5400
ccagttggaa gactctcagg actgcagcag agattttgtg gagatccgtg aaggaaatgc  5460
cacgggtcac ttggtgggac gatactgtgg aaactccttc cctctcaatt attcttccat  5520
cgttggacat accctgtggg tcagatttat ctcagatggt tctggcagcg gcacgggctt  5580
ccaggccaca tttatgaaga tatttggcaa tgataatatt gtgggaactc atgggaaagt  5640
cgcctctcct ttctggcctg aaaactaccc acataactcc aattaccaat ggacagtaaa  5700
tgtgaatgca tctcacgttg tccatggtag aatcttggag atggacatag aagaaataca  5760
aaactgctat tatgacaaat taaggatcta tgatgggcct agcattcacg cccgcctaat  5820
tggagcttac tgtggtaccc agactgaatc tttcagctcc actggaaatt ctttgacatt  5880
tcatttttac tccgactctt caatctcagg gaagggattc cttctggagt ggtttgcagt  5940
ggatgcacct gatggtgttt tacctaccat tgctccaggt gcttgtggtg gcttcctgag  6000
gacgggagat gcacccgtgt ttctcttctc cccgggctgg cctgacagtt acagtaatag  6060
agtggactgt acgtggctca tccaggctcc cgactctacc gtggaactca acattctttc  6120
cctggacatt gaatctcacc gaacgtgtgc ctatgatagc cttgtgatac gagatggaga  6180
taataacttg gcccagcagc tagcagttct ctgtggcaga gagatccctg ggcccatccg  6240
gtctactgga gagtacatgt tcatccgctt cacctcggac tccagtgtaa ccagggcagg  6300
cttcaatgca tcctttcaca agagctgcgg tggatatttg catgcagaca gagggatcat  6360
cacgtccccc aagtatccag agacttaccc atccaacctc aactgttctt ggcacgtcct  6420
ggtccaaagt ggcctgacca ttgctgtcca ttttgaacag cctttccaga ttccaaatgg  6480
agattcttct tgcaaccagg gggattactt ggtgctaaga aatggtcctg atatctgttc  6540
tccacccttg ggacccccctg gaggaaatgg tcatttttgt ggcagtcatg cttcatcaac  6600
tctgttcacc tcggataatc aaatgtttgt tcagtttatt tctgatcaca gtaatgaagg  6660
gcaaggattt aaaatcaaat atgaggcaaa gagtttagcc tgtgggggca acgtctacat  6720
ccatgatgct gattctgctg ggtatgtgac ctcccccaac caccctcata attatccccc  6780
gcacgctgat tgcatttgga tcttagcggc tccaccggaa acacgcatac agctgcaatt  6840
tgaagatcga ttcgatattg aagtaacacc caactgtact tccaactacc ttgagttgcg  6900
ggatggagtg gattcggatg caccaatact ttccaaattt tgtgggacat ctttgcccag  6960
cagtcagtgg tcctcaggag aggttatgta tttgagattt cgatctgaca acagccccac  7020
acatgtggga ttcaaggcca agtattctat agctcagtgt gggggaagag taccagggca  7080
aagtggtgtt gttgaaagca ttggacatcc aacacttcca tacagagaca acttattctg  7140
tgagtggcat ctccaggggc tctctggaca ctatctcacc atctcttttg aagactttaa  7200
ccttcagaat tcttctggct gtgaaaaaga cttcgtggag atctgggaca atcatacctc  7260
tggaaacatc ttgggcagat actgtggaaa caccattcct gacagcatag acacttctag  7320
caatactgct gtggtcaggt ttgtcacaga cggctctgtg actgcctcag gattcagact  7380
gcgatttgaa tccagtatgg aagagtgtgg tggggatctt cagggctcta ttggaacatt  7440
tacttctccc aactacccga acccaaatcc tcatggccgg atctgcgagt ggagaatcac  7500
```

-continued

```
tgccccggag ggaaggcgga tcaccctaat gtttaacaac ctgaggctgg ccacgcatcc  7560
gtcctgcaac aatgagcatg tgatagtatt caatggcatt agaagtaact caccccagct  7620
agagaaactg tgtagtagtg tgaatgtaag caatgagatt aaatcttcag gaaacacaat  7680
gaaagtcatt tttttcacgg atggatccag gccatatggc ggcttcactg cttcctatac  7740
ctccagtgaa gatgcagtgt gtggtgggtc tcttccaaat actcctgaag gaaactttac  7800
ttctcctggc tatgacggag tcaggaatta ctcaagaaac ctgaactgcg aatggactct  7860
cagcaatcca aatcagggaa attcatccat ttccattcac tttgaagatt tttacctaga  7920
aagtcaccaa gactgtcaat ttgatgtcct cgagtttcga gtgggtgatg ctgatgggcc  7980
cctgatgtgg agactttgtg gtccttcaaa gcctacattg ccattggtta taccttattc  8040
tcaggtatgg attcactttg tcaccaacga acgtgtagaa cacattggat tccatgcaaa  8100
gtattccttt acagattgtg gcggaataca gataggtgac agtggagtga tcacaagccc  8160
caactatcca aatgcttatg acagcctgac ccactgctct tcgctgttgg aggccccaca  8220
agggcacacc atcactctca catttagtga ctttgatatt gaaccccata caacttgtgc  8280
ttgggactct gtcactgtca ggaatggtgg gtcccctgaa tcacccatca taggacaata  8340
ctgtggaaat tcaaacccca ggacaataca gtcaggttcc aatcagctgg tcgtgacttt  8400
taactcagac cattcattgc aaggtggtgg attttatgct acgtggaaca cacaaacttt  8460
aggttgtggt ggaatatttc attctgataa tggtacaatc agatcccctc actggcctca  8520
gaattttccc gaaaacagca gatgttcctg gacggccatt actcacaaaa gtaaacactt  8580
ggagatcagc tttgacaaca acttcctaat ccccagcggt gatggacaat gtcagaatag  8640
cttcgtgaag gtgtgggcag gaactgagga ggtggacaaa gccctgctag ccactggctg  8700
tgggaacgtg gctccgggtc ccgttatcac accaagtaac acattcactg ccgtcttcca  8760
gtctcaggag gcaccagctc agggcttctc cgcgtccttt gttagccgat gtggaagtaa  8820
tttcactggc ccttcaggtt acatcatttc tccaaattac ccaaaacaat atgacaacaa  8880
catgaattgc acctatgtca tagaggctaa tcctctgtca gtggtcctct tgacttttgt  8940
gtccttccac ttagaagctc gttccgctgt gacgggaagc tgtgtcaacg atggcgtgca  9000
cattatcaga ggttacagcg tcatgtccac cccatttgct actgtgtgtg gggatgagat  9060
gccagctccc ctcaccatcg ctgggccggt tctgcttaac ttctactcca acgagcaaat  9120
cacagacttc ggattcaagt tttcctatag gataatctcc tgtggtggtg tgttcaattt  9180
ctcttctgga atcatcacaa gtcctgccta ttcatacgca gactacccaa atgatatgca  9240
ctgtctgtat accatcaccg ttagtgacga caaggtgatc gagctcaagt tcagtgattt  9300
tgatgtggtt ccctccacct cctgctccca tgactacctg gcaatttacg atggtgccaa  9360
taccagcgat ccccttcttg gcaaattctg cggttccaag cgcccaccaa atgtgaagag  9420
cagcaataat agtatgctcc tggtgttcaa gacagattca tttcagacag caaaaggctg  9480
gaagatgtct ttccggcaga cattggggcc tcagcaagga tgtggtggtt atctgacagg  9540
ctcgaataat acctttgcct ctcctgattc tgattcgaat ggaatgtatg acaagaattt  9600
aaactgtgta tggatcataa ttgcacctgt aaacaaagta attcacctca ccttcaatac  9660
atttgctctg gaggcagcaa gtactaggca aagatgcctt tatgattatg taaagttata  9720
tgatggggat agtgaaaatg cgaacttggc tggaacgttt tgtggttcca cagtacctgc  9780
tccttttatc tcttctggta acttccttac ggttcaattc atcagtgact taacattaga  9840
gagggaagga tttaatgcta catacaccat catggacatg ccttgtggtg gaacatacaa  9900
tgcaacttgg accccacaaa atatttcatc acccaattca tcagacccag atgtcccatt  9960
ttccatctgt acttgggtca ttgattcccc tccgcatcag caggtcaaga taactgtgtg  10020
ggcattacag ctgacctcgc aagactgcac gcagaattac ttacagcttc aggactcacc  10080
gcagggtcac ggaaattcaa gatttcagtt ctgtggcaga aatgcttcgg ctgtgccagt  10140
gttttattct tctatgagta ctgcaatggt cattttcaaa tctggagttg taaacagaaa  10200
ctctagaatg agtttcacct atcagattgc agattgcaac agagactatc acaaggcatt  10260
tggcaacctg agaagccctg gatggccaga taactacgac aatgacaagg attgcaccgt  10320
tactctcaca gccccccaga accacaccat ttccctcttt tttcattcac ttggcatcga  10380
gaactcagtt gaatgcagaa acgatttctt ggaggtgaga aatggaagta acagcaattc  10440
accattactg ggcaagtact gtggaactct gctgccaaac cctgtcttct ctcaaaataa  10500
tgaactatac ctacgattta agagtgatag tgtaacttct gatcgtggat atgaaatcat  10560
ctggacttca tcaccctctg gatgtggtgg aactctttat ggagacagag gctcattcac  10620
cagccccggc tatccaggca catacccaaa caacacgtac tgcgagtggg tccttgttgc  10680
tcctgctgga aggcttgtca ccatcaactt ctacttcatc agcattgacg atccaggaga  10740
ctgtgtccag aactatctca cactctatga tgggcccaac gccagctctc catcctctgg  10800
accatactgc ggaggcgaca ccagcatagc tcccttcgtg gcttcctcaa atcaggtctt  10860
cataaaattt catgctgatt atgcacggcg tccatccgca ttccgattaa cttgggacag  10920
ctaagtgggt aacaactcgt gttcactcag cactttccct ctgcagcacg ctggacagca  10980
ctctgccatc ctgatacatg accccctgctg atgccacaga gaataagctg aacttgtatg  11040
gtttttcacc aaaccatgga tagaatcaat atttgtaggc caggcgtggt ggctcacccc  11100
cctgtattct cagcactttg ggaggccgag gcaggttgat cacctgaggt caggagtttg  11160
agactagcct ggccagcatg gtgaaacctc atctctctaa caatataata attagccagg  11220
cgtggtggtg ggtgcctgta attccagcca ctcgagaggc tgaggcagga gaattgcttg  11280
aacccaggag gcagaggttg cagtgagcta agatcacacc actacactcc agcctgggcg  11340
agacggcaag actccatctc aaaaaaaaaa gaaacaaaaa aaaccagaat caatatttgt  11400
acattttctc gaacatagaa tatagcttct ttagtcttga gtgtgcattt cattctaata  11460
ttttgagctg aaatttaaaa aaactttgaa agagttggaa atgattatgg catatgtgac  11520
atacattttt aaaagttaat aataatagcc aggggcagtg gctcataccc ataatcccag  11580
cacgctggga ggccatgatg ggaggattgc ttgaacctag gagtttgaga ccagcctggg  11640
caacaaagtg agacctgatt tttacaaaaa atcaaaaaat tagccaggca tggtggcatg  11700
cacccgtggt tccagctaca caggaggttg aagcaggagg atcacttgag cccagtaggt  11760
taaggctgca gtgaaaccct gtgaattaac cactgtactc cagcctgggt gacagactga  11820
gaccctatct caaaaatgac aacaagaaca acaaaagtta atgataatat agaagcataa  11880
atttcctgtg aatgttcaat tacacataat aaacattatt gaattgtaca caa         11933
```

-continued

```
SEQ ID NO: 21          moltype = DNA  length = 3000
FEATURE                Location/Qualifiers
source                 1..3000
                       mol_type = other DNA
                       organism = Homo sapiens
SEQUENCE: 21
ctggaaccat ggagctcagc gtcctcctct tccttgcact cctcacaggc ctcttgctac  60
tcctggttca gcgtcaccct aactcccatg gcaccctccc accagggccc cgccctctgc  120
cccttttggg gaaccttctg cagatggaca gaagaggcct actcaaatcc tttctgaggt  180
tccgagagaa atatggggac gtcttcacgg tacacctggg accgaggccc gtggtcatgc  240
tgtgtggagt agaggccata cgggaggccc tggtggacaa cgctgaggcc ttctctggcc  300
ggggaaaaat cgtcatcatg gacccagtct accagggata tggcatgctc tttgccaatg  360
gaaaccgctg gaaggtgctt cggcgattct ctgtgaccac catgagggac ttcgggatgg  420
gaaagcggag tgtggaggag cggattcagg acgaggctca gtgtctgata gaggaacttc  480
ggaaatccaa gggagccctc gtggacccca ccttcctctt ccattccatt accgccaaca  540
tcatctgctc catcatcttt ggaaaacgct tccactacca agatcaagag ttcctgaaga  600
cgctgaactt gttctgccag agtttcttac tcatcagctc tatatccagc cagctgtttg  660
agctcttctc tggcttcttg aaatactttc ctggggcaca caggcaagtt tacaaaaacc  720
tacaggaaat caatgcttac attggccaca gtgtggagaa gcaccgtgaa accctggacc  780
ccagcgcccc cagggacctc atcgacacct acctgctcca catggaaaaa gagaaatcca  840
acccacacag tgaattcagc caccagaacc tcatcatcaa cacgctctcg ctcttctttg  900
ctggcactga gaccaccagc accactctcc gctacggctt cctgctcatg ctcaaatacc  960
ctcatgtcgc agagagagtc tacaaggaga ttgaacaggt ggttggccca catcgccctc  1020
cagcgcttga tgaccgagcc aaaatgccat acacagaggc agtcatccgt gagattcaga  1080
gatttgctga ccttctcccc atgggtgtgc cccacattgt cacccaacac accagcttct  1140
gagggtacac catccccaag gacacggaag tatttctcat cctgagcact gctctccgtg  1200
acccacacta ctttgaaaaa ccagacgcct tcaatcctga ccactttctg gatgccaatg  1260
gggcactgaa aaagaatgaa gcttttatcc ccttctcctt agggaagcgg atttgtcttg  1320
gtgaaggcat tgcccgtgcg gaattgttcc tcttcttcac caccatcctc cagaacttct  1380
ccgtggccag ccccgtggct cctgaagaca tcgatctgac accccaggag tgtggtgtgg  1440
gcaaaatacc cccaacatac cagatctgct tcctgccccg ctgaaggggc tgagggaagg  1500
gggtcaaagg attccagggt cattcagtgt ccccacctct gtagataatg gctctgactc  1560
cctgcaactt cctgcctctg agagacctgc tgcaagccag cttccttccc ttccatggca  1620
ccagttgtct gaggtcgcag tgcaaatgag tggaggagtg agattattga aaattataat  1680
atacaaaatt atatatatat attttgagac agagtctcac tcagttgccc aggctggagt  1740
gcagtggcgt gatctcggct cactgcaacc tccacccccg ggttcaaga aattctcctg  1800
cctcagcctc cctagtagct gggattacag gtgtgtgcta ccatgcctgg ctaatttttg  1860
tatttttagt agagatgggg tttcaccgtg ttggccaggc tgatctcaaa ctcctgaact  1920
caagtgattc acccacctta gcctcccaaa gtgctgggat tacaggtgtg agtcaccatg  1980
cccggccatg tatatatata attttaaaaa ttaagatgaa attcacataa aataaaatta  2040
gccattttaa agtgtacaat ttagtggtgt gtggttcatt cacaaagctg tacaaccacc  2100
accatctagt tccaaacatt ttcttttttt ctgagacgga gtctcactct gtcacccagg  2160
ttcgagttca gtggtcttga actcctgatg tcaggtgatt ctcctagttc caaatgtttt  2220
cattatctcc ccccaacaaa acccatacct atcaagctgt cactccccat accccattct  2280
ctttttcatc tcagcccctg tcaatctggt ttttgtcctt atggacttac caattctgaa  2340
tatttcctat aaacagaatc acacaatatt tgattttttt tttaaaacta agccttgctc  2400
tgtctcccag gctggagtgc tgtggcgtga ttttggttca ctgcaacctc cgccttccaa  2460
gttcaagaga ttctcctgcc tcagcttcca agtagctggg attacaggca tgtggtacca  2520
cgcctggcta atttcttgt atttttagta gggacatgtt ggccaggctg gttgtgagct  2580
cctggcctca ggtgatccac acgcctcagt gtcccagagt gctgatatta caggcgtaat  2640
atgtgatctt ttgtgtctgg ttcctttcac gttgaacgct atttttgagg ttcgtgcctg  2700
ttgtagacca cagtcacaca ctgctgtagt cttcccccat cctcattccc agctgcctcc  2760
tcctactgtt tccctctatc aaaaagcctc cttggcgcag gttccctgag ctgtgggatt  2820
ctgcactggt gctttggatt ccctgatatg ttccttcaaa tccactgaga attaaataaa  2880
catcgctaaa gcatgacctc cccacgtcaa aaaaaaaaaa aaaaaaaaaa aaaaaaaaaa  2940
aaaaaaaaaa aaaaaaaaaa aaaaaaaaaa aaaaaaaaaa aaaaaaaaaa aaaaaaaaaa  3000

SEQ ID NO: 22          moltype = DNA  length = 1418
FEATURE                Location/Qualifiers
source                 1..1418
                       mol_type = other DNA
                       organism = Homo sapiens
SEQUENCE: 22
agcagtcagc cggccggaga cagagacttc acgactccca gtctcctcct cgccgcggcc  60
gccgcctcct ccttctctcc tcctcctctt cctcctcctc cctcgctccc acagccatgt  120
ctgcttagac cagagcagcc ccacagccaa ctagggcagc tgccgccgcc acaacagcaa  180
ggacagccgc tgccgccgcc cgtgagcgat gacaggagtg tttgacagaa gggtccccag  240
catccgatcc ggcgacttcc aagctccgtt ccagacgtcc gcagctatgc accatccgtc  300
tcaggaatcg ccaactttgc ccgagtcttc agctaccgat tctgactact acagccctac  360
ggggggagcc ccgcacggct actgctctcc tacctcggct tcctatggca aagctctcaa  420
cccctaccag tatcagtatc acggcgtgaa cggctccgcc gggagctacc cagccaaagc  480
ttatgccgac tatagctacg ctagctccta ccaccagtac ggcggcgcct acaaccgcgt  540
cccaagcgcc accaaccagc cagagaaaga agtgaccgag cccgaggtga gaatggtgaa  600
tggcaaacca aagaaagttc gtaaacccag gactatttat tccagctttc agctggccgc  660
attacagaga aggtttcaga agactcagta cctcgccttg ccggaacgcg ccgagctggc  720
cgcctcgctg ggattgacac aaacacaggt gaaaatctgg tttcagaaca aaagatccaa  780
gatcaagaag atcatgaaaa acggggagat gcccccggag cacagtccca gctccagcga  840
cccaatggcg tgtaactcgc cgcagtctcc agcggtgtgg gagccccagg gctcgtcccg  900
ctcgctcagc caccaccctc atgcccaccc tccgacctcc aaccagtccc cagcgtccag  960
```

```
ctacctggag aactctgcat cctggtacac aagtgcagcc agctcaatca attcccacct  1020
gccgccgccg ggctccttac agcacccgct ggcgctggcc tccgggacac tctattagat  1080
gggctgctct ctcttactct ctttttggg actactgtgt tttgctgttc tagaaaatca  1140
taaagaaagg aattcatatg gggaagttcg gaaaactgaa aaagattcat gtgtaaagct  1200
tttttttgca tgtaagttat tgcatttcaa aagacccccc ctttttttac agaggacttt  1260
ttttgcgcaa ctgtggacac tttcaatggt gccttgaaat ctatgacctc aacttttcaa  1320
aagacttttt tcaatgttat tttagccatg taaataagtg tagatagagg aattaaactg  1380
tatattctgg ataaataaaa ttatttcgac catgaaaa                          1418

SEQ ID NO: 23          moltype = DNA  length = 3173
FEATURE                Location/Qualifiers
source                 1..3173
                       mol_type = other DNA
                       organism = Homo sapiens
SEQUENCE: 23
aggctgcccg ctggcctcgg agcaggcgcc tgcgccctcg gcctcggcct agtcatgctc  60
cgtcccggcg cgcagctgct gcggggcctc ctgctgcgga gctgcccgct gcagggctcc  120
cccgggcgcc cgcgctctgt ctgcggccgg gaaggagagg aaaaaccacc cttatctgca  180
gaaacacaat ggaaagacag agcagaaaca gtgataattg gaggtggctg tgttggtgtg  240
agtctggctt atcacctggc caaagcaggg atgaaagatg tggtcctgct ggagaaatca  300
gagctcacgg ctggatctac ctggcacgca gcaggtttaa caacttactt tcatcctgga  360
ataaacttga agaaaataca ttatgatagc atcaaacttt atgagaaact ggaagaagaa  420
actggtcagg tggtgggatt ccatcagcca ggtagtatca gacttgctac cacccctgta  480
agggtagatg aatttaaata tcaaatgact cggactggct ggcatgcaac agaacagtat  540
ctcattgaac ctgaaaaaat tcaagagatg ttccctttac tcaacatgaa taaggtttta  600
gctggattgt ataatcctgg agatggtcac attgatcctt attctctaac tatggcactg  660
gctgctgggg ctaggaaatg tggtgccctt ttaaaatatc ctgcaccagt aacttctctg  720
aaagccaggt cagatggaac atgggacgtt gaaacaccac aggggtctat gagagcaaat  780
agaattgtga atgctgcagg attttgggct cgtgaagtag gtaaaatgat tggactagaa  840
catcctctca ttccggttca acatcaatat gttgttacat cgactatatc tgaagtgaaa  900
gctttgaaac gagaactgcc tgtgctccgt gacctggaag gatcatatta tctccgacag  960
gaaagggatg ggcttttgtt tggtccatat gaaagtcaag agaaaatgaa agttcaggac  1020
tcctgggtca ccaatggagt tcctccaggt tttggaaagg aactctttga gtctgatcta  1080
gatcgaatca tggaacacat caaagctgcc atggaaatgg ttcctgtctt gaaaaaggct  1140
gacatcatca atgttgtcaa tggtcctatc acgtattctc ctgacattct gcctatggtg  1200
gggccccatc agggggtcag aaactactgg gtggctatag gctttggata tggcataatc  1260
cacgctggtg gggtagggaa atatctcagt gactggatcc tgcatggaga acctcctttt  1320
gatctgatag aattggatcc taatcgctat ggcaaatgga caacaaccca gtacactgag  1380
gccaaagcaa gagaatcata tggattcaac aatattgttg gttatcctaa agaagaacgg  1440
tttgctggga ggccgactca acgagtcagt gggctctatc aaaggctgga gtctaagtgt  1500
tccatggggt tccatgctgg ctgggagcag ccgcactggt tctacaaacc aggccaggac  1560
actcagtaca ggccaagttt tcgccgcaca aactggtttg agcctgtggg ctcggagtat  1620
aaacaggtta tgcaaagagt agcggtaact gacctatcac catttggcaa gtttaacatc  1680
aaaggccaag attccattag actactggac catctctttg caaatgtcat tccaaaggtg  1740
ggttttacaa atataagtca catgttaaca cccaagggtc gagtgtatgc tgagctgact  1800
gtttctcacc aatctcctgg ggagtttctt ttaattactg gctctggatc agaacttcat  1860
gatcttagat ggattgaaga agaagcagtc aaaggtggat atgatgttga aattaaaaac  1920
ataactgatg agcttggagt tcttggagtt gctgggccac aggcaagaaa ggtccttcag  1980
aaactgacct ctgaagatct tagtgatgat gttttcaagt ttcttcaaac caagtcctta  2040
aaggtttcca acattcctgt cactgctatt aggatatctt atactggtga gctgggttgg  2100
gagctgtatc acagaagaga agattctgtg gcgctgtatg acgctatcat gaatgcaggc  2160
caggaggagg gaatcgacaa ttttggaacc tatgccatga atgccttacg cctggagaaa  2220
gccttcagag cctggggggtt agagatgaac tgtgatacaa atcctttgga agctggactg  2280
gaatattttg tgaagttaaa taagccagca gacttcatag gaaagcaagc actgaaacag  2340
attaaagcca aggggctgaa acgaagactg gtctgcctca ccttggcaac ggatgatgtt  2400
gatccagagg gaaatgaaag catctggtac aatggcaagg tggttggcaa cacgacatct  2460
ggaagctata gctacagcat ccagaagagt ctggctttcg catatgtccc tgtacaacta  2520
agtgaagtgg gacagcaagt ggaagttgaa ctattaggca aaaattaccc agcagtcatc  2580
atacaagaac ctttggtatt gaccgaacca accagaaacc ggcttcagaa aaaaggtgga  2640
aaggacaaaa cttgaaaaaa gaccttcagc agtcaactga attagagttg ctaatgactg  2700
tccttgaaat tattataact ggctcccagg ggaatagagg aaaccaggaa ttcatttcaa  2760
aatcatcaaa gtctaaattt agaatcttaa tgaaaccttt ctgttaagtg ttttctaagc  2820
aagacagaat aatagataaa tgatttacat tgttctttta aatgaagaaa tttgaaatga  2880
atgtttttt atttacccca cattacccaa tcagtaaaac atttaggtgt ttgctaatat  2940
acacaatcat tactataacc taattaaggg acattttata attttagtaa caaatgcatt  3000
cggttcttga cagctgaaaa caaattaata aattatcttt tacataaaaa catgtacaat  3060
attgtttatg gatttacttc tttgagaaat ctttccttag atgaataaat gaaagtttta  3120
atttttcatg atatatctgt gatgaaaata gtaaaactta acattgacat ata         3173

SEQ ID NO: 24          moltype = DNA  length = 3104
FEATURE                Location/Qualifiers
source                 1..3104
                       mol_type = other DNA
                       organism = Homo sapiens
SEQUENCE: 24
aggctctatt tagagccggg taggggagcg cagcggccag atacctcagc gctacctggc  60
ggaactggat ttctctcccg cctgccggcc tgcctgccac agccggactc cgccactccg  120
gtagcctcat ggctgcaacc tgtgagatta gcaacatttt tagcaactac ttcagtgcga  180
tgtacagctc ggaggactcc accctggcct ctgttccccc tgctgccacc tttggggccg  240
```

-continued

```
atgacttggt actgaccctg agcaaccccc agatgtcatt ggagggtaca gagaaggcca  300
gctggttggg ggaacagccc cagttctggt cgaagacgca ggttctggac tggatcagct  360
accaagtgga gaagaacaag tacgacgcaa gcgccattga cttctcacga tgtgacatgg  420
atggcgccac cctctgcaat tgtgcccttg aggagctgcg tctggtcttt gggcctctgg  480
gggaccaact ccatgcccag ctgcgagacc tcacttccag ctcttctgat gagctcagtt  540
ggatcattga gctgctggag aaggatggca tggccttcca ggaggcccta gacccagggc  600
cctttgacca gggcagcccc tttgcccagg agctgctgga cgacggtcag caagccagcc  660
cctaccaccc cggcagctgt ggcgcaggag cccccctcccc tggcagctct gacgtctcca  720
ccgcagggac tggtgcttct cggagctccc actcctcaga ctccggtgga agtgacgtgg  780
acctggatcc cactgatggc aagctcttcc ccagcgatgg ttttcgtgac tgcaagaagg  840
gggatcccaa gcacgggaag cggaaacgag gccggccccg aaagctgagc aaagagtact  900
gggactgtct cgagggcaag aagagcaagc acgcgcccag aggcacccac ctgtgggagt  960
tcatccggga catcctcatc cacccggagc tcaacgaggg cctcatgaag tgggagaatc  1020
ggcatgaagg cgtcttcaag ttcctgcgct ccgaggctgt ggcccaacta tggggccaaa  1080
agaaaaagaa cagcaacatg acctacgaga agctgagccg ggccatgagg tactactaca  1140
aacgggagat cctggaacgg gtggatggcc ggcgactcgt ctacaagttt ggcaaaaact  1200
caagcggctg gaaggaggaa gaggttctcc agagtcggaa ctgagggttg gaactatacc  1260
cgggaccaaa ctcacggacc actcgaggcc tgcaaacctt cctgggagga caggcaggcc  1320
agatggcccc tccactgggg aatgctccca gctgtgctgt ggagagaagc tgatgttttg  1380
gtgtattgtc agccatcgtc ctgggactcg gagactatgg cctcgcctcc ccaccctcct  1440
cttggaatta caagccctgg ggtttgaagc tgactttata gctgcaagtg tatctccttt  1500
tatctggtgc ctcctcaaac ccagtctcag acactaaatg cagacaacac cttcctcctg  1560
cagacacctg gactgagcca aggaggcctg gggaggccct aggggagcac cgtgatggag  1620
aggacagagc aggggctcca gcaccttctt tctggactgg cgttcacctc cctgctcagt  1680
gcttgggctc cacgggcagg ggtcagagca ctccctaatt tatgtgctat ataaatatgt  1740
cagatgtaca tagagatcta ttttttctaa aacattcccc tccccactcc tctcccacag  1800
agtgctggac tgttccaggc cctccagtgg gctgatgctg ggacccttag gatggggctc  1860
ccagctcctt tctcctgtga atggaggcag agacctccaa taaagtgcct tctgggcttt  1920
ttctaacctt tgtcttagct acctgtgtac tgaaatttgg gcctttggat cgaatatggt  1980
caagaggttg gaggggagga aaatgaaggt ctaccaggct gagggtgagg gcaaaggctg  2040
acgaagaggg gagttacaga tttcctgtag caggtgtggg cttacagaca catggactgg  2100
gctgggaggc gagcaaagga agcagctgag actgttggag aacgcttaca agacttcatg  2160
caagcaagga catgaactca gaacactgag gtcagaagca tcctgctgtc atgacaccgc  2220
tcgagtgacc ttgaccttga ccaagtctgt cctgtttagg actgattttt cctattaggc  2280
tagggtttgg acctgatgtt ctcaagatgt ctagaattgc atggctggcc ttgtggaata  2340
gatggttttg cattccagcc aagtgtgctg taaactgtat atctgtaata tgaatcccag  2400
cttttgagtc tgacaaaatc agagttagga tcttgtaaag gaaaaaaaaa aaaaaacaaa  2460
acaaaatgga gatgagtact tgctgagaaa gaatgaggga aggagttggc atttgttgaa  2520
agtgtagtct ttttctcttt ttttttaat tgcaactttt actttagatt taggaggtcg  2580
tgcgcaggtt tgttacatgg gtatattgtg tgatgctgag cttgggatgc gaatgatcct  2640
gtcacccagg tagtgagtat agcacccagt gaaactgtag tctcatgcca ggcactgtgc  2700
tagcccactc tggctcattt aatcctctcc taagaagaga ggagacacag cgtccccatt  2760
tgacagatgc agaaagaggt tccacaggtg tgccttgatt ctgtcctaaa accgtttccc  2820
ggaagctttt cctggtgtgg gcgcttctaa cctaatcctc aatcgattcc agaactatta  2880
ctctgtttcc acagtgatac tgtgtctagg ttttagggag gacagttcat tgatgttact  2940
taagaatgct ttccaggtgg aaagttcctt aagtttgagg cttcaaattc catacagcac  3000
attaaaatcc cattcatgag tttgaaatac tgctctgttg tcttggaaat accaatcaga  3060
ttgttggctg aagtgatgtg gataaagaag ggatcttaga aaaa                   3104

SEQ ID NO: 25          moltype = DNA  length = 2595
FEATURE                Location/Qualifiers
source                 1..2595
                       mol_type = other DNA
                       organism = Homo sapiens
SEQUENCE: 25
gcacaacttg tgaagaagcg aacacttcca tggattgtcc ttggacttag ggcgccctgc  60
ccgccttttg cagaggagaa aaaacttttt tttttttttg cctcccccga gaactttccc  120
cccttctcct ccctgcctct aactccgatc cccccacgcc atctcgccaa aaaaaaaaaa  180
aaaaaaaaaa aagaaaaaaa aagaaaaaaa aagaaaaaaa attaccccaa tccacgcctg  240
caaattcttc tggaaggatt ttccccccctc tcttcaggtt gggcgcgttt ggtgcaagat  300
tctcgggatc ctcggctttg cctctccctc tccctccccc ctcctttcct ttttcctttc  360
ctttcctttc tttcttcctt tccttccccc cacccccacc cccaccccaa acaaacgagt  420
ccccaattct cgtccgtcct cgccgcgggc agcgggcggc ggaggcagcg tgcggcggtc  480
gccaggagct gggagcccag ggcgcccgct cctcggcgca gcatgttcca gccggcgccc  540
aagcgctgct tcaccatcga gtcgctggtg gccaaggaca gtcccctgcc cgcctcgcgc  600
tccgaggacc ccatccgtcc cgcggcactc agctacgcta actccagccc cataaatccg  660
ttcctcaacg gcttccactc ggccgccgcc gccgccgccg gtaggggcgt ctactccaac  720
ccggacttgg tgttcgccga ggcggtctcg cacccgccca accccgccgt gccagtgcac  780
ccggtgccgc cgccgcacgc cctggccgcc cacccccctac cctcctcgca ctcgccacac  840
cccctattcg cctcgcagca gcgggatccg tccaccttct acccctggct catccaccgc  900
taccgatatc tgggtcatcg cttccaaggg aacgacacta gccccgagag tttccttttg  960
cacaacgcgc tggcccgaaa gcccaagcgg atccgaaccg ccttctcccc gtcccagctt  1020
ctaaggctgg aacacgcctt tgagaagaat cactacgtgg tgggcgccga aaggaagcag  1080
ctggcacaca gcctcagcct cacggaaact caggtaaaag tatggtttca gaaccgaaga  1140
acaaagttca aaaggcagaa gctggaggaa gaaggctcag attcgcaaca aaagaaaaaa  1200
gggacgcacc atattaaccg gtggagaatc gccaccaagc aggcgagtcc ggaggaaata  1260
gacgtgacct cagatgatta aaaacataaa cctaacccca cagaaacgga caacatggag  1320
caaaagagac agggagaggt ggagaaggaa aaaaccctac aaaacaaaaa caaaccgcat  1380
acacgttcac cgagaaaggg agagggaatc ggagggagca gcggaatgcg gcgaagactc  1440
```

```
tggacagcga gggcacaggg tcccaaaccg aggccgcgcc aagatggcag aggatggagg  1500
ctccttcatc aacaagcgac cctcgtctaa agaggcagct gagtgagaga cacagagaga  1560
aggagaaaga gggagggaga gagagaaaga gagagaaaga gagagagaga gagagagaga  1620
gaaagctgaa cgtgcactct gacaagggga gctgtcaatc aaacaccaaa ccggggagac  1680
aagatgattg gcaggtattc cgtttatcac agtccactta aaaaatgatg atgatgataa  1740
aaaccacgac ccaaccaggc acaggacttt tttgtttttt gcacttcgct gtgtttcccc  1800
cccatcttta aaaataatta gtaataaaaa acaaaaattc catatctagc cccatcccac  1860
acctgtttca aatccttgaa atgcatgtag cagttgttgg gcgaatggtg tttaaagacc  1920
gaaaatgaat tgtaatttc ttttcctttt aaagacaggt tctgtgtgct ttttattttg  1980
atttttttc ccaagaaatg tgcagtctgt aaacactttt tgataccttc tgatgtcaaa  2040
gtgattgtgc aagctaaatg aagtaggctc agcgatagtg gtcctcttac agagaaacgg  2100
ggagcaggac gacgggggg ctgggggtgg cgggggaggg tgcccacaaa aagaatcagg  2160
acttgtactg ggaaaaaaac ccctaaatta attatatttc ttggacattc cctttcctaa  2220
catcctgagg cttaaaaccc tgatgcaaac ttctcctttc agtggttgga gaaattggcc  2280
gagttcaacc attcactgca atgcctattc caaactttaa atctatctat tgcaaaacct  2340
gaaggactgt agttagcggg gatgatgtta agtgtggcca agcgcacggc ggcaagtttt  2400
caagcactga gtttctattc caagatcata gacttactaa agagagtgac aaatgcttcc  2460
ttaatgtctt ctataccaga atgtaaatat ttttgtgttt tgtgttaatt tgttagaatt  2520
ctaacacact atatacttcc aagaagtatg tcaatgtcaa tattttgtca ataaagattt  2580
atcaatatgc cctca                                                   2595

SEQ ID NO: 26          moltype = DNA  length = 7282
FEATURE                Location/Qualifiers
source                 1..7282
                       mol_type = other DNA
                       organism = Homo sapiens
SEQUENCE: 26
gtgcttggct acagccgctg ctgcctctcg cgaactgggc tccggggctc ccggctcccg  60
agaactagaa gagaaacgcg agcgaaggga tcgaaacccg gggggttacc gacttgcaga  120
caccgccagg acagtctgta acgcaggaag atcccagcgg ctccgggtct ggtgagggga  180
ccataagcat gactgatagc gaatgaggaa gggcagccct aaacttttca agcaaagcct  240
cagagttttg ggttcactca ttagcatagg aaatcgattc accgaaaacc caaacaaaga  300
aaaacaagcc gacagtccag gcaggatgca ggcaaatcca gttcgggatt aagggtaaaa  360
ggctttttgg gtttttttc ctttggtttg atttttaaa atatggggag gggggtgaca  420
tctacccgat tctaggctcc ggcaggaacg caatgggtta atgaatggac aagccgcgga  480
gtattgatcg gctgccgccg gagaaagaaa gaaaaacaaa aaccagaccg aacctgcctt  540
cccgctgtgg ctgctcggcg ccccaattaa gcagggtcat ctcaggctgg ctgcatgcct  600
cagctgaaga tcccagctcc tgtcaatgcc acctctctgc ttgactgtct ccttccagat  660
tcgagcaggt atgagctggg aagaatgaag gcagggcatg cccgtgtgcc agctctgcac  720
agctggatag ctgaggaaag atgtggagga gaagccgggg attgtgtgga agtctaaggg  780
tgttgtttgc cctttgggtt ccagaagatg catgccagga ccctgggtgg cactgccagg  840
aagcaacaga gaggagataa aactcacagc agacagactt gccttaacaa caactccctt  900
gaattaaaac acgcttttca agaaaacaaa ttatcagttc gatcagcaaa cagcagagaa  960
gtttctctca taatggcaaa gaagggccgg gttgctgacc agtgaaagag cttcagaaaa  1020
ggagagggga gatgagatgg ccagaaggag caagagcacc gtacatccct ggacaacctc  1080
attctaatgg gtcaggggct gggacgtgca ttttggagtg caggagaagt ggcaactcac  1140
aaatgctaga ttttcttcta gagatgacca agctgtagtt cttaaagcag tggcactagg  1200
gcagaaaact ctcacacttt gatgtgcaca cacagcccct ggggatcttg ttgacatgta  1260
gattctgatt ccgtaagtcg ggctgagatt ctgcatttcc aacaagctcc tagatgaggt  1320
ccattttgct ggtccatgaa acacacttag aataagtagc aaggtatagg aggatactga  1380
ctttgctcag tgatgcttgg gcttccgtcc aaactaaaat aaaacaaaag cagacataaa  1440
tggcccaatt caacagcctg agaagtttgg tgataatgac ccaagccctg gcctggtgac  1500
caagtggctg ctcagagagc tctatctcca aactccttcc cttcctgcct cccctccaag  1560
agtgagtaat gtgccagagt tcattggggt ctgctgtccc cagggaaagg tggcccagtt  1620
gccaagtgca agtgtataga acggcttacc tgtgcaaagc tatcagccct ggacctatgg  1680
gcctagaaac attacttgcc actcactcac tcactatcat tcattcattt ctgcaacaaa  1740
cacttcctga gcatatgcta tacaccaggc cctgagctca gctctgggga tacaggatga  1800
atggcagatt gtgccatcag gaagccgact gcacagtcag cccgctggag cacatatgaa  1860
aaacaatacg gatgttttga tttattatca tattgatcat tatgatggta gcgtatactt  1920
ttggaaggct tgccatacat taggcattgt gctaagcaca ttatatggtt aatctcatca  1980
atcttcacaa cctatgtggc aggtactatt attaaaccca cttcaaagag gagggaactg  2040
aacctcagag agggtaagtg acttgcacaa ggacacaagc tagtgaggag aggaactgag  2100
aggaatggcc agacaggcca tcagcctctg tccccacatg ctgggtctga gtgtctgacg  2160
gtggacacat tcccttcctg gagggagagc tcctagggag ctgatggcag cactgagtct  2220
ggaatgtgat gggagtgcat tagatgacgt gggtgatctg atgagtacag aggcgtcaca  2280
ctgcaatgac ttcatgcaca tatctcccct tgaatgcaca gagattcagc agaggccagg  2340
agctcaagtt tctggcccag tgtccccctc ttcccctggg gaaagccagg gacacactgc  2400
ctggctttgc tacacctttc taggcaaagg cagtatgctc tccctctcct tggcctccct  2460
ggctgtccac acatccacac ccactcacac acacatgcac atgatcatac acattacaca  2520
agcccacatg cccacagaca tgctcacact cacactcaca tgcatacact gccatacaca  2580
acacacatac atacattcac acacacttgc acacacacac acacacacag ttctgatggc  2640
caatcttttg gggctatgtt gacactgtga agcaggtgaa acaaagtctt tgccactccc  2700
tgctttgggc ctattatgtt tgttttatag tttaactctc aaaagacaac tttattttcc  2760
aaaattattc aggttcccag ccaggtgcag tggctcacac ctgtaatccc agtactttgg  2820
gaggccaagg cgggcagatc acctgaggtc aggagtttga gaccagcttg gccaacatgg  2880
tgaaacccag tctctactaa aaatacaaaa attagccaga catggtggca cacacatgta  2940
atcccagcta ttcgggaggc tgaggcagga gaatcgcttg aacccgggag gcggaggttg  3000
cagtgggcca agatcgtgcc actgcactcc agcctgggca acagagcaag actccatctc  3060
aaaaaacaaa aacaaaatca ttcaggttct gtaggggacc ctcactgtgt cctggattcc  3120
```

-continued

```
attccacttt taaagtccca aacagcttgt atggccactt cccttgacac ccaaaccaga  3180
taggagtctt aaatgacaca gagtattgat ggtttcttta aaaggaaatc cactctcaat  3240
gggaagctgg ataacttcgc atccagattt catccatctt gggctttggt ggctgctgtt  3300
tgtttttgtg caggagaatc tctcccagcc aacgtcgatt tcactaacac agtggttaac  3360
ctttgctctc tactcctgca tcaatcttcc gcctaccgca tgttgagcca tgctgctttc  3420
tggcattcct tttggatttt cagtttacta cccaactacc agtcctaata acatcagata  3480
aaagggcttc cgctgtgctg cacttgtttt caaaaactat aaatgccatc gacccagagt  3540
taagtccagc ctcagagaga cagaatataa atacccaagt ggccctgggc cactgagttc  3600
ctcagacatt atgtgctatg ggagttccag aaagggggat tgcctggttt tgagtgcaga  3660
aggcttcctg gaggaggcga gatttctgat gggcctctgt tatgagctaa attgagtcca  3720
ccccaaaatt cagatgttca aatcctaacc tgtagtacct aagcatgtgg ccttatttgg  3780
aagcagaagc ataacagagg taattcgtta agatgaggtc acagtggaag agggtggacc  3840
ccaatctgat acaactcgtg tccttataaa aagcagaaat ttgaagacag acacacaaga  3900
agatgaaggc agagacctgg ctgatgcggc tataagccaa ggaacgccaa agattgccag  3960
caaagcacca gcagccaggg agaggcctcg aacaaattct ccctcccagc aaaaaggagg  4020
aaggaaggaa cctccaaaag aagcaggcca ggcacagtgg ctcacgcctg taatcccagt  4080
actttgggag gttaaggcag gcggatcacc tgagatcaag agttcaagac cagcctggcc  4140
aacatggtga aacctcatct ctacagaaaa atacaaaaat tagtcaggtg tagtggcgtg  4200
cacctgtagt cccagttact cgggaggctg aggcaagaga atcgcttgaa cctgggaggt  4260
ggaggttgca gtgagccaag atcgtgccat tgcactccag cctgggtgac agagcgagac  4320
tccatctcag aaaaacaaaa aagaacccta ctgacacctg gatttcagac ttccagcctc  4380
cagaactgtg agatgttaca tttctgtcat ttaaacaccc agtttgtagt actttgttgc  4440
aacagctcta gtgagctaat acagccttgt aggacaggta ggaatttgta atgcacagag  4500
aaagccaact ggccacagtt gttgaaaata atagaatcga agcgccccta tcactaccac  4560
cccaggccat cactttcaaa gctgttcaaa atgatgcagc cgcgtgagaa ggccggaagg  4620
ccagggcggg agatgggctc caggtgggcc caggctgcct gcagaaccag cttgcctcac  4680
tgcctggttg ccaaggagca cctgtggcta ggaggagatg cccaggaaga aaatttggcc  4740
acatccctgc ctgcctccct ggcaatgggt gatgctctct gccagctggc ccagctcccc  4800
caccacatac ctggctagga gtcagtagga aaacagtgtg tgtttgtagg gctctgcact  4860
gaagggcatt agatccatgc aaaggctaat aaattagaga taagtgggat ttgtagattt  4920
gctggaggtt agagctgcag ggtctggcat cagctctggg tcttttccat ggccccaggc  4980
tggctcaggt gtgagctgaa gaggcaaaac tgtctgttta ggttgcattg ggttcccctg  5040
aaagatctgt tgaagtccta acctcgggta cctctgtttg tgctatttgc aaacaggctc  5100
tttgcagatg taatcaagga aagatgaggc aacgctgatt tagtcaggcc ttaatccagt  5160
gactggtgtc ttcataagac aaggaaatct ggacacagac acacaaagag gaaaaagcca  5220
aagacacaga gacacatgta cacagggaga actccatggg acaacgcagg cacagatcgg  5280
agtgacgcgg ctgcaagcca aggagcgcca agattgccag caaccccctg gggctgcaag  5340
aggtgagaag gagccttcgg agggaacatg cactgctgat tccttgattc cagatttctg  5400
acctccagaa gcatgggaga acagatttcc cttgtttgaa ggcacccagt ctgtggtcct  5460
tcatcatggc agccctcagg aatggataca ggcccttccc tgcctgcctg gtggagcagc  5520
ctccaagggg agcctttgct agcaggaaga ggcatcgcat ggagctcaga cccgcctcag  5580
aggaacttct ctcagcctcc tctctccgca cacccgacca aggtgtgaaa tccctcccct  5640
ttacctctgc cacttgcagg tggcaggatg ctggagctgt ccctgcctct ttgtaaagtg  5700
agggaagggc agccctctct gctctttttt tttttttttt tgagacagag tctcactctg  5760
tctcccaggc tggagtgcaa tagcacgatc tcggctcact gcaacctccg cctcccaggt  5820
tcaagcgatt ctcctgcctc aacctcctga gtagctggaa ttacaggtgc ctgccaccac  5880
gcccagctaa ttttgtattg ttagtagagc cagggtttca ccatgtcggc caggctagtc  5940
tcaaactcct gacctcaggt gatccacctg cctcggcctc ccaaagtgct gcgattacag  6000
acatgagcca ccacgcccgg cctgctccac ttctaaggct tcttgtgaca atgtaagaga  6060
aaggagatga cagagctttg caacgggagg agggctatgt gttctggtga ccaattcact  6120
gtcttgtgtc gggacaggaa gaagcccttc atacgggcag caggctggga gccagggagg  6180
aggaaagatc acgatccact ccctggtaca tggcccttct gcaccccgca gtctccttcc  6240
aggtgccaca acgagaaggc acacatcctt ggcacagcac ttgaggcttt tcaccactgg  6300
ctgcactcac ccctccagac tcactgcctt gcaccaaccc ttttccgccc accccactct  6360
atgctgtcca cagcctccac cccagccacc tgattctgca ggccaatgtc acattcttcc  6420
agtccaggtt ctattctggc atttcttgtc attattttgc tgagaatgtg tctctcttga  6480
ctttgaactt attgagagca ggaatcatga ctcagccata tatcccagca cttggcccag  6540
ggcctgtcgt ttccagggta ggtggtctag gctgattgaa ggaatggcat ttagtcttta  6600
aaatgaaagc atgttgccta gcttggttat ttttgaactc tataatcaag gactacgttt  6660
acctgaatag cctctgcaga acaccaattc cgtaaggtgc ttcacacaca cacaccaatt  6720
ctatcattta atacattttg gaaaggctac atactactac agcctctttt acagattagc  6780
aatgtccatg agcgcactaa aggttgagac attctgcagt gaagaagcct atttcatttt  6840
gtttaaccaa gtatttctca aatttatttg atcatatgtg gcagaaaatg ctgtgtctgg  6900
cattcttcat ttccctcttc ctcctttaac atggaacccc tgatgtcttt agcttggcac  6960
atcgccaccc agaataaaaa ctacctttcc cagctcttcc tgcagctagg ggcagccctg  7020
ggataaattc tggacaatga aatacaggca gaagtaaatc atatacgatt tccatgaagg  7080
gaccttaaac agaagtgtgc ccttctcttc cccacacatt cctcctcctg tctgaaatgt  7140
agatgcaact gctggcattt gagcagccat cttgggccat gtggtagctt cttatggatg  7200
atctaggact aattcaaggg tctagattta cctccaaact ttgtttatct acaaaaaata  7260
aaactctatc ttcttaaagc ta                                            7282
```

```
SEQ ID NO: 27          moltype = DNA  length = 1731
FEATURE                Location/Qualifiers
source                 1..1731
                       mol_type = other DNA
                       organism = Homo sapiens
SEQUENCE: 27
aactgcagcg ccggggctgg gggaggggag cctactcact cccccaactc ccgggcggtg  60
actcatcaac gagcaccagc ggccagaggt gagcagtccc gggaaggggc cgagaggcgg  120
ggccgccagg tcgggcaggt gtgcgctccg ccccgccgcg cgcacagagc gctagtcctt  180
cggcgagcga gcaccttcga cgcggtccgg ggaccccctc gtcgctgtcc tcccgacgcg  240
gacccgcgtg ccccaggcct cgcgctgccc ggccggctcc tcgtgtccca ctcccggcgc  300
acgccctccc gcgagtcccg ggcccctccc gcgcccctct tctcggcgcg cgcgcagcat  360
ggcgcccccg caggtcctcg cgttcgggct tctgcttgcc gcggcgacgg cgacttttgc  420
cgcagctcag gaagaatgtg tctgtgaaaa ctacaagctg gccgtaaact gctttgtgaa  480
taataatcgt caatgccagt gtacttcagt tggtgcacaa aatactgtca tttgctcaaa  540
gctggctgcc aaatgtttgg tgatgaaggc agaaatgaat ggctcaaaac ttgggagaag  600
agcaaaacct gaaggggccc tccagaacaa tgatgggctt tatgatcctg actgcgatga  660
gagcgggctc tttaaggcca agcagtgcaa cggcacctcc atgtgctggt gtgtgaacac  720
tgctggggtc agaagaacag acaaggacac tgaaataacc tgctctgagc gagtgagaac  780
ctactggatc atcattgaac taaaacacaa agcaagagaa aaaccttatg atagtaaaag  840
tttgcggact gcacttcaga aggagatcac aacgcgttat caactggatc caaaatttat  900
cacgagtatt ttgtatgaga ataatgttat cactattgat ctggttcaaa attcttctca  960
aaaaactcag aatgatgtgg acatagctga tgtggcttat tattttgaaa aagatgttaa  1020
aggtgaatcc ttgtttcatt ctaagaaaat ggacctgaca gtaaatgggg aacaactgga  1080
tctggatcct ggtcaaactt taatttatta tgttgatgaa aaagcacctg aattctcaat  1140
gcagggtcta aaagctggtg ttattgctgt tattgtggtt gtggtgatag cagttgttgc  1200
tggaattgtt gtgctggtta tttccagaaa gaagagaatg gcaaagtatg agaaggctga  1260
gataaaggag atgggtgaga tgcataggga actcaatgca taactatata atttgaagat  1320
tatagaagaa gggaaatagc aaatggacac aaattacaaa tgtgtgtgcg tgggacgaag  1380
acatctttga aggtcatgag tttgttagtt taacatcata tatttgtaat agtgaaacct  1440
gtactcaaaa tataagcagc ttgaaactgg ctttaccaat cttgaaattt gaccacaagt  1500
gtcttatata tgcagatcta atgtaaaatc cagaacttgg actccatcgt taaaattatt  1560
tatgtgtaac attcaaatgt gtgcattaaa tatgcttcca cagtaaaatc tgaaaaactg  1620
atttgtgatt gaaagctgcc tttctattta cttgagtctt gtacatacat actttttat  1680
gagctatgaa ataaaacatt ttaaactgaa tttcttaaaa aaaaaaaaaa a           1731

SEQ ID NO: 28          moltype = DNA  length = 5765
FEATURE                Location/Qualifiers
source                 1..5765
                       mol_type = other DNA
                       organism = Homo sapiens
SEQUENCE: 28
actccagcct cgcgcgggag ggggcgcggc cgtgactcac ccccttccct ctgcgttcct  60
ccctccctct ctctctctct ctcacacaca cacacccctc ccctgccatc cctccccgga  120
ctccggctcc ggctccgatt gcaatttgca acctccgctg ccgtcgccgc agcagccacc  180
aattcgccag cggttcaggt ggctcttgcc tcgatgtcct agcctagggg cccccgggcc  240
ggacttggct gggctccctt caccctctgc ggagtcatga gggcgaacga cgctctgcag  300
gtgctgggct tgcttttcag cctggcccgg ggctccgagg tgggcaactc tcaggcagtg  360
tgtcctggga ctctgaatgg cctgagtgtg accggcgatg ctgagaacca ataccagaca  420
ctgtacaagc tctacgagag gtgtgaggtg gtgatgggga accttgagat tgtgctcacg  480
ggacacaatg ccgacctctc cttcctgcag tggattcgag aagtgacagg ctatgtcctc  540
gtggccatga atgaattctc tactctacca ttgcccaacc tccgcgtggt gcgagggacc  600
caggtctacg atgggaagtt tgccatcttc gtcatgttga actataacac caactccagc  660
cacgctctgc gccagctccg cttgactcag ctcaccgaga ttctgtcagg gggtgtttat  720
attgagaaga acgataagct ttgtcacatg gacacaattg actggaggga catcgtgagg  780
gaccgagatg ctgagatagt ggtgaaggac aatggcagaa gctgtccccc ctgtcatgag  840
gtttgcaagg ggcgatgctg gggtcctgga tcagaagact gccagacatt gaccaagacc  900
atctgtgctc ctcagtgtaa tggtcactgc tttgggccca accccaacca gtgctgccat  960
gatgagtgtg ccgggggctg ctcaggccct caggacacag actgctttgc ctgccggcac  1020
ttcaatgaca gtggagcctg tgtacctcgc tgtccacagc ctcttgtcta caacaagcta  1080
actttccagc tggaacccaa tccccacacc aagtatcagt atggaggagt ttgtgtagcc  1140
agctgtcccc ataactttgt ggtggatcaa acatcctgtg tcagggcctg tcctcctgac  1200
aagatggaag tagataaaaa tgggctcaag atgtgtgagc cttgtggggg actatgtccc  1260
aaagcctgtg agggaacagg ctctgggagc cgcttccaga ctgtggactc gagcaacatt  1320
gatggatttg tgaactgcac caagatcctg ggcaacctgg actttctgat caccggcctc  1380
aatggagacc cctggcacaa gatccctgcc ctggacccag agaagctcaa tgtcttccgg  1440
acagtacggg agatcacagg ttacctgaac atccagtcct ggccgcccca catgcacaac  1500
ttcagtgttt tttccaattt gacaaccatt ggaggcagaa gcctctacaa ccggggcttc  1560
tcattgttga tcatgaagaa cttgaatgtc acatctctgg gcttccgatc cctgaaggaa  1620
attagtgctg ggcgtatcta tataagtgcc aataggcagc tctgctacca ccactctttg  1680
aactggacca aggtgcttcg gggggcctacg gaagagcgac tagacatcaa gcataatcgg  1740
ccgcgcagag actgcgtggc agagggcaaa gtgtgtgacc cactgtgctc ctctggggga  1800
tgctggggcc caggccctgg tcagtgcttg tcctgtcgaa attatagccg aggaggtgtc  1860
tgtgtgaccc actgcaactt tctgaatggg gagcctcgag aatttgccca tgaggccgaa  1920
tgcttctcct gccacccgga atgccaaccc atggagggca ctgccacatg caatggctcg  1980
ggctctgata cttgtgctca atgtgcccat tttcgagatg ggccccactg tgtgagcagc  2040
tgcccccatg gagtcctagg tgccaagggc ccaatctaca agtacccaga tgttcagaat  2100
gaatgtcggc cctgccatga gaactgcacc caggggtgta aaggaccaga gcttcaagac  2160
tgtttaggac aaacactggt gctgatcggc aaaacccatc tgacaatggc tttgacagtg  2220
```

-continued

```
atagcaggat tggtagtgat tttcatgatg ctgggcggca cttttctcta ctggcgtggg  2280
cgccggattc agaataaaag ggctatgagg cgatacttgg aacggggtga gagcatagag  2340
cctctggacc ccagtgagaa ggctaacaaa gtcttggcca gaatcttcaa agagacagag  2400
ctaaggaagc ttaaagtgct tggctcgggt gtctttggaa ctgtgcacaa aggagtgtgg  2460
atccctgagg gtgaatcaat caagattcca gtctgcatta aagtcattga ggacaagagt  2520
ggacggcaga gttttcaagc tgtgacagat catatgctgg ccattggcag cctggaccat  2580
gcccacattg taaggctgct gggactatgc ccagggtcat ctctgcagct tgtcactcaa  2640
tatttgcctc tgggttctct gctggatcat gtgagacaac accgggggc actggggcca  2700
cagctgctgc tcaactgggg agtacaaatt gccaagggaa tgtactacct tgaggaacat  2760
ggtatggtgc atagaaacct ggctgcccga aacgtgctac tcaagtcacc cagtcaggtt  2820
caggtggcag attttggtgt ggctgacctg ctgcctcctg atgataagca gctgctatac  2880
agtgaggcca agactccaat taagtggatg gcccttgaga gtatccactt tgggaaatac  2940
acacaccaga gtgatgtctg gagctatggt gtgacagttt gggagttgat gaccttcggg  3000
gcagagccct atgcagggct acgattggct gaagtaccag acctgctaga gaagggggag  3060
cggttggcac agccccagat ctgcacaatt gatgtctaca tggtgatggt caagtgttgg  3120
atgattgatg agaacattcg cccaaccttt aaagaactag ccaatgagtt caccaggatg  3180
gcccgagacc caccacggta tctggtcata aagagagaga gtgggcctgg aatagcccct  3240
gggccagagc cccatggtct gacaaacaag aagctagagg aagtagagct ggagccagaa  3300
ctagacctag acctagactt ggaagcagag gaggacaacc tggcaaccac cacactgggc  3360
tccgccctca gcctaccagt tggaacactt aatcggccac gtgggagcca gagcctttta  3420
agtccatcat ctggatacat gcccatgaac cagggtaatc ttggggagtc ttgccaggag  3480
tctgcagttt ctgggagcag tgaacggtgc ccccgtccag tctctctaca cccaatgcca  3540
cggggatgcc tggcatcaga gtcatcagag ggcatgtaa caggctctga ggctgagctc  3600
caggagaaag tgtcaatgtg taggagccgg agcaggagcc ggagcccacg gccacgcgga  3660
gatagcgcct accattccca gcgccacagt ctgctgactc ctgttacccc actctcccca  3720
cccgggttag aggaagagga tgtcaacggt tatgtcatgc cagatacaca cctcaaaggt  3780
actccctcct cccgggaagg caccctttct tcagtgggtc tcagttctgt cctgggtact  3840
gaagaagaag atgaagatga ggagtatgaa tacatgaacc ggaggagaag gcacagtcca  3900
cctcatcccc ctaggccaag ttcccttgag gagctgggtt atgagtacat ggatgtgggg  3960
tcagacctca gtgcctctct gggcagcaca cagagttgcc cactccaccc tgtacccatc  4020
atgcccactg caggcacaac tccagatgaa gactatgaat atatgaatcg gcaacgagat  4080
ggaggtggtc ctgggggtga ttatgcagcc atgggggcct gcccagcatc tgagcaaggg  4140
tatgaagaga tgagagcttt tcaggggcct ggacatcagg ccccccatgt ccattatgcc  4200
cgcctaaaaa ctctacgtag cttagaggct acagactctg cctttgataa ccctgattac  4260
tggcatagca ggcttttccc caaggctaat gcccagagaa cgtaactcct gctccctgtg  4320
gcactcaggg agcatttaat ggcagctagt gcctttagag ggtaccgtct tctccctatt  4380
ccctctctct cccaggtccc agccccttttt ccccagtccc agacaattcc attcaatctt  4440
tggaggcttt taaacatttt gacacaaaat tcttatggta tgtagccagc tgtgcacttt  4500
cttctctttc ccaaccccag gaaaggtttt ccttattttg tgtgctttcc cagtcccatt  4560
cctcagcttc ttcacaggca ctcctggaga tatgaaggat tactctccat atcccttcct  4620
ctcaggctct tgactacttg gaactaggct cttatgtgtg cctttgtttc ccatcagact  4680
gtcaagaaga ggaaagggag gaaacctagc agaggaaagt gtaattttgg tttatgactc  4740
ttaacccccct agaaagacag aagcttaaaa tctgtgaaga aagaggttag gagtagatat  4800
tgattactat cataattcag cacttaacta tgagccaggc atcatactaa acttcaccta  4860
cattatctca cttagtcctt tatcatcctt aaaacaattc tgtgacatac atattatctc  4920
attttacaca aagggaagtc gggcatggtg gctcatgcct gtaatctcag cactttggga  4980
ggctgaggca gaaggattac ctgaggcaag gagtttgaga ccagcttagc caacatagta  5040
agacccccat ctctttaaaa aaaaaaaaaa aaaaaaaaaa aaaactttag aactgggtgc  5100
agtggctcat gcctgtaatc ccagccagca ctttgggagg ctgagatggg aagatcactt  5160
gagcccagaa ttagagataa gcctatggaa acatagcaag acactgtctc tacaggggaa  5220
aaaaaaaaaa gaaactgagc cttaaagaga tgaaataaat taagcagtag atccaggatg  5280
caaaatcctc ccaattcctg tgcatgtgct cttattgtaa ggtgccaaga aaaactgatt  5340
taagttacag cccttgttta aggggcactg tttcttgttt ttgcactgaa tcaagtctaa  5400
ccccaacagc cacatcctcc tatacctaga catctcatct caggaagtgg tggtggggt  5460
agtcagaagg aaaaataact ggacatcttt gtgtaaacca taatccacat gtgccgtaaa  5520
tgatcttcac tccttatccg agggcaaatt cacaaggatc cccaagatcc acttttagaa  5580
gccattctca tccagcagtg agaagcttcc aggtaggaca gaaaaaagat ccagcttcag  5640
ctgcacacct ctgtcccctt ggatggggaa ctaagggaaa acgtctgttg tatcactgaa  5700
gtttttgtt ttgtttttat acgtgtctga ataaaaatgc caaagttttt tttcagcaaa  5760
aaaaa                                                              5765

SEQ ID NO: 29          moltype = DNA  length = 6330
FEATURE                Location/Qualifiers
source                 1..6330
                       mol_type = other DNA
                       organism = Homo sapiens
SEQUENCE: 29
aggagctggc ggagggcgtt cgtcctggga ctgcacttgc tcccgtcggg tcgcccggct  60
tcaccggacc cgcaggctcc cggggcaggg ccggggccag agctcgcgtg tcggcgggac  120
atgcgctgcg tcgcctctaa cctcgggctg tgctcttttt ccaggtggcc cgccggtttc  180
tgagccttct gccctgcggg gacacggtct gcaccctgcc cgcggccacg gaccatgacc  240
atgaccctcc acaccaaagc atctgggatg gccctactgc atcagatcca agggaacgag  300
ctggagcccc tgaaccgtcc gcagctcaag atccccctgg agcggcccct gggcgaggtg  360
tacctggaca gcagcaagcc cgccgtgtac aactaccccg agggcgccgc ctacgagttc  420
aacgccgcgg ccgccgccaa cgcgcaggtc tacggtcaga ccggcctccc ctacggcccc  480
gggtctgagg ctgcggcgtt cggctccaac ggcctggggg gtttcccccc actcaacagc  540
gtgtctccga gcccgctgat gctactgcac ccgccgccgc agctgtcgcc tttcctgcag  600
ccccacggcc agcaggtgcc ctactacctg gagaacgagc ccagcggcta cacggtgcgc  660
gaggccggcc cgccggcatt ctacaggcca aattcagata atcgacgcca gggtggcaga  720
```

-continued

```
gaaagattgg ccagtaccaa tgacaaggga agtatggcta tggaatctgc caaggagact  780
cgctactgtg cagtgtgcaa tgactatgct tcaggctacc attatggagt ctggtcctgt  840
gagggctgca aggccttctt caagagaagt attcaaggac ataacgacta tatgtgtcca  900
gccaccaacc agtgcaccat tgataaaaac aggaggaaga gctgccaggc ctgccggctc  960
cgcaaatgct acgaagtggg aatgatgaaa ggtgggatac gaaaagaccg aagaggaggg  1020
agaatgttga aacacaagcg ccagagagat gatggggagg gcaggggtga agtggggtct  1080
gctggagaca tgagagctgc caacctttgg ccaagcccgc tcatgatcaa acgctctaag  1140
aagaacagcc tggccttgtc cctgacggcc gaccagatgg tcagtgcctt gttggatgct  1200
gagcccccca tactctattc cgagtatgat cctaccagac ccttcagtga agcttcgatg  1260
atgggcttac tgaccaacct ggcagacagg gagctggttc acatgatcaa ctgggcgaag  1320
agggtgccag gctttgtgga tttgaccctc catgatcagg tccaccttct agaatgtgcc  1380
tggctagaga tcctgatgat tggtctcgtc tggcgctcca tggagcaccc agggaagcta  1440
ctgtttgctc ctaacttgct cttggacagg aaccagggaa aatgtgtaga gggcatggtg  1500
gagatcttcg acatgctgct ggctacatca tctcggttcc gcatgatgaa tctgcaggga  1560
gaggagtttg tgtgcctcaa atctattatt ttgcttaatt ctggagtgta cacatttctg  1620
tccagcaccc tgaagtctct ggaagagaag gaccatatcc accgagtcct ggacaagatc  1680
acagacactt tgatccacct gatggccaag gcaggcctga ccctgcagca gcagcaccag  1740
cggctggccc agctcctcct catcctctcc cacatcaggc acatgagtaa caaaggcatg  1800
gagcatctgt acagcatgaa gtgcaagaac gtggtgcccc tctatgacct gctgctggag  1860
atgctggacg cccaccgcct acatgcgccc actagccgtg gaggggcatc cgtggaggag  1920
acggaccaaa gccacttggc cactgcgggc tctacttcat cgcattcctt gcaaaagtat  1980
tacatcacgg gggaggcaga gggtttccct gccacggtct gagagctccc tggctcccac  2040
acggttcaga taatccctgc tgcattttac cctcatcatg caccacttta gccaaattct  2100
gtctcctgca tacactccgg catgcatcca acaccaatgg ctttctagat gagtggccat  2160
tcatttgctt gctcagttct tagtggcaca tcttctgtct tctgttggga acagccaaag  2220
ggattccaag gctaaatctt tgtaacagct ctctttcccc cttgctatgt tactaagcgt  2280
gaggattccc gtagctcttc acagctgaac tcagtctatg ggttggggct cagataactc  2340
tgtgcattta agctacttgt agagacccag gcctggagag tagacatttt gcctctgata  2400
agcacttttt aaatggctct aagaataagc cacagcaaag aatttaaagt ggctccttta  2460
attggtgact tggagaaagc taggtcaagg gtttattata gcaccctctt gtattcctat  2520
ggcaatgcat ccttttatga aagtggtaca ccttaaagct tttatatgac tgtagcagag  2580
tatctggtga ttgtcaattc attcccccta taggaataca aggggcacac agggaaggca  2640
gatcccctag ttggcaagac tattttaact tgatacactg cagattcaga tgtgctgaaa  2700
gctctgcctc tggctttccg gtcatgggtt ccagttaatt catgcctccc atggacctat  2760
ggagagcagc aagttgatct tagttaagtc tccctatatg agggataagt tcctgatttt  2820
tgtttttatt tttgtgttac aaaagaaagc cctccctccc tgaacttgca gtaaggtcag  2880
cttcaggacc tgttccagtg ggcactgtac ttggatcttc ccggcgtgtg tgtgccttac  2940
acaggggtga actgttcact gtggtgatgc atgatgaggg taaatggtag ttgaaaggag  3000
caggggccct ggtgttgcat ttagccctgg ggcatggagc tgaacagtac ttgtgcagga  3060
ttgttgtggc tactagagaa caagagggaa agtagggcag aaactggata cagttctgag  3120
gcacagccag acttgctcag ggtggccctg ccacaggctg cagctaccta ggaacattcc  3180
ttgcagaccc cgcattgccc tttgggggtg ccctgggatc cctggggtag tccagctctt  3240
cttcatttcc cagcgtggcc ctggttggaa gaagcagctg tcacagctgc tgtagacagc  3300
tgtgttccta caattggccc agcaccctgg ggcacgggag aagggtgggg accgttgctg  3360
tcactactca ggctgactgg ggcctggtca gattacgtat gcccttggtg gtttagagat  3420
aatccaaaat cagggtttgg tttggggaag aaaatcctcc cccttcctcc cccgccccgt  3480
tccctaccgc ctccactcct gccagctcat ttccttcaat ttcctttgac ctataggcta  3540
aaaaagaaag gctcattcca gccacagggc agccttccct gggcctttgc ttctctagca  3600
caattatggg ttacttcctt tttcttaaca aaaaagaatg tttgatttcc tctgggtgac  3660
cttattgtct gtaattgaaa ccctattgag aggtgatgtc tgtgttagcc aatgacccag  3720
gtgagctgct cgggcttctc ttggtatgtc ttgtttggaa aagtggattt cattcatttc  3780
tgattgtcca gttaagtgat caccaaagga ctgagaatct gggagggcaa aaaaaaaaaa  3840
aaagttttta tgtgcactta aatttgggga caattttatg tatctgtgtt aaggatatgt  3900
ttaagaacat aattcttttg ttgctgtttg tttaagaagc accttagttt gtttaagaag  3960
caccttatat agtataatat atattttttt gaaattacat tgcttgttta tcagacaatt  4020
gaatgtagta attctgttct ggatttaatt tgactgggtt aacatgcaaa aaccaaggaa  4080
aaatatttag tttttttttt tttttttgta tacttttcaa gctaccttgt catgtataca  4140
gtcatttatg cctaaagcct ggtgattatt catttaaatg aagatcacat ttcatatcaa  4200
cttttgtatc cacagtagac aaaatagcac taatccagat gcctattgtt ggatactgaa  4260
tgacagacaa tcttatgtag caaagattat gcctgaaaag gaaaattatt cagggcagct  4320
aattttgctt ttaccaaaat atcagtagta atatttttgg acagtagcta atgggtcagt  4380
gggttctttt taatgtttat acttagattt tcttttaaaa aaattaaaat aaaacaaaaa  4440
aaaatttcta ggactagacg atgtaatacc agctaaagcc aaacaattat acagtggaag  4500
gttttacatt attcatccaa tgtgtttcta ttcatgttaa gatactacta catttgaagt  4560
gggcagagaa catcagatga ttgaaatgtt cgcccagggg tctccagcaa ctttggaaat  4620
ctctttgtat ttttacttga agtgccacta atggacagca gatattttct ggctgatgtt  4680
ggtattgggt gtaggaacat gatttaaaaa aaaactcttg cctctgcttt cccccactct  4740
gaggcaagtt aaaatgtaaa agatgtgatt tatctggggg gctcaggtat ggtggggaag  4800
tggattcagg aatctgggga atggcaaata tattaagaag agtattgaaa gtatttggag  4860
gaaaatggtt aattctgggt gtgcaccagg gttcagtaga gtccacttct gccctggaga  4920
ccacaaatca actagctcca tttacagcca tttctaaaat ggcagcttca gttctagaga  4980
agaaagaaca acatcagcag taaagtccat ggaatagcta gtggtctgtg tttcttttcg  5040
ccattgccta gcttgccgta atgattctat aatgccatca tgcagcaatt atgagaggct  5100
aggtcatcca aagagaagac cctatcaatg taggttgcaa aatctaaccc ctaaggaagt  5160
gcagtctttg atttgatttc cctagtaacc ttgcagatat gtttaaccaa gccatagccc  5220
atgccttttg agggctgaac aaataaggga cttactgata atttactttt gatcacatta  5280
aggtgttctc accttgaaat cttatacact gaaatggcca ttgatttagg ccactggctt  5340
agagtactcc ttcccctgca tgacactgat tacaaatact ttcctattca tactttccaa  5400
ttatgagatg gactgtgggt actgggagtg atcactaaca ccatagtaat gtctaatatt  5460
```

-continued

```
cacaggcaga tctgcttggg gaagctagtt atgtgaaagg caaatagagt catacagtag  5520
ctcaaaaggc aaccataatt ctctttggtg caggtcttgg gagcgtgatc tagattacac  5580
tgcaccattc ccaagttaat cccctgaaaa cttactctca actggagcaa atgaactttg  5640
gtcccaaata tccatctttt cagtagcgtt aattatgctc tgtttccaac tgcatttcct  5700
ttccaattga attaaagtgt ggcctcgttt ttagtcattt aaaattgttt tctaagtaat  5760
tgctgcctct attatggcac ttcaattttg cactgtcttt tgagattcaa gaaaaatttc  5820
tattcttttt tttgcatcca attgtgcctg aacttttaaa atatgtaaat gctgccatgt  5880
tccaaaccca tcgtcagtgt gtgtgtttag agctgtgcac cctagaaaca acatattgtc  5940
ccatgagcag gtgcctgaga cacagacccc tttgcattca cagagaggtc attggttata  6000
gagacttgaa ttaataagtg acattatgcc agtttctgtt ctctcacagg tgataaacaa  6060
tgctttttgt gcactacata ctcttcagtg tagagctctt gttttatggg aaaaggctca  6120
aatgccaaat tgtgtttgat ggattaatat gccctttttgc cgatgcatac tattactgat  6180
gtgactcggt tttgtcgcag ctttgctttg tttaatgaaa cacacttgta aacctctttt  6240
gcactttgaa aaagaatcca gcgggatgct cgagcacctg taaacaattt tctcaaccta  6300
tttgatgttc aaataaagaa ttaaactaaa                                    6330

SEQ ID NO: 30          moltype = DNA  length = 2634
FEATURE                Location/Qualifiers
source                 1..2634
                       mol_type = other DNA
                       organism = Homo sapiens
SEQUENCE: 30
cggctccggt cggagacaat cgcgctgagc gggcgccgca gcgggagcgg gagccggagc  60
tgcgaggcgc ggcgcagagc tggggctgcg cggggccggg cgagcgggac caggcgggag  120
ccatggaccg ctagggcccg gcctagcccc gcgatgccgc cggcgagtgg ccccagcgtc  180
ctcgcgcggc tgttgccgct gctggggctg ctgctcggca gcgcctcccg ggctcccggc  240
aagtcgccgc cggagccccc cagcccgcag gagatcctga tcaaggtgca ggtgtatgtg  300
agcggggagc tggtgcccct ggcccgggcc tcagtggatg tgtttgggaa ccggactctg  360
ctggcagctg gcaccacaga ctcagagggt gtggccaccc tgcccctcag ttatcgcttg  420
ggcacctggg tgctggtcac tgctgcccgc cctggcttcc tcaccaactc tgtgccctgg  480
cgtgttgaca agctgccctt gtatgcgtct gtcagcctct acctgctccc tgagcggccg  540
gccacgctca tcctctatga ggacctggtg cacattctcc taggctctcc cggtgcccgc  600
tcccagccct tggtgcagtt ccagcgccgg gctgcccgcc tgcctgtcag ctccacctac  660
agccagctct gggcgtcact tacgcctgcc agcacccagc aggaaatgcg ggctttccct  720
gccttcctgg gcactgaggc ctccagctca ggcaatggct cctggctgga gctgatgccc  780
ctgactgctg tgagcgtgca cctgctgaca ggtaatggga cagaggtgcc gctctcaggc  840
cccattcacc tgtccctgcc cgtgccctcc gagactcgtg ccctcaccgt gggcaccagc  900
attccagcct ggagatttga ccccaagagt gggctgtggg tgcgcaatgg cactggtgta  960
atccggaagg aaggccggca gctctactgg accttcgtct ccccccagct ggggtactgg  1020
gtggccgcca tggcctcccc cacggctggg ctggtcacca tcacgtcggg catccaggac  1080
atcggcacct accacaccat cttcttgctc accatcctgg cagccctggc cctgctggtg  1140
cttatcctgc tgtgtctgct catctactac tgccggaggc gctgcctgaa gccgaggcaa  1200
cagcaccgca agctgcagct ctcggggccc tctgacggta acaaacgaga ccaggccacc  1260
tcgatgtccc agctccacct catctgtggg ggacccctgg aacccgcccc gtcgggggac  1320
cccgaggctc cgcctccagg cccccctccac tcggccttct ccagctcccg ggacttggcc  1380
tcctcccggg atgacttctt ccgcaccaag ccgcgctctg ccagccgccc ggccgccgag  1440
ccttcgggtg cccgcggggg cgagagcgcc gggctcaagg gcgctcgctc ggccgagggc  1500
cccggcgggc tggagcccgg cctagaggag caccggcggg ggccctcggg ggctgcggcc  1560
ttcctgcacg agccgccctc gccgccgccg cccttcgacc actacctggg ccacaagggg  1620
gcggccgagg gcaagacccc cgacttcctg ctgtcgcagt cggtggacca gctggcgcgg  1680
ccgccgtcgc tgggccaggc ggggcagctc atcttctgcg gctccatcga ccacctcaag  1740
gacaacgtct accgcaacgt catgcccacc ctggtgatcc ccgcgcacta cgtgcgcctc  1800
ggcggcgagg cgggcgccgc cggcgtgggc gacgagccgg ccccgccgga gggcacggca  1860
cccggcccgg cgcgcgcttt tccccagccc gacccccagc gcccgcagat gccgggccac  1920
tcgggcccgg ggggcgaggg cggcgggggc ggcggcgagg gctggggggc cgggcgcgcg  1980
gcgcccgtca gtggctcagt caccatccct gtgctattca acgagtccac catggcgcag  2040
ctcaacgggg agctgcaggc cctgaccgag aagaagctgc tggaactggg cgtgaagccg  2100
cacccgcgcg cctggttcgt gtccctcgac gggcgctcca actcgcaagt gcgccactct  2160
tacatcgacc tgcaggcggg cggcggggca cgcagcaccg acgccagcct ggactcgggc  2220
gtagatgtcc acgaggcgcg gcccgcgcgc cgccggcccg cgagggagga gcgggagcgc  2280
gccccgcctg ccgcgccgcc gccgccgccc gcgcccccgc gcctggcgct cagcgaggac  2340
acggagccca gcagcagcga gagccgcacg ggcctctgct ctccggagga caactcgctg  2400
acgccgctgc tggacgaggt ggcggcgccc gagggccggg cggccacggt accccggggg  2460
cggggccgca gccgcgggga cagctcccgc agcagcgcca gcgagctgcg gcgcgactcg  2520
ctcaccagcc cggaggacga gctgggggcg gaggtgggcg acgaggcggg agacaagaag  2580
agcccgtggc agcggcggga ggagcggccg ctgatggtgt tcaacgtcaa gtag        2634

SEQ ID NO: 31          moltype = DNA  length = 4110
FEATURE                Location/Qualifiers
source                 1..4110
                       mol_type = other DNA
                       organism = Homo sapiens
SEQUENCE: 31
agtgcactct agaaacactg ctgtggtgga gaaactggac cccaggtctg gagcgaattc  60
cagcctgcag ggctgataag cgaggcatta gtgagattga gagagacttt accccgccgt  120
ggtggttgga gggcgcgcag tagagcagca gcacaggcgc gggtcccggg aggccggctc  180
tgctcgcgcc gagatgtgga atctccttca cgaaaccgac tcggctgtgg ccaccgcgcg  240
ccgcccgcgc tggctgtgcg ctggggcgct ggtgctggcg ggtggcttct ttctcctcgg  300
cttcctcttc gggtggttta taaaatcctc caatgaagct actaacatta ctccaaagca  360
```

```
taatatgaaa gcatttttgg atgaattgaa agctgagaac atcaagaagt tcttatataa  420
ttttacacag ataccacatt tagcaggaac agaacaaaac tttcagcttg caaagcaaat  480
tcaatcccag tggaaagaat ttggcctgga ttctgttgag ctagcacatt atgatgtcct  540
gttgtcctac ccaaataaga ctcatcccaa ctacatctca ataattaatg aagatggaaa  600
tgagatttc aacacatcat tatttgaacc acctcctcca ggatatgaaa atgtttcgga  660
tattgtacca cctttcagtg ctttctctcc tcaaggaatg ccagagggcg atctagtgta  720
tgttaactat gcacgaactg aagacttctt taaattggaa cgggacatga aaatcaattg  780
ctctgggaaa attgtaattg ccagatatgg gaaagttttc agaggaaata aggttaaaaa  840
tgcccagctg gcaggggcca aaggagtcat tctctactcc gaccctgctg actactttgc  900
tcctggggtg aagtcctatc cagatggttg gaatcttcct ggaggtggtg tccagcgtgg  960
aaatatccta aatctgaatg gtgcaggaga ccctctcaca ccaggttacc cagcaaatga  1020
atatgcttat aggcgtggaa ttgcagaggc tgttggtctt ccaagtattc ctgttcatcc  1080
aattggatac tatgatgcac agaagctcct agaaaaaatg ggtggctcag caccaccaga  1140
tagcagctgg agaggaagtc tcaaagtgcc ctacaatgtt ggacctggct ttactggaaa  1200
cttttctaca caaaaagtca agatgcacat ccactctacc aatgaagtga caagaattta  1260
caatgtgata ggtactctca gaggagcagt ggaaccagac agatatgtca ttctgggagg  1320
tcaccgggac tcatgggtgt ttggtggtat tgaccctcag agtggagcag ctgttgttca  1380
tgaaattgtg aggagctttg gaacactgaa aaaggaaggg tggagaccta gaagaacaat  1440
tttgtttgca agctgggatg cagaagaatt tggtcttctt ggttctactg agtgggcaga  1500
ggagaattca agactccttc aagagcgtgg cgtggcttat attaatgctg actcatctat  1560
agaaggaaac tacactctga gagttgattg tacaccgctg atgtacagct tggtacacaa  1620
cctaacaaaa gagctgaaaa gccctgatga aggctttgaa ggcaaatctc tttatgaaag  1680
ttggactaaa aaaagtcctt ccccagagtt cagtggcatg cccaggataa gcaaattggg  1740
atctggaaat gattttgagg tgttcttcca acgacttgga attgcttcag gcagagcacg  1800
gtatactaaa aattgggaaa caaacaaatt cagcggctat ccactgtatc acagtgtcta  1860
tgaaacatat gagttggtgg aaaagtttta tgatccaatg tttaaatatc acctcactgt  1920
ggcccaggtt cgaggaggga tggtgtttga gctagccaat tccatagtgc tcccttttga  1980
ttgtcgagat tatgctgtag ttttaagaaa gtatgctgac aaaatctaca gtatttctat  2040
gaaacatcca caggaaatga agacatacag tgtatcattt gattcacttt tttctgcagt  2100
aaagaatttt acagaaattg cttccaagtt cagtgagaga ctccaggact ttgacaaaag  2160
caacccaata gtattaagaa tgatgaatga tcaactcatg tttctggaaa gagcatttat  2220
tgatccatta gggttaccag acaggccttt ttataggcat gtcatctatg ctccaagcag  2280
ccacaacaag tatgcagggg agtcattccc aggaatttat gatgctctgt ttgatattga  2340
aagcaaagtg gacccttcca aggcctgggg agaagtgaag agacagattt atgttgcagc  2400
cttcacagtg caggcagctg cagagacttt gagtgaagta gcctaagagg attctttaga  2460
gaatccgtat tgaatttgtg tggtatgtca ctcagaaaga atcgtaatgg gtatattgat  2520
aaattttaaa attggtatat ttgaaataaa gttgaatatt atatatagtt atgtgagtgt  2580
ttatatatgt gtgtgtttat attgtttatc ttctccctat ggattaaaac tgaatttcat  2640
aattataaga ggttattctg aagtggaaaa atttaactca gtattaaatc taaggagaat  2700
ggcctaatat agtaaaactc tcatctggca ttatcaggga atcaagtcta atctattcat  2760
gtcacttcac acagaagaaa acatcagtat gtcagagagc acactgggga atatgcacaa  2820
gattatccca agccagaggc ctcacggcct acctggccag cctgggctga gaggatcact  2880
atctcagcac actatttggg aaatggatca aatcacactt ttagtaaatg ttatcactct  2940
atagcataag aaataattat tttttattta tataaaaggc tatagtataa aatatatgta  3000
tagtaattaa atgaacactt gtgaacctaa tagccatatg aagaaaataa catttctaat  3060
atctttggat gccccatgta ctaatgacag ttatgctttt gcattttctt gaattttatg  3120
tttatttatc tttcctctgt cattatttat aattttatca cacatggctg tatcctttac  3180
atgttttggc attatgtatt tttgaacttt ttgtaaagac aatcatacca tgtgtaattt  3240
tcagggactt gattttttc attgactttt aagggttcaa atatattatc actgtggctg  3300
tagtttgcca tattttgctg atatagagca ttcattcaca tgagggtagg attcagggtc  3360
catcaagaca gagaaaacat acagtaatgt gaatagggaa agttaatatg aagaattatt  3420
aattgttaca gcattggaac aatgaaatat tgtctagtaa tatgtaaaga gaagtctcaa  3480
gaatatgtga tgagcagatg taaggaattg ctcttgtctc catggtgaat ttggagcagc  3540
caatgaagag tcccctcaca ttgtggcctc gctcaaagtt aagaagtcgc tgtagtgttg  3600
cccttgaaga atctgcttca aattgacact tcagaactcc ccagaaactt gtcttctggg  3660
ccaatgtgta aagctgttta tgaagaaatg tcaagccaga ggggctctac tacaaatttg  3720
gcaaaggaca atttcaggag aagctcttgg ccgctgggtt ctcctggcca ccatgaactt  3780
caggaagtgg gtgccatagc agcagcctga actacagaat ctgggcactg gtgtagctct  3840
gtatgccctc cgtgtcagat gctggagatg tcatttgcat tgccagagtt tgccaagggt  3900
gcacacagaa agcagattga aaagcaccct cttggaacat ctctccaatg ccttctactc  3960
acaaagttta acatcattaa cacgtgacaa agaagaacta tttaatgggc ccagatctat  4020
ttatgaagac aatcaagtgg gagtttggag tggataaccc aaatttggat aactggtgaa  4080
taataaaatg tatttatttc tgctggtgta                                   4110
```

```
SEQ ID NO: 32          moltype = DNA  length = 3304
FEATURE                Location/Qualifiers
source                 1..3304
                       mol_type = other DNA
                       organism = Homo sapiens
SEQUENCE: 32
actccatctg agggtggctg cgtgtccaca tacgagggga cagggctgag gatgaggaga  60
accctgggga cccagaagac cgtgccttgc ctggaagtcc tgcctgtagg cctgaaggac  120
ttgccctaac agagcctcaa caactacctg gtgattccta cttcagcccc ttggtgtgag  180
cagcttctca acatgaacta cagcctccac ttggccttcg tgtgtctgag tctcttcact  240
gagaggatgt gcatccaggg gagtcagttc aacgtcgagg tcggcagaag tgacaagctt  300
tccctgcctg gctttgagaa cctcacagca ggatataaca aatttctcag gcccaatttt  360
ggtggagaac ccgtacagat agcgctgact ctggacattg caagtatctc tagcatttca  420
gagagtaaca tggactacac agccaccata tacctccgac agcgctggat ggaccagcgg  480
ctggtgtttg aaggcaacaa gagcttcact ctggatgccc gcctcgtgga gttcctctgg  540
```

```
gtgccagata cttacattgt ggagtccaag aagtccttcc tccatgaagt cactgtggga  600
aacaggctca tccgcctctt ctccaatggc acggtcctgt atgccctcag aatcacgaca  660
actgttgcat gtaacatgga tctgtctaaa taccccatgg acacacagac atgcaagttg  720
cagctggaaa gctggggcta tgatggaaat gatgtggagt tcacctggct gagagggaac  780
gactctgtgc gtggactgga acacctgcgg cttgctcagt acaccataga gcggtatttc  840
accttagtca ccagatcgca gcaggagaca ggaaattaca ctagattggt cttacagttt  900
gagcttcgga ggaatgttct gtatttcatt ttggaaacct acgttccttc cactttcctg  960
gtggtgttgt cctgggtttc attttggatc tctctcgatt cagtccctgc aagaacctgc  1020
attggagtga cgaccgtgtt atcaatgacc acactgatga tcgggtcccg cacttctctt  1080
cccaacacca actgcttcat caaggccatc gatgtgtacc tggggatctg ctttagcttt  1140
gtgtttgggg ccttgctaga atatgcagtt gctcactaca gttccttaca gcagatggca  1200
gccaaagata gggggacaac aaaggaagta gaagaagtca gtattactaa tatcatcaac  1260
agctccatct ccagctttaa acggaagatc agctttgcca gcattgaaat ttccagcgac  1320
aacgttgact acagtgactt gacaatgaaa accagcgaca agttcaagtt tgtcttccga  1380
gaaaagatgg gcaggattgt tgattatttc acaattcaaa accccagtaa tgttgatcac  1440
tattccaaac tactgtttcc tttgattttt atgctagcca atgtatttta ctgggcatac  1500
tacatgtatt tttgagtcaa tgttaaattt cttgcatgcc ataggtcttc aacaggacaa  1560
gataatgatg taaatggtat tttaggccaa gtgtgcaccc acatccaatg gtgctacaag  1620
tgactgaaat aatatttgag tctttctgct caaagaatga agctccaacc attgttctaa  1680
gctgtgtaga agtcctagca ttataggatc ttgtaataga aacatcagtc cattcctctt  1740
tcatcttaat caaggacatt cccatggagc ccaagattac aaatgtactc agggctgttt  1800
attcggtggc tccctggttt gcatttacct catataaaga atgggaagga gaccattggg  1860
taaccctcaa gtgtcagaag ttgtttctaa agtaactata catgtttttt actaaatctc  1920
tgcagtgctt ataaaataca ttgttgccta tttagggagt aacattttct agtttttgtt  1980
tctggttaaa atgaaatatg ggcttatgtc aattcattgg aagtcaatgc actaactcaa  2040
taccaagatg agtttttaaa taatgaatat tatttaatac cacaacagaa ttatccccaa  2100
tttccaataa gtcctatcat tgaaaattca aatataagtg aagaaaaaat tagtagatca  2160
acaatctaaa caaatccctc ggttctaaga tacaatggat tccccatact ggaaggactc  2220
tgaggcttta ttcccccact atgcatatct tatcatttta ttattataca cacatccatc  2280
ctaaactata ctaaagccct tttcccatgc atggatggaa atggaagatt ttttttaac  2340
ttgttctaga agtcttaata tgggctgttg ccatgaaggc ttgcagaatt gagtccattt  2400
tctagctgcc tttattcaca tagtgatggg gtactaaaag tactgggttg actcagagag  2460
tcgctgtcat tctgtcattg ctgctactct aacactgagc aacactctcc cagtggcaga  2520
tcccctgtat cattccaaga ggagcattca tccctttgct ctaatgatca ggaatgatgc  2580
ttattagaaa acaaactgct tgacccagga acaagtggct tagcttaagt aaacttggct  2640
ttgctcagat ccctgatcct tccagctggt ctgctatgag tggcttatcc cgcatgagca  2700
ggagcgtgct ggccctgagt actgaacttt ctgagtaaca atgagatacg ttacagaacc  2760
tatgttcagg ttgcgggtga gctgccctct ccaaatccag ccagagatgc acattcctcg  2820
gccagtctca gccaacagta ccaaaagtga tttttgagtg tgccagggta aaggcttcca  2880
gttcagcctc agttatttta gacaatctcg ccatctttaa tttcttagct tcctgttcta  2940
ataaatgcac ggctttacct ttcctgtcag aaataaacca aggctctaaa agatgatttc  3000
ccttctgtaa ctccctagag ccacaggttc tcattccttt tcccattata cttctcacaa  3060
ttcagtttct atgagtttga tcacctgatt tttttaacaa aatatttcta acgggaatgg  3120
gtgggagtgc tggtgaaaag aggtgaaatg tggttgtatg agccaatcat atttgtgatt  3180
ttttaaaaaa agtttaaaag gaaatatctg ttctgaaacc ccacttaagc attgttttta  3240
tataaaaaca atgataaaga tgtgaaactg tgaaataaat ataccatatt agctacccac  3300
caaa                                                                3304

SEQ ID NO: 33           moltype = DNA  length = 3083
FEATURE                 Location/Qualifiers
source                  1..3083
                        mol_type = other DNA
                        organism = Homo sapiens
SEQUENCE: 33
gaacactgag ctgcctggcg ccgtcttgat actttcagaa agaatgcatt ccctgtaaaa  60
aaaaaaaaaa aatactgaga gagggagaga gagagagaag aagagagaga gacggaggga  120
gagcgagaca gagcgagcaa cgcaatctga ccgagcaggt cgtacgccgc cgcctcctcc  180
tcctctctgc tcttcgctac ccaggtgacc cgaggaggga ctccgcctcc gagcggctga  240
ggaccccggt gcagaggagc ctggctcgca gaattgcaga gtcgtcgccc ctttttacaa  300
cctggtcccg ttttattctg ccgtacccag tttttggatt tttgtcttcc ccttcttctc  360
tttgctaaac gaccctcca agataatttt taaaaaacct tctcctttgc tcacctttgc  420
ttcccagcct tcccatcccc ccaccgaaag caaatcattc aacgaccccc gaccctccga  480
cggcaggagc cccccgacct cccaggcgga ccgccctccc tccccgcgcg cgggttccgg  540
gcccggcgag agggcgcgag cacagccgag gccatggagg tgacggcgga ccagccgcgc  600
tgggtgagcc accaccaccc cgccgtgctc aacgggcagc acccggacac gcaccacccg  660
ggcctcagcc actcctacat ggacgcggcg cagtacccgc tgccggagga ggtggatgtg  720
ctttttaaca tcgacggtca aggcaaccac gtcccgccct actacggaaa ctcggtcagg  780
gccacggtgc agaggtaccc tccgacccac cacgggagcc aggtgtgccg cccgcctctg  840
cttcatggat ccctaccctg gctggacggc ggcaaagccc tgggcagcca ccacaccgcc  900
tcccccctgga atctcagccc cttctccaag acgtccatcc accacggctc cccggggccc  960
ctctccgtct accccccggc ctcgtcctcc tccttgtcgg ggggccacgc cagcccgcac  1020
ctcttcacct tcccgcccac cccgccgaag gacgtctccc cggacccatc gctgtccacc  1080
ccaggctcgg ccggctcggc ccggcaggac gagaaagagt gcctcaagta ccaggtgccc  1140
ctgcccgaca gcatgaagct ggagtcgtcc cactcccgtg gcagcatgac cgccctgggt  1200
ggagcctcct cgtcgaccca ccaccccatc accacctacc cgccctacgt gcccgagtac  1260
agctccggac tcttcccccc cagcagcctg ctgggcggct cccccaccgg cttcggatgc  1320
aagtccaggc ccaaggcccg gtccagcaca gaaggcaggg agtgtgtgaa ctgtggggca  1380
acctcgaccc cactgtggcg gcgagatggc acgggacact acctgtgcaa cgcctgcggg  1440
ctctatcaca aaatgaacgg acagaaccgg cccctcatta agcccaagcg aaggctgtct  1500
```

```
gcagccagga gagcagggac gtcctgtgcg aactgtcaga ccaccacaac cacactctgg  1560
aggaggaatg ccaatgggga ccctgtctgc aatgcctgtg ggctctacta caagcttcac  1620
aatattaaca gacccctgac tatgaagaag gaaggcatcc agaccagaaa ccgaaaaatg  1680
tctagcaaat ccaaaaagtg caaaaaagtg catgactcac tggaggactt ccccaagaac  1740
agctcgttta acccggccgc cctctccaga cacatgtcct ccctgagcca catctcgccc  1800
ttcagccact ccagccacat gctgaccacg cccacgccga tgcacccgcc atccagcctg  1860
tcctttggac cacaccaccc ctccagcatg gtcaccgcca tgggttagag ccctgctcga  1920
tgctcacagg gcccccagcg agagtccctg cagtcccttt cgacttgcat tttgcagga   1980
gcagtatcat gaagcctaaa cgcgatggat atatgttttt gaaggcagaa agcaaaatta  2040
tgtttgccac tttgcaaagg agctcactgt ggtgtctgtg ttccaaccac tgaatctgga  2100
ccccatctgt gaataagcca ttctgactca tatcccctat ttaacagggt ctctagtgct  2160
gtgaaaaaaa aaatgctgaa cattgcatat aacttatatt gtaagaaata ctgtacaatg  2220
actttattgc atctgggtag ctgtaaggca tgaaggatgc caagaagttt aaggaatatg  2280
ggagaaatag tgtggaaatt aagaagaaac taggtctgat attcaaatgg acaaactgcc  2340
agttttgttt cctttcactg gccacagttg tttgatgcat taaaagaaaa taaaaaaaag  2400
aaaaaagaga aaagaaaaaa aaagaaaaaa gttgtaggcg aatcatttgt tcaaagctgt  2460
tggcctctgc aaaggaaata ccagttctgg gcaatcagtg ttaccgttca ccagttgccg  2520
ttgagggttt cagagagcct ttttctaggc ctacatgctt tgtgaacaag tccctgtaat  2580
tgttgtttgt atgtataatt caaagcacca aaataagaaa agatgtagat ttatttcatc  2640
atattataca gaccgaactg ttgtataaat ttatttactg ctagtcttaa gaactgcttt  2700
ctttcgtttg tttgtttcaa tattttcctt ctctctcaat ttttggttga ataaactaga  2760
ttacattcag ttggcctaag gtggttgtgc tcggagggtt tcttgtttct tttccatttt  2820
gtttttggat gatatttatt aaatagcttc taagagtccg gcggcatctg tcttgtccct  2880
attcctgcag cctgtgctga gggtagcagt gtatgagcta ccagcgtgca tgtcagcgac  2940
cctggcccga caggccacgt cctgcaatcg gcccggctgc ctcttcgccc tgtcgtgttc  3000
tgtgttagtg atcactgcct ttaatacagt ctgttggaat aatattataa gcataataat  3060
aaagtgaaaa tattttaaaa cta                                          3083

SEQ ID NO: 34          moltype = DNA  length = 4934
FEATURE                Location/Qualifiers
source                 1..4934
                       mol_type = other DNA
                       organism = Homo sapiens
SEQUENCE: 34
gagtcagagc ctcttctctc taagtcacgg gaactgccct tgctacttgt gacctgccct  60
ttactcagca gtttttgttc tgggaagccc tgggattctg ctaataccta tcactgtagg  120
tgctgaaggg aaacagatga agaacatgac ctcaaggagc ttcctgtcaa tgagaagacc  180
aagctgacgc ctggcaaaga tattaaagag gagcctgaaa ctgttccttg gacatcttat  240
gaatgtcaga aaataccttt tggagggtta gaagatcagg ggacatggtt gttcacattt  300
gctgccacgg aacaccgcca gtcttcactt ggaaacagaa tcacgccttg tgaagagatc  360
atccctaagc aggagagaag ctactaaagg attgtgtcct cctccacctt ccctgtgctc  420
ggtctccacc tgtctcccat tctgtgacga tggttcaatg gaagagactc tgccagctgc  480
attacttgtg ggctctgggc tgctatatgc tgctggccac tgtggctctg aaactttctt  540
tcaggttgaa gtgtgactct gaccacttgg gtctggagtc cagggaatct caaagccagt  600
actgtaggaa tatcttgtat aatttcctga aacttccagc aaagaggtct atcaactgtt  660
caggggtcac ccgaggggac caagaggcag tgcttcaggc tattctgaat aacctggagg  720
tcaagaagaa gcgagagcct ttcacagaca cccactacct ctccctcacc agagactgtg  780
agcacttcaa ggctgaaagg aagttcatac agttcccact gagcaaagaa gaggtggagt  840
tccctattgc atactctatg gtgattcatg agaagattga aaactttgaa aggctactgc  900
gagctgtgta tgcccctcag aacatatact gtgtccatgt ggatgagaag tccccagaaa  960
ctttcaaaga ggcggtcaaa gcaattattt cttgcttccc aaatgtcttc atagccagta  1020
agctggttcg ggtggtttat gcctcctggt ccagggtgca agctgacctc aactgcatgg  1080
aagacttgct ccagagctca gtgccgtgga aatacttcct gaatacatgt gggacggact  1140
ttcctataaa gagcaatgca gagatggtcc aggctctcaa gatgttgaat gggaggaata  1200
gcatggagtc agaggtacct cctaagcaca aagaaacccg ctggaaatat cactttgagg  1260
tagtgagaga cacattacac ctaaccaaca agaagaagga tcctccccct tataatttaa  1320
ctatgtttac agggaatgcg tacattgtgg cttcccgaga tttcgtccaa catgttttga  1380
agaaccctaa atcccaacaa ctgattgaat gggtaaaaga cacttatagc ccagatgaac  1440
acctctgggc caccccttcag cgtgcacggt ggatgcctgg ctctgttccc aaccacccca  1500
agtacgacat ctcagacatg acttctattg ccaggctggt caagtggcag ggtcatgagg  1560
gagacatcga taagggtgct ccttatgctc cctgctctgg aatccaccag cgggctatct  1620
gcgtttatgg ggctggggac ttgaattgga tgcttcaaaa ccatcacctg ttggccaaca  1680
agtttgaccc aaaggtagat gataatgctc ttcagtgctt agaagaatac ctacgttata  1740
aggccatcta tgggactgaa ctttgagaca cactatgaga gcgttgctac ctgtggggca  1800
agagcatgta caaacatgct cagaacttgc tgggacagtg tgggtgggag accagggctt  1860
tgcaattcgt ggcatccttt aggataagag ggctgctatt agagtgtggg taagtagatc  1920
ttttgccttg caaattgctg cctgggtgaa tgctgcttgt tctctcaccc ctaaccctag  1980
tagttcctcc actaactttc tcactaagtg agaatgagaa ctgctgtgat agggagagtg  2040
aaggagggat atgtggtaga gcacttgatt tcagttgaat gcctgctggt agcttttcca  2100
ttctgtggag ctgccgttcc taataattcc aggtttggta gcgtggagga gaactttgat  2160
ggaaagagaa ccttcccttc tgtactgtta acttaaaaat aaatagctcc tgattcaaag  2220
tattacctct actttttgcc tagtatgcca gaaataatat aaatataaac agataaagtg  2280
tgtgagactt tttctcataa ctattcatga catttaaaat ccctaggggc tggcaagaga  2340
gttctcatta ttctgaaatg gtcctgacaa gctgcatgaa tagcaatttt ttttttgaga  2400
cagagtcttg ctctgtcacc caggctggac tgcagtagtg caatctcagt tcactgcaac  2460
ctccgcctcc caggttcaag cgatactccc acctcagcct cctgagtagc tgggactaca  2520
ggcatgcagc accatgtctg gctaattttt gtatttttag tagaggccgg gtttcaccat  2580
attcgccagg ctggtcttga actcctgacc ttgtgatctg cccgcctcgg ccttccgaaa  2640
tgctgggatt acaggtggga actactgcgc ctggcctaca aatagcaaat tctaacgaag  2700
```

-continued

```
acaggggaac agggatggtt cttccattgt taaaagccat cctcattttg tttatattgc  2760
caggtttgtg atttttctgt aaaggaaaag gcagggtgat ttaaccagtt tgaccacctt  2820
tcctgtactc ttacaggaaa atcgcagcac taattctaat tttgtccact ttacagccaa  2880
agcttagcta atgttccata aaggagataa tagccaatca ggtaaggtaa tgtgtaattc  2940
attattcaaa gtggaacatg tttttgtagg gggagagtct gcactattaa taattgtatt  3000
gagaaataaa aataaactag gactattcag ttaaaccagg atgtcttatt attccatgtt  3060
taggcctctt gagtcaaaac tcttttttt tttttttttt ttttttttt tggagacagg  3120
ttctcactct gttgcccagg ctggagtgca gtggcatgat cttggctcac tgaagcctct  3180
gcctcccagg ttcaagtgat tctcccccca aaccttgcaa gtagctggga ttacagatgt  3240
gagccaccat gcccagctga tttttgtgta tttttagtaa agatggggtt tcaccatgtt  3300
ggccaggttg gtctcaaact cctggcctca agtgatccac ctgccccagc ctcccaaagt  3360
gctgggatta caggtgtgag ccaccatgcc tggtcccctc ttgagtcaaa actcttattt  3420
cagaatgcga atggaaggat cgctattagt gattctgcag attacacatt tccttgcggg  3480
gagacaataa ggtatgtgta aatacatata tgtgtgtgta tgtatacaca catacagcac  3540
gctacctccc aagtgttacc tagtgaaaca gtttcctttc cgaagctcca gagatggttg  3600
ttggctaagt tatactcttc tgtgatgggc aagggatact ataaaaacat aggcagtgcc  3660
ctttgaatat agtacagctc atcttctgca tacgatatgc cctggaaagg tgatttatat  3720
gcaagttaat tggtgtaatc tgaaggatgc tcccattaat acgtcatgat gtcattaata  3780
tgtttcttcc tttctgattt ttgttttttt tttttttttt gagacagagt ctcactctgt  3840
cacccaggtt ggagtgcaac gaatggcgca atcttggctc attacaacct ccgcctcctg  3900
ggtccaagcg attctcctgc ctcagcctcc tgagtaactg ggattacagg tgtgtgccac  3960
cttgcctggc taattttttt gtattttttt agtagaaaca gggtttcacc atgttggtca  4020
ggctggtctg aactcctgac ctcaagtgat ccacttgcct tggcttccca aagtgctggg  4080
attacaggcg tgagctaccg cacccagccc tttctgagtg ttgtcattca attcatcaag  4140
ttttctgtca tgatcaactt tctctatgca aaccctgtaa ctctgacagt tatcactgtg  4200
tctgacacag tgaatttttt atttataagg tagttacttt tggccaggtg tggtggctga  4260
cgcctgtaat cccagcactt tgggaggcca aggtaggcag atcacttgag gtcaggagtt  4320
caagatcagc ctggccaaca tggtgaatcc ccatctctac taaaaatata aaaattagcc  4380
agacatggtg gtgggtacct gtaatcccag ctacttggga ggctgaggca ggagaatcgc  4440
ttgaacatgg gaggcagagg ttgcagtgag ctgagatcgt accactgcac tccagcctgg  4500
gcgatagagc cagactgagt ctcaaaaaaa aaaaaaaagt taccttttt tggtaaggtt  4560
gtacttctta gataatggtc attgtcacta ccaacttgcc tgcattgtaa tagagtccta  4620
ttcactttgc tcccaacccc actacggaga tgactgatga ctagttgtat acacagtggg  4680
tgtgccctga gaggtctgtt gccagcagtg gtgatcgatc acggcctccc cctgctggct  4740
gatgtgatgg tccttggtcc tcctctgaag gaggtagaag gggcacacgg ccaccgtggg  4800
aagtaggcag aaaagcctcc ctgggtgcag attctctgag aaaagaactt tggcctcata  4860
gttaacttac tccaaaagct ttcatgtgaa ataatttata atttttata taaataaaaa  4920
gattaaaatg tgaa                                                    4934
```

```
SEQ ID NO: 35           moltype = DNA  length = 2546
FEATURE                 Location/Qualifiers
source                  1..2546
                        mol_type = other DNA
                        organism = Homo sapiens
SEQUENCE: 35
gctcccattg tctcggcaga tgccgcctgg tccagctatc gtgctcggta ttcagttttc  60
cggagcagcg ctctttctct ggcccgcgga gcggtcccgc ggccgagtac cggattcccg  120
agtttgggag gctctgcttt cctccttagg acccactttg ccgtcctggg gtggctgcag  180
ttatgtccgc gctgcgacct ctcctgcttc tgctgctgcc tctgtgtccc ggtcctggtc  240
ccggacccgg gagcgaggca aaggtcaccc ggagttgtgc agagacccgg caggtgctgg  300
gggcccgggg atatagctta aacctaatcc ctcccgccct gatctcaggt gagcacctcc  360
gggtctgtcc ccaggagtac acctgctgtt ccagtgagac agagcagagg ctgatcaggg  420
agactgaggc caccttccga ggcctggtgg aggacagcgg ctcctttctg gttcacacac  480
tggctgccag gcacagaaaa tttgatgagt tttttctgga gatgctctca gtagcccagc  540
actctctgac ccagctcttc tcccactcct acggccgcct gtatgcccag cacgccctca  600
tattcaatgg cctgttctct cggctgcgag acttctatgg ggaatctggt gaggggttgg  660
atgacaccct ggcggatttc tgggcacagc tcctggagag agtgttcccg ctgctgcacc  720
cacagtacag cttccccccct gactacctgc tctgcctctc acgcttggcc tcatctaccg  780
atggctctct gcagcccttt ggggactcac cccgccgcct ccgcctgcag ataacccgga  840
ccctggtggc tgcccgagcc tttgtgcagg gcctggagac tggaagagaat gtggtcagcg  900
aagcgcttaa ggtgccggtg tctgaaggct gcagccaggc tctgatgcgt ctcatcggct  960
gtcccctgtg ccgggggggtc ccctcactta tgccctgcca gggcttctgc ctcaacgtgg  1020
ttcgtggctg tctcagcagc aggggactgg agcctgactg gggcaactat ctggatggtc  1080
tcctgatcct ggctgataag ctccagggcc ccttttcctt tgagctgacg gccgagtcca  1140
ttggggtgaa gatctcggag ggtttgatgt acctgcagga aaacagtgcg aaggtgtccg  1200
cccaggtgtt tcaggagtgc ggccccccccg acccggtgcc tgcccgcaac cgtcgagccc  1260
cgccgccccg ggaagaggcg ggccggctgt ggtcgatggt gaccgaggag gagcggccca  1320
cgacggccgc aggcaccaac ctgcaccggc tggtgtggga gctccgcgag cgtctggccc  1380
ggatgcgggg cttctgggcc cggctgtccc tgacggtgtg cggagactct cgcatggcag  1440
cggacgcctc gctggaggcg gcgccctgct ggaccggagc cgggcggggc cggtacttgc  1500
cgccagtggt cgggggctcc ccggccgagc aggtcaacaa ccccgagctc aaggtggacg  1560
cctcgggccc cgatgtcccg acacggcggc gtcggctaca gctccgggcg gccacggcca  1620
gaatgaaaac ggccgcactg ggacacgacc tggacgggca ggacgcggat gaggatgcca  1680
gcggctctgg agggggacag cagtatgcag atgactggat ggctggggct gtggctcccc  1740
cagcccggcc tcctcggcct ccatacccctc ctagaaggga tggttctggg ggcaaaggag  1800
gaggtggcag tgcccgctac aaccagggcc ggagcaggag tgggggggca tctattggtt  1860
ttcacaccca aaccatcctc attctctccc tctcagccct ggccctgctt ggacctcgat  1920
aacgggggag gggtgcccta gcatcagaag ggttcatggc cctttcccct cctccccct  1980
cagctgggcc tggggaggag tcgaaggggg ctgcagagag ggtagagaag ggactttgca  2040
```

-continued

```
ggtgaatggc tggggcccca aatccaggag attttcatca gaggtgggtg ggtgttcaca  2100
atatttattt tttcatttgg taatgggagg ggggcctggg ggtatttatt taggagggag  2160
tgtggtttcc ttagaaggta tagtctctag ccctctaagg ctggggctgg tgatcagccc  2220
caacagagaa aatgaggagt ttagagttgc agctggggaa ggggtttgaa ggaagttgga  2280
agtggggagg ggtgggggca tctggtctca gaaatggacc agctggatgc agggcagggg  2340
actgagggtg cttgagtagg atgtgagact tcatgggcct gggttctgtt gagtttttc  2400
agtatcaatt tcttaaacca aattttaaaa aaaacaaggt ggggggtgc tcatctcgtg  2460
acctctgcca cccacatcct tcacaaactc catgtttcag tgtttgagtc catgtttatt  2520
ctgcaaataa atggtaatgt attgga                                         2546

SEQ ID NO: 36          moltype = DNA  length = 2293
FEATURE                Location/Qualifiers
source                 1..2293
                       mol_type = other DNA
                       organism = Homo sapiens
SEQUENCE: 36
acaccacctg cctgggttcc ttcctttagt cacttccagc tccaggcaca gcagttggtg  60
actccttggt gggagccgtg tcccacccgg tcctgatact gccgtcttct ctttcacagt  120
cctccaggct tgggccagcc ttgggggcag cagagcttct gggctgacat gggctcattg  180
ctccttctcc aagccctctg aggacatcaa aagcgtggac gcatcacttt ccaccatctt  240
gctgcccact gtccctccat cctgaggcct cctaagcaca tgtgtggggt ggcaggcaca  300
ctgctgatag ctgtggatgc ggccgtgaca tccttcaccc ctgcccccat ggcatgcatg  360
atccattagg gaggaccgtc tgcacaaagg tctcttgccc tgtgcagctt cctgcagact  420
ggacttgcaa agtccagcct gtatggctgg agttcccatg cctgccaatc tcctgtcgac  480
tgcgagtcag ctccgatact tcaccagatt cagccacctg gggagctgg aagtgaatct  540
cctcgtagct gagccttctg atgagactgc agccccggct gacacctgga ttgcagactc  600
atgaaagacc tgaaactcta ccaacagcca cctgggggag ctggaagtga atctcctcgt  660
agctgagcct tctgatgaga ctgcagcccc ggctgacacc tggattgcag actcatgaaa  720
gaccctgagc agaggaccca gtttggcaga gcccgaattc ctgacccaca ggaactggga  780
gataaaactc tgtggtttta atcttctcat tttagagtgc tcagtgtcct gtggtgtgaa  840
cacgcttcat tcaacctggg cccttgggag agatgctgag tggttcccgg gctgtcccca  900
ctccacaccg tggcagtgaa gagctgctga agtacatgct tcatagtcct tgcgtctctc  960
tgaccatgaa tggcacctac aacacctgtg gctccagcga cctcacctgg cccccagcga  1020
tcaagctggg cttctacgcc tacttgggcg tcctgctggt gctaggcctg ctgctcaaca  1080
gcctggcgct ctgggtgttc tgctgccgca tgcagcagtg gacggagacc cgcatctaca  1140
tgaccaacct ggcggtggcc gacctctgcc tgctgtgcac cttgcccttc gtgctgcact  1200
ccctgcgaga cacctcagac acgccgctgt gccagctctc ccagggcatc tacctgacca  1260
acaggtacat gagcatcagc ctggtcacgg ccatcgccgt ggaccgctat gtggccgtgc  1320
ggcacccgct gcgtgcccgc gggctgcggt cccccaggca ggctgcggcc gtgtgcgcgg  1380
tcctctgggt gctggtcatc ggctccctgg tggctcgctg gctcctgggg attcaggagg  1440
gcggcttctg cttcaggagc acccggcaca atttcaactc catggcgttc ccgctgctgg  1500
gattctacct gcccctggcc gtggtggtct tctgctccct gaaggtggtg actgccctgg  1560
cccagaggcc acccaccgac gtggggcagg cagaggccac ccgcaaggct gcccgcatgg  1620
tctgggccaa cctcctggtg ttcgtggtct gcttcctgcc cctgcacgtg gggctgacag  1680
tgcgcctcgc agtgggctgg aacgcctgtg ccctcctgga gacgatccgt cgcgccctgt  1740
acataaccag caagctctca gatgccaact gctgcctgga cgccatctgc tactactaca  1800
tggccaagga gttccaggag gcgtctgcac tggccgtggc tcccagtgct aaggcccaca  1860
aaagccagga ctctctgtgc gtgaccctcg cctaagaggc gtgctgtggg cgctgtgggc  1920
caggtctcgg gggctccggg aggtgctgcc tgccagggga agctggaacc agtagcaagg  1980
agcccgagat cagccctgaa ctcactgtgt attctcttgg agccttgggt gggcagggac  2040
ggcccaggta cctgctctct tgggaagaga gagggacagg gacaagggca agaggactga  2100
ggccagagca aggccaatgt cagagacccc cgggatgggg cctcacactt gccaccccca  2160
gaaccagctc acctggccag agtgggttcc tgctggccag ggtgcagcct tgatgacacc  2220
tgccgctgcc cctcggggct ggaataaaac tccccaccca gagtcagtcc taaaaaaaaa  2280
aaaaaaaaaa aaa                                                       2293

SEQ ID NO: 37          moltype = DNA  length = 2856
FEATURE                Location/Qualifiers
source                 1..2856
                       mol_type = other DNA
                       organism = Homo sapiens
SEQUENCE: 37
gcttcccata cggcagtggc tgggggagag tgatggagag aaaggctaag ctaaggtcaa  60
agaaaagtgga ggaaggctgg cttgtcccgc tggacttgac ggcggagctg ctgcaatctc  120
gcgggctggg cccttgcccc gggtggaccc gagtgcctgc ggggaggcgg gtgtggctcc  180
cccgggaggt gacagctggc ggggcccgta aggagctggt ctgctccggc tcccctctcg  240
tagccggcgc cctgggacca gcgcgtgagc acgtctcgga ggagtccgat gcgctgggca  300
gggccgggtg gtcacccccg cccagcttcc aggggtgact gtgcctctga cgtcagacgg  360
tttttgggtc attccctggc acggggactt tattttcata acagcatgaa gtgccgtgga  420
actggaatag gcgtgtcctc tccctcgacc ctccccctcc ttgtccctct gctcacccct  480
cgctcgttcc ctccctccgg cgagggccgc ctttataaca actgctcaga gtgcgagggc  540
gggatagctg tccaaggtct cccccagcac tgaggagctc gcctgctgcc ctcttgcgcg  600
cgggaagcag caccaagttc acggccaacg ccttggcact agggtccaga atggctacaa  660
cagtccctga tggttgccgc aatggcctga aatccaagta ctacagactt tgtgataagg  720
ctgaagcttg gggcatcgtc ctagaaacgg tggccacagc cggggttgtg acctcggtgg  780
ccttcatgct cactctcccg atcctcgtct gcaaggtgca ggactccaac aggcgaaaaa  840
tgctgcctac tcagtttctc ttcctcctgg gtgtgttggg catctttggc ctcaccttcg  900
ccttcatcat cggactggac gggagcacag ggcccacacg cttcttcctc tttgggatcc  960
tcttttccat ctgcttctcc tgcctgctgg ctcatgctgt cagtctgacc aagctcgtcc  1020
```

-continued

```
gggggaggaa gccccttcc ctgttggtga ttctgggtct ggccgtgggc ttcagcctag  1080
tccaggatgt tatcgctatt gaatatattg tcctgaccat gaataggacc aacgtcaatg  1140
tcttttctga gctttccgct cctcgtcgca atgaagactt tgtcctcctg ctcacctacg  1200
tcctcttctt gatggcgctg accttcctca tgtcctcctt caccttctgt ggttccttca  1260
cgggctggaa gagacatggg gcccacatct acctcacgat gctcctctcc attgccatct  1320
gggtggcctg gatcaccctg ctcatgcttc ctgactttga ccgcaggtgg gatgacacca  1380
tcctcagctc cgccttggct gccaatggct gggtgttcct gttggcttat gttagtcccg  1440
agttttggct gctcacaaag caacgaaacc ccatggatta tcctgttgag gatgctttct  1500
gtaaacctca actcgtgaag aagagctatg gtgtggagaa cagagcctac tctcaagagg  1560
aaatcactca aggttttgaa gagacagggg acacgctcta tgccccctat tccacacatt  1620
ttcagctgca gaaccagcct ccccaaaagg aattctccat cccacgggcc cacgcttggc  1680
cgagccctta caaagactat gaagtaaaga aagagggcag ctaactctgt cctgaagagt  1740
gggacaaatg cagccgggcg gcagatctag cgggagctca aagggatgtg ggcgaaatct  1800
tgagtcttct gagaaaactg tacaagacac tacgggaaca gtttgcctcc ctcccagcct  1860
caaccacaat tcttccatgc tggggctgat gtgggctagt aagactccag ttcttagagg  1920
cgctgtagta tttttttttt tttgtctcat cctttggata cttcttttaa gtgggagtct  1980
caggcaactc aagtttagac ccttactctt tttgtttgtt ttttgaaaca ggatcttgct  2040
ctgtcaccca ggcttgagtg cagtggtgcg atcacagccc agtgcagcct cgaccacctg  2100
tgctcaagca atcctcccat ctccatctcc caaagtgctg ggatgacagg cgtgagccac  2160
agctcccagc ctaggccctt aatcttgctg ttattttcca tggactaaag gtctggtcat  2220
ctgagctcac gctggctcac acagctctag gggcctgctc ctctaactca cagtgggttt  2280
tgtgaggctc tgtggcccag agcagacctg catatctgag caaaaatagc aaaagcctct  2340
ctcagcccac tggcctgaat ctacactgga agccaacttg ctggcacccc cgctccccaa  2400
cccttcttgc ctgggtagga gaggctaaag atcaccctaa atttactcat ctctctagtg  2460
ctgcctcaca ttgggcctca gcagctcccc agcaccaatt cacaggtcac ccctctcttc  2520
ttgcactgtc cccaaacttg ctgtcaattc cgagatctaa tctcccccta cgctctgcca  2580
ggaattcttt cagacctcac tagcacaagc ccggttgctc cttgtcagga gaatttgtag  2640
atcattctca cttcaaattc ctggggctga tacttctctc atcttgcacc ccaacctctg  2700
taaatagatt taccgcattt acggctgcat tctgtaagtg ggcatggtct cctaatggag  2760
gagtgttcat tgtataataa gttattcacc tgagtatgca ataaagatgt ggtggccact  2820
ctttcatggt ggtggcagca gttaccagta aaaaaa                           2856

SEQ ID NO: 38          moltype = DNA  length = 5231
FEATURE                Location/Qualifiers
source                 1..5231
                       mol_type = other DNA
                       organism = Homo sapiens
SEQUENCE: 38
agaaagttac ctgtggccgc ccaagtccgc cactttctgc tctgtgtctg cccattgcca  60
cgatccagga ggactccgcg ccgcccggcc gcctccgagc tcgggcccca tgtgaggggc  120
cccccttat cccacctttc cggctaggtg agggcgcgag cgggcgagcg agcgagagtg  180
gtgagggggg acggaaaagc agaattacct gtagctcttg ttctgccatc tcgggcgctc  240
tcacacacct tcacctgcac agacttgaaa gtccagtttc accagaggct gaggctccag  300
gaaaagcgga gcaagttcat tggatcaaac atgtcacaag agtcggacaa taataaaaga  360
ctagtggcct tagtgcccat gcccagtgac cctccattca atacccgaag agcctacacc  420
agtgaggatg aagcctggaa gtcatacttg gagaatcccc tgacagcagc caccaaggcc  480
atgatgagca ttaatggtga tgaggacagt gctgctgccc tcggcctgct ctatgactac  540
tacaaggttc ctcgagacaa gaggctgctg tctgtaagca aagcaagtga cagccaagaa  600
gaccaggaga aaagaaactg ccttggcacc agtgaagccc agagtaattt gagtggagga  660
gaaaaccgag tgcaagtcct aaagactgtt ccagtgaacc tttccctaaa tcaagatcac  720
ctggagaatt ccaagcggga acagtacagc atcagcttcc ccgagagctc tgccatcatc  780
ccggtgtcgg gaatcacggt ggtgaaagct gaagatttca caccagtttt catggcccca  840
cctgtgcact atccccgggg agatggggaa gagcaacgag tggttatctt tgaacagact  900
cagtatgacg tgccctcgct ggccacccac agcgcctatc tcaaagacga ccagcgcagc  960
actccggaca gcacatacag cgagagcttc aaggacgcag ccacagagaa atttcggagt  1020
gcttcagttg gggctgagga gtacatgtat gatcagacat caagtggcac atttcagtac  1080
accctggaag ccaccaaatc tctccgtcag aagcaggggg agggccccat gacctacctc  1140
aacaaaggac agttctatgc cataacactc agcgagaccg gagacaacaa atgcttccga  1200
caccccatca gcaaagtcag gagtgtggtg atggtggtct tcagtgaaga caaaaacaga  1260
gatgaacagc tcaaatactg gaaatactgg cactctcggc agcatacggc gaagcagagg  1320
gtccttgaca ttgccgatta caaggagagc tttaatacga ttggaaacat tgaagagatt  1380
gcatataatg ctgtttcctt tacctgggac gtgaatgaag aggcgaagat tttcatcacc  1440
gtgaattgct tgagcacaga tttctcctcc caaaaagggg tgaaaggact tcctttgatg  1500
attcagattg acacatacag ttataacaat cgtagcaata aacccattca tagagcttat  1560
tgccagatca aggtcttctg tgacaaagga gcagaaagaa aaatccgaga tgaagagcgg  1620
aagcagaaca ggaagaaagg gaaaggccag gcctcccaaa ctcaatgcaa cagctcctct  1680
gatgggaagt tggctgccat acctttacag aagaagagtg acatcaccta cttcaaaacc  1740
atgcctgatc tccactcaca gccagttctc ttcatacctg atgttcactt tgcaaacctg  1800
cagaggaccg gacaggtgta ttacaacacg gatgatgaac gagaaggtgg cagtgtcctt  1860
gttaaacgga tgttccggcc catggaagag gagtttggtc cagtgccttc aaagcagatg  1920
aaagaagaag ggacaaagcg agtgctcttg tacgtgagga aggagactga cgatgtgttc  1980
gatgcattga tgttgaagtc tcccacagtg aagggcctga tggaagcgat atctgagaaa  2040
tatgggctgc ccgtggagaa gatagcaaag ctttacaaga aaagcaaaaa aggcatcttg  2100
gtgaacatgg atgacaacat catcgagcac tactcgaacg aggacacctt catcctcaac  2160
atggagagca tggtggaggg cttcaaggtc acgctcatgg aaatctagcc ctgggtttgg  2220
catccgcttt ggctggagct ctcagtgcgt tcctccctga gagagacaga agccccagcc  2280
ccagaacctg gagacccatc tcccccatct cacaactgct gttacaagac cgtgctgggg  2340
agtggggcaa gggacaggcc ccactgtcgg tgtgcttggc ccatccactg gcacctacca  2400
cggagctgaa gcctgagccc ctcaggaagg tgccttaggc ctgttggatt cctatttatt  2460
```

```
gcccaccttt tcctggagcc caggtccagg cccgccagga ctctgcaggt cactgctagc  2520
tccagatgag accgtccagc gttccccctt caagagaaac actcatcccg aacagcctaa  2580
aaaattccca tcccttctct ctcacccctc catatctatc tcccgagtgg ctggacaaaa  2640
tgagctacgt ctgggtgcag tagttatagg tggggcaaga ggtggatgcc cactttctgg  2700
tcagacacct ttaggttgct ctggggaagg ctgtcttgct aaatacctcc agggttccca  2760
gcaagtggcc accaggcctt gtacaggaag acattcagtc accgtgtaat tagtaacaca  2820
gaaagtctgc ctgtctgcat tgtacatagt gtttataata ttgtaataat atattttacc  2880
tgtggtatgt gggcatgttt actgccactg gcctagagga gacacagacc tggagaccgt  2940
tttaatgggg gtttttgcct ctgtgcctgt tcaagagact tgcagggcta ggtagagggc  3000
ctttgggatg ttaaggtgac tgcagctgat gccaagatgg actctgcaat gggcatacct  3060
gggggctcgt tccctgtccc cagaggaagc cccctctcct tctccatggg catgactctc  3120
cttcgaggcc accacgttta tctcacaatg atgtgttttg cttgactttc cctttgcgct  3180
gtctcgtggg aaaggtcatt ctgtctgaga ccccagctcc ttctccagct ttggctgcgg  3240
gcatggcctg agctttctgg agagcctctg caggggggttt gccatcaggg ccctgtggct  3300
gggtctgctg cagagctcct tggctatcag gagaatcctg gacactgtac tgtgcctccc  3360
agtttacaaa cacgcccttc atctcaagtg gccctttaaa aggcctgctg ccatgtgaga  3420
gctgtgaaca gctcagctct gagtcggcag gctggggctt cctcctgggc caccagatgg  3480
aaagggggta ttgtttgcct cactcctgga tgctgcgttt taaggaagtg agtgagaaag  3540
aatgtgccaa gatacctggc tcctgtgaaa ccagcctcag gagggaaact gggagagaga  3600
agctgtggtc tcctgctaca tgccctggga gctggaagag aaaaacactc ccctaaacaa  3660
tcgcaaaatg atgaaccatc atgggccact gttctctttg aggggacagg tttaggggtt  3720
tgcgttcgcc cttgtgggct gaagcactag ctttttggta gctagacaca tcctgcaccc  3780
aaaggttctc tacaaaggcc cagatttgtt tgtaaagcac tttgactctt acctggaggc  3840
ccgctctcta agggcttcct gcgctcccac ctcatctgtc cctgagatgc agagcaggat  3900
ggagggtctg cttctagctc agctgtttct ccttgaggtt gcggaggaat tgaattgaat  3960
gggacagagg gcaggtgctg tggccaagaa gatctccgag cagcagtgac ggggcacctt  4020
gctgtgtgtc ctctgggcat gttaaccctt ctgtggggcc aaaggtttgc atcgtggatc  4080
cagctgtgct ccagtctgtc ccctcctcct ccactctgac tgccacgccc cggaccagca  4140
gcttggggac cctccagggt actaatgggg ctctgttctg agatggacaa attcagtgtt  4200
ggaaatacat gttgtactat gcacttccca tgctcctagg gttaggaata gtttcaaaca  4260
tgattggcag acataacaac ggcaaatact cggactgggg cataggactc cagagtagga  4320
aaaagacaaa agatttggca gcctgacaca ggcaacctac ccctctctct ccagcctctt  4380
tatgaaactg tttgtttgcc agtcctgccc taaggcagaa gatgaattga agatgctgtg  4440
catgtttcct aagtccttga gcaatcatgg tggtgacaat tgccacaagg gatatgaggc  4500
cagtgccacc agagggtggt gccaagtgcc acatcccttc cgatccattc ccctctgcat  4560
cctcggagca ccccagtttg cctttgatgt gtccgctgtg tatgttagct gaactttgat  4620
gagcaaaatt tcctgagcga aacactccaa agagatagga aaacttgccg cctcttcttt  4680
tttgtccctt aatcaaactc aaataagctt aaaaaaaatc catggaagat catggacatg  4740
tgaaatgagc atttttttct ttttttttt taacaaagtc tgaactgaac agaacaagac  4800
tttttcctca tacatctcca aattgtttaa acttacttta tgagtgtttg tttagaagtt  4860
cggaccaaca gaaaaatgca gtcagatgtc atcttggaat tggtttctaa aagagtaagg  4920
catgtccctg cccagaaact taggaagcat gaaataaatc aaatgtttat tttccttctt  4980
atttaaaatc atgcaaatgc aacagaaata gagggtttgt gccaaatgct atgaacggcc  5040
ctttcttaaa gacaagcaag ggagattgat atatgtacaa tttgctctca tgttttaaaa  5100
aaaaaaaggt aaatgtaact taatagtttt gtaaatggga gagggggaat ctataaacta  5160
taaatacagt tattttattt tttgtacatt tttaaggaga aaaaataaat attcataaca  5220
taagagtaaa a                                                       5231
```

```
SEQ ID NO: 39          moltype = DNA  length = 3417
FEATURE                Location/Qualifiers
source                 1..3417
                       mol_type = other DNA
                       organism = Homo sapiens
SEQUENCE: 39
ggggccctga ttcacgggcc gctggggcca gggttggggg ttgggggtgc ccacagggct  60
tggctagtgg ggttttgggg gggcagtggg tgcaaggagt ttggtttgtg tctgccggcc  120
ggcaggcaaa cgcaacccac gcggtggggg aggcggctag cgtggtggac ccgggccgcg  180
tggccctgtg gcagccgagc catggtttct aaactgagcc agctgcagac ggagctcctg  240
gcggccctgc tcgagtcagg gctgagcaaa gaggcactga tccaggcact gggtgagccg  300
gggccctacc tcctggctgg agaaggcccc ctggacaagg gggagtcctg cggcggcggt  360
cgaggggagc tggctgagct gcccaatggg ctgggggaga ctcggggctc cgaggacgag  420
acggacgacg atggggaaga cttcacgcca cccatcctca aagagctgga gaacctcagc  480
cctgaggagg cggcccacca gaaagccgtg gtggagaccc ttctgcagga ggacccgtgg  540
cgtgtggcga agatggtcaa gtcctacctg cagcagcaca acatcccaca gcgggaggtg  600
gtcgatacca ctggcctcaa ccagtcccac ctgtcccaac acctcaacaa gggcactccc  660
atgaagacgc agaagcgggc cgccctgtac acctggtacg tccgcaagca gcgagaggtg  720
gcgcagcagt tcacccatgc agggcaggga gggctgattg aagagcccac aggtgatgag  780
ctaccaacca agaagggggcg gaggaaccgt ttcaagtggg gcccagcatc ccagcagatc  840
ctgttccagg cctatgagag gcagaagaac cctagcaagg aggagcgaga gacgctagtg  900
gaggagtgca atagggcgga atgcatccag agaggggtgt ccccatcaca ggcacagggg  960
ctgggctcca acctcgtcac ggaggtgcgt gtctacaact ggtttgccaa ccggcgcaaa  1020
gaagaagcct tccggcacaa gctggccatg gacacgtaca gcgggccccc cccagggcca  1080
ggcccgggac ctgcgctgcc cgctcacagc tcccctggcc tgcctccacc tgccctctcc  1140
cccagtaagg tccacggtgt gcgctatgga cagcctgcga ccagtgagac tgcagaagta  1200
ccctcaagca gcggcggtcc cttagtgaca gtgtctacac ccctccacca agtgtccccc  1260
acgggcctgg agcccagcca cagcctgctg agtacagaag ccaagctggt ctcagcagct  1320
gggggccccc tccccctgt cagcaccctg acagcactgc acagcttgga gcagacatcc  1380
ccaggcctca accagcagcc ccagaacctc atcatggcct cacttcctgg ggtcatgacc  1440
atcgggcctg gtgagcctgc ctccctgggt cctacgttca ccaacacagg tgcctccacc  1500
```

```
ctggtcatcg gcctggcctc cacgcaggca cagagtgtgc cggtcatcaa cagcatgggc  1560
agcagcctga ccaccctgca gcccgtccag ttctcccagc cgctgcaccc ctcctaccag  1620
cagccgctca tgccacctgt gcagagccat gtgacccaga gcccccttcat ggccaccatg  1680
gctcagctgc agagccccca cgccctctac agccacaagc ccgaggtggc ccagtacacc  1740
cacacgggcc tgctcccgca gactatgctc atcaccgaca ccaccaacct gagcgccctg  1800
gccagcctca cgcccaccaa gcaggtcttc acctcagaca ctgaggcctc cagtgagtcc  1860
gggcttcaca cgccggcatc tcaggccacc accctccacg tccccagcca ggaccctgcc  1920
ggcatccagc acctgcagcc ggcccaccgg ctcagcgcca gccccacagt gtcctccagc  1980
agcctggtgc tgtaccagag ctcagactcc agcaatggcc agagccacct gctgccatcc  2040
aaccacagcg tcatcgagac cttcatctcc acccagatgg cctcttcctc ccagtaacca  2100
cggcacctgg gccctggggc ctgtactgcc tgcttggggg gtgatgaggg cagcagccag  2160
ccctgcctgg aggacctgag cctgccgagc aaccgtggcc cttcctggac agctgtgcct  2220
cgctccccac tctgctctga tgcatcagaa agggagggct ctgaggcgcc ccaacccgtg  2280
gaggctgctc ggggtgcaca ggagggggtc gtggagagct aggagcaaag cctgttcatg  2340
gcagatgtag gagggactgt cgctgcttcg tgggatacag tcttcttact tggaactgaa  2400
gggggcggcc tatgacttgg gcacccccag cctgggccta tggagagccc tgggaccgct  2460
acaccactct ggcagccaca cttctcagga cacaggcctg tgtagctgtg acctgctgag  2520
ctctgagagg ccctggatca gcgtggcctt gttctgtcac caatgtaccc accgggccac  2580
tccttcctgc cccaactcct tccagctagt gacccacatg ccatttgtac tgaccccatc  2640
acctactcac acaggcattt cctgggtggc tactctgtgc cagagcctgg ggctctaacg  2700
cctgagccca gggaggccga agctaacagg gaaggcaggc agggctctcc tggcttccca  2760
tccccagcga ttccctctcc caggccccat gacctccagc tttcctgtat ttgttcccaa  2820
gagcatcatg cctctgaggc cagcctggcc tcctgcctct actgggaagg ctacttcggg  2880
gctgggaagt cgtccttact cctgtgggag cctcgcaacc cgtgccaagt ccaggtcctg  2940
gtggggcagc tcctctgtct cgagcgccct gcagaccctg cccttgtttg gggcaggagt  3000
agctgagctc acaaggcagc aaggcccgag cagctgagca gggccgggga actggccaag  3060
ctgaggtgcc caggagaaga aagaggtgac cccagggcac aggagctacc tgtgtggaca  3120
ggactaacac tcagaagcct gggggcctgg ctggctgagg gcagttcgca gccaccctga  3180
ggagtctgag gtcctgagca ctgccaggag ggacaaagga gcctgtgaac ccaggacaag  3240
catggtccca catccctggg cctgctgctg agaacctggc cttcagtgta ccgcgtctac  3300
cctgggattc aggaaaaggc ctggggtgac ccggcacccc ctgcagcttg tagccagccg  3360
gggcgagtgg cacgtttatt taacttttag taaagtcaag gagaaatgcg gtggaaa     3417

SEQ ID NO: 40          moltype = DNA  length = 1575
FEATURE                Location/Qualifiers
source                 1..1575
                       mol_type = other DNA
                       organism = Homo sapiens
SEQUENCE: 40
gtcctgtggc ctctgcagct cagcatggct agggtactgg gagcacccgt tgcactgggg  60
ttgtggagcc tatgctggtc tctggccatt gccacccctc ttcctccgac tagtgcccat  120
gggaatgttg ctgaaggcga gaccaagcca gacccagacg tgactgaacg ctgctcagat  180
ggctggagct ttgatgctac caccctggat gacaatggaa ccatgctgtt ttttaaaggg  240
gagtttgtgt ggaagagtca caaatgggac cgggagttaa tctcagagag atggaagaat  300
ttccccagcc ctgtggatgc tgcattccgt caaggtcaca acagtgtctt tctgatcaag  360
ggggacaaag tctgggtata ccctcctgaa aagaaggaga aaggataccc aaagttgctc  420
caagatgaat ttcctggaat cccatcccca ctggatgcag ctgtggaatg tcaccgtgga  480
gaatgtcaag ctgaaggcgt cctcttcttc caaggtgacc gcgagtggtt ctgggacttg  540
gctacgggaa ccatgaagga gcgttcctgg ccagctgttg ggaactgctc ctctgccctg  600
agatggctgg gccgctacta ctgcttccag ggtaaccaat tcctgcgctt cgaccctgtc  660
aggggagagg tgcctcccag gtacccgcgg gatgtccgag actacttcat gccctgccct  720
ggcagaggcc atggacacag gaatgggact ggccatggga acagtaccca ccatggccct  780
gagtatatgc gctgtagccc acatctagtc ttgtctgcac tgacgtctga caaccatggt  840
gccacctatg ccttcagtgg gacccactac tggcgtctgg acaccagccg ggatggctgg  900
catagctggc ccattgctca tcagtggccc cagggtcctt cagcagtgga tgctgccttt  960
tcctgggaag aaaaactcta tctggtccag ggcacccagg tatatgtctt cctgacaaag  1020
ggaggctata ccctagtaag cggttatccg aagcggctgg agaaggaagt cgggacccct  1080
catgggatta tcctggactc tgtggatgcg gcctttatct gccctgggtc ttctcggctc  1140
catatcatgg caggacggcg gctgtggtgg ctggacctga agtcaggagc ccaagccacg  1200
tggacagagc ttccttggcc ccatgagaag gtagacggag ccttgtgtat ggaaaagtcc  1260
cttggcccta actcatgttc cgccaatggt cccggcttgt acctcatcca tggtcccaat  1320
ttgtactgct acagtgatgt ggagaaactg aatgcagcca aggcccttcc gcaaccccag  1380
aatgtgacca gtctcctggg ctgcactcac tgaggggcct tctgacatga gtctggcctg  1440
gccccacctc ctagttcctc ataataaaga cagattgctt cttcgcttct cactgagggg  1500
ccttctgaca tgagtctggc ctggccccac ctccccagtt tctcataata aagacagatt  1560
gcttcttcac ttgaa                                                  1575

SEQ ID NO: 41          moltype = DNA  length = 7419
FEATURE                Location/Qualifiers
source                 1..7419
                       mol_type = other DNA
                       organism = Homo sapiens
SEQUENCE: 41
gaagagttct gcactttgtt ccttccctgg cacacctgtg tctgcattcc ttctatctcc  60
cggcattctc cactcctgtc tctgtgtgtt taaaaaccgg tgtgggaagt gtgcacgcct  120
gtgacgtcag actccagacc atgtatttcc tgactcccat cttggtagcc attctctgca  180
ttttggttgt gtggatcttt aaaaatgccg acagaagcat ggagaaaaag aaggggggagc  240
ctagaaccag ggccgaagct cgcccctggg tggatgaaga cttaaaagac agcagtgacc  300
tgcaccaagc agaagaagat gctgatgaat ggcaagaatc agaagaaaat gttgaacaca  360
```

-continued

```
tccccttctc tcataaccac tatcctgaga aggaaatggt taagaggtct caggaatttt  420
atgaacttct caataagaga cggtcagtca ggttcataag taatgagcaa gtcccaatgg  480
aagtcattga taatgtcatc agaacggcag gaacagcccc gagtggggct cacacagagc  540
cctggacctt cgtggttgtg aaggacccag acgtgaagca caagattcga aagatcattg  600
aggaggaaga ggagatcaac tacatgaaaa ggatgggaca tcgctgggtc acagacctca  660
agaaactgag aaccaactgg attaaagagt acttggatac tgcccctatt ttgattctca  720
ttttcaaaca agtacatggt ttcgccgcaa atggcaagaa aaaagtccac tactacaatg  780
agatcagtgt ttccatcgct tgtggcatcc tgctagctgc cctgcagaat gcaggtctgg  840
tgactgtcac taccactcct ctcaactgtg gccctcgact gagggtgctc ctgggccgcc  900
ccgcacatga aaagctgctg atgctgctcc ccgtggggta ccccagcaag gaggccacgg  960
tgcctgacct caagcgcaaa cctctggacc agatcatggt gacagtgtag gcagggcccc  1020
ccaagggagt ggcagggaga tggcgcccct gcttttccct gagcctctcg cctgctcctc  1080
ttgggtctct tggctgctct ttctccaggt gtcaggtccc ctcattgctc ttctcaggtg  1140
gccacactat gtcaagaagc ctctccacac tctgtggcac ttccagtccc ataaatcctg  1200
tttcttatcc actttggaaa tgcatgaaca ctttacaaag aacatgcccg ggtttttaca  1260
ttttaaaagt tattctagac aatcactatt ggcttttttc ttttattttt aaaaaactca  1320
catagaggag acaatcagaa atttaccata gtcccaagaa ttcagctaca tgatgactcg  1380
aatttaaatt tagattaatc aaatggtctc ctgttctctg atttctggtg gcttttagac  1440
actaattttt gagaactact tttttttttt taccaaactt cagggacact ctgctagttt  1500
tgaataagta accatcaaag ttactaaaac atggccaggc gcagtggctc atgcctgtaa  1560
tcccagcact ttgggaggcc gaggtgggca gattgcctga gctcaagagt tcgagaccag  1620
cctggccaac atggtgaaac cccatctcta ctaaaaatac aaaaaattag ctgggcatgc  1680
acttgtaatt ccagctactc aggaggctga ggcaagagaa ctgcttgaat ccgggaggta  1740
gagattgcag tgagtcaaga tgctgagatg ccaccactgc actccagcct gggcaacaga  1800
gcgagaacct gtctcaaaaa aaacaaaaac aaagttacta aaatgtcacc ttcacagaac  1860
aggacagggt acccttgggt cgcacgggcc tggctggcat gtaaacggtc agttgcactg  1920
cctagtggtt tggtagatct gacttgtaag cagttcatag aagctgctca atactcaaga  1980
atcttgcaag acagttatta aacattcata gcttgaaatt gcccatggtg ggagagttta  2040
catcacaacc actacaaatc agcacttgct ttcttcttct taaagagagc tgcttaccat  2100
acatagcacc cacagtgtct cccttctctt ctaccccaac ccctgaaaca cactgacccc  2160
tattctccag atgacagcac agctgtttgg gactgatagg gtcacagttg ccaggttggg  2220
aatgctagat gtagtcttca cccatcacct tctgtcgtcc tcccaggggt gtcatattta  2280
cagaggcaaa ctcttacagc ttggatgatt tctcatcaag caactctact cacctctttt  2340
tccccttttcc ctgtgcgttt cttcttcttg tcctcatttt ccttgagaaa actctctcta  2400
taaaaaattt ccatagagta tgtggctgat aaacaacaga aatttgtttc tcacagttct  2460
ggaggctgga agtccaaggt cggggtgccc tcatggtcag gtgctggtga ggaccctgat  2520
ctgggttgca gactgctgac ttcttattgt gtcctcgtgg tagaaagagg gttagagcct  2580
ctggcatgcc ttttataagg gtactaatcc catcatgagg ccccgtcctt atgacctcat  2640
cacctcccaa aggacccccct cctaatacca tcacattggg ggttagggtt tcaacatatg  2700
aattgcgggg gacacaaaca ttccgtccat ggcacctact tcatagggtt tggcatgctg  2760
ctcggtacat ggttaacatt cataaatggt gggggccctt actgtggtag aaaccattgt  2820
cactgcaagg cagccctgct tgggattcag gtgaacaaat gtaacgtggg tgggtgaggg  2880
actccctcct cttcagagaa gccctcctgt ggctcagggg cagctgcagg gccagatgga  2940
gttggcctgc agggagtcag ccttacccca tcagagacca acttgaaaga tttttttctc  3000
tgtgtagttc gtgttatcaa tctgatctgc agccaggtta tttacttctg aagcattgga  3060
gttatcgatt gccattgccc catggttctc actctttgca ggcactcttc aaatttttat  3120
tttaaaaatt ataatgcaaa catctggcca tcaccttaac caagtgacaa agtcctagca  3180
caccattaat ggtaggataa ctgacattaa gtgttcctgc tgggatgaat tatgaagtat  3240
tccttccaaa gatgtcaatg gaaactaatc gagtcttaca cctaattttc agtttacagt  3300
aaatacagag gataaagaag ttaatggcat ggtggaataa ccaaaatgtg tatcattcta  3360
caaaaaaata ggcctggact atttaaggag tgagtgtcac tgtgggaaga ataagagggg  3420
gactgtcttg tccttgctac tcaaagagtg gtcctgggcc tgtatcatca ttgggaccac  3480
ctgggcgctt gttagaatca aagactctca ggcctcacct agacatccag aatcaaaatc  3540
tgcattttaa caagatgccc aggtgatctg catgcctgtt aaagtctgag ctctgttgca  3600
gataaccaga gacccaacaa ccaaaggcaa agcgtaagcc ttgattggat tttggtttag  3660
gaaaaatctc ataggtataa aagacaactg ggaatgttga atgtggatct ggtggtaggt  3720
gatattgtta gtgatgtgag tgatgcctgc tgaagtactg agagatgaag catcatattg  3780
acaacttact ccaggaaaaa aggtgtgtgt ataggtgtgt gtttggagag tgtgagcgag  3840
aactaacatg gtaaaatgtt aggtggagca tatacagttc tcattatact cttattttaa  3900
atttatattt gaacacagtc aaatctgaat ggaaatacat ttaaataagc atttctttca  3960
gtcatataag taatttgcct aaaaatgccc tctaagtcca tcattaggtt aagcgattta  4020
ctgaaggtgc agatatcatg cttatttcat tgggttgttt tggaatgtcc cccacttgga  4080
gagtttgagg aatggaaatg agaatcggag gagaaataag gccagaggct cacattgctt  4140
gcagggaacc gactgagtaa tgaagaagag gaaggaagcc cttggaagga acgtaaaatc  4200
catttcagcc tgccgcccct tggaatggag ggtcttctag ggaccagaaa caccagacac  4260
ttcttctgcc ccaagcacac cccacactaa tttctgctgc agcatcacga tcagggcaaa  4320
tcagcacagc cccccagcca tcagtggtgt ctagaaaagt aaggataatt ttcttccttc  4380
tcactgcagc cccaagctct tattaacctt cttttatgtg ttcattaaat gcagtcatgt  4440
gacaactgtg ttcaaagtta gaaatagtgg tcggggaggc ttatagatcc tcttgctgtt  4500
ctgaggcctt aaaaccaaaa aaataatgga atgattgcat cactgcgagg aagtatactt  4560
aattaagaaa gttgaaaatg gtttgtgtct tactaatagg actcacctga agactctact  4620
ttgccaagag ggaattttta actcaaagtt gtgtcagcca gcacggggta gagccatggt  4680
cctcatactt gctggcatcc ctcatctggt ggtctgttaa agcacagatt gctgggccgc  4740
accctcaggg tgtgtgattg tgtgattcag tattgctggg tggtgcccaa atgctccagt  4800
tctaatgtat tcccaggtgt tgctgatgct ggtgattggg taccacattt tgagaaccat  4860
ggggcattgg caatcaacaa atgcaatgct tgtgacttga cgtgataaaa gttcatttat  4920
tgggcaggca aagtcctctg caggcctgga aaccctccga gacaattact tgcatggggt  4980
aacccagtaa tactgtggga tgcaacttct agggcatggc tgcctccttc ctagaggcag  5040
cagggggaga aaacactgga agaggtcacc ccaacaattc catcgtacct tggcctagga  5100
```

```
gtgacctcct cagtctcaca accctttggc tagaactagt catgtgacct cacaggaggt  5160
ggagcagtgt cgtcaatgtt atcatccccc tgcacctgca aggaaggagg cccagatgtg  5220
tgtaggtgct ggatgtctct tccccaaaac atataactct ggatttggaa aacaaaactg  5280
gatataacag aaaagaaaag gaggggagaa ggaaagttga agaaattggt gaaatcagaa  5340
taggacagtg aaaggcataa agattttctt ctgaaacgct aagatcggtt gatatttgtc  5400
taatacagct ttaaatagag tatcactttg ggccaaagaa aattgatata aacatacata  5460
aagtggaact aagattgact tcttcctaga catctctgcc tctgtccaca aaatggaaac  5520
ttccatcaag gagtactgga ggacagttca gtatttcttc ttatttgctc ctccctatga  5580
aaggaagagt gacttctctg ctgcatgata ttgggggtaa atagttattg cacatttgct  5640
caaaccccag caaagtgcac cccattttaa gccaaattta caaacttaca aagatgatcc  5700
accaatagtt ttctctattt actttattct tgctctgtca cccaggctag aatgcagtgg  5760
tgtgattata gctcactgca gcctccaact tctggactca agtgatcctc ccaccttagc  5820
ttcccaggta gctgggatac aggtgcacgc caccacaccc aggctagttt ttctaaatat  5880
tggagttccc aaagagtatt caaactgatg tgatatttta aaagacattt tgtaagcatc  5940
ttttaggaat atcagtaagt ggaagaaaaa cacatagtta tcagtggata ttatgccaga  6000
gaggcatgag aaatataatt ttattttgct aggtatcagc agagtgccct cttataattt  6060
gtgtgaaatg gaaacaaagg taacatcgtg ttttcaattc acacatatat acaagtaatg  6120
agaggtccag aagaaatgtg gcttcagctc tgctgctact gtgcctccct tctcctgccc  6180
cactcagccc acaaaatagg ctggacactc aaaaaacgtt gcgtttatct accttttaga  6240
gagggtgaat agcagagaac tggaggtggg aatggtaagg aactcccagc agggtagtgg  6300
agggaatggg ctgacgcatc taaggctgat gccaggtctg ctccctatct gggtggcctc  6360
agcaaatgac gtccagcaca tccaggggca ggctcaaggg agaacagccc ccaaagctaa  6420
gatcctgcca agctaaatac agtagttcta atgaaatgtg agaggctata atcccatttg  6480
ggaaattcct aaaaagtcat gaggcagggg attggtttat gttattatca tgacctgaga  6540
gtcatggctc agagccaaat gttcaggatt gaattcaaca gcatttaaat gtctttagag  6600
caggatggaa atatgttagc aatgcctgca gagtgccaag taaacgcaaa agccaatgag  6660
atcataaagg aagttgttag ctaacctagg tggagtcgcc aacttccttc tactctaata  6720
attaaaaata aaaataatac ttgggaggta actggaataa aggttctaaa atcaaaaccc  6780
tctgaagggt gaaaactggg agcctcctgt tcccatagta accacagcac tcagggcact  6840
gtctcccagc gctggagtac tgtcttatga ccagagatcc taagcaacct ctgctcatct  6900
gagttgtcca ccatattgtg ggcatgagtc cttgacaata gtaaatagca cctctgttcc  6960
cttattgggt aaatgatttt ccaactctgg gaatgtgtag aattcattat ggaaataatg  7020
caataattca aatccataat attgatactt tcatgttaag tttaggacta atcttgtgta  7080
tgctccttaa gtgatttgaa tctttaaaaa gcttatgatt ccaatttgaa atgtgaaatt  7140
gattttacgt ttgtgatttg aagttgaaag gtataagaat atttaactta gctcatgaaa  7200
agtattagac tagatttact ataagtttaa tgtattagat ttacaagaga tgcttaaata  7260
tatgagaatg ttttgtctta attggttata atcttgtcat atcaatgatt tgaagtgcta  7320
aaatagaaaa ttaaatatga taaattacac aagaagttta gaatgtttaa aagattttaa  7380
taaacaaagc ctataactaa gaaaaaaaaa aaaaaaaaa                         7419
```

```
SEQ ID NO: 42           moltype = DNA  length = 1413
FEATURE                 Location/Qualifiers
source                  1..1413
                        mol_type = other DNA
                        organism = Homo sapiens
SEQUENCE: 42
gccgccaccg tcgtccgcaa agcctgagtc ctgtcctttc tctctccccg gacagcatga  60
gcttcaccac tcgctccacc ttctccacca actaccggtc cctgggctct gtccaggcgc  120
ccagctacgg cgcccggccg gtcagcagcg cggccagcgt ctatgcaggc gctgggggct  180
ctggttcccg gatctccgtg tcccgctcca ccagcttcag gggcggcatg gggtccgggg  240
gcctggccac cgggatagcc gggggtctgg caggaatggg aggcatccag aacgagaagg  300
agaccatgca aagcctgaac gaccgcctgg cctcttacct ggacagagtg aggagcctgg  360
agaccgagaa ccggaggctg gagagcaaaa tccgggagca cttggagaag aagggacccc  420
aggtcagaga ctggagccat tacttcaaga tcatcgagga cctgagggct cagatcttcg  480
caaatactgt ggacaatgcc cgcatcgttc tgcagattga caatgcccgt cttgctgctg  540
atgactttag agtcaagtat gagacagagc tggccatgcg ccagtctgtg gagaacgaca  600
tccatgggct ccgcaaggtc attgatgaca ccaatatcac acgactgcag ctggagacag  660
agatcgaggc tctcaaggag gagctgctct tcatgaagaa gaaccacgaa gaggaagtaa  720
aaggcctaca agcccagatt gccagctctg ggttgaccgt ggaggtagat gcccccaaat  780
ctcaggacct cgccaagatc atggcagaca tccgggccca atatgacgag ctggctcgga  840
agaaccgaga ggagctagac aagtactggt ctcagcagat tgaggagagc accacagtgg  900
tcaccacaca gtctgctgag gttggagctg ctgagacgac gctcacagag ctgagacgta  960
cagtccagtc cttggagatc gacctggact ccatgagaaa tctgaaggcc agcttggaga  1020
acagcctgag ggaggtggag gcccgctacg ccctacagat ggagcagctc aacgggatcc  1080
tgctgcacct tgagtcagag ctggcacaga cccgggcaga gggacagcgc caggcccagg  1140
agtatgaggc cctgctgaac atcaaggtca agctggaggc tgagatcgcc acctaccgcc  1200
gcctgctgga agatggcgag gactttaatc ttggtgatgc cttggacagc agcaactcca  1260
tgcaaaccat ccaaaagacc accacccgcc ggatagtgga tggcaaagtg gtgtctgaga  1320
ccaatgacac caaagttctg aggcattaag ccagcagaag cagggtaccc tttggggagc  1380
aggaggccaa taaaaagttc agagttcatt gga                               1413
```

```
SEQ ID NO: 43          moltype = DNA  length = 2308
FEATURE                Location/Qualifiers
source                 1..2308
                       mol_type = other DNA
                       organism = Homo sapiens
SEQUENCE: 43
agtcctgctt ctcttccctc tctcctccag cctctcacac tctcctcagc tctctcatct  60
cctggaacca tggccagcac atccaccacc atcaggagcc acagcagcag ccgccggggt  120
ttcagtgcca actcagccag gctccctggg gtcagccgct ctggcttcag cagcgtctcc  180
gtgtcccgct ccaggggcag tggtggcctg ggtggtgcat gtggaggagc tggctttggc  240
agccgcagtc tgtatggcct ggggggctcc aagaggatct ccattggagg gggcagctgt  300
gccatcagtg gcggctatgg cagcagagcc ggaggcagct atggctttgg tggcgccggg  360
agtggatttg gtttcggtgg tggagccggc attggctttg gtctgggtgg tggagccggc  420
cttgctggtg gctttggggg ccctggcttc cctgtgtgcc cccctggagg catccaagag  480
gtcaccgtca accagagtct cctgactccc ctcaacctgc aaatcgatcc caccatccag  540
cgggtgcggg ctgaggagcg tgaacagatc aagaccctca acaacaagtt tgcctccttc  600
atcgacaagg tgcggttcct ggagcagcag aacaaggttc tggaaacaaa gtggaccctg  660
ctgcaggagc agggcaccaa gactgtgagg cagaacctgg agccgttgtt cgagcagtac  720
atcaacaacc tcaggaggca gctggacagc attgtcgggg aacggggccg cctggactca  780
gagctcagag gcatgcagga cctggtggag gacttcaaga acaaatatga ggatgaaatc  840
aacaagcgca cagcagcaga gaatgaattt gtgactctga agaaggatgt ggatgctgcc  900
tacatgaaca aggttgaact gcaagccaag gcagacactc tcacagacga gatcaacttc  960
ctgagagcct tgtatgatgc agagctgtcc cagatgcaga cccacatctc agacacatct  1020
gtggtgctgt ccatggacaa caaccgcaac ctggacctgg acagcatcat cgctgaggtc  1080
aaggcccaat atgaggagat tgctcagaga agccgggctg aggctgagtc ctggtaccag  1140
accaagtacg aggagctgca ggtcacagca ggcagacatg gggacgacct gcgcaacacc  1200
aagcaggaga ttgctgagat caaccgcatg atccagaggc tgagatctga gatcgaccac  1260
gtcaagaagc agtgcgccaa cctgcaggcc gccattgctg atgctgagca gcgtggggag  1320
atggccctca aggatgccaa gaacaagctg gaagggctgg aggatgccct gcagaaggcc  1380
aagcaggacc tggcccggct gctgaaggag taccaggagc tgatgaatgt caagctggcc  1440
ctggacgtgg agatcgccac ctaccgcaag ctgctggagg gtgaggagtg caggctgaat  1500
ggcgaaggcg ttggacaagt caacatctct gtggtgcagt ccaccgtctc cagtggctat  1560
ggcggtgcca gtggtgtcgg cagtggctta ggcctgggtg gaggaagcag ctactcctat  1620
ggcagtggtc ttggcgttgg aggtggcttc agttccagca gtggcagagc cattgggggt  1680
ggcctcagct ctgttggagg cggcagttcc accatcaagt acaccaccac ctcctcctcc  1740
agcaggaaga gctataagca ctaaagtgcg tctgctagct ctcggtccca cagtcctcag  1800
gcccctctct ggctgcagag ccctctcctc aggttgcctt tcctctcctg gcctccagtc  1860
tcccctgctg tcccaggtag agctgggtat ggatgcttag tgccctcact tcttctctct  1920
ctctctatac catctgagca cccattgctc accatcagat caacctctga ttttacatca  1980
tgatgtaatc accactggag cttcactgtt actaaattat taatttcttg cctccagtgt  2040
tctatctctg aggctgagca ttataagaaa atgacctctg ctccttttca ttgcagaaaa  2100
ttgccagggg cttatttcag aacaacttcc acttacttc cactggctct caaactctct  2160
aacttataag tgttgtgaac cccccacccag gcagtatcca tgaaagcaca agtgactagt  2220
cctatgatgt acaaagcctg tatctctgtg atgatttctg tgctcttcgc tgtttgcaat  2280
tgctaaataa agcagattta taatacaa                                2308

SEQ ID NO: 44          moltype = DNA  length = 2302
FEATURE                Location/Qualifiers
source                 1..2302
                       mol_type = other DNA
                       organism = Homo sapiens
SEQUENCE: 44
gtcctgcttc tcctccctct cgcctccagc ctctcacact ctcctaagcc ctctcatctc  60
ctggaaccat ggccagcaca tccaccacca tcaggagcca cagcagcagc cgccggggtt  120
tcagtgccaa ctcagccagg ctccctgggg tcagccgctc tggcttcagc agcatctccg  180
tgtcccgctc caggggcagt ggtggcctgg gtggcgcatg tggaggagct ggctttggca  240
gccgcagtct gtatggcctg gggggctcca agaggatctc cattggaggg ggcagctgtg  300
ccatcagtgg cggctatggc agcagagccg gaggcagcta tggctttggt ggcgccggga  360
gtggatttgg tttcggtggt ggagccggca ttggctttgg tctgggtggt ggagccggcc  420
ttgctggtgg ctttgggggc cctggcttcc ctgtgtgccc ccctggaggc atccaagagg  480
tcactgtcaa ccagagtctc ctgactcccc tcaacctgca aattgacccc gccatccagc  540
gggtgcgggc cgaggagcgt gagcagatca agaccctcaa caacaagttt gcctccttca  600
tcgacaaggt gcggttccta gagcagcaga acaaggttct ggacaccaag tggaccctgc  660
tgcaggagca gggcaccaag actgtgaggc agaacctgga gccgttgttc gagcagtaca  720
tcaacaacct caggaggcag ctggacaaca tcgtgggggga acggggtcgt ctggactcgg  780
agctgagaaa catgcaggac ctggtggagg acctcaagaa caaatatgag gatgaaatca  840
acaagcgcac agcagcagag aatgaatttg tgactctgaa gaaggatgtg gatgctgcct  900
acatgaacaa ggttgaactg caagccaagg cagacactct tacagatgag atcaacttcc  960
tgagagcctt gtatgatgca gagctgtccc agatgcagac ccacatctca gacacatccg  1020
tggtgctatc catggacaac aaccgcaacc tggacctgga cagcatcatc gctgaggtca  1080
aggcccaata tgaggagatt gctcagagga gcagggctga ggctgagtcc tggtaccaga  1140
caaagtacga ggagctgcag atcacagcag gcagacatgg ggacgacctg cgcaacacca  1200
agcaggagat tgctgagatc aaccgcatga tccagaggct gagatctgag atcgaccacg  1260
tcaagaagca gtgtgccaac ctacaggccg ccattgctga tgctgagcag cgtggggaga  1320
tggccctcaa ggatgctaag aacaagctgg aagggctgga ggatgccctg cagaaggcca  1380
agcaggacct ggcccggctg ctgaaggagt accaggagct gatgaacgtc aagctggccc  1440
tggatgtgga gatcgccacc taccgcaagc tgctggaggg cgaggagtgc aggctgaatg  1500
gcgaaggcgt tggacaagtc aacatctctg tagtgcagtc caccgtctcc agtggctatg  1560
gcggtgccag cggtgtcggc agtggcttag gcctgggtgg aggaagcagc tactcctatg  1620
```

```
gcagtggtct tggcgttgga ggcggcttta gttccagcag cggcagagcc actgggggtg  1680
gcctcagctc tgttggaggc ggcagttcca ccatcaagta caccaccacc tcctcctcca  1740
gcaggaagag ctacaagcac tgaagtgctg ccgccagctc tcagtcccac agctctcagg  1800
cccctctctg gcagcagagc cctctcctca ggttgcttgt cctcccctgg cctccagtct  1860
cccctgccct cccgggtaga gctgggatgc cctcactttt cttctcatca atacctgttc  1920
cactgagctc ctgttgctta ccatcaagtc aacagttatc agcactcaga catgcgaatg  1980
tcctttttag ttcccgtatt attacaggta tctgagtctg ccataattct gagaagaaaa  2040
tgacctatat ccccataaga actgaaactc agtctaggtc cagctgcaga tgaggagtcc  2100
tctctttaat tgctaaccat cctgcccatt atagctacac tcaggagttc tcatctgaca  2160
agtcagttgt cctgatcttc tcttgcagtg tccctgaatg gcaagtgatg taccttctga  2220
tgcagtctgc attcctgcac tgctttctct gctctctttg ccttcttttg ttctgttgaa  2280
taaagcatat tgagaatgtg aa                                             2302

SEQ ID NO: 45          moltype = DNA  length = 1926
FEATURE                Location/Qualifiers
source                 1..1926
                       mol_type = other DNA
                       organism = Homo sapiens
SEQUENCE: 45
actccaggtc ccctatcctg tcctctgcaa cccaaacgtc caggaggatc atgacctgcg  60
gatcaggatt tggtgggcgc gccttcagct gcatctcggc ctgcgggccg cggcccggcc  120
gctgctgcat caccgccgcc ccctaccgtg gcatctcctg ctaccgcggc ctcaccgggg  180
gcttcggcag ccacagcgtg tgcggaggct ttcgggccgg ctcctgcgga cgcagcttcg  240
gctaccgctc cgggggcgtg tgcgggccca gtcccccatg catcaccacc gtgtcggtca  300
acgagagcct cctcacgccc ctcaacctgg agatcgaccc caacgcgcag tgcgtgaagc  360
aggaggagaa ggagcagatc aagtccctca acagcaggtt cgcggccttc atcgacaagg  420
tgcgcttcct ggagcagcag aacaaactgc tggagacaaa gctgcagttc taccagaacc  480
gcgagtgttg ccagagcaac ctggagcccc tgtttgaggg ctacatcgag actctgcggc  540
gggaggccga gtgcgtggag gccgacagcg ggaggctggc ctcagagctt aaccacgtgc  600
aggaggtgct ggagggctac aagaagaagt atgaggagga ggtttctctg agagcaacag  660
ctgagaacga gtttgtggct ctgaagaagg atgtggactg cgcctacctc cgcaagtcag  720
acctggaggc caacgtggag gccctgatcc aggagatcga cttcctgagg cggctgtatg  780
aggaggagat cctcattctc cagtcgcaca tctcagacac ctccgtggtt gtcaagctgg  840
acaacagccg ggacctgaac atggactgca tcattgccga gattaaggca cagtatgacg  900
acattgtcac ccgcagccgg gccgaggccg agtcctggta ccgcagcaag tgtgaggaga  960
tgaaggccac ggtgatcagg cacggggaga ccctgcgccg caccaaggag gagatcaatg  1020
agctgaaccg catgatccaa aggctgacgg ccgaggtgga gaatgccaag tgccagaact  1080
ccaagctgga ggccgcggtg gcccagtctg agcagcaggg tgaggcggcc ctcagtgatg  1140
cccgctgcaa gctggccgag ctggagggcg ccctgcagaa ggccaagcag gacatggcct  1200
gcctgatcag ggagtaccag gaggtgatga actccaagct gggcctggac atcgagatcg  1260
ccacctacag gcgcctgctg gagggcgagg agcagaggct atgtgaaggc attggggctg  1320
tgaatgtctg tgtcagcagc tcccggggcg gggtcgtgtg cggggacctc tgcgtgtcag  1380
gctcccggcc agtgactggc agtgtctgca gcgctccgtg caacgggaac gtggcggtga  1440
gcaccggcct gtgtgcgccc tgcggccaat tgaacaccac ctgcggaggg ggttcctgcg  1500
gcgtgggctc ctgtggtatc agctccctgg gtgtggggtc ttgcggcagc agctgccgga  1560
aatgttaggc accccaactc aagtcccagg ccccaggcat ctttcctgcc ctgccttgct  1620
tggcccatcc agtccaggcg cctggagcaa gtgctcagct acttctcctg cactttgaaa  1680
gacccctccc actcctggcc tcacatttct ctgtgtgatc ccccacttct gggctctgcc  1740
accccacagt gggaaaggcc accctagaaa gaagtccgct ggcacccata ggaaggggcc  1800
tcaggagcag gaagggccag gaccagaacc ttgcccacgg caactgcctt cctgcctctc  1860
cccttcctcc tctgctcttg atctgtgttt caataaatta atgtagccaa aaaaaaaaaa  1920
aaaaaa                                                               1926

SEQ ID NO: 46          moltype = DNA  length = 1802
FEATURE                Location/Qualifiers
source                 1..1802
                       mol_type = other DNA
                       organism = Homo sapiens
SEQUENCE: 46
aaaaggccat tcctgagagc tctcctcacc aagaagcagc ttctccgctc cttctaggat  60
ctccgcctgg ttcggcccgc ctgcctccac tcctgcctct accatgtcca tcagggtgac  120
ccagaagtcc tacaaggtgt ccacctctgg cccccgggcc ttcagcagcc gctcctacac  180
gagtgggccc ggttcccgca tcagctcctc gagcttctcc cgagtgggca gcagcaactt  240
tcgcggtggc ctgggcggcg gctatggtgg ggccagcggc atgggaggca tcaccgcagt  300
tacggtcaac cagagcctgc tgagccccct tgtcctggag gtggacccca acatccaggc  360
cgtgcgcacc caggagaagg agcagatcaa gaccctcaac aacaagtttg cctccttcat  420
agacaaggta cggttcctgg agcagcagaa caagatgctg gagaccaagt ggagcctcct  480
gcagcagcag aagacggctc gaagcaacat ggacaacatg ttcgagagct acatcaacaa  540
ccttaggcgg cagctggaga ctctgggcca ggagaagctg aagctggagg cggagcttgg  600
caacatgcag gggctggtgg aggacttcaa gaacaagtat gaggatgaga tcaataagcg  660
tacagagatg gagaacgaat ttgtcctcat caagaaggat gtggatgaag cttacatgaa  720
caaggtagag ctggagtctc gcctggaagg gctgaccgac gagatcaact tcctcaggca  780
gctatatgaa gaggagatcc gggagctgca gtcccagatc tcggacacat ctgtggtgct  840
gtccatggac aacagccgct ccctggacat ggacagcatc attgctgagg tcaaggcaca  900
gtacgaggat attgccaacc gcagccgggc tgaggctgag agcatgtacc agatcaagta  960
tgaggagctg cagagcctgg ctgggaagca cggggatgac ctgcggcgca caaagactga  1020
gatctctgag atgaaccgga acatcagccg gctccaggct gagattgagg gcctcaaagg  1080
ccagagggct tccctggagg ccgccattgc agatgccgag cagcgtggag agctggccat  1140
taaggatgcc aacgccaagt tgtccgagct ggaggccgcc ctgcagcggg ccaagcagga  1200
```

-continued

```
catggcgcgg cagctgcgtg agtaccagga gctgatgaac gtcaagctgg ccctggacat  1260
cgagatcgcc acctacagga agctgctgga gggcgaggag agccggctgg agtctgggat  1320
gcagaacatg agtattcata cgaagaccac cagcggctat gcaggtggtc tgagctcggc  1380
ctatgggggc ctcacaagcc ccggcctcag ctacagcctg ggctccagct ttggctctgg  1440
cgcgggctcc agctccttca gccgcaccag ctcctccagg gccgtggttg tgaagaagat  1500
cgagacacgt gatgggaagc tggtgtctga gtcctctgac gtcctgccca agtgaacagc  1560
tgcggcagcc cctcccagcc tacccctcct gcgctgcccc agagcctggg aaggaggccg  1620
ctatgcaggg tagcactggg aacaggagac ccacctgagg ctcagcccta gccctcagcc  1680
cacctgggga gtttactacc tggggacccc ccttgcccat gcctccagct acaaaacaat  1740
tcaattgctt tttttttttg gtccaaaata aaacctcagc tagctctgcc aatgtcaaaa  1800
aa                                                                  1802

SEQ ID NO: 47          moltype = DNA  length = 2869
FEATURE                Location/Qualifiers
source                 1..2869
                       mol_type = other DNA
                       organism = Homo sapiens
SEQUENCE: 47
ggtccaccca gtgcttgcgg cctcgcggcc gggccggcct gggctgcaat caatgcggct  60
ttgtctggga cgcccacatc ccagaggcca ttcccgggtc ggcaaatcgg agcgcggccg  120
gggcgcgcgg gggtgagata agcggccatg tgatcccacc tgggctggaa ggggaggggc  180
gccaggtgag gcggcggccg gcggggcgcg ggcggccacg cggggctcct gcagcatggc  240
tgtcagcagg aaggactggt ccgcgctgtc cagccttgcc cggcagagga ctctggagga  300
tgaggaggaa caggagcgcg agcgcaggcg gcggcaccgc aacctgagct ccaccacgga  360
cgatgaggct cccaggctca gccagaatgg agaccggcag gcctctgctt ctgagagact  420
accgagcgtg gaagaagcag aggtgcccaa gccactgccc ccagcctcca aagatgagga  480
cgaggacatc cagagcatcc tcagaacacg gcaggagcgg aggcagaggc ggcaggtggt  540
ggaggctgca caggccccca tccaggagag gctggaggca gaggagggga ggaacagctt  600
gagccctgtg caggccacac agaaacccct agtctccaag aaggaactgg aaatcccacc  660
tcgccggaga ctgagtcggg aacagcgggg cccctgggcc ctggaggagg agagcttggt  720
gggcagggag ccagaagaga ggaagaaagg ggttccagaa aagtccccag tcttggagaa  780
gtcctccatg ccaaagaaga cggcacctga aaagagcctg gtctccgata aaacctccat  840
ctctgagaag gtgctggcct cagagaagac atctctatca gagaagatag cagtgtcaga  900
gaaaagaaac agctcagaga agaagtctgt tctagaaaaa accagtgtct ctgagaagtc  960
gctggcccca gggatggcac tgggctcagg aaggaggctg gtgtctgaga aagcttccat  1020
ctttgagaag gcactggcct cagagaagag cccaactgca gatgctaagc cggcccccaaa  1080
gagggccaca gcctcagagc agcccctggc gcaggagccg ccagcctctg gggaagcccc  1140
agccaccacc aaggagcaga gaggaagggc cctccctggg aagaacctgc cctctttggc  1200
aaagcagggg gcttcagacc ctccgactgt ggcctcccgc ctcccacccg tcacactcca  1260
ggtgaaaatc cccagcaagg aggaagaggc agatatgtcc tcacccacac agcgaaccta  1320
cagcagctcc ctcaaacgct ccagccccag gaccatctcc tttcggatga aacccaagaa  1380
agaaaactcg gaaacaaccc taactcgcag tgccagcatg aagctcccag acaacacagt  1440
gaagttggga gagaagctgg agagatacca cacggccata cggagatcag aatctgtcaa  1500
gtctcggggt ctgccttgca ctgagttatt cgtggctcct gtgggtgtag ccagcaagcg  1560
ccacctcttt gagaaggaac tggcgggcca gagccgagca gaaccagcct ccagccggaa  1620
ggagaacttg aggctctcag gggttgtgac atcaaggctc aacctgtgga tcagcaggac  1680
ccaggaatct ggagatcagg acccccagga ggcacagaaa gcatcatctg caaccgagag  1740
gactcagtgg ggacagaaat ctgactcctc gctggacgct gaggtgtgac aagccccgcc  1800
aagacagacc tgcaagtctt cgtctcaagg gacctccctc atgccaggcc cctgcctctc  1860
acagcagcac cctttcctct cattgtccct gttccctttt tgcctgtgga tctgtttggc  1920
cagggtccct ggggtcagga atatttgcaa gactcagcca gctccttccc agcccagcct  1980
cttggggctg ggactttctc accctgcggc aggcacaaca gatgctggga cccagtctct  2040
gcccaggtca cagcacaagt gcacatcagc actatggggc ctatgtcctg cccagagacc  2100
tctgctcctt cctgctcaca tccacagtca gggcacggcg cccctcaaga actccagagt  2160
cacctgtctc atcggctccc agcaagtgcc tctttgtcta tgatgtcccc cttctctgag  2220
gcctggaccc acccatcttt gtccctgggg cctgctccca gccactgagg cccgctctgg  2280
ccaggggaga aggagctgcc gtgcgtcttc cctgtgcccc gtctccctgc ttggttctcc  2340
cctcccttcc ctggccggct gccatggcca ggagctaagt gcctttttgt gtgcaaccac  2400
ttaccctttc tctgaaaaac ctgttctcag gaaggatctg ataaactcat ttactctcag  2460
gtgtaagaga ctgatgagac cttagaagcg aattcctctc tggaggcctt gctttctagc  2520
agaggtcacc tgaagtgtgt gaggaggatc atcattttcc tcatcccccc tcttctcaca  2580
ttaaggtggt ggcttgccac tcagcagtcc tagcttggtg actgggaact gccacataca  2640
gggccaggcc taccctcctt ccccacaagc cccctccaac ccccaccccc atgctctgga  2700
cctcatggct cctatgagct tggagcatgg tgaaccatca gagaatctag aaccaaccaa  2760
gctaggaaca tcagcctggt gccctgttaa ccccttaaag ctgtggttta caacttttca  2820
aaaatttaaa tcattagaaa aaaaaaaaaa aaaaaaaaaa aaaaaaaaa             2869

SEQ ID NO: 48          moltype = DNA  length = 2091
FEATURE                Location/Qualifiers
source                 1..2091
                       mol_type = other DNA
                       organism = Homo sapiens
SEQUENCE: 48
gagacaggtg gtggctacga cggcgaaggg agctgagact gtccaggcag ccaggttagg  60
ccaggaggac catgtgaatg gggccagagg gctcccgggc tgggcaggga ccatgggctg  120
tggctgcagc tcacacccgg aagatgactg gatggaaaac atcgatgtgt gtgagaactg  180
ccattatccc atagtcccac tggatggcaa gggcacgctg ctcatccgaa atggctctga  240
ggtgcgggac ccactggtta cctacgaagg ctccaatccg ccggcttccc cactgcaaga  300
caacctggtt atcgctctgc acagctatga gccctctcac gacggagatc tgggctttga  360
```

-continued

```
gaagggggaa cagctccgca tcctggagca gagcggcgag tggtggaagg cgcagtccct  420
gaccacgggc caggaaggct tcatcccctt caattttgtg gccaaagcga acagcctgga  480
gccccgaaccc tggttcttca agaacctgag ccgcaaggac gcggagcggc agctcctggc  540
gcccgggaac actcacggct ccttcctcat ccgggagagc gagagcaccg cgggatcgtt  600
ttcactgtcg gtccgggact tcgaccagaa ccagggagag gtggtgaaac attacaagat  660
ccgtaatctg gacaacggtg gcttctacat ctcccctcga atcacttttc ccggcctgca  720
tgaactggtc cgccattaca ccaatgcttc agatgggctg tgcacacggt tgagccgccc  780
ctgccagacc cagaagcccc agaagccgtg gtgggaggac gagtgggagg ttcccaggga  840
gacgctgaag ctggtggagc ggctgggggc tggacagttc ggggaggtgt ggatggggta  900
ctacaacggg cacacgaagg tggcggtgaa gagcctgaag cagggcagca tgtccccgga  960
cgccttcctg gccgaggcca acctcatgaa gcagctgcaa caccagcggc tggttcggct  1020
ctacgctgtg gtcacccagg agcccatcta catcatcact gaatacatgg agaatgggag  1080
tctagtggat tttctcaaga ccccttcagg catcaagttg accatcaaca aactcctgga  1140
catggcagcc caaattgcag aaggcatggc attcattgaa gagcggaatt atattcatcg  1200
tgaccttcgg gctgccaaca ttctggtgtc tgacaccctg agctgcaaga ttgcagactt  1260
tggcctagca cgcctcattg aggacaacga gtacacagcc agggaggggg ccaagtttcc  1320
cattaagtgg acagcgccag aagccattaa ctacgggaca ttcaccatca agtcagatgt  1380
gtggtctttt gggatcctgc tgacggaaat tgtcacccac ggccgcatcc cttacccagg  1440
gatgaccaac ccggaggtga ttcagaacct ggagcgaggc taccgcatgg tgcgccctga  1500
caactgtcca gaggagctgt accaactcat gaggctgtgc tggaaggagc gcccagagga  1560
ccggcccacc tttgactacc tgcgcagtgt gctggaggac ttcttcacgg ccacagaggg  1620
ccagtaccag cctcagcctt gagaggcctt gagaggccct ggggttctcc ccctttctct  1680
ccagcctgac ttggggagat ggagttcttg tgccatagtc acatggccta tgcacatatg  1740
gactctgcac atgaatccca cccacatgtg acacatatgc accttgtgtc tgtacacgtg  1800
tcctgtagtt gcgtggactc tgcacatgtc ttgtacatgt gtagcctgtg catgtatgtc  1860
ttggacactg tacaaggtac ccctttctgg ctctcccatt tcctgagacc acagagagag  1920
gggagaagcc tgggattgac agaagcttct gcccacctac ttttctttcc tcagatcatc  1980
cagaagttcc tcaagggcca ggactttatc taatacctct gtgtgctcct ccttggtgcc  2040
tggcctggca cacatcagga gttcaataaa tgtctgttga tgactgttgt a           2091

SEQ ID NO: 49           moltype = DNA  length = 1121
FEATURE                 Location/Qualifiers
source                  1..1121
                        mol_type = other DNA
                        organism = Homo sapiens
SEQUENCE: 49
accatctccc actcctgcag ctcttctcac aggaccagcc actagcgcag cctcgagcga  60
tggcctatgt ccccgcaccg ggctaccagc ccacctacaa cccgacgctg ccttactacc  120
agcccatccc gggcgggctc aacgtgggaa tgtctgttta catccaagga gtggccagcg  180
agcacatgaa gcggttcttc gtgaactttg tggttgggca ggatccgggc tcagacgtcg  240
ccttccactt caatccgcgg tttgacggct gggacaaggt ggtcttcaac acgttgcagg  300
gcgggaagtg gggcagcgag gagaggaaga ggagcatgcc cttcaaaaag ggtgccgcct  360
ttgagctggt cttcatagtc ctggctgagc actacaaggt ggtggtaaat ggaaatccct  420
tctatgagta cgggcaccgg cttcccctac agatggtcac ccacctgcaa gtggatgggg  480
atctgcaact tcaatcaatc aacttcatcg gaggccagcc cctccggccc cagggacccc  540
cgatgatgcc accttaccct ggtcccggac attgccatca acagctgaac agcctgccca  600
ccatggaagg acccccaacc ttcaacccgc ctgtgccata tttcgggagg ctgcaaggag  660
ggctcacagc tcgaagaacc atcatcatca agggctatgt gcctcccaca ggcaagagct  720
ttgctatcaa cttcaaggtg ggctcctcag gggacatagc tctgcacatt aatccccgca  780
tgggcaacgg taccgtggtc cggaacagcc ttctgaatgg ctcgtgggga tccgaggaga  840
agaagatcac ccacaaccca tttggtcccg gacagttctt tgatctgtcc attcgctgtg  900
gcttggatcg cttcaaggtt tacgccaatg gccagcacct ctttgacttt gcccatcgcc  960
tctcggcctt ccagagggtg gacacattgg aaatccaggg tgatgtcacc ttgtcctatg  1020
tccagatcta atctattcct ggggccataa ctcatgggaa aacagaatta tcccctagga  1080
ctcctttcta agcccctaat aaaatgtctg agggtgtctc a                      1121

SEQ ID NO: 50           moltype = DNA  length = 3646
FEATURE                 Location/Qualifiers
source                  1..3646
                        mol_type = other DNA
                        organism = Homo sapiens
SEQUENCE: 50
gcgggagaag aggaagacag gaagggggtg gggatgtgaa gcgaccgtcc cagccttccc  60
cgcccgccac ccccacccca actcggcagc cgtcacgtga tgcctggagt gggaggtggg  120
gagaaaaggc gagacttttg tgggtgctcc cgatcgccag tagttccttc agtctcagcc  180
gccaactccg gaggcgcggt gctcggcccg ggagcgcgag cgggaggagc agagacccgc  240
agccgggagc ccgagcgcgg gcgatgcagg ctccgcgagc ggcacctgcg gctcctctaa  300
gctacgaccg tcgtctccgc ggcagcagcg cgggccccag cagcctcggc agccacagcc  360
gctgcagccg gggcagcctc cgctgctgtc gcctcctctg atgcgcttgc cctctcccgg  420
ccccgggact ccgggagaat gtgggtccta ggcatcgcgg caactttttg cggattgttc  480
ttgcttccag gctttgcgct gcaaatccag tgctaccagt gtgaagaatt ccagctgaac  540
aacgactgct cctcccccga gttcattgtg aattgcacgg tgaacgttca agacatgtgt  600
cagaaagaag tgatggagca aagtgccggg atcatgtacc gcaagtcctg tgcatcatca  660
gcggcctgtc tcatcgcctc tgccgggtac cagtccttct gctccccagg gaaactgaac  720
tcagtttgca tcagctgctg caacacccct ctttgtaacg ggccaaggcc caagaaaagg  780
ggaagttctg cctcggccct caggccaggg ctccgcacca ccatcctgtt cctcaaatta  840
gccctcttct cggcacactg ctgaagctga aggagatgcc acccccctcct gcattgttct  900
tccagccctc gcccccaacc ccccacctcc ctgagtgagt ttcttctggg tgtcctttta  960
ttctgggtag ggagcgggag tccgtgttct cttttgttcc tgtgcaaata atgaaagagc  1020
```

```
tcggtaaagc attctgaata aattcagcct gactgaattt tcagtatgta cttgaaggaa  1080
ggaggtggag tgaaagttca cccccatgtc tgtgtaaccg gagtcaaggc caggctggca  1140
gagtcagtcc ttagaagtca ctgaggtggg catctgcctt ttgtaaagcc tccagtgtcc  1200
attccatccc tgatgggggc atagtttgag actgcagagt gagagtgacg ttttcttagg  1260
gctggagggc cagttcccac tcaaggctcc ctcgcttgac attcaaactt catgctcctg  1320
aaaaccattc tctgcagcag aattggctgg tttcgcgcct gagttgggct ctagtgactc  1380
gagactcaat gactgggact tagactgggg ctcggcctcg ctctgaaaag tgcttaagaa  1440
aatcttctca gttctccttg cagaggactg gcgccgggac gcgaagagca acgggcgctg  1500
cacaaagcgg gcgctgtcgg tggtggagtg cgcatgtacg cgcaggcgct tctcgtggtt  1560
ggcgtgctgc agcgacaggc ggcagcacag cacctgcacg aacacccgcc gaaactgctg  1620
cgaggacacc gtgtacagga gcgggttgat gaccgagctg aggtagaaaa acgtctccga  1680
gaaggggagg aggatcatgt acgcccggaa gtaggacctc gtccagtcgt gcttgggttt  1740
ggccgcagcc atgatcctcc gaatctggtt gggcatccag catacggcca atgtcacaac  1800
aatcagccct gggcagacac gagcaggagg gagagacaga gaaaagaaaa acacagcatg  1860
agaacacagt aaatgaataa aaccataaaa tatttagccc ctctgttctg tgcttactgg  1920
ccaggaaatg gtaccaattt ttcagtgttg gacttgacag cttcttttgc cacaagcaag  1980
agagaattta acactgtttc aaacccgggg gagttggctg tgttaaagaa agaccattaa  2040
atgctttaga cagtgtattt ataccagttg atgtctgtta attttaaaaa aatgttttca  2100
ttggtgtttg tttgcgtatc cagaaagcag ttcatgttat ccataaatct ggttttgtct  2160
tttttgttt taaagaaaaa gatgtataca tacagtatag ctgcattaga taaagcagtg  2220
tttgtatttt aaaggatgtc tgcacaaaga agacctagtg atatttttaa atcaaatgga  2280
agaagtgtcc ctttggcaac aaagcagcat atttaatgac actggttttg cattcagttt  2340
caggggaagc aaagtcagga atagcctgtc gccaagaatg tttttggac atatacatac  2400
taggtatgca cacctataat catgatgctc atatctgcaa cagcatatgt gtttcttttc  2460
agacactttt agatccctca tgtggggaaa aagaattatt cagagatggc aaatataaaa  2520
cttccttcta gttcagccag taacatgttc ccttccttg cagcactgag ctgtgctgtc  2580
aacagcccag aagcaatcag gccctagaga agagaccact caaaggccct tctgtagatc  2640
aaatgtttac tgcatgtaca tttgtttgca tgcccacata tttgtattcc aacttaagta  2700
accaccacca gttctgcaat tctgactgac agagataaag atgctacata gaccacaaac  2760
aactgaaatc acaggtatca tgagagttta gttacagtga caaaagcaaa aaagaacaaa  2820
ggaagatcag gggatctgtg aagcatttgc tctctctttt cgtaaggagc caagacaccc  2880
acagtaaatt cccctgtaga gagctgctac cttaaagcag gatttgcatt ttcagaaatg  2940
cttccttcct ctcctacatt tcaatcgtag taagaaacat ttactcacat tttcaatctt  3000
ctgattttct agaaacccta gggaagtgac agttggcaat gaatgcttcc tgcctatgac  3060
ccatggtaaa tattctatta ataaatgggg gccagacatg gtggcgcatg cctgatatct  3120
caatactctg ggaggccaag gcagaaggat cacttaagcc tagaaatttg agacccacct  3180
aggcaacata gcaagacccc atctctacaa aaaaagaaaa acttagccag gcatggtggt  3240
acatacacac ctgtggtctc agatactttt tgggggctga ggcgggagga tcacttgagc  3300
ccaggaggtg aaggctacag tgagacacga atgtgccact gcactccagc ctggctgaca  3360
gagtgaaact gtctcaataa accaataaat aaatgctcca ggaaaaaaca gccacattca  3420
cacatccaga attgagcctc ctgtatgcac tggcctgagt attccttgcc tgctgttgga  3480
ggggacccta gctgtgttca aatcctccac aaatccatat gtgagcaagg aaggccttgg  3540
aaactcttct cctttgttaa tttccacagg tttctcctgt caactcccag cctaaaactt  3600
tgaaatataa gccaatttgt ttattttta aaaaaaaaaa aaaaaa                 3646

SEQ ID NO: 51          moltype = DNA  length = 2698
FEATURE                Location/Qualifiers
source                 1..2698
                       mol_type = other DNA
                       organism = Homo sapiens
SEQUENCE: 51
gggcttggcc acctgcccaa gaaacttgtt ggttgttgcc ctcaggtcgc tcccgggcgc  60
ggacacggaa cccggccatg gaagatccgt cgggggctcg cgagccccgg gcccggccga  120
gagagcggga cccgggacgg cgccccccacc cagaccaagg ccgcacccac gatcgaccgc  180
gggaccgacc cggggacccg cgcaggaagc gaagcagcga cgggaaccgg cgaagggacg  240
gggaccggga cccggagaga gaccaggaga gggacgggaa ccgcgaccgg aaccgggacc  300
gggagaggga gagagagagg gaaagagacc cggaccgagg cccccgccgg gacacacaca  360
gggacgcggg ccctcgcgca ggtgaacacg gagtttggga aaaaccgcgc caaagccgga  420
cgcgggacgg agcccgggga ctgacctggg acgcagccgc gcctcctggg cccgcgccct  480
gggaagcccc ggagccgccg cagccgcaga ggaagggaga ccccgggcgc cgcagacccg  540
aaagtgaacc cccttcggag agatatctgc cctcgacccc caggcctgga cgagaggagg  600
tggaatatta ccagtcagag gcggaaggac tcctggaatg ccacaaatgc aaatacttgt  660
gcactgggag agcctgctgc caaatgctgg aggttctcct gaacttgctg atcctggcct  720
gcagctctgt gtcttacagt tccacagggg gctacacggg catcaccagc ttgggggggca  780
tttactacta tcagttcgga ggggcttaca gtggctttga tggtgctgac ggggagaagg  840
cccagcaact ggatgtccag ttctaccagc taaagctgcc catggtcact gtggcaatgg  900
cctgtagtgg agccctcaca gccctctgct gcctcttcgt tgccatgggt gtcctgcggg  960
tcccgtggca ttgtccactg ttgctggtga ccgaaggctt gttggacatg ctcatcgcgg  1020
gggggtacat cccggccttg tacttctact tccactacct ctctgctgcc tatggctctc  1080
ctgtgtgtaa agagaggcag gcgctgtacc aaagcaaagg ctacagcggt ttcggctgca  1140
gtttccacgg agcagatata ggagctggaa tctttgctgc cctgggcatt gtggtctttg  1200
ccctgggggc tgtcctggcc ataaagggct accgaaaagt taggaagcta aaagagaagc  1260
cagcagaaat gtttgaattt taagggtttc taaaacgctc tgacagatgc aagtggtggt  1320
ggaaggtagt ctgagccact gcctttccca agaatccctt gttgtggaag tttccagtgc  1380
tggaaaagca gcgagccagc gttggtgtgg tgggcggagc tcccagtcgc atggagcggt  1440
gttcatggat gcaacagacc ctggcttctg gagtcctctg tgagtgaggg accaatcaaa  1500
attatttttc aaaaagcaaa aaaatggccg gcctcggcgg ctcacacctg taaccccagc  1560
actttgggag gctgaggtgg gtggatcact tgaggtcagg agctcgagac cagcttggcc  1620
aacatggtga gcccccgtct ctactaaaat acaaaaaaat tagccaggcg tggtggcggg  1680
```

```
cgcctgtaat cccagctact tgggaggctg aggcaggaga atcgcttgaa tctgggaggc  1740
ggagattgca gtgagccgag atcccgccac tgcactccag cccaggtgac agagcgagac  1800
tccatctcaa aaaaaaaaaa aagcaaaaaa actggacccc aagagccaca aggaaaaagc  1860
atgtactaca acagagtgca cctcttcatt cagtaaaggg aggtcaccaa gagaatttga  1920
tgaaccttac cttcaaagtt cctgggcaca gtggctcaca cctgtaatcc cagagctttg  1980
ggaggctgag gtaggaggat tgcttgaacc caggagttca agtttgcagt gcgctatgat  2040
tgtcccacta cactctagcc tgagcaacag accaagaccg tattgccaaa ataccaaaaa  2100
aaaaaaaagt tcatggagag ccacatagac atgagaccac acttcagcct gaatttttct  2160
aaaacacagt tgtctcaagc agattactcc acacgttttt ccacactgaa ctctccagtc  2220
cttccacttc cttaattctg caaatggagg gggtggggac tcttgggaaa ctactcctgt  2280
aaaattgaag ttggaggtag gcgtgggctg aggaaagagg aatcagatta attctctggg  2340
ttgcaaagag gctattctgc aagcccctta cagtggccct gaaagctcaa taagtgtttt  2400
gtacctcttg taaatgtgcc attgtgtgaa gcattaaacc caacatctag aattcaggat  2460
tcatccagaa taaaaggatg taaaatcttt cccaacagaa gagtgttact tttggtcaga  2520
caacttcatg ggttcttact gcacattaaa ttatgactta tggaacattg caatatattc  2580
tcggtcctta agttatgact tatggaacat tacaatatat tctcggtcca agtgagtaag  2640
ttctttgctt tatgtgaatc caataaaaaa tccaaagaat tttaaaaaaa aaaaaaaa    2698

SEQ ID NO: 52          moltype = DNA  length = 9701
FEATURE                Location/Qualifiers
source                 1..9701
                       mol_type = other DNA
                       organism = Homo sapiens
SEQUENCE: 52
agcccctagc gcagacggcg gagagcagag agggagcgcg ccttggctcg ctggccttgg  60
cggcggctcc tcaggagagc tggggcgccc acgagaggat ccctcacccg ggtctctcct  120
cagggatgac atcatccgtc cacctccttg tcttcaagga ccacctcctc tccatgctga  180
gctgctgcca aggggcctgc tgcccatcta cacctcacga gggcactagg agcacggttt  240
cctggatccc accaacatac aaagcagcca ctcactgacc cccaggacca ggatggcaaa  300
ggatgaagag gaccggaact gaccagccag ctgtccctct tacctaaaga cttaaaccaa  360
tgccctagtg agggggcatt gggcattaag ccctgacctt tgctatgctc atactttgac  420
tctatgagta ctttcctata agtctttgct tgtgttcacc tgctagcaaa ctggagtgtt  480
tccctcccca agggggtgtc agtctttgtc gactgactct gtcatcaccc ttatgatgtc  540
ctgaatggaa ggatcccttt gggaaattct caggaggggg acctgggcca agggcttggc  600
cagcatcctg ctggcaactc caaggccctg ggtgggcttc tggaatgagc atgctactga  660
atcaccaaag gcacgcccga cctctctgaa gatcttccta tccttttctg gggaatgggg  720
gtcgatgaga gcaacctcct agggttgttg tgagaattaa atgagataaa agaggcctca  780
ggcaggatct ggcatagagg aggtgatcag caaatgtttg ttgaaaaggt ttgacaggtc  840
agtcccttcc cacccctctt gcttgtctta cttgtcttat ttattctcca acagcactcc  900
aggcagccct tgtccacggg ctctccttgc atcagccaag cttcttgaaa ggcctgtcta  960
cacttgctgt cttccttcct cacctccaat ttcctcttca acccactgct tcctgactcg  1020
ctctactccg tggaagcacg ctcacaaagg cacgtgggcc gtggcccggc tgggtcggct  1080
gaagaactgc ggatggaagc tgcggaagag gccctgatgg ggcccaccat cccggaccca  1140
agtcttcttc ctggcgggcc tctcgtctcc ttcctggttt gggcggaagc catcacctgg  1200
atgcctacgt gggaagggac ctcgaatgtg ggaccccagc ccctctccag ctcgaaatcg  1260
gcagactagg atggaagtgc cctgtgagct ggggggccct tcaaagggcc aaggagaaaa  1320
cgcaggccga gggaccagcc ttccaaatgg gcttcaagct ccaatgacct ccgctcgccc  1380
cctcgaaatg tctggaaaac ataatgggca gattttctgt cttcaaagtt tccggctaaa  1440
cctcttcaag ttctttattg tttgggactg agacactcag ccatgttaat gggtagtttc  1500
ttttgtattt gccttgaaag gccaaaatat ttttatattg ccacagacaa agccacctat  1560
ttaaaaatga actccatgtc cgtcgtttcc caccaggaga ctatgtacca tgtgtgtgtc  1620
tctatgtatt ctggggtctt gaaacaggtt tctcatgggg atggtcattc accacggtcc  1680
agagggggcag aacaggcggc gcttgccttg cccagggggc ctggggaacg tgggccctca  1740
tctcagatct gcccccagta tgtttaggac gcgagcccca gaaggatctg ggagtaaact  1800
taacattcac tgtgtctctg ctctgcatcc gccatttgtg tgtgtttctg gactgtgggc  1860
tgtgtgtacc ttggttggtg actcagtgag aagaagcagg aatgccaaag atactgtgaa  1920
tgttctgagt tttgttgctg ttgttgttga gaggttgttt cactggtatc tattgcattg  1980
tataataaat gaccagatga atgaatgagt gaagcaagag agaatgaata aacaagtaaa  2040
taggtaaaga agtaagcaag ccaggatgag agtgtgtgta cacaagacca tggttcatcc  2100
gctttgatgg ctaggcaatc aatatataaa tagaaaaaaa ccagtgaatc actaagtaat  2160
agggcaacac acaaagcgat atcaggtgat tatggactaa ggggtatgtg taactcaaat  2220
atatgcctct gacatttgac aatgaaaaag aacctaaatg aaagaaagaa tggatgtatg  2280
agtagtgaag tgcagaatga gacatagatt ttgaggcccg tcaaaatgaa aagatgcaag  2340
ttagggaaca agtgatcaaa agggagaagg gaaaggtttt ttttaaaaaa ccaaaacaac  2400
aaagaaaggt taaaaaaaaa aacagactag aggatgagta atgagtaact ctgtaaggag  2460
gaccatgtca gactattgta agctaagcat taggactgat acaaataata tatgctcctg  2520
gcatagaaaa ataaaccaca gagaacgagt tcaaagaata gcaaagaaag aaagaggacc  2580
cagtgggcga aagatgagag tgtactttta ccaaaagtta tctaagcctg agcacttgaa  2640
gtctgcacat aaataaataa atgacaaaag aaagaaaaaa aggccaaaaa gtctacattg  2700
cgtgtgtgga tggatgaatg agcagtggga gtgcagcgcc aggtgacaag atgttgtgag  2760
gggttttgag tcatccagtc ctgggcactg aggtctgtta gatgaaagga tatgagaaag  2820
gtaatattgg taaataaaga aataggaaac aatgtaacaa atgttaagta cagaaataca  2880
ttaatgggtg gtaaataaag atgtaaaaga aggcaatgcg atcgatggtg gcaaaagatc  2940
atcacagatt aagggctatg gctggtccac ttctagaaaa ccacaggctg tccattaaat  3000
aatgaacatc taagtgaaca agtcagtgag tacctaaata gacaaggatg aggtgaatga  3060
gaagacatgg ccccatgggt cctcctgatg agggtgttgg ggtccccccct gggcacccca  3120
gctgcatgaa aatgaaggac aggaggtatg gaaagctatg acagaagaga gaaaggaacg  3180
gtaaaaagaa ataacaacca aatggataaa tgggtagatc cacgagaaga gttaggctag  3240
gacttgtcat aagggcacct gactccacta atagaggaat aaatgcctaa taaaaagaga  3300
```

-continued

```
gcaagcagga aggaaggatg ctatgaatgc aggaaggaag taatgagtga gacgtggaac  3360
cgcacggcca aggatggacg tttgcgggtg gctttttgat gcgtacagcc aagccactcc  3420
atggcaatga gctccgaaga caaagtgcaa gagagaatga gtgagagagt gagagagaga  3480
gaaacaataa aaaatgggaa gaaatgtaaa aaggaagaaa ggaagagagg taatatatta  3540
aggaataaat acatgcatgc agatttaaga cagagccatg ctagaacagg aatgaaaggc  3600
tgtgtgaacc aagcagaccg cttaattggc accagtgctg ctggtatggt caatcaccta  3660
ctcaactaag gaacggctca aagcatacac atgggaggga ggagtggggc cacagagaga  3720
gggcccatta gttgcagatt acgatgtatc cagttaggtg cacctgcctt cgagaagtgt  3780
aaaaataagt atttacatag aaagaaagac tgaatggatg cacggtgaat gcatgaatga  3840
ttgaacgaca gaaaagattt gcattgaccg atgaggaggg cattgtagac agggatgagg  3900
gtcattgatc ctgggtgcag atctccaaaa gaatgacaga aagaaagagg gagtggtgga  3960
aagaaacaat aggatgggaa aaaatgaaaa tagaaaaaag gaagtgaaag agataataaa  4020
taattagatc aaataagttg atgaaagggg actggtttag cacaagccat ccacattaat  4080
tcaaacctgt ggctctgaag tttgtttttt aaatgaccac aagtgtaaga ctgaatgaaa  4140
gaataaatgc gtgcattcca taggatgcaa gaaaaggagt gaggaatggg aaaattggaa  4200
gaacgagaga gggagagatg taagaaaaga aaggaaaagt gaagtaggca tatgaaagaa  4260
aaggcacttc ttggacaagc actgaaatat aatgagacag ttttacccat taaatataat  4320
aaacagtaaa cgttgaggtt catcaataaa agcacagata cctgaataga ggagtgacct  4380
gaatagaatt cgttcagccg aacgaatgag aatggatgat tttcactatc ctgtgcactc  4440
aaggcccaaa agagaaagca agagaggaga gaatatggaa acgtatgaca ggatgtatat  4500
aagcaataca aacatattga atgaataaat aaagacataa atatgtggga gagtggacca  4560
cgcaaggaca aaaagaggag agaaggcagc aagaattatg actaattcaa aactgggttc  4620
ctgagatagt taaataaatc ctgcaccaaa tccccagggg gagaaattaa caaacaaaag  4680
acagccccac acggaccagt gtgcagaagg ctccaggaac cgcagattat ggttaatcca  4740
attctgtgca cctgaggtcc ataaataaaa gaataagtat tgaaatgaaa gaatgacaga  4800
aagaatgaat ggacacatga acgactgaat tagaaatgga aatgcctggc acagccagga  4860
aggagctgcc catgggattg tcattcatct cactctgggc acctgaggtc cataagcgtg  4920
aaaagaggca ggaagagaag tgtcagggag tcaaagatag agctaaggaa aggcaaaaat  4980
gaaactaaat gaaagcgaaa gggaaaataa agaaaaacca ataaaaaaga gaacgaatac  5040
gtgggtgtat ctgtaagagt aggatctgtt aggattagtc ataagactgt cagtaatcct  5100
gaagatggat gagataatcc aggcccaggt tcccaggggg agggaaaatg gagaaaatat  5160
aaaaagatgt gaaaaaggaa aaaggaaagg taataaacaa acaaccaaag tgataaatgg  5220
atagttaagg gaggttgtct gaacagggat tataattagt ttacatacat actccttaaa  5280
cagataaata cattacacct ttcaaagaat aaatgaaaaa tagagagaca tacctggctc  5340
caaaacaagg ctgtatcttc tgccactgta ataaaataga tgcaattgag gttcataaat  5400
aaaagaataa atacttaaac gtgaaaggtg actaaatgcg gggaagaaag attgcaaata  5460
aatacatggg ccaaagatgt ttggtttgcc catggagttt taattaaaaa aattaataag  5520
gaaaacaaat acccaaaata aggaagactg acaaatgagt gagtggatga gagagtgaat  5580
ggtgcttgac gtaggagcag tagtgcttta gggaccagca tgaaggtggt gaccgggagc  5640
cctgattcat gggattctgt ccacctgact ttataagaac caagaatggc tgggaatggt  5700
ggctcacgcc tgtaatccca gcactttggg aggccgaggt gggcggatca tgaggtcagg  5760
agtttgagac cagccagttt gagatcagcc tggccaacat ggtgaaattc catctctact  5820
aaaaaaatac aaaaattatg ggcgtggtgg cacctgtctg taatcctagc tactcgggag  5880
gctgagagag gagaattgct tgaacccggg aggtggaggt tgtagtgagc caagattgca  5940
ccactgcact ccagcctggg ctacagagca agacactatc ttagatcaaa aaagaaaaaa  6000
aaaaaaagaa ggagaaagaa ccagagaaac ataaggaaga gtgagaggaa gaaagaaaga  6060
tgcaatttgg gaagaaatga aaaagaaatg aataaagaat aaaataatgt aacggtcaat  6120
aaataggact tgtgaatgga ggcctttagg ccaaaggcta tgattaattt caagctatgt  6180
tactgaagtc cataaacaaa ggactcagat ctaaatggat gaacgaatga ctggaagaaa  6240
gggtggtagg aaggtaggaa gaaaggaagg agggaaaaag ggaagagagg aaggaacctt  6300
ctttccagtc ctgtgttcta gacagtggaa tgaagtggtc cccagggagg gtggctgtag  6360
gcatgtcatg tgcttgtcac atgcacttgc cctggcaggg aggagctggc tcaggaagac  6420
cctggtcttg ggtgctgtt  gccctatctt ggctgtgtgg gccatttcac tgcatctgtc  6480
tcttcctcag tttccccatc tgtaaacctg gagtggcacc agctgcctac tagagttgat  6540
cttatgtgtc tctgttgatg gtaccccatc tatggcctgg ataggcagga agggcttgga  6600
ccctgagccc cgcagaaggt tgcatgaacg agtggtgtga agcctgttgg gtagcttggc  6660
cactcccgcg gcatgggtca cctgcacagg aggttttgcc caccaggggg cagcagaggg  6720
tcagggagca ataggccctg ggtggagcat gggccccgcc tgctgtgtgc caccctgggt  6780
gtggcaccta ctcacatcca ggggttggtg cagggaaagg ccagaaggtg gccaggcgca  6840
cctgagaagg gggacccaga agccccggga cccaggagcc ctgggcaagc caccagaaac  6900
cttgttcttg caactctctg cagtgtgccc aggccaccct ctggcctggt cttccatggg  6960
gcagggcgcc cacccttctc aactcaggtt tccctgggca gcaggtgcac ctcagcaccc  7020
ctggggttgc agaagtggtc cggggaccct ggcttccttg acatgccatc cccagagcct  7080
ggttcaaggc ctctctgtct tctcggctgt ttcacgacgt gttttgtaac ttggcgggat  7140
tgcgtttcgc tgtgtcgagg ttgtctcttc tctgactcgc cctccggggg actgccgggg  7200
taaatctgga gagttgctcg tgctgacagt cctcccccag ggcctccccg gttctgttga  7260
gtctcctttc tctgtagtgg aggaaatgtg tgtagttttg tgttgtgtgc ctgtgtttgt  7320
ctgtaaaagc aaggaccaaa gtctcccttg ttgacctctc aattcctatt tgggacatat  7380
aaaaacactg gattcttaac aagcgcccgg agcagtagga gcacagcttg gatggactca  7440
ggacttgtgg cagggagcac gtgggaggca ggggagtggg gtggggccag gccatctgga  7500
gtgggaggcg tcatgctcag agtgactctg tagacgctgg gtgggatggg gagtgcgggc  7560
gcaggcatgg atggggctgt tagctagtgt gatgcttgag gtctgagctg atggcagcaa  7620
agtggggtgc tcaggaatca aagctatggg gttatagaca ggatatgaag gagggaggga  7680
ggcaagaaga agggggtggt tcccacgctt ctagctccgg ccgagtggat ggcaacagca  7740
tttggaaggc ggaggacatg gaattcatgt gtcaggagcc accttccgag cctccagtac  7800
cacgtgtcag ggccacatga gctgggcctc gtgggcctga tgtggtgctg ggcctcagg   7860
ggtctgctct tcttctcttt cagaatctgg ggctccaggc tatgccttgg ctggactgag  7920
gtctggggt  gcacttatta tccctgggga cacctgctga agcttctccc tgacaagctg  7980
tgtcactgtt ggatgaggat ggggcgggag gggttcaggg cagaagaaga ccgggagggt  8040
```

```
ctttcaaaag aactcatgta cggctgttaa aaaaagtcag cagaggctca ggaagactta  8100
aagtgtgcag aaggcgggga agggagggcc cattgcatgc accaagagga aattggaagg  8160
aacaagcgac gttggctgct aggagagcct gctcccaaca tctaggggct gtcctgacgg  8220
gtcacagtgg gtcgaactga gccaatgaga gcagctctgg ggagacccac tggtgccctg  8280
gaggctgggt gggtttgggt tggatgaatt ctgtgtgtcc ttttggaaat gtggaggcca  8340
tgagggggga tcagggctct tagggttttg acccttaaga gttttgtatc tgtaattcaa  8400
aggttcttta gttctgggat gctgagattc gggatagggt tcctaatggc acaaaagcca  8460
gagataaaac atccttcacg tgctccctac ccggttcttt ctgtaccaga cccacaaggt  8520
ccgagttggg atcctagtgc tcctgtctgg tcagggccta tctttatgtg ttcgttaaac  8580
ttttaacaat gagaattaat tctgtctctt gacattgtca tttgcatgct ccccacacac  8640
aaatcctttc ctggtgacac caggagctac aactctcctt ggcctcctct tgtgactccc  8700
aactccctcc ttgggaagct tggcctcagg acctctggga tagacaggcc acgaatcctg  8760
ctgtgtcccg ttgtgttcct aatataaatg gtgtggatgg cacttgacct agagcagtgg  8820
gaaatgcatg caccactcaa cattctgaca tgtcacccat tttacattct tacaggcata  8880
cttttttaa aaaaagagtg tctattcttt aatgagcatc ccttctttaa aaaaacctaa  8940
ttgccattat tcaccacata cacttttttt tttttgtatc ctgcctcttc tatttaattt  9000
tctgtcatca acattttccc ttgttccatg aatcttcata acctcacttg ctgcgttgtg  9060
ccttgttgag tggctatggc atcattcaca gaaccattct gttattctta tgtataacca  9120
ccttttaaaa atattatgaa taatgccaca actaactgct taaaacaccc ttttttttcat  9180
tcttaagaat tatgttcttc cacccagaaa ttatcattgc ttcactacag atcagtttcc  9240
cctgctagac tgtgagcccc ataagggcaa ggagcttatt gaattggcct ttgtatctct  9300
gatgcccaac atgttgtaga ctataaataa atgatgaatg agtggatgga agaatggagg  9360
aaggagcgag tgagtgagtg tttggctgat ggataagagg gtggaaggat aggcggaagg  9420
atggattggt gaatgaatga atgaatttcc tttggttaag tctcttgaaa gaaaggctat  9480
ggatctttgt atggatgttg aataatttca gtaagcttac agcattttac aatgttcagc  9540
aatgtatgac cacttaatta agatatggct agtttgtctc tgttataaag tacttttgca  9600
ttactttaac ttgcattgct ttaattacta atgatgggtg aacactttga cctatgtttg  9660
ttaacaaatt gtattttatc ttctgtgaaa aaaaaaaaaa a                      9701

SEQ ID NO: 53          moltype = DNA  length = 2879
FEATURE                Location/Qualifiers
source                 1..2879
                       mol_type = other DNA
                       organism = Homo sapiens
SEQUENCE: 53
atcatttcct cctcagatta ccaagcaaga acagctaaaa tgaaagccat cattcatctt  60
actcttcttg ctctcctttc tgtaaacaca gccaccaacc aaggcaactc agctgatgct  120
gtaacaacca cagaaactgc gactagtggt cctacagtag ctgcagctga taccactgaa  180
actaatttcc ctgaaactgc tagcaccaca gcaaatacac cttctttccc aacagctact  240
tcacctgctc cccccataat tagtacacat agttcctcca caattcctac acctgctccc  300
cccataatta gtacacatag ttcctccaca attcctatac ctactgctgc agacagtgag  360
tcaaccacaa atgtaaattc attagctacc tctgacataa tcaccgcttc atctccaaat  420
gatggattaa tcacaatggt tccttctgaa acacaaagta acaatgaaat gtcccccacc  480
acagaagaca atcaatcatc agggcctccc actggcaccg ctttattgga gaccagcacc  540
ctaaacagca caggtcccag caatccttgc caagatgatc cctgtgcaga taattcgtta  600
tgtgttaagc tgcataatac aagtttttgc ctgtgtttag aagggtatta ctacaactct  660
tctacatgta agaaaggaaa ggtattccct gggaagattt cagtgacagt atcagaaaca  720
tttgacccag aagagaaaca ttccatggcc tatcaagact tgcatagtga aattactagc  780
ttgtttaaag atgtatttgg cacatctgtt tatggacaga ctgtaattct tactgtaagc  840
acatctctgt caccaagatc tgaaatgcgt gctgatgaca agtttgttaa tgtaacaata  900
gtaacaattt tggcagaaac cacaagtgac aatgagaaga ctgtgactga gaaaattaat  960
aaagcaatta gaagtagctc aagcaacttt ctaaactatg atttgaccct tcggtgtgat  1020
tattatggct gtaaccagac tgcggatgac tgcctcaatg gtttagcatg cgattgcaaa  1080
tctgacctgc aaaggcctaa cccacagagc cctttctgcg ttgcttccag tctcaagtgt  1140
cctgatgcct gcaacgcaca gcacaagcaa tgcttaataa agaagagtgg tggggcccct  1200
gagtgtgcgt gcgtgcccgg ctaccaggaa gatgctaatg ggaactgcca aaagtgtgca  1260
tttggctaca gtggactcga ctgtaaggac aaatttcagc tgatcctcac tattgtgggc  1320
accatcgctg gcattgtcat tctcagcatg ataattgcat tgattgtcac agcaagatca  1380
aataacaaaa cgaagcatat tgaagaagag aacttgattg acgaagactt tcaaaatcta  1440
aaactgcggt cgacaggctt caccaatctt ggagcagaag ggagcgtctt tcctaaggtc  1500
aggataacgg cctccagaga cagccagatg caaaatccct attcaagaca cagcagcatg  1560
ccccgccctg actattagaa tcataagaat gtggaacccg ccatggcccc caaccaatgt  1620
acaagctatt atttagagtg tttagaaaga ctgatggaga agtgagcacc agtaaagatc  1680
tggcctccgg ggtttttctt ccatctgaca tctgccagcc tctctgaatg gaagttgtga  1740
atgtttgcaa cgaatccagc tcacttgcta aataagaatc tatgacatta aatgtagtag  1800
atgctattag cgcttgtcag agaggtggtt ttcttcaatc agtacaaagt actgagacaa  1860
tggttagggt tgttttctta attcttttcc tggtagggca acaagaacca tttccaatct  1920
agaggaaagc tccccagcat tgcttgctcc tgggcaaaca ttgctcttga gttaagtgac  1980
ctaattcccc tgggagacat acgcatcaac tgtggaggtc cgaggggatg agaagggata  2040
cccaccatct ttcaagggtc acaagctcac tctctgacaa gtcagaatag ggacactgct  2100
tctatccctc caatggagag attctggcaa cctttgaaca gcccagagct tgcaacctag  2160
cctcacccaa gaagactgga aagagacata tctctcagct tttcaggag gcgtgcctgg  2220
gaatccagga actttttgat gctaattaga aggcctggac taaaaatgtc cactatgggg  2280
tgcactctac agtttttgaa atgctaggag gcagaagggg cagagagtaa aaaacatgac  2340
ctggtagaag gaagagaggc aaaggaaact gggtggggag gatcaattag agaggaggca  2400
cctgggatcc accttcttcc ttaggtcccc tcctccatca gcaaaggagc acttctctaa  2460
tcatgccctc ccgaagactg gctgggagaa ggtttaaaaa caaaaaatcc aggagtaaga  2520
gccttaggtc agtttgaaat tggagacaaa ctgtctggca aagggtgcga gagggagctt  2580
gtgctcagga gtccagccgt ccagcctcgg ggtgtaggtt tctgaggtgt gccattgggg  2640
```

```
cctcagcctt ctctggtgac agaggctcag ctgtggccac caacacacaa ccacacacac  2700
acaaccacac acacaaatgg gggcaaccac atccagtaca agcttttaca aatgttatta  2760
gtgtcctttt ttatttctaa tgccttgtcc tcttaaaagt tattttattt gttattatta  2820
tttgttcttg actgttaatt gtgaatggta atgcaataaa gtgcctttgt tagatggtg   2879

SEQ ID NO: 54          moltype = DNA  length = 43816
FEATURE                Location/Qualifiers
source                 1..43816
                       mol_type = other DNA
                       organism = Homo sapiens
SEQUENCE: 54
aagcgttgca caattccccc aacctccata catacggcag ctcttctaga cacaggtttt  60
cccaggtcaa atgcggggac cccagccata tctcccaccc tgagaaattt tggagtttca  120
gggagctcag aagctctgca gaggccaccc tctctgaggg gattcttctt agacctccat  180
ccagaggcaa atgttgacct gtccatgctg aaaccctcag gccttcctgg gtcatcttct  240
cccacccgct ccttgatgac agggagcagg agcactaaag ccacaccaga aatggattca  300
ggactgacag gagccacctt gtcacctaag acatctacag gtgcaatcgt ggtgacagaa  360
catactctgc cctttacttc cccagataag accttggcca gtcctacatc ttcggttgtg  420
ggaagaacca cccagtcttt gggggtgatg tcctctgctc tccctgagtc aacctctaga  480
ggaatgacac actccgagca aagaaccagc ccatcgctga gtccccaggt caatggaact  540
ccctctagga actaccctgc tacaagcatg gtttcaggat tgagttcccc aaggaccagg  600
accagttcca cagaaggaaa ttttaccaaa gaagcatcta catacacact cactgtagag  660
accacaagtg gcccagtcac tgagaagtac acagtcccca ctgagacctc aacaactgaa  720
ggtgacagca cagagacccc ctgggacaca agatatattc ctgtaaaaat cacatctcca  780
atgaaaacat ttgcagattc aactgcatcc aaggaaaatg ccccagtgtc tatgactcca  840
gctgagacca cagttactga ctcacatact ccaggaagga caaacccatc atttgggaca  900
ctttattctt ccttccttga cctatcacct aaagggaccc caaattccag aggtgaaaca  960
agcctggaac tgattctatc aaccactgga tatcccttct cctctcctga acctggctct  1020
gcaggacaca gcagaataag taccagtgcg cctttgtcat catctgcttc agttctcgat  1080
aataaaatat cagagaccag catattctca ggccagagtc tcacctcccc tctgtctcct  1140
ggggtgcccg aggccagagc cagcacaatg cccaactcag ctatcccttt ttccatgaca  1200
ctaagcaatg cagaaacaag tgccgaaagg gtcagaagca caatttcctc tctggggact  1260
ccatcaatat ccacaaagca gacagcagag actatcctta ccttccatgc cttcgctgag  1320
accatggata tacccagcac ccacatagcc aagactttgg cttcagaatg gttgggaagt  1380
ccaggtaccc ttggtggcac cagcacttca gcgctgacaa ccacatctcc atctaccact  1440
ttagtctcag aggagaccaa cacccatcac tccacgagtg gaaaggaaac agaaggaact  1500
ttgaatacat ctatgactcc acttgagacc tctgctcctg gagaagagtc cgaaatgact  1560
gccaccttgg tccccactct aggttttaca actcttgaca gcaagatcag aagtccatct  1620
caggtctctt catcccaccc aacaagagag ctcagaacca caggcagcac ctctgggagg  1680
cagagttcca gcacagctgc ccacgggagc tctgacatcc tgagggcaac cacttccagc  1740
acctcaaaag catcatcatg gaccagtgaa agcacagctc agcaatttag tgaaccccag  1800
cacacacagt gggtggagac aagtcctagc atgaaaacag agagaccccc agcatcaacc  1860
agtgtggcag cccctatcac cacttctgtt ccctcagtgg tctctggctt caccaccctg  1920
aagaccagct ccacaaaagg gatttggctt gaagaaacat ctgcagacac actcatcgga  1980
gaatccacag ctggcccaac cacccatcag tttgctgttc ccactgggat ttcaatgaca  2040
ggaggcagca gcaccagggg aagccagggc acaacccacc tactcaccag agccacagca  2100
tcatctgaga catccgcaga tttgactctg gccacgaacg gtgtcccagt ctccgtgtct  2160
ccagcagtga gcaagacggc tgctggctca agtcctccag gagggacaaa gccatcatat  2220
acaatggttt cttctgtcat ccctgagaca tcatctctac agtcctcagc tttcagggaa  2280
ggaaccagcc tgggactgac tccattaaac actagacatc ccttctcttc ccctgaacca  2340
gactctgcag gacacaccaa gataagcacc agcattcctc tgttgtcatc tgcttcagtt  2400
cttgaggata aagtgtcagc gaccagcaca ttctcacacc acaaagccac ctcatctatt  2460
accacaggga ctcctgaaat ctcaacaaag acaaagccca gctcagccgt tctttcctcc  2520
atgaccctaa gcaatgcagc aacaagtcct gaaagagtca gaaatgcaac ttcccctctg  2580
actcatccat ctccatcagg ggaagagaca gcagggagtg tcctcactct cagcacctct  2640
gctgagacta cagactcacc taacatccac ccaactggga cactgacttc agaatcgtca  2700
gagagtccta gcactctcag cctcccaagt gtctctggag tcaaaaccac atttcttca   2760
tctactcctt ccactcatct atttactagt ggagaagaaa cagaggaaac ttcgaatcca  2820
tctgtgtctc aacctgagac ttctgtttcc agagtaagga ccaccttggc cagcacctct  2880
gtccctaccc cagtattccc caccatggac acctggccta cacgttcagc tcagttctct  2940
tcatcccacc tagtgagtga gctcagagct acgagcagta cctcagttac aaactcaact  3000
ggttcagctc ttcctaaaat atctcacctc actgggacgg caacaatgtc acagaccaat  3060
agagacacgt ttaatgactc tgctgcaccc caaagcacaa cttggccaga gactagtccc  3120
agattcaaga cagggttacc ttcagcaaca accactgttt caacctctgc cacttctctc  3180
tctgctactg taatggtctc taaattcact tctccagcaa ctagttccat ggaagcaact  3240
tctatcaggg aaccatcaac aaccatcctc acaacagaga ccacgaatgg cccaggctct  3300
atggctgtgg cttctaccaa catcccaatt ggaaagggct acattactga aggaagattg  3360
gacacaagcc atctgcccat tggaaccaca gcttcctctg agacatctat ggattttacc  3420
atggccaaag aaagtgtctc aatgtcagta tctccatctc agtccatgga tgctgctggc  3480
tcaagcactc caggaaggac aagccaattc gttgacacat tttctgatga tgtctatcat  3540
ttaacatcca gagaaattac aatacctaga gatggaacaa gctcagctct gactccacaa  3600
atgactgcaa ctcaccctcc atctcctgat cctggctctg ctagaagcac ctggcttggc  3660
atcttgtcct catctccttc ttctcctact cccaaagtca caatgagctc cacattttca  3720
actcagagag tcaccacaag catgataatg gacacagttg aaactagtcg gtggaacatg  3780
cccaacttac cttccacgac ttccttgaca ccaagtaata ttccaacaag tggtgccata  3840
ggaaaaagca ccctggttcc cttggacact ccatctccag ccacatcatt ggaggcatca  3900
gaagggggac ttccaaccct cagcacctac cctgaatcaa caaacacacc cagcatccac  3960
ctcggagcac acgctagttc agaaagtcca agcaccatca aacttaccat ggcttcagta  4020
gtaaaacctg gctcttacac acctctcacc ttcccctcaa tagagaccca cattcatgta  4080
```

```
tcaacagcca gaatggctta ctcttctggg tcttcacctg agatgacagc tcctggagag  4140
actaacactg gtagtacctg ggaccccacc acctacatca ccactacgga tcctaaggat  4200
acaagttcag ctcaggtctc tacaccccac tcagtgagga cactcagaac cacagaaaac  4260
catccaaaga cagagtccgc caccccagct gcttactctg gaagtcctaa aatctcaagt  4320
tcacccaatc tcaccagtcc ggccacaaaa gcatggacca tcacagacac aactgaacac  4380
tccactcaat tacattacac aaaattggca gaaaaatcat ctggatttga gacacagtca  4440
gctccaggac ctgtctctgt agtaatccct acctccccta ccattggaag cagcacattg  4500
gaactaactt ctgatgtccc aggggaaccc ctggtccttg ctcccagtga gcagaccaca  4560
atcactctcc ccatggcaac atggctgagt accagtttga cagaggaaat ggcttcaaca  4620
gaccttgata tttcaagtcc aagttcaccc atgagtacat ttgctatttt tccacctatg  4680
tccacacctt ctcatgaact ttcaaagtca gaggcagata ccagtgccat tagaaataca  4740
gattcaacaa cgttggatca gcacctagga atcaggagtt tgggcagaac tggggactta  4800
acaactgttc ctatcacccc actgacaacc acgtggacca gtgtgattga acactcaaca  4860
caagcacagg acaccctttc tgcaacgatg agtcctactc acgtgacaca gtcactcaaa  4920
gatcaaacat ctataccagc ctcagcatcc ccttcccatc ttactgaagt ctaccctgag  4980
ctcgggacac aagggagaag ctcctctgag gcaaccactt tttggaaacc atctacagac  5040
acactgtcca gagagattga gactggccca acaaacattc aatccactcc acccatggac  5100
aacacaacaa cagggagcag tagtagtgga gtcaccctgg gcatagccca ccttcccata  5160
ggaacatcct ccccagctga gacatccaca aacatggcac tggaaagaag aagttctaca  5220
gccactgtct ctatggctgg gacaatggga ctccttgtta ctagtgctcc aggaagaagc  5280
atcagccagt cattaggaag agtttcctct gtcctttctg agtcaactac tgaaggagtc  5340
acagattcta gtaagggaag cagcccaagg ctgaacacac agggaaatac agctctctcc  5400
tcctctcttg aacccagcta tgctgaagga agccagatga gcacaagcat ccctctaacc  5460
tcatctccta caactcctga tgtggaattc ataggggggca gcacattttg gaccaaggag  5520
gtcaccacag ttatgacctc agacatctcc aagtcttcag caaggacaga gtccagctca  5580
gctaccctta tgtccacagc tttgggaagc actgaaaata caggaaaaga aaaactcaga  5640
actgcctcta tggatcttcc atctccaact ccatcaatgg aggtgacacc atggatttct  5700
ctcactctca gtaatgcccc caataccaca gattcacttg acctcagcca tggggtgcac  5760
accagctctg cagggacttt ggccactgac aggtcattga atactggtgt cactagagcc  5820
tccagattgg aaaacggctc tgatacctct tctaagtccc tgtctatggg aaacagcact  5880
cacacttcca tgacttacac agagaagagt gaagtgtctt cttcaatcca tccccgacct  5940
gagacctcag ctcctggagc agagaccact ttgacttcca ctcctggaaa cagggccata  6000
agcttaacat tgccttttc atccattcca gtggaagaag tcatttctac aggcataacc  6060
tcaggaccag acatcaactc agcacccatg acacattctc ccatcacccc accaacaatt  6120
gtatggacca gtacaggcac aattgaacag tccactcaac cactacatgc agtttcttca  6180
gaaaaagttt ctgtgcagac acagtcaact ccatatgtca actctgtggc agtgtctgct  6240
tcccctaccc atgagaattc agtctcttct ggaagcagca catcctctcc atattcctca  6300
gcctcacttg aatccttgga ttccacaatc agtaggagga atgcaatcac ttcctggcta  6360
tgggacctca ctacatctct ccccactaca acttggccaa gtactagttt atctgaggca  6420
ctgtcctcag gccattctgg ggtttcaaac ccaagttcaa ctacgactga atttccactc  6480
ttttcagctg catccacatc tgctgctaag caaagaaatc cagaaacaga gacccatggt  6540
ccccagaata cagccgcgag tactttgaac actgatgcat cctcggtcac aggtctttct  6600
gagactcctg tgggggcaag tatcagctct gaagtccctc ttccaatggc cataacttct  6660
agatcagatg tttctggcct tacatctgag agtactgcta acccgagttt aggcacagcc  6720
tcttcagcag ggaccaaatt aactaggaca atatccctgc ccacttcaga gtctttggtt  6780
tcctttagaa tgaacaagga tccatggaca gtgtcaatcc ctttggggtc ccatccaact  6840
actaatacag aaacaagcat cccagtaaac agcgcaggtc cacctggctt gtccacagta  6900
gcatcagatg taattgacac accttcagat ggggctgaga gtattcccac tgtctccttt  6960
tccccctccc ctgatactga agtgacaact atctcacatt tcccagaaaa gacaactcat  7020
tcatttagaa ccatttcatc tctcactcat gagttgactt caagagtgac acctattcct  7080
ggggattgga tgagttcagc tatgtctaca aagcccacag gagccagtcc ctccattaca  7140
ctgggagaga gaaggacaat cacctctgct gctccaacca cttcccccat agttctcact  7200
gctagtttca cagagaccag cacagtttca ctggataatg aaactacagt aaaaacctca  7260
gatatccttg acgcacggaa aacaaatgag ctccccctcag atagcagttc ttcttctgat  7320
ctgatcaaca cctccatagc ttcttcaact atggatgtca ctaaaacagc ctccatcagt  7380
cccactagca tctcaggaat gacagcaagt tcctccccat ctctcttctc ttcagataga  7440
ccccaggttc ccacatctac aacagagaca aatacagcca cctctccatc tgtttccagt  7500
aacacctatt ctcttgatgg gggctccaat gtgggtggca ctccatccac tttaccaccc  7560
tttacaatca cccaccctgt cgagacaagc tcggccctat tagcctggtc tagaccagta  7620
agaactttca gcaccatggt cagcactgac actgcctccg gagaaaatcc tacctctagc  7680
aattctgtgg tgacttctgt tccagcacca ggtacatgga ccagtgtagg cagtactact  7740
gacttacctg ccatgggctt tctcaagaca agtcctgcag gagaggcaca ctcacttcta  7800
gcatcaacta ttgaaccagc cactgccttc actccccatc tctcagcagc agtggtcact  7860
ggatccagtg ctacatcaga agccagtctt ctcactacga gtgaaagcaa agccattcat  7920
tcttcaccac agaccccaac tacaccccacc tctggagcaa actgggaaac ttcagctact  7980
cctgagagcc ttttggtagt cactgagact tcagacacaa cacttacctc aaagattttg  8040
gtcacagata ccatcttgtt ttcaactgtg tccacgccac cttctaaatt tccaagtacg  8100
gggactctgt ctggagcttc cttccctact ttactcccgg acactccagc catccctctc  8160
actgccactg agccaacaag ttcattagct acatcctttg attccacccc actggtgact  8220
atagcttcgg atagtcttgg cacagtccca gagactaccc tgaccatgtc agagacctca  8280
aatggtgatg cactggttct taagacagta agtaacccag ataggagcat ccctggaatc  8340
actatccaag gagtaacaga aagtccactc catccttctt ccacttcccc ctctaagatt  8400
gttgctccac ggaatacaac ctatgaaggt tcgatcacag tggcactttc tactttgcct  8460
gcgggaacta ctggttccct tgtattcagt cagagttctg aaaactcaga gacaacggct  8520
ttggtagact catcagctgg gcttgagagg gcatctgtga tgccactaac cacaggaagc  8580
cagggtatgg ctagctctgg aggaatcaga agtgggtcca ctcactcaac tggaaccaaa  8640
acattttctt ctctccctct gaccatgaac ccaggtgagg ttacagccat gtctgaaatc  8700
accacgaaca gactgacagc tactcaatca acagcaccca aagggatacc tgtgaagccc  8760
accagtgctg agtcaggcct cctaacacct gtctctgcct cctcaagccc atcaaaggcc  8820
```

-continued

```
tttgcctcac tgactacagc tcccccaact tgggggatcc cacagtctac cttgacattt  8880
gagttttctg aggtcccaag tttggatact aagtccgctt ctttaccaac tcctggacag  8940
tccctgaaca ccattccaga ctcagatgca agcacagcat cttcctcact gtccaagtct  9000
ccagaaaaaa acccaagggc aaggatgatg acttccacaa aggccataag tgcaagctca  9060
tttcaatcaa caggttttac tgaaacccct gagggatctg cctccccttc tatggcaggg  9120
catgaaccca gagtccccac ttcaggaaca ggggacccta gatatgcctc agagagcatg  9180
tcttatccag acccaagcaa ggcatcatca gctatgacat cgacctctct tgcatcaaaa  9240
ctcacaactc tcttcagcac aggtcaagca gcaaggtctg gttctagttc ctctcccata  9300
agcctatcca ctgagaaaga aacaagcttc ctttccccca ctgcatccac ctccagaaag  9360
acttcactat ttcttgggcc ttccatggca aggcagccca acatattggt gcatcttcag  9420
acttcagctc tgacactttc tccaacatcc actctaaata tgtcccagga ggagcctcct  9480
gagttaacct caagccagac cattgcagaa gaagagggaa caacagctga aacacagacg  9540
ttaaccttca caccatctga gaccccaaca tccttgttac ctgtctcttc tcccacagaa  9600
cccacagcca gaagaaagag ttctccagaa acatgggcaa gctctatttc agttcctgcc  9660
aagacctcct tggttgaaac aactgatgga acgctagtga ccaccataaa gatgtcaagc  9720
caggcagcac aaggaaattc cacgtggcct gccccagcag aggagacggg gagcagtcca  9780
gcaggcacat ccccaggaag cccagaaatg tctaccactc tcaaaatcat gagctccaag  9840
gaacccagca tcagcccaga gatcaggtcc actgtgagaa attctccttg gaagactcca  9900
gaaacaactg ttcccatgga gaccacagtg gaaccagtca cccttcagtc cacagcccta  9960
ggaagtggca gcaccagcat ctctcacctg cccacaggaa ccacatcacc aaccaagtca  10020
ccaacagaaa atatgttggc tacagaaagg gtctccctct ccccatcccc acctgaggct  10080
tggaccaacc tttattctgg aactccagga gggaccaggc agtcactggc cacaatgtcc  10140
tctgtctccc tagagtcacc aactgctaga agcatcacag ggactggtca gcaaagcagt  10200
ccagaactgg tttcaaagac aactggaatg gaattctcta tgtggcatgg ctctactgga  10260
gggaccacag gggacacaca tgtctctctg agcacatctt ccaatatcct tgaagaccct  10320
gtaaccagcc caaactctgt gagctcattg acagataaat ccaaacataa aaccgagaca  10380
tgggtaagca ccacagccat tccctccact gtcctgaata ataagataat ggcagctgaa  10440
caacagacaa gtcgatctgt ggatgaggct tattcatcaa ctagttcttg gtcagatcag  10500
acatctggga gtgacatcac ccttggtgca tctcctgatg tcacaaacac attatacatc  10560
acctccacag cacaaaccac ctcactagtg tctctgccct ctggagacca aggcattaca  10620
agcctcacca atccctcagg aggaaaaaca agctctgcgt catctgtcac atctccttca  10680
atagggcttg agactctgag ggccaatgta agtgcagtga aaagtgacat tgcccctact  10740
gctgggcatc tatctcagac ttcatctcct gcggaagtga gcatcctgga cgtaaccaca  10800
gctcctactc caggtatctc caccaccatc accaccatgg gaaccaactc aatctcaact  10860
accacaccca acccagaagt gggtatgagt accatggaca gcaccccggc cacagagagg  10920
cgcacaactt ctacagaaca cccttccacc tggtcttcca cagctgcatc agattcctgg  10980
actgtcacag acatgacttc aaacttgaaa gttgcaagat ctcctggaac aatttccaca  11040
atgcatacaa cttcattctt agcctcaagc actgaattag actccatgtc tactccccat  11100
ggccgtataa ctgtcattgg aaccagcctg gtcactccat cctctgatgc ttcagctgta  11160
aagacagaga ccagtacaag tgaaagaaca ttgagtcctt cagacacaac tgcatctact  11220
cccatctcaa ctttttctcg tgtccagagg atgagcatct cagttcctga cattttaagt  11280
acaagttgga ctcccagtag tacagaagca gaagatgtgc ctgtttcaat ggtttctaca  11340
gatcatgcta gtacaaagac tgacccaaat acgcccctgt ccacttttct gtttgattct  11400
ctgtccactc ttgactggga cactgggaga tctctgtcat cagccacagc cactacctca  11460
gctcctcagg gggccacaac tccccaggaa ctcactttgg aaaccatgat cagcccagct  11520
acctcacagt tgcccttctc tatagggcac attacaagtg cagtcacacc agctgcaatg  11580
gcaaggagct ctggagttac tttttcaaga ccagatccca caagcaaaaa ggcagagcag  11640
acttccactc agcttcccac caccacttct gcacatccag ggcaggtgcc cagatcagca  11700
gcaacaactc tggatgtgat cccacacaca gcaaaaactc cagatgcaac ttttcagaga  11760
caagggcaga cagctcttac aacagaggca agagctacat ctgactcctg gaatgagaaa  11820
gaaaaatcaa ccccaagtgc accttggatc actgagatga tgaattctgt ctcagaagat  11880
accatcaagg aggttaccag ctcctccagt gtattaagga ccctgaatac gctggacata  11940
aacttggaat ctgggacgac ttcatcccca agttggaaaa gcagcccata tgagagaatt  12000
gccccttctg agtccaccac agacaaagag gcaattcacc cttctacaaa cacagtagag  12060
accacaggct gggtcacaag ttccgaacat gcttctcatt ccactatccc agcccactca  12120
gcgtcatcca aactcacatc tccagtggtt acaacctcca ccagggaaca agcaatagtt  12180
tctatgtcaa caaccacatg gccagagtct acaagggcta gaacagagcc taattccttc  12240
ttgactattg aactgaggga cgtcagccct tacatggaca ccagctcaac cacacaaaca  12300
agtattatct cttccccagg ttccactgcg atcaccaagg ggcctagaac agaaattacc  12360
tcctctaaga gaatatccag ctcattcctt gcccagtcta tgaggtcgtc agacagcccc  12420
tcagaagcca tcaccaggct gtctaacttt cctgccatga cagaatctgg aggaatgatc  12480
cttgctatgc aaacaagtcc acctggcgct acatcactaa gtgcacctac tttggataca  12540
tcagccacag cctcctggac agggactcca ctggctacga ctcagagatt tacatactca  12600
gagaagacca ctctctttag caaaggtcct gaggatacat cacagccaag ccctccctct  12660
gtggaagaaa ccagctcttc ctcttccctg gtacctatcc atgctacaac ctcgccttcc  12720
aatattttgt tgacatcaca aggcacagt ccctcctcta ctccacctgt gacctcagtt  12780
ttcttgtctg agacctctgg cctggggaag accacagaca tgtcgaggat aagcttggaa  12840
cctggcacaa gtttacctcc caatttgagc agtacagcag gtgaggcgtt atccacttat  12900
gaagcctcca gagatacaaa ggcaattcat cattctgcag acacagcagt gacgaatatg  12960
gaggcaacca gttctgaata ttctcctatc ccaggccata caaagccatc caaagccaca  13020
tctccattgg ttacctccca catcatgggg gacatcactt cttccacatc agtatttggc  13080
tcctccgaga ccacagagat tgagacagtg tcctctgtga accagggact tcaggagaga  13140
agcacatccc aggtggccag ctctgctaca gagacaagca ctgtcattac ccatgtgtct  13200
agtggtgatg ctactactca tgtcaccaag acacaagcca ctttctctag cggaacatcc  13260
atctcaagcc ctcatcagtt tataacttct accaacacat ttacagatgt gagcaccaac  13320
ccctccacct ctctgataat gacagaatct tcaggagtga ccatcaccac ccaaacaggt  13380
cctactggag ctgcaacaca gggtccatat ctcttggaca catcaaccat gccttacttg  13440
acagagactc cattagctgt gactccagat tttatgcaat cagagaagac cactctcata  13500
agcaaaggtc ccaaggatgt gtcctggaca agccctccct ctgtggcaga aaccagctat  13560
```

-continued

```
ccctcttccc tgacaccttt cttggtcaca accatacctc ctgccacttc cacgttacaa  13620
gggcaacata catcctctcc tgtttctgcg acttcagttc ttacctctgg actggtgaag  13680
accacagata tgttgaacac aagcatggaa cctgtgacca attcacctca aaatttgaac  13740
aatccatcaa atgagatact ggccactttg gcagccacca cagatataga gactattcat  13800
ccttccataa acaaagcagt gaccaatatg ggactgccca gttcagcaca tgtactgcat  13860
tccactctcc cagtcagctc agaaccatct acagccacat ctccaatggt tcctgcctcc  13920
agcatggggg acgctcttgc ttctatatca atacctggtt ctgagaccac agacattgag  13980
ggagagccaa catcctccct gactgctgga cgaaaagaga acagcaccct ccaggagatg  14040
aactcaacta cagagtcaaa catcatcctc tccaatgtgt ctgtgggggc tattactgaa  14100
gccacaaaaa tggaagtccc ctcttttgat gcaacattca taccaactcc tgctcagtca  14160
acaaagttcc cagatatttt ctcagtagcc agcagtagac tttcaaactc tcctcccatg  14220
acaatatcta cccacatgac caccacccag acagggtctt ctggagctac atcaaagatt  14280
ccacttgcct tagacacatc aaccttggaa acctcagcag ggactccatc agtggtgact  14340
gaggggtttg cccactcaaa aataaccact gcaatgaaca atgatgtcaa ggacgtgtca  14400
cagacaaacc ctccctttca ggatgaagcc agctctccct cttctcaagc acctgtcctt  14460
gtcacaacct taccttcttc tgttgctttc acaccgcaat ggcacagtac ctcctctcct  14520
gtttctatgt cctcagttct tacttcttca ctggtaaaga ccgcaggcaa ggtggataca  14580
agcttagaaa cagtgaccag ttcacctcaa agtatgagca acactttgga tgacatatcg  14640
gtcacttcag cagccaccac agatatagag acaacgcatc cttccataaa cacagtagtt  14700
accaatgtgg ggaccaccgg ttcagcattt gaatcacatt ctactgtctc agcttaccca  14760
gagccatcta aagtcacatc tccaaatgtt accacctcca ccatggaaga caccacaatt  14820
tccagatcaa tacctaaatc ctctaagact acaagaactg agactgagac aacttcctcc  14880
ctgactccta aactgaggga gaccagcatc tcccaggaga tcacctcgtc cacagagaca  14940
agcactgttc cttacaaaga gctcactggt gccactaccg aggtatccag gacagatgtc  15000
acttcctcta gcagtacatc cttccctggc cctgatcagt ccacagtgtc actagacatc  15060
tccacagaaa ccaacaccag gctgtctacc tccccaataa tgacagaatc tgcagaaata  15120
accatcacca cccaaacagg tcctcatggg gctacatcac aggatacttt taccatggac  15180
ccatcaaata caacccccca ggcagggatc cactcagcta tgactcatgg attttcacaa  15240
ttggatgtga ccactcttat gagcagaatt ccacaggatg tatcatggac aagtcctccc  15300
tctgtggata aaaccagctc cccctcttcc tttctgtcct cacctgcaat gaccacacct  15360
tccctgattt cttctacctt accagaggat aagctctcct ctcctatgac ttcacttctc  15420
acctctggcc tagtgaagat tacagacata ttacgtacac gcttggaacc tgtgaccagc  15480
tcacttccaa atttcagcag cacctcagat aagatactgg ccacttctaa agacagtaaa  15540
gacacaaagg aaatttttcc ttctataaac acagaagaga ccaatgtgaa agccaacaac  15600
tctggacatg aatcccattc ccctgcactg gctgactcag agacacccaa agccacaact  15660
caaatggtta tcaccaccac tgtgggagat ccagctcctt ccacatcaat gccagtgcat  15720
ggttcctctg agactacaaa cattaagaga gagccaacat atttcttgac tcctagactg  15780
agagagacca gtacctctca ggagtccagc tttcccacgg acacaagttt tctactttcc  15840
aaagtcccca ctggtactat tactgaggtc tccagtacag ggtcaactc  ttctagcaaa  15900
atttccaccc cagaccatga taagtccaca gtgccacctg acaccttcac aggagagatc  15960
cccagggtct tcacctcctc tattaagaca aaatctgcag aaatgacgat caccacccaa  16020
gcaagtcctc ctgagtctgc atcgcacagt acccttccct tggacacatc aaccacactt  16080
tcccagggag ggactcattc aactgtgact cagggattcc catactcaga ggtgaccact  16140
ctcatgggca tgggtcctgg gaatgtgtca tggatgacaa ctccccctgt ggaagaaacc  16200
agctctgtgt cttccctgat gtcttcacct gccatgacat ccccttctcc tgtttcctcc  16260
acatcaccac agagcatccc ctcctctcct cttcctgtga ctgcacttcc tacttctgtt  16320
ctggtgacaa ccacagatgt gttgggcaca acaagcccag agtctgtaac cagttcacct  16380
ccaaatttga gcagcatcac tcatgagaga ccggccactt acaaagacac tgcacacaca  16440
gaagccgcca tgcatcattc cacaaacacc gcagtgacca atgtagggac ttccgggtct  16500
ggacataaat cacaatcctc tgtcctagct gactcagaga catcgaaagc cacacctctg  16560
atgagtacca cctccaccct gggggacaca agtgtttcca catcaactcc taatatctct  16620
cagactaacc aaattcaaac agagccaaca gcatccctga gccctagact gagggagagc  16680
agcacgtctg agaagaccag ctcaacaaca gagacaaata ctgccttttc ttatgtgccc  16740
acaggtgcta ttactcaggc ctccagaaca gaaatctcct ctagcagaac atccatctca  16800
gaccttgatc ggcccacaat agcacccgac atctccacag gaatgatcac caggctcttc  16860
acctccccca tcatgacaaa atctgcagaa atgaccgtca ccactcaaac aactactcct  16920
ggggctacat cacagggtat ccttccctgg gacacatcaa ccacactttt ccagggaggg  16980
actcattcaa ccgtgtctca gggattccca cactcagaga taaccactct tcggagcaga  17040
acccctggag atgtgtcatg gatgacaact ccccctgtgg aagaaaccag ctctgggttt  17100
tccctgatgt caccttccat gacatcccct tctcctgttt cctccacatc accagagagc  17160
atcccctcct ctcctctccc tgtgactgca cttcttactt ctgttctggt gacaaccaca  17220
aatgtattgg gcacaacaag cccagagccc gtaacgagtt cacctccaaa tttaagcagc  17280
cccacacagg agagactgac cacttacaaa gacactgcgc acacagaagc catgcatgct  17340
tccatgcata caaacactgc agtggccaac gtggggacct ccatttctgg acatgaatca  17400
caatcttctg tcccagctga ttcacacaca tccaaagcca catctccaat gggtatcacc  17460
ttcgccatgg gggatacaag tgtttctaca tcaactcctg ccttctttga gactagaatt  17520
cagactgaat caacatcctc tttgattcct ggattaaggg acaccaggac gtctgaggag  17580
atcaacactg tgacagagac cagcactgtc ctttcagaag tgcccactac tactactact  17640
gaggtctcca ggacagaagt tatcacttcc agcagaacaa ccatctcagg gcctgatcat  17700
tccaaaatgt caccctacat ctccacagaa accatcacca ggctctccac ttttcctttt  17760
gtaacaggat ccacagaaat ggccatcacc aaccaaacag gtcctatagg gactatctca  17820
caggctaccc ttaccctgga cacatcaagc acagcttcct gggaagggac tcactcacct  17880
gtgactcaga gatttccaca ctcagaggag accactacta tgagcagaag tactaagggc  17940
gtgtcatggc aaagccctcc ctctgtggaa gaaaccagtt ctccttcttc cccagtgcct  18000
ttacctgcaa taacctcaca ttcatctctt tattccgcag tatcaggaag tagcccccact  18060
tctgctctcc cctgtgacttc ccttctcacc tctggcagga ggaagaccat agacatgttg  18120
gacacacact cagaacttgt gaccagctcc ttaccaagtg caagtagctt ctcaggtgag  18180
atactcactt ctgaagcctc cacaaataca gagacaattc acttttcaga gaacacagca  18240
gaaaccaata tggggaccac caattctatg cataaactac attcctctgt ctcaatccac  18300
```

-continued

```
tcccagccat ccggacacac acctccaaag gttactggat ctatgatgga ggacgctatt  18360
gtttccacat caacacctgg ttctcctgag actaaaaatg ttgacagaga ctcaacatcc  18420
cctctgactc ctgaactgaa agaggacagc accgccctgg tgatgaactc aactacagag  18480
tcaaacactg ttttctccag tgtgtccctg gatgctgcta ctgaggtctc cagggcagaa  18540
gtcacctact atgatcctac attcatgcca gcttctgctc agtcaacaaa gtccccagac  18600
atttcacctg aagccagcag cagtcattct aactctcctc ccttgacaat atctacacac  18660
aagaccatcg ccacacaaac aggtccttct ggggtgacat ctcttggcca actgaccctg  18720
gacacatcaa ccatagccac ctcagcagga actccatcag ccagaactca ggattttgta  18780
gattcagaaa caaccagtgt catgaacaat gatctcaatg atgtgttgaa gacaagccct  18840
ttctctgcag aagaagccaa ctctctctct tctcaggcac ctctccttgt gacaacctca  18900
ccttctcctg taacttccac attgcaagag cacagtacct cctctcttgt ttctgtgacc  18960
tcagtaccca cccctacact ggcgaagatc acagacatgg acacaaactt agaacctgtg  19020
actcgttcac ctcaaaattt aaggaacacc ttggccactt cagaagccac cacagataca  19080
cacacaatgc atccttctat aaacacagca gtggccaatg tggggaccac cagttcacca  19140
aatgaattct attttactgt ctcacctgac tcagacccat ataaagccac atccgcagta  19200
gttatcactt ccacctcggg ggactcaata gtttccacat caatgcctag atcctctgcg  19260
atgaaaaaga ttgagtctga gacaactttc tccctgatat ttagactgag ggagactagc  19320
acctcccaga aaattggctc atcctcagac acaagcacgg tctttgacaa agcattcact  19380
gctgctacta ctgaggtctc cagaacagaa ctcacctcct ctagcagaac atccatccaa  19440
ggcactgaaa agcccacaat gtcaccggac acctccacaa gatctgtcac catgctttct  19500
acttttgctg gcctgacaaa atccgaagaa aggaccattg ccacccaaac aggtcctcat  19560
agggcgacat cacagggtac ccttacctgg gacacatcaa tcacaacctc acaggcaggg  19620
acccactcag ctatgactca tggattttca caattagatt tgtccactct tacgagtaga  19680
gttcctgagt acatatcagg gacaagccca ccctctgtgg aaaaaaccag ctcttcctct  19740
tcccttctgt ctttaccagc aataacctca ccgtcccctg tacctactac attaccagaa  19800
agtaggccgt cttctcctgt tcatctgact tcactcccca cctctggcct agtgaagacc  19860
acagatatgc tggcatctgt ggccagttta cctccaaact tgggcagcac ctcacataag  19920
ataccgacta cttcagaaga cattaaagat acagagaaaa tgtatccttc cacaaacata  19980
gcagtaacca atgtggggac caccacttct gaaaaggaat cttattcgtc tgtcccagcc  20040
tactcagaac cacccaaagt cacctctcca atggttacct ctttcaacat aagggacacc  20100
attgtttcca catccatgcc tggctcctct gagattacaa ggattgagat ggagtcaaca  20160
ttctccctgg ctcatgggct gaagggaacc agcacctccc aggaccccat cgtatccaca  20220
gagaaaagtg ctgtccttca caagttgacc actggtgcta ctgagacctc taggacagaa  20280
gttgcctctt ctagaagaac atccattcca ggccctgatc attccacaga gtcaccagac  20340
atctccactg aagtgatccc cagcctgcct atctcccttg gcattacaga atcttcaaat  20400
atgaccatca tcactcgaac aggtcctcct cttggctcta catcacaggg cacatttacc  20460
ttggacacac caactacatc ctccagggca ggaacacact cgatggcgac tcaggaattt  20520
ccacactcag aaatgaccac tgtcatgaac aaggaccctg agattctatc atggacaatc  20580
cctccttcta tagagaaaac cagcttctcc tcttccctga tgccttcacc agccatgact  20640
tcacctcctg tttcctcaac attaccaaag accattcaca ccactccttc tcctatgacc  20700
tcactgctca cccctagcct agtgatgacc acagacacat tgggcacaag cccagaacct  20760
acaaccagtt cacctccaaa tttgagcagt acctcacatg agatactgac aacagatgaa  20820
gacaccacag ctatagaagc catgcatcct tccacaagca cagcagcgac taatgtggaa  20880
accaccagtt ctggacatgg gtcacaatcc tctgtcctag ctgactcaga aaaaaccaag  20940
gccacagctc caatggatac cacctccacc atggggcata caactgtttc cacatcaatg  21000
tctgtttcct ctgagactac aaaaattaag agagagtcaa catattcctt gactcctgga  21060
ctgagagaga ccagcatttc ccaaaatgcc agcttttcca ctgacacaag tattgttctt  21120
tcagaagtcc ccactggtac tactgctgag gtctccagga cagaagtcac ctcctctggt  21180
agaacatcca tccctggccc ttctcagtcc acagttttgc cagaaatatc cacaagaaca  21240
atgacaaggc tctttgcctc gcccaccatg acagaatcag cagaaatgac catcccccact  21300
caaacaggtc cttctgggtc tacctcacag gataccctta ccttggacac atccaccaca  21360
aagtcccagg caaagactca ttcaactttg actcagagat ttccacactc agagatgacc  21420
actctcatga gcagaggtcc tggagatatg tcatggcaaa gctctccctc tctggaaaat  21480
cccagctctc tcccttccct gctgtcttta cctgccacaa cctcacctcc tcccatttcc  21540
tccacattac cagtgactat ctcctcctct cctcttcctg tgacttcact tctcacctct  21600
agcccggtaa cgaccacaga catgttacac acaagcccag aacttgtaac cagttcacct  21660
ccaaagctga gccacacttc agatgagaga ctgaccactg gcaaggacac cacaaataca  21720
gaagctgtgc atccttccac aaacacagca gcgtccaatg tggagattcc cagctctgga  21780
catgaatccc cttcctctgc cttagctgac tcagagacat ccaaagccac atcaccaatg  21840
tttattacct ccacccagga ggatacaact gttgccatat caacccctca cttcttggag  21900
actagcagaa ttcagaaaga gtcaatttcc tccctgagcc ctaaattgag ggagacaggc  21960
agttctgtgg agacaagctc agccatagag acaagtgctg tcctttctga agtgtccatt  22020
ggtgctacta ctgagatctc caggacagaa gtcacctcct ctagcagaac atccatctct  22080
ggttctgctg agtccacaat gttgccagaa atatccacca caagaaaaat cattaagttc  22140
cctacttccc ccatcctggc agaatcatca gaaatgacca tcaagaccca aacaagtcct  22200
cctgggtcta catcagagag taccttaca ttagacacat caaccactcc ctccttggta  22260
ataacccatt cgactatgac tcagagattg ccacactcag agataaccac tcttgtgagt  22320
agaggtgctg gggatgtgcc acggcccagc tctctccctg tggaagaaac aagccctcca  22380
tcttcccagc tgtctttatc tgccatgatc tcaccttctc ctgtttcttc cacattacca  22440
gcaagtagcc actcctcttc tgcttctgtg acttcacttc tcacaccagg ccaagtgaag  22500
actactgagg tgttggacgc aagtgcagaa cctgaaacca gttcacctcc aagtttgagc  22560
agcacctcag ttgaaatact ggccacctct gaagtcacca cagatacgga gaaaattcat  22620
cctttctcaa acacggcagt aaccaaagtt ggaacttcca gttctggaca tgaatcccct  22680
tcctctgtcc tacctgactc agagacaacc aaagccacat cggcaatggg taccatctcc  22740
attatggggg atacaagtgt ttctacatta actcctgcct tatctaacac taggaaaatt  22800
cagtcagagc cagcttcctc actgaccacc agattgaggg agaccagcac ctctgaagag  22860
accagcttag ccacagaagc aaacactgtt ctttctaaag tgtccactgg tgctactact  22920
gaggtctcca ggacagaagc catctccttt agcagaacat ccatgtcagg ccctgagcag  22980
tccacaatgt cacaagacat ctccatagga accatcccca ggatttctgc ctcctctgtc  23040
```

-continued

```
ctgacagaat ctgcaaaaat gaccatcaca acccaaacag gtccttcgga gtctacacta  23100
gaaagtaccc ttaatttgaa cacagcaacc acaccctctt gggtggaaac ccactctata  23160
gtaattcagg gatttccaca cccagagatg accacttcca tgggcagagg tcctggaggt  23220
gtgtcatggc ctagccctcc ctttgtgaaa gaaaccagcc ctccatcctc cccgctgtct  23280
ttacctgccg tgacctcacc tcatcctgtt tccaccacat tcctagcaca tatccccccc  23340
tctccccttc ctgtgacttc acttctcacc tctggcccgg cgacaaccac agatatcttg  23400
ggtacaagca cagaacctgg aaccagttca tcttcaagtt tgagcaccac ctcccatgag  23460
agactgacca cttacaaaga cactgcacat acagaagccg tgcatccttc cacaaacaca  23520
ggagggacca atgtggcaac caccagctct ggatataaat cacagtcctc tgtcctagct  23580
gactcatctc caatgtgtac cacctccacc atggggggata caagtgttct cacatcaact  23640
cctgccttcc ttgagactag gaggattcag acagagctag cttcctccct gacccctgga  23700
ttgagggagt ccagcggctc tgaagggacc agctcaggca ccaagatgag cactgtcctc  23760
tctaaagtgc ccactggtgc tactactgag atctccaagg aagacgtcac ctccatccca  23820
ggtcccgctc aatccacaat atcaccagac atctccacaa gaaccgtcag ctggttctct  23880
acatcccctg tcatgacaga atcagcagaa ataaccatga acacccatac aagtccttta  23940
ggggccacaa cacaaggcac cagtactttg gacacgtcaa gcacaacctc tttgacaatg  24000
acacactcaa ctatatctca aggatttca cactcacaga tgagcactct tatgaggagg  24060
ggtcctgagg atgtatcatg gatgagccct cccccttctgg aaaaaactag accttccttt  24120
tctctgatgt cttcaccagc cacaacttca ccttctcctg tttcctccac attaccagag  24180
agcatctctt cctctcctct tcctgtgact tcactcctca cgtctggctt ggcaaaaact  24240
acagatatgt tgcacaaaag ctcagaacct gtaaccaact cacctgcaaa tttgagcagc  24300
acctcagttg aaatactggc cacctctgaa gtcaccacag atacagagaa aactcatcct  24360
tcttcaaaca gaacagtgac cgatgtgggg acctccagtt ctggacatga atccacttcc  24420
tttgtcctag ctgactcaca gacatccaaa gtcacatctc caatggttat tacctccacc  24480
atggaggata cgagtgtctc cacatcaact cctggctttt ttgagactag cagaattcag  24540
acagaaccaa catcctccct gacccttgga ctgagaaaga ccagcagctc tgaggggacc  24600
agcttagcca cagagatgag cactgtcctt tctggagtgc ccactggtgc cactgctgaa  24660
gtctccagga cagaagtcac ctcctctagc agaacatcca tctcaggctt tgctcagctc  24720
acagtgtcac cagagacttc cacagaaacc atcaccagac tccctacctc cagcataatg  24780
acagaatcag cagaaatgat gatcaagaca caaacagatc ctcctgggtc tacaccagag  24840
agtactcata ctgtggacat atcaacaaca cccaactggg tagaaaccca ctcgactgtg  24900
actcagagat tttcacactc agagatgacc actcttgtga gcagaagccc tggtgatatg  24960
ttatggccta gtcaatcctc tgtggaagaa accagctctg cctcttccct gctgtctctg  25020
cctgccacga cctcaccttc tcctgtttcc tctacattag tagaggattt cccttccgct  25080
tctcttcctg tgacttctct tctcaaccct ggcctggtga taaccacaga caggatgggc  25140
ataagcagag aacctggaac cagttccact tcaaatttga gcagcacctc ccatgagaga  25200
ctgaccactt tggaagacac tgtagataca gaagacatgc agccttccac acacacagca  25260
gtgaccaacg tgaggacctc catttctgga catgaatcac aatcttctgt cctatctgac  25320
tcagagacac ccaaagccac atctccaatg ggtaccacct acaccatggg ggaaacgagt  25380
gtttccatat ccacttctga cttctttgag accagcagaa ttcagataga accaacatcc  25440
tccctgactt ctggattgag ggagaccagc agctctgaga ggatcagctc agccacagag  25500
ggaagcactg tcctttctga agtgcccagt ggtgctacca ctgaggtctc caggacagaa  25560
gtgatatcct ctaggggaac atccatgtca gggcctgatc agttcaccat atcaccagac  25620
atctctactg aagcgatcac caggctttct acttccccca ttatgacaga atcagcagaa  25680
agtgccatca ctattgagac aggttctcct ggggctacat cagagggtac cctcaccttg  25740
gacacctcaa caacaacctt ttggtcaggg acccactcaa ctgcatctcc aggattttca  25800
cactcagaga tgaccactct tatgagtaga actcctggag atgtgccatg gccgagcctt  25860
ccctctgtgg aagaagccag ctctgtctct tcctcactgt cttcacctgc catgacctca  25920
acttcttttt tctccacatt accagagagc atctcctcct ctcctcatcc tgtgactgca  25980
cttctcaccc ttggcccagt gaagaccaca gacatgttgc gcacaagctc agaacctgaa  26040
accagttcac ctccaaattt gagcagcacc tcagctgaaa tattagccac gtctgaagtc  26100
accaaagata gagagaaaat tcatccctcc tcaaacacac ctgtagtcaa tgtagggact  26160
gtgatttata aacatctatc cccttcctct gttttggctg acttagtgac aacaaaaccc  26220
acatctccaa tggctaccac ctccactctg gggaatacaa gtgtttccac atcaactcct  26280
gccttcccag aaactatgat gacacagcca acttcctccc tgacttctgg attaagggag  26340
atcagtacct ctcaagagac cagctcagca acagagagaa gtgcttctct ttctggaatg  26400
cccactggtg ctactactaa ggtctccaga acagaagccc tctccttagg cagaacatcc  26460
accccaggtc ctgctcaatc cacaatatca ccagaaatct ccacggaaac catcactaga  26520
atttctactc ccctcaccac gacaggatca gcagaaatga ccatcacccc caaaacaggt  26580
cattctgggg catcctcaca aggtaccttt accttggaca catcaagcag agcctcctgg  26640
ccaggaactc actcagctgc aactcacaga tctccacact cagggatgac cactcctatg  26700
agcagaggtc ctgaggatgt gtcatggcca agccgcccat cagtggaaaa aactagccct  26760
ccatcttccc tggtgtcttt atctgcagta acctcacctt cgccacttta ttccacacca  26820
tctgagagta gccactcatc tcctctccgg gtgacttctc ttttcacccc tgtcatgatg  26880
aagaccacag acatgttgga cacaagcttg gaacctgtga ccacttcacc tcccagtatg  26940
aatatcacct cagatgagag tctggccact tctaaagcca ccatggagac agaggcaatt  27000
cagctttcag aaaacacagc tgtgactcag atgggcacca tcagcgctag acaagaattc  27060
tattcctctt atccaggcct cccagagcca tccaaagtga catctccagt ggtcacctct  27120
tccaccataa aagacattgt ttctacaacc atacctgctt cctctgagat aacaagaatt  27180
gagatggagt caacatccac cctgaccccc acaccaaggg agaccagcac ctcccaggag  27240
atccactcag ccacaaagcc aagcactgtt ccttacaagg cactcactag tgccacgatt  27300
gaggactcca tgacacaagt catgtcctct agcagaggac ctagccctga tcagtccaca  27360
atgtcacaag acatatccac tgaagtgatc accaggctct ctacctcccc catcaagaca  27420
gaatctacag aaatgaccat taccacccaa acaggttctc ctggggctac atcaaggggt  27480
acccttacct tggacacttc aacaactttt atgtcaggga cccactcaac tgcatctcaa  27540
ggattttcac actcacagat gaccgctctt atgagtagaa ctcctggaga tgtgccatgg  27600
ctaagccatc cctctgtgga agaagccagc tctgcctctt tctcactgtc ttcacctgtc  27660
atgacctcat cttctcccgt ttcttccaca ttaccagaca gcatccactc ttcttcgctt  27720
cctgtgacat cacttctcac ctcagggctg gtgaagacca cagagctgtt gggcacaagc  27780
```

-continued

```
tcagaacctg aaaccagttc acccccaaat ttgagcagca cctcagctga aatactggcc  27840
atcactgaag tcactacaga tacagagaaa ctggagatga ccaatgtggt aacctcaggt  27900
tatacacatg aatctccttc ctctgtccta gctgactcag tgacaacaaa ggccacatct  27960
tcaatgggta tcacctaccc cacaggagat acaaatgttc tcacatcaac ccctgccttc  28020
tctgacacca gtaggattca aacaaagtca aagctctcac tgactcctgg gttgatggag  28080
accagcatct ctgaagagac cagctctgcc acagaaaaaa gcactgtcct ttctagtgtg  28140
cccactggtg ctactactga ggtctccagg acagaagcca tctcttctag cagaacatcc  28200
atcccaggcc ctgctcaatc cacaatgtca tcagacacct ccatggaaac catcactaga  28260
atttctaccc ccctcacaag gaaagaatca acagacatgg ccatcacccc caaaacaggt  28320
ccttctgggg ctacctcgca gggtaccttt accttggact catcaagcac agcctcctgg  28380
ccaggaactc actcagctac aactcagaga tttccacagt cagtggtgac aactcctatg  28440
agcagaggtc ctgaggatgt gtcatggcca agcccgctgt ctgtggaaaa aaacagccct  28500
ccatcttccc tggtatcttc atcttcagta acctcacctt cgccacttta ttccacacca  28560
tctgggagta gccactcctc tcctgtccct gtcacttctc ttttcacctc tatcatgatg  28620
aaggccacag acatgttgga tgcaagtttg gaacctgaga ccacttcagc tcccaatatg  28680
aatatcacct cagatgagag tctggccgct tctaaagcca ccacggagac agaggcaatt  28740
cacgtttttg aaaatacagc agcgtcccat gtggaaacca ccagtgctac agaggaactc  28800
tattcctctt ccccaggctt ctcagagcca acaaaagtga tatctccagt ggtcacctct  28860
tcctctataa gagacaacat ggtttccaca acaatgcctg gctcctctgg cattacaagg  28920
attgagatag agtcaatgtc atctctgacc cctggactga gggagaccag aacctcccag  28980
gacatcacct catccacaga gacaagcact gtcctttaca agatgccctc tggtgccact  29040
cctgaggtct ccaggacaga agttatgccc tctagcagaa catccattcc tggccctgct  29100
cagtccacaa tgtcactaga catctccgat gaagttgtca ccaggctgtc tacctctccc  29160
atcatgacag aatctgcaga aataaccatc accacccaaa caggttattc tctggctaca  29220
tcccaggtta cccttccctt gggcacctca atgacctttt tgtcagggac ccactcaact  29280
atgtctcaag gactttcaca ctcagagatg accaatctta tgagcagggg tcctgaaagt  29340
ctgtcatgga cgagccctcg ctttgtggaa acaactagat cttcctcttc tctgacatca  29400
ttacctctca cgacctcact ttctcctgtg tcctccacat tactagacag tagcccctcc  29460
tctcctcttc ctgtgacttc acttatcctc ccaggcctgg tgaagactac agaagtgttg  29520
gatacaagct cagagcctaa aaccagttca tctccaaatt tgagcagcac ctcagttgaa  29580
ataccggcca cctctgaaat catgacagat acagagaaaa ttcatccttc ctcaaacaca  29640
gcggtggcca aagtgaggac ctccagttct gttcatgaat ctcattcctc tgtcctagct  29700
gactcagaaa caaccataac cataccttca atgggtatca cctccgctgt ggacgatacc  29760
actgttttca catcaaatcc tgccttctct gagactagga ggattccgac agagccaaca  29820
ttctcattga ctcctggatt cagggagact agcacctctg aagagaccac ctcaatcaca  29880
gaaacaagtg cagtccttta tggagtgccc actagtgcta ctactgaagt ctccatgaca  29940
gaaatcatgt cctctaatag aatacacatc cctgactctg atcagtccac gatgtctcca  30000
gacatcatca ctgaagtgat caccaggctc tcttcctcat ccatgatgtc agaatcaaca  30060
caaatgacca tcaccaccca aaaaagttct cctggggcta cagcacagag tactcttacc  30120
ttggccacaa caacagcccc cttggcaagg acccactcaa ctgttcctcc tagattttta  30180
cactcagaga tgacaactct tatgagtagg agtcctgaaa atccatcatg gaagagctct  30240
ctctttgtgg aaaaaactag ctcttcatct tctctgttgt ccttacctgt cacgacctca  30300
ccttctgttt cttccacatt accgcagagt atcccttcct cctctttttc tgtgacttca  30360
ctcctcaccc caggcatggt gaagactaca gacacaagca cagaacctgg aaccagttta  30420
tctccaaatc tgagtggcac ctcagttgaa atactggctg cctctgaagt caccacagat  30480
acagagaaaa ttcatccttc ttcaagcatg gcagtgacca atgtgggaac caccagttct  30540
ggacatgaac tatattcctc tgtttcaatc cactcggagc catccaaggc tacataccca  30600
gtgggtactc cctcttccat ggctgaaacc tctatttcca catcaatgcc tgctaatttt  30660
gagaccacag gatttgaggc tgagccattt tctcatttga cttctggatt taggaagaca  30720
aacatgtccc tggacaccag ctcagtcaca ccaacaaata caccttcttc tcctgggtcc  30780
actcaccttt tacagagttc caagactgat ttcacctctt ctgcaaaaac atcatcccca  30840
gactggcctc cagcctcaca gtatactgaa attccagtgg acataatcac cccctttaat  30900
gcttctccat ctattacgga gtccactggg ataacctcct tcccagaatc caggtttact  30960
atgtctgtaa cagaaagtac tcatcatctg agtacagatt tgctgccttc agctgagact  31020
atttccactg gcacagtgat gccttctcta tcagaggcca tgacttcatt tgccaccact  31080
ggagttccac gagccatctc aggttcaggt agtccattct ctaggacaga gtcaggccct  31140
ggggatgcta ctctgtccac cattgcagag agcctgcctt catccactcc tgtgccattc  31200
tcctcttcaa ccttcactac cactgattct tcaaccatcc cagccctcca tgagataact  31260
tcctcttcag ctaccccata tagagtggac accagtcttg ggacagagag cagcactact  31320
gaaggacgct tggttatggt cagtactttg gacacttcaa gccaaccagg caggacatct  31380
tcatcaccca ttttggatac cagaatgaca gagagcgttg agctgggaac agtgacaagt  31440
gcttatcaag ttccttcact ctcaacacgg ttgacaagaa ctgatggcat tatggaacac  31500
atcacaaaaa tacccaatga agcagcacac agaggtacca taagaccagt caaaggccct  31560
cagacatcca cttcgcctgc cagtcctaaa ggactacaca caggagggac aaaaagaatg  31620
gagaccacca ccacagctct gaagaccacc accacagctc tgaagaccac ttccagagcc  31680
accttgacca ccagtgtcta tactcccact ttgggaacac tgactcccct caatgcatca  31740
atgcaaatgg ccagcacaat ccccacagaa atgatgatca caaccccata tgttttccct  31800
gatgttccag aaacgacatc ctcattggct accagcctgg gagcagaaac cagcacagct  31860
cttcccagga caaccccatc tgttttcaat agagaatcag agaccacagc ctcactggtc  31920
tctcgttctg gggcagagag aagtccggtt attcaaactc tagatgtttc ttctagtgag  31980
ccagatacaa cagcttcatg ggttatccat cctgcagaga ccatcccaac tgtttccaag  32040
acaaccccca atttttcca cagtgaatta gacactgtat cttccacagc caccagtcat  32100
ggggcagacg tcagctcagc cattccaaca aatatctcac ctagtgaact agatgcactg  32160
accccactgg tcactatttc ggggacagat actagtacaa cattcccaac actgactaag  32220
tccccacatg aaacagagac aagaaccaca tggctcactc atcctgcaga gaccagctca  32280
actattccca gaacaatccc caatttttct catcatgaat cagatgccac accttcaata  32340
gccaccagtc ctggggcaga aaccagttca gctattccaa ttatgactgt ctcacctggt  32400
gcagaagatc tggtgacctc acaggtcact agttctggga cagacagaaa tatgactatt  32460
ccaactttga ctctttctcc tggtgaacca aagacgatag cctcattagt cacccatcct  32520
```

-continued

```
gaagcacaga caagttcggc cattccaact tcaactatct cgcctgctgt atcacggttg  32580
gtgacctcaa tggtcaccag tttggcggca aagacaagta caactaatcg agctctgaca  32640
aactcccctg gtgaaccagc tacaacagtt tcattggtca cgcatcctgc acagaccagc  32700
ccaacagttc cctggacaac ttccattttt ttccatagta aatcagacac cacaccttca  32760
atgaccacca gtcatggggc agaatccagt tcagctgttc caactccaac tgtttcaact  32820
gaggtaccag gagtagtgac ccctttggtc accagttcta gggcagtgat cagtacaact  32880
attccaattc tgactctttc tcctggtgaa ccagagacca caccttcaat ggccaccagt  32940
catggggaag aagccagttc tgctattcca actccaactg tttcacctgg ggtaccagga  33000
gtggtgacct ctctggtcac tagttctagg gcagtgacta gtacaactat tccaattctg  33060
actttttctc ttggtgaacc agagaccaca ccttcaatgg ccaccagtca tgggacagaa  33120
gctggctcag ctgttccaac tgttttacct gaggtaccag gaatggtgac ctctctggtt  33180
gctagttcta gggcagtaac cagtacaact cttccaactc tgactctttc tcctggtgaa  33240
ccagagacca caccttcaat ggccaccagt catggggcag aagccagctc aactgttcca  33300
actgtttcac ctgaggtacc aggagtggtg acctctctgg tcactagttc tagtggagta  33360
aacagtacaa gtattccaac tctgattctt tctcctggtg aactagaaac cacaccttca  33420
atggccacca gtcatggggc agaagccagc tcagctgttc caactccaac tgtttcacct  33480
ggggtatcag gagtggtgac ccctctggtc actagttcca gggcagtgac cagtacaact  33540
attccaattc taactctttc ttctagtgag ccagagacca caccttcaat ggccaccagt  33600
catggggtag aagccagctc agctgttcta actgtttcac ctgaggtacc aggaatggtg  33660
acctctctgg tcactagttc tagagcagta accagtacaa ctattccaac tctgactatt  33720
tcttctgatg aaccagagac cacaacttca ttggtcaccc attctgaggc aaagatgatt  33780
tcagccattc caactttagc tgtctcccct actgtacaag ggctggtgac ttcactggtc  33840
actagttctg ggtcagagac cagtgcgttt tcaaatctaa ctgttgcctc aagtcaacca  33900
gagaccatag actcatgggt cgctcatcct gggacagaag caagttctgt tgttccaact  33960
ttgactgtct ccactggtga gccgtttaca aatatctcat tggtcaccca tcctgcagag  34020
agtagctcaa ctcttcccag gacaacctca aggttttccc acagtgaatt agacactatg  34080
ccttctacag tcaccagtcc tgaggcagaa tccagctcag ccatttcaac aactatttca  34140
cctggtatac caggtgtgct gacatcactg gtcactagct ctgggagaga catcagtgca  34200
acttttccaa cagtgcctga gtccccacat gaatcagagg caacagcctc atgggttact  34260
catcctgcag tcaccagcac aacagttccc aggacaaccc ctaattattc tcatagtgaa  34320
ccagacacca caccatcaat agccaccagt cctggggcag aagccacttc agattttcca  34380
acaataactg tctcacctga tgtaccagat atggtaacct cacaggtcac tagttctggg  34440
acagacacca gtataactat tccaactctg actctttctt ctggtgagcc agagaccaca  34500
acctcattta tcacctattc tgagacacac acaagttcag ccattccaac tctccctgtc  34560
tcccctggtg catcaaagat gctgacctca ctggtcatca gttctgggac agacagcact  34620
acaactttcc caacactgac ggagacccca tatgaaccag agacaacagc catacagctc  34680
attcatcctg cagagaccaa cacaatggtt cccaggacaa ctcccaagtt ttcccatagt  34740
aagtcagaca ccacactccc agtagccatc accagtcctg ggccagaagc cagttcagct  34800
gtttcaacga caactatctc acctgatatg tcagatctgg tgacctcact ggtccctagt  34860
tctgggacag acaccagtac aaccttccca acattgagtg agaccccata tgaaccagag  34920
actacagcca cgtggctcac tcatcctgca gaaaccagca caacggtttc tgggacaatt  34980
cccaactttt cccatagggg atcagacact gcaccctcaa tggtcaccag tcctggagta  35040
gacacgaggt caggtgttcc aactacaacc atcccaccca gtataccagg ggtagtgacc  35100
tcacaggtca ctagttctgc aacagacact agtacagcta ttccaacttt gactccttct  35160
cctggtgaac cagagaccac agcctcatca gctacccatc ctgggacaca gactggcttc  35220
actgttccaa ttcggactgt tccctctagt gagccagata caatggcttc ctgggtcact  35280
catcctccac agaccagcac acctgtttcc agaacaacct ccagtttttc ccatagtagt  35340
ccagatgcca cacctgtaat ggccaccagt cctaggacag aagccagttc agctgtactg  35400
acaacaatct cacctggtgc accagagatg gtgacttcac agatcactag ttctggggca  35460
gcaaccagta caactgttcc aactttgact cattctcctg gtatgccaga gaccacagcc  35520
ttattgagca cccatcccag aacagagaca agtaaaacat ttcctgcttc aactgtgttt  35580
cctcaagtat cagagaccac agcctcactc accattagac ctggtgcaga gactagcaca  35640
gctctcccaa ctcagacaac atcctctctc ttcaccctac ttgtaactgg aaccagcaga  35700
gttgatctaa gtccaactgc ttcacctggt gtttctgcaa aaacagcccc actttccacc  35760
catccaggga cagaaaccag cacaatgatt ccaacttcaa ctctttccct tggtttacta  35820
gagactacag gcttactggc caccagctct tcagcagaga ccagcacgag tactctaact  35880
ctgactgttt cccctgctgt ctctgggctt tccagtgcct ctataacaac tgataagccc  35940
caaactgtga cctcctggaa cacagaaacc tcaccatctg taacttcagt tggaccccca  36000
gaattttcca ggactgtcac aggcaccact atgaccttga taccatcaga gatgccaaca  36060
ccacctaaaa ccagtcatgg agaaggagtg agtccaacca ctatcttgag aactacaatg  36120
gttgaagcca ctaatttagc taccacaggt tccagtccca ctgtggccaa gacaacaacc  36180
accttcaata cactggctgg aagcctcttt actcctctga ccacacctgg gatgtccacc  36240
ttggcctctg agagtgtgac ctcaagaaca agttataacc atcggtcctg gatctccacc  36300
accagcagtt ataaccgtcg gtactggacc cctgccacca gcactccagt gacttctaca  36360
ttctccccag ggatttccac atcctccatc cccagctcca cagcagccac agtcccattc  36420
atggtgccat tcaccctcaa cttcaccatc accaacctgc agtacgagga ggacatgcgg  36480
caccctggtt ccaggaagtt caacgccaca gagagagaac tgcagggtct gctcaaaccc  36540
ttgttcagga atagcagtct ggaatacctc tattcaggct gcagactagc ctcactcagg  36600
ccagagaagg atagctcagc cacggcagtg gatgccatct gcacacatcg ccctgaccct  36660
gaagacctcg gactggacag agagcgactg tactgggagc tgagcaatct gacaaatggc  36720
atccaggagc tgggccccta caccctggac cggaacagtc tctatgtcaa tggtttcacc  36780
catcgaagct ctatgcccac caccagcact cctgggacct ccacagtgga tgtgggaacc  36840
tcagggactc catcctccag ccccagcccc acgactgctg gccctctcct gatgccgttc  36900
accctcaact tcaccatcac caacctgcag tacgaggagg acatgcgtcg cactggctcc  36960
aggaagttca acaccatgga gagtgtcctg cagggtctgc tcaagccctt gttcaagaac  37020
accagtgttg gccctctgta ctctggctgc agattgacct tgctcaggcc cgagaaagat  37080
ggggcagcca ctggagtgga tgccatctgc acccaccgcc ttgaccccaa aagccctgga  37140
ctcaacaggg agcagctgta ctgggagcta agcaaactga ccaatgacat tgaagagctg  37200
ggcccctaca ccctggacag gaacagtctc tatgtcaatg gtttcaccca tcagagctct  37260
```

-continued

```
gtgtccacca ccagcactcc tgggacctcc acagtggatc tcagaacctc agggactcca 37320
tcctccctct ccagccccac aattatggct gctggccctc tcctggtacc attcaccctc 37380
aacttcacca tcaccaacct gcagtatggg gaggacatgg gtcaccctgg ctccaggaag 37440
ttcaacacca cagagagggt cctgcagggt ctgcttggtc ccatattcaa gaacaccagt 37500
gttggccctc tgtactctgg ctgcagactg acctctctca ggtctgagaa ggatggagca 37560
gccactggag tggatgccat ctgcatccat catcttgacc ccaaaagccc tggactcaac 37620
agagagcggc tgtactggga gctgagccaa ctgaccaatg gcatcaaaga gctgggcccc 37680
tacaccctgg acaggaacag tctctatgtc aatggtttca cccatcggac ctctgtgccc 37740
accagcagca ctcctgggac ctccacagtg gaccttggaa cctcagggac tccattctcc 37800
ctcccaagcc ccgcaactgc tggccctctc ctggtgctgt tcaccctcaa cttcaccatc 37860
accaacctga agtatgagga ggacatgcat cgccctggct ccaggaagtt caacaccact 37920
gagagggtcc tgcagactct gcttggtcct atgttcaaga acaccagtgt tggccttctg 37980
tactctggct gcagactgac cttgctcagg tccgagaagg atggagcagc cactggagtg 38040
gatgccatct gcacccaccg tcttgacccc aaaagccctg gagtggacag ggagcagcta 38100
tactgggagc tgagccagct gaccaatggc atcaaagagc tgggccccta caccctggac 38160
aggaacagtc tctatgtcaa tggtttcacc cattggatcc ctgtgcccac cagcagcact 38220
cctgggacct ccacagtgga ccttgggtca gggactccat cctccctccc cagccccaca 38280
actgctggcc ctctcctggt gccgttcacc ctcaacttca ccatcaccaa cctgaagtac 38340
gaggaggaca tgcattgccc tggctccagg aagttcaaca ccacagagag agtcctgcag 38400
agtctgcttg gtcccatgtt caagaacacc agtgttggcc ctctgtactc tggctgcaga 38460
ctgaccttgc tcaggtccga gaaggatgga gcagccactg gagtggatgc catctgcacc 38520
caccgtcttg accccaaaag ccctggagtg gacagggagc agctatactg ggagctgagc 38580
cagctgacca atggcatcaa agagctgggt ccctacaccc tggacagaaa cagtctctat 38640
gtcaatggtt tcacccatca gacctctgcg cccaacacca gcactcctgg gacctccaca 38700
gtggaccttg ggacctcagg gactccatcc tccctcccca gccctacatc tgctggccct 38760
ctcctggtgc cattcaccct caacttcacc atcaccaacc tgcagtacga ggaggacatg 38820
catcacccag gctccaggaa gttcaacacc acggagcggg tcctgcaggg tctgcttggt 38880
cccatgttca agaacaccag tgtcggcctt ctgtactctg gctgcagact gaccttgctc 38940
aggcctgaga agaatggggc agccactgga atggatgcca tctgcagcca ccgtcttgac 39000
cccaaaagcc ctggactcaa cagagagcag ctgtactggg agctgagcca gctgacccat 39060
ggcatcaaag agctgggccc ctacaccctg gacaggaaca gtctctatgt caatggtttc 39120
acccatcgga gctctgtggc ccccaccagc actcctggga cctccacagt ggaccttggg 39180
acctcaggga ctccatcctc cctccccagc cccacaacag ctgttcctct cctggtgccg 39240
ttcaccctca actttaccat caccaatctg cagtatgggg aggacatgcg tcaccctggc 39300
tccaggaagt tcaacaccac agagagggtc ctgcagggtc tgcttggtcc cttgttcaag 39360
aactccagtg tcggccctct gtactctggc tgcagactga tctctctcag gtctgagaag 39420
gatggggcag ccactggagt ggatgccatc tgcacccacc accttaaccc tcaaagccct 39480
ggactggaca gggagcagct gtactggcag ctgagccaga tgaccaatgg catcaaagag 39540
ctgggcccct acaccctgga ccggaacagt ctctacgtca atggtttcac ccatcggagc 39600
tctgggctca ccaccagcac tccttggact tccacagttg accttggaac ctcagggact 39660
ccatcccccg tccccagccc cacaaccacc ggccctctcc tggtgccatt cacactcaac 39720
ttcaccatca ctaacctaca gtatgaggag aacatgggtc accctggctc caggaagttc 39780
aacatcacgg agagtgttct gcagggtctg ctcaagccct tgttcaagag caccagtgtt 39840
ggccctctgt attctggctg cagactgacc ttgctcaggc ctgagaagga tggagtagcc 39900
accagagtgg acgccatctg cacccaccgc cctgacccca aaatccctgg gctagacaga 39960
cagcagctat actgggagct gagccagctg acccacagca tcactgagct gggaccctac 40020
accctggata gggacagtct ctatgtcaat ggtttcaccc agcggagctc tgtgcccacc 40080
accagcactc ctgggacttt cacagtacag ccggaaacct ctgagactcc atcatccctc 40140
cctggcccca cagccactgg ccctgtcctg ctgccattca ccctcaattt taccatcact 40200
aacctgcagt atgaggagga catgcgtcgc cctggctcca ggaagttcaa caccacggag 40260
agggtccttc agggtctgct tatgcccttg ttcaagaaca ccagtgtcag ctctctgtac 40320
tctggttgca gactgacctt gctcaggcct gagaaggatg gggcagccac cagagtggat 40380
gctgtctgca cccatcgtcc tgaccccaaa agccctggac tggacagaga gcggctgtac 40440
tggaagctga gccagctgac ccacggcatc actgagctgg gcccctacac cctggacagg 40500
cacagtctct atgtcaatgg tttcacccat cagagctcta tgacgaccac cagaactcct 40560
gatacctcca caatgcacct ggcaacctcg agaactccag cctccctgtc tggacccatg 40620
accgccagcc ctctcctggt gctattcaca attaacttca ccatcactaa cctgcggtat 40680
gaggagaaca tgcatcaccc tggctctaga aagtttaaca ccacggagag agtccttcag 40740
ggtctgctca ggcctgtgtt caagaacacc agtgttggcc ctctgtactc tggctgcaga 40800
ctgaccttgc tcaggcccaa gaaggatggg gcagccacca aagtggatgc catctgcacc 40860
taccgccctg atcccaaaag ccctggactg gacagagagc agctatactg ggagctgagc 40920
cagctgaccc acagcatcac tgagctgggc ccctacaccc tggacaggga cagtctctat 40980
gtcaatggtt tcacacagcg gagctctgtg cccaccacta gcattcctgg gacccccaca 41040
gtggacctgg gaacatctgg gactccagtt tctaaacctg gtccctcggc tgccagccct 41100
ctcctggtgc tattcactct caacttcacc atcaccaacc tgcggtatga ggagaacatg 41160
cagcaccctg gctccaggaa gttcaacacc acggagaggg tccttcaggg cctgctcagg 41220
tccctgttca agagcaccag tgttggccct ctgtactctg gctgcagact gactttgctc 41280
aggcctgaaa aggatgggac agccactgga gtggatgcca tctgcaccca ccaccctgac 41340
cccaaaagcc ctaggctgga cagagagcag ctgtattggg agctgagcca gctgacccac 41400
aatatcactg agctgggccc ctatgccctg gacaacgaca gcctctttgt caatggtttc 41460
actcatcgga gctctgtgtc caccaccagc actcctggga cccccacagt gtatctggga 41520
gcatctaaga ctccagcctc gatatttggc ccttcagctg ccagccatct cctgatacta 41580
ttcaccctca acttcaccat cactaacctg cggtatgagg agaacatgtg gcctggctcc 41640
aggaagttca acactacaga gagggtcctt cagggcctgc taaggccctt gttcaagaac 41700
accagtgttg gccctctgta ctctggctgc aggctgacct tgctcaggcc agagaaagat 41760
ggggaagcca ccggagtgga tgccatctgc acccaccgcc ctgaccccac aggccctggg 41820
ctggacagag agcagctgta tttggagctg agccagctga cccacagcat cactgagctg 41880
ggcccctaca cactggacag ggacagtctc tatgtcaatg gtttcaccca tcggagctct 41940
gtacccacca ccagcaccgg ggtggtcagc gaggagccat tcacactgaa cttcaccatc 42000
```

```
aacaacctgc gctacatggc ggacatgggc caacccggct ccctcaagtt caacatcaca  42060
gacaacgtca tgcagcacct gctcagtcct ttgttccaga ggagcagcct gggtgcacgg  42120
tacacaggct gcagggtcat cgcactaagg tctgtgaaga acggtgctga gacacgggtg  42180
gacctcctct gcacctacct gcagcccctc agcggcccag gtctgcctat caagcaggtg  42240
ttccatgagc tgagccagca gacccatggc atcacccggc tgggccccta ctctctggac  42300
aaagacagcc tctaccttaa cggttacaat gaacctggtc cagatgagcc tcctacaact  42360
cccaagccag ccaccacatt cctgcctcct ctgtcagaag ccacaacagc catggggtac  42420
cacctgaaga ccctcacact caacttcacc atctccaatc tccagtattc accagatatg  42480
ggcaagggct cagctacatt caactccacc gagggggtcc ttcagcacct gctcagaccc  42540
ttgttccaga agagcagcat gggcccctc tacttgggtt gccaactgat ctccctcagg  42600
cctgagaagg atggggcagc cactggtgtg gacaccacct gcacctacca ccctgaccct  42660
gtgggccccg ggctggacat acagcagctt tactgggagc tgagtcagct gacccatggt  42720
gtcacccaac tgggcttcta tgtcctggac agggatagcc tcttcatcaa tggctatgca  42780
ccccagaatt tatcaatccg gggcgagtac cagataaatt tccacattgt caactggaac  42840
ctcagtaatc cagaccccac atcctcagag tacatcaccc tgctgaggga catccaggac  42900
aaggtcacca cactctacaa aggcagtcaa ctacatgaca cattccgctt ctgcctggtc  42960
accaacttga cgatggactc cgtgttggtc actgtcaagg cattgttctc ctccaatttg  43020
gaccccagcc tggtggagca agtctttcta gataagaccc tgaatgcctc attccattgg  43080
ctgggctcca cctaccagtt ggtggacatc catgtgacag aaatggagtc atcagtttat  43140
caaccaacaa gcagctccag cacccagcac ttctacctga atttcaccat caccaaccta  43200
ccatattccc aggacaaagc ccagccaggc accaccaatt accagaggaa caaaaggaat  43260
attgaggatg cgctcaacca actcttccga aacagcagca tcaagagtta tttttctgac  43320
tgtcaagttt caacattcag gtctgtcccc aacaggcacc acaccggggt ggactccctg  43380
tgtaacttct cgccactggc tcggagagta gacagagttg ccatctatga ggaatttctg  43440
cggatgaccc ggaatggtac ccagctgcag aacttcaccc tggacaggag cagtgtcctt  43500
gtggatgggt attctcccaa cagaaatgag cccttaactg ggaattctga ccttcccttc  43560
tgggctgtca tcctcatcgg cttggcagga ctcctgggag tcatcacatg cctgatctgc  43620
ggtgtcctgg tgaccacccg ccggcggaag aaggaaggag aatacaacgt ccagcaacag  43680
tgcccaggct actaccagtc acacctagac ctggaggatc tgcaatgact ggaacttgcc  43740
ggtgcctggg gtgcctttcc cccagccagg gtccaaagaa gcttggctgg ggcagaaata  43800
aaccatattg gtcgga                                                  43816

SEQ ID NO: 55          moltype = DNA  length = 16756
FEATURE                Location/Qualifiers
source                 1..16756
                       mol_type = other DNA
                       organism = Homo sapiens
SEQUENCE: 55
gcacttggtt cgggccagcc gcctgagggg acgggctcac gtctgctcct cacactgcag  60
ctgctgggcc gtggagcttc cccagggagc caggggggact tttgccgcag ccatgaaggg  120
ggcacgctgg aggagggtcc cctgggtgtc cctgagctgc ctgtgtctct gcctccttcc  180
gcatgtggtc ccaggaacca cagaggacac attaataact ggaagtaaaa ctgctgcccc  240
agtcacctca acaggctcaa caacagcgac actagaggga caatcaactg cagcttcttc  300
aaggacctct aatcaggaca tatcagcttc atctcagaac caccagacta agagcacgga  360
gaccaccagc aaagctcaaa ccgacaccct cacgcagatg atgacatcaa ctctttttttc  420
ttccccaagt gtacacaatg tgatggagac agctcctcca gatgaaatga ccacatcatt  480
tccctccagt gtcaccaaca cactcatgat gacatcaaag actataacaa tgacaacctc  540
cacagactcc actcttggaa acacagaaga gacatcaaca gcaggaactg aaagttctac  600
cccagtgacc tcagcagtct caataacagc tggacaggaa ggacaatcac gaacaacttc  660
ctggaggacc tctatccaag acacatcagc ttcttctcag aaccactgga ctcggagcac  720
gcagaccacc agggaatctc aaaccagcac cctaacacac agaaccactt caactccttc  780
tttctctcca agtgtacaca atgtgacagg gactgtttct cagaagacat ctccttcagg  840
tgaaacagct acctcatccc tctgtagtgt cacaaacaca tccatgatga catcagagaa  900
gataacagtg acaacctcca caggctccac tcttggaaac ccaggggaga catcatcagt  960
acctgttact ggaagtctta tgccagtcac ctcagcagcc ttagtaacat ttgatccaga  1020
aggacaatca ccagcaactt tctcaaggac ttctactcag gacacaacag ctttttctaa  1080
gaaccaccag actcagagcg tggagaccac cagagtatct caaatcaaca ccctcaacac  1140
cctcacaccg gttacaacat caactgtttt atcctcacca agtggattca acccaagtgg  1200
aacagtttct caggagacat tcccttctgg tgaaacaacc acctcatccc cttccagtgt  1260
cagcaataca ttcctggtaa catcaaaggt gttcagaatg ccaacctcca gagactctac  1320
tcttggaaac acagaggaga catcactatc tgtaagtgga accatttctg caatcacttc  1380
caaagtttca accatatggt ggtcagacac tctgtcaaca gcactctccc ccagttctct  1440
acctccaaaa atatccacag ctttccacac ccagcagagt gaaggtgcag agaccacagg  1500
acggcctcat gagaggagct cattctctcc aggtgtgtct caagaaatat ttactctaca  1560
tgaaacaaca acatggcctt cctcattctc cagcaaaggc cacacaactt ggtcacaaac  1620
agaactgccc tcaacatcaa caggtgctgc cactaggctt gtcacaggaa atccatctac  1680
agggacagct ggcactattc caagggtccc ctctaaggtc tcagcaatag ggggaaccagg  1740
agagcccacc acatactcct cccacagcac aactctccca aaaacaacag gggcaggcgc  1800
ccagacacaa tggacacaag aaacggggac cactggagag gctcttctca gcagcccaag  1860
ctacagtgtg actcagatga taaaaacggc cacatcccca tcttcttcac ctatgctgga  1920
tagacacaca tcccaacaaa ttacaacggc accatcaaca aatcattcaa caatacattc  1980
cacaagcacc tctcctcagg aatcaccagc tgtttcccaa aggggtcaca ctcaagcccc  2040
gcagaccaca caagaatcac aaaccacgag gtccgtctcc cccatgactg acaccaagac  2100
agtcaccacc ccaggttctt ccttcacagc cagtgggcac tcgccctcag aaattgttcc  2160
tcaggacgca cccaccataa gtgcagcaac aacctttgcc ccagctccca ccggggatgg  2220
tcacacaacc caggccccga ccacagcact gcaggcagca cccagcagcc atgatgccac  2280
cctggggccc tcaggaggca cgtcactttc caaaacaggt gcccttactc tggccaactc  2340
tgtagtgtca acaccagggg gcccagaagg acaatggaca tcagcctctg ccagcacctc  2400
acctgacaca gcagcagcca tgacccatac ccaccaggct gagagcacag aggcctctgg  2460
```

-continued

```
acaaacacag accagcgaac cggcctcctc agggtcacga accacctcag cgggcacagc  2520
taccccttcc tcatccgggg cgagtggcac aacaccttca ggaagcgaag gaatatccac  2580
ctcaggagag acgacaaggt tttcatcaaa cccctccagg gacagtcaca caacccagtc  2640
aacaaccgaa ttgctgtccg cctcagccag tcatggtgcc atcccagtaa gcacaggaat  2700
ggcgtcttcg atcgtccccg gcacctttca tcccaccctc tctgaggcct ccactgcagg  2760
gagaccgaca ggacagtcaa gcccaacttc tcccagtgcc tctcctcagg agacagccgc  2820
catttcccgg atggcccaga ctcagaggac aagaaccagc agagggtctg acactatcag  2880
cctggcgtcc caggcaaccg acaccttctc aacagtccca cccacacctc catcgatcac  2940
atccactggg cttacatctc cacaaaccga gacccacact ctgtcacctt cagggtctgg  3000
taaaaccttc accacggccc tcatcagcaa cgccacccct cttcctgtca cctacgcttc  3060
ctcggcatcc acaggtcaca ccacccctct tcatgtcacc gatgcttcct cagtatccac  3120
aggtcacgcc acccctcttc ctgtcaccag cccttcctca gtatccacag gtcacaccac  3180
ccctcttcct gtcaccgaca cttcctcaga atccacaggt cacgtcaccc ctcttcctgt  3240
caccagcttt tcctcagcat ccacaggtga cagcacccct cttcctgtca ctgacacttc  3300
ctcagcatcc acaggtcacg tcacccctct tcctgtcacc agcctttcct cagcatccac  3360
aggtgacacc acccctcttc ctgtcactga cacttcctca gcatccacag gtcacgccac  3420
ctctcttcct gtcaccgaca cttcctcagt atccacaggt cacaccaccc ctcttcctgt  3480
caccgacact tcctcagcat ccacaggtca cgccacctct cttcctgtca ccgacacttc  3540
ctcagtatcc acaggtcaca ccacccctct tcatgtcact gatgcttcct cagcatccac  3600
aggtcaggcc acccctcttc ctgtcaccag cctttcctca gtatccacag gtgacaccac  3660
gcctcttcct gtcactagcc cttcctcagc atccacaggt cacgccaccc ctcttcttgt  3720
caccgacact tcctcagcat ccacaggaca cgccacccct cttcctgtca ccgacgcttc  3780
ctcagtgtcc acagatcacg ccacctctct tcctgtaacc atcccttccg cagcatccac  3840
aggtcacacc acccctcttc ctgtcaccga cacttcctca gcatccacag gtcaggccac  3900
ctctcttctt gtcaccgaca cttcctcagt atccacaggt gacaccacgc ctcttcctgt  3960
cactagcact tcctcagcat ccacaggtca cgtcactcct cttcatgtca ccagcccttc  4020
ctcagcatcc acaggtcacg ccacccctct tcctgtcacc agcctttcct cagcatccac  4080
aggtgacacc atgcctcttc ctgtcactag cccttcctca gcatccacag gtgacaccac  4140
ccctcttcct gtcaccgacg cttcctcagt atccacaggt cacaccaccc ctcttcatgt  4200
cactgatgct tcctcagcat ccacaggtca ggccacccct cttcctgtca ccagcctttc  4260
ctcagtatcc acaggtgaca ccacgcctct tcctgtcact agcccttcct cagcatccac  4320
aggtcacgcc acccctcttc ttgtcaccga cacttcctca gcatccacag gacacgccac  4380
ccctcttcct gtcaccgacg cttcctcagt gtccacagat cacgccacct ctcttcctgt  4440
aaccatccct tccgcagcat ccacaggtca caccacccct cttcctgtca ccgacacttc  4500
ctcagcatcc acaggtcagg ccacctctct tcttgtcacc gacacttcct cagtatccac  4560
aggtgacacc acgcctcttc ctgtcactag cacttcctca gcatccacag gtcacgtcac  4620
tcctcttcat gtcaccagcc cttcctcagc atccacaggt cacgccaccc ctcttcctgt  4680
caccagcctt tcctcagcat ccacaggtga caccatgcct cttcctgtca ctagcccttc  4740
ctcagcatcc acaggtgaca ccacccctct tcctgtcacc gacgcttcct cagtatccac  4800
aggtcacacc acccctcttc ctgtcaccag cccttcctca gcatctacag gtcacaccac  4860
ccctcttcct gtcaccgaca cttcctcagc atccaaaggt gacaccaccc ctcttcctgt  4920
caccagccct tcctcagcat ctacaggtca caccacccct cttcctgtca ccgacacttc  4980
ctcagcatcc acaggtgaca ccacccctct tcctgtcacc aatgcttcct cattatccac  5040
aggtcacgcc acccctcttc atgtcaccag cccttcctca gcatccacag gtcacgccac  5100
ccctcttcct gtcaccagca cttcctcagc atccaccggt cacgccaccc ctcttcctgt  5160
caccggcctt tcctcagcta ccacagatga caccacccgt cttcctgtca ccgacgtttc  5220
ctcggcatcc acaggtcagg ccacccctct tcctgtcacc agcctttcct cagtatccac  5280
aggtgacacc acgcctcttc ctgtcactag cccttcctca gcatccacag gtcacgccag  5340
ccctcttctt gtcactgacg cttcctcagc atccacaggt caggccaccc ctcttcctgt  5400
caccgacact tcctcagtat ccacagctca cgccacccca cttcctgtca ccggcctttc  5460
ttcagcttcc acagatgaca ccacccgtct tcctgtcacc gacgtttcct cggcatccac  5520
aggtcaggcc atccctcttc ctgtcaccag cccttcctca gcatccacag gtgacaccac  5580
ccctcttcct gtcaccgacg cttcctcagc atccacaggt gacaccacct ctcttcctgt  5640
caccatccct tcctcagcat cttcaggtca caccacctct cttcctgtca ccgacgcttc  5700
ctcagtgtcc acaggtcacg ccacctctct tcttgtcacc gacgcttcct cagtatccac  5760
aggtgacacc acccctcttc ctgtcaccga cactaactca gcatccacag gtgacaccac  5820
ccctcttcat gtcaccgacg cttcctcagt atccacaggt cacgccacct ctcttcctgt  5880
caccagcctt tcctcagcat ccacaggtga caccacgcct cttcctgtca ctagcccttc  5940
ctcagcatcc tcaggtcaca ccacccctct tcctgtcacc gacgcttcct cagtacccac  6000
aggtcacgcc acctctcttc ctgtcaccga cgcttcctca gtgtccacag gtcacgccac  6060
ccctcttcct gtcaccgacg cttcctcagt gtccacaggt catgccaccc ctcttccggt  6120
caccgacact tcctcagtat ctacaggaca ggccacccct cttcctgtca ccagcctttc  6180
ctcagcatcc actggtgaca ccacgccgct tcctgtcacc gatacttcct cagcatccac  6240
aggtcaggac acccctcttc ctgtcaccag cctttcctca gtatccacag gtgacaccac  6300
gcctcttcct gtcactaacc cttcctcagc atccacaggt cacgccaccc ctcttcttgt  6360
caccgacgct tcctcaatat ccacaggtca cgccacctct cttcttgtca ccgacgcttc  6420
ctcagtatcc acaggtcacg ccaccgctct tcatgacacc gatgcttcct cattatccac  6480
aggggacacc acccctcttc ctgtcaccag cccttcctca acatccacag gtgacaccac  6540
ccctcttcct gtcaccgaaa cttcctcagt atccacaggt cacgccacct ctcttcctgt  6600
caccgacact tcctcagcat ccacaggtca cgccacctct cttcctgtca ccgacacttc  6660
ctcagcatcc acaggtcacg ccacccctct tcctgtcacc gacacttcct cagcatccac  6720
aggtcaggcc acccctcttc ctgtcaccag cccttcctca gcatccacag gtcacgccat  6780
ccctcttctt gtcaccgaca cttcctcagc atccacagga caggccaccc ctcttcctgt  6840
caccagcctt tcctcagcat ccacaggtga caccacccct cttcctgtca ccgacgcttc  6900
ctcagtgtcc acaggtcacg ccacctctct tcctgtcacc agcctttcct cagtatccac  6960
aggtgacacc actcctcttc ctgtcactag cccttcctca gcatccacag gtcacgccac  7020
ccctcttcat gtcaccgacg cttcctcagc atccacaggt cacgccaccc ctcttcctgt  7080
caccagcctt tcctcagcat ccacaggtga caccacgcct cttcctgtca ctagcccttc  7140
ctcagcatcc acaggtcacg ccacccctct tcatgtcacc gacgcttcct cagtatccac  7200
```

-continued

```
aggtgacacc acccctcttc ctgtcaccag ctcttcctca gcatcctcag gtcacaccac  7260
ccctcttcct gtcaccgacg cttcctcagc atccacaggt gacaccaccc ctcttcctgt  7320
caccgacact tcctcagcat ccacaggtca cgccacccat cttcctgtca ccggcctttc  7380
ctcagcttcc acaggtgaca ccacccgtct tcctgtcacc aacgtttcct cggcatccac  7440
aggtcatgcc acccctcttc ctgtcaccag cacttcctca gcatccacag gtgacaccac  7500
ccctcttcct ggcaccgaca cttcctcagt atccacaggt cacaccaccc ctcttcttgt  7560
caccgacgct tcgtcagtat ccacaggtga caccacccgt cttcctgtca ccagcccttc  7620
ctcagcatct acaggtcaca ccacccctct acctgtcacc gacactccct cagcatccac  7680
aggtgacacc acccctcttc ctgtcaccaa tgcttcctca ttatccacac gtcacgccac  7740
ctctcttcat gtcaccagcc cttcctcagc atccacaggt cacgccacct ctcttcctgt  7800
caccgacact tccgcagcat ccacaggtca cgccacccct cttcctgtca ccagcacttc  7860
ctcagcatcc acaggtgaca ccacccctct tcctgtcacc gacacttact cagcatccac  7920
aggtcaggcc acccctcttc ctgtcaccag cctttcctca gtatccacag gtgacaccac  7980
gcctcttcct gtcactagcc cttcctcagc atccacaggt cacgccactc ctcttcttgt  8040
caccgacgct tcctcagcat ccacaggtca ggccacccct cttcctgtca ccagcctttc  8100
ctcagtatcc acaggtgaca ccacgcctct tcctgtcact agcccttcct cagcatccac  8160
cggtcatgcc acctctcttc ctgtcaccga cacttcctca gcatccacag gtgacaccac  8220
ctctcttcct gtcaccgaca cttcctcagc atacacaggt gacaccacct ctcttcctgt  8280
caccgacact tcctcatcat ccacaggtga caccacccct cttcttgtca ccgagacttc  8340
ctcagtatcc acaggtgaca ccacccctct tcctgtcacc gacacttcct cagcatccac  8400
aggtcacgcc acccctcttc ctgtcaccaa cacttcctca gtatccacag gtcacgccac  8460
ccctcttcat gtcaccagcc cttcctcagc atccacaggt cacaccaccc ctcttcctgt  8520
caccgacgct tcgtcagtgt ccacaggtca cgccacctct cttcctgtca ccgacgcttc  8580
ctcagtgttc acaggtcatg ccacctctct tcctgtcacc atcccttcct cagcatcctc  8640
aggtcacacc acccctcttc ctgtcaccga cgcttcctca gtgtccacag gtcacgccac  8700
ctctcttcct gtcaccgacg cttcctcagt gtccacaggt catgccaccc ctcttcctgt  8760
caccgacgct tcctcagtgt ccacaggtca cgctacccct cttcctctca ccagcctttc  8820
ctcagtatcc acaggtgaca ccacgcctct tcctgtcacc gacacttcct cagcatccac  8880
aggtcaggcc acccctcttc ctgtcaccag cctttcctca gtatccacag gtgacaccac  8940
ccctcttcct gtcaccgaca cttcctcagc atccacaggt cacgccacct ctcttcctgt  9000
caccgacact tcctcagcat ccacaggtca cgccacccct cttcctgaca ccgacacttc  9060
ctcagcatcc acaggtcacg ccacccttct tcctgtcacc gacacttcct cagcatccat  9120
aggtcacgcc acctctcttc ctgtcaccga cacttcctca atatccacag gtcacgccac  9180
ccctcttcat gtcaccagcc cttcctcagc atccaccggt cacgccaccc cgcttcctgt  9240
caccgacact tcctcagcat ccacaggtca cgccaaccct cttcatgtca ccagcccttc  9300
ctcagcatcc accggtcacg ccaccccgct tcctgtcacc gacacttcct cagcatccac  9360
aggtcacgcc acccctcttc ctgtcaccag cctttcctca gtatccacag gtgacaccac  9420
gcctcttcct gtcactagcc cttcctcagc atccacaggt cacaccaccc ctcttcctgt  9480
caccgacact tcctcagcat ccacaggtca ggccaccgct cttcctgtca ccagcacttc  9540
ctcagcatcc acaggtgaca ccacccctct tcctgtcacc gacacttcct cagcatccac  9600
aggtcaggcc acccctcttc ctgtcaccag cctttcctca gtatccacag gtgacaccac  9660
gcctcttcct gtcactagcc cttcctcagc atccacaggt cacgccactc ctcttcttgt  9720
caccgacgct tcctcagcat ccacaggtca ggccacccct cttcctgtca ccagcctttc  9780
ctcagtatcc acaggtgaca ccacgcctct tcctgtcact agcccttcct cagcatccac  9840
cggtcatgcc acctctcttc ctgtcaccga cacttcctca gcatccacag gtgacaccac  9900
ctctcttcct gtcaccgaca cttcctcagc atacacaggt gacaccacct ctcttcctgt  9960
caccgacact tcctcatcat ccacaggtga caccacccct cttcttgtca ccgagacttc  10020
ctcagtatcc acaggtcacg ccactcctct tcttgtcacc gacgcttcct cagcatccac  10080
aggtcacgcc acccctcttc atgtcaccag cccttcctca gcatccacag gtgacaccac  10140
ccctgtgcct gtcaccgaca cttcctcagt atccacaggt cacgccaccc ctcttcctgt  10200
caccggcctt tcctcagctt ccacaggtga caccacccgt cttcctgtca ccgacatttc  10260
ctcggcatcc acaggtcagg ccacccctct tcctgtcacc aacacttcct cagtatccac  10320
aggtgacacc atgcctcttc ctgtcactag cccttcctca gcatccacag gtcacgccac  10380
ccctcttcct gtcaccagca cttcctcagc atccaccggt cacgccaccc ctgttcctgt  10440
caccagcact tcctcagcat ctacaggtca caccacccct cttcctgtca ccgacacttc  10500
ctcagcatcc acaggtgaca ccacccctct tcctgtcacc agcccttcct cagcatctac  10560
aggtcacacc acccctcttc atgtcaccat cccttcctca gcatccacag gtgacaccag  10620
cactcttcct gtcaccggcg cttcctcagc atccaccggt cacgccaccc ctcttcctgt  10680
caccgacact tcctcagtat ccaccggtca cgccacgcct cttcctgtca ccagcctttc  10740
ctcagtatcc acaggtgaca ccacccctct tcctgtcacc gacgcttcct cggcatccac  10800
aggtcaggcc acccctcttc ctgtcaccag cctttcctca gtatccacag gtgacaccac  10860
ccctcttctt gtcaccgacg cttcctcagt atccacaggt cacgccaccc ctcttcctgt  10920
caccgacact tcctcagcat ccacaggtga caccacccgt cttcctgtca cggacacttc  10980
ctcagcatcc acaggtcagg ccacccctct tcctgtcacc agcctttcct cagtatccac  11040
aggtgacacc acccctcttc ttgtcaccga cgcttcctca gtatccacag gtcacgccac  11100
ccctcttcct gtcaccgaca cttcctcagc atccacaggt gacaccaccc gtcttcctgt  11160
cacggacact tcctcagcat ccacaggtca ggccacccct cttcctgtca ccatcccttc  11220
ctcatcatcc tcaggtcaca ccacccctct tcctgtcacc agcacttcct cagtatctac  11280
aggtcacgtc acccctcttc atgtcaccag cccttcctca gcatccacag gtcacgtcac  11340
ccctcttcct gtcaccagca cttcctcagc atccacaggt cacgccaccc ctcttcttgt  11400
caccgacgct tcctcagtgt ccacaggtca cgccacgcct cttcctgtca ccgacgcttc  11460
ctcagcatcc acaggtgaca ccacccctct tcctgtcacc gacacttcct cagcatccac  11520
aggtcaggcc acccctcttc ctgtcaccag cctttcctca gtatccacag gtgacaccac  11580
ccctcttcct gtcaccgacg cttcctcagc atccacaggt cacgccaccc ctcttcctgt  11640
caccatccct tcctcagtat ccacaggtga caccatgcct cttcctgtca ctagcccttc  11700
ctcagcatcc acaggtcacg ccacccctct tcctgttacc ggcctttcct cagcttccac  11760
aggtgacacc acccctcttc ctgtcaccga cacttcctca gcatccacac gtcacgccac  11820
ccctcttcct gtcaccgaca cttcctcagc ttccacagat gacaccaccc gtcttcctgt  11880
caccgacgtt tcctcggcat ccacaggaca tgccacccct cttcctgtca ccagcacttc  11940
```

-continued

```
ctcagcatcc acaggtgaca ccacccctct tcctgtcacc gacacttcct cagtatccac  12000
aggtcacgcc acctctcttc ctgtcaccag ccgttcctca gcatccacag gtcacgccac  12060
ccccttcct gtcaccgaca cttcctcagt atccacaggt cacgccaccc ctcttcctgt  12120
caccagcact tcctcagtat ctacaggtca cgccacccct cttcctgtca ccagcccttc  12180
ctcagcatcc acaggtcacg ccacccctgt tcctgtcacc agcacttcct cagcatccac  12240
aggtgacacc acccctcttc ctgtcaccaa tgcttcctca ttatccacag gtcacgccac  12300
ccctcttcat gtcaccagcc cttcctcagc atccagaggt gacaccagca ctcttcctgt  12360
caccgatgct tcctcagcat ccaccggtca cgccacccct cttcctctca ccagcctttc  12420
ctcagtatcc acaggtgaca ccacgcctct tcctgtcacc gacacttcct ctgcatccac  12480
aggtcaggcc acccctcttc ctgtcaccag cctttcctca gtatccacag gtgacaccac  12540
gcctcttcct gtcaccatcc cttcctcagc atcctcaggt cacaccacct ctcttcctgt  12600
caccgacgct tcctcagtgt ccacaggtca cggcacccct cttcctgtca ccagcacttc  12660
ctcagcatcc acaggtgaca ccacccctct tcctgtcacc gacacttcct cagcatccac  12720
aggtcacgcc acccctcttc ctgtcaccga cacttcctca gcatccacag gtcacgccac  12780
ccctcttcct gtcaccagcc tttcctcagt atccacaggt cacgccaccc ctcttgctgt  12840
cagcagtgct acctcagctt ccacagtatc ctcggactcc cctctgaaga tggaaacacc  12900
aggaatgaca acaccgtcac tgaagacaga cggtgggaga cgcacagcca catcaccacc  12960
ccccacaacc tcccagacca tcatttccac cattcccagc actgccatgc acacccgctc  13020
cacagctgcc cccatcccca tcctgcctga gagaggagtt tccctcttcc cctatggggc  13080
aggcgccggg gacctggagt tcgtcaggag gaccgtggac ttcacctccc cactcttcaa  13140
gccggcgact ggcttccccc ttggctcctc tctccgtgat tccctctact tcacagacaa  13200
tggccagatc atcttcccag agtcagacta ccagattttc tcctacccca acccactccc  13260
aacaggcttc acaggccggg accctgtggc cctggtggct ccgttctggg acgatgctga  13320
cttctccact ggtcgggga ccacatttta tcaggaatac gagacgttct atggtgaaca  13380
cagcctgcta gtccagcagg ccgagtcttg gattagaaag atgacaaaca acggggcta  13440
caaggccagg tgggccctaa aggtcacgtg ggtcaatgcc cacgcctatc ctgcccagtg  13500
gaccctcggg agcaacacct accaagccat cctctccacg gacgggagca ggtcctatgc  13560
cctgtttctc taccagagcg gtgggatgca gtgggacgtg gcccagcgct caggcaaccc  13620
ggtgctcatg ggcttctcta gtggagatgg ctatttcgaa aacagcccac tgatgtccca  13680
gccagtgtgg gagaggtatc gccctgatag attcctgaat tccaactcag gcctccaagg  13740
gctgcagttc tacaggctac accgggaaga aaggcccaac taccgtctcg agtgcctgca  13800
gtggctgaag agccagcctc ggtggcccag ctggggctgg aaccaggtct cctgcccttg  13860
ttcctggcag cagggacgac gggacttacg attccaaccc gtcagcatag gtcgctgggg  13920
cctcggcagt aggcagctgt gcagcttcac ctcttggcga ggaggcgtgt gctgcagcta  13980
cgggccctgg ggagagtttc gtgaaggctg gcacgtgcag cgtccttggc agttggccca  14040
ggaactggag ccacagagct ggtgctgccg ctggaatgac aagccctacc tctgtgccct  14100
gtaccagcag aggcggcccc acgtgggctg tgctacatac aggcccccac agcccgcctg  14160
gatgttcggg gacccccaca tcaccacctt ggatggtgtc agttacacct tcaatgggct  14220
gggggacttc ctgctggtcg gggcccaaga cgggaactcc tccttcctgc ttcagggccg  14280
caccgcccag actggctcag cccaggccac caacttcatc gcctttgcgg ctcagtaccg  14340
ctccagcagc ctgggccccg tcacggtcca atggctcctt gagcctcacg acgcaatccg  14400
tgtcctgctg gataaccaga ctgtgacatt tcagcctgac catgaagacg gcggaggcca  14460
ggagacgttc aacgccaccg gagtcctcct gagccgcaac ggctctgagg tctcggccag  14520
cttcgacggc tgggccaccg tctcggtgat cgcgctctcc aacatcctcc acgcctccgc  14580
cagcctcccg cccgagtacc agaaccgcac ggaggggctc ctgggggtct ggaataacaa  14640
tccagaggac gacttcagga tgcccaatgg ctccaccatt cccccaggga gccctgagga  14700
gatgcttttc cactttggaa tgacctggca gatcaacggg acaggcctcc ttggcaagag  14760
gaatgaccag ctgccttcca acttcacccc tgttttctac tcacaactgc aaaaaaacag  14820
ctcctgggct gaacatttga tctccaactg tgacggagat agctcatgca tctatgacac  14880
cctggccctg cgcaacgcaa gcatcggact tcacacgagg gaagtcagta aaaactacga  14940
gcaggcgaac gccaccctca atcagtaccc gccctccatc aatggtggtc gtgtgattga  15000
agcctacaag ggcagacca cgctgattca gtacaccagc aatgctgagg atgccaactt  15060
cacgctcaga gacagctgca ccgacttgga gctctttgag aatgggacgt tgctgtggac  15120
acccaagtcg ctggagccat tcactctgga gattctagca agaagtgcca agattggctt  15180
ggcatctgca ctccagccca ggactgtggt ctgccattgc aatgcagaga gccagtgttt  15240
gtacaatcag accagcaggg tgggcaactc ctccctggag gtggctggct gcaagtgtga  15300
cgggggcacc ttcggccgct actgcgaggg ctccgaggat gcctgtgagg agccgtgctt  15360
cccgagtgtc cactgcgttc ctgggaaggg ctgcgaggcc tgccctccaa acctgactgg  15420
ggatgggcgg cactgtgcgg ctctggggag ctctttcctg tgtcagaacc agtcctgccc  15480
tgtgaattac tgctacaatc aaggccactg ctacatctcc cagactctgg gctgtcagcc  15540
catgtgcacc tgcccccag ccttcactga cagccgctgc ttcctggctg ggaacaactt  15600
cagtccaact gtcaacctag aacttccctt aagagtcatc cagctcttgc tcagtgaaga  15660
ggaaaatgcc tccatggcag aagtcaacgc ctcggtggca tacagactgg ggaccctgga  15720
catgcgggcc tttctccgca acagccaagt ggaacgaatc gattctgcag caccggcctc  15780
gggaagcccc atccaacact ggatggtcat ctcggagttc cagtaccgcc ctcggggccc  15840
ggtcattgac ttcctgaaca accagctgct ggccgcggtg gtggaggcgt tcttatacca  15900
cgttccacgg aggagtgagg agcccaggaa cgacgtggtc ttccagccca tctccgggga  15960
agacgtgcgc gatgtgacag ccctgaacgt gagcacgctg aaggcttact tcagatgcga  16020
tggctacaag ggctacgacc tggtctacag cccccagagc ggcttcacct gcgtgtcccc  16080
gtgcagtagg ggctactgtg accatggagg ccagtgccag cacctgccca gtgggccccg  16140
ctgcagctgt gtgtccttct ccatctacac ggcctggggc gagcactgtg agcacctgag  16200
catgaaactc gacgcgttct tcggcatctt ctttggggcc ctgggcggcc tcttgctgct  16260
gggggtcggg acgttcgtgg tcctgcgctt ctggggttgc tccggggcca ggttctccta  16320
tttcctgaac tcagctgagg ccttgccttg aaggggcagc tgtggcctag gctacctcaa  16380
gactcacctc atccttaccg cacatttaag gcgccattgc ttttgggaga ctggaaaagg  16440
gaaggtgact gaaggctgtc aggattcttc aaggagaatg aatactggga atcaagacaa  16500
```

-continued

```
gactatacct tatccatagg cgcaggtgca caggggggagg ccataaagat caaacatgca  16560
tggatgggtc ctcacgcaga cacacccaca gaaggacact agcctgtgca cgcgcgcgtg  16620
cacacacaca cacacacaca cgagttcata atgtggtgat ggccctaagt taagcaaaat  16680
gcttctgcac acaaaactct ctggtttact tcaaattaac tctatttaaa taaagtctct  16740
ctgacttttt gtgtct                                                  16756
```

```
SEQ ID NO: 56          moltype = DNA  length = 2613
FEATURE                Location/Qualifiers
source                 1..2613
                       mol_type = other DNA
                       organism = Homo sapiens
SEQUENCE: 56
aggctgtgac agtcatctgt ctggacgcgc tgggtggatg cggggggctc ctgggaactg  60
tgttggagcc gagcaagcgc tagccaggcg caagcgcgca cagactgtag ccatccgagg  120
acacccccgc ccccccggcc cacccggaga cacccgcgca gaatcgcctc cggatcccct  180
gcagtcggcg ggagtgttgg aggtcggcgc cggcccccgc cttccgcgcc ccccacggga  240
aggaagcacc cccggtatta aaacgaacgg ggcggaaaga agccctcagt cgccggccgg  300
gaggcgagcc gatgccgagc tgctccacgt ccaccatgcc gggcatgatc tgcaagaacc  360
cagacctcga gtttgactcg ctacagccct gcttctaccc ggacgaagat gacttctact  420
tcggcggccc cgactcgacc cccccggggg aggacatctg gaagaagttt gagctgctgc  480
ccacgccccc gctgtcgccc agccgtggct tcgcggagca cagctccgag cccccgagct  540
gggtcacgga gatgctgctt gagaacgagc tgtggggcag cccggccgag gaggacgcgt  600
tcggcctggg gggactgggt ggcctcaccc ccaacccggt catcctccag gactgcatgt  660
ggagcggctt ctccgcccgc gagaagctgg agcgcgccgt gagcgagaag ctgcagcacg  720
gccgcgggcc gccaaccgcc ggttccaccg cccagtcccc gggagccggc gccgccagcc  780
ctgcgggtcg cgggcacggc ggggctgcgg gagccggccg cgccggggcc gccctgcccg  840
ccgagctcgc ccacccggcc gccgagtgcg tggatcccgc cgtggtcttc ccctttcccg  900
tgaacaagcg cgagccagcg cccgtgcccg cagccccggc cagtgccccg gcggcgggcc  960
ctgcggtcgc ctcgggggcg ggtattgccg ccccagccgg ggccccgggg gtcgcccctc  1020
cgcgcccagg cggccgccag accagcggcg gcgaccacaa ggccctcagt acctccggag  1080
aggacaccct gagcgattca gatgatgaag atgatgaaga ggaagatgaa gaggaagaaa  1140
tcgacgtggt cactgtggag aagcggcgtt cctcctccaa caccaaggct gtcaccacat  1200
tcaccatcac tgtgcgtccc aagaacgcag ccctgggtcc cgggagggct cagtccagcg  1260
agctgatcct caaacgatgc cttcccatcc accagcagca caactatgcc gccccctctc  1320
cctacgtgga gagtgaggat gcacccccac agaagaagat aaagagcgag gcgtccccac  1380
gtccgctcaa gagtgtcatc cccccaaagg ctaagagctt gagcccccga aactctgact  1440
cggaggacag tgagcgtcgc agaaaccaca acatcctgga gcgccagcgc cgcaacgacc  1500
ttcggtccag ctttctcacg ctcagggacc acgtgccgga gttggtaaag aatgagaagg  1560
ccgccaaggt ggtcattttg aaaaaggcca ctgagtatgt ccactccctc caggccgagg  1620
agcaccagct tttgctggaa aaggaaaaat tgcaggcaag acagcagcag ttgctaaaga  1680
aaattgaaca cgctcggact tgctagacgc ttctcaaaac tggacagtca ctgccacttt  1740
gcacattttg attttttttt taaacaaaca ttgtgttgac attaagaatg ttggtttact  1800
ttcaaatcgg tcccctgtcg agttcggctc tgggtgggca gtaggaccac cagtgtgggg  1860
ttctgctggg accttggaga gcctgcatcc caggatgctg ggtggccctg cagcctcctc  1920
cacctcacct ccatgacagc gctaaacgtt ggtgacggtt gggagcctct ggggctgttg  1980
aagtcacctt gtgtgttcca agtttccaaa caacagaaag tcattccttc tttttaaaat  2040
ggtgcttaag ttccagcaga tgccacataa ggggtttgcc atttgatacc cctggggaac  2100
atttctgtaa ataccattga cacatccgcc ttttgtatac atcctgggta atgagaggtg  2160
gcttttgcgg ccagtattag actggaagtt catacctaag tactgtaata atacctcaat  2220
gtttgaggag catgttttgt atacaaatat attgttaatc tctgttatgt actgtactaa  2280
ttcttacact gcctgtatac tttagtatga cgctgataca taactaaatt tgatacttat  2340
attttcgtat gaaaatgagt tgtgaaagtt ttgagtagat attactttat cactttttga  2400
actaagaaac ttttgtaaag aaatttacta tatatatatg ccttttttcct agcctgtttc  2460
ttcctgttaa tgtatttgtt catgtttggt gcatagaact gggtaaatgc aaagttctgt  2520
gtttaatttc ttcaaaatgt atatatttag tgctgcatct tatagcactt tgaaatacct  2580
catgtttatg aaaataaata gcttaaaatt aaa                               2613
```

```
SEQ ID NO: 57          moltype = DNA  length = 1357
FEATURE                Location/Qualifiers
source                 1..1357
                       mol_type = other DNA
                       organism = Homo sapiens
SEQUENCE: 57
acacccaggt ccccagcgat gtctccacca ccgctgctgc aacccctgct gctgctgctg  60
cctctgctga atgtggagcc ttccggggcc acactgatcc gcatccctct tcatcgagtc  120
caacctggac gcaggatcct gaacctactg aggggatgga gagaaccagc agagctcccc  180
aagttggggg ccccatcccc tggggacaag cccatcttcg tacctctctc gaactacagg  240
gatgtgcagt attttgggga aattgggctg ggaacgcctc cacaaaactt cactgttgcc  300
tttgacactg gctcctccaa tctctgggtc ccgtccagga gatgccactt cttcagtgtg  360
ccctgctggt tacaccaccg atttgatccc aaagcctcta gctccttcca ggccaatggg  420
accaagtttg ccattcaata tggaactggg cgggtagatg gaatcctgag cgaggacaag  480
ctgactattg gtggaatcaa gggtgcatca gtgattttcg gggaggctct ctgggagccc  540
agcctggtct tcgcttttgc ccattttgat gggatattgg gcctcggttt tcccattctg  600
tctgtggaag gagttcggcc cccgatggat gtactggtgg agcaggggct attggataag  660
cctgtcttct ccttttacct caacagggac cctgaagagc ctgatggagg agagctggtc  720
ctgggggct cggacccggc acactacatc ccacccctca ccttcgtgcc agtcacggtc  780
cctgcctact ggcagatcca catggagcgt gtgaaggtgg gcccagggct gactctctgt  840
gccaagggct gtgctgccat cctggatacg ggcacgtccc tcatcacagg acccactgag  900
gagatccggg ccctgcatgc agccattggg ggaatcccct tgctggctgg ggagtacatc  960
```

-continued

```
atcctgtgct cggaaatccc aaagctcccc gcagtctcct tccttcttgg gggggtctgg  1020
tttaacctca cggcccatga ttacgtcatc cagactactc gaaatggcgt ccgcctctgc  1080
ttgtccggtt tccaggccct ggatgtccct ccgcctgcag ggcccttctg gatcctcggt  1140
gacgtcttct tggggacgta tgtggccgtc ttcgaccgcg gggacatgaa gagcagcgcc  1200
cgggtgggcc tggcgcgcgc tcgcactcgc ggagcggacc tcggatgggg agagactgcg  1260
caggcgcagt tccccgggtg acgcccaagt gaagcgcatg cgcagcgggt ggtcgcggag  1320
gtcctgctac ccagtaaaaa tccactattt ccattga                         1357

SEQ ID NO: 58          moltype = DNA  length = 3278
FEATURE                Location/Qualifiers
source                 1..3278
                       mol_type = other DNA
                       organism = Homo sapiens
SEQUENCE: 58
agcggtgcgg gccgggcggg tgcattcagg ccaaggcggg gccgccggga tgctcagggt  60
tccggagccg cggcccgggg aggcgaaagc ggagggggcc gcgccgccga ccccgtccaa  120
gccgctcacg tccttcctca tccaggacat cctgcgggac ggcgcgcagc ggcaaggcgg  180
ccgcacgagc agccagagac agcgcgaccc ggagccggag ccagagccag agccagaggg  240
aggacgcagc cgcgccgggg cgcagaacga ccagctgagc accgggcccc gcgccgcgcc  300
ggaggaggcc gagacgctgg cagagaccga gccagaaagg cacttggggt cttatctgtt  360
ggactctgaa aacacttcag gcgcccttcc aaggcttccc caaacccccta agcagccgca  420
gaagcgctcc cgagctgcct tctcccacac tcaggtgatc gagttggaga ggaagttcag  480
ccatcagaag tacctgtcgg cccctgaacg ggcccacctg gccaagaacc tcaagctcac  540
ggagacccaa gtgaagatat ggttccagaa cagacgctat aagactaagc gaaagcagct  600
ctcctcggag ctgggagact tggagaagca ctcctctttg ccggccctga aagaggaggc  660
cttctcccgg gcctccctgg tctccgtgta taacagctat ccttactacc catacctgta  720
ctgcgtgggc agctggagcc cagctttttg gtaatgccag ctcaggtgac aaccattatg  780
atcaaaaact gccttcccca gggtgtctct atgaaaagca caaggggcca aggtcaggga  840
gcaagaggtg tgcacaccaa agctattgga gatttgcgtg gaaatctcag attcttcact  900
ggtgagacaa tgaaacaaca gagacagtga aagttttaat acctaagtca ttcctccagt  960
gcatactgta ggtcattttt tttgcttctg gctacctgtt tgaaggggag agagggaaaa  1020
tcaagtggta ttttccagca ctttgtatga ttttggatga gttgtacacc caaggattct  1080
gttctgcaac tccatcctcc tgtgtcactg aatatcaact ctgaaagagc aaacctaaca  1140
ggagaaagga caaccaggat gaggatgtca ccaactgaat taaacttaag tccagaagcc  1200
tcctgttggc cttggaatat ggccaaggct ctctctgtcc ctgtaaaaga gaggggcaaa  1260
tagagagtct ccaagagaac gccctcatgc tcagcacata tttgcatggg agggggagat  1320
gggtgggagg agatgaaaat atcagctttt cttattcctt tttattcctt ttaaaatggt  1380
atgccaactt aagtatttac agggtggccc aaatagaaca agatgcactc gctgtgattt  1440
taagacaagc tgtataaaca gaactccact gcaagagggg gggccgggcc aggagaatct  1500
ccgcttgtcc aagacagggg cctaaggagg gtctccacac tgctgctagg ggctgttgca  1560
tttttttatt agtagaaagt ggaaaggcct cttctcaact tttttccctt gggctggaga  1620
atttagaatc agaagtttcc tggagttttc aggctatcat atatactgta tcctgaaagg  1680
caacataatt cttccttccc tccttttaaa attttgtgtt cctttttgca gcaattactc  1740
actaaagggc ttcattttag tccagatttt tagtctggct gcacctaact tatgcctcgc  1800
ttatttagcc cgagatctgg tctttttttt tttttttttt tttttttttc cgtctcccca  1860
aagctttatc tgtcttgact ttttaaaaaa gtttgggggc agattctgaa ttggctaaaa  1920
gacatgcatt tttaaaacta gcaactctta tttctttcct ttaaaaatac atagcattaa  1980
atcccaaatc ctatttaaag acctgacagc ttgagaaggt cactactgca tttataggac  2040
cttctggtgg ttctgctgtt acgtttgaag tctgacaatc cttgagaatc tttgcatgca  2100
gaggaggtaa gaggtattgg attttcacag aggaagaaca cagcgcagaa tgaagggcca  2160
ggcttactga gctgtccagt ggagggctca tgggtgggac atggaaaaga aggcagccta  2220
ggccctgggg agcccagtcc actgagcaag caagggactg agtgagcctt ttgcaggaaa  2280
aggctaagaa aaaggaaaac cattctaaaa cacaacaaga aactgtccaa atgctttggg  2340
aactgtgttt attgcctata atgggtcccc aaaatgggta acctagactt cagagagaat  2400
gagcagagag caaaggagaa atctggctgt ccttccattt tcattctgtt atctcaggtg  2460
agctggtaga ggggagacat tagaaaaaaa tgaaacaaca aaacaattac taatgaggta  2520
cgctgaggcc tgggagtctc ttgactccac tacttaattc cgtttagtga gaaacctttc  2580
aattttcttt tattagaagg gccagcttac tgttggtggc aaaattgcca acataagtta  2640
atagaaagtt ggccaatttc accccatttt ctgtggtttg ggctccacat tgcaatgttc  2700
aatgccacgt gctgctgaca ccgaccggag tactagccag cacaaaaggc agggtagcct  2760
gaattgcttt ctgctcttta catttctttt aaaataagca tttagtgctc agtccctact  2820
gagtactctt tctctcccct cctctgaatt taattctttc aacttgcaat ttgcaaggat  2880
tacacatttc actgtgatgt atattgtgtt gcaaaaaaaa aaaaaaagtg tctttgttta  2940
aaattacttg gtttgtgaat ccatcttgct ttttccccat tggaactagt cattaaccca  3000
tctctgaact ggtagaaaaa catctgaaga gctagtctat cagcatctga caggtgaatt  3060
ggatggttct cagaaccatt tcacccagac agcctgtttc tatcctgttt aataaattag  3120
tttgggttct ctacatgcat aacaaaccct gctccaatct gtcacataaa agtctgtgac  3180
ttgaagttta gtcagcaccc ccaccaaact ttatttttct atgtgttttt tgcaacatat  3240
gagtgttttg aaaataaagt acccatgtct ttattaga                        3278

SEQ ID NO: 59          moltype = DNA  length = 4185
FEATURE                Location/Qualifiers
source                 1..4185
                       mol_type = other DNA
                       organism = Homo sapiens
SEQUENCE: 59
acactccctg gggcaggcgc tcacgcacgc tacaaacaca cactcctctt tcctccctcg  60
cgcgccctct ctcatccttc ttcacgaagc gctcactcgc accctttctc tctctctctc  120
tctctctcta acacgcacgc acactcccag ttgttcacac tcgggtcctc tccagcccga  180
```

```
cgttctcctg gcacccacct gctccgcggc gccctgcgcg ccccccctcgg tcgcgcccct  240
tgcgctctcg gcccagaccg tcgcagctac agggggcctc gagccccggg gtgagcgtcc  300
ccgtcccgct cctgctcctt cccataggga cgcgcctgat gcctgggacc ggccgctgag  360
cccaagggga ccgaggaggc catggtagga gcgctcgcct gctgcggtgc ccgctgaggc  420
catgccgggg ccccggcgcc ccgctggctc ccgcctgcgc ctgctcctgc tcctgctgct  480
gccgccgctg ctgctgctgc tccggggcag ccacgcgggc aacctgacgg tagccgtggt  540
actgccgctg gccaatacct cgtacccctg gtcgtgggcg cgcgtgggac ccgccgtgga  600
gctggccctg gcccaggtga aggcgcgccc cgacttgctg ccgggctgga cggtccgcac  660
ggtgctgggc agcagcgaaa acgcgctggg cgtctgctcc gacaccgcag cgcccctggc  720
cgcggtggac ctcaagtggg agcacaaccc cgctgtgttc ctgggccccg gctgcgtgta  780
cgccgccgcc ccagtggggc gcttcaccgc gcactggcgg gtcccgctgc tgaccgccgg  840
cgcccccggcg ctgggcttcg gtgtcaagga cgagtatgcg ctgaccaccc gcgcggggcc  900
cagctacgcc aagctggggg acttcgtggc ggcgctgcac cgacggctgg gctgggagcg  960
ccaagcgctc atgctctacg cctaccggcc gggtgacgaa gagcactgct tcttcctcgt  1020
ggaggggctg ttcatgcggg tccgcgaccg cctcaatatt acggtggacc acctggagtt  1080
cgccgaggac gacctcagcc actacaccag gctgctgcgg accatgccgc gcaaaggccg  1140
agttatctac atctgcagct cccctgatgc cttcagaacc ctcatgctcc tggccctgga  1200
agctggcttg tgtggggagg actacgtttt cttccacctg gatatctttg ggcaaagcct  1260
gcaaggtgga cagggccctg ctccccgcag gccctgggag agaggggatg ggcaggatgt  1320
cagtgcccgc caggcctttc aggctgccaa aatcattaca tataaagacc cagataatcc  1380
cgagtacttg gaattcctga agcagttaaa acacctggcc tatgagcagt tcaacttcac  1440
catggaggat ggcctggtga acaccatccc agcatccttc cacgacgggc tcctgctcta  1500
tatccaggca gtgacggaga ctctggcaca tgggggaact gttactgatg ggagaacat  1560
cactcagcgg atgtggaacc gaagctttca aggtgtgaca ggatacctga aaattgatag  1620
cagtggcgat cgggaaacag acttctccct ctgggatatg gatcccgaga atggtgcctt  1680
cagggttgta ctgaactaca atgggacttc ccaagagctg gtggctgtgt cggggcgcaa  1740
actgaactgg cccctggggt accctcctcc tgacatcccc aaatgtggct ttgacaacga  1800
agacccagca tgcaaccaag atcacctttc caccctggag gtgctggctt tggtgggcag  1860
cctctccttg ctcggcattc tgattgtctc cttcttcata tacaggaaga tgcagctgga  1920
gaaggaactg gcctcggagc tgtggcgggt gcgctgggag gacgttgagc ccagtagcct  1980
tgagaggcac ctgcggagtg caggcagccg gctgaccctg agcgggagag gctccaatta  2040
cggctccctg ctaaccacag agggccagtt ccaagtcttt gccaagacag catattataa  2100
gggcaacctc gtggctgtga aacgtgtgaa ccgtaaacgc attgagctga cacgaaaagt  2160
cctgtttgaa ctgaagcata tgcgggatgt gcagaatgaa cacctgacca ggtttgtggg  2220
agcctgcacc gaccccccca atatctgcat cctcacagag tactgtcccc gtgggagcct  2280
gcaggacatt ctggagaatg agagcatcac cctggactgg atgttccggt actcactcac  2340
caatgacatc gtcaagggca tgctgtttct acacaatggg gctatctgtt cccatgggaa  2400
cctcaagtca tccaactgcg tggtagatgg gcgctttgtg ctcaagatca ccgactatgg  2460
gctggagagc ttcagggacc tggacccaga gcaaggacac accgtttatg ccaaaaagct  2520
gtggacggcc cctgagctcc tgcgaatggc ttcacccccct gtgcggggct cccaggctgg  2580
tgacgtatac agctttggga tcatccttca ggagattgcc ctgaggagtg gggtcttcca  2640
cgtggaaggt ttggacctga gccccaaaga gatcatcgag cgggtgactc ggggtgagca  2700
gccccccttc cggccctccc tggccctgca gagtcacctg gaggagttgg ggctgctcat  2760
gcagcggtgc tgggctgagg acccacagga gaggccacca ttccagcaga tccgcctgac  2820
gttgcgcaaa tttaacaggg agaacagcag caacatcctg gacaacctgc tgtcccgcat  2880
ggagcagtac gcgaacaatc tggaggaact ggtggaggag cggacccagg catacctgga  2940
ggagaagcgc aaggctgagg ccctgctcta ccagatcctg cctcactcag tggctgagca  3000
gctgaagcgt ggggagacgg tgcaggccga agcctttgac agtgttacca tctacttcag  3060
tgacattgtg ggtttcacag cgctgtcggc ggagagcaca cccatgcagg tggtgaccct  3120
gctcaatgac ctgtacactt gctttgatgc tgtcatagac aactttgatg tgtacaaggt  3180
ggagacaatt ggcgatgcct acatggtggt gtcagggctc cctgtgcgga acgggcggct  3240
acacgcctgc gaggtagccc gcatggccct ggcactgctg gatgctgtgc gctccttccg  3300
aatccgccac cggccccagg agcagctgcg cttgcgcatt ggcatccaca caggacctgt  3360
gtgtgctgga gtggtgggac tgaagatgcc ccgttactgt ctctttgggg atacagtcaa  3420
cacagcctca agaatggagt ctaatgggga agccctgaag atccacttgt cttctgagac  3480
caaggctgtc ctggaggagt ttggtggttt cgagctggag cttcgagggg atgtagaaat  3540
gaagggcaaa ggcaaggttc ggacctactg gctccttggg gagaggggga gtagcacccg  3600
aggctgacct gcctcctctc ctatccctcc acacctccct accctgtgcc agaagcaaca  3660
gaggtgccag gcctcagcct cacccacagc agccccatcg ccaaaggatg gaagtaattt  3720
gaatagctca ggtgtgctga ccccagtgaa gacaccagat aggacctctg agaggggact  3780
ggcatggggg gatctcagag cttacaggct gagccaagcc cacggccatg cacagggaca  3840
ctcacacagg cacacgcacc tgctctccac ctggactcag gccgggctgg gctgtggatt  3900
cctgatcccc tcccctcccc atgctctcct ccctcagcct tgctaccctg tgacttactg  3960
ggaggagaaa gagtcacctg aaggggaaca tgaaaagaga ctaggtgaag agagggcagg  4020
ggagcccaca tctggggctg gcccacaata cctgctcccc cgaccccctc cacccagcag  4080
tagacacagt gcacagggga gaagagggggt ggcgcagaag ggttgggggc ctgtatgcct  4140
tgcttctacc atgagcagag acaattaaaa tctttattcc agtga                 4185
```

```
SEQ ID NO: 60          moltype = DNA  length = 4055
FEATURE                Location/Qualifiers
source                 1..4055
                       mol_type = other DNA
                       organism = Homo sapiens
SEQUENCE: 60
gggaacaaac ttcagaagga ggagagacac cgggcccagg gcaccctcgc gggcggaccc  60
aagcagtgag ggcctgcagc cggccggcca gggcagcggc aggcgcggcc cggacctacg  120
ggaggaagcc ccgagccctc ggcgggctgc gagcgactcc ccggcgatgc ctcacaactc  180
catcagatct ggccatggag ggctgaacca gctgggaggg gcctttgtga atggcagacc  240
tctgccggaa gtggtccgcc agcgcatcgt agacctggcc caccagggtg taaggccctg  300
```

-continued

```
cgacatctct cgccagctcc gcgtcagcca tggctgcgtc agcaagatcc ttggcaggta  360
ctacgagact ggcagcatcc ggcctggagt gatagggggc tccaagccca aggtggccac  420
ccccaaggtg gtggagaaga ttggggacta caaacgccag aaccctacca tgtttgcctg  480
ggagatccga gaccggctcc tggctgaggg cgtctgtgac aatgacactg tgcccagtgt  540
cagctccatt aatagaatca tccggaccaa agtgcagcaa ccattcaacc tccctatgga  600
cagctgcgtg gccaccaagt ccctgagtcc cggacacacg ctgatcccca gctcagctgt  660
aactcccccg gagtcacccc agtcggattc cctgggctcc acctactcca tcaatgggct  720
cctgggcatc gctcagcctg gcagcgacaa gaggaaaatg gatgacagtg atcaggatag  780
ctgccgacta agcattgact cacagagcag cagcagcgga ccccgaaagc accttcgcac  840
ggatgccttc agccagcacc acctcgagcc gctcgagtgc ccatttgagc ggcagcacta  900
cccagaggcc tatgcctccc ccagccacac caaaggcgag cagggcctct acccgctgcc  960
cttgctcaac agcaccctgg acgacgggaa ggccaccctg acccccttcca acacgccact  1020
ggggcgcaac ctctcgactc accagaccta ccccgtggtg gcagatcctc actcaccctt  1080
cgccataaag caggaaaccc ccgaggtgtc cagttctagc tccacccctt cctctttatc  1140
tagctccgcc tttttggatc tgcagcaagt cggctccggg gtcccgccct tcaatgcctt  1200
tccccatgct gcctccgtgt acgggcagtt cacgggccag gccctcctct cagggcgaga  1260
gatggtgggg cccacgctgc ccggataccc accccacatc ccccaccagcg gacagggcag  1320
ctatgcctcc tctgccatcg caggcatggt ggcaggaagt gaatactctg gcaatgccta  1380
tggccacacc ccctactcct cctacagcga ggcctggcgc ttccccaact ccagcttgct  1440
gagttcccca tattattaca gttccacatc aaggccgagt gcaccgccca ccactgccac  1500
ggcctttgac catctgtagt tgccatgggg acagtgggag cgactgagca acaggaggac  1560
tcagcctggg acaggcccca gagagtcaca caaaggaatc tttatttatt acatgaaaaa  1620
taaccacaag tccagcattg cggcacactc cctgtgtggt taatttaatg aaccatgaaa  1680
gacaggatga ccttggacaa ggccaaactg tcctccaaga ctccttaatg aggggcagga  1740
gtcccaggga aagagaacca tgccatgctg aaaaagacaa aattgaagaa gaaatgtagc  1800
ccccagccgg tacccaccaa aggagagaag aagcaatagc cgaggaactt gggggggatgg  1860
cgaatggttc ctgcccgggc ccaaggggtg cacagggcac ctccatggct ccattattaa  1920
cacaactcta gcaattatgg accataagca cttccctcca gcccacaagt cacagcctgg  1980
tgccgaggct ctcctcacca gccacccagg gagtcacctc cctcagcctc ccgcctgccc  2040
cacacggagg ctctggctgt cctctttctc cactccattt gcttggctct ttctacacct  2100
ccctcttggg catgggctga gggctggagc gagtccctca gaaattccac caggctgtca  2160
gctgacctct tttgcctgct gctgtgaagg tatagcacca ccccaggtcc tcctgcagtg  2220
cggcatcccc ttggcagctg ccgtcagcca ggccagcccc agggagctta aaacagacat  2280
tccacagggc ctgggcccct gggaggtgag gtgtggtgtg cggcttcacc cagggcagaa  2340
caaggcagaa tcgcaggaaa cccgcttccc cttcctgaca gctcctgcca agccaaatgt  2400
gcttcctgca gctcacgccc accagctact gaagggaccc aaggcacccc ctgaagccag  2460
cgatagaggg tccctctctg ctccccagca gctcctgccc ccaaggcctg actgtatata  2520
ctgtaaatga aactttgttt gggtcaagct tccttcttc taacccccag actttggcct  2580
ctgagtgaaa tgtctctctt tgccctgtgg ggcttctctc cttgatgctt ctttcttttt  2640
ttaaagacaa cctgccatta ccacatgact caataaacca ttgctcttca tctcaggctt  2700
tggggttggc tggggaagga ggcatcccgg ggctgggctt tctcccaaga acatcagagc  2760
tgagtagccg acaaactcac tttggggccg tgggctggaa gggaccatct gatgccccag  2820
agctctggct tggccttctc cctctgcctt taattcacgt tgaacgctgg gtacctcact  2880
catcccaagt tcttcaacac tgagcaaatg caaggatagc acagtactga gccaaccata  2940
gactccccac aaggagttgc tgttgttatt aacaggaagc cagagaatca gcagggtggg  3000
ttagtgaggg atccgggaat agctgtgact ggagcctgca taaacagctc tgaagggaga  3060
gagaagactg ggctctcttg tgtgccaggc acagtatgga aggcttcata taagttaagc  3120
tgaaattagc cctgttttac atacagcttc attttacata tgaggaaact gaggctttga  3180
aaaaaatgag atgtcttgtc caagatgaaa agtagtagat tcaaccaagt cctcttactc  3240
taagcccaac gcttttaccc aaaaccccag agtcctcatc agggatgcca aatggttcta  3300
gacccagtgg aggttctgga gctgccactg ggatttaat ttcttttgat ttgctaaaga  3360
tttgacctga ctgaatggag aggtagagtg tagtgtggcc aggacaaggt gagggaggct  3420
gtagagactt agcactttag gccaaccacc tccaggaaat ctgggaaatg caatgtgaca  3480
gctcgggctc tgcactccag ggggctgtct ggtgtccaca tggaccttct ccatgtggga  3540
cacagctgga acaaggggggc aggggcctgc agctgggatg cccaggtgaa tatgggcagc  3600
tggacaaaca acactgggat tgagtcagat agaaggggcc caaggactcc agggctggga  3660
ggacagaggc tgggagagag ggctcttacc tccttaggcc tcccaaagag cggttaggga  3720
tgctgccatg gatggcatgg cagggggaac cctcctggaa gaaaatccat ctcttctgaa  3780
gggatctgag atgcggctgg tttttcaatg gcagaacttc cctctgcagc gcgactccga  3840
atccatgaca tctgagagtc ttcctgacca caaacctctg ggatcccgag ggctccctac  3900
ccaagaatca ctttgagcac agcatcccaa ggagcccata gagcgatccc ttgcattcac  3960
agccacagcc cctctgggga cactctgtac ccccggcaga ccctttccaa ctcacaacca  4020
ataaagggggc ttgggctgtg ctttgactaa ggtga                            4055
```

```
SEQ ID NO: 61          moltype = DNA  length = 2304
FEATURE                Location/Qualifiers
source                 1..2304
                       mol_type = other DNA
                       organism = Homo sapiens
SEQUENCE: 61
acagctcccc cgcagccaga agccgggcct gcagcgcctc agcaccgctc cgggacaccc  60
cacccgcttc ccaggcgtga cctgtcaaca ggtctgtatt ggcgacaaaa ggagcagccc  120
tgaatgtagg gaaagcaggg cggagtcctc tgcaggctcg ggggaggggga ggggcgtgaa  180
tgcgtggatt tctgtggaga gtggaaacac ggggagtcga ggggagcatg cgcgggcctc  240
agaaagttct gggaaaccga ctcccgggag cagggaggaa cgcgcgctcc agagacaact  300
tcgcggtgtg gtgaactctc tgaggaaaaa cacgtgcgtg gcaacaagtg actgagacct  360
agaaatccaa gcgttggagg tcctgaggcc agcctaagtc gcttcaaaat ggaacgaagg  420
cgtttgtggg gttccattca gagccgatac atcagcatga gtgtgtggac aagcccacgg  480
agacttgtgg agctggcagg gcagagcctg ctgaaggatg aggccctggc cattgccgcc  540
```

-continued

```
ctggagttgc tgcccaggga gctcttcccg ccactcttca tggcagcctt tgacgggaga  600
cacagccaga ccctgaaggc aatggtgcag gcctggccct tcacctgcct ccctctggga  660
gtgctgatga agggacaaca tcttcacctg gagaccttca aagctgtgct tgatggactt  720
gatgtgctcc ttgcccagga ggttcgcccc aggaggtgga aacttcaagt gctggattta  780
cggaagaact ctcatcagga cttctggact gtatggtctg gaaacagggc cagtctgtac  840
tcatttccag agccagaagc agctcagccc atgacaaaga agcgaaaagt agatggtttg  900
agcacagagg cagagcagcc cttcattcca gtagaggtgc tcgtagacct gttcctcaag  960
gaaggtgcct gtgatgaatt gttctcctac ctcattgaga aagtgaagcg aaagaaaaat  1020
gtactacgcc tgtgctgtaa gaagctgaag atttttgcaa tgcccatgca ggatatcaag  1080
atgatcctga aaatggtgca gctggactct attgaagatt tggaagtgac ttgtacctgg  1140
aagctaccca ccttggcgaa attttctcct tacctgggcc agatgattaa tctgcgtaga  1200
ctcctcctct cccacatcca tgcatcttcc tacatttccc cggagaagga agagcagtat  1260
atcgcccagt tcacctctca gttcctcagt ctgcagtgcc tgcaggctct ctatgtggac  1320
tctttatttt tccttagagg ccgcctggat cagttgctca ggcacgtgat gaacccccttg  1380
gaaaccctct caataactaa ctgccggctt tcggaagggg atgtgatgca tctgtcccag  1440
agtcccagcg tcagtcagct aagtgtcctg agtctaagtg gggtcatgct gaccgatgta  1500
agtcccgagc ccctccaagc tctgctggag agagcctctg ccaccctcca ggacctggtc  1560
tttgatgagt gtgggatcac ggatgatcag ctccttgccc tcctgccttc cctgagccac  1620
tgctcccagc ttacgacctt aagcttctac gggaattcca tctccatatc tgccctgcag  1680
agtctcctgc agcacctcat cgggctgagc aatctgaccc acgtgctgta tcctgtcccc  1740
ctggagagtt atgaggacat ccatggtacc ctccacctgg agaggcttgc ctatctgcat  1800
gccaggctca gggagttgct gtgtgagttg ggcggcccca gcatggtctg gcttagtgcc  1860
aacccctgtc ctcactgtgg ggacagaacc ttctatgacc cggagcccat cctgtgcccc  1920
tgtttcatgc ctaattagct gggtgcacat atcaaatgct tcattctgca tacttggaca  1980
ctaaagccag gatgtgcatg catcttgaag caacaaagca gccacagttt cagacaaatg  2040
ttcagtgtga gtgaggaaaa catgttcagt gaggaaaaaa cattcagaca aatgttcagt  2100
gaggaaaaaa aggggaagtt gggggtaggc agatgttgac ttgaggagtt aatgtgatct  2160
ttggggagat acatcttata gagttagaaa tagaatctga atttctaaag ggagattctg  2220
gcttgggaag tacatgtagg agttaatccc tgtgtagact gttgtaaaga aactgttgaa  2280
aataaagaga agcaatgtga agca                                        2304
```

```
SEQ ID NO: 62          moltype = DNA  length = 982
FEATURE                Location/Qualifiers
source                 1..982
                       mol_type = other DNA
                       organism = Homo sapiens
SEQUENCE: 62
acagcccacc agtgaccacg aaggctgtgc tgcttgccct gttgatggca ggcttggccc  60
tgcagccagg cactgccctg ctgtgctact cctgcaaagc ccaggtgagc aacgaggact  120
gcctgcaggt ggagaactgc acccagctgg gggagcagtg ctggaccgcg cgcatccgcg  180
cagttggcct cctgaccgtc atcagcaaag gctgcagctt gaactgcgtg gatgactcac  240
aggactacta cgtgggcaag aagaacatca cgtgctgtga caccgacttg tgcaacgcca  300
gcggggccca tgccctgcag ccggctgctg ccatccttgc gctgctccct gcactcggcc  360
tgctgctctg ggacccggc cagctctagg ctctgggggg ccccgctgca gcccacactg  420
ggtgtggtgc cccaggcctc tgtgccactc ctcacacacc cggcccagtg ggagcctgtc  480
ctggttcctg aggcacatcc taacgcaagt ctgaccatgt atgtctgcgc ccctgtcccc  540
caccctgacc ctcccatggc cctctccagg actcccaccc ggcagatcgg ctctattgac  600
acagatccgc ctgcagatgg cccctccaac cctctctgct gctgtttcca tggcccagca  660
ttctccaccc ttaaccctgt gctcaggcac ctcttccccc aggaagcctt ccctgcccac  720
cccatctatg acttgagcca ggtctggtcc gtggtgtccc ccgcacccag caggggacag  780
gcactcagga gggcccggta aaggctgaga tgaagtggac tgagtagaac tggaggacag  840
gagtcgacgt gagttcctgg gagtctccag agatggggcc tggaggcctg gaggaagggg  900
ccaggcctca cattcgtggg gctccctgaa tggcagcctc agcacagcgt aggcccttaa  960
taaacacctg ttggataagc ca                                          982
```

```
SEQ ID NO: 63          moltype = DNA  length = 3458
FEATURE                Location/Qualifiers
source                 1..3458
                       mol_type = other DNA
                       organism = Homo sapiens
SEQUENCE: 63
gccgtcgttg ttggccacag cgtgggaagc agctctgggg gagctcggag ctcccgatca  60
cggcttcttg gggtagcta cggctgggtg tgtagaacgg ggccggggct ggggctgggt  120
cccctagtgg agacccaagt gcgagaggca agaactctgc agcttcctgc cttctgggtc  180
agttccttat tcaagtctgc agccggctcc cagggagatc tcggtggaac ttcagaaacg  240
ctgggcagtc tgcctttcaa ccatgcccct gtccctggga gccgagatgt gggggcctga  300
ggcctggctg ctgctgctgc tactgctggc atcatttaca ggccggtgcc ccgcgggtga  360
gctggagacc tcagacgtgg taactgtggt gctgggccag gacgcaaaac tgccctgctt  420
ctaccgaggg gactccggcg agcaagtggg gcaagtggca tgggctcggg tggacgcggg  480
cgaaggcgcc caggaactag cgctactgca ctccaaatac gggcttcatg tgagcccggc  540
ttacgagggc cgcgtggagc agccgccgcc cccacgcaac cccctggacg gctcagtgct  600
cctgcgcaac gcagtgcagg cggatgaggg cgagtacgag tgccgggtca gcaccttccc  660
cgccggcagc ttccaggcgc ggctgcggct ccgagtgctg gtgcctcccc tgccctcact  720
gaatcctggt ccagcactag aagagggcca gggcctgacc ctggcagcct cctgcacagc  780
tgagggcagc ccagccccca gcgtgacctg ggacacggag gtcaaaggca caacgtccag  840
ccgttccttc aagcactccc gctctgctgc cgtcacctca gagttccact tggtgcctag  900
ccgcagcatg aatgggcagc cactgacttg tgtggtgtcc catcctggcc tgctccagga  960
ccaaaggatc acccacatcc tccacgtgtc cttccttgct gaggcctctg tgaggggcct  1020
tgaagaccaa aatctgtggc acattggcag agaaggagct atgctcaagt gcctgagtga  1080
```

```
agggcagccc cctccctcat acaactggac acggctggat gggcctctgc ccagtggggt  1140
acgagtggat ggggacactt tgggctttcc cccactgacc actgagcaca gcggcatcta  1200
cgtctgccat gtcagcaatg agttctcctc aagggattct caggtcactg tggatgttct  1260
tgacccccag gaagactctg ggaagcaggt ggacctagtg tcagcctcgg tggtggtggt  1320
gggtgtgatc gccgcactct tgttctgcct tctggtggtg gtggtggtgc tcatgtcccg  1380
ataccatcgg cgcaaggccc agcagatgac ccagaaatat gaggaggagc tgaccctgac  1440
cagggagaac tccatccgga ggctgcattc ccatcacacg gaccccagga gccagccgga  1500
ggagagtgta gggctgagag ccgagggcca ccctgatagt ctcaaggaca acagtagctg  1560
ctctgtgatg agtgaagagc ccgagggccg cagttactcc acgctgacca cggtgaggga  1620
gatagaaaca cagactgaac tgctgtctcc aggctctggg cgggccgagg aggaggaaga  1680
tcaggatgaa ggcatcaaac aggccatgaa ccattttgtt caggagaatg ggaccctacg  1740
ggccaagccc acgggcaatg gcatctacat caatgggcgg ggacacctgg tctgacccag  1800
gcctgcctcc cttccctagg cctggctcct tctgttgaca tgggagattt tagctcatct  1860
tgggggcctc cttaaacacc cccatttctt gcggaagatg ctccccatcc cactgactgc  1920
ttgaccttta cctccaaccc ttctgttcat cgggagggct ccaccaattg agtctctccc  1980
accatgcatg caggtcactg tgtgtgtgca tgtgtgcctg tgtgagtgtt gactgactgt  2040
gtgtgtgtgg aggggtgact gtccgtggag gggtgactgt gtccgtggtg tgtattatgc  2100
tgtcatatca gagtcaagtg aactgtggtg tatgtgccac gggatttgag tggttgcgtg  2160
ggcaacactg tcagggtttg gcgtgtgtgt catgtggctg tgtgtgacct ctgcctgaaa  2220
aagcaggtat tttctcagac cccagagcag tattaatgat gcagaggttg gaggagagag  2280
gtggagactg tggctcagac ccaggtgtgc gggcatagct ggagctggaa tctgcctccg  2340
gtgtgaggga acctgtctcc taccacttcg gagccatggg ggcaagtgtg aagcagccag  2400
tccctgggtc agccagaggc ttgaactgtt acagaagccc tctgccctct ggtggcctct  2460
gggcctgctg catgtacata ttttctgtaa atatacatgc gccgggagct tcttgcagga  2520
atactgctcc gaatcacttt taattttttt cttttttttt tcttgccctt tccattagtt  2580
gtatttttta tttattttta ttttatttt tttttagaga tggagtctca ctatgttgct  2640
caggctggcc ttgaactcct gggctcaagc aatcctcctg cctcagcctc cctagtagct  2700
gggactttaa gtgtacacca ctgtgcctgc tttgaatcct ttacgaagag aaaaaaaaaa  2760
ttaaagaaag cctttagatt tatccaatgt ttactactgg gattgcttaa agtgaggccc  2820
ctccaacacc agggggttaa ttcctgtgat tgtgaaaggg gctacttcca aggcatcttc  2880
atgcaggcag ccccttggga gggcacctga gagctggtag agtctgaaat tagggatgtg  2940
agcctcgtgg ttactgagta aggtaaaatt gcatccacca ttgtttgtga taccttaggg  3000
aattgcttgg acctggtgac aagggctcct gttcaatagt ggtgttgggg agagagagag  3060
cagtgattat agaccgagag agtaggagtt gaggtgaggt gaaggaggtg ctgggggtga  3120
gaatgtcgcc tttcccctg ggttttggat cactaattca aggctcttct ggatgtttct  3180
ctgggttggg gctggagttc aatgaggttt atttttagct ggcccaccca gatacactca  3240
gccagaatac ctagatttag tacccaaact cttcttagtc tgaaatctgc tggatttctg  3300
gcctaaggga gaggctccca tccttcgttc cccagccagc ctaggacttc gaatgtggag  3360
cctgaagatc taagatccta acatgtacat tttatgtaaa tatgtgcata tttgtacata  3420
aaatgatatt ctgtttttaa ataaacagac aaaacttg                          3458

SEQ ID NO: 64          moltype = DNA  length = 471
FEATURE                Location/Qualifiers
source                 1..471
                       mol_type = other DNA
                       organism = Homo sapiens
SEQUENCE: 64
acattttctc ggccctgcca gcccccagga ggaaggtggg tctgaatcta gcaccatgac  60
ggaactagag acagccatgg gcatgatcat agacgtcttt tcccgatatt cgggcagcga  120
gggcagcacg cagaccctga ccaaggggga gctcaaggtg ctgatggaga aggagctacc  180
aggcttcctg cagagtggaa aagacaagga tgccgtggat aaattgctca aggacctgga  240
cgccaatgga gatgcccagg tggacttcag tgagttcata gtgttcgtgg ctgcaatcac  300
gtctgcctgt cacaagtact ttgagaaggc aggactcaaa tgatgccctg gagatgtcac  360
agattcctgg cagagccatg gtcccaggct tcccaaaagt gtttgttggc aattattccc  420
ctaggctgag cctgctcatg tacctctgat taataaatgc ttatgaaatg a           471

SEQ ID NO: 65          moltype = DNA  length = 5209
FEATURE                Location/Qualifiers
source                 1..5209
                       mol_type = other DNA
                       organism = Homo sapiens
SEQUENCE: 65
aattactggg acatgcgcgt tccggccgaa ggggggtaaa tttcccaact ccaggaattt  60
gtggcggaga gggcaaataa ctgcggctct cccggcgccc cgatgctcgc accatgtcga  120
ggcgcaagca ggcgaaaccc cagcacatca actcggagga ggaccagggc gagcagcagc  180
cgcagcagca gaccccggag tttgcagatg cggccccagc ggcgcccgcg gcgggggagc  240
tgggtgctcc agtgaaccac ccagggaatg acgaggtggc gagtgaggat gaagccacag  300
taaagcggct tcgtcgggag gagacgcacg tctgtgagaa atgctgtgcg gagttcttca  360
gcatctctga gttcctggaa cataagaaaa attgcactaa aaatccacct gtcctcatca  420
tgaatgacag cgaggggcct gtgccttcag aagacttctc cggagctgta ctgagccacc  480
agcccaccag tcccggcagt aaggactgtc acagggagaa tggcggcagc tcagaggaca  540
tgaaggagaa gccggatgcg gagtctgtgg tgtacctaaa gacagagaca gccctgccac  600
ccacccccca ggacataagc tatttagcca aaggcaaagt ggccaacact aatgtgacct  660
tgcaggcact acggggcacc aaggtggcgg tgaatcagcg gagcgcggat gcactccctg  720
cccccgtgcc tggtgccaac agcatcccgt gggtcctcga gcagatcttg tgtctgcagc  780
agcagcagct acagcagatc cagctcaccg agcagatccg catccaggtg aacatgtggg  840
cctcccacgc cctccactca agcggggcag gggccgacac tctgaagacc ttgggcagcc  900
acatgtctca gcaggtttct gcagctgtgg ctttgctcag ccagaaagct ggaagccaag  960
gtctgtctct ggatgccttg aaacaagcca agctacctca cgccaacatc ccttctgcca  1020
```

-continued

```
ccagctccct gtccccaggg ctggcaccct tcactctgaa gccggatggg acccgggtgc  1080
tcccgaacgt catgtcccgc ctcccgagcg ctttgcttcc tcaggccccg ggctcggtgc  1140
tcttccagag ccctttctcc actgtggcgc tagacacatc caagaaaggg aaggggaagc  1200
caccgaacat ctccgcggtg gatgtcaaac ccaaagacga ggcggccctc tacaagcaca  1260
agtgtaagta ctgtagcaag gtttttggga ctgatagctc cttgcagatc cacctccgct  1320
cccacactgg agagagaccc ttcgtgtgct ctgtctgtgg tcatcgcttc accaccaagg  1380
gcaacctcaa ggtgcacttt caccgacatc cccaggtgaa ggcaaacccc cagctgtttg  1440
ccgagttcca ggacaaagtg gcggccggca atggcatccc ctatgcactc tctgtacctg  1500
accccataga tgaaccgagt ctttctttag acagcaaacc tgtccttgta accacctctg  1560
tagggctacc tcagaatctt tcttcgggga ctaatcccaa ggacctcacg ggtggctcct  1620
tgcccggtga cctgcagcct gggccttctc cagaaagtga gggtggaccc acactccctg  1680
gggtgggacc aaactataat tccccaaggg ctggtggctt ccaagggagt gggacccctg  1740
agccagggtc agagaccctg aaattgcagc agttggtgga gaacattgac aaggccacca  1800
ctgatcccaa cgaatgtctc atttgccacc gagtcttaag ctgtcagagc tccctcaaga  1860
tgcattatcg cacccacacc ggggagagac cgttccagtg taagatctgt ggccgagcct  1920
tttctaccaa aggtaacctg aagacacacc ttggggttca ccgaaccaac acatccatta  1980
agacgcagca ttcgtgcccc atctgccaga agaagttcac taatgccgtg atgctgcagc  2040
aacatattcg gatgcacatg ggcggtcaga ttcccaacac gcccctgcca gagaatccct  2100
gtgactttac gggttctgag ccaatgaccg tgggtgagaa cggcagcacc ggcgctatct  2160
gccatgatga tgtcatcgaa agcatcgatg tagaggaagt cagctcccag gaggctccca  2220
gcagctcctc caaggtcccc acgcctcttc ccagcatcca ctcggcatca cccacgctag  2280
ggtttgccat gatggcttcc ttagatgccc cagggaaagt gggtcctgcc ccttttaacc  2340
tgcagcgcca gggcagcaga gaaaacggtt ccgtggagag cgatggcttg accaacgact  2400
catcctcgct gatgggagac caggagtatc agagccgaag cccagatatc ctggaaacca  2460
catccttcca ggcactctcc ccggccaata gtcaagccga aagcatcaag tcaaagtctc  2520
ccgatgctgg gagcaaagca gagagctccg agaacagccg cactgagatg gaaggtcgga  2580
gcagtctccc ttccacgttt atccgagccc cgccgaccta tgtcaaggtt gaagttcctg  2640
gcacatttgt gggaccctcg acattgtccc cagggatgac ccctttgtta gcagcccagc  2700
cacgccgaca ggccaagcaa catggctgca cacggtgtgg gaagaacttc tcgtctgcta  2760
gcgctcttca gatccacgag cggactcaca ctggagagaa gccttttgtg tgcaacattt  2820
gtgggcgagc ttttaccacc aaaggcaact taaaggttca ctacatgaca cacggggcga  2880
acaataactc agcccgccgt ggaaggaagt tggccatcga gaacaccatg gctctgttag  2940
gtacggacgg aaaaagagtc tcagaaatct ttcccaagga aatcctggcc ccttcagtga  3000
atgtggaccc tgttgtgtgg aaccagtaca ccagcatgct caatggcggt ctggccgtga  3060
agaccaatga gatctctgtg atccagagtg ggggggttcc taccctcccg gtttccttgg  3120
gggccacctc cgttgtgaat aacgccactg tctccaagat ggatggctcc cagtcgggta  3180
tcagtgcaga tgtggaaaaa ccaagtgcta ctgacggcgt tcccaaacac cagtttcctc  3240
acttcctgga agaaaacaag attgcggtca gctaaggggag aacttgcgtg gaaggagcaa  3300
tgcagacaca gtgaaatctc tagaatctgc tttgttttgt aagaactcat ctcctcctgt  3360
tttctttttc ttactgatat gcaaatgatg tttactacgt tggttgtgac cacaacctca  3420
ggcaagtgct acaatcacga ttgttgctat gctgctttgc aaaaagttga aaaaataaaa  3480
aaaaaatgca taccaaaaca aatacagact cttttttttt gagatggagt ctcgctctat  3540
cacccaggct ggagtgcagt ggcatgatct cggctcactg caacctcccc attctgggtt  3600
caagtgattc tcctgcctta gcctccagag tagctgggat tacaggcagg tgccaccacg  3660
cccggctaat tttgtatttt gagtagagac tgggtttcac catgttggtc aggctggtct  3720
cgaactgctg acctcgtgat ccacccgcct tggcctccca aagtgctggg attacaggca  3780
tgagctacca cgcctggcac tttttttttt tttttctaat tttggaaaga agcgggtctt  3840
gcaaagtagc tttgttactt gtaacagacg tatacataga acctttgtac aacctagagt  3900
gactttttcc aaagactgtt acctatttca aggtagaatc gttggaactt actgaacaac  3960
agtggaaaag acaactacac agcctcattg aggggagatg ggtactgtat acttactggt  4020
aactggacac gggtaaaagg acaaggtctg tcatctcttt agggacctgt tttatatgcc  4080
ccaaccctgt ccccatctta ttgttttttt ttgaatgtac ttaaaaaagg aacaacaaaa  4140
aactagggtt gtagaattat aaaactgctt caaccttaga accttaagta ggaggccctc  4200
aaatggactt acgttagtcc ttagggagtc aatgtgtgtg ttgctgctta tttaaataca  4260
gttcagttgg agccccgaga gtgccaatgt tttccccaca cctcttggat gccttcctct  4320
tcccaaatcc cagaagaggt gggcacctga gcggggaatc tcaggtgact tagtttgcca  4380
gtgcctactc tattgaagaa ctgggttttc atgctcgaga agaaactcgt ggaagggcgt  4440
gtttcccatc acaggttcac atactgattg cttttgttga atttccttgg tgcgacttat  4500
gccaagtaat tatgacgatt ttttgttttg ttttgtttcc ttgctgaata tttcatgaag  4560
gctacgaagt tagaacaggc acgtcctggg tgtgaaagct ttaatttatc tacctcattt  4620
atttttattt ttttgtagcc atagtgtcta ttttcctatt ttaagaccgc tgaagtattc  4680
ccaggccctg tctaaagcct aagagttgat gtattggtgg gaagaggtga acgttcaaga  4740
tgattttgtg atgccttttt tttttgtagt ttcctttgta aatgtgatat tgagcaaacg  4800
aaacattgct cttggtttaa caagaaagaa agaaaaaaac tctaatttct gggagaaaag  4860
tctttcccct ctatgtggaa ggtcctgacg gaaatatgca tccaagacga ttagccaaag  4920
tgttgtctct tcatcgttgc acctgacttt aggattccgc cccccttttt tttttttttt  4980
tttttttttg ccaagttgtg cctttccttc tggaattgta agtgaacacg ataatagtac  5040
ctgtttacac tgtgaagtgg atattgttac agaaaacaca ccagtggctt tctcactgtt  5100
gagctaataa tgccttgtga atgtatgatc tacggagaaa cccctgtagt tgtacctgct  5160
gatgctgtct gtctgttgga aaataaaatt tgaatgtttt tttttctca               5209
```

-continued

```
SEQ ID NO: 66           moltype = DNA  length = 1283
FEATURE                 Location/Qualifiers
source                  1..1283
                        mol_type = other DNA
                        organism = Homo sapiens
SEQUENCE: 66
agtttgcttg gagctcctgg ggcctaacaa aaagaaacct gccatgctgc tcttcctcct  60
ctctgcactg gtcctgctca cacagcccct gggctacctg gaagcagaaa tgaagaccta  120
ctcccacaga acaatgccca gtgcttgcac cctggtcatg tgtagctcag tggagagtgg  180
cctgcctggt cgcgatggac gggatgggag agagggccct cggggcgaga agggggaccc  240
aggtttgcca ggagctgcag ggcaagcagg gatgcctgga caagctggcc cagttgggcc  300
caaaggggac aatggctctg ttggagaacc tggaccaaag ggagacactg ggccaagtgg  360
acctccagga cctcccggtg tgcctggtcc agctggaaga gaaggtcccc tggggaagca  420
ggggaacata ggacctcagg gcaagccagg cccaaaagga gaagctgggc ccaaaggaga  480
agtaggtgcc ccaggcatgc agggctcggc aggggcaaga ggcctcgcag gccctaaggg  540
agagcgaggt gtccctggtg agcgtggagt ccctggaaac acaggggcag cagggtctgc  600
tggagccatg ggtccccagg gaagtccagg tgccagggga cccccgggat tgaaggggga  660
caaaggcatt cctggagaca aaggagcaaa gggagaaagt gggcttccag atgttgcttc  720
tctgaggcag caggttgagg ccttacaggg acaagtacag cacctccagg ctgctttctc  780
tcagtataag aaagttgagc tcttcccaaa tggccaaagt gtcggggaga agattttcaa  840
gacagcaggc tttgtaaaac catttacgga ggcacagctg ctgtgcacac aggctggtgg  900
acagttggcc tctccacgct ctgccgctga gaatgccgcc ttgcaacagc tggtcgtagc  960
taagaacgag gctgctttcc tgagcatgac tgattccaag acagagggca agttcaccta  1020
ccccacagga gagtccctgg tctattccaa ctgggcccca ggggagccca acgatgatgg  1080
cgggtcagag gactgtgtgg agatcttcac caatggcaag tggaatgaca gggcttgtgg  1140
agaaaagcgt cttgtggtct gcgagttctg agccaactgg ggtgggtggg gcagtgcttg  1200
gcccaggagt ttggccagaa gtcaaggctt agaccctcat gctgccaata tcctaataaa  1260
aaggtgacca tctgtgccgg gaa                                          1283

SEQ ID NO: 67           moltype = DNA  length = 2195
FEATURE                 Location/Qualifiers
source                  1..2195
                        mol_type = other DNA
                        organism = Homo sapiens
SEQUENCE: 67
cccagcgctc ctccccgcaa atgatcccgc cccaggggcc tatcccagtc cccccagtgc  60
ctttggttgc tggagggaag aacacaatgg atctggtgct aaaaagatgc cttcttcatt  120
tggctgtgat aggtgctttg ctggctgtgg gggctacaaa agtacccaga aaccaggact  180
ggcttggtgt ctcaaggcaa ctcagaacca aagcctggaa caggcagctg tatccagagt  240
ggacagaagc ccagagactt gactgctgga gaggtggtca agtgtccctc aaggtcagta  300
atgatgggcc tacactgatt ggtgcaaatg cctccttctc tattgccttg aacttccctg  360
gaagccaaaa ggtattgcca gatgggcagg ttatctgggt caacaatacc atcatcaatg  420
ggagccaggt gtggggagga cagccagtgt atccccagga aactgacgat gcctgcatct  480
tccctgatgg tggaccttgc ccatctggct cttggtctca gaagagaagc tttgtttatg  540
tctggaagac ctggggccaa tactggcaag ttctaggggg cccagtgtct gggctgagca  600
ttgggacagg cagggcaatg ctgggcacac acaccatgga agtgactgtc taccatcgcc  660
ggggatcccg gagctatgtg cctcttgctc attccagctc agccttcacc attactgacc  720
aggtgccttt ctccgtgagc gtgtcccagt tgcgggcctt ggatggaggg aacaagcact  780
tcctgagaaa tcagcctctg acctttgccc tccagctcca tgaccccagt ggctatctgg  840
ctgaagctga cctctcctac acctgggact ttggagacag tagtggaacc ctgatctctc  900
gggcacttgt ggtcactcat acttacctgg agcctggccc agtcactgcc caggtggtcc  960
tgcaggctgc cattcctctc acctcctgtg gctcctcccc agttccaggc accacagatg  1020
ggcacaggcc aactgcagag gcccctaaca ccacagctgg ccaagtgcct actacagaag  1080
ttgtgggtac tacacctggt caggcgccaa ctgcagagcc ctctggaacc acatctgtgc  1140
aggtgccaac cactgaagtc ataagcactg cacctgtgca gatgccaact gcagagagca  1200
caggtatgac acctgagaag gtgccagttt cagaggtcat gggtaccaca ctggcagaga  1260
tgtcaactcc agaggctaca ggtatgacac ctgcagaggt atcaattgtg gtgctttctg  1320
gaaccacagc tgcacaggta acaactacag agtgggtgga gaccacagct agagagctac  1380
ctatccctga gcctgaaggt ccagatgcca gctcaatcat gtctacggaa agtattacag  1440
gttccctggg cccccctgctg gatggtacag ccaccttaag gctggtgaag agacaagtcc  1500
ccctggattg tgttctgtat cgatatggtt cctttttccgt caccctggac attgtccagg  1560
gtattgaaag tgccgagatc ctgcaggctg tgccgtccgg tgaggggggat gcatttgagc  1620
tgactgtgtc ctgccaaggc gggctgccca aggaagcctg catggagatc tcatcgccag  1680
ggtgccagcc ccctgcccag cggctgtgcc agcctgtgct acccagccca gcctgccagc  1740
tggttctgca ccagatactg aagggtggct cggggacata ctgcctcaat gtgtctctgg  1800
ctgataccaa cagcctggca gtggtcagca cccagcttat catgcctggt caagaagcag  1860
gccttgggca ggttccgctg atcgtgggca tcttgctggt gttgatggct gtggtccttg  1920
catctctgat atataggcgc agacttatga agcaagactt ctccgtaccc cagttgccac  1980
atagcagcag tcactggctg cgtctacccc gcatcttctg ctcttgtccc attggtgaga  2040
acagccccct cctcagtggg cagcaggtct gagtactctc atatgatgct gtgattttcc  2100
tggagttgac agaaacacct atatttcccc cagtcttccc tgggagacta ctattaactg  2160
aaataaatac tcagagcctg aaaaaaaaaa aaaaa                             2195
```

```
SEQ ID NO: 68          moltype = DNA  length = 1222
FEATURE                Location/Qualifiers
source                 1..1222
                       mol_type = other DNA
                       organism = Homo sapiens
SEQUENCE: 68
agtattgggg atgctgagct gcggggtacg ggcctgagga gggatgggag taagaagtgc  60
tgtggaaacc gtcaggccat gaaccaggct gaccctcggc tcagagcagt gtgcttgtgg  120
actctcacat ctgcagccat gagcagaggc gacaactgca cggatctact cgcactggga  180
atcccctcca taacccaggc ctggggactg tgggtcctct taggggctgt gacgctgcta  240
tttctcatct cgctggctgc acacttgtcc cagtggacca ggggccggag caggagccat  300
ccggggcagg gacgctctgg agagtctgtg gaagaggtcc cgctgtatgg gaacctgcat  360
tatctacaga caggacggct gtctcaagac ccagagccag accagcagga tccaactctt  420
ggaggccctg ccagggctgc agaggaggtg atgtgctata ccagcctgca gctgcggcct  480
cctcagggtc ggatccccgg tcctggaacc cccgtcaagt actcggaggt ggtgctggac  540
tctgagccaa agtcccaggc ctcgggcccc gagccggagc tctatgcctc agtatgtgcc  600
cagacccgca gggcccgggc ctccttcccg gatcaggcct atgccaacag ccagcctgca  660
gccagctgag atggagggcc tggcacagcg gggcgtgcac tgccccagcc ccccgtagca  720
ggggcatgac tgtttcccaa ccagcaccca aagacgggcg ccattgccaa gtcacaggat  780
gtgatctacc ccggacttcc tatctgagct tcaagggaga catctcaggg caaagctttc  840
gtgatggagg aggcaaagac agtagccccc tccttatttc ttttttctat ctgttcctct  900
tagcccccaa actcccaggt tctcacttcc ttcttctgga gtttaaccag atcctcccca  960
cccccgctcc ctcatagtct acccccacgc ctcagtgtct cctcaggcac aggaagtggg  1020
cggtggggga ggggtaaggg cctgacagtg ggtgggtggg tatattcctc aggagtccac  1080
agactggagt ggacctggaa cttagagacg ggagggaccc gagcctggct tttgacctaa  1140
gaaccctagc aggagaatac agtctccatc ctgctgtctc tgtcctgtcc ccaagttttc  1200
aaataaaact ttccaaaaag tg                                            1222

SEQ ID NO: 69          moltype = DNA  length = 4930
FEATURE                Location/Qualifiers
source                 1..4930
                       mol_type = other DNA
                       organism = Homo sapiens
SEQUENCE: 69
ctcagccttc ccggttcggg aaaggggaag aatgcaggag gggtaggatt tctttcctga  60
taggatcggt tgggaaagac cgcagcctgt gtgtgtcttt cccttcgacc aaggtgtctg  120
ttgctccgta aataaaacgt cccactgcct tctgagagcg ctataaaggc agcggaaggg  180
tagtccgcgg ggcattccgg gcggggcgcg agcagagaca ggtcatggca gcgccaggcg  240
gcaggtcgga gccgccgcag ctccccgagt acagctgcag ctacatggtg tcgcggccgg  300
tctacagcga gctcgctttc cagcaacagc acgagcggcg cctgcaggag cgcaagacgc  360
tgcgggagag cctggccaag tgctgcagtt gttcaagaaa gagagccttt ggtgtgctaa  420
agactcttgt gcccatcttg gagtggctcc ccaaataccg agtcaaggaa tggctgctta  480
gtgacgtcat ttcgggagtt agtactgggc tagtggccac gctgcaaggg atggcatatg  540
ccctactagc tgcagttcct gtcggatatg gtctctactc tgcttttttc cctatcctga  600
catactttat ctttggaaca tcaagacata tctcagttgg acctttttcca gtggtgagtt  660
taatggtggg atctgttgtt ctgagcatgg cccccgacga acactttctc gtatccagca  720
gcaatggaac tgtattaaat actactatga tagacactgc agctagagat acagctagag  780
tcctgattgc cagtgccctg actctgctgg ttggaattat acagttgata tttggtggct  840
tgcagattgg attcatagtg aggtacttgg cagatccttt ggttggtggc ttcacaacag  900
ctgctgcctt ccaagtgctg gtctcacagc taaagattgt cctcaatgtt tcaaccaaaa  960
actacaatgg agttctctct attatctata cgctggttga gatttttcaa aatattggtg  1020
ataccaatct tgctgatttc actgctggat tgctcaccat tgtcgtctgt atggcagtta  1080
aggaattaaa tgatcggttt agacacaaaa tcccagtccc tattcctata gaagtaattg  1140
tgacgataat tgctactgcc atttcatatg gagccaacct ggaaaaaaat tacaatgctg  1200
gcattgttaa atccatccca aggggggtttt tgcctcctga acttccacct gtgagcttgt  1260
tctcggagat gctggctgca tcattttcca tcgctgtggt ggcttatgct attgcagtgt  1320
cagtaggaaa agtatatgcc accaagtatg attacaccat cgatgggaac caggaattca  1380
ttgcctttgg gatcagcaac atcttctcag gattcttctc ttgttttgtg gccaccactg  1440
ctctttcccg cacggccgtc caggagagca ctggaggaaa gacacaggtt gctggcatca  1500
tctctgctgc gattgtgatg atcgccattc ttgccctggg gaagcttctg gaacccttgc  1560
agaagtcggt cttggcagct gttgtaattg ccaacctgaa agggatgttt atgcagctgt  1620
gtgacattcc tcgtctgtgg agacagaata agattgatgc tgttatctgg gtgtttacgt  1680
gtatagtgtc catcattctg gggctggatc tcggtttact agctggcctt atatttggac  1740
tgttgactgt ggtcctgaga gttcagtttc cttcttggaa tggccttgga agcatcccta  1800
gcacagatat ctacaaaagt accaagaatt acaaaaacat tgaagaacct caaggagtga  1860
agattcttag attttccagt cctattttct atggcaatgt cgatggtttt aaaaaatgta  1920
tcaagtccac agttggattt gatgccatta gagtatataa taagaggctg aaagcgctga  1980
ggaaaataca gaaactaata aaaagtggac aattaagagc aacaaagaat ggcatcataa  2040
gtgatgctgt ttcaacaaat aatgcttttg agcctgatga ggatattgaa gatctggagg  2100
aacttgatat cccaaccaag gaaatagaga ttcaagtgga ttggaactct gagcttccag  2160
tcaaagtgaa cgttcccaaa gtgccaatcc atagccttgt gcttgactgt ggagctatat  2220
ctttcctgga cgttgttgga gtgagatcac tgcgggtgat tgtcaaagaa ttccaaagaa  2280
ttgatgtgaa tgtgtatttt gcatcacttc aagattatgt gatagaaaag ctggagcaat  2340
gcgggttctt tgacgacaac attagaaagg acacattctt tttgacggtc catgatgcta  2400
tactctatct acagaaccaa gtgaaatctc aagagggtca aggttccatt ttagaaacga  2460
tcactctcat tcaggattgt aaagataccc ttgaattaat agaaacagag ctgacggaag  2520
aagaacttga tgtccaggat gaggctatgc gtacacttgc atcctgaaag tgggttcggg  2580
aggtctctat gagcaaggaa tacaagacaa aacttcctca atgcattgac tatttcttca  2640
gactcaaaac actcattctt ttttctatta agccattgaa agagaagcac taagactgct  2700
```

-continued

```
tctaggcttt atttataaaa taaacacctt atccctaaca tgggcaaaat ggctagaatt  2760
attcagacga tttggcagcg tccagggtaa gctggtgtta taatacgctg ctgatctaca  2820
tcacagattt gctaataatg ttcacgtggg ccctggcata tctctgttca gttagagtga  2880
gtgctgaccc aacagcctct gtggtcaagc gagtcacgaa tgattaatca taaagaaaaa  2940
tcagtttttg actgacctgg atatccatga gctgcactga tcaccatgta aggtcacatt  3000
tagtaaatgc tgaaataaaa tgattaatgc atttatcaat aaaagccttt gaaaatactt  3060
tggataataa attggagttt taaaaatgca aatttgctta gtatctaata atgaagtgtt  3120
attacatata gccggaattg aggatctctt tgatcctgga aatggtttac ctaaaagcta  3180
cagaaccagg ccaatatatt ttgaaatatt gatgcagaca aatgaaataa taaagagatt  3240
ttcatggttt ataaaaatct tttttgatat gataataatc atgatcacaa ctgagatcaa  3300
aaaaatatat gacagattat tttgtttaaa aatgcagttt taattatctt agtctataga  3360
aatgatcatt gcatggaggc atgtataggt atgatctgtg taaaatctga cataaaaaca  3420
gtgctattct gagtgaaaat ttttttgatg tgcttacata accatggtga ttaaaatgag  3480
tttatatttt ttctcaaaaa ttttagcagt gtgtaaagta agtaatcttt aactgaactc  3540
tgaccactta aaaaaaaatc taaaaattga actacctata gtagtctgtg tttaaagtga  3600
atttttaaag acaaagcatt ctaaatgaac tcaatataaa aacattcatt tggaatgtac  3660
atactgaaaa atacaggttt ttttgaccaa aagtttttat atcttttctt tttatttatt  3720
tttttcctaa gtgccaacaa ttttctagat attatataca acacaggctt tgatcttggg  3780
gacttttccc atatatttca cactggagtg aatgaagttg tacttcattt ctagagaaaa  3840
gttataccca ggtccccaat tgagaatgtc ttgcttgatt gaaaacgaca tcatcccttg  3900
gtatactcca gggattggtt tcaggacccc tgcatttacc aaaatttgtg cacactcaag  3960
tcctgcagtc acccctgcct aaagatagaa tggcttctct gtttttcttc tgaaatacaa  4020
ccagaaacaa tgtgtctatt tctgaaagaa taggattaat gatcatacaa atgggttaat  4080
cctgaattct ggttgtaaat ctggttacag cataactagg attataatgc tgcctcattt  4140
tcacagcact acttgcttat attgacaaca aatcatctcg ctaaagagtg aatgtaggcc  4200
aggcgcggtg gctcatgcct gtaatcccag cactttggga ggccgaggcg ggtggatcac  4260
gaggtcagga gatcgagacc atcctggcta acatggtaaa accccgtctc tactaaaaat  4320
agaaaaaaag aaattagcct agcgtggtgg ctggcgggcg cctgtagtcc cagctatttg  4380
ggaggctaag gcaggagaat ggcgtgaacc cgggaggcgg agcttgcagt gagccgaggt  4440
cgtgccactg cactccagcc tgggcgacag agcaagactc cgtctcaaaa aaaaaaaaaa  4500
aaaaaaaaaa agagtgaatg taatagtctt gcagaaaatg aatgaatacc tttgttcaat  4560
aaaggaaata tgcactgctc actttttga aggaaatgcc aaagttacgt tttacaacaa  4620
ggctagagtt tgtaaattct gggttcattt gtgatgacat aagtcagcaa actgcgggaa  4680
tactgtctct tctatgtatt ttgtgaatag taagcataat tttagttttg tattatcaat  4740
gaaaatttca cttgaaatta aagctgcctt ttgttatatt tttaacctat aggataagat  4800
tccagtattg tatatgagtt ttaacaaatt aaaaaatcaa atcatgtaca tttgaaaata  4860
tttgcacaca tttaaaaata aatgtaaagt tgtcttttaa actactcgga tgtgtccttt  4920
ctgaacaaaa                                                          4930

SEQ ID NO: 70           moltype = DNA  length = 2353
FEATURE                 Location/Qualifiers
source                  1..2353
                        mol_type = other DNA
                        organism = Homo sapiens
SEQUENCE: 70
aagaccaagc attcagcaag ccactcttcc acctccctta ctgcaggaag gcactccgaa  60
gacataagtc ggtgagacat ggctgaagat aaaagcaaga gagactccat cgagatgagt  120
atgaagggat gccagacaaa caacgggttt gtccataatg aagacattct ggagcagacc  180
ccggatccag gaagctcaac agacaacctg aagcacagca ccaggggcat ccttggctcc  240
caggagcccg acttcaaggg cgtccagccc tatgcgggga tgcccaagga ggtgctgttc  300
cagttctctg gccaggcccg ctaccgcata cctcgggaga tcctcttctg gctcacagtg  360
gcttctgtgc tggtgctcat cgcggccacc atagccatca ttgccctctc tccaaagtgc  420
ctagactggt ggcaggaggg gcccatgtac cagatctacc caaggtcttt caaggacagt  480
aacaaggatg ggaacggaga tctgaaaggt attcaagata aactggacta catcacagct  540
ttaaatataa aaactgtttg gattacttca ttttataaat cgtcccttaa agatttcaga  600
tatggtgttg aagatttccg ggaagttgat cccatttttg gaacgatgga agattttgag  660
aatctggttg cagccataca tgataaaggt ttaaaattaa tcatcgattt cataccaaac  720
cacacgagtg ataaacatat ttggtttcaa ttgagtcgga cacggacagg aaaatatact  780
gattattata tctggcatga ctgtacccat gaaaatggca aaaccattcc acccaacaac  840
tggttaagtg tgtatggaaa ctccagttgg cactttgacg aagtgcgaaa ccaatgttat  900
tttcatcagt ttatgaaaga gcaacctgat ttaaatttcc gcaatcctga tgttcaagaa  960
gaaataaaag aaattttacg gttctggctc acaaagggtg ttgatggttt tagtttggat  1020
gctgttaaat tcctcctaga agcaaagcac ctgagagatg agatccaagt aaataagacc  1080
caaatcccgg acacggtcac acaatactcg gagctgtacc atgacttcac caccacgcag  1140
gtgggaatgc acgacattgt ccgcagcttc cggcagacca tggaccaata cagcacggag  1200
cccggcagat acaggttcat ggggactgaa gcctatgcag agagtattga caggaccgtg  1260
atgtactatg gattgccatt tatccaagaa gctgattttc ccttcaacaa ttacctcagc  1320
atgctagaca ctgtttctgg gaacagcgtg tatgaggtta tcacatcctg gatggaaaac  1380
atgccagaag gaaaatggcc taactggatg attggtggac cagacagttc acggctgact  1440
tcgcgtttgg ggaatcagta tgtcaacgtg atgaacatgc ttcttttcac actccctgga  1500
actcctataa cttactatgg agaagaaatt ggaatgggaa atattgtagc cgcaaatctc  1560
aatgaaagct atgatattaa taccccttcgc tcaaagtcac caatgcagtg ggacaatagt  1620
tcaaatgctg gtttttctga agctagtaac acctggttac ctaccaattc agattaccac  1680
actgtgaatg ttgatgtcca aaagactcag cccagatcgg ctttgaagtt atatcaagat  1740
ttaagtctac ttcatgccaa tgagctactc ctcaacaggg gctggttttg ccatttgagg  1800
aatgacagcc actatgttgt gtacacaaga gagctggatg gcatcgacag aatctttatc  1860
gtggttctga attttggaga atcaacactg ttaaatctac ataatatgat ttcgggcctt  1920
```

```
cccgctaaaa tgagaataag gttaagtacc aattctgccg acaaaggcag taaagttgat  1980
acaagtggca tttttctgga caagggagag ggactcatct ttgaacacaa cacgaagaat  2040
ctccttcatc gccaaacagc tttcagagat agatgctttg tttccaatcg agcatgctat  2100
tccagtgtac tgaacatact gtatacctcg tgttaggcac ctttatgaag agatgaagac  2160
actggcattt cagtgggatt gtaagcattt gtaatagctt catgtacagc atgctgcttg  2220
gtgaacaatc attaattctt cgatatttct gtagcttgaa tgtaactgct ttaagaaagg  2280
ttctcaaatg ttttgaaaaa aataaaatgt ttaaaagtaa aaaaaaaaaa aaaaaaaaaa  2340
aaaaaaaaaa aaa                                                     2353

SEQ ID NO: 71          moltype = DNA  length = 3391
FEATURE                Location/Qualifiers
source                 1..3391
                       mol_type = other DNA
                       organism = Homo sapiens
SEQUENCE: 71
gcggagtaac ctggagattt aaaagccgcc ggctggcgcg cgtggggggc aaggaagggg  60
gggcggaacc agcctgcacg cgctggctcc gggtgacagc cgcgcgcctc ggccaggatc  120
tgagtgatga gacgtgtccc cactgaggtg ccccacagca gcaggtgttg agcatgggct  180
gagaagctgg accggcacca aagggctggc agaaatgggc gcctggctga ttcctaggca  240
gttggcggca gcaaggagga gaggccgcag cttctggagc agagccgaga cgaagcagtt  300
ctggagtgcc tgaacggccc cctgagccct acccgcctgg cccactatgg tccagaggct  360
gtgggtgagc cgcctgctgc ggcaccggaa agcccagctc ttgctggtca acctgctaac  420
ctttggcctg gaggtgtgtt tggccgcagg catcacctat gtgccgcctc tgctgctgga  480
agtgggggta gaggagaagt tcatgaccat ggtgctgggc attggtccag tgctgggcct  540
ggtctgtgtc ccgctcctag gctcagccag tgaccactgg cgtggacgct atggccgccg  600
ccggcccttc atctgggcac tgtccttggg catcctgctg agcctctttc tcatcccaag  660
ggccggctgg ctagcagggc tgctgtgccc ggatcccagg cccctggagc tggcactgct  720
catcctgggc gtggggctgc tggacttctg tggccaggtg tgcttcactc cactggaggc  780
cctgctctct gacctcttcc gggacccgga ccactgtcgc caggcctact ctgtctatgc  840
cttcatgatc agtcttgggg gctgcctggg ctacctcctg cctgccattg actgggacac  900
cagtgccctg gccccctacc tgggcaccca ggaggagtgc ctctttggcc tgctcaccct  960
catcttcctc acctgcgtag cagccacact gctggtggct gaggaggcag cgctgggccc  1020
caccgagcca gcagaagggc tgtcggcccc ctccttgtcg ccccactgct gtccatgccg  1080
ggcccgcttg gctttccgga acctgggcgc cctgcttccc cggctgcacc agctgtgctg  1140
ccgcatgccc cgcaccctgc gccggctctt cgtggctgag ctgtgcagct ggatggcact  1200
catgaccttc acgctgtttt acacggattt cgtgggcgag gggctgtacc agggcgtgcc  1260
cagagctgag ccgggcaccg aggcccggag acactatgat gaaggcgttc ggatgggcag  1320
cctggggctg ttcctgcagt gcgccatctc cctggtcttc tctctggtca tggaccggct  1380
ggtgcagcga ttcggcactc gagcagtcta tttggccagt gtggcagctt tccctgtggc  1440
tgccggtgcc acatgcctgt cccacagtgt ggccgtggtg acagcttcag ccgccctcac  1500
cgggttcacc ttctcagccc tgcagatcct gccctacaca ctggcctccc tctaccaccg  1560
ggagaagcag gtgttcctgc ccaaataccg aggggacact ggaggtgcta gcagtgagga  1620
cagcctgatg accagcttcc tgccaggccc taagcctgga gctcccttcc ctaatggaca  1680
cgtgggtgct ggaggcagtg gcctgctccc acctccaccc gcgctctgcg gggcctctgc  1740
ctgtgatgtc tccgtacgtg tggtggtggg tgagcccacc gaggccaggg tggttccggg  1800
ccggggcatc tgcctggacc tcgccatcct ggatagtgcc ttcctgctgt cccaggtggc  1860
cccatccctg tttatgggct ccattgtcca gctcagccag tctgtcactg cctatatggt  1920
gtctgccgca ggcctgggtc tggtcgccat ttactttgct acacaggtag tatttgacaa  1980
gagcgacttg gccaaatact cagcgtagaa aacttccagc acattggggt ggagggcctg  2040
cctcactggg tcccagctcc ccgctcctgt tagccccatg gggctgccgg gctggccgcc  2100
agtttctgtt gctgccaaag taatgtggct ctctgctgcc accctgtgct gctgaggtgc  2160
gtagctgcac agctgggggc tggggcgtcc ctctcctctc tccccagtct ctagggctgc  2220
ctgactggag gccttccaag gggtttcag  tctggactta tacagggagg ccagaagggc  2280
tccatgcact ggaatgcggg gactctgcag gtggattacc caggctcagg gttaacagct  2340
agcctcctag ttgagacaca cctagagaag ggtttttggg agctgaataa actcagtcac  2400
ctggtttccc atctctaagc cccttaacct gcagcttcgt ttaatgtagc tcttgcatgg  2460
gagtttctag gatgaaacac tcctccatgg gatttgaaca tatgaaagtt atttgtaggg  2520
gaagagtcct gaggggcaac acacaagaac caggtcccct cagcccacag cactgtcttt  2580
ttgctgatcc accccccctct taccttttat caggatgtgg cctgttggtc cttctgttgc  2640
catcacagag acacaggcat ttaaatattt aacttattta tttaacaaag tagaagggaa  2700
tccattgcta gcttttctgt gttggtgtct aatatttggg tagggtgggg gatccccaac  2760
aatcaggtcc cctgagatag ctggtcattg ggctgatcat tgccagaatc ttcttctcct  2820
ggggtctggc cccccaaaat gcctaaccca ggaccttgga aattctactc atcccaaatg  2880
ataattccaa atgctgttac ccaaggttag ggtgttgaag gaaggtagag ggtggggctt  2940
caggtctcaa cggcttccct aaccacccct cttctcttgg cccagcctgg ttccccccac  3000
ttccactccc ctctactctc tctaggactg ggctgatgaa ggcactgccc aaaatttccc  3060
ctacccccaa ctttccccta cccccaactt tccccaccag ctccacaacc ctgtttggag  3120
ctactgcagg accagaagca caaagtgcgg tttcccaagc ctttgtccat ctcagccccc  3180
agagtatatc tgtgcttggg gaatctcaca cagaaactca ggagcacccc ctgcctgagc  3240
taagggaggt cttatctctc aggggggggtt taagtgccgt ttgcaataat gtcgtcttat  3300
ttatttagcg gggtgaatat tttatactgt aagtgagcaa tcagagtata atgtttatgg  3360
tgacaaaatt aaaggctttc ttatatgttt a                                 3391
```

-continued

```
SEQ ID NO: 72          moltype = DNA  length = 2346
FEATURE                Location/Qualifiers
source                 1..2346
                       mol_type = other DNA
                       organism = Homo sapiens
SEQUENCE: 72
gcagtgtcac taggccggct gggggccctg ggtacgctgt agaccagacc gcgacaggcc  60
agaacacggg cggcggcttc gggccgggag acccgcgcag ccctcggggc atctcagtgc  120
ctcactcccc acccccctccc ccgggtcggg ggaggcggcg cgtccggcgg agggttgagg  180
ggagcggggc aggcctggag cgccatgagc agcccggatg cgggatacgc cagtgacgac  240
cagagccaga cccagagcgc gctgcccgcg gtgatggccg ggctgggccc ctgcccctgg  300
gccgagtcgc tgagccccat cggggacatg aaggtgaagg gcgaggcgcc ggcgaacagc  360
ggagcaccgg ccggggccgc gggccgagcc aagggcgagt cccgtatccg gcggccgatg  420
aacgctttca tggtgtgggc taaggacgag cgcaagcggc tggcgcagca gaatccagac  480
ctgcacaacg ccgagttgag caagatgctg ggcaagtcgt ggaaggcgct gacgctggcg  540
gagaagcggc ccttcgtgga ggaggcagag cggctgcgcg tgcagcacat gcaggaccac  600
cccaactaca agtaccggcc gcggcggcgc aagcaggtga agcggctgaa gcgggtggag  660
ggcggcttcc tgcacggcct ggctgagccg caggcggccg cgctgggccc cgagggcggc  720
cgcgtggcca tggacggcct gggcctccag ttccccgagc agggcttccc cgccggcccg  780
ccgctgctgc ctccgcacat gggcggccac taccgcgact gccagagtct gggcgcgcct  840
ccgctcgacg gctacccgtt gcccacgccc gacacgtccc cgctggacgg cgtggacccc  900
gacccggctt tcttcgccgc cccgatgccc ggggactgcc cggcggccgg cacctacagc  960
tacgcgcagg tctcggacta cgctggcccc ccggagcctc ccgccggtcc catgcacccc  1020
cgactcggcc cagagcccgc gggtccctcg attccgggcc tcctggcgcc acccagcgcc  1080
cttcacgtgt actacggcgc gatgggctcg cccggggcgg gcggcgggcg cggcttccag  1140
atgcagccgc aacaccagca ccagcaccag caccagcacc accccccggg ccccggacag  1200
ccgtcgcccc ctccggaggc actgccctgc cgggacggca cggaccccag tcagcccgcc  1260
gagctcctcg ggagggtgga ccgcacggaa tttgaacagt atctgcactt cgtgtgcaag  1320
cctgagatgg gcctccccta ccaggggcat gactccggtg tgaatctccc cgacagccac  1380
ggggccattt cctcggtggt gtccgacgcc agctccgcgg tatattactg caactatcct  1440
gacgtgtgac aggtccctga tccgccccag cctgcaggcc agaagcagtg ttacacactt  1500
cctggaggag ctaaggaaat cctcagactc ctgggttttt gttgttgctg ttgttgtttt  1560
ttaaaaggtg tgttggcata taatttatgg taatttattt tgtctgccac ttgaacagtt  1620
tgggggggtg aggtttcatt taaaatttgt tcagagattt gtttcccata gttggattgt  1680
caaaaaccta tttccaagtt caagttaact agctttgaat gtgtcccaaa acagcttcct  1740
ccatttcctg aaagtttatt gatcaaagaa atgttgtcct gggtgtgttt tttcaatctt  1800
ctaaaaaata aaatctggaa tcctgctttt ttgctctact agtacctctg tcacactagt  1860
cttatcaaaa accagttctt aagatcaatg ttaagtttat tagttaatgt aaatttctca  1920
tcctcgaaaa gggtgaacat aaatgccttt aaggagtata tctaaaaata aacattagga  1980
tatctaagtt tgatgtaatt gtttcaggaa ggaaaaaaga aaagcattct ggaatgagcc  2040
tacttcaagt aatcttagtt tctaaaacta acagttaata ttttcaattc cagtatatca  2100
ctttaagtag aaggggatgt ccaagtaatt ttggtttttct aactgttgaa tcataagctt  2160
gacctgcccc cagaggcttt ttggatgttt ttatctgtgt tttgccatct ctttacactc  2220
ctcgacattc agtttacctt aatcttcaca tttttacacc ttgggaagtg gcaagcatcg  2280
ctgggtttaa gataaaggag tcacaaaaac taatcaaaat aaaatttgca ttatgacaac  2340
ttttaa                                                             2346

SEQ ID NO: 73          moltype = DNA  length = 1910
FEATURE                Location/Qualifiers
source                 1..1910
                       mol_type = other DNA
                       organism = Homo sapiens
SEQUENCE: 73
cttcatctcg cggctgtctg acttcctccc agcacattcc tgcactctgc cgtgtccaca  60
ctgccccaca gacccagtcc tccaagcctg ctgccagctc cctgcaagcc cctcaggttg  120
ggccttgcca cggtgccagc aggcagccct gggctggggg taggggactc cctacaggca  180
cgcagccctg agacctcaga gggccacccc ttgagggtgg ccaggccccc agtggccaac  240
ctgagtgctg cctctgccac cagccctgct ggcccctggt tccgctggcc ccccagatgc  300
ctggctgaga cacgccagtg gcctcagctg cccacacctc ttcccggccc ctgaagttgg  360
cactgcagca gacagctccc tgggcaccag gcagctaaca gacacagccg ccagcccaaa  420
cagcagcggc atgggcagcg ccagcccggg tctgagcagc gtatccccca gccacctcct  480
gctgcccccc gacacggtgt cgcggacagg cttggagaag gcggcagcgg gggcagtggg  540
tctcgagaga cgggactgga gtcccagtcc acccgccacg cccgagcagg gcctgtccgc  600
cttctacctc tcctactttg acatgctgta ccctgaggac agcagctggg cagccaaggc  660
ccctggggcc agcagtcggg aggagccacc tgaggagcct gagcagtgcc cggtcattga  720
cagccaagcc ccagcgggca gcctggactt ggtgcccggc gggctgacct tggaggagca  780
ctcgctggag caggtgcagt ccatggtggt gggcgaagtg ctcaaggaca tcgagacggc  840
ctgcaagctg ctcaacatca ccgcagatcc catggactgg agccccagca atgtgcagaa  900
gtggctcctg tggacagagc accaataccg gctgccccccc atgggcaagg ccttccagga  960
gctggcgggc aaggagctgt gcgccatgtc ggaggagcag ttccgccagc gctcgcccct  1020
gggtggggat gtgctgcacg cccacctgga catctggaag tcagcggcct ggatgaaaga  1080
gcggacttca cctggggcga ttcactactg tgcctcgacc agtgaggaga gctggaccga  1140
cagcgaggtg gactcatcat gctccgggca gcccatccac ctgtggcagt tcctcaagga  1200
gttgctactc aagccccaca gctatggccg cttcattagg tggctcaaca aggagaaggg  1260
catcttcaaa attgaggact cagcccaggt ggcccggctg tggggcatcc gcaagaaccg  1320
tcccgccatg aactacgaca agctgagccg ctccatccgc cagtattaca agaagggcat  1380
catccggaag ccagacatct cccagcgcct cgtctaccag ttcgtgcacc ccatctgagt  1440
gcctggccca gggcctgaaa cccgccctca ggggcctctc tcctgcctgc cctgcctcag  1500
ccaggccctg agatgggggga aaacgggcag tctgctctgc tgctctgacc ttccagagcc  1560
```

```
caaggtcagg gaggggcaac caactgcccc agggggatat gggtcctctg gggccttcgg  1620
gaccctgggg caggggtgct tcctcctcag gcccagctgc tcccctggag gacagaggga  1680
gacagggctg ctccccaaca cctgcctctg accccagcat ttccagagca gagcctacag  1740
aagggcagtg actcgacaaa ggccacaggc agtccaggcc tctctctgct ccatccccct  1800
gcctcccatt ctgcaccaca cctggcatgg tgcagggaga catctgcacc cctgagttgg  1860
gcagccagga gtgcccccgg gaatggataa taaagatact agagaactga            1910

SEQ ID NO: 74          moltype = DNA  length = 1688
FEATURE                Location/Qualifiers
source                 1..1688
                       mol_type = other DNA
                       organism = Homo sapiens
SEQUENCE: 74
gccattggct ctggcgacct ccgcgcgttg ggaggtgtag cgcggctctg aacgcgctga  60
gggccgttga gtgtcgcagg cggcgagggc gcgagtgagg agcagaccca ggcatcgcgc  120
gccgagaagg ccgggcgtcc ccacactgaa ggtccggaaa ggcgacttcc gggggctttg  180
gcacctggcg gaccctcccg gagcgtcggc acctgaacgc gaggcgctcc attgcgcgtg  240
cgcgttgagg ggcttcccgc acctgatcgc gagaccccaa cggctggtgg cgtcgcctgc  300
gcgtctcggc tgagctggcc atggcgcagc tgtgcgggct gaggcggagc cgggcgtttc  360
tcgccctgct gggatcgctg ctcctctctg ggggtcctggc ggccgaccga gaacgcagca  420
tccacgactt ctgcctggtg tcgaaggtgg tgggcagatg ccgggcctcc atgcctaggt  480
ggtggtacaa tgtcactgac ggatcctgcc agctgtttgt gtatgggggc tgtgacggaa  540
acagcaataa ttacctgacc aaggaggagt gcctcaagaa atgtgccact gtcacagaga  600
atgccacggg tgacctggcc accagcagga atgcagcgga ttcctctgtc ccaagtgctc  660
ccagaaggca ggattctgaa gaccactcca gcgatatgtt caactatgaa gaatactgca  720
ccgccaacgc agtcactggg ccttgccgtg catccttccc acgctggtac tttgacgtgg  780
agaggaactc ctgcaataac ttcatctatg gaggctgccg ggcaataag aacagctacc  840
gctctgagga ggcctgcatg ctccgctgct tccgccagca ggagaatcct cccctgcccc  900
ttggctcaaa ggtggtggtt ctggcggggc tgttcgtgat ggtgttgatc ctcttcctgg  960
gagcctccat ggtctacctg atccgggtgg cacggaggaa ccaggagcgt gccctgcgca  1020
ccgtctggag ctccggagat gacaaggagc agctggtgaa gaacacatat gtcctgtgac  1080
cgccctgtcg ccaagaggac tggggaaggg aggggagact atgtgtgagc tttttttaaa  1140
tagagggatt gactcggatt tgagtgatca ttagggctga ggtctgtttc tctgggaggt  1200
aggacggctg cttcctggtc tggcagggat gggtttgctt tggaaatcct ctaggaggct  1260
cctcctcgca tggcctgcag tctggcagca gccccgagtt gtttcctcgc tgatcgattt  1320
ctttcctcca ggtagagttt tctttgctta tgttgaattc cattgcctct tttctcatca  1380
cagaagtgat gttggaatcg tttcttttgt ttgtctgatt tatggttttt ttaagtataa  1440
acaaaagttt tttattagca ttctgaaaga aggaaagtaa aatgtacaag tttaataaaa  1500
aggggccttc ccctttagaa taaatttcag catgtgcttt ctttatggga gtcctaattt  1560
caaccctacc aaaatgatca caagacacta tctgaggtgt cccattctag aaatagaccc  1620
ctcaaaatag cgtctttcag atctttttga atgaatccac aagatgaaat aaatgtccta  1680
ttactgag                                                          1688

SEQ ID NO: 75          moltype = DNA  length = 1046
FEATURE                Location/Qualifiers
source                 1..1046
                       mol_type = other DNA
                       organism = Homo sapiens
SEQUENCE: 75
accagatccc tgtttccgtg gaggaaggca gacttcagac tgaaggacag agaaggcaac  60
tgccctacag ccctgcaggt cttcaagtct gtggttgtgg gcactaaccc agacaagaaa  120
aggaaagacc tgcagtatcg gtgcaggaaa ggcaaagaag ggaacatctc aacatggaaa  180
agctctacaa agaaaatgaa ggaaagccag agaatgaaag aaacctagaa agtgagggaa  240
agccagagga tgagggaagt acagaagatg aaggaaagtc agacgaggaa gaaaagccgg  300
acatggaggg gaagacagaa tgcgagggaa agcgagagga tgagggagag ccaggtgatg  360
agggacaact ggaagatgag ggaaaccagg aaaagcaggg caagtctgaa ggtgaggaca  420
agccacaaag tgagggcaag ccagcctccc aggccaagcc agagagccag ccgcgggccg  480
ccgaaaagcg cccggctgaa gattatgtgc cccggaaagc aaaaagaaaa accgacaggg  540
ggacggacga ttcccccaag gactctcagg aggacttaca agaaaggcat ctgagcagtg  600
aggagatgat gagagaatgt ggagatgtgt caagggctca ggaggagcta aggaaaaaac  660
agaaaatggg tggttttcat tggatgcaaa gagatgtaca ggatccattc gccccaaggg  720
gccaacgggg tgtgaggga gtgaggggcg gaggtagggg ccagaaagac ttagaagatg  780
tcccatatgt ttaatgtctt tggcctttaa ttctgatttc tctgatggga atattgccag  840
tcctgctttt cctggcaggc atttgccggc ctatgtgctt taaccttaag ctgatacttt  900
cctttaggtg tcactcttgt taccagcaga cttttgaccc aactacagtg ctctgtcttt  960
tagtagagga ttttcaccca tgtgcatgga ataaatgttc atggtacatt gtaaaataac  1020
aataaaaaag agttttcaga accatg                                      1046

SEQ ID NO: 76          moltype = DNA  length = 8455
FEATURE                Location/Qualifiers
source                 1..8455
                       mol_type = other DNA
                       organism = Homo sapiens
SEQUENCE: 76
aagcagtggt ttctcctcct tcctcccagg aagggccagg aaaatggccc tggtcctgga  60
gatcttcacc ctgctggcct ccatctgctg ggtgtcggcc aatatcttcg agtaccaggt  120
ggatgcccag ccccttcgtc cctgtgagct gcagagggaa acggcctttc tgaagcaagc  180
agactacgtg ccccagtgtg cagaggatgg cagcttccag actgtccagt gccagaacga  240
cggccgctcc tgctggtgtg tgggtgccaa cggcagtgaa gtgctgggca gcaggcagcc  300
```

-continued aggacggcct gtggcttgtc tgtcattttg tcagctacag aaacagcaga tcttactgag 360
tggctacatt aacagcacag acacctccta cctccctcag tgtcaggatt caggggacta 420
cgcgcctgtt cagtgtgatg tgcagcaggt ccagtgctgg tgtgtggacg cagaggggat 480
ggaggtgtat gggacccgcc agctggggag gccaaagcga tgtccaagga gctgtgaaat 540
aagaaatcgt cgtcttctcc acggggtggg agataagtca ccaccccagt gttctgcgga 600
gggagagttt atgcctgtcc agtgcaaatt tgtcaacacc acagacatga tgatttttga 660
tctggtccac agctacaaca ggtttccaga tgcatttgtg accttcagtt ccttccagag 720
gaggttccct gaggtatctg ggtattgcca ctgtgctgac agccaagggc gggaactggc 780
tgagacaggt ttggagttgt tactggatga aatttatgac accatttttg ctggcctgga 840
ccttccttcc accttcactg aaaccaccct gtaccggata ctgcagagac ggttcctcgc 900
agttcaatca gtcatctctg gcagattccg atgccccaca aaatgtgaag tggagcggtt 960
tacagcaacc agctttggtc accccctatgt tccaagctgc cgccgaaatg gcgactatca 1020
ggcggtgcag tgccagacgg aagggccctg ctggtgtgtg gacgcccagg ggaaggaaat 1080
gcatggaacc cggcagcaag gggagccgcc atcttgtgct gaaggccaat cttgtgcctc 1140
cgaaaggcag caggccttgt ccagactcta ctttgggacc tcaggctact tcagccagca 1200
cgacctgttc tcttccccag agaaaagatg ggcctctcca agagtagcca gatttgccac 1260
atcctgccca cccacgatca aggagctctt tgtggactct gggcttctcc gcccaatggt 1320
ggagggacag agccaacagt tttctgtctc agaaaatctt ctcaaagaag ccatccgagc 1380
aatttttccc tcccgagggc tggctcgtct tgcccttcag tttaccacca acccaaagag 1440
actccagcaa aacctttttg gagggaaatt tttggtgaat gttggccagt ttaacttgtc 1500
tggagccctt ggcacaagag gcacatttaa cttcagtcaa tttttccagc aacttggtct 1560
tgcaagcttc ttgaatggag ggagacaaga agatttggcc aagccactct ctgtgggatt 1620
agattcaaat tcttccacag gaacccctga agctgctaag aaggatggta ctatgaataa 1680
gccaactgtg ggcagctttg gctttgaaat taacctacaa gagaaccaaa atgccctcaa 1740
attccttgct tctctcctgg agcttccaga attccttctc ttcttgcaac atgctatctc 1800
tgtgccagaa gatgtggcaa gagatttagg tgatgtgatg gaaacggtac tcagctccca 1860
gacctgtgag cagacacctg aaaggctatt tgtcccatca tgcacgacag aaggaagcta 1920
tgaggatgtc caatgctttt ccggagagtg ctggtgtgtg aattcctggg gcaaagagct 1980
tccaggctca agagtcagag gtggacagcc aaggtgcccc acagactgtg aaaagcaaag 2040
ggctcgcatg caaagcctca tgggcagcca gcctgctggc tccaccttgt ttgtccctgc 2100
ttgtactagt gagggacatt tcctgcctgt ccagtgcttc aactcagagt gctactgtgt 2160
tgatgctgag ggtcaggcca ttcctggaac tcgaagtgca atagggaagc ccaagaaatg 2220
ccccacgccc tgtcaattac agtctgagca agctttcctc aggacggtgc aggccctgct 2280
ctctaactcc agcatgctac ccaccctttc cgacacctac atcccacagt gcagcaccga 2340
tgggcagtgg agacaagtgc aatgcaatgg gcctcctgag caggtcttcg agttgtacca 2400
acgatgggag gctcagaaca agggccagga tctgacgcct gccaagctgc tagtgaagat 2460
catgagctac agagaagcag cttccggaaa cttcagtctc tttattcaaa gtctgtatga 2520
ggctggccag caagatgtct tcccggtgct gtcacaatac ccttctctgc aagatgtccc 2580
actagcagca ctggaaggga aacggcccca gcccagggag aatatcctcc tggagcccta 2640
cctcttctgg cagatcttaa atggccaact cagccaatac ccggggtcct actcagactt 2700
cagcactcct ttggcacatt ttgatcttcg gaactgctgg tgtgtggatg aggctggcca 2760
agaactggaa ggaatgcggt ctgagccaag caagctccca acatgtcctg gctcctgtga 2820
ggaagcaaag ctccgtgtac tgcagttcat tagggaaacg gaagagattg tttcagcttc 2880
caacagttct cggttccctc tgggggagag tttcctggtg gccaagggaa tccggctgag 2940
gaatgaggac ctcggccttc ctccgctctt cccgccccgg gaggctttcg cggagcagtt 3000
tctgcgtggg agtgattacg ccattcgcct ggcggctcag tctaccttaa gcttctatca 3060
gagacgccgc ttttccccgg acgactcggc tggagcatcc gcccttctgc ggtcgggccc 3120
ctacatgcca cagtgtgatg cgtttggaag ttgggagcct gtgcagtgcc acgctgggac 3180
tgggcactgc tggtgtgtag atgagaaagg agggttcatc cctggctcac tgactgcccg 3240
ctctctgcag attccacagt gcccgacaac ctgcgagaaa tctcgaacca gtgggctgct 3300
ttccagttgg aaacaggcta gatcccaaga aaacccatct ccaaaagacc tgttcgtccc 3360
agcctgccta gaaacaggag agtatgccag gctgcaggca tcgggggctg gcacctggtg 3420
tgtggaccct gcatcaggag aagagttgcg gcctggctcg agcagcagtg cccagtgccc 3480
aagcctctgc aatgtgctca agagtggagt cctctccagg agagtcagcc caggctatgt 3540
cccagcctgc agggcagagg atgggggctt ttccccagtg caatgtgacc aggcccaggg 3600
cagctgctgg tgtgtcatgg acagcggaga agaggtgcct gggacgcgcg tgaccggggg 3660
ccagcccgcc tgtgagagcc cgcggtgtcc gctgccattc aacgcgtcgg aggtggttgg 3720
tggaacaatc ctgtgtgaga caatctcggg ccccacaggc tctgccatgc agcagtgcca 3780
attgctgtgc cgccagggct cctggagcgt gtttccacca gggccattga tatgtagcct 3840
ggagagcgga cgctgggagt cacagctgcc tcagccccgg gcctgccaac ggccccagct 3900
gtggcagacc atccagaccc aagggcactt tcagctccag ctcccgccgg gcaagatgtg 3960
cagtgctgac tacgcggatt tgctgcagac tttccaggtt ttcatattgg atgagctgac 4020
agcccgcggc ttctgccaga tccaggtgaa gacttttggc accctggttt ccattcctgt 4080
ctgcaacaac tcctctgtgc aggtgggttg tctgaccagg gagcgtttag gagtgaatgt 4140
tacatggaaa tcacggcttg aggacatccc agtggcttct cttcctgact tacatgacat 4200
tgagagagcc ttggtgggca aggatctcct tgggcgcttc acagatctga tccagagtgg 4260
ctcattccag cttcatctgg actccaagac gttcccagcg gaaaccatcc gcttcctcca 4320
aggggaccac tttggcacct ctcccaggac atggtttggg tgctcggaag gattctacca 4380
agtcttgaca agtgaggcca gtcaggacgg actgggatgc gttaagtgtc ctgaaggaag 4440
ctattcccaa gatgaggaat gcattccttg tcctgttgga ttctaccaag aacaggcagg 4500
gagcttggcc tgtgtcccat gtcctgtggg cagaacgacc atttctgctg gagctttcag 4560
ccagactcac tgtgtcactg actgtcagag gaacgaagca ggcctgcaat gtgaccagaa 4620
tggccagtat cgagccagcc agaaggacag gggcagtggg aaggccttct gtgtggacgg 4680
cgagggggcgg aggctgccat ggtgggaaac agaggcccct cttgaggact cacagtgttt 4740
gatgatgcag aagtttgaga aggttccaga atcaaaggtg atcttcgacg ccaatgctcc 4800
tgtggctgtc agatccaaag ttcctgattc tgagttcccc gtgatgcagt gcttgacaga 4860
ttgcacagag gacgaggcct gcagcttctt caccgtgtcc acgacggagc cagagatttc 4920
ctgtgatttc tatgcttgga caagtgacaa tgttgcctgc atgacttctg accagaaacg 4980
agatgcactg ggaactcaa aggccaccag ctttggaagt cttcgctgcc aggtgaaagt 5040

-continued

```
gaggagccat ggtcaagatt ctccagctgt gtatttgaaa aagggccaag gatccaccac  5100
aacacttcag aaacgctttg aacccactgg tttccaaaac atgctttctg gattgtacaa  5160
ccccattgtg ttctcagcct caggagccaa tctaaccgat gctcacctct tctgtcttct  5220
tgcatgcgac cgtgatctgt gttgcgatgg cttcgtcctc acacaggttc aaggaggtgc  5280
catcatctgt gggttgctga gctcacccag tgtcctgctt tgtaatgtca aagactggat  5340
ggatccctct gaagcctggg ctaatgctac atgtcctggt gtgacatatg accaggagag  5400
ccaccaggtg atattgcgtc ttggagacca ggagttcatc aagagtctga caccccttaga  5460
aggaactcaa gacaccttta ccaattttca gcaggtttat ctctggaaag attctgacat  5520
ggggtctcgg cctgagtcta tgggatgtag aaaagacaca gtgccaaggc cagcatctcc  5580
aacagaagca ggtttgacaa cagaactttt ctcccctgtg gacctcaacc aggtcattgt  5640
caatggaaat caatcactat ccagccagaa gcactggctt ttcaagcacc tgttttcagc  5700
ccagcaggca aacctatggt gcctttctcg ttgtgtgcag gagcactctt tctgtcagct  5760
cgcagagata acagagagtg catccttgta cttcacctgc accctctacc cagaggcaca  5820
ggtgtgtgat gacatcatgg agtccaatgc ccagggctgc agactgatcc tgcctcagat  5880
gccaaaggcc ctgttccgga agaaagttat actggaagat aaagtgaaga acttttacac  5940
tcgcctgccg ttccaaaaac tgatggggat atccattaga aataaagtgc ccatgtctga  6000
aaaatctatt tctaatgggt tctttgaatg tgaacgacgg tgcgatgcgg acccatgctg  6060
cactggcttt ggatttctaa atgtttccca gttaaaagga ggagaggtga catgtctcac  6120
tctgaacagc ttgggaattc agatgtgcag tgaggagaat ggaggagcct ggcgcatttt  6180
ggactgtggc tctcctgaca ttgaagtcca cacctatccc ttcggatggt accagaagcc  6240
cattgctcaa aataatgctc ccagtttttg ccctttggtt gttctgcctt ccctcacaga  6300
gaaagtgtct ctggactcgt ggcagtccct ggccctctct tcagtggttg ttgatccatc  6360
cattaggcac tttgatgttg cccatgtcag cactgctgcc accagcaatt tctctgctgt  6420
ccgagacctc tgtttgtcgg aatgttccca acatgaggcc tgtctcatca ccactctgca  6480
aacccaacct ggggctgtga gatgtatgtt ctatgctgat actcaaagct gcacacatag  6540
tctgcagggt cagaactgcc gacttctgct tcgtgaagag gccacccaca tctaccggaa  6600
gccaggaatc tctctgctca gctatgaggc atctgtacct tctgtgccca tttccaccca  6660
tggccggctg ctgggcaggt cccaggccat ccaggtgggt acctcatgga agcaagtgga  6720
ccagttcctt ggagttccat atgctgcccc gcccctggca gagaggcgct tccaggcacc  6780
agagcccttg aactggacag gctcctggga tgccagcaag ccaagggcca gctgctggca  6840
gccaggcacc agaacatcca cgtctcctgg agtcagtgaa gattgtttgt atctcaatgt  6900
gttcatccct cagaatgtgg cccctaacgc gtctgtgctg gtgttcttcc acaacaccat  6960
ggacagggag gagagtgaag gatggccggc tatcgacggc tccttcttgg ctgctgttgg  7020
caacctcatc gtggtcactg ccagctaccg agtgggtgtc ttcggcttcc tgagttctgg  7080
gtccggagag gtgagtggca actgggggct gctggaccag gtggcggctc tgacctgggt  7140
gcagacccac atccgaggat ttggcgggga ccctcggcgc gtgtccctgg cagcagaccg  7200
tggcggggct gatgtggcca gcatccacct tctcacggcc agggccacca actcccaact  7260
tttccggaga gctgtgctga tgggaggctc cgcactctcc ccggccgccg tcatcagcca  7320
tgagagggct cagcagcagg caattgcttt ggcaaaggag gtcagttgcc ccatgtcatc  7380
cagccaagaa gtggtgtcct gcctccgcca gaagcctgcc aatgtcctca atgatgccca  7440
gaccaagctc ctggccgtga gtggcccttt ccactactgg ggtcctgtga tcgatggcca  7500
cttcctccgt gagcctccag ccagagcact gaagaggtct ttatgggtag aggtcgatct  7560
gctcattggg agttctcagg acgacgggct catcaacaga gcaaaggctg tgaagcaatt  7620
tgaggaaagt cgaggccgga ccagtagcaa aacagccttt taccaggcac tgcagaattc  7680
tctgggtggc gaggactcag atgcccgcgt cgaggctgct gctacatggt attactctct  7740
ggagcactcc acggatgact atgcctcctt ctcccgggct ctggagaatg ccacccggga  7800
ctactttatc atctgcccta taatcgacat ggccagtgcc tgggcaaaga gggcccgagg  7860
aaacgtcttc atgtaccatg ctcctgaaaa ctacggccat ggcagcctgg agctgctggc  7920
ggatgttcag tttgccttgg ggcttccctt ctacccagcc tacgaggggc agttttctct  7980
ggaggagaag agcctgtcgc tgaaaatcat gcagtacttt tcccacttca tcagatcagg  8040
aaatcccaac tacccttatg agttctcacg gaaagtaccc acatttgcaa ccccctggcc  8100
tgactttgta ccccgtgctg gtggagagaa ctacaaggag ttcagtgagc tgctccccaa  8160
tcgacagggc ctgaagaaag ccgactgctc cttctggtcc aagtacatct cgtctctgaa  8220
gacatctgca gatggagcca agggcgggca gtcagcagag agtgaagagg aggagttgac  8280
ggctggatct gggctaagag aagatctcct aagcctccag gaaccaggct ctaagaccta  8340
cagcaagtga ccagcccttg agctccccaa aaacctcacc cgaggctgcc cactatggtc  8400
atctttttct ctaaaatagc cacttacctt caataaagta tctacatgcg gtgaa       8455
```

```
SEQ ID NO: 77          moltype = DNA  length = 1352
FEATURE                Location/Qualifiers
source                 1..1352
                       mol_type = other DNA
                       organism = Homo sapiens
SEQUENCE: 77
actttgcctt gtgttttcca ccctgaaaga atgttgtggc tgctcttttt tctggtgact  60
gccattcatg ctgaactctg tcaaccaggt gcagaaaatg cttttaaagt gagacttagt  120
atcagaacag ctctgggaga taaagcatat gcctgggata ccaatgaaga atacctcttc  180
aaagcgatgg tagctttctc catgagaaaa gttcccaaca gagaagcaac agaaatttcc  240
catgtcctac tttgcaatgt aacccagagg gtatcattct ggtttgtggt tacagaccct  300
tcaaaaaatc acacccttcc tgctgttgag gtgcaatcag ccataagaat gaacaagaac  360
cggatcaaca atgccttctt tctaaatgac caaactctgg aatttttaaa aatcccttcc  420
acacttgcac cacccatgga cccatctgtg cccatctgga ttattatatt tggtgtgata  480
ttttgcatca tcatagttgc aattgcacta ctgattttat cagggatctg gcaacgtaga  540
agaaagaaca aagaaccatc tgaagtggat gacgctgaag ataagtgtga aaacatgatc  600
acaattgaaa atggcatccc ctctgatccc ctggacatga agggagggca tattaatgat  660
gccttcatga cagaggatga gaggctcacc cctctctgaa gggctgttgt tctgcttcct  720
caagaaatta aacatttgtt tctgtgtgac tgctgagcat cctgaaatac caagagcaga  780
tcatatattt tgtttcacca ttcttctttt gtaataaatt ttgaatgtgc ttgaaagtga  840
aaagcaatca attataccca ccaacaccac tgaaatcata agctattcac gactcaaaat  900
```

-continued

```
attctaaaat atttttctga cagtatagtg tataaatgtg gtcatgtggt atttgtagtt  960
attgatttaa gcatttttag aaataagatc aggcatatgt atatattttc acacttcaaa  1020
gacctaagga aaaataaatt ttccagtgga gaatacatat aatatggtgt agaaatcatt  1080
gaaaatggat ccttttgac gatcacttat atcactctgt atatgactaa gtaaacaaaa  1140
gtgagaagta attattgtaa atggatggat aaaaatggaa ttactcatat acagggtgga  1200
attttatcct gttatcacac caacagttga ttatatattt tctgaatatc agcccctaat  1260
aggacaattc tatttgttga ccatttctac aatttgtaaa agtccaatct gtgctaactt  1320
aataaagtaa taatcatctc tttttgattg tg                                1352

SEQ ID NO: 78          moltype = DNA  length = 4944
FEATURE                Location/Qualifiers
source                 1..4944
                       mol_type = other DNA
                       organism = Homo sapiens
SEQUENCE: 78
ctatgtctga tagcatttga ccctattgct tttagcctcc cggctttata tctatatata  60
cacaggtata tgtgtatatt ttatataatt gttctccgtt cgttgatatc aaagacagtt  120
gaaggaaatg aattttgaaa cttcacggtg tgccacccta cagtactgcc ctgaccctta  180
catccagcgt ttcgtagaaa ccccagctca tttctcttgg aaagaaagtt attaccgatc  240
caccatgtcc cagagcacac agacaaatga attcctcagt ccagaggttt tccagcatat  300
ctgggatttt ctggaacagc ctatatgttc agttcagccc attgacttga actttgtgga  360
tgaaccatca gaagatggtg cgacaaacaa gattgagatt agcatggact gtatccgcat  420
gcaggactcg gacctgagtg accccatgtg gccacagtac acgaacctgg ggctcctgaa  480
cagcatggac cagcagattc agaacggctc ctcgtccacc agtccctata acacagacca  540
cgcgcagaac agcgtcacgg cgccctcgcc ctacgcacag cccagctcca ccttcgatgc  600
tctctctcca tcacccgcca tcccctccaa caccgactac ccaggcccgc acagtttcga  660
cgtgtccttc cagcagtcga gcaccgccaa gtcggccacc tggacgtatt ccactgaact  720
gaagaaactc tactgccaaa ttgcaaagac atgccccatc cagatcaagg tgatgacccc  780
acctcctcag ggagctgtta tccgcgccat gcctgtctac aaaaaagctg agcacgtcac  840
ggaggtggtg aagcggtgcc ccaaccatga gctgagccgt gaattcaacg agggacagat  900
tgcccctcct agtcatttga ttcgagtaga ggggaacagc catgcccagt atgtagaaga  960
tcccatcaca ggaagacaga gtgtgctggt accttatgag ccaccccagg ttggcactga  1020
attcacgaca gtcttgtaca atttcatgtg taacagcagt tgtgttggag ggatgaaccg  1080
ccgtccaatt ttaatcattg ttactctgga aaccagagat gggcaagtcc tgggccgacg  1140
ctgctttgag gcccggatct gtgcttgccc aggaagagac aggaaggcgg atgaagatag  1200
catcagaaag cagcaagttt cggacagtac aaagaacggt gatggtacga agcgcccgtt  1260
tcgtcagaac acacatggta tccagatgac atccatcaag aaacgaagat ccccagatga  1320
tgaactgtta tacttaccag tgaggggccg tgagacttat gaaatgctgt tgaagatcaa  1380
agagtccctg gaactcatgc agtaccttcc tcagcacaca attgaaacgt acaggcaaca  1440
gcaacagcag cagcaccagc acttacttca gaaacagacc tcaatacagt ctccatcttc  1500
atatggtaac agctccccac ctctgaacaa aatgaacagc atgaacaagc tgccttctgt  1560
gagccagctt atcaaccctc agcagcgcaa cgccctcact cctacaacca ttcctgatgg  1620
catgggagcc aacattccca tgatgggcac ccacatgcca atggctggag acatgaatgg  1680
actcagcccc acccaggcac tccctccccc actctccatg ccatccacct cccactgcac  1740
acccccacct ccgtatccca cagattgcag cattgtcagt ttcttagcga ggttgggctg  1800
ttcatcatgt ctggactatt tcacgaccca ggggctgacc accatctatc agattgagca  1860
ttactccatg gatgatctgg caagtctgaa aatccctgag caatttcgac atgcgatctg  1920
gaagggcatc ctggaccacc ggcagctcca cgaattctcc tcccccttctc atctcctgcg  1980
gaccccaagc agtgcctcta cagtcagtgt gggctccagt gagacccggg gtgagcgtgt  2040
tattgatgct gtgcgattca ccctccgcca gaccatctct ttcccacccc gagatgagtg  2100
gaatgacttc aactttgaca tggatgctcg ccgcaataag caacagcgca tcaaagagga  2160
gggggagtga gcctcaccat gtgagctctt cctatccctc tcctaactgc cagcccccta  2220
aaagcactcc tgcttaatct tcaaagcctt ctccctagct cctccccttc ctcttgtctg  2280
atttcttagg ggaaggagaa gtaagaggct acctcttacc taacatctga cctggcatct  2340
aattctgatt ctggctttaa gccttcaaaa ctatagcttg cagaactgta gctgccatgg  2400
ctaggtagaa gtgagcaaaa aagagttggg tgtctcctta agctgcagag atttctcatt  2460
gacttttata aagcatgttc acccttatag tctaagacta tatatataaa tgtataaata  2520
tacagtatag atttttgggt gggggggcatt gagtattgtt taaaatgtaa tttaaatgaa  2580
agaaaattga gttgcactta ttgaccattt tttaatttac ttgttttgga tggcttgtct  2640
atactccttc ccttaagggg tatcatgtat ggtgataggt atctagagct taatgctaca  2700
tgtgagtgac gatgatgtac agattctttc agttctttgg attctaaata catgccacat  2760
caaacctttg agtagatcca tttccattgc ttattatgta ggtaagactg tagatatgta  2820
ttcttttctc agtgttggta tattttatat tactgacatt tcttctagtg atgatggttc  2880
acgttggggt gatttaatcc agttataaga agaagttcat gtccaaacgt cctctttagt  2940
ttttggttgg gaatgaggaa aattcttaaa aggcccatag cagccagttc aaaaacaccc  3000
gacgtcatgt atttgagcat atcagtaacc cccttaaatt taataccaga taccttatct  3060
tacaatattg attgggaaaa catttgctgc cattacagag gtattaaaac taaatttcac  3120
tactagattg actaactcaa atacacattt gctactgttg taagaattct gattgatttg  3180
attgggatga atgccatcta tctagttcta acagtgaagt tttactgtct attaatattc  3240
agggtaaata ggaatcattc agaaatgttg agtctgtact aaacagtaag atatctcaat  3300
gaaccataaa ttcaactttg taaaaatctt ttgaagcata gataatattg tttggtaaat  3360
gtttcttttg tttggtaaat gtttctttta aagaccctcc tattctataa aactctgcat  3420
gtagaggctt gtttaccttt ctctctctaa ggtttacaat aggagtggtg atttgaaaaa  3480
tataaaatta tgagattggt tttcctgtgg cataaattgc atcactgtat catttctttt  3540
tttaaccggt aagagtttca gtttgttgga aagtaactgt gagaacccag tttcccgtcc  3600
atctccctta gggactaccc atagacatga aaggtcccca cagagcaaga gataagtctt  3660
tcatggctgc tgttgcttaa accacttaaa cgaagagttc ccttgaaact ttgggaaaac  3720
atgttaatga caatattcca gatctttcag aaatataaca catttttttg catgcatgca  3780
aatgagctct gaaatcttcc catgcattct ggtcaagggc tgtcattgca cataagcttc  3840
```

```
cattttaatt ttaaagtgca aaagggccag cgtggctcta aaaggtaatg tgtggattgc  3900
ctctgaaaag tgtgtatata ttttgtgtga aattgcatac tttgtatttt gattattttt  3960
tttttcttct tgggatagtg ggatttccag aaccacactt gaaacctttt tttatcgttt  4020
ttgtattttc atgaaaatac catttagtaa gaataccaca tcaaataaga aataatgcta  4080
caattttaag aggggaggga agggaaagtt ttttttattt attttttaa aattttgtat  4140
gttaaagaga atgagtcctt gatttcaaag ttttgttgta cttaaatggt aataagcact  4200
gtaaacttct gcaacaagca tgcagctttg caaacccatt aaggggaaga atgaaagctg  4260
ttccttggtc ctagtaagaa gacaaactgc ttcccttact ttgctgaggg tttgaataaa  4320
cctaggactt ccgagctatg tcagtactat tcaggtaaca ctagggcctt ggaaattcct  4380
gtactgtgtc tcatggattt ggcactagcc aaagcgaggc acccttactg gcttacctcc  4440
tcatggcagc ctactctcct tgagtgtatg agtagccagg gtaaggggta aaaggatagt  4500
aagcatagaa accactagaa agtgggctta atggagttct tgtggcctca gctcaatgca  4560
gttagctgaa gaattgaaaa gtttttgttt ggagacgttt ataaacagaa atggaaagca  4620
gagttttcat taaatccttt tacctttttt ttttcttggt aatcccctaa aataacagta  4680
tgtgggatat tgaatgttaa aggatattt ttttctatta tttttataat tgtacaaaat  4740
taagcaaatg ttaaaagttt tatatgcttt attaatgttt tcaaaaggta ttatacatgt  4800
gatacatttt ttaagcttca gttgcttgtc ttctggtact ttctgttatg ggcttttggg  4860
gagccagaag ccaatctaca atctcttttt gtttgccagg acatgcaata aaatttaaaa  4920
aataaataaa aactaattaa gaaa                                        4944
```

```
SEQ ID NO: 79          moltype = DNA  length = 9859
FEATURE                Location/Qualifiers
source                 1..9859
                       mol_type = other DNA
                       organism = Homo sapiens
SEQUENCE: 79
ttcctccgcg aaggctcctt tgatattaat agtgttggtg tcttgaaact gacgtaatgc  60
gcggagactg aggtcctgac aagcgataac atttctgata aagacccgat cttactgcaa  120
tctctagcgt cctctttttt ggtgctgctg gtttctccag acctcgcgtc ctctcgattg  180
ctctctcgcc ttcctatttc tttttttttt ttttaaacaa aaaacaacac cccctcccct  240
ctcccacccg gcaccgggca catccttgct ctatttcctt tctctttctc tctctctctc  300
tctctctctc ttttttaata agggtggggg agggaaaggg gggggaggca ggaaagacct  360
ttttctctcc cccccgcaat aatccaagat caactctgca aacaacagaa gacggttcat  420
ggctttggcc gccgcgccac catctttcgg gctgccgagg gtgttcttga cgattaatca  480
acagatatgg tccggaaaaa gaaccccct ctgagaaacg ttgcaagtga aggcgagggc  540
cagatcctgg agcctatagg tacagaaagc aaggtatctg gaaagaacaa agaattttct  600
gcagatcaga tgtcagaaaa tacggatcag agtgatgctg cagaactaaa tcataaggag  660
gaacatagct tgcatgttca agatccatct tctagcagta agaaggactt gaaaagcgca  720
gttctgagtg agaaggctgg cttcaattat gaaagcccca gtaagggagg aaactttccc  780
tcctttccgc atgatgaggt gacagacaga aatatgttgg ctttctcatc tccagctgct  840
gggggagtct gtgagccctt gaagtctccg caaagagcag aggcagatga ccctcaagat  900
atggcctgca ccccctcagg ggactcactg gagacaaagg aagatcagaa gatgtcacca  960
aaggctacag aggaaacagg gcaagcacag agtggtcaag ccaattgtca aggtttgagc  1020
ccagtttcag tggcctcaaa aaacccacaa gtgccttcag atggggggtgt aagactgaat  1080
aaatccaaaa ctgacttact ggtgaatgac aacccagacc cggcacctct gtctccagag  1140
cttcaggact ttaaatgcaa tatctgtgga tatggttact acggcaacga ccccacagat  1200
ctgattaagc acttccgaaa gtatcactta ggactgcata accgcaccag gcaagatgct  1260
gagctggaca gcaaaatctt ggcccttcat aacatggtgc agttcagcca ttccaaagac  1320
ttccagaagg tcaaccgttc tgtgttttct ggtgtgctgc aggacatcaa ttcttcaagg  1380
cctgttttac taaatgggac ctatgatgtg caggtgactt caggtggaac attcattggc  1440
attggacgga aaacaccaga ttgccaaggg aacaccaagt atttccgctg taaattctgc  1500
aatttcactt atatgggcaa ctcatccacc gaattagaac aacattttct tcagactcac  1560
ccaaacaaaa taaaagcttc tctcccctcc tctgaggttg caaaaccttc agagaaaaac  1620
tctaacaagt ccatccctgc acttcaatcc agtgattctg gagacttggg aaaatggcag  1680
gacaagataa cagtcaaagc aggagatgac actcctgttg ggtactcagt gcccataaag  1740
cccctcgatt cctctagaca aaatggtaca gaggccacca gttactactg gtgtaaattt  1800
tgtagtttca gctgtgagtc atctagctca cttaaactgc tagaacatta tggcaagcag  1860
cacggagcag tgcagtcagg cggccttaat ccagagttaa atgataagct ttccaggggc  1920
tctgtcatta atcagaatga tctagccaaa agttcagaag gagagacaat gaccaagaca  1980
gacaagagct cgagtggggc taaaaagaag gacttctcca gcaagggagc cgaggataat  2040
atggtaacga gctataattg tcagttctgt gacttccgat attccaaaag ccatggccct  2100
gatgtaattg tagtggggcc acttctccgt cattatcaac agctccataa cattcacaag  2160
tgtaccatta aacactgtcc attctgtccc agaggacttt gcagcccaga aaagcacctt  2220
ggagaaatta cttatccgtt tgcttgtaga aaaagtaatt gttcccactg tgcactcttg  2280
cttctgcact tgtctcctgg ggcggctgga agctcgcgag tcaaacatca gtgccatcag  2340
tgttcattca ccacccctga cgtagatgta ctcctctttc actatgaaag tgtgcatgag  2400
tcccaagcat cggatgtcaa acaagaagca aatcacctgc aaggatcgga tgggcagcag  2460
tctgtcaagg aaagcaaaga acactcatgt accaaatgtg attttattac ccaagtggaa  2520
gaagagattt cccgacacta caggagagca cacagctgct acaaatgccg tcagtgcagt  2580
tttacagctg ccgatactca gtcactactg gagcacttca acactgttca ctgccaggaa  2640
caggacatca ctacagccaa cggcgaagag gacggtcatg ccatatccac catcaaagag  2700
gagcccaaaa ttgacttcag ggtctacaat ctgctaactc cagactctaa aatgggagag  2760
ccagtttctg agagtgtggt gaagagagag aagctggaag agaaggacgg gctcaaagag  2820
aaagtttgga ccgagagttc cagtgatgac cttcgcaatg tgacttggag aggggcagac  2880
atcctgcggg ggagtccgtc atacacccaa gcaagcctgg ggctgctgac gcctgtgtct  2940
ggcacccaag agcagacaaa gactctaagg gatagtccca atgtggaggc cgcccatctg  3000
gcgcgaccta tttatggctt ggctgtggaa accaagggat tcctgcaggg ggcgccagct  3060
ggcggagaga agtctggggc cctcccccag cagtatcctg catcgggaga aaacaagtcc  3120
aaggatgaat cccagtccct gttacggagg cgtagaggct ccggtgtttt ttgtgccaat  3180
```

-continued

```
tgcctgacca caaagacctc tctctggcga aagaatgcaa atggcggata tgtatgcaac  3240
gcgtgtggcc tctaccagaa gcttcactcg actcccaggc ctttaaacat cattaaacaa  3300
aacaacggtg agcagattat taggaggaga acaagaaagc gccttaaccc agaggcactt  3360
caggctgagc agctcaacaa acagcagagg ggcagcaatg aggagcaagt caatggaagc  3420
ccgttagaga ggaggtcaga agatcatcta actgaaagtc accagagaga aattccactc  3480
cccagcctaa gtaaatacga agcccagggt tcattgacta aaagccattc tgctcagcag  3540
ccagtcctgg tcagccaaac tctggatatt cacaaaagga tgcaaccttt gcacattcag  3600
ataaaaagtc ctcaggaaag tactggagat ccaggaaata gttcatccgt atctgaaggg  3660
aaaggaagtt ctgagagagg cagtcctata gaaaagtaca tgagacctgc gaaacaccca  3720
aattattcac caccaggcag ccctattgaa aagtaccagt acccactttt tggacttccc  3780
tttgtacata atgacttcca gagtgaagct gattggctgc ggttctggag taaatataag  3840
ctctccgttc ctgggaatcc gcactacttg agtcacgtgc ctggcctacc aaatccttgc  3900
caaaactatg tgccttatcc caccttcaat ctgcctcctc atttttcagc tgttggatca  3960
gacaatgaca ttcctctaga tttggcgatc aagcattcca gacctgggcc aactgcaaac  4020
ggtgcctcca aggagaaaac gaaggcacca ccaaatgtaa aaaatgaagg tcccttgaat  4080
gtagtaaaaa cagagaaagt tgatagaagt actcaagatg aactttcaac aaaatgtgtg  4140
cactgtggca ttgtctttct ggatgaagtg atgtatgctt tgcatatgag ttgccatggt  4200
gacagtggac ctttccagtg cagcatatgc cagcatcttt gcacggacaa atatgacttc  4260
acaacacata tccagagggg cctgcatagg aacaatgcac aagtggaaaa aaatggaaaa  4320
cctaaagagt aaaaccttag cacttagcac aattaaatag aaataggttt tcttgatggg  4380
aattcaatag cttgtaatgt cttatgaaga cctattaaaa aaatacttca tagagcctgc  4440
cttatccaac atgaaattcc cttctttgt tattctttct tttgatgagt aggttaccaa  4500
gattaaaaag tgagataaat ggtcaatgag aaagaatgga agatggtaaa caatcacttt  4560
ttaaaacctg ttaagtcaaa accatcttgg ctaatatgta ctggggaaat aatccataag  4620
agatatcacc agactagaat taatatattt ataaagaaag agaccaaaac tgtctagaat  4680
ttgaaagggt ttacatatta ttatactaaa gcagtactgg actggccatt ggaccatttg  4740
ttccaaaacc cataaattgt tgcctaaatt tataatgatc atgaaaccct aggcagagga  4800
ggagaaattg aaggtccagg gcaatgaaag aaaaatggcg ccctctcaat ttagtcttct  4860
ctcattggcc atgtttcaga ttttgaccta gaaatgcgag ctgtggttag gcttggttag  4920
agtgcagcaa gcaacatgac agatggtggc acgctgtttt tacccagccc tgcctgtaca  4980
tacacatgca caccctctct gatattttg tcctttagat gttcaaatac tcagtagtcc  5040
ttttgtttgc ggtttagatt cattttgtcc acacatgtac ccattttaaa aaacaatgtc  5100
ctcgatgctt ctgtagtgat ttcattttag ccaggtattt ctttcttgtg tgtgatgaac  5160
cagtatggat ttgcttttct aagcctcctg ttggttacta atctcacttg gcacattata  5220
actaaaggaa tcccctcaat tcaaaagcat agatggatac aaatgtcaga ccgtgggttt  5280
aatttgttta gaacacatgg catttcttca caaggtaacc tgctgtattt atttattttc  5340
ttttggttaa atataatttc caaactttgt ggtcaggcag cgtctaaggt tacgttacca  5400
cagactgaca gttggtatat gtaccagcca atcccttcat taaatgtata cagatttagt  5460
taagtagcat taaataggat tcttagaagt atgtcctcat agaactttta atacttaagg  5520
ctttgtaaaa actatccatg aagggaaagc tcctcagcat aactgctcag ggaaataggg  5580
ctaaataact gaacattaaa taattggtta aaggtgctgt tagtcgagcc tcaatgcttg  5640
ctacaaggat gtatgtacaa ggactgactt taataatttg cattatattg tcccaaccag  5700
tagtttattt tttgccacgg agatgtagaa gatattacaa gctactggat gcactgtcag  5760
attaacttat ttcattaaag aagttgggag aacaaatagg aaaaaaaaaa cttattttc  5820
tagtaaatat taatgtatta catttcaaat aatggtgcct gacatattga ataattattt  5880
tctacagtgt acgtatgcaa caaagatatt ccatcatgca ttagagtcag ttctggctct  5940
gcctagctgt ttacatttgc aaatgtagca aacaaggtaa tgaagcaact atttctattg  6000
cagtagatat ccttttgtgt gtgtgtgtgt gcattaaagt tgtaaacggt aacatgaaac  6060
aaatgaaagt tcttgctata atggtatgga aaacaagaag gaaatgaaaa tatttttatg  6120
cctacttagg aaaaaaaggg tagcacttat tcattccaag tacttttttt tttttaattt  6180
ttaagctctt aactcacatt gttatgctta agatgataaa catatatcct ctttttattg  6240
ctttgtctat gtttcatatg aaacatttca gaaattattt tgataagtgt tgctggaatc  6300
tgcaacgctg attttttttt gcattctgta gtcgcatttg cactccattt ttacattaat  6360
tcgcagttgc tttgtatcat tgtttttgttt gggttttgtt tctttttcac agtgccgggt  6420
cttcgtttct taaagttgga tggcaggtag agttcaacca gttcgtgact gttgtagcga  6480
atgaagttaa aaaaatgtct ttctgatgtt gtgttgtcat tttcattttt gcattttttt  6540
gtttgcatat taaaaaaaga gaaaagagaa agcaagagac agaaatcagg actaagtcct  6600
ctgcttcagt ttcattgtta acgggcctta ttctgatctc acctgtcgcg tagctctaat  6660
attcacataa actgaaataa agaagtggaa tgaggagctt tgacattcaa attatgtgat  6720
gtaatttatc ttccttagga attttgatgg atgcatctca aaatgtatag ccagacttga  6780
gaggtgacaa ttaaagatct aaaaaagaga ggagattccc ccaaacaaca atatttaatt  6840
ttcttagtaa aaagaataac agaatgcatc gtggcaatcc ttaagcaaca ttatctatgt  6900
ggactgctta aatcagcaaa acaccagaag tttggttaac ttgggcaata tgacaagtat  6960
tactttttgg gcaaaactac tcattaagca atttctctag tgtgtcggac acaaataggt  7020
tctttatttt tggcatgtat gcctttttat tttcattcaa tttttttttt ttctcagaca  7080
gacatagtag taacgactag cattggaaaa tacatatcac tattcttgga atatttatgg  7140
tcagtctact ttttagtaga atatttttgg atagcgttga cacgatagat cttattccat  7200
acttctttat tattgataat tttattttca ttttttgctt tcattattat acatattttg  7260
gtggagaaga ggttgggctt ttttgaaaga gacaaaaatt tattataaca ctaaacactc  7320
cttttttgac atattaaagc ctttattcca tctctcaaga tatattataa aatttatttt  7380
tttaatttaa gatttctgaa ttattttatc ttaaattgtg attttaaacg agctattatg  7440
gtacggaact ttttttaatg aggaatttca tgatgattta ggaattttct ctcttggaaa  7500
aggcttcccc tgtgatgaaa atgatgtgcc agctaaaatt gtgtgccatt taaaaactga  7560
aaatatttta aaattatttg tctatattct aaattgagct ttggatcaaa ctttaggcca  7620
ggaccagctc atgcgttctc attcttcctt ttctcactct ttctctcatc actcacctct  7680
gtattcattc tgttgtttgg gatagaaaaa tcataaagag ccaacccatc tcagaacgtt  7740
gtggattgag agagacacta catgactcca agtatatgag aaaaggacag agctctaatt  7800
gataactctg tagttcaaaa ggaaaagagt atgcccaatt ctctctacat gacatattga  7860
gatttttttt aatcaacttt taagatagtg atgttctgtt ctaaactgtt ctgttttagt  7920
```

-continued

```
gaaggtagat ttttataaaa caagcatggg gattcttttc taaggtaata ttaatgagaa  7980
gggaaaaaag tatctttaac agctctttgt tgaagcctgt ggtagcacat tatgtttata  8040
attgcacatg tgcacataat ctattatgat ccaatgcaaa tacagctcca aaaatattaa  8100
atgtatatat attttaaaat gcctgaggaa atacattttt cttaataaac tgaagagtct  8160
cagtatggct attaaaataa ttattagcct cctgttgtgt ggctgcaaaa catcacaaag  8220
tgaccggtct tgagacctgt gaactgctgc cctgtttagt aaataaaatt aatgcatttc  8280
tagaggggga atatctgcca tccagtggtg gaaatgtgga gtaaagaagc tggtggtctg  8340
cttctgtgct gtatgccagc cttttgcctt aagttgagag gaggtcaact ttagctactg  8400
tctttggttt gagagccatg gcaaaaaaaa aaaaagaaaa aaagatcaag tcgtctttgg  8460
tgagccagta aggtgaaagc ttgctgactg tccaaggcac aagagaaaat tgaggaattg  8520
aaatgcaacc tgagtatcaa actaaatatt ctaatcaaag gtaggtactg ttaggtggaa  8580
ttctatcagc aggcaactgc aaatgagaag aagatagaag gacgcccgtc gggactttgg  8640
agggcattgt tattttccca aagaaagacg gccaagggca gaggcatgga ttctttgcag  8700
agcacttcct tttggttttt cagtactgtt tcatagacag tgggctcaca tgttcctgat  8760
agtgctgcag ttgcttagaa agcatcccag ttaattgcag taattagaac ttctggaata  8820
tgctagggca gaagtatgtc aagtatgtca catgaagaaa atgtgaaatt caagagtaat  8880
ccacacgtga gaaactagac aatgtacatt catgtgttct cttgaaagga aagggagagc  8940
tgtaagcttc actctgtcct acaccggaga aaagcaggaa taactttacc gtggaaataa  9000
tgtttagctt ttatcagaga aaattgtcct tctagagcat agagtcccaa aactcaattc  9060
tggttttccc ctgttttttt tttttttttt tttcccaaca tataaactgc agcatatcac  9120
tttttctttt tgtgcctcag gttcctcagc tgtaaaattg aaaaatatat gtattaataa  9180
tattattaat aataataatg gtaatgtagt acttgtttgt aaagcacttt gagatccttg  9240
gttgaaaggc accataggag tgccaagtat tattatgtgg ccaagggggt tatttaaact  9300
gtcagttccc aaaggccagg aaaggttggg gtcatttttc ttaaagacga gctgtaaata  9360
tcaactaggc agccaatagt gttgactatg aagatgcaaa actattacta ggctgataaa  9420
atcatagttt cttaatggct accaataagg caaatatcac aataataaac gccaaattcc  9480
ttagggcgga ctatttgaca accacatgga aaactttggg ggaggcatga ggggggaaca  9540
tctcaaaatg ccaatgtaaa atttaactta cagcaatatt caccagcaga aaatgtcttt  9600
catatggaat gatttcatgt tgctaagaaa aagaattcaa tttgtagtcc tgatttgaat  9660
actagaatgt tggctataat agttctgttc ttacaacaca tgaaattttt tcgttttatt  9720
ttattttgtt ttcatagtgc atgttcattt ctactcacaa acatgttctt ggtgtatttc  9780
ttatgcaaac aatcttcagg cagcaaagat gtctgttaca tctaaacttg aataataaag  9840
ttttaccacc agttacaca                                               9859

SEQ ID NO: 80          moltype = DNA  length = 1131
FEATURE                Location/Qualifiers
source                 1..1131
                       mol_type = other DNA
                       organism = Homo sapiens
SEQUENCE: 80
agtgccccag gagctatgac aagcaaagga acatacttgc ctggagatag cctttgcgat  60
atttaaatgt ccgtggatac agaaatctct gcaggcaagt tgctccagag catattgcag  120
gacaagcctg taacgaatag ttaaattcac ggcatctgga ttcctaatcc ttttccgaaa  180
tggcaggtgt gagtgcctgt ataaaatatt ctatgtttac cttcaacttc ttgttctggc  240
tatgtggtat cttgatccta gcattagcaa tatgggtacg agtaagcaat gactctcaag  300
caatttttgg ttctgaagat gtaggctcta gctcctacgt tgctgtggac atattgattg  360
ctgtaggtgc catcatcatg attctgggct tcctgggatg ctgcggtgct ataaaagaaa  420
gtcgctgcat gcttctgttg tttttcatag gcttgcttct gatcctgctc ctgcaggtgg  480
cgacaggtat cctaggagct gttttcaaat ctaagtctga tcgcattgtg aatgaaactc  540
tctatgaaaa cacaaagctt ttgagcgcca caggggaaag tgaaaaacaa ttccaggaag  600
ccataattgt gtttcaagaa gagtttaaat gctgcggttt ggtcaatgga gctgctgatt  660
ggggaaataa ttttcaacac tatcctgaat tatgtgcctg tctagataag cagagaccat  720
gccaaagcta taatggaaaa caagtttaca aagagacctg tatttctttc ataaaagact  780
tcttggcaaa aaatttgatt atagttattg gaatatcatt tggactggca gttattgaga  840
tactgggttt ggtgtttttct atggtcctgt attgccagat cgggaacaaa tgaatctgtg  900
gatgcatcaa cctatcgtca gtcaaacccc tttaaaatgt tgctttggct ttgtaaattt  960
aaatatgtaa gtgctatata agtcaggagc agctgtcttt ttaaaatgtc tcggctagct  1020
agaccacaga tatcttctag acatattgaa cacatttaag atttgaggga tataagggaa  1080
aatgatatga atgtgtattt ttactcaaaa taaaagtaac tgtttacgtt g           1131

SEQ ID NO: 81          moltype = DNA  length = 2459
FEATURE                Location/Qualifiers
source                 1..2459
                       mol_type = other DNA
                       organism = Homo sapiens
SEQUENCE: 81
gagagactgg gaggggcccc aatccaggct ccgggatggc ctggctggca tctggggttc  60
cagtggcccc tctcccttgg ccctggcagt ggggctggat actggcctgc ctcccaccag  120
agtcccccca gctcctccct gctgtgggct ggcctgggag gaagggggtg gggtgcactt  180
acatttgcag gtctttccag cccctggggc agcctgatta accagcttct ccagggccaa  240
gctgttgggg gtgaggtgca gcccgaagca gccagaccag cccctgagcc tcccgggtgc  300
tggcagctgt catggggcta ccctgggggc agcctcacct agggctgcag atgctcctcc  360
tggcgttgaa ctgtctccgg cccagcctga gcctggagct ggtgccctac acaccacaga  420
taacagcttg ggacctggaa gggaaggtca cagccaccac cttctccctg gagcagccgc  480
gctgtgtctt cgatgggctt gccagcgcca gcgataccgt ctggctcgtg gtggccttca  540
gcaatgcctc caggggcttc cagaacccgg agacactggc tgacattccg gcctccccac  600
agctgctgac cgatggccac tacatgacgc tgcccctgtc tccggaccag ctgccctgtg  660
gcgaccccat ggcgggcagc ggaggcgccc ccgtgctgcg ggtgggccat gaccacggct  720
gccaccagca gcccttctgc aacgcgcccc tccctggccc tggaccctat cgggtgaagt  780
```

```
tcctcctgat ggacaccagg ggctcaccca gggctgagac caagtggtca gaccccatca  840
ctctccacca agggaagacc cccggatcca tcgacacctg gccagggcgg cgaagtggca  900
gcatgatcgt cattacctcc atcctctctt ctctggccgg cctcctactc ttggccttct  960
tggcagcctc taccatgcgc ttctccagcc tgtggtggcc ggaggaggcc ccggagcagc  1020
tgcggatcgg ctccttcatg ggcaagcgct acatgaccca ccacatccca cccagagagg  1080
ccgccacact gccggtgggc tgcaagcctg gcctggaccc cctccccagc ctcagcccct  1140
agcctggcct ctttgcatgg ggctggggga gatggggcgc tgggagtgag tgcatggtgc  1200
tttgtcccag ctcctgcacc cacaggcccc ctcagggctc cttgcctttc ccccccacca  1260
gcacaccccg taccctgcct ggaatcccag caccagcccc cctgcctctc ctctgccttt  1320
ctggtttctc tccctctcca agcatctgta agttgcactc aggagggttt aggggagggc  1380
catgggcagg ctggataccc agtccccacc tccatcccca cctctgtctc acctgacctc  1440
ctgcgaggga ggctggagac tgtgtggaca ggccgccctg accgcaagct tccagaccct  1500
gggaggaggc ctgcagagga ctgtgctttg cctgatgcag ggagctgggc ccatcctggg  1560
gcctatgaga cctgagccac cctccgtccc ccatcccaca catcagtggc tgggcggggt  1620
gaggattcag aggcatctct actgcccctg ggcacagcac ctttctgaga gtgggactct  1680
ccatggtcat ctgactacca attctggcca ccacctccaa ccctcttgtg catatggatg  1740
gctctagccc ttatccaccc cctcaagcat ttattaagca tctgctgtat gctacataca  1800
gtgttagact tggggcttca ggcatagccg gtcctgacct tggggagatg ccttctctag  1860
acctgagacg accacgtgtc cagatgtgac ctgttgctgt cgggggtcta tcaggccctt  1920
agaccgtcac cccagtaggc tctccaggac ccaggagcct ccatcacctg gaaggaccct  1980
ctgtgcaaaa cctcaagcgt ccatctgtgc acaaggccgg tggttcccgt cgtcgccact  2040
cggggtcgcc ggtgagccgc agccaggccg cctcacggcc agtgtgcatg ctcgctgcta  2100
ttcgctgccc cttctgcctc cgaggcggta gcagatgcca cgttggcggg gtcggtgaag  2160
gtcaggactc taggcctccc tccgccaagc cagagggatg agcaatcacg cctgagagcc  2220
cactgcgtgc catgcagtcc gcacagccgc agcggttttc tagatggaga aactgaggct  2280
cagtgacttg cccgctgcac tctgtccacg gccgctgcac acgccccctt gggctgcgct  2340
cccggacctt ctaatgtgac cacggctccc ggcatgcagg ccctgccagc ggagggagcc  2400
cggtggtgac ccttggtctg cagccctctt tggaggtgaa taaatgcggt ctggagccc   2459

SEQ ID NO: 82          moltype = DNA  length = 1626
FEATURE                Location/Qualifiers
source                 1..1626
                       mol_type = other DNA
                       organism = Homo sapiens
SEQUENCE: 82
ctccttccct gtctctgcct ctccctccct tcctcaggca tcagagcgga gacttcaggg  60
agaccagagc ccagcttgcc aggcactgag ctagaagccc tgccatggca cccctgagac  120
cccttctcat actggccctg ctggcatggg ttgctctggc tgaccaagag tcatgcaagg  180
gccgctgcac tgagggcttc aacgtggaca agaagtgcca gtgtgacgag ctctgctctt  240
actaccagag ctgctgcaca gactatacgg ctgagtgcaa gccccaagtg actcgcgggg  300
atgtgttcac tatgccggag gatgagtaca cggtctatga cgatggcgag gagaaaaaca  360
atgccactgt ccatgaacag gtgggggggcc cctccctgac ctctgacctc caggcccagt  420
ccaaagggaa tcctgagcag acacctgttc tgaaacctga ggaagaggcc cctgcgcctg  480
aggtgggcgc ctctaagcct gaggggatag actcaaggcc tgagaccctt catccaggga  540
gacctcagcc cccagcagag gaggagctgt gcagtgggaa gcccttcgac gccttcaccg  600
acctcaagaa cggttccctc tttgccttcc gagggcagta ctgctatgaa ctggacgaaa  660
aggcagtgag gcctgggtac cccaagctca tccgagatgt ctggggcatc gagggcccca  720
tcgatgccgc cttcacccgc atcaactgtc aggggaagac ctacctcttc aagggtagtc  780
agtactggcg ctttgaggat ggtgtcctgg accctgatta cccccgaaat atctctgacg  840
gcttcgatgg catcccggac aacgtggatg cagccttggc cctccctgcc catagctaca  900
gtggccggga gcgggtctac ttcttcaagg ggaaacagta ctgggagtac cagttccagc  960
accagcccag tcaggaggag tgtgaaggca gctccctgtc ggctgtgttt gaacactttg  1020
ccatgatgca gcgggacagc tgggaggaca tcttcgagct tctcttctgg ggcagaacct  1080
ctgctggtac cagacagccc cagttcatta gccgggactg gcacggtgtg ccagggcaag  1140
tggacgcagc catggctggc cgcatctaca tctcaggcat ggcaccccgc ccctccttgg  1200
ccaagaaaca aaggtttagg catcgcaacc gcaaaggcta ccgttcacaa cgaggccaca  1260
gccgtggccg caaccagaac tcccgccggc catcccgcgc cacgtggctg tccttgttct  1320
ccagtgagga gagcaacttg ggagccaaca actatgatga ctacaggatg gactggcttg  1380
tgcctgccac ctgtgaaccc atccagagtg tcttcttctt ctctggagac aagtactacc  1440
gagtcaatct tcgcacacgg cgagtggaca ctgtggaccc tccctaccca cgctccatcg  1500
ctcagtactg gctgggctgc ccagctcctg gccatctgta ggagtcagag cccacatggc  1560
cgggccctct gtagctccct cctcccatct ccttccccca gcccaataaa ggtcccttag  1620
ccccga                                                             1626

SEQ ID NO: 83          moltype = DNA  length = 6768
FEATURE                Location/Qualifiers
source                 1..6768
                       mol_type = other DNA
                       organism = Homo sapiens
SEQUENCE: 83
agtttcctga agacccggaa gccgatcgcg tggggagccg gtcttggagc agcgggatta  60
gcttctaaag tctctttcat ctctcctaag gaagaagcct agaagaggag gaagaggaaa  120
gaaaaggagt caggaatgcc tcttagatat ctcttccaaa tgcatgatga aaaaggtggg  180
aagattactt gagccaggga gttgaaggct gcagtgagcc ctgtttttgc caccacactc  240
cagcttggga ttgatttcta aagactcatg ttacatgagg aagcagctca gaagaggaaa  300
ggaaaggagc caggcatggc tcttcctcag ggacgcttga ctttcaggga tgtggctata  360
gaattctcat tggcagagtg gaaattcctg aaccctgcgc agagggcttt gtacagggaa  420
gtgatgttgg agaactacag gaacctggag gctgtggata tctcttccaa acgcatgatg  480
aaggaggtct tgtcaacagg gcaaggcaat acagaagtga tccacacagg gatgttgcaa  540
```

-continued

```
agacatgaaa gttatcacac tggagatttt tgcttccagg aaattgaaaa agatattcat  600
gactttgagt ttcagtcaca aaaagatgaa agaaatggcc atgaagcatc catgccaaaa  660
atcaaagagt tgatgggtag cacagaccga catgatcaaa ggcatgctgg aaacaagcct  720
attaaagatc agcttggatt aagctttcat ttgcatcttc ctgaactcca catatttcag  780
cccgaagaga aaattgctaa tcaagtggag aagtctgtca acgatgcttc ctcaatttca  840
acatcccaaa gaatttcttg taggcctgaa acacatactc ctaataacta tgggaataat  900
tttttccatt catcattact cacacaaaaa caggaagtac acatgagaga aaaatctttc  960
caatgtaatg agactggcga agcctttaat tgtagctcat ttgtaaggaa acatcagata  1020
atccatttag gagaaaaaca atataaattt gatatatgtg gcaaagtctt taatgagaag  1080
cgataccttg cacgccatcg tagatgtcac actagtgaga aaccttacaa gtgtaatgaa  1140
tgtggaaagt ccttcagtta caagtcatcc ctgacatgcc atcgtagatg tcacactggt  1200
gagaaacctt acaagtgtaa tgaatgtgga aagtccttca gttacaagtc atcccttaca  1260
tgccatcata ggtgtcacac tggtgagaaa ccttacaagt gtaatgaatg tggaaagtcc  1320
ttcagttaca agtcatccct tagatgccat cgtagacttc atactggaat aaaaccttac  1380
aagtgtaatg agtgtggcaa gatgtttggt caaaattcaa cccttgtaat tcataaggca  1440
attcatactg gagagaaacc ttacaagtgt aatgaatgtg gcaaggcttt taatcaacaa  1500
tcacaccttt cacgtcatca tagacttcat actggagaga aaccttacaa gtgtaatgac  1560
tgtggtaagg cttttattca tcagtcaagc cttgcacgtc atcatagact tcatactgga  1620
gagaaatctt acaaatgtga agaatgtgac agagttttca gtcagaaatc aaaccttgag  1680
agacacaaga taattcatac tggagagaaa ccttacaagt gtaatgagtg tcacaagacc  1740
ttcagtcaca ggtcatctct tccatgccat cgtagacttc atagtggtga gaaaccttac  1800
aagtgtaatg aatgtgggaa gacttttaat gtacagtcac acctttcacg tcatcataga  1860
cttcatactg gagagaaacc ttacaaatgt aaggtttgtg acaaggcttt catgtgccat  1920
tcttatctgg caaaccatac tagaattcat agcggagaga aaccttacaa gtgtaatgag  1980
tgtggtaagg ctcacaatca cttgattgat tcatcaatca agccttgcat gtcatcatag  2040
acttcatact ggagagaaac cttacaaatg tgaagcatgt gacaaagttt tcagtcacag  2100
atcacgcctt aaaagacata ggagaattca tactggagag aaaccttaca agtgtaatga  2160
gtgtggcaaa gcctttagtg accagtcaac acttaccatc aggccattca tggtgtaggg  2220
aaacttgact aatgtaatga ttgtcacaaa gtcttcagta acgctacaac gattgcaaat  2280
cattggagaa tccataatga agagagatct tccgagtgta ataaatgtgg caaatttttc  2340
agacatcgtt cataccttgc agttcatcag tgaactcata ctggagagaa accttacaaa  2400
tgtcatgact tgtggcaaggt cttcagtcaa gcttcatcct atgcaaaaca taggagaatt  2460
catgcaggag agaaatgtca caagtgtgat gagtgttgca aagcctttac ttcatgttca  2520
cacctcatta gacatcagag aatccctact ggagagaaat cttacaaatg tcatcagtgt  2580
ggcaaggtct tcagtccgag gtcactcctt gcagaacatc agaaaattca tttttgagat  2640
aactgttccc aatgcagtga gtatagcaaa ccatcaagca ttaattgaca ttggagtcaa  2700
ttcagcattg acttgagttt gtgttgactt aacattgagt tcaagcctta attgacatgc  2760
aggtgtttat gataagagga ttgggccagg tgcagtggat cacgcctgta atcccagcac  2820
attgggaggc caaggcacat aggtcacttg aggtcaagag tttgaaacaa gcatggccaa  2880
gagatgtgag ccagttttcc cagcctgttt attattattt tttgagatgg agtgttgctc  2940
ttgctgccca ggctagagtg caatggtgcg atcttgactc acagcaacct ccgcctcctg  3000
ggttcaagcg attcctctgc ctcagcctcc ctagttgctg ggattacagg tatatgccac  3060
gacgcctggc taattttttg tatttttagt agggaaaggg tttctccatg ttggtcaggc  3120
tggtctcaaa ctcccgatct caggtgatcc gcccacctca gcctcccaaa gtgatgagat  3180
tacaggcata tgccaccgcg cctggcattg tttcttcttt tccttttttt tttttttttt  3240
ttttttgag atagtacttt ttaaagagat agtacttttt tgagatagta ctttttaaa  3300
gggatatacc atagtagttt taaaagggat atcaggctgg gtgtggcagc tcacgccggt  3360
aatcccagca ctttgggagg ccaaggcagg cagataacaa agtcaggaga ttgagaccgt  3420
cctggctaac acggtgaaac ctcgtctcta ctaaaaatac aaaaacttag ccgggcatgg  3480
tggtgggcac ctgtagtctc agctactcag ggggctgagg ctggacaatg gtgtgaaccc  3540
aggaggcggt gcttgcaggg agccgagatc gtgccactgc actccaggct gggcgacaga  3600
gtgagagtct gtctcaaaaa aaaaaaaaaa aagatatcaa acccggggtg tctcatccca  3660
cagcactttg gaagactgaa gtgagtggat catctaagat cagagttcaa gagcaccctg  3720
gctaacatgg tgaaacccca tctctactaa aaatacaaaa gttagccagg ggtgggggtg  3780
tgcaccttta gttccagcta cttgggacac tgaggcatga gaatcactta aacctgggag  3840
gtagaggtta cagcgaatca aaaccgtgcc actgtactgc agcgaggttg gcagagtgag  3900
tctccatctc aaacaaacaa atgaaaaaaa cagacatcaa aaatgctttt gttctcgttg  3960
tgtcatagac ttcccttttt tttccttctg gttcctcttc agttctctat ttattttttc  4020
tttttgcag attgagtttg agatatatct tagttttaat agttttattt cttaacacat  4080
aatgacttct gaaagatgcc tttgcagcat cctgtaatca gctcacatca ttcgtttctg  4140
tacttgtata ttttccagtt gttttccggt tgaccccaaa attcgtgaga ttttttttcct  4200
acaacaattt caaaagagtt gctgtttgaa attagttgca tccagttcag atcgaggtct  4260
gcatgctttc tagtctttgt tatttattgg aaggctgtgg tacctactac ttaagtttga  4320
ttgttgcagt gtgtacttgg taaagatgtc agtgaccttt taaataaaca tcaaaatgta  4380
gtttaagcag ttagtctgtt tttcagtttt ctttccttat gtcatttttt aaaatcttga  4440
gctgggagct atttattgtg tgtttccctc aaggccctgt ggtccattct ggaaaaatgt  4500
tgaaacatgg gctggagtgg catagagcgc tgctccaaaa gcacccatgt attcttttct  4560
tttttggaaa tggagtctcg ctctgtcagc ttggatggag tgcagtggtg cgatctcagc  4620
tcactgcaac ctctacctcc ttggatcaag tgatgctcct gcctcagtct cctgaggagc  4680
tggaattaca ggcacccacc agcacaccca gctagttttt gtatttttag tagagacagg  4740
gtttcaccat gtttgtcagg ctggtctcaa actcctgacc tcgcgatcca cccgactcag  4800
cctcccactg tgatgggatt acaggcatga gctaccacgt cgagactctt tttttttttt  4860
ttttttagat ggagttttgc ttttgttgct gaggctggag tgcaatggtg cgatctggtg  4920
tcactccaat gtcttcctcc tgggttcaag tgatttctcc tgcctcatcc tactgagtag  4980
ttgggattac aggtgccctc caccactccc ggctcatttt ttgcattttt agtagagaca  5040
gggtttcatc atgttggcag gctggtcttg aactcctgac ttcaggtgat ctgcccacct  5100
cgacctccca aaatgctagg attacaagcg tgagccattg tgcctgacca ctcatgtatt  5160
cttgattgaa ataatttgct tatttcttag ttctacagct gaccctcttt cactgtttcc  5220
aaggtcaata gctgtgtgtt cacacttctg cattttataa atgttcctgt gagtttttttg  5280
```

-continued

```
taaggaagaa ttaactgtca ggaatcaatg tcatcagaac cttgcaaaag aagtttcttt  5340
agcccaggtt tgtgaaagag gtttctctaa ttttcaagga tgggggtgat aagagcaacc  5400
tttgccatta gcccttccag gaccccatgt aagactttag acaccttctc actcatctca  5460
gaccttctca gggtaacttg gtgaaaatgt cttccgatct gagccccagt gagcctccct  5520
gcaacttggc gacgaggggc ttgaccagaa aaggtcaacc cgagtgtccc tgaccgttga  5580
aatgattggc aaaatggagt gcgtgtctgg gtgtggcttt ttttttttg aggagtgccc  5640
agttgtgatt agaatttca atgggatgca gtgccctaaa aatgaaaaac aaaagcagaa  5700
gaatggaaga aatagaggta gactcagaca cagagaccat cttcaaggcc tttctctgta  5760
tgaggacatc acagcaaaat ctaaagcagg tcacgtcaat ccctggcagg gaaccctcca  5820
ccggcttccc gtgttcccca ggacaaaagc ccaacccctc actgtggctc cacagccccg  5880
tgtgcagggc ccctgccagt gtccagcctc ctcctggcag cttgccctca tctcatgact  5940
ccctctgccc cagtcacatt tgcttttctc ttttcccaaa catcaaaacc cttcctgtct  6000
caggtcattg tccctgctct taccctatgt accctgtccc tttctcctcc ttcaggtcta  6060
ggctcagagc tctctcccat gccctcccac ccctggtctc aagctcctga gctcaagtga  6120
tctacccacc tcggcctcct agagtgctgg gatgacaggc atgagccact gcaaccagcc  6180
tctgcatggg gtttcctcaa ctttaggtct gtgccctgaa ggggagctca ttccagccca  6240
gttcccaact gctgcagcat gtgtgtgtgg gcttctccag aaggggagcc agagtttccc  6300
tgtaggagtt tatcctccat ggtgaggagg gccgcagggg ggactgtatt tgctcagggt  6360
gaggtctcct ttgtgtcagg cctctgagcc caagctaagc catcgtatcc cctgtcacct  6420
gcacgtatac atccagatgg cctgaagcaa ctgaagatcc acgaaagaag tgaaaatacc  6480
cttaagtgat gacattccac cattgtgatt tatttctgca ccatcttgac tgatcaatgt  6540
gctttgtaat ctcccccacc cttcagaagg ctctttgtaa tcctccccac ccttgagaat  6600
ggacttggtg agatccaccc cctgcctgca aagcattgcc cctaactcca ccgcctgtcc  6660
caaaagctac aagaactaat gataatccca ccatactttg ctgactctct tttcacactc  6720
agcccgcctg cacccaggtg aaataaacag cctcgttgct cacacaaa              6768

SEQ ID NO: 84          moltype = DNA  length = 3341
FEATURE                Location/Qualifiers
source                 1..3341
                       mol_type = other DNA
                       organism = Homo sapiens
SEQUENCE: 84
ctttgtctcc ttgcggccgg cggggtgctg ggttcccgtc tgctgcctct cggagagtcc  60
cgggtgactg ccgcaggctc catcgccctg tggcctgcag gtattgcgag atttataggg  120
aggacgctgg gacccccaaa agctgggaaa tgggactatt ggcattcagg gatgtggctc  180
tagaattctc tccagaggag tgggaatgcc tggacccagc tcagcggagt ttgtataggg  240
atgtgatgtt agagaactac agaaacctga tctcccttgg tgaggatagc ttcaatatgc  300
aattcctatt tcacagtctt gctatgtcta agccagaact gatcatctgt ctggaggcaa  360
ggaaagagcc ctggaacgtg aacacagaga agacagccag acactcagtt ttgtcttctt  420
atcttactga agacatttg ccagagcagg gcctgcaagt ttcattccaa aaagtgatgc  480
tgagaagata tgaaagatgt tgtcttgaga aattacgctt aaggaatgac tgggaaattg  540
tgggtgagtg gaaagggcag aaggcaagtt ataatggact tgacctatgc tcagcaacta  600
ctcatagcaa aaactttcaa tgcaataaat gtgtgaaagg ttttagtaaa tttgcaaatc  660
taaataaatg taagataagc catactggag aaaaaccatt caaatgcaaa gaatgtggca  720
atgtctcttg catgtcttta ataatgactc aacagcagag aatccatatt ggagagaacc  780
cgtaccaatg taaaaaatgt ggcaaagcct ttaatgagtg ctcatgcttt actgactgta  840
agagaattca tgttggagag aaacattgca aatgtgaaga atgtaataac atttttaagt  900
cttgctcaag tcttgctgtt gttgagaaaa atcatactga aaagaaaacc tacagatgtg  960
aagaatgtgg caaagctttt aacctgtgct cagttcttac taaacataag aaaattcata  1020
ctggagagaa accatacaaa tgtgaagaat gtggcaaatc ctttaagttg ttcccatacc  1080
ttactcaaca caagagaatt catagtagag agaaacccta caagtgtgaa gaatgtggca  1140
aagtctttaa attgttgtca taccttactc aacatagaag aattcatact ggagagaaaa  1200
ccttccgatg tgaagaatgt ggaaaagcct ttaaccagag ctcacatctg actgaacata  1260
ggagaattca tactggtgag aaaccataca aatgtgagga atgtggcaaa gcttttacct  1320
ggttctcata ccttattcag cataagagaa ttcatactgg gcagaaaccc tacaaatgtg  1380
aggaatgtgg caaagctttt acctggtttt catacettac tcaacataag agaattcata  1440
ctggagagaa accctacaaa tgtgatgaat gtggcaaagc ttttaactgg ttttcatatc  1500
ttactaatca taagagaatt catactggag agaaacccta caaatgtgaa gaatgtggca  1560
aagcctttgg ccagagctca cacctttcta aacataagac aattcatacc agagagaaac  1620
catacaagtg tgaggaatgt ggcaaagcct ttaaccactc tgcacaactt gctgtacatg  1680
agaaaactca tacctgagaa aaaccctaca attctaaaca atatggcata gtctttaata  1740
cctattcaca acttcacagc agaatatttt tactgaataa gagtgttaca aatgtaatga  1800
ctgtcaaaag gccatttaca gtctatgagc ctttgagtgc actaaaatgt ttaggctacg  1860
aacaatacaa atagaccggt tcaacacctc cacttatatc acagctctta ctgtacacag  1920
aagaatttat actggaggga aaccctccag ttgctcaaac tgtattcaat ttcaaagact  1980
ttgtattgga gagaaaccct acaaatgtaa taaatgcaga aacaacattt gttcaaaaaa  2040
tatacctcag aaaacaccag agtgttcaca ctaaaaactg ttttacagat gcagtaaatg  2100
tgaaaaaatg tctaatcaaa aattacatca aaacacatcc aagaattcat agtaaaaagc  2160
actaagtcac tgacactttc agacattact gtaaatctga gtgttggtta tagagaataa  2220
ttcaaagtta agttaaagta agtaggagat tcaccttttg gggaagttat aattacattt  2280
caagtatacc ttttggtgcc aggcacggtg gctctttcct atagttgctg cacttttgga  2340
tgccgaggtc gggggattgc ttgagcccag gagtttggga ccaggctggg caacatggca  2400
aaacctcatc tctacaaaaa gtaaaataaa agccaggctt ggtggcacat gcctgttgtc  2460
ccagctactt ggaaggctca ggtgggagga ttgcttgagc ctggaggttg aggatgcagt  2520
gagctgctat ctggcaactt cactcctgcc tgggcaacag agcaagaccc tttctcaata  2580
ataataataa caacataata ataaagtata ctcggtgcac tgaaagagtt ttagcttttt  2640
tgaaaatcac atatttatgt aattcaagtc ttaaatcact tgataccatg ccttcatttc  2700
tagtgtttat gtgaaggcat gaggcctact gttgctacat gaaagctgtg agagtttctt  2760
ctatattcgg gtgggtgttg ttcatatcct tttctttgga agattatgga cattgcattg  2820
```

-continued

```
taagcttcct gaagaaattt aactggagag gctctttgta cttgtcttat aatagggttg  2880
taagtgattc atgagatagg tcttcagagt actattctgc attatattta agaaagaaac  2940
atttgagttt tacaagtcag ttgtttttcc tattgcacat taaggtaata aaattcagtg  3000
gattttgaaa tgctcttttt agactgtttg aacttaattt gttttaataa gacattgttt  3060
taatgtcttt ggaccgttgt acattaagtg atgcgtatcc taccaccaac gttaacctat  3120
ctcaccttag ttacggttgt aggtaacaaa tggtaacaat acaatagtgg gtaacatggt  3180
ggaatagtat ctctaatgat cccttctccc agtggcatta aacttcaaat aatttgaaaa  3240
atattgttcc cacacgttac accttcattc tgtttgctct ttttgtaatg acagtgtcat  3300
tattaaggct ataataaagc ctatatagga ttataatcaa a                      3341
```

DETECTING CANCER CELL OF ORIGIN

CROSS REFERENCE TO RELATED APPLICATIONS

This application is a continuation of U.S. application Ser. No. 17/284,310, filed Apr. 9, 2021, which is a U.S. National Stage application under 35 U.S.C. 371 of International Application No. PCT/US2019/055318, filed Oct. 9, 2019, which claims the benefit of priority to U.S. Provisional Application No. 62/743,256 filed Oct. 9, 2018 and U.S. Provisional Application No. 62/819,893 filed Mar. 18, 2019, each of which is incorporated by reference herein in its entirety for all purposes.

FIELD

The present invention relates to methods for determining an integrated, pan-cancer subtype and for predicting the prognosis of a patient inflicted with said integrated subtype of cancer.

REFERENCE TO AN ELECTRONIC SEQUENCE LISTING

The contents of the electronic sequence listing (GNCN_016_03US_SeqList_ST26.xml; Size: 407,556 bytes; and Date of Creation: Aug. 17, 2022) is herein incorporated by reference in its entirety.

BACKGROUND

Cancers are typically classified using pathologic criteria that rely heavily on the tissue site of origin. Recently, large-scale genomics projects spearheaded by The Cancer Genome Atlas (TCGA) have been undertaken in order to provide a detailed molecular characterization of thousands of tumors, thereby making a systematic molecular-based taxonomy of cancer possible (see, for example, The_Cancer_Genome_Atlas_Network. Comprehensive genomic characterization defines human glioblastoma genes and core pathways. Nature. 2008; 455:1061-1068; The_Cancer_Genome_Atlas_Network. Integrated genomic analyses of ovarian carcinoma. Nature. 2011; 474:609-615; The_Cancer_Genome_Atlas_Network. Comprehensive genomic characterization of squamous cell lung cancers. Nature. 2012a; 489:519-525; The_Cancer_Genome_Atlas_Network. Comprehensive molecular characterization of human colon and rectal cancer. Nature. 2012b; 487:330-337; The_Cancer_Genome_Atlas_Network. Comprehensive molecular portraits of human breast tumours. Nature. 2012c; 490: 61-70; The_Cancer_Genome_Atlas_Network. Comprehensive molecular characterization of clear cell renal cell carcinoma. Nature. 2013a; 499:43-49; The_Cancer_Genome_Atlas_Network. Genomic and epigenomic landscapes of adult de novo acute myeloid leukemia. The New England journal of medicine. 2013b; 368:2059-2074; The_Cancer_Genome_Atlas_Network. Comprehensive molecular characterization of urothelial bladder carcinoma. Nature. 2014; 507:315-322; each of which is herein incorporated by reference). These large-scale genomics projects have shown that each single-tissue cancer type can be further divided into three to four molecular subtypes and meaningful differences in clinical behavior can often be correlated with the single-tissue tumor types. In fact, in a few cases, single-tissue subtype identification has led to therapies that target the driving subtype-specific molecular alteration(s). EGFR-mutant lung adenocarcinomas and ERBB2-amplified breast cancer are two well-established examples.

Building off these projects, more recent studies have undertaken multi-platform integrative analysis of thousands of cancers from numerous tumor types in The Cancer Genome Atlas (TCGA) project in order to determine whether tissue-of-origin categories split into sub-types based upon multi-platform genomic analyses, what molecular alterations are shared across cancers arising from different tissues and if previously recognized disease subtypes in fact span multiple tissues of origin (see Hoadley et al., Cell. 2014 Aug. 14; 158(4):929-944 and Hoadley et al., Cell. 2018 Apr. 5; 173(2):291-304, each of which is herein incorporated by reference). While these studies have helped to elucidate a molecular taxonomy of cancer with newly defined integrated subtypes that can provide a significant increase in the accuracy for the prediction of clinical outcomes, they have relied on performing a second-level cluster analysis (i.e., clustering of cluster assignments (COCA)) using as input data from five 'omic' platforms. The 'omic' platforms used in the studies for the COCA analysis included whole-exome DNA sequence (Illumina HiSeq and GAII), DNA methylation (Illumina 450,000-feature microarrays), genome-wide mRNA levels (Illumina mRNA-seq), microRNA levels (Illumina microRNA-seq), and protein levels and/or phosphorylated proteins (Reverse Phase Protein Arrays; RPPA).

While the benefits of such a pan-cancer analysis from a clinical standpoint are clear, the resources necessary to perform said analysis can be laborious, time-consuming and expensive. Accordingly, there is need in the art for methods and resources for molecularly characterizing tumor samples in a rapid, efficient and reliable manner regardless of tissue of origin.

The present disclosure addresses the limitations of the current methods and other needs in the field for an efficient method for pan-cancer tumor classification that may inform prognosis and patient management based on underlying genomic and biologic tumor characteristics shared across tumor samples from multiple tissues of origin.

SUMMARY

The methods disclosed herein include determination of a cell of origin subtype, treatment of cancer based on a cell of origin subtype, prediction of overall survival of patients based on a cell of origin subtype, and application of an algorithm to gene expression data for one or a plurality of classifier biomarkers for categorization of tumor sample into one of 21 a clustering of cluster assignments (COCA) subtypes C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and C28 (THCA)) such that the COCA subtype is indicative of the cell of origin of the tumor sample regardless of the anatomical location of said tumor sample. The algorithm can be a classification to the nearest centroid (CLaNC algorithm). The C1 COCA subtype can indicate that a tumor sample is substantially similar to or is adrenocortical carcinoma. The C2 COCA subtype can indicate that a tumor sample is substantially similar to or is glioblastoma. The C3 COCA subtype can indicate that a tumor sample is substantially similar to or is an ovarian serous cystadenocarcinoma (epithelial ovarian cancer). The C4 COCA subtype can indicate that a tumor sample is substantially similar to or is squamous cell carcinoma of the lung, the head and neck or the bladder. The C6 COCA subtype can indicate that a tumor sample is substantially similar to or is lung adenocarcinoma. The C8 COCA subtype can indicate that a tumor sample is substantially similar to or is pancreatic adenocarcinoma. The C9 COCA subtype can indicate that a tumor sample is substantially similar to or is uterine carcinosarcoma. The C10 COCA subtype can indicate that a tumor sample is substantially similar to or is the basal subtype of breast cancer. The C12 COCA subtype can indicate that a tumor sample is substantially similar to or is uterine corpus endometrial cancer. The C14 COCA subtype can indicate that a tumor sample is substantially similar to or is prostate cancer. The C15 COCA subtype can indicate that a tumor sample is substantially similar to or is non-squamous cervical cancer. The C16 COCA subtype can indicate that a tumor sample is substantially similar to or is a bladder urothelial carcinoma. The C17 COCA subtype can indicate that a tumor sample is substantially similar to or is a testicular germ cell tumor. The C19 COCA subtype can indicate that a tumor sample is substantially similar to or is a colon, rectal, esophageal or stomach adenocarcinoma. The C20 COCA subtype can indicate that a tumor sample is substantially similar to or is a sarcoma. The C21 COCA subtype can indicate that a tumor sample is substantially similar to or is a kidney chromophobe, kidney renal papillary cell carcinoma or kidney renal clear cell carcinoma. The C22 COCA subtype can indicate that a tumor sample is substantially similar to or is liver hepatocellular carcinoma. The C24 COCA subtype can indicate that a tumor sample is substantially similar to or is the luminal subtype of breast cancer. The C25 COCA subtype can indicate that a tumor sample is substantially similar to or is thymoma. The C26 COCA subtype can indicate that a tumor sample is substantially similar to or is melanoma. The C28 COCA subtype can indicate that a tumor sample is substantially similar to or is thyroid cancer.

In one aspect, provided herein is a method for determining a clustering of cluster assignments (COCA) subtype of a tumor cancer sample obtained from a patient, the method comprising detecting an expression level of at least one classifier biomarker of Table 1, wherein the detection of the expression level of the classifier biomarker specifically identifies a C1, C2, C3, C4, C6, C8, C9, C10, C12, C14, C15, C16, C17, C19, C20, C21, C22, C24, C25, C26 or C28 COCA subtype. In some cases, the method further comprises comparing the detected levels of expression of the at least one classifier biomarker of Table 1 to the expression of the at least one classifier biomarker of Table 1 in at least one sample training set(s), wherein the at least one sample training set(s) comprises expression data of the at least one classifier biomarker of Table 1 from a reference C1 sample, expression data of the at least one classifier biomarker of Table 1 from a reference C2 sample, expression data of the at least one classifier biomarker of Table 1 from a reference C3 sample, expression data of the at least one classifier biomarker of Table 1 from a reference C4 sample, expression data of the at least one classifier biomarker of Table 1 from a reference C6 sample, expression data of the at least one classifier biomarker of Table 1 from a reference C8 sample, expression data of the at least one classifier biomarker of Table 1 from a reference C9 sample, expression data of the at least one classifier biomarker of Table 1 from a reference C10 sample, expression data of the at least one classifier biomarker of Table 1 from a reference C12 sample, expression data of the at least one classifier biomarker of Table 1 from a reference C14 sample, expression data of the at least one classifier biomarker of Table 1 from a reference C15 sample, expression data of the at least one classifier biomarker of Table 1 from a reference C16 sample, expression data of the at least one classifier biomarker of Table 1 from a reference C17 sample, expression data of the at least one classifier biomarker of Table 1 from a reference C19 sample, expression data of the at least one classifier biomarker of Table 1 from a reference C20 sample, expression data of the at least one classifier biomarker of Table 1 from a reference C21 sample, expression data of the at least one classifier biomarker of Table 1 from a reference C22 sample, expression data of the at least one classifier biomarker of Table 1 from a reference C24 sample, expression data of the at least one classifier biomarker of Table 1 from a reference C25 sample, expression data of the at least one classifier biomarker of Table 1 from a reference C26 sample, expression data of the at least one classifier biomarker of Table 1 from a reference C28 sample or a combination thereof; and classifying the sample as the C1, C2, C3, C4, C6, C8, C9, C10, C12, C14, C15, C16, C17, C19, C20, C21, C22, C24, C25, C26 or C28 COCA subtype based on the results of the comparing step. In some cases, the comparing step comprises applying a statistical algorithm which comprises determining a correlation between the expression data obtained from the sample and the expression data from the at least one training set(s); and classifying the sample as a C1, C2, C3, C4, C6, C8, C9, C10, C12, C14, C15, C16, C17, C19, C20, C21, C22, C24, C25, C26 or C28 COCA subtype based on the results of the statistical algorithm. In some cases, the expression level of the classifier biomarker is detected at the nucleic acid level. In some cases, the nucleic acid level is RNA or cDNA. In some cases, the detecting an expression level comprises performing a quantitative real time reverse transcriptase polymerase chain reaction (qRT-PCR), RNAseq, microarray analysis, gene chips, an nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing RNAseq. In some cases, the detection of the expression level comprises using at least one pair of oligonucleotide primers specific for at least one classifier biomarker of Table 1. In some cases, the sample is a formalin-fixed, paraffin-embedded (FFPE) tissue sample, a fresh or a frozen tissue sample, an exosome, wash fluids, cell pellets, or a bodily fluid obtained from the patient. In some cases, the bodily fluid is blood or fractions thereof (i.e., serum or plasma), urine, saliva, or sputum. In some cases, the at least one classifier biomarker comprises a plurality of classifier biomarkers. In some cases, the plurality of classifier biomarkers comprises, consists essentially of or consists of at least 2 classifier biomarkers, at least 4 classifier biomarkers, at least 6 classifier biomarkers, at least 8 classifier biomarkers, at least 10 classifier biomarkers, at least 12 classifier biomarkers, at least 14 classifier biomarkers, at least 16 classifier biomarkers, at least 18 classifier biomarkers, at least 20 classifier biomarkers, at least 30 classifier biomarkers, at least 40 classifier biomarkers, at least 50 classifier biomarkers, at least 60 classifier biomarkers, at least 70 classifier biomarkers or at least 80 classifier biomarkers of Table 1. In some cases, the at least one classifier biomarker comprises, consists essentially of or consists of all the classifier biomarkers of Table 1.

In another aspect, provided herein is a method of detecting a biomarker in a tumor sample obtained from a patient, the method comprising measuring the expression level of a plurality of classifier biomarker nucleic acids selected from Table 1 using an amplification, hybridization and/or sequencing assay. In some cases, the patient is suffering from or is suspected of suffering from kidney renal papillary cell carcinoma (KIRP); breast invasive carcinoma (BRCA); thyroid cancer (THCA); bladder urothelial carcinoma (BLCA); prostate adenocarcinoma (PRAD); kidney chromophobe (KICH); cervical squamous cell carcinoma and endocervical adenocarcinoma (CESC); kidney renal clear cell carcinoma (KIRC); liver hepatocellular carcinoma (LIHC); low grade glioma (LGG); sarcoma (SARC); lung adenocarcinoma (LUAD); colon adenocarcinoma (COAD); head and neck squamous cell carcinoma (HNSC); uterine corpus endometrial carcinoma (UCEC); glioblastoma multiforme (GBM); esophageal carcinoma (ESCA); stomach adenocarcinoma (STAD); ovarian serous cystadenocarcinoma (OV); rectum adenocarcinoma (READ); adrenocortical carcinoma (ACC); uveal melanoma (UVM); mesothelioma (MESO); pheochromocytoma and paraganglioma (PCPG); skin cutaneous melanoma (SKCM); uterine carcinosarcoma (UCS); lung squamous cell carcinoma (LUSC); testicular germ cell tumors (TGCT); cholangiocarcinoma (CHOL); pancreatic adenocarcinoma (PAAD); thymoma (THYM); or Lymphoid Neoplasm Diffuse Large B-cell Lymphoma (DLBC). In some cases, the amplification, hybridization and/or sequencing assay comprises performing quantitative real time reverse transcriptase polymerase chain reaction(s) (qRT-PCR), RNAseq, microarray analysis, gene chips, nCounter Gene Expression Assay(s), Serial Analysis of Gene Expression (SAGE), Rapid Analysis of Gene Expression (RAGE), nuclease protection assays, Northern blotting, or any other equivalent gene expression detection techniques. In some cases, the expression level is detected by performing RNAseq. In some cases, the detection of the expression level comprises using at least one pair of oligonucleotide primers per each of the plurality of biomarker nucleic acids selected from Table 1. In some cases, the sample is a formalin-fixed, paraffin-embedded (FFPE) tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, at least 60 classifier biomarkers, at least 70 classifier biomarkers or at least 80 classifier biomarkers of Table 1. In some cases, the plurality of biomarker nucleic acids comprises, consists essentially of or consists of all the classifier biomarker nucleic acids of Table 1.

In yet another aspect, provided herein is a method of treating cancer in a subject, the method comprising: measuring the expression level of at least one biomarker nucleic acid in a tumor sample obtained from the subject, wherein the at least one biomarker nucleic acid is selected from a set of biomarkers listed in Table 1, wherein the presence, absence and/or level of the at least one biomarker indicates a COCA subtype of the cancer; and administering a therapeutic agent based on the COCA subtype of the cancer. In some cases, the at least one biomarker nucleic acid selected from the set of biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, at least 60 classifier biomarkers, at least 70 classifier biomarkers or at least 80 classifier biomarkers of Table 1. In some cases, the method further comprises measuring the expression of at least one biomarker from an additional set of biomarkers. In some cases, the additional set of biomarkers comprises at least an immune cell signature, a cell proliferation signature, or drug target genes. In some cases, the measuring the expression level is conducted using an amplification, hybridization and/or sequencing assay. In some cases, the amplification, hybridization and/or sequencing assay comprises performing quantitative real time reverse transcriptase polymerase chain reaction(s) (qRT-PCR), RNAseq, microarray analysis, gene chips, nCounter Gene Expression Assay(s), Serial Analysis of Gene Expression (SAGE), Rapid Analysis of Gene Expression (RAGE), nuclease protection assays, Northern blotting, or any other equivalent gene expression detection techniques. In some cases, the expression level is detected by performing RNAseq. In some cases, the sample is a formalin-fixed, paraffin-embedded (FFPE) tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the subject's COCA subtype is selected from C1, C2, C3, C4, C6, C8, C9, C10, C12, C14, C15, C16, C17, C19, C20, C21, C22, C24, C25, C26 or C28.

In still another aspect, provided herein is a method of predicting overall survival in a cancer patient, the method comprising detecting an expression level of at least one classifier biomarker of Table 1 in a tumor sample obtained from a patient, wherein the detection of the expression level of the at least one classifier biomarker specifically identifies a COCA subtype, and wherein identification of the COCA subtype is predictive of the overall survival in the patient. In some cases, the method further comprises comparing the detected levels of expression of the at least one classifier biomarker of Table 1 to the expression of the at least one classifier biomarker of Table 1 in at least one sample training set(s), wherein the at least one sample training set(s) comprises expression data of the at least one classifier biomarker of Table 1 from a reference C1 sample, expression data of the at least one classifier biomarker of Table 1 from a reference C2 sample, expression data of the at least one classifier biomarker of Table 1 from a reference C3 sample, expression data of the at least one classifier biomarker of Table 1 from a reference C4 sample, expression data of the at least one classifier biomarker of Table 1 from a reference C6 sample, expression data of the at least one classifier biomarker of Table 1 from a reference C8 sample, expression data of the at least one classifier biomarker of Table 1 from a reference C9 sample, expression data of the at least one classifier biomarker of Table 1 from a reference C10 sample, expression data of the at least one classifier biomarker of Table 1 from a reference C12 sample, expression data of the at least one classifier biomarker of Table 1 from a reference C14 sample, expression data of the at least one classifier biomarker of Table 1 from a reference C15 sample, expression data of the at least one classifier biomarker of Table 1 from a reference C16 sample, expression data of the at least one classifier biomarker of Table 1 from a reference C17 sample, expression data of the at least one classifier biomarker of Table 1 from a reference C19 sample, expression data of the at least one classifier biomarker of Table 1 from a reference C20 sample, expression data of the at least one classifier biomarker of Table 1 from a reference C21 sample, expression data of the at least one classifier biomarker of Table 1 from a reference C22 sample, expression data of the at least one classifier biomarker of Table 1 from a reference C24 sample, expression data of the at least one classifier biomarker of Table 1 from a reference C25 sample, expression data of the at least one classifier biomarker of Table 1 from a reference C26 sample, expression data of the at least one classifier biomarker of Table 1 from a reference C28 sample or a combination thereof; and classifying the sample as the C1, C2, C3, C4, C6, C8, C9, C10, C12, C14, C15, C16, C17, C19, C20, C21, C22, C24, C25, C26 or C28 COCA subtype based on the results of the comparing step. In some cases, the comparing step comprises applying a statistical algorithm which comprises determining a correlation between the expression data obtained from the sample and the expression data from the at least one training set(s); and classifying the sample as a C1, C2, C3, C4, C6, C8, C9, C10, C12, C14, C15, C16, C17, C19, C20, C21, C22, C24, C25, C26 or C28 COCA subtype based on the results of the statistical algorithm. In some cases, the expression level of the classifier biomarker is detected at the nucleic acid level. In some cases, the nucleic acid level is RNA or cDNA. In some cases, the detecting an expression level comprises performing quantitative real time reverse transcriptase polymerase chain reaction(s) (qRT-PCR), RNAseq, microarray analysis, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing RNAseq. In some cases, the detection of the expression level comprises using at least one pair of oligonucleotide primers specific for at least one classifier biomarker of Table 1. In some cases, the sample is a formalin-fixed, paraffin-embedded (FFPE) tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the at least one classifier biomarker comprises a plurality of classifier biomarkers. In some cases, the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, at least 60 classifier biomarkers, at least 70 classifier biomarkers or at least 80 classifier biomarkers of Table 1. In some cases, the at least one classifier biomarker comprises, consists essentially of or consists of all the classifier biomarkers of Table 1.

BRIEF DESCRIPTION OF THE DRAWINGS

FIG. 1 shows a cross-tabulation of the TCGA tumor type and COCA subtype from Hoadley et al., Cell. 2018 Apr. 5; 173(2):291-304 for samples with qualifying expression data as described in Example 1. FIG. 1 also provides the integrated tumor subtypes provided herein.

FIG. 4 illustrates agreement and disagreement between the GS subtype (rows) and the subtype based on the 84-gene subtyper (columns) (left panel) for the test set described in Example 1. The right panel shows agreement for each COCA subtype listed. Overall agreement was 90%. Overall agreement with COCA on the training set was 91%.

FIG. 5 shows the proportion of COCA subtypes in the test set that were called correctly by the 84-gene typer developed in Example 1.

FIG. 6 shows results of within cancer-type survival analysis for bladder cancer (BLCA) via testing for association of COCA subtypes from BLCA sample with overall survival. p=0.0204 for COCA subtype C4 as determined using the 84 gene COCA subtyper provided herein.

FIG. 7 shows results of within cancer-type survival analysis for breast cancer (BRCA) via testing for association of COCA subtypes from BRCA sample with overall survival. p=0.00013 for COCA subtype C24 as determined using the 84 gene COCA subtyper provided herein.

FIG. 8 shows results of within cancer-type survival analysis for stomach adenocarcinoma (STAD) via testing for association of COCA subtypes from STAD sample with overall survival. p=0.00689 for COCA subtype C8 as determined using the 84 gene COCA subtyper provided herein.

DETAILED DESCRIPTION

Definitions

Figure 2:
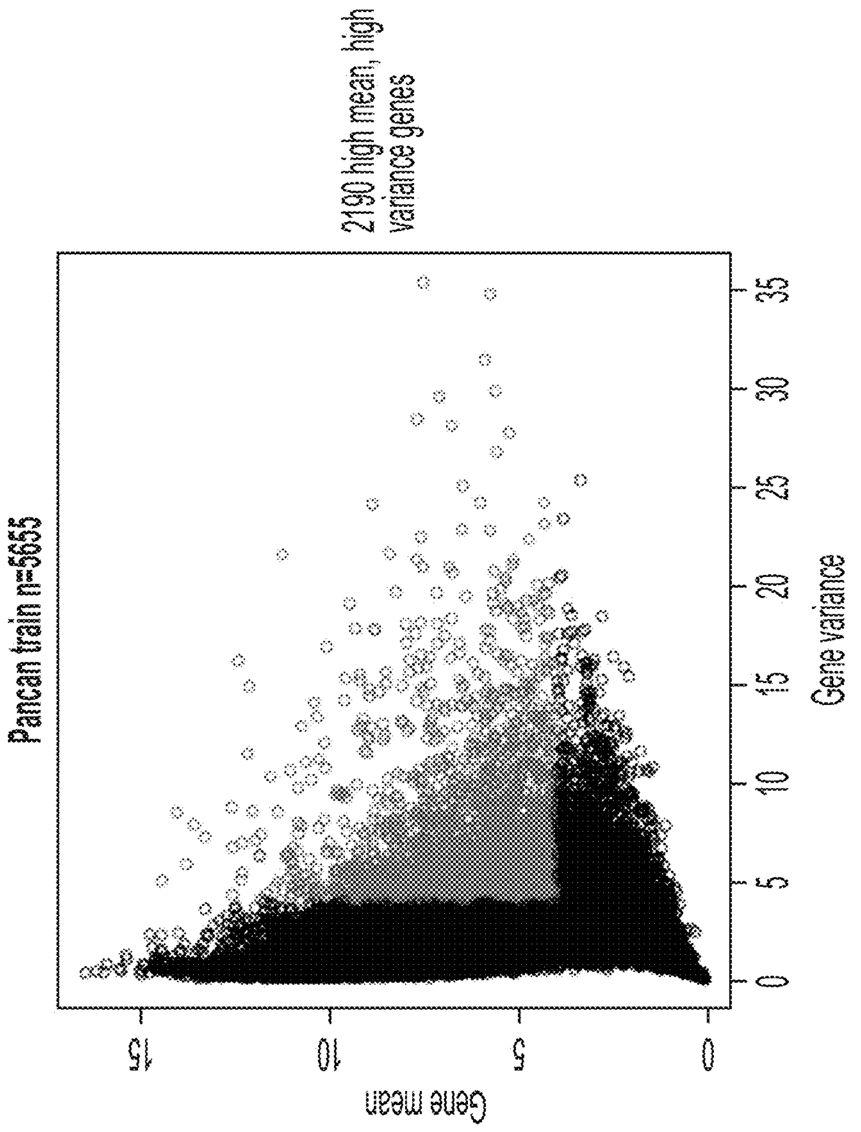
FIG. 2 illustrates how the TCGA samples were divided into a training set (⅔ of the data set; n=5696) and test set (⅓ of the data set), balancing for uniform tumor type of origin distributions for development of the 84-gene subtyper described herein (see the Table in FIG. 2). As illustrated in the graph on FIG. 2, using the training set, genes with low variance and/or low mean were filtered out, while genes with mean variance and mean expression values greater than 4 were kept resulting in gene expression data for 2190 genes.

While the following terms are believed to be well understood by one of ordinary skill in the art, the following definitions are set forth to facilitate explanation of the presently disclosed subject matter.

As used herein, the singular forms “a”, “an” and “the” are intended to include the plural forms as well, unless the context clearly indicates otherwise. Additionally, the use of “or” is intended to include “and/or” unless the context clearly indicates otherwise. Furthermore, to the extent that the terms “including”, “includes”, “having”, “has”, “with”, or variants thereof are used in either the detailed description and/or the claims, such terms are intended to be inclusive in a manner similar to the term “comprising”. The term “about” as used herein can refer to a range that is 15%, 10%, 8%, 6%, 4%, or 2% plus or minus from a stated numerical value.

Unless the context requires otherwise, throughout the present specification and claims, the word “comprise” and variations thereof, such as, “comprises” and “comprising” are to be construed in an open, inclusive sense that is as “including, but not limited to”. The use of the alternative (e.g., “or”) should be understood to mean either one, both, or any combination thereof of the alternatives. As used herein, the terms “about” and “consisting essentially of” mean+/−20% of the indicated range, value, or structure, unless otherwise indicated.

Reference throughout this specification to “one embodiment” or “an embodiment” means that a particular feature, structure or characteristic described in connection with the embodiment may be included in at least one embodiment of the present disclosure. Thus, the appearances of the phrases “in one embodiment” or “in an embodiment” in various places throughout this specification may not necessarily all be referring to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

Throughout this disclosure, various aspects of the methods and compositions provided herein can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Unless otherwise indicated, the methods and compositions provided herein can utilize conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Gait, "Oligonucleotide Synthesis: A Practical Approach" 1984, IRL Press, London, Nelson and Cox (2000), Lehninger et al., (2008) Principles of Biochemistry 5th Ed., W.H. Freeman Pub., New York, N.Y. and Berg et al. (2006) Biochemistry, 6.sup.th Ed., W.H. Freeman Pub., New York, N.Y., all of which are herein incorporated in their entirety by reference for all purposes.

Conventional software and systems may also be used in the methods and compositions provided herein. Computer software products for use herein typically include computer readable medium having computer-executable instructions for performing the logic steps of any of the methods provided herein. Suitable computer readable medium include floppy disk, CD-ROM/DVD/DVD-ROM, hard-disk drive, flash memory, ROM/RAM, magnetic tapes, etc. The computer-executable instructions may be written in a suitable computer language or combination of several languages. Basic computational biology methods are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2.sup.nd ed., 2001). See U.S. Pat. No. 6,420,108.

The methods and compositions provided herein may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Computer methods related to genotyping using high density microarray analysis may also be used in the present methods, see, for example, US Patent Pub. Nos. 20050250151, 20050244883, 20050108197, 20050079536 and 20050042654.

Additionally, the present disclosure may have preferred embodiments that include methods for providing genetic information over networks such as the Internet as shown in U.S. Patent Pub. Nos. 20030097222, 20020183936, 20030100995, 20030120432, 20040002818, 20040126840, and 20040049354.

As used herein, the terms "individual," "patient," and "subject" can refer to any single animal, more preferably a mammal (including such non-human animals as, for example, dogs, cats, horses, rabbits, zoo animals, cows, pigs, sheep, and non-human primates) for which treatment is desired. In particular embodiments, the individual or patient herein is a human.

It will be appreciated that the term "healthy" as used herein, is relative to cancer status, as the term "healthy" cannot be defined to correspond to any absolute evaluation or status. Thus, an individual defined as healthy with reference to any specified disease or disease criterion, can in fact be diagnosed with any other one or more diseases, or exhibit any other one or more disease criterion, including one or more other cancers.

The term "tumor," as used herein, can refer to all neoplastic cell growth and proliferation, whether malignant or benign, and all pre-cancerous and cancerous cells and tissues. The terms "cancer," "cancerous," and "tumor" are not mutually exclusive and can be used interchangeably.

The term "detection" can include any means of detecting, including direct and indirect detection.

The terms "substantially" or "substantial" as used herein can mean substantially similar in function or capability or otherwise competitive to the products, items (e.g., type of cancer, nucleic acid complement), services or methods recited herein. Substantially similar products, items (e.g., type of cancer, nucleic acid complement), services or methods are at least 80%, 81%, 82%, 83%, 83%, 84%, 85%, 86%, 87%, 88%, 89%, 90%, 91%, 92%, 93%, 94%, 95%, 96%, 97%, 98%, 99% or 99.5% similar or the same as a product, item (e.g., type of cancer, nucleic acid complement), service or method recited herein.

Overview

Provided herein are kits, compositions and methods for identifying, determining, detecting or diagnosing integrated, pan-cancer clustering of cluster assignment (COCA) subtypes. That is, the methods can be useful for molecularly defining subsets of cancer regardless of tissue of origin. The methods provide a pan-cancer classification of a tumor sample obtained from subject that can be prognostic and predictive for therapeutic response. The therapeutic response can include chemotherapy, immunotherapy, angiogenesis inhibitor therapy, surgical intervention and/or radiotherapy. The methods can be also provide a prognosis of overall survival for cancer patients according to their pan-cancer, integrated COCA subtype. The kits, compositions and methods provided herein can be used to classify a tumor sample as being any type of COCA subtype known in the art. In one embodiment, the COCA subtype determined or diagnosed by the methods and compositions provided herein are selected from C1 (ACC/PCPG), C2 (GBM/LGG), C3 (OV), C4 (Squamous-like), C6 (LUAD-Enriched), C8

(PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and C28 (THCA).

The COCA subtype determined using the kits, compositions or methods provided herein can indicate or disclose the cell or tissue of origin of a tumor sample obtained from a subject. For example, the C1 COCA subtype can indicate that a tumor sample is substantially similar to or is adrenocortical carcinoma; the C2 COCA subtype can indicate that a tumor sample is substantially similar to or is glioblastoma; the C3 COCA subtype can indicate that a tumor sample is substantially similar to or is an ovarian serous cystadenocarcinoma (epithelial ovarian cancer); the C4 COCA subtype can indicate that a tumor sample is substantially similar to or is squamous cell carcinoma of the lung, the head and neck or the bladder; the C6 COCA subtype can indicate that a tumor sample is substantially similar to or is lung adenocarcinoma; the CR COCA subtype can indicate that a tumor sample is substantially similar to or is pancreatic adenocarcinoma; the C9 COCA subtype can indicate that a tumor sample is substantially similar to or is uterine carcinosarcoma; the C10 COCA subtype can indicate that a tumor sample is substantially similar to or is the basal subtype of breast cancer; the C12 COCA subtype can indicate that a tumor sample is substantially similar to or is uterine corpus endometrial cancer; the C14 COCA subtype can indicate that a tumor sample is substantially similar to or is prostate cancer; the C15 COCA subtype can indicate that a tumor sample is substantially similar to or is non-squamous cervical cancer; the C16 COCA subtype can indicate that a tumor sample is substantially similar to or is a bladder urothelial carcinoma; the C17 COCA subtype can indicate that a tumor sample is substantially similar to or is a testicular germ cell tumor; the C19 COCA subtype can indicate that a tumor sample is substantially similar to or is a colon, rectal, esophageal or stomach adenocarcinoma; the C20 COCA subtype can indicate that a tumor sample is substantially similar to or is a sarcoma; the C21 COCA subtype can indicate that a tumor sample is substantially similar to or is a kidney chromophobe, kidney renal papillary cell carcinoma or kidney renal clear cell carcinoma; the C22 COCA subtype can indicate that a tumor sample is substantially similar to or is liver hepatocellular carcinoma; the C24 COCA subtype can indicate that a tumor sample is substantially similar to or is the luminal subtype of breast cancer; the C25 COCA subtype can indicate that a tumor sample is substantially similar to or is thymoma; the C26 COCA subtype can indicate that a tumor sample is substantially similar to or is melanoma; or the C28 COCA subtype can indicate that a tumor sample is substantially similar to or is thyroid cancer.

"Determining a COCA subtype" can include, for example, diagnosing or detecting the presence, sub-type and cell-of-origin of a cancer, monitoring the progression of the disease, and identifying or detecting cells or samples that are indicative of said pan-cancer subtypes.

In one embodiment, the COCA subtype is assessed or determined through the evaluation of expression patterns, or profiles, of one or a plurality of classifier biomarkers or biomarkers in one or more subject samples. The term subject, or subject sample, may refer to an individual regardless of health and/or disease status. A subject can be a subject, a study participant, a test subject, a control subject, a screening subject, or any other class of individual from whom a sample is obtained and assessed in the context of the methods and compositions provided herein. Accordingly, a subject can be previously diagnosed with one type of a myriad of cancers, can present with one or more symptoms of said type of cancer, or a predisposing factor, such as a family (genetic) or medical history (medical) factor for said type of cancer, can be undergoing treatment or therapy for said cancer, or the like. Alternatively, a subject can be healthy as defined herein with respect to any of the aforementioned factors or criteria.

The myriad of cancers from which a subject may be suffering from or suspected of suffering from can be any cancer known in the art. The classifier biomarkers provided herein (e.g., the classifier biomarkers of Table 1) and methods of using said classifier biomarkers can be used to determine an integrated, pan-cancer COCA subtype of the cancer that said subject may be or is suspected of suffering from. Further to any of the embodiments provided herein, the cancer can include, but is not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. Examples of a cancer can also include, but are not limited to, a lung cancer (e.g., a non-small cell lung cancer (NSCLC) or small cell lung cancer), a kidney cancer (e.g., a kidney urothelial carcinoma or RCC), a bladder cancer (e.g., a bladder urothelial (transitional cell) carcinoma (e.g., locally advanced or metastatic urothelial cancer, including 1 L or 2 L+ locally advanced or metastatic urothelial carcinoma)), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycosis fungoides, a Merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, a Ewing's tumor, a squamous cell carcinoma, a basal cell carcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor.

In one embodiment, the cancer is selected from kidney renal papillary cell carcinoma (KIRP); breast invasive carcinoma (BRCA); thyroid cancer (THCA); bladder urothelial carcinoma (BLCA); prostate adenocarcinoma (PRAD); kidney chromophobe (KICH); cervical squamous cell carcinoma and endocervical adenocarcinoma (CESC); kidney renal clear cell carcinoma (KIRC); liver hepatocellular carcinoma (LIHC); low grade glioma (LGG); sarcoma (SARC); lung adenocarcinoma (LUAD); colon adenocarcinoma (COAD); head and neck squamous cell carcinoma (HNSC); uterine corpus endometrial carcinoma (UCEC); glioblastoma multiforme (GBM); esophageal carcinoma (ESCA); stomach adenocarcinoma (STAD); ovarian serous cystadenocarcinoma (OV); rectum adenocarcinoma (READ); adrenocortical carcinoma (ACC); uveal melanoma (UVM); mesothelioma (MESO); pheochromocytoma and paraganglioma (PCPG); skin cutaneous melanoma (SKCM); uterine carcinosarcoma (UCS); lung squamous cell carcinoma (LUSC); testicular germ cell tumors (TGCT); cholangiocarcinoma (CHOL); pancreatic adenocarcinoma (PAAD); thymoma (THYM); Lymphoid Neoplasm Diffuse Large B-cell Lymphoma (DLBC); and Acute Myeloid Leukemia [LAML] in another embodiment, the cancer is selected from kidney renal papillary cell carcinoma (KIRP); breast invasive carcinoma (BRCA); thyroid cancer (THCA); bladder urothelial carcinoma (BLCA); prostate adenocarcinoma (PRAD); kidney chromophobe (KICH); cervical squamous cell carcinoma and endocervical adenocarcinoma (CESC); kidney renal clear cell carcinoma (KIRC); liver hepatocellular carcinoma (LIHC); low grade glioma (LGG); sarcoma (SARC); lung adenocarcinoma (LUAD); colon adenocarcinoma (COAD); head and neck squamous cell carcinoma (HNSC); uterine corpus endometrial carcinoma (UCEC); glioblastoma multiforme (GBM); esophageal carcinoma (ESCA); stomach adenocarcinoma (STAD); ovarian serous cystadenocarcinoma (OV); rectum adenocarcinoma (READ); adrenocortical carcinoma (ACC); uveal melanoma (UVM); mesothelioma (MESO); pheochromocytoma and paraganglioma (PCPG); skin cutaneous melanoma (SKCM); uterine carcinosarcoma (UCS); lung squamous cell carcinoma (LUSC); testicular germ cell tumors (TGCT); cholangiocarcinoma (CHOL); pancreatic adenocarcinoma (PAAD); thymoma (THYM); and Lymphoid Neoplasm Diffuse Large B-cell Lymphoma (DLBC).

As used herein, an "expression profile" or an "expression pattern" or a "biomarker profile" or a "gene signature" can comprise one or more values corresponding to a measurement of the relative abundance, level, presence, or absence of expression of a discriminative or classifier biomarker or biomarker. An expression profile can be derived from a subject prior to or subsequent to a diagnosis of a type of cancer, can be derived from a biological sample collected from a subject at one or more time points prior to or following treatment or therapy, can be derived from a biological sample collected from a subject at one or more time points during which there is no treatment or therapy (e.g., to monitor progression of disease or to assess development of disease in a subject diagnosed with or at risk for a type of cancer), or can be collected from a healthy subject. The term subject can be used interchangeably with patient. The patient can be a human patient. The one or a plurality of classifier biomarkers that can make up an expression profile as provided herein can be selected from one or more biomarkers of Table 1 and/or any additional set of biomarker classifiers disclosed herein.

As used herein, the term "determining an expression level" or "determining an expression profile" or "detecting an expression level" or "detecting an expression profile" as used in reference to a biomarker or classifier can mean the application of a biomarker specific reagent such as a probe, primer or antibody and/or a method applied to a sample, for example a sample of the subject or patient and/or a control sample, for ascertaining or measuring quantitatively, semi-quantitatively or qualitatively the amount of a biomarker or biomarkers, for example the amount of biomarker polypeptide or mRNA (or cDNA derived therefrom). The level of a biomarker as provided herein can be determined by any number of methods known in the art and/or provided herein. The methods can include for example immunoassays including for example immunohistochemistry, ELISA, Western blot, immunoprecipitation and the like, where a biomarker detection agent such as an antibody for example, a labeled antibody, specifically binds the biomarker and permits for example relative or absolute ascertaining of the amount of polypeptide biomarker, hybridization and PCR protocols where a probe or primer or primer set are used to ascertain the amount of nucleic acid biomarker, including for example probe based and amplification based methods including for example microarray analysis, RT-PCR such as quantitative RT-PCR (qRT-PCR), serial analysis of gene expression (SAGE), Northern Blot, digital molecular barcoding technology, for example Nanostring Counter Analysis, and TaqMan quantitative PCR assays. Other methods of mRNA detection and quantification can be applied, such as mRNA in situ hybridization in formalin-fixed, paraffin-embedded (FFPE) tissue samples or cells. This technology is currently offered by the QuantiGene ViewRNA (Affymetrix), which uses probe sets for each mRNA that bind specifically to an amplification system to amplify the hybridization signals; these amplified signals can be visualized using a standard fluorescence microscope or imaging system. This system for example can detect and measure transcript levels in heterogeneous samples; for example, if a sample has normal and tumor cells present in the same tissue section. As mentioned, TaqMan probe-based gene expression analysis (PCR-based) can also be used for measuring gene expression levels in tissue samples, and this technology has been shown to be useful for measuring mRNA levels in FFPE samples. In brief, TaqMan probe-based assays utilize a probe that hybridizes specifically to the mRNA target. This probe contains a quencher dye and a reporter dye (fluorescent molecule) attached to each end, and fluorescence is emitted only when specific hybridization to the mRNA target occurs. During the amplification step, the exonuclease activity of the polymerase enzyme causes the quencher and the reporter dyes to be detached from the probe, and fluorescence emission can occur. This fluorescence emission is recorded and signals are measured by a detection system; these signal intensities are used to calculate the abundance of a given transcript (gene expression) in a sample.

In one embodiment, the "expression profile" or a "biomarker profile" or "gene signature" associated with the classifier biomarkers described herein (e.g., Table 1 and/or any additional set of biomarker classifiers as disclosed herein) can be useful for distinguishing between normal and tumor samples. In another embodiment, the tumor samples are one type of cancer as determined based on tissue of origin. The one type of cancer can be any type of cancer known in the art and/or provided herein. In another embodiment, the cancer can be further classified as a specific clustering of cluster assignment (COCA) subtype based upon an expression profile of one or more classifier biomarkers (e.g., Table 1) determined using the methods provided herein. The specific COCA subtype can be any COCA subtype as described in Hoadley, Katherine A., Christina Yau, Toshinori Hinoue, Denise M. Wolf, Alexander J. Lazar, Esther Drill, Ronglai Shen et al. "Cell-of-origin patterns dominate the molecular classification of 10,000 tumors from 33 types of cancer." Cell173, no. 2 (2018): 291-304. In one embodiment, the specific COCA subtype can be selected from C1 ACC/PCPG, C2 GBM/LGG, C3 OV, C4 Squamous-like, C6 LUAD-Enriched, C8 PAAD/some STAD, C9 UCS, C10 BRCA/Basal, C12 UCEC, C14 PRAD, C15 CESC (subset of cervical), C16 BLCA, C17 TGCT, C19 COAD/READ, C20 SARC/MESO, C21 KIRK/KICH/KIRP, C22 Liver, C24 BRCA/Luminal, C25 THYM, C26 SKCM/UVM and C28 THCA. Expression profiles using the classifier biomarkers disclosed herein (e.g., Table 1, Table 2 and any additional set of biomarker classifiers as disclosed herein) can provide valuable molecular tools for specifically identifying COCA subtypes, and for treating a cancer based on its COCA subtype. Accordingly, provided herein are methods for screening and classifying a subject for pan-cancer COCA subtypes.

In some instances, a single classifier biomarker or a plurality of classifier biomarkers provided herein (e.g., from Table 1) is capable of identifying COCA subtypes of cancer with a predictive success of at least about 70%, at least about 71%, at least about 72%, at least about 73%, at least about 74%, at least about 75%, at least about 76%, at least about 77%, at least about 78%, at 1 east about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, inclusive of all ranges and subranges therebetween.

In some instances, a single classifier biomarker or a plurality of classifier biomarkers as provided herein (e.g., from Table 1) is capable of determining COCA subtypes of cancer with a sensitivity or specificity of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, inclusive of all ranges and subranges therebetween.

Also encompassed herein is a system capable of distinguishing various COCA subtypes of cancer not detectable using current methods. This system can b e capable of processing a large number of subjects and subject variables such as expression profiles and other diagnostic criteria. In one embodiment, the methods for determining a COCA subtype as provided herein using one or a plurality of classifier biomarkers as provided herein (e.g., Table 1) can be part of system capable of distinguishing various COCA subtypes that also utilizes data accumulated from other diagnostic methods. The other diagnostic methods can include additional genome-wide molecular assays or platforms, histochemical, immunohistochemical, cytologic, immunocytologic, visual diagnostic methods including histologic or morphometric evaluation of cancer or tumor tissue or any combination thereof. The additional genome-wide molecular assays or platforms can be selected from whole-exome DNA sequencing assays (e.g., Illumina HiSeq and GAII), DNA copy-number variation assays (e.g., Affymetrix 6.0 microarrays), DNA methylation assays (e.g., Illumina 450,000-feature microarrays), genome-wide mRNA level assays (e.g., Illumina mRNA-seq), microRNA level assays (e.g., Illumina microRNA-seq), and protein level assays for proteins and/or phosphorylated proteins (e.g., Reverse Phase Protein Arrays; RPPA).

In various embodiments, the expression profile derived from a subject (e.g., from a sample obtained from said subject) is compared to a reference expression profile. A "reference expression profile" or "control expression profile" can be a profile derived from the subject prior to treatment or therapy; can be a profile produced from the subject sample at a particular time point (usually prior to or following treatment or therapy, but can also include a particular time point prior to or following diagnosis of a type of cancer); or can be derived from a healthy individual or a pooled reference from healthy individuals. A reference expression profile can be specific to different COCA subtypes of cancer. The COCA reference expression profile can be from any tissues from which a specific COCA has been found. As provided herein, in one embodiment, the specific COCA subtype can be any COCA subtype as described in Hoadley, Katherine A., Christina Yau, Toshinori Hinoue, Denise M. Wolf, Alexander J. Lazar, Esther Drill, Ronglai Shen et al. "Cell-of-origin patterns dominate the molecular classification of 10,000 tumors from 33 types of cancer." Cell173, no. 2 (2018): 291-304. In one embodiment, the specific COCA subtype can be selected from a C1 ACC/PCPG, C2 GBM/LGG, C3 OV, C4 Squamous-like, C6 LUAD-Enriched, C8 PAAD/some STAD, C9 UCS, C10 BRCA/Basal, C12 UCEC, C14 PRAD, C15 CESC (subset of cervical), C16 BLCA, C17 TGCT, C19 COAD/READ, C20 SARC/MESO, C21 KIRK/KICH/KIRP, C22 Liver, C24 BRCA/Luminal, C25 THYM, C26 SKCM/UVM or C28 THCA COCA subtype.

The reference expression profile can be compared to a test expression profile or vice versa. A "test expression profile" can be derived from the same subject as the reference expression profile except at a subsequent time point (e.g., one or more days, weeks or months following collection of the reference expression profile) or can be derived from a different subject. In summary, any test expression profile of a subject can be compared to a previously collected profile from a subject that has a specific COCA subtype. The specific COCA subtype can be any COCA subtype as described in Hoadley, Katherine A., Christina Yau, Toshinori Hinoue, Denise M. Wolf, Alexander J. Lazar, Esther Drill, Ronglai Shen et al. "Cell-of-origin patterns dominate the molecular classification of 10,000 tumors from 33 types of cancer." Cell173, no. 2 (2018): 291-304. In one embodiment, the specific COCA subtype can be selected from a C1 ACC/PCPG, C2 GBM/LGG, C3 OV, C4 Squamous-like, C6 LUAD-Enriched, C8 PAAD/some STAD, C9 UCS, C10

BRCA/Basal, C12 UCEC, C14 PRAD, C15 CESC (subset of cervical), C16 BLCA, C17 TGCT, C19 COAD/READ, C20 SARC/MESO, C21 KIRK/KICH/KIRP, C22 Liver, C24 BRCA/Luminal, C25 THYM, C26 SKCM/UVM or C28 THCA COCA subtype.

The classifier biomarkers provided herein (e.g., Table 1) for use in the methods, compositions or kits provided herein can include nucleic acids (RNA, cDNA, and DNA) and proteins, and variants and fragments thereof. Such biomarkers can include DNA comprising the entire or partial sequence of the nucleic acid sequence encoding the biomarker, or the complement of such a sequence. The biomarkers described herein can include RNA comprising the entire or partial sequence of any of the nucleic acid sequences of interest, or their non-natural cDNA products, obtained synthetically in vitro in a reverse transcription reaction. The biomarker nucleic acids can also include any expression product or portion thereof of the nucleic acid sequences of interest. A biomarker protein can be a protein encoded by or corresponding to a DNA biomarker provided herein. A biomarker protein can comprise the entire or partial amino acid sequence of any of the biomarker proteins or polypeptides. The biomarker nucleic acid can be extracted from a bodily fluid (e.g., blood or fractions thereof, urine, saliva, CSF, etc.), a cell or can be cell free or extracted from an extracellular vesicular entity such as an exosome.

A “classifier biomarker” or “biomarker” or “classifier gene” can be any nucleic acid (DNA, RNA or cDNA) or protein whose level of expression in a tissue or cell is altered compared to that of a normal or healthy cell or tissue or any other reference or control as provided herein. For example, a “classifier biomarker” or “biomarker” or “classifier gene” can be any nucleic acid (DNA, RNA or cDNA) or protein whose level of expression in a tissue or cell is altered in a specific COCA subtype. The detection of the biomarkers provided herein can permit the determination of the specific COCA subtype. The “classifier biomarker” or “biomarker” or “classifier gene” may be one that is up-regulated (e.g. expression is increased) or down-regulated (e.g. expression is decreased) relative to a reference or control as provided herein. The reference or control can be any reference or control as provided herein. In some embodiments, the expression values of nucleic acids (DNA, RNA or cDNA) that are up-regulated or down-regulated in a particular COCA subtype of cancer can be pooled into one gene signature. The overall expression level in each gene signature is referred to herein as the “expression profile” and is used to classify a test sample (i.e., a sample obtained from a subject suffering from or suspected of suffering from cancer) according to the COCA subtype of cancer. However, it is understood that independent evaluation of expression for each of the genes disclosed herein can be used to classify tumor subtypes without the need to group up-regulated and down-regulated genes into one or more gene signatures. In some cases, as shown in Tables 1 and 2, a total of 84 biomarkers can be used for COCA subtype determination. For a specific COCA subtype, for example, expression of 4 of the 84 biomarkers of Table 1 can have altered expression that is correlated therewith. Further, the correlation of the 4 of the 84 biomarkers of Table 1 with the specific COCA subtype can be positive, negative or a combination thereof.

The classifier biomarkers for use in the methods provided herein can include any nucleic acid (DNA, RNA or cDNA) or protein that is selectively expressed in COCA subtypes of cancer, as defined herein above. Sample biomarker genes are listed in Table 1 below.

In one embodiment, the 84-gene gene signature for COCA subtyping is found in Table 1. The relative gene expression levels as represented by nearest centroid coefficients of the classifier biomarkers for the 84-gene pan-cancer subtyper of Table 1 are shown in Table 2.

TABLE 1

84 Gene Classifier Biomarker Signature for Pan-Cancer COCA subtyping.

| SEQ ID NO. | Gene Symbol | Gene Name | GenBank Accession Number* |
|---|---|---|---|
| 1 | A1BG | Alpha-1-B Glycoprotein | NM_130786.3 |
| 2 | ACPP | Acid Phosphatase, Prostate | NM_001099.5 |
| 3 | APC2 | APC2, WNT Signaling Pathway Regulator | NM_001351273.1 |
| 4 | AQP5 | Aquaporin 5 | NM_001651.4 |
| 5 | ASGR1 | asialoglycoprotein receptor 1 | NM_001671.5 |
| 6 | BCAN | brevican | NM_021948.5 |
| 7 | BCL2L15 | BCL2 like 15 | NM_001010922.3 |
| 8 | C1orf172 | keratinocyte differentiation factor 1 | NM_152365.3 |
| 9 | CAPS | calcyphosine | NM_004058.5 |
| 10 | CBLC | Cbl proto-oncogene C | NM_012116.4 |
| 11 | CDH1 | cadherin 1 | NM_004360.5 |
| 12 | CEACAM5 | carcinoembryonic antigen related cell adhesion molecule 5 | NM_004363.5 |
| 13 | CEACAM6 | carcinoembryonic antigen related cell adhesion molecule 6 | NM_002483.7 |
| 14 | CHMP4C | multivesicular body protein 4C | NM_152284.4 |
| 15 | CLCA2 | chloride channel accessory 2 | NM_006536.7 |
| 16 | CLDN4 | claudin 4 | NM_001305.4 |
| 17 | COL11A2 | collagen type XI alpha 2 chain | NM_080680.2 |
| 18 | CRB3 | crumbs cell polarity complex component 3 | NM_139161.5 |
| 19 | CTSE | cathepsin E | NM_001910.4 |
| 20 | CUBN | cubilin | NM_001081.3 |
| 21 | CYP2B7P1 | cytochrome P450 family 2 subfamily B member 7, pseudogene | NR_001278.1 |
| 22 | DLX5 | distal-less homeobox 5 | NM_005221.6 |
| 23 | DMGDH | dimethylglycine dehydrogenase | NM_013391.3 |
| 24 | ELF3 | E74 like ETS transcription factor 3 | NM_004433.5 |
| 25 | EMX2 | empty spiracles homeobox 2 | NM_004098.4 |
| 26 | EMX2OS | EMX2 opposite strand/antisense RNA | NR_002791.2 |
| 27 | EPCAM | epithelial cell adhesion molecule | NM_002354.2 |
| 28 | ERBB3 | erb-b2 receptor tyrosine kinase 3 | NM_001982.3 |
| 29 | ESR1 | estrogen receptor 1 | NM_000125.3 |
| 30 | FAM171A2 | family with sequence similarity 171 member A2 | NM_198475.2 |
| 31 | FOLH1 | folate hydrolase 1 | NM_004476.3 |
| 32 | GABRP | gamma-aminobutyric acid type A receptor pi subunit | NM_014211.3 |
| 33 | GATA3 | GATA binding protein 3 | NM_001002295.2 |
| 34 | GCNT3 | glucosaminyl (N-acetyl) transferase 3, mucin type | NM_004751.3 |

TABLE 1-continued

84 Gene Classifier Biomarker Signature for Pan-Cancer COCA subtyping.

| SEQ ID NO. | Gene Symbol | Gene Name | GenBank Accession Number* |
|---|---|---|---|
| 35 | GPC2 | glypican 2 | NM_152742.3 |
| 36 | GPR35 | G protein-coupled receptor 35 | NM_001195381.1 |
| 37 | GPRC5A | G protein-coupled receptor class C group 5 member A | NM_003979.3 |
| 38 | GRHL2 | grainyhead like transcription factor 2 | NM_024915.3 |
| 39 | HNF1A | HNF1 homeobox A | NM_000545.6 |
| 40 | HPX | hemopexin | NM_000613.3 |
| 41 | IYD | iodotyrosine deiodinase | NM_203395.2 |
| 42 | KRT18 | keratin 18 | NM_000224.3 |
| 43 | KRT6A | keratin 6A | NM_005554.4 |
| 44 | KRT6B | keratin 6B | NM_005555.4 |
| 45 | KRT81 | keratin 81 | NM_002281.3 |
| 46 | KRT8 | keratin 8 | NM_002273.3 |
| 47 | LAD1 | ladinin 1 | NM_005558.3 |
| 48 | LCK | LCK proto-oncogene, Src family tyrosine kinase | NM_005356.5 |
| 49 | LGALS4 | galectin 4 | NM_006149.4 |
| 50 | LYPD1 | LY6/PLAUR domain containing 1 | NM_144586.6 |
| 51 | MARVELD3 | MARVEL domain containing 3 | NM_052858.5 |
| 52 | MEG3 | maternally expressed 3 | NR_046473.1 |
| 53 | MUC13 | mucin 13, cell surface associated | NM_033049.4 |
| 54 | MUC16 | mucin 16, cell surface associated | NM_024690.2 |
| 55 | MUC4 | mucin 4, cell surface associated | NM_018406.7 |
| 56 | MYCN | MYCN proto-oncogene, bHLH transcription factor | NM_005378.6 |
| 57 | NAPSA | napsin A aspartic peptidase | NM_004851.3 |
| 58 | NKX3-1 | NK3 homeobox 1 | NM_006167.4 |
| 59 | NPR1 | natriuretic peptide receptor 1 | NM_000906.4 |
| 60 | PAX8 | paired box 8 | NM_003466.4 |
| 61 | PRAME | preferentially expressed antigen in melanoma | NM_206956.3 |
| 62 | PSCA | prostate stem cell antigen | NM_005672.5 |
| 63 | PVRL4 | nectin cell adhesion molecule 4 | NM_030916.3 |
| 64 | S100P | calcium binding protein P | NM_005980.3 |
| 65 | SALL4 | spalt like transcription factor 4 | NM_020436.5 |
| 66 | SFTPD | surfactant protein D | NM_003019.5 |
| 67 | SILV | premelanosome protein | NM_006928.4 |
| 68 | SIT1 | signaling threshold regulating transmembrane adaptor 1 | NM_014450.3 |
| 69 | SLC26A4 | solute carrier family 26 member 4 | NM_000441.1 |
| 70 | SLC3A1 | solute carrier family 3 member 1 | NM_000341.3 |
| 71 | SLC45A3 | solute carrier family 45 member 3 | NM_033102.3 |
| 72 | SOX17 | SRY-box 17 | NM_022454.4 |
| 73 | SPDEF | SAM pointed domain containing ETS transcription factor | NM_012391.3 |
| 74 | SPINT2 | serine peptidase inhibitor, Kunitz type 2 | NM_021102.4 |
| 75 | TCEAL5 | transcription elongation factor A like 5 | NM_001012979.3 |
| 76 | TG | thyroglobulin | NM_003235.5 |
| 77 | TMEM27 | collectrin, amino acid transport regulator | NM_020665.6 |
| 78 | TP63 | tumor protein p63 | NM_003722.5 |
| 79 | TRPS1 | transcriptional repressor GATA binding 1 | NM_001330599.1 |
| 80 | TSPAN8 | tetraspanin 8 | NM_004616.3 |
| 81 | UPK3B | uroplakin 3B | NM_001347684.1 |
| 82 | VTN | vitronectin | NM_000638.4 |
| 83 | ZNF578 | zinc finger protein 578 | NM_001099694.2 |
| 84 | ZNF695 | zinc finger protein 695 | NM_020394.5 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 2

Nearest centroid classifier coefficients of 84 Gene Classifier Biomarker Signature for Pan-Cancer COCA subtyping.

| # | Gene Symbol | C1 (ACC/PCPG) | C2 (GBM/LGG) | C3 (OV) | C4 (Squamous-like) | C6 (LUAD enriched) | C8 (PAAD/ some STAD) | C9 (UCS) |
|---|---|---|---|---|---|---|---|---|
| 1 | A1BG | 1.591560699 | 0.190424 | 0.486501004 | −0.428197254 | 0.412635759 | −0.184279 | 2.001627705 |
| 2 | ACPP | −3.165733781 | −3.12929 | 1.422642856 | 1.55810748 | 1.220541761 | 0.3613543 | −0.523609534 |
| 3 | APC2 | 5.927921166 | 9.535164 | −0.596869926 | 0.426709368 | −0.235550248 | 0.211678867 | 0.296218394 |
| 4 | AQP5 | 0.913265915 | −1.5756 | 6.077199618 | 0.038435948 | 3.968116521 | 5.439757901 | 4.689537595 |
| 5 | ASGR1 | 0.200382941 | 2.23723 | −0.270715575 | −0.385421722 | 0.9311113 | 0.377002269 | 1.767020071 |
| 6 | BCAN | 3.407338299 | 11.97624 | −1.053982755 | −0.662093738 | −0.729179033 | 0.649031299 | 0.667042943 |
| 7 | BCL2L15 | −0.658510708 | 0.077946 | 0.865164587 | −0.382856173 | 4.273114175 | 5.648586443 | −0.38038599 |
| 8 | C1orf172 | −7.367511726 | −8.11012 | 0.639328401 | 0.482516142 | 0.16674242 | −0.401651641 | −2.035170988 |
| 9 | CAPS | −0.328076695 | −0.34918 | 2.841784698 | −1.13544035 | 1.075257629 | 0.923666447 | 0.259472216 |
| 10 | CBLC | −8.155167351 | −8.15517 | 0.559363299 | 1.283503926 | 0.054904876 | 0.803955968 | −1.909451133 |
| 11 | CDH1 | −11.31993378 | −6.63507 | −0.611897157 | 0.320830787 | 0.259254437 | 0.32354087 | −2.417624306 |
| 12 | CEACAM5 | −4.263447619 | −4.26345 | −2.162761329 | 5.453807243 | 8.01040042 | 8.25154716 | −1.643025427 |
| 13 | CEACAM6 | −6.692665202 | −6.69267 | −1.411084364 | 3.660636032 | 8.117243572 | 7.181029674 | −2.853743681 |
| 14 | CHMP4C | −4.851564145 | −6.7881 | 0.477705202 | 0.092903499 | 0.246039693 | 0.425978288 | −1.619930594 |

TABLE 2-continued

Nearest centroid classifier coefficients of 84 Gene Classifier Biomarker Signature for Pan-Cancer COCA subtyping.

| | | | | | | | | |
|---|---|---|---|---|---|---|---|---|
| 15 | CLCA2 | −1.916026013 | −0.55212 | −2.135469493 | 10.56468928 | 0.196047759 | −0.982688048 | 0.230995571 |
| 16 | CLDN4 | −7.769800248 | −8.52437 | 1.293661429 | −0.21590352 | 0.923225733 | 0.698989001 | −2.196157068 |
| 17 | COL11A2 | 0.994719726 | 3.794411 | 0.981227344 | −0.355884432 | −0.290171902 | −0.134024256 | 5.747006193 |
| 18 | CRB3 | −6.855921321 | −6.69387 | 0.314038459 | −0.051924366 | 0.42596628 | 0.230134355 | −2.12978152 |
| 19 | CTSE | −2.769179309 | −2.76918 | 0.690060563 | −0.068850571 | 8.211338748 | 10.27849106 | −1.795164025 |
| 20 | CUBN | 1.417595067 | 1.109969 | −1.06751464 | −1.098119051 | 0.200954954 | 0.214406457 | 1.001364945 |
| 21 | CYP2B7P1 | −0.494004573 | 0.493388 | −0.20904464 | −0.38882331 | 7.020240242 | 1.642138931 | 0.554846851 |
| 22 | DLX5 | 0.646764837 | −0.46515 | −0.543489219 | 3.043312263 | −1.037762982 | −0.615048606 | 3.664621768 |
| 23 | DMGDH | 1.35983288 | 1.246526 | −0.621678415 | −1.957477961 | 0.403167757 | 0.050041264 | −0.042151268 |
| 24 | ELF3 | −9.499613685 | −8.35834 | 1.621031579 | 0.270463158 | 1.261978364 | 1.664172061 | −1.774337463 |
| 25 | EMX2 | −1.445515678 | 4.196057 | 7.930390253 | −0.743521137 | −3.08024833 | −1.20337606 | 5.823681705 |
| 26 | EMX2OS | −1.40599953 | 4.680959 | 6.731039756 | −1.182024547 | −3.142205278 | −1.044827924 | 5.399413819 |
| 27 | EPCAM | −4.140528206 | −8.15621 | 1.301641135 | −0.969949548 | 1.349981921 | 1.210777667 | −0.808127169 |
| 28 | ERBB3 | −6.795539466 | −2.20761 | −0.171425783 | −0.850309305 | 0.543205553 | 0.488891046 | −1.571378197 |
| 29 | ESR1 | −1.563757872 | −2.7205 | 4.824366357 | −0.395784527 | 0.80814913 | −0.646508959 | −0.041535695 |
| 30 | FAM171A2 | 2.31912146 | 3.133851 | 2.782191887 | −0.20635555 | 0.23640564 | −0.553185081 | 4.13232199 |
| 31 | FOLH1 | 0.35530613 | 1.32629 | 0.070865602 | −0.437336881 | −0.404293953 | −0.516227658 | 0.984459412 |
| 32 | GABRP | −3.114382282 | −3.80051 | 2.138616034 | 2.054140007 | −0.13455569 | 5.495459292 | 0.876924899 |
| 33 | GATA3 | 3.645314335 | −4.46319 | 1.041365419 | 0.137891422 | −0.30939716 | 0.245236202 | −0.485018337 |
| 34 | GCNT3 | −3.715677872 | −4.43208 | −0.425219053 | 1.24405515 | 3.332011974 | 6.140028092 | −2.627063776 |
| 35 | GPC2 | 0.327681714 | 3.748559 | 0.567306982 | 0.383564177 | 0.020301437 | −0.493055636 | 4.27187925 |
| 36 | GPR35 | −1.123275158 | 0.288748 | 0.479762937 | −0.401845781 | 0.612377482 | 3.964562506 | 1.02539215 |
| 37 | GPRC5A | −5.029113731 | −6.47264 | −1.03988769 | 0.471927094 | 2.504432044 | 2.440959491 | −1.902607145 |
| 38 | GRHL2 | −9.186320721 | −9.01009 | 0.20905294 | 0.759772508 | 0.222957527 | −0.501711577 | −2.025188838 |
| 39 | HNF1A | −0.226398309 | 0.326606 | −0.566429337 | −0.634513541 | −0.056397283 | 3.532952512 | 0.664824374 |
| 40 | HPX | 0.285105569 | −0.08725 | −0.761181725 | −0.99545754 | 0.077064824 | 0.031571949 | 0.655698572 |
| 41 | IYD | −3.48501457 | −3.48501 | −2.700731814 | −1.942508868 | 2.764256302 | 4.516203307 | −2.338163874 |
| 42 | KRT18 | −6.139551755 | −9.93225 | 0.824379787 | −1.150398992 | 0.366193169 | 0.669054426 | −1.559549225 |
| 43 | KRT6A | −3.978012535 | −3.97801 | 3.985705153 | 13.04837042 | 1.834983617 | 2.826759232 | 0.495449701 |
| 44 | KRT6B | −3.679513879 | −3.67951 | −0.284781052 | 10.86983161 | −0.095874456 | 4.031758881 | −0.319655407 |
| 45 | KRT81 | −1.52156723 | −2.24431 | 1.219674513 | 0.808360415 | 0.685287495 | 0.157557306 | 1.332452992 |
| 46 | KRT8 | −9.333378281 | −12.0127 | 0.923200159 | −0.888982445 | 0.25864778 | 1.104030262 | −1.049517897 |
| 47 | LAD1 | −9.54391772 | −9.93659 | 0.152727678 | 2.525900274 | 1.096406409 | 2.02745431 | −1.338565911 |
| 48 | LCK | −2.653249024 | −4.15782 | −0.449932121 | 0.595456972 | 1.114873169 | 1.294851611 | −0.905250193 |
| 49 | LGALS4 | −1.069860082 | −0.88856 | −0.804776299 | −0.636711502 | 0.902648195 | 9.957840161 | 0.300844381 |
| 50 | LYPD1 | 0.161356715 | 4.620573 | 6.06218977 | 0.619464566 | 0.866852785 | 1.287462226 | 2.488687449 |
| 51 | MARVELD3 | −6.499693064 | −1.92762 | −0.006137317 | 0.236649367 | 0.110533207 | 0.419749056 | −1.459194862 |
| 52 | MEG3 | 6.987769361 | 4.00401 | 0.481443128 | −0.367973396 | 0.187829444 | 2.037867641 | 5.549924389 |
| 53 | MUC13 | −1.096164161 | −1.549 | −0.857929123 | −0.216081121 | 3.60927036 | 9.342999034 | −0.087884353 |
| 54 | MUC16 | −2.940429889 | −2.94043 | 8.971152269 | 3.553030115 | 5.922759027 | 2.391002348 | 2.159619147 |
| 55 | MUC4 | −2.659938287 | −1.76141 | 1.013937899 | 4.360400601 | 6.293886393 | 4.455995593 | 0.8936279 |
| 56 | MYCN | 2.635001351 | 3.722476 | 3.48370589 | −0.476428956 | −0.4996297 | −0.139261692 | 4.259965299 |
| 57 | NAPSA | −1.134449647 | −0.6277 | −0.350262749 | 0.121656227 | 11.53466505 | −0.206023725 | −0.551300842 |
| 58 | NKX3-1 | 0.643122217 | −0.8988 | −1.012928267 | 0.87446207 | 0.131533121 | 0.091873999 | −0.013147747 |
| 59 | NPR1 | 1.562673445 | −1.70035 | 4.826134025 | −0.898468302 | 0.426172792 | 0.791217063 | 0.909336394 |
| 60 | PAX8 | −1.207977403 | −2.70163 | 6.131772035 | −0.109570392 | −0.507568017 | 0.425575927 | 0.567460764 |
| 61 | PRAME | −2.720513358 | −3.0116 | 7.417738065 | 4.107800576 | 1.634537806 | −0.732218434 | 8.835740874 |
| 62 | PSCA | −2.62692522 | −1.51466 | 1.088832807 | 2.403172672 | 0.853737331 | 6.468730165 | −0.867506614 |
| 63 | PVRL4 | −7.123332103 | −7.84158 | 0.298515276 | 2.072952358 | 1.11395964 | 0.537458726 | −2.175556637 |
| 64 | S100P | −4.176354266 | −4.39339 | −2.039708839 | 2.60206496 | 3.54339421 | 5.588006332 | −0.835327459 |
| 65 | SALL4 | −0.350139755 | −1.98283 | 0.992610931 | 0.242440795 | 0.631851425 | 1.50741502 | 2.172219002 |
| 66 | SFTPD | 1.229072592 | 0.156327 | 1.095837733 | 0.844728495 | 6.616682345 | −0.138899031 | −0.528759079 |
| 67 | SILV | −1.601355906 | −3.16131 | 0.436716938 | −0.17041022 | 0.318281992 | 0.27070394 | 0.049533868 |
| 68 | SIT1 | −2.339171989 | −3.35217 | −0.160872017 | 0.621892503 | 1.468402409 | 0.74432008 | −1.226672618 |
| 69 | SLC26A4 | −0.01413008 | 0.420072 | −1.783069972 | −0.415510022 | 0.74827946 | −0.100896769 | −0.464161483 |
| 70 | SLC3A1 | 1.225854746 | 0.996711 | −0.32436489 | −1.197295399 | −0.603148658 | 5.542018189 | 0.717943528 |
| 71 | SLC45A3 | −2.005759994 | −0.41185 | −0.428424528 | −0.241045139 | 0.557739049 | 1.726290953 | 0.128310421 |
| 72 | SOX17 | 0.824116164 | −0.22888 | 6.125476978 | −1.080390132 | −0.166935984 | 0.604218197 | 1.286142427 |
| 73 | SPDEF | −2.615781968 | −2.0345 | 3.94966981 | −0.755535616 | 4.925193925 | 4.243866593 | 0.699764031 |
| 74 | SPINT2 | −2.997432839 | −4.83916 | 1.007795827 | 0.294659358 | 0.15758716 | 0.166037725 | −0.979250422 |
| 75 | TCEAL5 | 4.349410995 | 5.379822 | 1.642558611 | −0.898540151 | −0.528496105 | 0.788010053 | 4.759050684 |
| 76 | TG | 2.696748103 | −0.10465 | −1.217878931 | 0.390892921 | −0.793389805 | −0.297668711 | 1.286415669 |
| 77 | TMEM27 | −0.42619294 | −0.29365 | −0.1091435 | −0.496636878 | 0.747255703 | 0.386605101 | −0.460703305 |
| 78 | TP63 | −2.443322255 | −2.69429 | −1.072539715 | 8.079773017 | 1.080093521 | −0.122917429 | 0.715521461 |
| 79 | TRPS1 | −0.827302587 | 0.82757 | 1.115573024 | 0.379838983 | −0.553191739 | −0.163032265 | 1.067422295 |
| 80 | TSPAN8 | −1.517176876 | −1.38543 | 1.264805902 | −0.971215985 | 4.123187886 | 8.120119283 | 1.88608684 |
| 81 | UPK3B | −1.800031107 | −1.79259 | 6.496391778 | 2.591465189 | 1.916362767 | 1.31370249 | 1.253864936 |
| 82 | VTN | 4.532732542 | 0.962046 | −0.35391519 | −0.827839727 | 0.374371855 | 3.646375202 | 0.21090879 |
| 83 | ZNF578 | 1.940365745 | 2.606116 | 1.274215935 | −2.128937852 | −0.532541888 | −0.12176826 | 1.417239081 |
| 84 | ZNF695 | −2.395893789 | −0.97465 | 2.29727236 | 1.015039672 | −0.170693901 | −0.682198412 | 2.909908974 |

| # | Gene Symbol | C10 (BRCA/Basal) | C12 (UCEC) | C14 (PAAD) | C15 (CESC) | C16 (BLCA) | C17 (TGCT) | C19 (COAD/READ) |
|---|---|---|---|---|---|---|---|---|
| 1 | A1BG | 0.142304769 | −0.093163359 | −1.141696682 | −1.152290675 | −1.29740042 | 0.256130124 | −1.788698924 |
| 2 | ACPP | −1.398401725 | −0.082101813 | 10.45064724 | 1.42121 | 0.266257162 | 0.477828173 | 0.992457174 |
| 3 | APC2 | −0.572616388 | −0.977273763 | 0.32549264 | 0.054659498 | 0.405219188 | 1.45040744 | 0.15536217 |
| 4 | AQP5 | 3.702869943 | 6.247684679 | −1.136288477 | 8.250686508 | −2.413179516 | 2.019598373 | −0.061400955 |

TABLE 2-continued

Nearest centroid classifier coefficients of 84 Gene Classifier Biomarker Signature for Pan-Cancer COCA subtyping.

| | | | | | | | | |
|---|---|---|---|---|---|---|---|---|
| 5 | ASGR1 | −0.374333329 | −0.307671908 | −1.422479203 | −0.69544287 | −0.284590427 | 0.811900301 | 0.284656903 |
| 6 | BCAN | −0.843138597 | −0.389425497 | −2.101665722 | 0.113052513 | −0.411742591 | 2.451102537 | 1.398031108 |
| 7 | BCL2L15 | −0.509343675 | 2.21556825 | −0.416331352 | 5.642847062 | −0.076320616 | −0.539990486 | 5.956925607 |
| 8 | C1orf172 | 0.377167732 | 0.541078744 | 0.28000935 | 0.529249282 | 0.78721152 | −0.331669012 | 0.205165485 |
| 9 | CAPS | 1.236614303 | 3.401999923 | 1.140742546 | 3.129590389 | 3.356392461 | −1.598575877 | −1.041036365 |
| 10 | CBLC | 0.528896861 | 0.860866464 | 0.983689368 | 1.366858965 | 2.004650922 | −1.590854285 | 1.462118274 |
| 11 | CDH1 | 0.147729378 | 0.016506631 | 0.816575199 | 0.187211685 | 0.578678097 | −1.440668807 | 0.796827631 |
| 12 | CEACAM5 | −0.578531195 | −0.226926702 | 0.223892364 | 8.216176042 | 2.697562315 | −3.025546808 | 11.26786682 |
| 13 | CEACAM6 | 0.378171192 | −0.861664584 | −1.150176451 | 5.321201782 | 1.780316958 | 0.990910873 | 7.545948521 |
| 14 | CHMP4C | 0.932335566 | 0.332852097 | 0.654936052 | −0.061505461 | 0.701272543 | −2.076344669 | 0.955706036 |
| 15 | CLCA2 | 1.252518338 | −0.870513832 | 0.834994065 | 0.083375317 | 5.899414972 | 0.277783481 | −1.434642506 |
| 16 | CLDN4 | 0.596506064 | 0.783384706 | 0.695706592 | 0.872264084 | 1.666131843 | −4.130304775 | 1.506307594 |
| 17 | COL11A2 | 1.152615114 | 1.094477267 | −0.512589565 | 0.34882784 | −0.277012497 | 0.921823497 | −0.972050734 |
| 18 | CRB3 | −0.252190917 | 0.447730499 | 0.314262173 | 0.485822293 | 0.422819651 | −1.015012817 | 0.63102577 |
| 19 | CTSE | −1.579272399 | −0.27402142 | −0.123593233 | 4.329326574 | 3.964690014 | 0.131319517 | 6.509851516 |
| 20 | CUBN | −0.042341755 | 0.692484506 | −0.083311834 | −1.016397158 | −1.291707376 | −0.060942034 | −1.2605976 |
| 21 | CYP2B7P1 | −0.793782659 | −1.135804901 | −0.048029795 | 2.920741779 | −1.769335752 | −1.106667891 | 0.57204011 |
| 22 | DLX5 | 1.065680224 | 6.63897818 | 1.203219318 | 0.244733336 | 2.095413211 | −0.874548488 | −2.278703058 |
| 23 | DMGDH | −1.016515828 | −0.716060074 | 0.747670367 | −1.492260644 | −2.335607422 | −0.511890494 | −1.983626926 |
| 24 | ELF3 | 0.867636291 | 1.089943222 | −0.33693125 | 2.161246514 | 1.979945601 | −2.024525261 | 1.906780054 |
| 25 | EMX2 | 0.398485049 | 7.622270699 | −1.139800617 | 3.497783132 | 2.434679878 | −0.070065196 | −2.337175682 |
| 26 | EMX2OS | 0.35047227 | 6.672513444 | −0.771169469 | 2.651126602 | 1.918119816 | 0.003917034 | −2.749389229 |
| 27 | EPCAM | 1.070959088 | 1.65345969 | 0.656584363 | 1.491420181 | −0.23366156 | 0.118017267 | 2.502744305 |
| 28 | ERBB3 | 0.156681689 | −0.354419176 | 0.85480606 | 0.70559009 | 0.245664699 | −1.125976575 | 1.142628311 |
| 29 | ESR1 | −0.114307986 | 4.969542469 | 1.603982283 | 2.334162784 | −0.866991852 | −1.616321139 | −2.643912362 |
| 30 | FAM171A2 | 1.110078033 | 2.742226868 | −0.598712372 | 1.23539718 | 0.196442464 | 2.52966238 | −2.299101465 |
| 31 | FOLH1 | 1.342626401 | 1.95199662 | 7.506581427 | −1.68931756 | −1.160417237 | −1.194199537 | −0.990382338 |
| 32 | GABRP | 8.062957771 | 3.497605248 | 3.292130436 | 7.257298478 | −1.104614063 | −2.409859347 | 1.866998203 |
| 33 | GATA3 | 2.883744656 | −1.322536343 | 0.362300268 | 0.172939031 | 5.863126341 | 0.347938903 | −1.305257494 |
| 34 | GCNT3 | −2.229182519 | 1.453042898 | −1.612817806 | 4.45653155 | −2.101854264 | −1.198296139 | 5.978745374 |
| 35 | GPC2 | 1.844529239 | 1.87662419 | −0.31412767 | −0.281008532 | 1.248099969 | 3.603718475 | −0.446098297 |
| 36 | GPR35 | −0.201147094 | 1.145430196 | −0.633581001 | 3.403228537 | −0.074926063 | 0.037914492 | 4.997511501 |
| 37 | GPRC5A | 0.136594075 | −0.047037042 | −1.729389157 | 1.713890286 | 0.947387044 | 1.099444707 | 2.341085357 |
| 38 | GRHL2 | 0.887932851 | 0.608466746 | 1.846078681 | 0.587744821 | 0.927526179 | −4.112841993 | 0.296403053 |
| 39 | HNF1A | −0.757149534 | 0.998266857 | −0.224121716 | 3.083804118 | −0.876897763 | −0.071449343 | 4.816960704 |
| 40 | HPX | 0.083502266 | 0.467027224 | 1.898436273 | −0.011129604 | −0.443467655 | 1.739428473 | −0.713289667 |
| 41 | IYD | −1.986600368 | −1.163865741 | 1.126629676 | 1.43730223 | 0.098371764 | −3.48501457 | 5.821174506 |
| 42 | KRT18 | −0.774406938 | 0.534341861 | 0.455271746 | 1.038944818 | 0.900515088 | −0.471025112 | 1.117607068 |
| 43 | KRT6A | 3.285148104 | 2.483810663 | −0.073242302 | 4.424176683 | 4.698929835 | −3.375318162 | 0.482454829 |
| 44 | KRT6B | 6.929849448 | −0.029392703 | −0.881504967 | 3.541676869 | 2.041513217 | −3.679513879 | 2.619439855 |
| 45 | KRT81 | 3.704809399 | 1.125852117 | −1.180411884 | 1.855047045 | −0.224822743 | −1.682654755 | −1.136304837 |
| 46 | KRT8 | 0.117987473 | 0.541422454 | −0.071910723 | 1.371770589 | 1.338626534 | −0.317434922 | 1.536661174 |
| 47 | LAD1 | 1.117718225 | 0.900829355 | −0.184554726 | 1.845819432 | 2.28378527 | −1.0294741 | 2.021237694 |
| 48 | LCK | 0.323828061 | −0.2698455 | −0.135093489 | 0.809447978 | −0.427656591 | 1.876095595 | 0.766125516 |
| 49 | LGALS4 | −1.049805056 | −0.658445291 | 0.33823429 | 2.270150332 | 1.671819995 | 1.025358005 | 10.63263886 |
| 50 | LYPD1 | 0.318704537 | 2.561660067 | −1.46291243 | 0.106783622 | −0.846380974 | 0.579452651 | −1.457927861 |
| 51 | MARVELD3 | 0.594064846 | 0.59864298 | 0.746088507 | 0.673220178 | 0.379141989 | −1.349340309 | 0.960362538 |
| 52 | MEG3 | −0.760697048 | −0.559506246 | 0.124435896 | −0.790286218 | 0.176547542 | 7.212428882 | −0.102624496 |
| 53 | MUC13 | −0.415482063 | 2.373448458 | 3.347855433 | 9.337472272 | −1.260341969 | −1.137285921 | 11.16914163 |
| 54 | MUC16 | 5.749271478 | 7.257302838 | −0.380117549 | 9.47128499 | −0.667829704 | 2.503910209 | −1.68279375 |
| 55 | MUC4 | −0.533649289 | 1.580638241 | 1.704056599 | 7.6185769 | 1.358543899 | 3.416007758 | 4.848907641 |
| 56 | MYCN | 1.167011131 | 1.749261819 | −3.028046397 | 0.244478213 | 0.693171089 | 6.57493164 | 0.586544197 |
| 57 | NAPSA | −0.568068159 | 0.272590794 | −0.267650347 | 0.491103798 | −0.068387887 | 0.784909839 | −0.516593433 |
| 58 | NKX3-1 | 0.636142588 | −0.165152927 | 8.791444726 | 1.213527947 | 0.111824365 | 0.401176282 | −1.098810432 |
| 59 | NPR1 | −0.108559874 | −0.014674711 | −0.783482295 | −1.047763786 | −1.086165265 | −0.51156436 | −1.013472417 |
| 60 | PAX8 | −1.679043287 | 6.175626455 | −1.300676688 | 3.829761838 | −0.264941996 | 0.019241642 | 0.199759138 |
| 61 | PRAME | 5.753805128 | 8.637405593 | −1.641025038 | 2.240303364 | −1.86413095 | 6.249324024 | 0.732324816 |
| 62 | PSCA | 2.380934424 | 0.822962284 | 5.024448953 | 5.074590237 | 9.409030075 | −1.378514517 | 0.823284273 |
| 63 | PVRL4 | 1.983169736 | 0.54330796 | 0.274629626 | 1.209370824 | 2.956273849 | −1.709650966 | −0.443057331 |
| 64 | S100P | 3.387292842 | 0.722588023 | 0.264728445 | 6.102225171 | 7.587401555 | −0.745010036 | 6.222215668 |
| 65 | SALL4 | 0.212011363 | −0.183118884 | −0.428196415 | 1.736697609 | 1.763666611 | 6.22003894 | 1.160887388 |
| 66 | SFTPD | −0.864741869 | 0.18743199 | 0.85637944 | −0.169964303 | −1.953003098 | 0.810342471 | −3.059355397 |
| 67 | SILV | −0.445152541 | 0.023561013 | −0.906600385 | 1.276911935 | 0.671250555 | −0.419750375 | 0.364343543 |
| 68 | SIT1 | 0.404484797 | −0.245179126 | −0.698370063 | −0.228329389 | −0.700949754 | 1.862224753 | 0.160038551 |
| 69 | SLC26A4 | −0.242562803 | −0.736362299 | 4.542023228 | 0.049925703 | −1.244893781 | −1.393279547 | −0.773795962 |
| 70 | SLC3A1 | −0.811991759 | 1.503175223 | 0.81337641 | 0.685335393 | −0.830561409 | 0.02998455 | 4.234950007 |
| 71 | SLC45A3 | 0.50351858 | −0.257430773 | 7.798304016 | 0.259038112 | 0.761165507 | 1.057588337 | 1.253011444 |
| 72 | SOX17 | −0.436621464 | 6.590489885 | 0.258734252 | 0.190327448 | −0.537074063 | 4.1051736 | −0.639722737 |
| 73 | SPDEF | 2.428928058 | 4.878948809 | 9.396200085 | 5.896810841 | 0.785079512 | −1.183433789 | 3.426972043 |
| 74 | SPINT2 | 0.199553149 | 0.669655069 | 0.202002754 | 0.813009857 | 0.747461864 | −0.67968284 | 0.224352664 |
| 75 | TCEAL5 | −0.580215651 | 0.283236555 | 1.291973501 | −0.314854034 | −0.207630749 | 1.239038231 | −1.642797685 |
| 76 | TG | −1.043977276 | −1.109552249 | 1.299196722 | −1.24118987 | −0.588195791 | −0.92548737 | 0.175292614 |
| 77 | TMEM27 | 0.248102359 | 0.030206129 | 0.611157159 | −0.754191803 | −0.750158332 | 1.251273614 | −1.235570332 |
| 78 | TP63 | 1.282401189 | −1.071684619 | 3.203409462 | −1.13139572 | 6.245170227 | −0.345850774 | −2.304303836 |
| 79 | TRPS1 | 3.153356243 | 1.248382334 | 0.226726961 | 0.003939999 | −2.35803211 | −1.170459499 | −1.794640325 |
| 80 | TSPAN8 | −1.77985797 | 0.74692949 | 6.457395474 | 4.704465483 | −0.385074926 | −0.435573001 | 8.97062099 |
| 81 | UPK3B | 0.43781618 | 1.273683944 | −0.408516441 | 2.151943812 | 7.898733759 | −0.735658973 | −0.139912799 |
| 82 | VTN | −1.022686104 | −1.195484585 | −0.273276881 | −1.471670906 | 0.728314508 | 3.181634913 | −0.582351194 |

TABLE 2-continued

Nearest centroid classifier coefficients of 84 Gene Classifier Biomarker Signature for Pan-Cancer COCA subtyping.

| | | | | | | | | |
|---|---|---|---|---|---|---|---|---|
| 83 | ZNF578 | −0.128482728 | −0.291752675 | 0.60523606 | −2.466912276 | −1.115858745 | 5.469695435 | −1.515460348 |
| 84 | ZNF695 | 2.994868611 | 2.77909196 | −1.075168344 | 2.286781576 | 1.644923103 | 3.609635955 | 1.952089723 |

| # | Gene Symbol | C20 (SARC/MESO) | C21 (KIRK/KICH/KIRP) | C22 (Liver) | C24 (BRCA/Luminal) | C25 (THYM) | C26 (SKCM/UVM) | C28 (THCA) |
|---|---|---|---|---|---|---|---|---|
| 1 | A1BG | 0.070192984 | −0.940840591 | 8.703413543 | 0.936369381 | 1.706237879 | 1.914831468 | 0.703529067 |
| 2 | ACPP | −2.032541038 | −2.305500467 | −4.40459131 | −1.024439493 | −2.066553063 | −3.741468299 | 0.699426376 |
| 3 | APC2 | 0.552360013 | −0.679752407 | −0.062564922 | −0.527174725 | −0.177801985 | 1.332087657 | −1.406046015 |
| 4 | AQP5 | −1.419094969 | −2.627502329 | −2.379706191 | −0.280015058 | 0.67166607 | −1.438430189 | 3.948999547 |
| 5 | ASGR1 | 0.462676231 | −0.369411855 | 9.174063668 | −1.440166184 | −0.048667321 | −1.316415138 | 1.003468362 |
| 6 | BCAN | −0.209671799 | 0.222422862 | 0.598814814 | −0.685014857 | −2.971866954 | 7.441867064 | −2.689173959 |
| 7 | BCL2L15 | −0.946597411 | 0.308006633 | −0.847993525 | −0.339415371 | 0.44529515 | −1.396188006 | −1.219332417 |
| 8 | C1orf172 | −7.714313141 | −2.053892696 | −1.961055619 | 0.097896284 | −1.121520119 | −5.883858505 | 0.420348593 |
| 9 | CAPS | −0.499052174 | −1.362494555 | −0.691670099 | 0.575620059 | 0.228128949 | −0.326249828 | 1.883752499 |
| 10 | CBLC | −8.155167351 | −3.648064102 | 0.283666077 | 0.197383744 | −8.155167351 | −8.155167351 | −4.683902455 |
| 11 | CDH1 | −7.229104847 | −1.902809546 | −0.803408059 | 0.453092886 | −1.794492653 | −0.380697254 | 1.07759058 |
| 12 | CEACAM5 | −4.263447619 | −4.263447619 | −4.263447619 | 3.43408992 | −4.263447619 | −3.826859325 | −3.766911393 |
| 13 | CEACAM6 | −6.003097658 | −6.22642964 | −6.020466183 | 2.793954656 | −5.749231419 | −6.088214272 | −1.029763418 |
| 14 | CHMP4C | −6.433893852 | −0.448980057 | −0.477565154 | 0.166274869 | −3.416609246 | −6.4170014 | 0.423295456 |
| 15 | CLCA2 | 1.090083657 | −1.916425099 | −2.448293094 | 2.423949605 | 0.511588318 | −0.16703996 | −0.923829634 |
| 16 | CLDN4 | −6.877306455 | −0.800472122 | −4.850938463 | −0.062787487 | −6.750496629 | −8.258170243 | 1.193098579 |
| 17 | COL11A2 | 0.407171494 | −0.522028403 | −1.162577547 | −1.391989324 | 2.822133446 | 4.012255459 | 0.998530701 |
| 18 | CRB3 | −6.899881762 | 0.409378715 | 0.082599609 | −0.202979549 | −3.405323461 | −5.927493049 | 0.442041688 |
| 19 | CTSE | −2.104241431 | 0.366273475 | −1.243260786 | −2.250040026 | −2.122740123 | −1.826195711 | 5.586773138 |
| 20 | CUBN | 0.713604848 | 7.281399905 | −1.384529654 | −0.145536797 | 1.410829201 | 3.566340978 | 3.20938295 |
| 21 | CYP2B7P1 | −0.654635147 | −1.447176918 | 5.139802834 | 6.622628205 | −1.379336644 | −1.212199304 | −0.964049728 |
| 22 | DLX5 | 0.462490967 | 0.017699215 | −3.265329736 | −0.745686562 | −2.117303943 | −0.829299281 | −0.068606829 |
| 23 | DMGDH | 0.028856242 | 6.060504719 | 6.702437958 | −0.060898439 | −0.46134749 | −1.489004211 | 2.38214753 |
| 24 | ELF3 | −7.606527581 | −0.555341599 | −0.334664939 | 0.302735788 | −5.416983065 | −8.778305188 | −1.61788093 |
| 25 | EMX2 | 2.802771238 | 7.074822861 | −3.08024833 | 1.035384246 | −1.557188268 | −0.213597469 | −1.488833995 |
| 26 | EMX2OS | 2.520378612 | 7.353718721 | −3.593640608 | 1.294980889 | −1.893334068 | −0.333268626 | −1.117234841 |
| 27 | EPCAM | −8.94327619 | −1.582907817 | −6.179887918 | 0.150227096 | −3.89203662 | −9.927578427 | 1.469515171 |
| 28 | ERBB3 | −7.397006842 | 0.362674201 | 0.676372657 | 1.354976731 | −7.751611174 | 1.393383686 | −0.864197462 |
| 29 | ESR1 | −0.204263771 | 0.353961842 | −0.001186471 | 7.045755877 | −0.917732083 | −0.567345455 | 1.658056187 |
| 30 | FAM171A2 | 0.843521911 | −1.147803639 | −1.94488491 | −0.67709113 | −0.913518602 | −0.123166538 | 2.177241264 |
| 31 | FOLH1 | −0.285087483 | 2.107020634 | 2.114399746 | −0.44262496 | −3.693628465 | −1.90866141 | −0.126630866 |
| 32 | GABRP | −2.303619388 | −1.113604356 | −2.60527593 | 2.880519078 | −2.969804846 | −0.477412964 | −2.451544871 |
| 33 | GATA3 | −0.479072713 | −0.694342037 | −2.42000097 | 7.039537351 | 2.449239776 | −2.642455615 | 1.305924613 |
| 34 | GCNT3 | −3.369932214 | 3.012084991 | 0.745283917 | −3.199989256 | 0.677330491 | −4.065793513 | −0.452261295 |
| 35 | GPC2 | −0.655639972 | −1.345174813 | −2.097850016 | −0.520643983 | 2.326152106 | −0.721335705 | −2.085120953 |
| 36 | GPR35 | −0.15384199 | 0.320806564 | −0.470378252 | −0.642499168 | 1.115849375 | −1.434965852 | −1.068214302 |
| 37 | GPRC5A | −1.978637673 | −3.708321529 | −7.617162596 | 1.869297678 | −7.799087331 | −2.526958538 | 1.836642695 |
| 38 | GRHL2 | −8.760984555 | −8.300732853 | −8.41380076 | 0.977699908 | −2.733003314 | −9.346544321 | −0.260490678 |
| 39 | HNF1A | −0.460004648 | 5.003097445 | 5.740038488 | −0.419983585 | −0.254057708 | −0.06916107 | −1.339783101 |
| 40 | HPX | 0.428825996 | −0.644318213 | 12.34302566 | 4.13452407 | −0.715914255 | −1.121106629 | −0.927626931 |
| 41 | IYD | −3.48501457 | 1.83359512 | 5.111462206 | 0.63980155 | −3.48501457 | −3.48501457 | 9.864317761 |
| 42 | KRT18 | −5.393634178 | −0.214336662 | 0.659378292 | 0.645722621 | −3.361767124 | −6.292360598 | 0.141599862 |
| 43 | KRT6A | −2.750394666 | −3.593741642 | −3.978012535 | −1.007177282 | 1.775950277 | −1.756754105 | −1.199299426 |
| 44 | KRT6B | −2.809563532 | −3.679513879 | −3.007677051 | 3.038039173 | 1.074967474 | −0.771604139 | −2.767720312 |
| 45 | KRT81 | −0.708340478 | −0.549017438 | −1.474487037 | 1.719278698 | 0.293233459 | −2.832035518 | 1.29934714 |
| 46 | KRT8 | −6.585518291 | −0.445328958 | 0.292357177 | 0.583940663 | −1.211875599 | −7.214684995 | 0.11941998 |
| 47 | LAD1 | −6.366889981 | −3.487703983 | −0.03314457 | −0.937855879 | −2.032988069 | −4.586601984 | −0.415235244 |
| 48 | LCK | −0.077998068 | 0.355214635 | −0.747932263 | −0.312039768 | 5.221543649 | −1.853755715 | −0.526016141 |
| 49 | LGALS4 | −0.883963009 | 1.366073433 | 9.773901918 | −1.137042557 | 0.240641913 | −1.598817352 | −0.203473823 |
| 50 | LYPD1 | 0.387124296 | −0.528951531 | 0.547288234 | −0.876913408 | 0.13379984 | 0.661428164 | −0.897772519 |
| 51 | MARVELD3 | −5.995262907 | −0.510050567 | −0.675659361 | 0.322410532 | −2.735366823 | −6.383666653 | −0.153513769 |
| 52 | MEG3 | 2.478280919 | −2.166933932 | −0.320863598 | 0.160100014 | 2.853324939 | −2.730675804 | −3.166451005 |
| 53 | MUC13 | −0.981854002 | 1.997077234 | 6.771194467 | −1.618112428 | −1.772933448 | −2.419188288 | −1.948580943 |
| 54 | MUC16 | −1.427646768 | −1.678538069 | −2.940429889 | 1.60919 | −1.668765178 | −2.940429889 | 1.33450999 |
| 55 | MUC4 | −3.199831606 | −0.551376679 | −2.460727016 | −2.202007274 | −1.442945771 | −4.022799483 | −1.386650033 |
| 56 | MYCN | −1.115153774 | −1.072643704 | −0.572987836 | −0.563222061 | 2.256763699 | −1.121103788 | 0.383429385 |
| 57 | NAPSA | −0.441224683 | 5.357444831 | −0.330311961 | −0.680826272 | 1.54889432 | −1.10948967 | 3.230552348 |
| 58 | NKX3-1 | 0.34424304 | −0.695607881 | −0.636037275 | 1.380598103 | −0.358807355 | −1.225980043 | −1.347772078 |
| 59 | NPR1 | 3.611141372 | 2.936608674 | 0.739290647 | −0.02018339 | −0.04911732 | −1.692369146 | 0.560520251 |
| 60 | PAX8 | −0.438408776 | 5.138704009 | −0.439224734 | −1.115572722 | −0.742610195 | −1.098989328 | 7.330352514 |
| 61 | PRAME | −2.28601297 | 3.648546027 | −1.904681098 | −1.204180981 | 3.601719603 | 9.250663624 | −3.172944285 |
| 62 | PSCA | −1.664873567 | −2.372135296 | −2.32137749 | 1.204841172 | −1.580925941 | 0.391748243 | −3.189626014 |
| 63 | PVRL4 | −4.983285402 | −6.308620694 | −6.330798801 | 1.140190077 | −3.872718208 | −6.359272034 | 0.126583059 |
| 64 | S100P | −4.27172475 | −4.04897439 | 0.499095434 | 2.122747189 | −4.765549062 | −4.663901764 | −4.574712189 |
| 65 | SALL4 | −0.701854731 | −2.670674063 | −1.068969101 | 0.308484856 | −1.113633609 | 2.219699773 | 0.019104844 |
| 66 | SFTPD | −2.015504097 | −0.059979562 | −1.883528068 | −0.664564777 | −1.784683096 | −1.174451747 | 2.77077955 |
| 67 | SILV | −0.404015329 | 0.403352323 | 1.696442392 | 0.346443524 | −1.809580739 | 12.3265592 | −0.064184971 |
| 68 | SIT1 | 0.560522874 | 0.56641542 | −0.448541127 | 0.083905789 | 6.077538122 | −1.010014644 | −0.588029822 |
| 69 | SLC26A4 | 0.245073029 | 0.600404783 | −1.143209401 | 0.077251179 | 0.024544315 | 0.276126125 | 7.424523266 |
| 70 | SLC3A1 | −0.360884127 | 10.50265557 | 1.764194349 | −0.750224836 | −0.620498156 | −0.303626634 | −0.228977476 |
| 71 | SLC45A3 | −1.119761006 | 0.021163292 | 0.733358084 | −0.480014382 | −2.00381626 | −1.453023157 | −2.254242818 |

TABLE 2-continued

Nearest centroid classifier coefficients of 84 Gene Classifier Biomarker Signature for Pan-Cancer COCA subtyping.

| | | | | | | | | |
|---|---|---|---|---|---|---|---|---|
| 72 | SOX17 | 0.817442439 | 0.837037779 | 0.345260582 | 0.26054328 | −0.203888143 | −1.596069152 | 0.733884158 |
| 73 | SPDEF | 2.697057213 | −2.838870874 | −2.854924213 | 7.609282727 | −3.084262875 | −2.745456716 | −2.779572185 |
| 74 | SPINT2 | −3.920290094 | −0.542550342 | −5.841694183 | 0.163004523 | −0.712680222 | −5.966064445 | 0.738611694 |
| 75 | TCEAL5 | 0.881390897 | −0.79947069 | −2.066499307 | 0.638825329 | 0.319737925 | −0.114766242 | 0.788194285 |
| 76 | TG | 0.984073587 | 0.60666684 | −1.221557274 | −1.111088643 | 1.124956459 | −0.727984197 | 15.10003804 |
| 77 | TMEM27 | −1.803900196 | 6.875082323 | 0.633259141 | −0.517663186 | −0.292695792 | −0.470425257 | 1.189669219 |
| 78 | TP63 | −0.665339268 | −2.068568045 | −1.9563835 | 1.974020464 | 5.386578658 | −2.022259539 | −0.159043543 |
| 79 | TRPS1 | 0.01584306 | −0.129451899 | −2.232072347 | 4.425365059 | −1.181551745 | −1.947966145 | −0.277029596 |
| 80 | TSPAN8 | −1.889160765 | −1.739590705 | 5.986779156 | −2.397233332 | −1.9296585 | −4.08731649 | −2.677540765 |
| 81 | UPK3B | −0.660628051 | −0.514196839 | −0.477166533 | −0.755620892 | −0.069584588 | −1.061067781 | −0.712380093 |
| 82 | VTN | 2.923525274 | −0.52452731 | 14.37513361 | −0.702306293 | −0.029929938 | 1.884788007 | −0.627880077 |
| 83 | ZNF578 | 1.22614863 | 0.540308545 | −1.87596215 | −0.083197077 | 0.429479376 | −0.209295458 | 2.232739055 |
| 84 | ZNF695 | −0.449132017 | −2.051634999 | −3.038221841 | 0.76346101 | 0.74872153 | −0.970490477 | −1.99162398 |

In one embodiment, a subset of one or more of the 84 genes of Table 1 can be used to classify or determine the COCA subtype of a tumor sample. In one embodiment, all 84 genes of Table 1 can be used to classify or determine the COCA subtype of a tumor sample. In some embodiments, the up-regulation of a classifier biomarker (e.g. expression is increased) can refer to an expression value that is positive (i.e., higher than zero) relative to a reference or control as provided herein. In some embodiments, the down-regulation of a classifier biomarker (e.g. expression is decreased) can refer to an expression value that is negative (i.e., lower than zero) relative to a reference or control as provided herein. In some embodiments, a classifier biomarker may have no specific effects on a certain COCA subtype when the expression level equals to zero.

In some embodiments, determining integrated, pan-cancer COCA subtypes can further include measuring the expression of at least one biomarker from an additional set of biomarker classifiers. In one embodiment, an additional set of biomarker classifiers can include measuring gene signatures related to cell proliferation. The gene signatures related to cell proliferation for use in the methods provided herein can include the 11 gene signature comprising BIRC5, CCNB1, CDC20, CDCA1, CEP55, KNTC2, MKI67, PTTG1, RRM2, TYMS, and UBE2C found in Martin M. et al., Breast Cancer Res Treat, 138: 457-466 (2013), the 18 gene signature found in US 20160115551 and/or the 26 gene signature found in 62/789,668 filed Jan. 8, 2019, each of which is herein incorporated by reference. In one embodiment, an additional set of biomarker classifiers can include a 5 gene signature comprising tumor driver genes such as TP53 and RB1, and receptor tyrosine kinases including FGFR2, FGFR3, and ERBB2. In one embodiment, the 5 gene signature is related to the signature of tumor driver genes. In one embodiment, the biomarker classifiers can also include immune cell signatures that are known in the art (Bindea G. et al., Immunity, 39(4): 782-95 (2013); Faruki H. et al., JTO, 12(6): 943-953 (2017); Charoentong P. et al., Cell reports, 18, 248-262 (2017); Thorsson, V., Gibbs, D. L., Brown, S. D., Wolf, D., Bortone, D. S., Yang, T. H. O., Porta-Pardo, E., Gao, G. F., Plaisier, C. L., Eddy, J. A. and Ziv, E., 2018, The immune landscape of cancer. *Immunity,* 48(4), pp. 812-830; and/or WO2017/201165, and WO2017/201164), each of which is herein incorporated by reference). In one embodiment, an additional set of biomarker classifiers can include assessing tumor purity ABSOLUTE derived from the TCGA supplementary data. In one embodiment, the additional set of biomarker can be gene signatures known in the art for specific types of cancer. In one embodiment, the cancer is lung cancer and the gene signature is selected from the gene signatures found in WO2017/201165, WO2017/201164, US20170114416 or U.S. Pat. No. 8,822,153, each of which is herein incorporated by reference in their entirety. In one embodiment, the cancer is head and neck squamous cell carcinoma (HNSCC) and the gene signature is selected from the gene signatures found in PCT/US18/45522 or PCT/US18/48862, each of which is herein incorporated by reference in their entirety. In one embodiment, the cancer is breast cancer and the gene signature is the PAM50 sub-typer found in Parker J S et al., (2009) Supervised risk predictor of breast cancer based on intrinsic subtypes. J Clin Oncol 27:1160-1167, which is herein incorporated by reference in its entirety. In one embodiment, the cancer is bladder cancer and the gene signature can include the bladder cancer biomarker signature described in Gene Expression Omnibus (GEO) dataset: GSE87304, Seiler R. et al., Eur Urol, 72(4):544-554 (2017); Gene Expression Omnibus (GEO) dataset: GSE32894, Sjödahl G. et al., Clin Cancer Res, 18(12):3377-86 (2012), each of which is herein incorporated by reference). In one embodiment, the cancer is bladder cancer (e.g., MIBC) and the gene signature can include the bladder cancer biomarker signatures described in 62/629,975 filed Feb. 13, 2018, which is herein incorporated by reference. In one embodiment, the cancer is bladder cancer (e.g., MIBC) and the gene signature can include the bladder cancer biomarker signature described in The Cancer Genome Atlas Research Network. Comprehensive molecular characterization of urothelial bladder carcinoma. Nature volume 507, pages 315-322 (2014), or Robertson, A G, et al., Cell, 171(3): 540-556 (2017), each of which is herein incorporated by reference.

In some embodiments, determining integrated, pan-cancer COCA subtypes can further include assessing tumor mutation burden (TMB) and/or TMB rate. In one embodiment, the TMB value and/or rate can be calculated from RNA (e.g., via transcriptome profiling or RNA sequencing)) as provided in U.S. 62/771,702 filed Nov. 27, 2018 and U.S. 62/743,257 filed Oct. 9, 2018, which is herein incorporated by reference herein.

As provided herein, the expression levels of the at least one of the classifier biomarkers (such as the classifier biomarkers of Table 1 or any additional set of biomarker classifiers as disclosed herein) determined, measured or detected from the sample obtained from the subject can then be compared to reference expression levels of the at least one of the classifier biomarkers (such as the classifier biomarkers of Table 1 or any additional set of biomarker classifiers as disclosed herein) from at least one sample training set. The at least one sample training set can comprise, (i) expression levels of the at least one biomarker from a sample that overexpresses the at least one biomarker or (ii) expression levels from a reference sample for a specific COCA subtype (e.g., C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and C28 (THCA)) and classifying the sample obtained from the subject sample as a specific COCA subtype (e.g., C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and C28 (THCA)) based on the results of the comparing step. In one embodiment, the comparing step can comprise applying a statistical algorithm which comprises determining a correlation between the expression data obtained from the sample obtained from the subject and the expression data from the at least one training set(s); and classifying the sample obtained from the subject as a specific COCA subtype (e.g., C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and C28 (THCA)) based on the results of the statistical algorithm. The statistical algorithm can be any statistical algorithm found in the art and/or provided herein.

In one embodiment, the statistical algorithm for the comparing step can be an algorithm that comprises determining a correlation between the expression data obtained from the tumor sample obtained from the subject (i.e., test sample) and centroids constructed from the expression levels or profiles measured or detected for the at least one classifier biomarkers (such as the classifier biomarkers of Table 1 or subsets thereof or any additional set of biomarker classifiers or subsets thereof as disclosed herein) from the at least one training set. The COCA subtype for the tumor sample (i.e., test sample) can then be assigned by finding the centroid to which it is nearest from the centroids constructed from the expression data from the at least one training set, using any distance measure e.g. Euclidean distance or correlation. The centroids can be constructed using any method known in the art for generating centroids such as, for example, those found in Mullins et al. (2007) Clin Chem. 53(7):1273-9 or Dabney (2005) Bioinformatics 21(22):4148-4154 The COCA subtype can then be assigned to the tumor sample obtained from subject based on the use of a classification to the nearest centroid (CLaNC) algorithm as applied to the expression data generated or measured from the tumor sample and the centroid(s) constructed for the at least one training sets. The CLaNC algorithm for use in the methods, compositions and kits provided herein can be the CLaNC algorithm implemented by the CLaNC software found in Dabney A R. ClaNC: Point-and-click software for classifying microarrays to nearest centroids. Bioinformatics. 2006; 22: 122-123 or equivalents or derivatives thereof.

Sample Types/Methods of Detection

The methods and compositions provided herein allow for the differentiation or diagnosis of a sample obtained from a subject as being a specific COCA subtype. The COCA subtype can be one of 21 integrated, pan-cancer COCA subtypes of cancer selected from C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and C28 (THCA). The differentiation, detection or diagnosis of the sample obtained from the subject as being a COCA subtype as provided herein can be accomplished by measuring or detecting the presence and/or level of one or more classifier biomarkers from a publically available pan-cancer dataset and/or a pan-cancer dataset provided herein (e.g., Table 1). The measuring can be at the nucleic acid or protein level.

A sample for use in any of the methods and compositions provided herein can be a tumor sample obtained from a subject or patient suffering from or suspected of suffering from a type of cancer. The type of cancer can be any type of cancer provided herein and/or known in the art. The tumor sample used for the detection or differentiation methods described herein can be a sample previously determined or diagnosed as a type of cancer sample using traditional tissue-of-origin methods. The previous diagnosis can be based on a histological analysis. The histological analysis can be performed by one or more pathologists.

The sample (e.g., tumor sample) can be any sample (e.g., tumor) isolated from the subject or patient. In one embodiment, the subject or patient is a human subject or patient. For example, in one embodiment, the analysis is performed on biopsies that are embedded in paraffin wax. In one embodiment, the sample can be a fresh frozen tissue sample. In another embodiment, the sample can be a bodily fluid obtained from the patient. The bodily fluid can be blood or fractions thereof (i.e., serum, plasma), urine, saliva, sputum or cerebrospinal fluid (CSF). The sample can contain cellular as well as extracellular sources of nucleic acid or protein for use in the methods provided herein. The extracellular sources can be cell-free DNA and/or exosomes. In one embodiment, the sample can be a cell pellet or a wash. This aspect of the methods provided herein provides a means to improve current diagnostics by accurately identifying the major histological types, even from small biopsies. The methods provided herein, including the RT-PCR methods, are sensitive, precise and have multi-analyte capability for use with paraffin-embedded samples. See, for example, Cronin et al. (2004) *Am. J Pathol.* 164(1):35-42, herein incorporated by reference.

Formalin fixation and tissue embedding in paraffin wax is a universal approach for tissue processing prior to light microscopic evaluation. A major advantage afforded by formalin-fixed paraffin-embedded (FFPE) specimens is the preservation of cellular and architectural morphologic detail in tissue sections. (Fox et al. (1985) J Histochem Cytochem 33:845-853). The standard buffered formalin fixative in which biopsy specimens are processed is typically an aqueous solution containing 37% formaldehyde and 10-15% methyl alcohol. Formaldehyde is a highly reactive dipolar compound that results in the formation of protein-nucleic acid and protein-protein crosslinks in vitro (Clark et al. (1986) J Histochem Cytochem 34:1509-1512; McGhee and von Hippel (1975) Biochemistry 14:1281-1296, each incorporated by reference herein).

In one embodiment, the sample used herein is obtained from an individual, and comprises formalin-fixed paraffin-embedded (FFPE) tissue. However, other tissue and sample types are amenable for use herein. In one embodiment, the other tissue and sample types can be fresh frozen tissue, wash fluids, cell pellets, or the like. In one embodiment, the sample can be a bodily fluid obtained from the individual. The bodily fluid can be blood or fractions thereof (e.g., serum, plasma), urine, sputum, saliva or cerebrospinal fluid (CSF). A biomarker nucleic acid as provided herein can be extracted from a cell, can be cell free or extracted from an extracellular vesicular entity such as an exosome.

Methods are known in the art for the isolation of nucleic acid (e.g., RNA) from FFPE tissue. In one embodiment, total RNA can be isolated from FFPE tissues as described by Bibikova et al. (2004) American Journal of Pathology 165: 1799-1807, herein incorporated by reference. Likewise, the High Pure RNA Paraffin Kit (Roche) can be used. Paraffin is removed by xylene extraction followed by ethanol wash. RNA can be isolated from sectioned tissue blocks using the MasterPure Purification kit (Epicenter, Madison, Wis.); a DNase I treatment step is included. RNA can be extracted from frozen samples using Trizol reagent according to the supplier's instructions (Invitrogen Life Technologies, Carlsbad, Calif.). Samples with measurable residual genomic DNA can be resubjected to DNaseI treatment and assayed for DNA contamination. All purification, DNase treatment, and other steps can be performed according to the manufacturer's protocol. After total RNA isolation, samples can be stored at −80° C. until use.

General methods for mRNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker (Lab Invest. 56:A67, 1987) and De Andres et al. (Biotechniques 18:42-44, 1995). In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Other commercially available RNA isolation kits include MasterPure™. Complete DNA and RNA Purification Kit (Epicentre, Madison, Wis.) and Paraffin Block RNA Isolation Kit (Ambion, Austin, Tex.). Total RNA from tissue samples can be isolated, for example, using RNA Stat-60 (Tel-Test, Friendswood, Tex.). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155, incorporated by reference in its entirety for all purposes).

In one embodiment, a sample comprises cells harvested from a tumor sample. Cells can be harvested from a biological sample using standard techniques known in the art. For example, in one embodiment, cells are harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract nucleic acid, e.g, messenger RNA. All samples obtained from a subject, including those subjected to any sort of further processing, are considered to be obtained from the subject.

The sample, in one embodiment, is further processed before the detection of the biomarker levels of the combination of biomarkers set forth herein. For example, mRNA in a cell or tissue sample can be separated from other components of the sample. The sample can be concentrated and/or purified to isolate mRNA in its non-natural state, as the mRNA is not in its natural environment. For example, studies have indicated that the higher order structure of mRNA in vivo differs from the in vitro structure of the same sequence (see, e.g., Rouskin et al. (2014). Nature 505, pp. 701-705, incorporated herein in its entirety for all purposes).

mRNA from the sample in one embodiment, is hybridized to a synthetic DNA probe, which in some embodiments, includes a detection moiety (e.g., detectable label, capture sequence, barcode reporting sequence). Accordingly, in these embodiments, a non-natural mRNA-cDNA complex is ultimately made and used for detection of the biomarker. In another embodiment, mRNA from the sample is directly labeled with a detectable label, e.g., a fluorophore. In a further embodiment, the non-natural labeled-mRNA molecule is hybridized to a cDNA probe and the complex is detected.

In one embodiment, once the mRNA is obtained from a sample, it is converted to complementary DNA (cDNA) prior to the hybridization reaction or is used in a hybridization reaction together with one or more cDNA probes. cDNA does not exist in vivo and therefore is a non-natural molecule. Furthermore, cDNA-mRNA hybrids are synthetic and do not exist in vivo. Besides cDNA not existing in vivo, cDNA is necessarily different than mRNA, as it includes deoxyribonucleic acid and not ribonucleic acid. The cDNA is then amplified, for example, by the polymerase chain reaction (PCR) or other amplification method known to those of ordinary skill in the art. For example, other amplification methods that may be employed include the ligase chain reaction (LCR) (Wu and Wallace, Genomics, 4:560 (1989), Landegren et al., Science, 241:1077 (1988), incorporated by reference in its entirety for all purposes, transcription amplification (Kwoh et al., *Proc. Natl. Acad. Sci. USA,* 86:1173 (1989), incorporated by reference in its entirety for all purposes), self-sustained sequence replication (Guatelli et al., *Proc. Nat. Acad. Sci. USA,* 87:1874 (1990), incorporated by reference in its entirety for all purposes), incorporated by reference in its entirety for all purposes, and nucleic acid based sequence amplification (NASBA). Guidelines for selecting primers for PCR amplification are known to those of ordinary skill in the art. See, e.g., McPherson et al., PCR Basics: From Background to Bench, Springer-Verlag, 2000, incorporated by reference in its entirety for all purposes. The product of this amplification reaction, i.e., amplified cDNA is also necessarily a non-natural product. First, as mentioned above, cDNA is a non-natural molecule. Second, in the case of PCR, the amplification process serves to create hundreds of millions of cDNA copies for every individual cDNA molecule of starting material. The numbers of copies generated are far removed from the number of copies of mRNA that are present in vivo.

In one embodiment, cDNA is amplified with primers that introduce an additional DNA sequence (e.g., adapter, reporter, capture sequence or moiety, barcode) onto the fragments (e.g., with the use of adapter-specific primers), or mRNA or cDNA biomarker sequences are hybridized directly to a cDNA probe comprising the additional sequence (e.g., adapter, reporter, capture sequence or moiety, barcode). Amplification and/or hybridization of mRNA to a cDNA probe therefore serves to create non-natural double stranded molecules from the non-natural single stranded cDNA, or the mRNA, by introducing additional sequences and forming non-natural hybrids. Further, as known to those of ordinary skill in the art, amplification procedures have error rates associated with them. Therefore, amplification introduces further modifications into the cDNA molecules. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature, and (iv) the chemical addition of a detectable label to the cDNA molecules.

In some embodiments, the expression of a biomarker of interest is detected at the nucleic acid level via detection of non-natural cDNA molecules.

The biomarkers described herein can include RNA comprising the entire or partial sequence of any of the nucleic acid sequences of interest, or their non-natural cDNA product, obtained synthetically in vitro in a reverse transcription reaction. The term "fragment" is intended to refer to a portion of the polynucleotide that generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein as provided herein.

Isolated mRNA can be used in hybridization or amplification assays that include, but are not limited to, Southern or Northern analyses, PCR analyses and probe arrays, NanoString Assays. One method for the detection of mRNA levels involves contacting the isolated mRNA or synthesized cDNA with a nucleic acid molecule (probe) that can hybridize to the mRNA encoded by the gene being detected. The nucleic acid probe can be, for example, a cDNA, or a portion thereof, such as an oligonucleotide of at least 7, 15, 30, 50, 100, 250, or 500 nucleotides in length and sufficient to specifically hybridize under stringent conditions to the non-natural cDNA or mRNA biomarker provided herein.

In one embodiment, the measuring or detecting step in any method provided herein is at the nucleic acid level by performing RNA-seq, a reverse transcriptase polymerase chain reaction (RT-PCR) or a hybridization assay with oligonucleotides that are substantially complementary to portions of cDNA molecules of the at least one classifier biomarker (such as the classifier biomarkers of Table 1 or any additional set of biomarker classifiers as disclosed herein) under conditions suitable for RNA-seq, RT-PCR or hybridization and obtaining expression levels of the at least one classifier biomarkers based on the detecting step.

In some embodiments, the method for COCA subtyping includes not only detecting expression levels of a classifier biomarker set in a sample obtained from a subject, but can further comprise detecting expression levels of said classifier biomarker set in one or more control or reference samples. The one or more control or reference samples can be selected from a normal or cancer-free sample, a cancer sample of a specific COCA subtype (e.g., C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and C28 (THCA)) or any combination thereof. In some embodiments, the detecting includes all of the classifier biomarkers of Table 1 or any additional set of biomarker classifiers as disclosed herein at the nucleic acid level or protein level. In some embodiments, the detecting includes all of the classifier biomarkers of Table 1 at the nucleic acid level or protein level. In another embodiment, a single or a subset or a plurality of the classifier biomarkers of Table 1 are detected, for example, from about 1 to about 4, from about 4 to about 8, from about 8 to about 12, from about 12 to about 16, from about 16 to about 20, from about 20 to about 24, from about 24 to about 28, from about 28 to about 32, from about 32 to about 36, from about 36 to about 40, from about 40 to about 44, from about 44 to about 48, from about 48 to about 52, from about 52 to about 56, from about 56 to about 60, from about 60 to about 64, from about 64 to about 68, from about 68 to about 72, from about 72 to about 76, from about 76 to about 80 of the biomarkers in Table 1 are detected in a method to determine the COCA subtype. In another embodiment, each of the biomarkers from Table 1 is detected in a method to determine the COCA subtype. In another embodiment, any of 84 of the biomarkers from Table 1 are selected as the gene signatures for a specific COCA subtype. The detecting can be performed by any suitable technique including, but not limited to, RNA-seq, a reverse transcriptase polymerase chain reaction (RT-PCR), a microarray hybridization assay, or another hybridization assay, e.g., a NanoString assay for example, with primers and/or probes specific to the classifier biomarkers, and/or the like. In some cases, the primers useful for the amplification methods (e.g., RT-PCR or qRT-PCR) are any forward and reverse primers suitable for binding to a classifier biomarker provided herein, such as the classifier biomarkers of Table 1 or any additional set of biomarker classifiers as disclosed herein.

As explained above, in one embodiment, once the mRNA is obtained from a sample (e.g., form a subject suffering from or suspected of suffering from cancer or a control subject), it is converted to complementary DNA (cDNA) in a hybridization reaction. Conversion of the mRNA to cDNA can be performed with oligonucleotides or primers comprising sequence that is complementary to a portion of a specific mRNA. Conversion of the mRNA to cDNA can be performed with oligonucleotides or primers comprising random sequence. Conversion of the mRNA to cDNA can be performed with oligonucleotides or primers comprising sequence that is complementary to the poly(A) tail of an mRNA. cDNA does not exist in vivo and therefore is a non-natural molecule. In a further embodiment, the cDNA is then amplified, for example, by the polymerase chain reaction (PCR) or other amplification method known to those of ordinary skill in the art. PCR can be performed with the forward and/or reverse primers comprising sequence complementary to at least a portion of a classifier biomarker provided herein, such as the classifier biomarkers of Table 1 or any additional set of biomarker classifiers as disclosed herein. The product of this amplification reaction, i.e., amplified cDNA is necessarily a non-natural product. As mentioned above, cDNA is a non-natural molecule. Second, in the case of PCR, the amplification process serves to create hundreds of millions of cDNA copies for every individual cDNA molecule of starting material. The number of copies generated is far removed from the number of copies of mRNA that are present in vivo.

In one embodiment, cDNA is amplified with primers that introduce an additional DNA sequence (adapter sequence) onto the fragments (with the use of adapter-specific primers). The adaptor sequence can be a tail, wherein the tail sequence is not complementary to the cDNA. For example, the forward and/or reverse primers comprising sequence complementary to at least a portion of a classifier biomarker provided herein, such as the classifier biomarkers of Table 1 or any additional set of biomarker classifiers as disclosed herein can comprise tail sequence. Amplification therefore serves to create non-natural double stranded molecules from the non-natural single stranded cDNA, by introducing barcode, adapter and/or reporter sequences onto the already non-natural cDNA. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (ii) adapter sequences are added to the ends of cDNA molecules to make DNA sequences that do not exist in vivo, (iii) the error rate associated with amplification further creates DNA sequences that do not exist in vivo, (iv) the disparate structure of the cDNA molecules as compared to what exists in nature, and (v) the chemical addition of a detectable label to the cDNA molecules.

In one embodiment, the synthesized cDNA (for example, amplified cDNA) is immobilized on a solid surface via hybridization with a probe, e.g., via a microarray. In another embodiment, cDNA products are detected via real-time polymerase chain reaction (PCR) via the introduction of fluorescent probes that hybridize with the cDNA products. For example, in one embodiment, biomarker detection is assessed by quantitative fluorogenic RT-PCR (e.g., with TaqMan® probes). For PCR analysis, well known methods are available in the art for the determination of primer sequences for use in the analysis.

In one embodiment, the measuring or detecting step in any method provided herein is performed via a hybridization assay that comprises probing the levels of at least one of the classifier biomarkers provided herein, such as the classifier biomarkers of Table 1 or any additional set of biomarker classifiers disclosed herein, at the nucleic acid level, in a tumor sample obtained from the patient. The probing step, in one embodiment, comprises mixing the sample with one or more oligonucleotides that are substantially complementary to portions of cDNA molecules of the at least one classifier biomarkers provided herein, such as the classifier biomarkers of Table 1 or any additional set of biomarker classifiers disclosed herein under conditions suitable for hybridization of the one or more oligonucleotides to their complements or substantial complements; detecting whether hybridization occurs between the one or more oligonucleotides to their complements or substantial complements; and obtaining hybridization values of the at least one classifier biomarkers based on the detecting step. The hybridization values of the at least one classifier biomarkers are then compared to reference hybridization value(s) from at least one sample training set. The tumor sample is classified, for example, as a COCA subtype (e.g., C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and C28 (THCA)) based on the results of the comparing step. In one embodiment, the hybridization values of the tumor sample can be compared to centroid(s) constructed from the hybridization values of the training set.

In one embodiment, the hybridization reaction utilized in methods provided herein employs a capture probe and/or a reporter probe. For example, the hybridization probe is a probe derivatized to a solid surface such as a bead, glass or silicon substrate. In another embodiment, the capture probe is present in solution and mixed with the patient's sample, followed by attachment of the hybridization product to a surface, e.g., via a biotin-avidin interaction (e.g., where biotin is a part of the capture probe and avidin is on the surface). The hybridization assay, in one embodiment, employs both a capture probe and a reporter probe. The reporter probe can hybridize to either the capture probe or the biomarker nucleic acid. Reporter probes e.g., are then counted and detected to determine the level of biomarker(s) in the sample. The capture and/or reporter probe, in one embodiment contain a detectable label, and/or a group that allows functionalization to a surface.

For example, the nCounter gene analysis system (see, e.g., Geiss et al. (2008) Nat. Biotechnol. 26, pp. 317-325, incorporated by reference in its entirety for all purposes, is amenable for use with the methods provided herein.

Hybridization assays described in U.S. Pat. Nos. 7,473,767 and 8,492,094, the disclosures of which are incorporated by reference in their entireties for all purposes, are amenable for use with the methods provided herein, i.e., to detect the biomarkers and biomarker combinations described herein.

Biomarker levels may be monitored using a membrane blot (such as used in hybridization analysis such as Northern, Southern, dot, and the like), or microwells, sample tubes, gels, beads, or fibers (or any solid support comprising bound nucleic acids). See, for example, U.S. Pat. Nos. 5,770,722, 5,874,219, 5,744,305, 5,677,195 and 5,445,934, each incorporated by reference in their entireties.

In one embodiment, microarrays are used to detect biomarker levels. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316, each incorporated by reference in their entireties. High-density oligonucleotide arrays are particularly useful for determining the gene expression profile for a large number of RNAs in a sample.

Techniques for the synthesis of these arrays using mechanical synthesis methods are described in, for example, U.S. Pat. No. 5,384,261. Although a planar array surface is generally used, the array can be fabricated on a surface of virtually any shape or even a multiplicity of surfaces. Arrays can be nucleic acids (or peptides) on beads, gels, polymeric surfaces, fibers (such as fiber optics), glass, or any other appropriate substrate. See, for example, U.S. Pat. Nos. 5,770,358, 5,789,162, 5,708,153, 6,040,193 and 5,800,992, each incorporated by reference in their entireties. Arrays can be packaged in such a manner as to allow for diagnostics or other manipulation of an all-inclusive device. See, for example, U.S. Pat. Nos. 5,856,174 and 5,922,591, each incorporated by reference in their entireties.

Serial analysis of gene expression (SAGE) in one embodiment is employed in the methods described herein. SAGE is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. See, Velculescu et al. Science 270:484-87, 1995; Cell 88:243-51, 1997, incorporated by reference in its entirety.

In another embodiment, the measuring or detecting step in any method provided herein is performed via an amplification assay. The amplification assay can be coupled with a sequencing method. In one embodiment, a method of biomarker level analysis at the nucleic acid level as provided herein utilizes an amplification reaction coupled with a sequencing method such as, for example, RNAseq, next generation sequencing, and massively parallel signature sequencing (MPSS) as described by Brenner et al. (Nat. Biotech. 18:630-34, 2000, incorporated by reference in its entirety). MPSS is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3.0\times10^6$ microbeads/$cm^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

The expression level values of the at least one classifier biomarkers obtained from the amplification and/or sequencing assay are then compared to reference expression level value(s) from at least one sample training set. The tumor sample is classified, for example, as a COCA subtype (e.g., C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and C28 (THCA)) based on the results of the comparing step. In one embodiment, the expression level values of the tumor sample can be compared to centroid(s) constructed from the expression level values obtained from the training set.

Another method of biomarker level analysis at the nucleic acid level for use in any method provided herein is the use of an amplification method such as, for example, RT-PCR or quantitative RT-PCR (qRT-PCR). Methods for determining the level of biomarker mRNA in a sample may involve the process of nucleic acid amplification, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. Numerous different PCR or qRT-PCR protocols are known in the art and can be directly applied or adapted for use using the presently described compositions for the detection and/or quantification of expression of discriminative genes in a sample. See, for example, Fan et al. (2004) Genome Res. 14:878-885, herein incorporated by reference. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR.

Quantitative RT-PCR (qRT-PCR) (also referred as real-time RT-PCR) is preferred under some circumstances because it provides not only a quantitative measurement, but also reduced time and contamination. As used herein, "quantitative PCR" (or "real time qRT-PCR") refers to the direct monitoring of the progress of a PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time. A DNA binding dye (e.g., SYBR green) or a labeled probe can be used to detect the extension product generated by PCR amplification. Any probe format utilizing a labeled probe comprising the sequences provided herein may be used.

Immunohistochemistry methods are also suitable for detecting the levels of the biomarkers provided herein. Samples can be frozen for later preparation or immediately placed in a fixative solution. Tissue samples can be fixed by treatment with a reagent, such as formalin, glutaraldehyde, methanol, or the like and embedded in paraffin. Methods for preparing slides for immunohistochemical analysis from formalin-fixed, paraffin-embedded tissue samples are well known in the art.

In one embodiment, COCA subtypes can be evaluated using levels of protein expression of one or more of the classifier biomarkers provided herein, such as the classifier biomarkers of Table 1 or any additional set of biomarker classifiers disclosed herein. The level of protein expression can be measured using an immunological detection method. Immunological detection methods which can be used herein include, but are not limited to, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. Such assays are routine and well known in the art (see, e.g., Ausubel et al, eds, 1994, *Current Protocols in Molecular Biology*, Vol. I, John Wiley & Sons, Inc., New York, which is incorporated by reference herein in its entirety).

In one embodiment, antibodies specific for biomarker proteins are utilized to detect the expression of a biomarker protein in a sample (e.g., tumor sample). The method comprises obtaining a sample from a patient or a subject, contacting the sample with at least one antibody directed to a biomarker that is selectively expressed in cancer cells, and detecting antibody binding to determine if the biomarker is expressed in the patient sample. Also provided herein is an immunocytochemistry technique for diagnosing COCA subtypes. One of skill in the art will recognize that the immunocytochemistry method described herein below may be performed manually or in an automated fashion.

In some embodiments, the expression level of a classifier biomarker(s) (e.g., from Table 1) as determined using any methods or compositions provided herein or its expression product, is determined by normalization to the level of reference nucleic acid(s) (e.g., RNA transcripts) or their expression products (e.g., proteins), which can be all measured nucleic acids (e.g., transcripts (or their products)) in the sample or a particular reference set of nucleic acids (e.g., RNA transcripts (or their non-natural cDNA products)). Normalization is performed to correct for or normalize away both differences in the amount of nucleic acid (e.g., RNA or cDNA) assayed and variability in the quality of the nucleic acid (e.g., RNA or cDNA) used. Therefore, an assay typically measures and incorporates the expression of certain normalizing genes, including well known housekeeping genes, such as, for example, GAPDH and/or β-Actin. Alternatively, normalization can be based on the mean or median signal of all of the assayed biomarkers or a large subset thereof (global normalization approach).

In one embodiment, the levels of the biomarkers provided herein, such as the classifier biomarkers of Table 1 (or subsets thereof, for example, 1 to 4, 4 to 8, 8 to 12, 12 to 16, 16 to 20, 20 to 24, 24 to 28, 28 to 32, 32 to 36, 36 to 40, 40 to 44, 44 to 48, 48 to 52, 52 to 56, 56 to 60, 60 to 64, 64 to 68, 68 to 72, 72 to 76, 76 to 80, 80 to 84 of the classifier biomarkers) are normalized against the expression levels of all RNA transcripts or their non-natural cDNA expression products, or protein products in the sample, or of a reference set of RNA transcripts or a reference set of their non-natural cDNA expression products, or a reference set of their protein products in the sample. In one embodiment, the levels of the biomarkers provided herein, such as any of the additional set of classifier biomarkers disclosed herein are normalized against the expression levels of all RNA transcripts or their non-natural cDNA expression products, or protein products in the sample, or of a reference set of RNA transcripts or a reference set of their non-natural cDNA expression products, or a reference set of their protein products in the sample.

Statistical Methods

As provided throughout, the methods set forth herein provide a method for determining the COCA subtype of a patient. Once the biomarker levels (e.g., Table 1 or any other gene signature provided herein) are determined, for example by measuring non-natural cDNA biomarker levels or non-natural mRNA-cDNA biomarker complexes, the biomarker levels are compared to reference values or a reference sample as provided herein, for example with the use of statistical methods or direct comparison of detected levels, to make a determination of the COCA subtype. Based on the comparison, the patient's tumor sample is classified, e.g., as a specific COCA subtype (e.g., C1 ACC/PCPG, C2 GBM/LGG, C3 OV, C4 Squamous-like, C6 LUAD-Enriched, C8 PAAD/some STAD, C9 UCS, C10 BRCA/Basal, C12 UCEC, C14 PRAD, C15 CESC (subset of cervical), C16 BLCA, C17 TGCT, C19 COAD/READ, C20 SARC/MESO, C21 KIRK/KICH/KIRP, C22 Liver, C24 BRCA/Luminal, C25 THYM, C26 SKCM/UVM and C28 THCA).

In one embodiment, expression level values of the at least one classifier biomarkers provided herein, such as the classifier biomarkers of Table 1 are compared to reference expression level value(s) from at least one sample training set, wherein the at least one sample training set comprises expression level values from a reference sample(s). In a further embodiment, the at least one sample training set comprises expression level values of the at least one classifier biomarkers provided herein, such as the classifier biomarkers of Table 1 or any additional set of biomarker classifiers disclosed herein from a specific COCA subtype (e.g., C1 ACC/PCPG, C2 GBM/LGG, C3 OV, C4 Squamous-like, C6 LUAD-Enriched, C8 PAAD/some STAD, C9 UCS, C10 BRCA/Basal, C12 UCEC, C14 PRAD, C15 CESC (subset of cervical), C16 BLCA, C17 TGCT, C19 COAD/READ, C20 SARC/MESO, C21 KIRK/KICH/KIRP, C22 Liver, C24 BRCA/Luminal, C25 THYM, C26 SKCM/UVM and C28 THCA) or a combination thereof.

In a separate embodiment, for methods provided herein employing a hybridization assay, hybridization values of the at least one classifier biomarkers provided herein, such as the classifier biomarkers of Table 1 or any additional set of biomarker classifiers disclosed herein are compared to reference hybridization value(s) from at least one sample training set, wherein the at least one sample training set comprises hybridization values from a reference sample(s). In a further embodiment, the at least one sample training set comprises hybridization values of the at least one classifier biomarker provided herein, such as the classifier biomarkers of Table 1 or any additional set of biomarker classifiers disclosed herein from a specific COCA subtype (e.g., C1 ACC/PCPG, C2 GBM/LGG, C3 OV, C4 Squamous-like, C6 LUAD-Enriched, C8 PAAD/some STAD, C9 UCS, C10 BRCA/Basal, C12 UCEC, C14 PRAD, C15 CESC (subset of cervical), C16 BLCA, C17 TGCT, C19 COAD/READ, C20 SARC/MESO, C21 KIRK/KICH/KIRP, C22 Liver, C24 BRCA/Luminal, C25 THYM, C26 SKCM/UVM and C28 THCA) or a combination thereof. Methods for comparing detected levels of biomarkers to reference values and/or reference samples are provided herein. Based on this comparison, in one embodiment a correlation between the biomarker levels obtained from the subject's sample and the reference values is obtained. An assessment of the COCA subtype is then made.

Various statistical methods can be used to aid in the comparison of the biomarker levels obtained from the patient and reference biomarker levels, for example, from at least one sample training set.

In one embodiment, a supervised pattern recognition method is employed. Examples of supervised pattern recognition methods can include, but are not limited to, the nearest centroid methods (Dabney (2005) Bioinformatics 21(22):4148-4154 and Tibshirani et al. (2002) Proc. Natl.

Acad. Sci. USA 99(10):6576-6572); soft independent modeling of class analysis (SIMCA) (see, for example, Wold, 1976); partial least squares analysis (PLS) (see, for example, Wold, 1966; Joreskog, 1982; Frank, 1984; Bro, R., 1997); linear discriminant analysis (LDA) (see, for example, Nillson, 1965); K-nearest neighbor analysis (KNN) (sec, for example, Brown et al., 1996); artificial neural networks (ANN) (see, for example, Wasserman, 1989; Anker et al., 1992; Hare, 1994); probabilistic neural networks (PNNs) (see, for example, Parzen, 1962; Bishop, 1995; Speckt, 1990; Broomhead et al., 1988; Patterson, 1996); rule induction (RI) (see, for example, Quinlan, 1986); and, Bayesian methods (see, for example, Bretthorst, 1990a, 1990b, 1988). In one embodiment, the classifier for identifying COCA subtypes based on gene expression data is used in a centroid based method as described in Mullins et al. (2007) Clin Chem. 53(7):1273-9, which is incorporated herein by reference in its entirety. In another embodiment, the classifier for identifying tumor subtypes based on gene expression data is used in a nearest centroid based method as described in Dabney (2005) Bioinformatics 21(22):4148-4154, which is incorporated herein by reference in its entirety. The nearest centroid based method can be performed using CLaNC software as described in Dabney A R. ClaNC: Point-and-click software for classifying microarrays to nearest centroids. Bioinformatics. 2006; 22: 122-123 or equivalents or derivatives thereof.

In other embodiments, an unsupervised training approach is employed, and therefore, no training set is used.

Referring to sample training sets for supervised learning approaches again, in some embodiments, a sample training set(s) can include expression data of a plurality or all of the classifier biomarkers (e.g., all the classifier biomarkers of Table 1) from a specific COCA subtype sample. The plurality of classifier biomarkers can comprise at least 4 classifier biomarkers, at least 8 classifier biomarkers, at least 12 classifier biomarkers, at least 16 classifier biomarkers at least 20 classifier biomarkers, at least 24 classifier biomarkers, at least 28 classifier biomarkers, at least 32 classifier biomarkers, at least 36 classifier biomarkers, at least 40 classifier biomarkers, at least 44 classifier biomarkers, at least 48 classifier biomarkers, at least 52 classifier biomarkers, at least 56 classifier biomarkers, at least 60 classifier biomarkers, at least 64 classifier biomarkers, at least 68 classifier biomarkers, at least 72 classifier biomarkers, at least 76 classifier biomarkers or at least 80 classifier biomarkers of Table 1. In some embodiments, the plurality of classifier biomarkers comprises all 84 biomarkers of Table 1. In some embodiments, the sample training set(s) are normalized to remove sample-to-sample variation.

In some embodiments, comparing can include applying a statistical algorithm, such as, for example, any suitable multivariate statistical analysis model, which can be parametric or non-parametric. In some embodiments, applying the statistical algorithm can include determining a correlation between the expression data obtained from the tumor sample obtained from the subject suffering from or suspected of suffering from cancer (i.e., the test subject) and the expression data from the COCA subtyping training set(s). In some embodiments, cross-validation is performed, such as (for example), leave-one-out cross-validation (LOOCV). In some embodiments, integrative correlation is performed. In some embodiments, a Spearman correlation is performed. In some embodiments, a centroid based method based on gene expression data is employed for the statistical algorithm. The centroids can be constructed using any method known in the art for generating centroids such as, for example, those found in Mullins et al. (2007) Clin Chem. 53(7):1273-9 or the nearest centroid method found in Dabney (2005) Bioinformatics 21(22):4148-4154, which is herein incorporated by reference in its entirety. In one embodiment, a correlation analysis is performed on the expression data obtained from the tumor sample and the centroid(s) constructed from the expression data from the COCA training set(s). The correlation analysis can be a Spearman correlation or a Pearson correlation. In one embodiment, a distance measure analysis (e.g., Euclidean distance) is performed on the expression data obtained from the tumor sample and the centroid(s) constructed on the expression data from the COCA training set(s).

Results of the gene expression analysis performed on a sample from a subject (test sample) may be compared to a biological sample(s) or data derived from a biological sample(s) (e.g., expression data or levels from at least one classifier biomarker provided herein, e.g., Table 1) that is known or suspected to be normal ("reference sample" or "normal sample", e.g., non-cancer sample). In some embodiments, a reference sample or reference gene expression data (e.g., expression data or levels from at least one classifier biomarker provided herein, e.g., Table 1) is obtained or derived from an individual known to have a particular COCA subtype of cancer, e.g., C1 ACC/PCPG, C2 GBM/LGG, C3 OV, C4 Squamous-like, C6 LUAD-Enriched, C8 PAAD/some STAD, C9 UCS, C10 BRCA/Basal, C12 UCEC, C14 PRAD, C15 CESC (subset of cervical), C16 BLCA, C17 TGCT, C19 COAD/READ, C20 SARC/MESO, C21 KIRK/KICH/KIRP, C22 Liver, C24 BRCA/Luminal, C25 THYM, C26 SKCM/UVM and C28 THCA. In one embodiment, the gene expression levels or profile measured for the at least one classifier biomarkers from Table 1 measured or detected in the test sample (i.e., tumor sample obtained from the subject) may be compared to centroids constructed from the gene expression performed on the reference or normal sample or training set and classification can be based on determining which is the nearest centroid based on distance measure such as, for example, a Euclidean distance or a correlation. The centroids can be constructed using any of the methods provided herein such as, for example, using the ClaNC software described in Dabney A R. ClaNC: Point-and-click software for classifying microarrays to nearest centroids. Bioinformatics. 2006; 22: 122-123 or equivalents or derivatives related thereto. Classification or determination of the subtype of the test sample can then be ascertained by determining the nearest centroid from the reference or normal sample to which the expression levels or profile from said test sample is nearest based on a distance measure or correlation. The distance measure can be a Euclidean distance.

The reference sample may be assayed at the same time, or at a different time from the sample obtained from the test subject (i.e., test sample). Alternatively, the biomarker level information from a reference sample may be stored in a database or other means for access at a later date.

The biomarker level results of an assay on the test sample may be compared to the results of the same assay on a reference sample. In some cases, the results of the assay on the reference sample are from a database, or a reference value(s). In some cases, the results of the assay on the reference sample are a known or generally accepted value or range of values by those skilled in the art. In some cases, the comparison is qualitative. In other cases, the comparison is quantitative. In some cases, qualitative or quantitative comparisons may involve but are not limited to one or more of the following: comparing expression levels of a test sample to gene centroids constructed from expression level data from a reference sample (e.g., constructed from expression level data for one or a plurality of genes from Table 1), fluorescence values, spot intensities, absorbance values, chemiluminescent signals, histograms, critical threshold values, statistical significance values, expression levels of the genes described herein, mRNA copy numbers.

In one embodiment, an odds ratio (OR) is calculated for each biomarker level panel measurement. Here, the OR is a measure of association between the measured biomarker values for the patient and an outcome, e.g., COCA subtype. For example, see, *J. Can. Acad. Child Adolesc. Psychiatry* 2010; 19(3): 227-229, which is incorporated by reference in its entirety for all purposes.

In one embodiment, a specified statistical confidence level may be determined in order to provide a confidence level regarding the COCA subtype. For example, it may be determined that a confidence level of greater than 90% may be a useful predictor of the COCA subtype. In other embodiments, more or less stringent confidence levels may be chosen. For example, a confidence level of about or at least about 50%, 60%, 70%, 75%, 80%, 85%, 90%, 95%, 97.5%, 99%, 99.5%, or 99.9% may be chosen. The confidence level provided may in some cases be related to the quality of the sample, the quality of the data, the quality of the analysis, the specific methods used, and/or the number of gene expression values (i.e., the number of genes) analyzed. The specified confidence level for providing the likelihood of response may be chosen on the basis of the expected number of false positives or false negatives. Methods for choosing parameters for achieving a specified confidence level or for identifying markers with diagnostic power include but are not limited to Receiver Operating Characteristic (ROC) curve analysis, binomial ROC, principal component analysis, odds ratio analysis, partial least squares analysis, singular value decomposition, least absolute shrinkage and selection operator analysis, least angle regression, and the threshold gradient directed regularization method.

Determining the COCA subtype in some cases can be improved through the application of algorithms designed to normalize and or improve the reliability of the gene expression data. In some embodiments, the data analysis utilizes a computer or other device, machine or apparatus for application of the various algorithms described herein due to the large number of individual data points that are processed. A "machine learning algorithm" refers to a computational-based prediction methodology, also known to persons skilled in the art as a "classifier," employed for characterizing a gene expression profile or profiles, e.g., to determine the COCA subtype. The biomarker levels, determined by, e.g., microarray-based hybridization assays, sequencing assays, NanoString assays, etc., are in one embodiment subjected to the algorithm in order to classify the profile. Supervised learning generally involves "training" a classifier to recognize the distinctions among COCA subtypes such as, for example, C1 ACC/PCPG positive, C2 GBM/LGG positive, C3 OV positive, C4 Squamous-like positive, C6 LUAD-Enriched positive, C8 PAAD/some STAD positive, C9 UCS positive, C10 BRCA/Basal positive, C12 UCEC positive, C14 PRAD positive, C15 CESC (subset of cervical) positive, C16 BLCA positive, C17 TGCT positive, C19 COAD/READ positive, C20 SARC/MESO positive, C21 KIRK/KICH/KIRP positive, C22 Liver positive, C24 BRCA/Luminal positive, C25 THYM positive, C26 SKCM/UVM positive and C28 THCA positive, and then "testing" the accuracy of the classifier on an independent test set. Therefore, for new, unknown samples the classifier can be used to predict, for example, the class (e.g., C1 ACC/PCPG, C2 GBM/LGG, C3 OV, C4 Squamous-like, C6 LUAD-Enriched, C8 PAAD/some STAD, C9 UCS, C10 BRCA/Basal, C12 UCEC, C14 PRAD, C15 CESC (subset of cervical), C16 BLCA, C17 TGCT, C19 COAD/READ, C20 SARC/MESO, C21 KIRK/KICH/KIRP, C22 Liver, C24 BRCA/Luminal, C25 THYM, C26 SKCM/UVM and C28 THCA) in which the samples belong. The machine learning algorithm can be a CLaNC algorithm as provided herein.

In some embodiments, a robust multi-array average (RMA) method may be used to normalize raw data. The RMA method begins by computing background-corrected intensities for each matched cell on a number of microarrays. In one embodiment, the background corrected values are restricted to positive values as described by Irizarry et al. (2003). Biostatistics April 4 (2): 249-64, incorporated by reference in its entirety for all purposes. After background correction, the base-2 logarithm of each background corrected matched-cell intensity is then obtained. The background corrected, log-transformed, matched intensity on each microarray is then normalized using the quantile normalization method in which for each input array and each probe value, the array percentile probe value is replaced with the average of all array percentile points, this method is more completely described by Bolstad et al. Bioinformatics 2003, incorporated by reference in its entirety. Following quantile normalization, the normalized data may then be fit to a linear model to obtain an intensity measure for each probe on each microarray. Tukey's median polish algorithm (Tukey, J. W., Exploratory Data Analysis. 1977, incorporated by reference in its entirety for all purposes) may then be used to determine the log-scale intensity level for the normalized probe set data.

Various other software programs may be implemented. In certain methods, feature selection and model estimation may be performed by logistic regression with lasso penalty using glmnet (Friedman et al. (2010). *Journal of statistical software* 33(1): 1-22, incorporated by reference in its entirety). Raw reads may be aligned using TopHat (Trapnell et al. (2009). *Bioinformatics* 25(9): 1105-11, incorporated by reference in its entirety). In methods, top features (N ranging from 10 to 200) are used to train a linear support vector machine (SVM) (Suykens J A K, Vandewalle J. Least Squares Support Vector Machine Classifiers. *Neural Processing Letters* 1999; 9(3): 293-300, incorporated by reference in its entirety) using the e1071 library (Meyer D. Support vector machines: the interface to libsvm in package e1071. 2014, incorporated by reference in its entirety). Confidence intervals, in one embodiment, are computed using the pROC package (Robin X, Turck N, Hainard A, et al. pROC: an open-source package for R and S+ to analyze and compare ROC curves. *BMC bioinformatics* 2011; 12: 77, incorporated by reference in its entirety).

In addition, data may be filtered to remove data that may be considered suspect. In one embodiment, data derived from microarray probes that have fewer than about 4, 5, 6, 7 or 8 guanosine+cytosine nucleotides may be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine+cytosine nucleotides may in one embodiment be considered unreliable due to their aberrant hybridization propensity or secondary structure issues.

In some embodiments, data from probe-sets may be excluded from analysis if they are not identified at a detectable level (above background).

In some embodiments, probe-sets that exhibit no, or low variance may be excluded from further analysis. Low-variance probe-sets are excluded from the analysis via a Chi-Square test. In one embodiment, a probe-set is considered to be low-variance if its transformed variance is to the left of the 99 percent confidence interval of the Chi-Squared distribution with (N−1) degrees of freedom. (N−1)*Probe-set Variance/(Gene Probe-set Variance). Chi-Sq(N−1) where N is the number of input CEL files, (N−1) is the degrees of freedom for the Chi-Squared distribution, and the "probe-set variance for the gene" is the average of probe-set variances across the gene. In some embodiments, probe-sets for a given mRNA or group of mRNAs may be excluded from further analysis if they contain less than a minimum number of probes that pass through the previously described filter steps for GC content, reliability, variance and the like. For example in some embodiments, probe-sets for a given gene or transcript cluster may be excluded from further analysis if they contain less than about 1, 2, 3, 4, 5, 6, 7, 8, 9, 10, 11, 12, 13, 14, 15, or less than about 20 probes.

Methods of biomarker level data analysis in one embodiment, further include the use of a feature selection algorithm as provided herein. In some embodiments, feature selection is provided by use of the LIMMA software package (Smyth, G. K. (2005). Limma: linear models for microarray data. In: Bioinformatics and Computational Biology Solutions using R and Bioconductor, R. Gentleman, V. Carey, S. Dudoit, R. Irizarry, W. Huber (eds.), Springer, New York, pages 397-420, incorporated by reference in its entirety for all purposes).

Methods of biomarker level data analysis, in one embodiment, include the use of a pre-classifier algorithm. For example, an algorithm may use a specific molecular fingerprint to pre-classify the samples according to their composition and then apply a correction/normalization factor. This data/information may then be fed in to a final classification algorithm which would incorporate that information to aid in the final diagnosis.

Methods of biomarker level data analysis, in one embodiment, further include the use of a classifier algorithm as provided herein. In one embodiment, a diagonal linear discriminant analysis, k-nearest neighbor algorithm, support vector machine (SVM) algorithm, linear support vector machine, random forest algorithm, or a probabilistic model-based method or a combination thereof is provided for classification of microarray data. In some embodiments, identified markers that distinguish samples (e.g., of varying biomarker level profiles, and/or varying COCA subtypes of cancer are selected based on statistical significance of the difference in biomarker levels between classes of interest. In some cases, the statistical significance is adjusted by applying a Benjamin Hochberg or another correction for false discovery rate (FDR).

In some cases, the classifier algorithm may be supplemented with a meta-analysis approach such as that described by Fishel and Kaufman et al. 2007 Bioinformatics 23(13): 1599-606, incorporated by reference in its entirety for all purposes. In some cases, the classifier algorithm may be supplemented with a meta-analysis approach such as a repeatability analysis.

Methods for deriving and applying posterior probabilities to the analysis of biomarker level data are known in the art and have been described for example in Smyth, G. K. 2004 *Stat. Appi. Genet. Mol. Biol.* 3: Article 3, incorporated by reference in its entirety for all purposes. In some cases, the posterior probabilities may be used in the methods provided herein to rank the markers provided by the classifier algorithm.

A statistical evaluation of the results of the biomarker level profiling may provide a quantitative value or values indicative of one or more of the following: COCA subtype of cancer; the likelihood of the success of a particular therapeutic intervention, e.g., angiogenesis inhibitor therapy, chemotherapy, or immunotherapy. In one embodiment, the data is presented directly to the physician in its most useful form to guide patient care, or is used to define patient populations in clinical trials or a patient population for a given medication. The results of the molecular profiling can be statistically evaluated using a number of methods known to the art including, but not limited to: the students T test, the two sided T test, Pearson rank sum analysis, hidden Markov model analysis, analysis of q-q plots, principal component analysis, one way ANOVA, two way ANOVA, LIMMA and the like.

In some cases, accuracy may be determined by tracking the subject over time to determine the accuracy of the original diagnosis. In other cases, accuracy may be established in a deterministic manner or using statistical methods. For example, receiver operator characteristic (ROC) analysis may be used to determine the optimal assay parameters to achieve a specific level of accuracy, specificity, positive predictive value, negative predictive value, and/or false discovery rate.

In some cases, the results of the biomarker level profiling assays, are entered into a database for access by representatives or agents of a molecular profiling business, the individual, a medical provider, or insurance provider. In some cases, assay results include sample classification, identification, or diagnosis by a representative, agent or consultant of the business, such as a medical professional. In other cases, a computer or algorithmic analysis of the data is provided automatically. In some cases, the molecular profiling business may bill the individual, insurance provider, medical provider, researcher, or government entity for one or more of the following: molecular profiling assays performed, consulting services, data analysis, reporting of results, or database access.

In some embodiments, the results of the biomarker level profiling assays are presented as a report on a computer screen or as a paper record. In some embodiments, the report may include, but is not limited to, such information as one or more of the following: the levels of biomarkers (e.g., as reported by copy number or fluorescence intensity, etc.) as compared to the reference sample or reference value(s); the likelihood the subject will respond to a particular therapy, based on the biomarker level values and the COCA subtype and proposed therapies.

In one embodiment, the results of the gene expression profiling may be classified into one or more of the following: C1 ACC/PCPG positive, C2 GBM/LGG positive, C3 OV positive, C4 Squamous-like positive, C6 LUAD-Enriched positive, C8 PAAD/some STAD positive, C9 UCS positive, C10 BRCA/Basal positive, C12 UCEC positive, C14 PRAD positive, C15 CESC (subset of cervical) positive, C16 BLCA positive, C17 TGCT positive, C19 COAD/READ positive, C20 SARC/MESO positive, C21 KIRK/KICH/KIRP positive, C22 Liver positive, C24 BRCA/Luminal positive, C25 THYM positive, C26 SKCM/UVM positive or C28 THCA positive, C1 ACC/PCPG negative, C2 GBM/LGG negative, C3 OV negative, C4 Squamous-like negative, C6 LUAD-Enriched negative, C8 PAAD/some STAD negative, C9 UCS negative, C10 BRCA/Basal negative, C12

UCEC negative, C14 PRAD negative, C15 CESC (subset of cervical) negative, C16 BLCA negative, C17 TGCT negative, C19 COAD/READ negative, C20 SARC/MESO negative, C21 KIRK/KICH/KIRP negative, C22 Liver negative, C24 BRCA/Luminal negative, C25 THYM negative, C26 SKCM/UVM negative or C28 THCA negative or a combination thereof.

In some embodiments, results are classified using a trained algorithm. Trained algorithms provided herein include algorithms that have been developed using a reference set of known gene expression values and/or normal samples, for example, samples from individuals diagnosed with a particular molecular COCA subtype of cancer. In some cases, a reference set of known gene expression values are obtained from individuals who have been diagnosed with a particular COCA subtype of cancer. In some cases, a reference set of known gene expression values are obtained from individuals who have been diagnosed with a particular COCA subtype of cancer, and are also known to possess certain immune cell signature. In some cases, a reference set of known gene expression values are obtained from individuals who have been diagnosed with a particular COCA subtype of cancer, and are also known to have certain expression of tumor driver genes.

Algorithms suitable for categorization of samples include but are not limited to k-nearest neighbor algorithms, support vector machines, linear discriminant analysis, centroid algorithms (e.g., CLaNC), diagonal linear discriminant analysis, updown, naive Bayesian algorithms, neural network algorithms, hidden Markov model algorithms, genetic algorithms, or any combination thereof.

When a binary classifier is compared with actual true values (e.g., values from a biological sample), there are typically four possible outcomes. If the outcome from a prediction is p (where "p" is a positive classifier output, such as the presence of a deletion or duplication syndrome) and the actual value is also p, then it is called a true positive (TP); however if the actual value is n then it is said to be a false positive (FP). Conversely, a true negative has occurred when both the prediction outcome and the actual value are n (where "n" is a negative classifier output, such as no deletion or duplication syndrome), and false negative is when the prediction outcome is n while the actual value is p. In one embodiment, consider a test that seeks to determine whether a person is likely or unlikely to respond to angiogenesis inhibitor therapy. A false positive in this case occurs when the person tests positive, but actually does respond. A false negative, on the other hand, occurs when the person tests negative, suggesting they are unlikely to respond, when they actually are likely to respond. The same holds true for classifying a COCA subtype.

The positive predictive value (PPV), or precision rate, or post-test probability of disease, is the proportion of subjects with positive test results who are correctly diagnosed as likely or unlikely to respond, or diagnosed with the correct COCA subtype, or a combination thereof. It reflects the probability that a positive test reflects the underlying condition being tested for. Its value does however depend on the prevalence of the disease, which may vary. In one example, the following characteristics are provided: FP (false positive); TN (true negative); TP (true positive); FN (false negative). False positive rate $(\alpha)=FP/(FP+TN)-specificity$; False negative rate $(\beta)=FN/(TP+FN)-sensitivity$; $Power=sensitivity=1-\beta$; Likelihood-ratio $positive=sensitivity/(1-specificity)$; Likelihood-ratio $negative=(1-sensitivity)/specificity$. The negative predictive value (NPV) is the proportion of subjects with negative test results who are correctly diagnosed.

In some embodiments, the results of the biomarker level analysis of the subject methods provide a statistical confidence level that a given diagnosis is correct. In some embodiments, such statistical confidence level is at least about, or more than about 85%, 90%, 91%, 92%, 93%, 94%, 95%, 96%, 97%, 98%, 99% 99.5%, or more.

In some embodiments, the method further includes classifying the tumor tissue sample as a particular COCA subtype based on the comparison of biomarker levels in the sample and reference biomarker levels, for example present in at least one training set. In some embodiments, the tumor tissue sample is classified as a particular subtype if the results of the comparison meet one or more criterion such as, for example, a minimum percent agreement, a value of a statistic calculated based on the percentage agreement such as (for example) a kappa statistic, a minimum correlation (e.g., Pearson's correlation) and/or the like.

It is intended that the methods described herein can be performed by software (stored in memory and/or executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including Unix utilities, C, C++, Java™, Ruby, SQL, SAS®, the R programming language/software environment, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Some embodiments described herein relate to devices with a non-transitory computer-readable medium (also can be referred to as a non-transitory processor-readable medium or memory) having instructions or computer code thereon for performing various computer-implemented operations and/or methods disclosed herein. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

In some embodiments, a single biomarker, or from about 1 to about 4, from about 4 to about 8, from about 8 to about 12, from about 12 to about 16, from about 16 to about 20, from about 20 to about 24, from about 24 to about 30, from about 34 to about 38, from about 38 to about 42, from about 42 to about 46, from about 46 to about 50, from about 50 to about 54, from about 54 to about 58, from about 58 to about 62, from about 62 to about 66, from about 66 to about 72, from about 72 to about 76, from about 76 to about 80, from about 80 to about 84 (e.g., as disclosed in Table 1) is capable of classifying COCA subtypes of cancer with a predictive success of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, and all values in between. In some embodiments, any combination of biomarkers disclosed herein (e.g., in Table 1) can be used to obtain a predictive success of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, and all values in between.

In some embodiments, a single biomarker, or from about 1 to about 4, from about 4 to about 8, from about 8 to about 12, from about 12 to about 16, from about 16 to about 20, from about 20 to about 24, from about 24 to about 30, from about 34 to about 38, from about 38 to about 42, from about 42 to about 46, from about 46 to about 50, from about 50 to about 54, from about 54 to about 58, from about 58 to about 62, from about 62 to about 66, from about 66 to about 72, from about 72 to about 76, from about 76 to about 80, from about 80 to about 84 (e.g., as disclosed in Table 1) is capable of classifying COCA subtypes of cancer with a sensitivity or specificity of at least about 70%, at least about 71%, at least about 72%, at least about 73%, at least about 74%, at least about 75%, at least about 76%, at least about 77%, at least about 78%, at 1 east about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, and all values in between. In some embodiments, any combination of biomarkers disclosed herein can be used to obtain a sensitivity or specificity of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, and all values in between.

Classifier Biomarker Selection

In one embodiment, the methods and compositions provided herein are useful for determining the clustering of cluster assignments (COCA) subtype of a sample (e.g., tumor sample) from a patient by analyzing the expression of a set of biomarkers, whereby use of the set of biomarkers in detecting a COCA subtype comprises use of a fewer number of biomarkers from a single genome-wide platform as compared to methods known in the art for molecularly classifying a cell of origin cancer subtype (e.g., Hoadley et al. "Cell-of-origin patterns dominate the molecular classification of 10,000 tumors from 33 types of cancer." Cell173, no. 2 (2018): 291-304, and Hoadley et al. "Multiplatform analysis of 12 cancer types reveals molecular classification within and across tissues of origin." Cell 158, no. 4 (2014): 929-944, both of which are herein incorporated by reference). In some cases, the set of biomarkers is less than 300, 290, 280, 270, 260, 250, 240, 230, 220, 210, 200, 150, 100 or 90 biomarkers. In some cases, the set of biomarkers is between 4 and 84 biomarkers. In some cases, the set of biomarkers is the set of 84 biomarkers listed in Table 1. In some cases, the set of biomarkers is a sub-set of biomarkers listed Table 1 such as, for example 2, 4, 6, 8, 10, 12, 14, 16, 18, 20, 22, 24, 26, 28, 30, 32, 34, 36, 40, 42, 44, 46, 48, 50, 52, 54, 56, 58, 60, 62, 64, 66, 68, 70, 72, 74, 76, 78, 80 or 82 of the biomarkers listed in Table 1. The biomarkers or classifier biomarkers useful in the methods and compositions provided herein can be selected from one or more cancer datasets from one or more databases. The cancers can be any cancer known in the art. The cancers can include hematologic and lymphatic malignancies, solid tumor types, cancers of the central nervous system, cancers from neural-crest-derived tissues, and melanocytic cancers of the skin. The cancers for use in the methods herein can be the cancers studied in The Cancer Genome Atlas (TCGA) or a subset thereof. The cancers for use in the method provided herein can be those cancers listed herein. The databases can be public databases.

Figure 3:
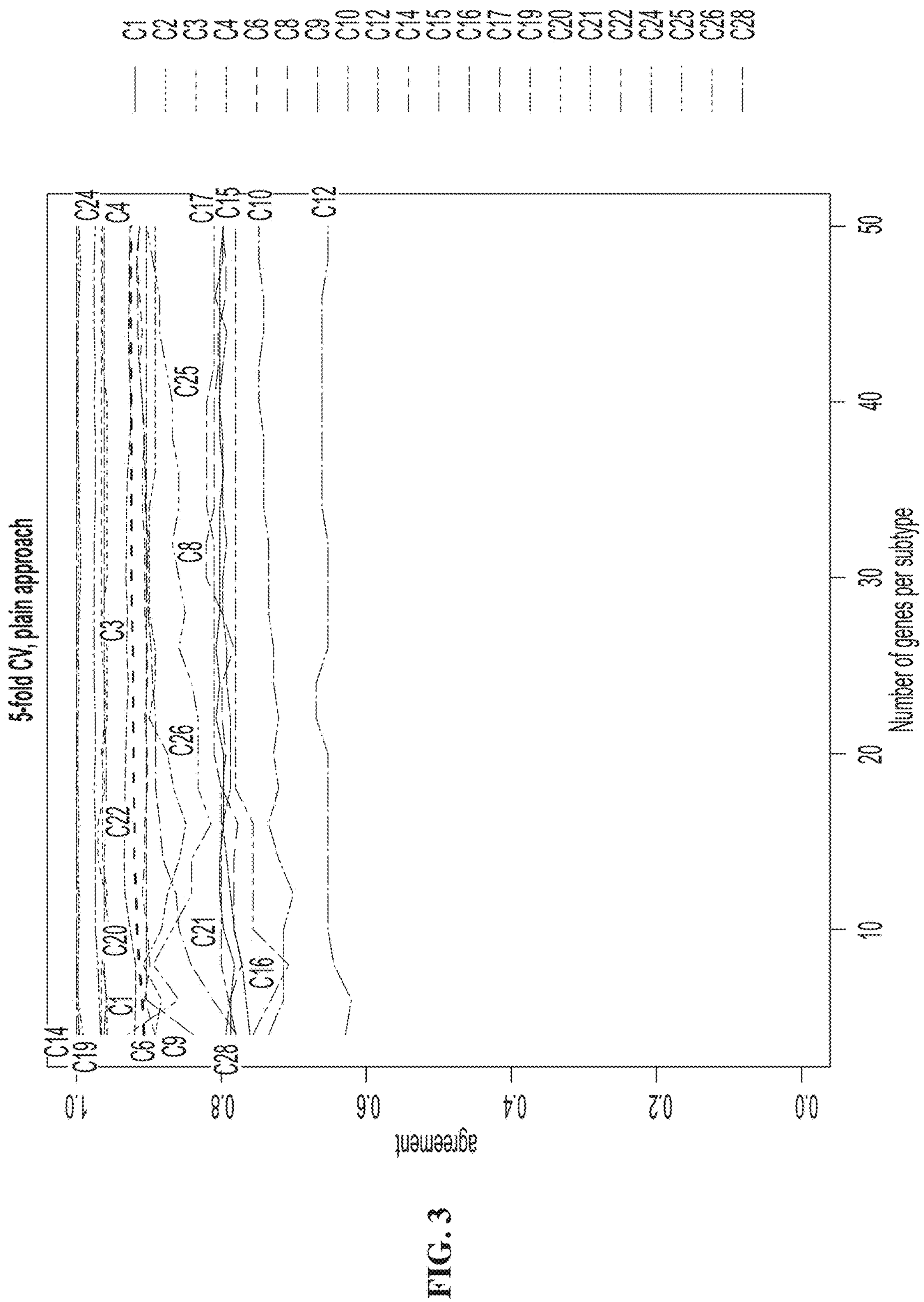
FIG. 3 illustrates five-fold cross validation curves using classification to the nearest centroid (ClaNC) on the TCGA-2018 training dataset (n=408) to guide the selection of the number of genes per subtype to include in the signature for COCA subtyping provided herein.

In one embodiment, classifier biomarkers (e.g., one or more genes listed in Table 1) useful in the methods and compositions provided herein for detecting or diagnosing subtypes were selected from a large data set of potential classifier biomarkers. In one embodiment, classifier biomarkers useful for the methods and compositions provided herein such as those in Table 1 are selected by subjecting a large set of classifier biomarkers to an in silico based process in order to determine the minimum number of genes whose expression profile can be used to determine a pan-cancer COCA subtype of a subject from a sample obtained from said subject. In some cases, the large set of classifier biomarkers can be a pan-cancer dataset such as, for example, the mRNA expression data (i.e., RNA-seq data) from TCGA found at gdc.cancer.gov/about-data/publications/pancanatlas. In some cases, the large set of classifier biomarkers can be the genes derived from the mRNA expression profile data derived from more than 10,000 tumors across more than 30 tumor types as described in Hoadley et al. "Cell-of-origin patterns dominate the molecular classification of 10,000 tumors from 33 types of cancer." Cell 173, no. 2 (2018): 291-304, which comprised one of several genome-wide molecular platforms that together can serve to define the gold standard (GS) COCA subtyper. The in silico process for selecting a gene signature as provided herein (e.g., Table 1 and 2) for determining a COCA subtype of a sample from a patient can comprise applying or using a Classification to Nearest Centroid (CLaNC) algorithm on the pan-cancer mRNA expression data (i.e., RNA-seq data) from TCGA to choose a minimum number of correlated genes for each subtype. For determination of the optimal number of genes (e.g., 84 genes as shown in Table 1) to include in the signature, the process can further comprise performing a 5-fold cross validation using the TCGA pan-cancer dataset following application of the CLaNC algorithm as provided herein to produce cross-validation curves to test different numbers of correlated genes as shown in FIG. 3 in order to determine the minimum number of correlated genes needed per subtype. To get the final list of gene classifiers, the method can further comprise applying the CLaNC algorithm to the entire TCGA mRNA expression pan-cancer dataset. The CLaNC software used in the methods provided herein can be as found in or derived from Alan R. Dabney; ClaNC: point-and-click software for classifying microarrays to nearest centroids, Bioinformatics, Volume 22, Issue 1, 1 Jan. 2006, Pages 122-123).

In one embodiment, the method further comprises validating the gene classifiers. Validation can comprise testing the expression of the classifiers in a test set of samples and comparing the COCA subtype determined using the signature of Table 1 with the COCA subtype determined using the gold standard COCA subtyper method described in Hoadley et al. "Cell-of-origin patterns dominate the molecular classification of 10,000 tumors from 33 types of cancer." Cell173, no. 2 (2018): 291-304. The test set of samples can be any sample type provided herein such as, for example, fresh frozen or archived formalin-fixed paraffin-embedded (FFPE) cancer samples. In one embodiment, validation can comprise testing the expression of the classifiers in several fresh frozen publicly available array and/or RNAseq datasets and calling the subtype based on said expression levels and subsequently comparing the COCA subtype determined using the signature of Table 1 with the COCA subtype determined using the gold standard COCA subtyper method described in Hoadley et al. "Cell-of-origin patterns dominate the molecular classification of 10,000 tumors from 33 types of cancer." Cell 173, no. 2 (2018): 291-304. In other words, validation can comprise calling the subtypes of the several fresh frozen publicly available array and RNAseq test datasets using their expression levels and the CLaNC algorithm as described herein and comparing the subtype calls with the gold standard subtype calls as defined in Hoadley et al. "Cell-of-origin patterns dominate the molecular classification of 10,000 tumors from 33 types of cancer." Cell 173, no. 2 (2018): 291-304. Final validation of the gene signature (e.g., Table 1) can then be performed in a newly collected dataset of archived formalin-fixed paraffin-embedded (FFPE) cancer samples to assure comparable performance in the FFPE samples. In one embodiment, the classifier biomarkers of Table 1 were selected based on the in silico CLaNC process described herein. The gene symbols and official gene names are listed in Table 1. Further to the above embodiments, the in silico CLaNC process can entail use of the CLaNC process described in Dabney (2005) Bioinformatics 21(22):4148-4154. In one embodiment, the in silico CLaNC process can entail use of CLaNC software described in Dabney A R. ClaNC: Point-and-click software for classifying microarrays to nearest centroids. Bioinformatics. 2006; 22: 122-123 or equivalents or derivatives related thereto.

In one embodiment, the methods provided herein require the detection of the expression level of at least 1, at least 2, at least 3, at least 4, at least 5, at least 6, at least 7, at least 8, at least 9, at least 10, at least 11, at least 12, at least 13, at least 14, at least 15, at least 16, at least 18, at least 20, at least 22, at least 24, at least 26, at least 28, at least 30, at least 32, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83 or up to 84 classifier biomarkers (e.g., from Table 1) in a cancer sample obtained from a patient whose expression is altered in order to identify a COCA cancer subtype. The same applies for other classifier biomarker expression datasets as provided herein.

In another embodiment, the methods provided herein require the detection of the expression level of a total of at least 2, at least 4, at least 6, at least 8, at least 10, at least 12, at least 14, at least 16, at least 18, at least 20, at least 22, at least 24, at least 26, at least 28, at least 30, at least 32, at least 34, at least 36, at least 38, at least 40, at least 42, at least 44, at least 46, at least 48, at least 50, at least 52, at least 54, at least 56, at least 58, at least 60, at least 62, at least 64, at least 66, at least 68, at least 70, at least 72, at least 74, at least 76, at least 78, at least 80, at least 82 or up to 84 classifier biomarkers out of the 84 gene biomarkers of Table 1 in a cancer cell sample obtained from a patient in order to identify a COCA cancer subtype. In another embodiment, the methods provided herein require the detection of the expression level of a total of at least 4, at least 8, at least 12, at least 16, at least 20, at least 24, at least 28, at least 32, at least 36, at least 40, at least 44, at least 48, at least 52, at least 56, at least 60, at least 64, at least 68, at least 72, at least 76, at least 80 or up to 84 classifier biomarkers out of the 84 gene biomarkers of Table 1 in a cancer cell sample obtained from a patient in order to identify a COCA cancer subtype. The same applies for other classifier biomarker expression datasets as provided herein.

In one embodiment, the expression level of one or more classifier biomarkers of Table 1 can be altered in a specific COCA subtype as detected in a sample obtained from a subject as described in any of the methods provided herein. The alteration of the expression level can be an "up-regulation" or "down-regulation" of the one or more classifier biomarkers of Table 1. In one embodiment, at least 1, at least 2, at least 3, at least 4, at least 5, at least 6, at least 7, at least 8, at least 9, at least 10, at least 11, at least 12, at least 13, at least 14, at least 15, at least 16, at least 18, at least 20, at least 22, at least 24, at least 26, at least 28, at least 30, at least 32, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83 or up to 84 classifier biomarkers out of the 84 gene biomarkers of Table 1 are "up-regulated" in a specific COCA subtype of cancer. In another embodiment, at least 1, at least 2, at least 3, at least 4, at least 5, at least 6, at least 7, at least 8, at least 9, at least 10, at least 11, at least 12, at least 13, at least 14, at least 15, at least 16, at least 18, at least 20, at least 22, at least 24, at least 26, at least 28, at least 30, at least 32, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83 or up to 84 classifier biomarkers out of the 84 gene biomarkers of Table 1 are "down-regulated" in a specific COCA subtype of cancer. In a still further embodiment, in methods provided herein utilizing more than one classifier biomarker (e.g., more than one classifier biomarker from Table 1) to determine a COCA subtype, the alteration in expression levels of the more than one classifier biomarkers can either be an up-regulation, a down-regulation or any combination thereof. Further to any of the above embodiments, the alteration of the expression level can be relative to or compared to a sample isolated from a healthy subject as defined herein. The sample obtained from the healthy subject can be form the same anatomical area of the body. The same applies for other classifier biomarker expression datasets as provided herein.

In one embodiment, the expression level of an "up-regulated" biomarker as provided herein is increased by about 0.2-fold, about 0.5-fold, about 1-fold, about 1.5-fold, about 2-fold, about 2.5-fold, about 3-fold, about 3.5-fold, about 4-fold, about 4.5-fold, about 5-fold, and any values in between. In another embodiment, the expression level of a "down-regulated" biomarker as provided herein is decreased by about 0.2-fold, about 0.5-fold, about 1-fold, about 1.5-fold, about 2-fold, about 2.5-fold, about 3-fold, about 3.5-fold, about 4-fold, about 4.5-fold, about 5-fold, and any values in between.

It is recognized that additional genes or proteins or molecular platforms can be used in the practice of the methods provided herein. In general, genes useful in classifying the COCA subtypes of cancer include those that are independently capable of distinguishing between normal versus tumor, or between different classes or grades of cancer. A gene is considered to be capable of reliably distinguishing between COCA subtypes if the area under the receiver operator characteristic (ROC) curve is approximately 1. Further, in general, molecular platforms that generate data that can be useful in classifying the COCA subtypes of cancer can include genome-wide platforms such as, for example, whole-exome DNA sequencing assays (e.g., Illumina HiSeq and GAII), DNA copy-number variation assays (e.g., Affymetrix 6.0 microarrays), DNA methylation assays (e.g., Illumina 450,000-feature microarrays), genome-wide mRNA level assays (e.g., Illumina mRNA-seq), microRNA level assays (e.g., Illumina microRNA-seq), and protein level assays for proteins and/or phosphorylated proteins (e.g., Reverse Phase Protein Arrays; RPPA).

Clinical/Therapeutic Uses

In one embodiment, a method is provided herein for determining a disease outcome or prognosis for a patient suffering from cancer. In some cases, the cancer can be any cancer known in the art and/or provided herein. The disease outcome or prognosis can be measured by examining the overall survival for a period of time or intervals (e.g., 0 to 36 months or 0 to 60 months). In one embodiment, survival is analyzed as a function of COCA subtype. In one embodiment, survival is analyzed as a function of COCA subtype across tissue of origin tumor types. In one embodiment, survival is analyzed as a function of COCA subtype within a tissue of origin tumor type (see, for example, FIGS. 6-8). The COCA subtype can be determined using the methods provided herein such as, for example, determining the expression of all or subsets of the genes in Table 1. Relapse-free and overall survival can be assessed using standard Kaplan-Meier plots as well as Cox proportional hazards modeling.

In one embodiment, the methods and compositions as provided herein for determining a COCA subtype of a patient suffering or suspected of suffering from cancer is used to determine whether or not said patient is a candidate for treatment with a specific type or types of cancer therapy. The sample can be any type of sample obtained from the patient as provided herein. The cancer can be any type of cancer known in the art and/or provided herein. In one embodiment, determining the COCA subtype is one of a number of methods that can be employed to characterize the sample obtained from the patient such that the determining the COCA subtype alone or in combination with one or more of the number of methods can be used to determine whether or not said patient is a candidate for treatment with a specific type or types of cancer therapy. In addition to assessing or determining a COCA subtype, the number of methods for characterizing the sample can entail determining a proliferation score, the tumor mutation burden (TMB), the tissue of origin subtype, the level of immune activation or any combination thereof. In one embodiment, one or all of the methods for characterizing the sample can be performed on RNA sequencing data obtained from the sample.

In one embodiment, in addition to assessing the COCA subtype as provided herein, the characterization entails determining proliferation or proliferation score. In one embodiment, proliferation or the proliferation score is determined using any method known in the art such as, for example, as provided in U.S. 62/789,668 filed Jan. 8, 2019, which is herein incorporated by reference herein.

In one embodiment, in addition to determining the COCA subtype as provided herein, the characterization entails calculating a TMB value and/or rate. The TMB value and/or rate can be calculated using any method known in the art. In one embodiment, the TMB value and/or rate can be calculated from RNA (e.g., via transcriptome profiling or RNA sequencing)) as provided in U.S. 62/771,702 filed Nov. 27, 2018 and U.S. 62/743,257 filed Oct. 9, 2018, which is herein incorporated by reference herein.

The determination of whether or not said patient is a candidate for treatment with a specific type or types of cancer therapy can be based on the COCA subtype alone or in combination with other methods known in the art for characterizing a sample obtained from a patient suffering from or suspected of suffering from cancer. The other methods for characterizing said sample can be histologically based methods, gene expression based methods or a combination thereof. The histologically based methods can include histological cancer subtyping by one or more trained pathologists as well as the histological based methods of assessing proliferation such as, for example, determining the mitotic activity index. The gene expression based methods can include subtyping, assessment of TMB, assessment of tissue of origin subtype, immune subtyping or any combination thereof. The gene expression based methods can be assessed from DNA, RNA or a combination thereof. In one embodiment, the characterization of the sample obtained from the patient suffering from or suspected of suffering from cancer is performed on RNA obtained or isolated from the sample.

The gene expression based tissue of origin cancer subtyping can be determined using gene signatures known in the art for specific types of cancer. In one embodiment, the tissue of origin of the cancer is the lung and the gene signature is selected from the gene signatures found in WO2017/201165, WO2017/201164, US20170114416 or U.S. Pat. No. 8,822,153, each of which is herein incorporated by reference in their entirety. In one embodiment, the tissue of origin cancer is head and neck squamous cell carcinoma (HNSCC) and the gene signature is selected from the gene signatures found in PCT/US18/45522 or PCT/US18/48862, each of which is herein incorporated by reference in their entirety. In one embodiment, the tissue of origin cancer is breast cancer and the gene signature is the PAM50 subtyper found in Parker J S et al., (2009) Supervised risk predictor of breast cancer based on intrinsic subtypes. J Clin Oncol 27:1160-1167, which is herein incorporated by reference in its entirety. In one embodiment, the tissue of origin cancer is bladder cancer (e.g., MIBC) and the gene signature is selected from the gene signatures found in 62/629,975 filed Feb. 13, 2018, which is herein incorporated by reference in their entirety. In one embodiment, the tissue of origin cancer is bladder cancer (e.g., MIBC) and the gene signature is selected from the gene signature found in The Cancer Genome Atlas Research Network. Comprehensive molecular characterization of urothelial bladder carcinoma. Nature volume 507, pages 315-322 (2014), or Robertson, A G, et al., Cell, 171(3): 540-556 (2017), each of which is herein incorporated by reference, which is herein incorporated by reference in their entirety.

The gene expression based immune subtyping or immune cell activation can be determined using immune expression signatures known in the art such as, for example, the gene signatures found in Thorsson, V., Gibbs, D. L., Brown, S. D., Wolf, D., Bortone, D. S., Yang, T. H. O., Porta-Pardo, E., Gao, G. F., Plaisier, C. L., Eddy, J. A. and Ziv, E., 2018, The immune landscape of cancer. *Immunity,* 48(4), pp. 812-830, which is herein incorporated by reference in its entirety. In one embodiment, immune cell activation is determined by monitoring the immune cell signatures of Bindea et al (Immunity 2013; 39(4); 782-795), the contents of which are herein incorporated by reference in its entirety. In one embodiment, the method further comprises measuring single gene immune biomarkers, such as, for example, CTLA4, PDCD1 and CD274 (PD-LI), PDCDLG2(PD-L2) and/or IFN gene signatures. In one embodiment, the level of immune cell activation is determined by measuring gene expression signatures of immunomarkers. The immunomarkers can be measured in the same and/or different sample used to determine the COCA subtype as described herein. The immunomarkers can be those found in WO2017/201165, and WO2017/201164, each of which is herein incorporated by reference in their entirety.

The gene expression based method for calculating a TMB value and/or rate can be any method known in the art. In one embodiment, the TMB value and/or rate can be calculated from RNA (e.g., via transcriptome profiling or RNA sequencing)) as provided in U.S. 62/771,702 filed Nov. 27, 2018 and U.S. 62/743,257 filed Oct. 9, 2018, which is herein incorporated by reference herein.

In one embodiment, upon determining a patient's COCA subtype (e.g., by measuring the expression of all or subsets of the genes in Table 1), the patient is selected for suitable therapy, for example, radiotherapy (radiation therapy), surgical intervention, target therapy, chemotherapy or drug therapy with an angiogenesis inhibitor or immunotherapy or combinations thereof. In some embodiments, the suitable treatment can be any treatment or therapeutic method that can be used for a cancer patient. In one embodiment, upon determining a patient's COCA subtype, the patient is administered a suitable therapeutic agent, for example chemotherapeutic agent(s) or an angiogenesis inhibitor or immunotherapeutic agent(s). In one embodiment, the therapy is immunotherapy, and the immunotherapeutic agent is a checkpoint inhibitor, monoclonal antibody, biological response modifier, therapeutic vaccine or cellular immunotherapy. In some embodiments, the determination of a suitable treatment can identify treatment responders. In some embodiments, the determination of a suitable treatment can identify treatment non-responders. In some embodiments, upon determining a patient's COCA subtype, the cancer patient can be selected for any combination of suitable therapies. For example, chemotherapy or drug therapy with a radiotherapy, a tumor dissection with an immunotherapy or a chemotherapeutic agent with a radiotherapy. In some embodiments, immunotherapy, or immunotherapeutic agent can be a checkpoint inhibitor, monoclonal antibody, biological response modifier, therapeutic vaccine or cellular immunotherapy.

The methods provided herein are also useful for evaluating clinical response to therapy, as well as for endpoints in clinical trials for efficacy of new therapies. The extent to which sequential diagnostic expression profiles move towards normal can be used as one measure of the efficacy of the candidate therapy.

In one embodiment, the methods provided herein also find use in predicting response to different lines of therapies based on the COCA subtype of cancer alone or in combination with other characterization methods as described herein (e.g., tissue of origin cancer subtype, immune subtype, proliferation and/or TMB status). For example, chemotherapeutic response can be improved by more accurately assigning tumor cell of origin subtypes. Likewise, treatment regimens can be formulated based on the COCA subtype alone or in combination with other characterization methods as described herein (e.g., tissue of origin cancer subtype, immune subtype, proliferation and/or TMB status).

Immunotherapy

In one embodiment, provided herein is a method for determining whether a cancer patient is likely to respond to immunotherapy by determining the COCA subtype of cancer of a sample obtained from the patient and, based on the COCA subtype, assessing whether the patient is likely to respond to immunotherapy. In another embodiment, provided herein is a method of selecting a patient suffering from cancer for immunotherapy by determining a COCA subtype of a sample from the patient and, based on the COCA subtype, selecting the patient for immunotherapy. The determination of the COCA subtype of the sample obtained from the patient can be performed using any method for COCA subtyping known in the art. The determination of the COCA subtype of the sample obtained from the patient can be performed using any method for COCA subtyping provided herein. In one embodiment, the sample obtained from the patient has been previously diagnosed as being a particular type of cancer, and the methods provided herein are used to determine the COCA subtype of the sample. The previous diagnosis can be based on a histological analysis. The histological analysis can be performed by one or more pathologists. In one embodiment, the COCA subtyping is performed via gene expression analysis of a set or panel of biomarkers or subsets thereof in order to generate an expression profile. The gene expression analysis can be performed on a tumor sample obtained from a patient in order to determine the presence, absence or level of expression of one or more biomarkers selected from a publically available pan-cancer database described herein and/or Table 1 provided herein. The COCA subtype can be selected from the group consisting of C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and C28 (THCA). The immunotherapy can be any immunotherapy provided herein. In one embodiment, the immunotherapy comprises administering one or more checkpoint inhibitors. The checkpoint inhibitors can be any checkpoint inhibitor provided herein such as, for example, a checkpoint inhibitor that targets PD-1, PD-LI or CTLA4.

As disclosed herein, the biomarkers panels, or subsets thereof, can be those disclosed in any publically available pan-cancer gene expression dataset or datasets. In one embodiment, the biomarker panel or subset thereof is, for example, the cancer genome atlas pan-cancer mRNA expression dataset. In one embodiment, the biomarker panel or subset thereof is, for example, the pan-cancer mRNA expression dataset disclosed in Hoadley, Katherine A., Christina Yau, Toshinori Hinoue, Denise M. Wolf, Alexander J. Lazar, Esther Drill, Ronglai Shen et al. "Cell-of-origin patterns dominate the molecular classification of 10,000 tumors from 33 types of cancer." Cell173, no. 2 (2018): 291-304, the contents of which are herein incorporated by reference in its entirety. In one embodiment, the biomarker panel or subset thereof is, for example, the gene expression signature disclosed in Table 1 in combination with one or more biomarkers from a publically available pan-cancer expression dataset.

In one embodiment, from about 1 to about 4, about 4 to about 8, from about 4 to about 12, from about 4 to about 16, from about 4 to about 20, from about 4 to about 24, from about 4 to about 28, from about 4 to about 32, from about 4 to about 36, from about 4 to about 40, from about 4 to about 44, from about 4 to about 48, from about 4 to about 52, from about 4 to about 56, from about 4 to about 60, from about 4 to about 64, from about 4 to about 68, from about 4 to about 72, from about 4 to about 76, from about 4 to about 80 or from about 4 to about 84 of the biomarkers in any of the pan-cancer gene expression datasets provided herein, including, for example, Table 1 for a tumor sample are detected in a method to determine the COCA subtype as provided herein. In another embodiment, each of the biomarkers from any one of the pan-cancer gene expression datasets provided herein, including, for example, Table 1 for a tumor sample are detected in a method to determine the COCA subtype as provided herein.

In one embodiment, the methods provided herein further comprise determining the presence, absence or level of immune activation in a COCA subtype. The presence or level of immune cell activation can be determined by creating an expression profile or detecting the expression of one or more biomarkers associated with innate immune cells and/or adaptive immune cells associated with each COCA subtype in a sample obtained from a patient. In one embodiment, immune cell activation associated with a COCA subtype of cancer is determined by monitoring the immune cell signatures of Thorsson, V. et al., 2018, The immune landscape of cancer. *Immunity,* 48(4), pp. 812-830, Bindea et al (Immunity 2013; 39(4); 782-795) Faruki H. et al., JTO, 12(6): 943-953 (2017), Charoentong P. et al., Cell reports, 18, 248-262 (2017) and/or WO2017/201165 and WO2017/201164, the contents of each of which are herein incorporated by reference in its entirety. In one embodiment, the method further comprises measuring single gene immune biomarkers, such as, for example, CTLA4, PDCD1 and CD274 (PD-LI), PDCDLG2(PD-L2) and/or IFN gene signatures. The presence or a detectable level of immune activation (Innate and/or Adaptive) associated with a COCA subtype can indicate or predict that a patient with said COCA subtype may be amendable to immunotherapy. The immunotherapy can be treatment with a checkpoint inhibitor as provided herein. In one embodiment, a method is provided herein for detecting the expression of at least one classifier biomarker provided herein in a sample (e.g., tumor sample) obtained from a patient further comprises administering an immunotherapeutic agent following detection of immune activation as provided herein in said sample.

In one embodiment, the method comprises determining a COCA subtype of a tumor sample and subsequently determining a level of immune cell activation of said sub-type. In one embodiment, the subtype is determined by determining the expression levels of one or more classifier biomarkers at the nucleic acid level using sequencing (e.g., RNASeq), amplification (e.g., qRT-PCR) or hybridization assays (e.g., microarray analysis) as described herein. The one or more biomarkers can be selected from a publically available database (e.g., TCGA pan-cancer mRNA expression datasets or any other publically available pan-cancer gene expression datasets provided herein). In some embodiments, the biomarkers of Table 1 can be used to specifically determine the COCA subtype of a tumor sample obtained from a patient. In one embodiment, the level of immune cell activation is determined by measuring gene expression signatures of immunomarkers. The immunomarkers can be measured in the same and/or different sample used to subtype the tumor sample as described herein. The immunomarkers that can be measured can comprise, consist of, or consistently essentially of innate immune cell (IIC) and/or adaptive immune cell (AIC) gene signatures, interferon (IFN) gene signatures, individual immunomarkers, major histocompatibility complex class II (MHC class II) genes or a combination thereof. The gene expression signatures for IICs, AICs, IFN and MHC class II can be any known gene signatures for said cell types or genes known in the art. For example, the immune gene signatures can be those from Bindea et al. (Immunity 2013; 39(4); 782-795), Faruki H. et al., JTO, 12(6): 943-953 (2017), Charoentong P. et al., Cell reports, 18, 248-262 (2017) and/or WO2017/201165 and WO2017/201164. The individual immunomarkers can be CTLA4, PDCD1 and CD274 (PD-L1). In one embodiment, immune subtyping or immune cell activation can be determined using the gene signatures found in Thorsson, V., Gibbs, D. L., Brown, S. D., Wolf, D., Bortone, D. S., Yang, T. H. O., Porta-Pardo, E., Gao, G. F., Plaisier, C. L., Eddy, J. A. and Ziv, E., 2018, The immune landscape of cancer. *Immunity,* 48(4), pp. 812-830.

In one embodiment, upon determining a patient's COCA cancer subtype using any of the methods and classifier biomarkers panels or subsets thereof as provided herein, the patient is selected for treatment with or administered an immunotherapeutic agent. The immunotherapeutic agent can be a checkpoint inhibitor, monoclonal antibody, biological response modifiers, therapeutic vaccine or cellular immunotherapy.

In another embodiment, the immunotherapeutic agent is a checkpoint inhibitor. In some cases, a method for determining the likelihood of response to one or more checkpoint inhibitors is provided. In one embodiment, the checkpoint inhibitor is a PD-1/PD-LI checkpoint inhibitor. The PD-1/PD-LI checkpoint inhibitor can be nivolumab, pembrolizumab, atezolizumab, durvalumab, lambrolizumab, or avelumab. In one embodiment, the checkpoint inhibitor is a CTLA-4 checkpoint inhibitor. The CTLA-4 checkpoint inhibitor can be ipilimumab or tremelimumab. In one embodiment, the checkpoint inhibitor is a combination of checkpoint inhibitors such as, for example, a combination of one or more PD-1/PD-LI checkpoint inhibitors used in combination with one or more CTLA-4 checkpoint inhibitors.

In one embodiment, the immunotherapeutic agent is a monoclonal antibody. In some cases, a method for determining the likelihood of response to one or more monoclonal antibodies is provided. The monoclonal antibody can be directed against tumor cells or directed against tumor products. The monoclonal antibody can be panitumumab, matuzumab, necitumunab, trastuzumab, amatuximab, bevacizumab, ramucirumab, bavituximab, patritumab, rilotumumab, cetuximab, immu-132, or demcizumab.

In yet another embodiment, the immunotherapeutic agent is a therapeutic vaccine. In some cases, a method for determining the likelihood of response to one or more therapeutic vaccines is provided. The therapeutic vaccine can be a peptide or tumor cell vaccine. The vaccine can target MAGE-3 antigens, NY-ESO-1 antigens, p53 antigens, survivin antigens, or MUC1 antigens. The therapeutic cancer vaccine can be GVAX (GM-CSF gene-transfected tumor cell vaccine), belagenpumatucel-L (allogeneic tumor cell vaccine made with four irradiated NSCLC cell lines modified with TGF-beta2 antisense plasmid), MAGE-A3 vaccine (composed of MAGE-A3 protein and adjuvant AS15), (1)-BLP-25 anti-MUC-1 (targets MUC-1 expressed on tumor cells), CimaVax EGF (vaccine composed of human recombinant Epidermal Growth Factor (EGF) conjugated to a carrier protein), WT1 peptide vaccine (composed of four Wilms' tumor suppressor gene analogue peptides), CRS-207 (live-attenuated *Listeria monocytogenes* vector encoding human mesothelin), Bec2/BCG (induces anti-GD3 antibodies), GV1001 (targets the human telomerase reverse transcriptase), TG4010 (targets the MUC1 antigen), racotumomab (anti-idiotypic antibody which mimicks the NGcGM3 ganglioside that is expressed on multiple human cancers), tecemotide (liposomal BLP25; liposome-based vaccine made from tandem repeat region of MUC1) or DRibbles (a vaccine made from nine cancer antigens plus TLR adjuvants).

In one embodiment, the immunotherapeutic agent is a biological response modifier. In some cases, a method for determining the likelihood of response to one or more biological response modifiers is provided. The biological response modifier can trigger inflammation such as, for example, PF-3512676 (CpG 7909) (a toll-like receptor 9 agonist), CpG-ODN 2006 (downregulates Tregs), *Bacillus* Calmette-Guerin (BCG), *Mycobacterium* vaccae (SRL172) (nonspecific immune stimulants now often tested as adjuvants). The biological response modifier can be cytokine therapy such as, for example, IL-2+ tumor necrosis factor alpha (TNF-alpha) or interferon alpha (induces T-cell proliferation), interferon gamma (induces tumor cell apoptosis), or Mda-7 (IL-24) (Mda-7/IL-24 induces tumor cell apoptosis and inhibits tumor angiogenesis). The biological response modifier can be a colony-stimulating factor such as, for example granulocyte colony-stimulating factor. The biological response modifier can be a multi-modal effector such as, for example, multi-target VEGFR: thalidomide and analogues such as lenalidomide and pomalidomide, cyclophosphamide, cyclosporine, denileukin diftitox, talactoferrin, trabecetedin or all-trans-retinoic acid.

In one embodiment, the immunotherapy is cellular immunotherapy. In some cases, a method for determining the likelihood of response to one or more cellular therapeutic agents. The cellular immunotherapeutic agent can be dendritic cells (DCs) (ex vivo generated DC-vaccines loaded with tumor antigens), T-cells (ex vivo generated lymphokine-activated killer cells; cytokine-induce killer cells; activated T-cells; gamma delta T-cells), or natural killer cells.

In some cases, specific COCA subtypes of cancer have different levels of immune activation (e.g., innate immunity and/or adaptive immunity) such that COCA subtypes with elevated or detectable immune activation (e.g., innate immunity and/or adaptive immunity) are selected for treatment with one or more immunotherapeutic agents described herein. In some cases, specific COCA subtypes of cancer have high or elevated levels of immune activation. In some cases, the C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and/or C28 (THCA) subtype has elevated levels of immune activation (e.g., innate immunity and/or adaptive immunity) as compared to other blaCOCA subtypes. In some cases, the C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and/or C28 (THCA) subtype has reduced levels of immune activation (e.g., innate immunity and/or adaptive immunity) as compared to other COCA subtypes. In one embodiment, COCA subtypes with low levels of or no immune activation (e.g., innate immunity and/or adaptive immunity) are not selected for treatment with one or more immunotherapeutic agents described herein.

Angiogenesis Inhibitors

In one embodiment, upon determining a patient's or subject's COCA subtype alone or in combination with other characterization methods as described herein (e.g., determining tissue of origin cancer subtype, proliferation signature or score, immune subtype and/or TMB status, etc.), the patient is selected for drug therapy with an angiogenesis inhibitor.

In one embodiment, the angiogenesis inhibitor is a vascular endothelial growth factor (VEGF) inhibitor, a VEGF receptor inhibitor, a platelet derived growth factor (PDGF) inhibitor or a PDGF receptor inhibitor.

In general, methods of determining whether a patient is likely to respond to angiogenesis inhibitor therapy, or methods of selecting a patient for angiogenesis inhibitor therapy are provided herein. In one embodiment, the method comprises determining a COCA subtype alone or in combination with other characterization methods as described herein (e.g., determining tissue of origin cancer subtype, proliferation signature or score, immune subtype and/or TMB status, etc.) and probing a sample from the patient for the levels of at least five hypoxia biomarkers selected from the group consisting of RRAGD, FABP5, UCHL1, GAL, PLOD, DDIT4, VEGF, ADM, ANGPTL4, NDRG1, NP, SLC16A3, and C14ORF58 (see Table A) at the nucleic acid level. In a further embodiment, the probing step comprises mixing the sample with five or more oligonucleotides that are substantially complementary to portions of nucleic acid molecules of the at least five biomarkers under conditions suitable for hybridization of the five or more oligonucleotides to their complements or substantial complements, detecting whether hybridization occurs between the five or more oligonucleotides to their complements or substantial complements; and obtaining hybridization values of the sample based on the detecting steps. The hybridization values of the sample are then compared to reference hybridization value(s) from at least one sample training set, wherein the at least one sample training set comprises (i) hybridization value(s) of the at least five biomarkers from a sample that overexpresses the at least five biomarkers, or overexpresses a subset of the at least five biomarkers, (ii) hybridization values of the at least five biomarkers from a reference cancer of COCA subtype specific sample, or (iii) hybridization values of the at least five biomarkers from a control or healthy sample. A determination of whether the patient is likely to respond to angiogenesis inhibitor therapy, or a selection of the patient for angiogenesis inhibitor is then made based upon (i) the patient's COCA subtype alone or in combination with other characterization methods as described herein (e.g., determining tissue of origin cancer subtype, proliferation signature or score, immune subtype and/or TMB status, etc.) and (ii) the results of comparison.

TABLE A

| Biomarkers for hypoxia profile | | |
|---|---|---|
| Name | Abbreviation | GenBank Accession No. |
| RRAGD | Ras-related GTP binding D | BC003088 |
| FABP5 | fatty acid binding protein 5 | M94856 |
| UCHL1 | ubiquitin carboxyl-terminal esterase L1 | NM_004181 |
| GAL | Galanin | BC030241 |
| PLOD | procollagen-lysine, 2-oxoglutarate 5-dioxygenase lysine hydroxylase | M98252 |
| DDIT4 | DNA-damage-inducible transcript 4 | NM_019058 |
| VEGF | vascular endothelial growth factor | M32977 |
| ADM | Adrenomedullin | NM_001124 |
| ANGPTL4 | angiopoietin-like 4 | AF202636 |
| NDRG1 | N-myc downstream regulated gene 1 | NM_006096 |
| NP | nucleoside phosphorylase | NM 000270 |
| SLC16A3 | solute carrier family 16 monocarboxylic acid transporters, member 3 | NM_004207 |
| C14ORF58 | chromosome 14 open reading frame 58 | AK000378 |

The aforementioned set of thirteen biomarkers, or a subset thereof, is also referred to herein as a "hypoxia profile".

In one embodiment, the method provided herein includes determining the levels of at least five biomarkers, at least six biomarkers, at least seven biomarkers, at least eight biomarkers, at least nine biomarkers, or at least ten biomarkers, or five to thirteen, six to thirteen, seven to thirteen, eight to thirteen, nine to thirteen or ten to thirteen biomarkers selected from RRAGD, FABP5, UCHL1, GAL, PLOD, DDIT4, VEGF, ADM, ANGPTL4, NDRG1, NP, SLC16A3, and C140RF58 in a sample obtained from a subject. Biomarker expression in some instances may be normalized against the expression levels of all RNA transcripts or their expression products in the sample, or against a reference set of RNA transcripts or their expression products. The reference set as explained throughout, may be an actual sample that is tested in parallel with the sample, or may be a reference set of values from a database or stored dataset. Levels of expression, in one embodiment, are reported in number of copies, relative fluorescence value or detected fluorescence value. The level of expression of the biomarkers of the hypoxia profile together with the COCA subtype alone or in combination with other characterization methods as described herein (e.g., determining tissue of origin cancer subtype, proliferation signature or score, immune subtype and/or TMB status, etc.) as determined using the methods provided herein can be used in the methods described herein to determine whether a patient is likely to respond to angiogenesis inhibitor therapy.

In one embodiment, the levels of expression of the thirteen biomarkers (or subsets thereof, as described above, e.g., five or more, from about five to about 13), are normalized against the expression levels of all RNA transcripts or their non-natural cDNA expression products, or protein products in the sample, or of a reference set of RNA transcripts or a reference set of their non-natural cDNA expression products, or a reference set of their protein products in the sample.

In one embodiment, angiogenesis inhibitor treatments include, but are not limited to an integrin antagonist, a selectin antagonist, an adhesion molecule antagonist, an antagonist of intercellular adhesion molecule (ICAM)-1, ICAM-2, ICAM-3, platelet endothelial adhesion molecule (PCAM), vascular cell adhesion molecule (VCAM)), lymphocyte function-associated antigen 1 (LFA-1), a basic fibroblast growth factor antagonist, a vascular endothelial growth factor (VEGF) modulator, a platelet derived growth factor (PDGF) modulator (e.g., a PDGF antagonist).

In one embodiment of determining whether a subject is likely to respond to an integrin antagonist, the integrin antagonist is a small molecule integrin antagonist, for example, an antagonist described by Paolillo et al. (Mini Rev Med Chem, 2009, volume 12, pp. 1439-1446, incorporated by reference in its entirety), or a leukocyte adhesion-inducing cytokine or growth factor antagonist (e.g., tumor necrosis factor-α (TNF-α), interleukin-1β (IL-1β), monocyte chemotactic protein-1 (MCP-1) and a vascular endothelial growth factor (VEGF)), as described in U.S. Pat. No. 6,524,581, incorporated by reference in its entirety herein.

The methods provided herein are also useful for determining whether a subject is likely to respond to one or more of the following angiogenesis inhibitors: interferon gamma 1β, interferon gamma 1β (Actimmune®) with pirfenidone, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with *salvia* and *Schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260, XV615 or a combination thereof.

In another embodiment, a method is provided for determining whether a subject is likely to respond to one or more endogenous angiogenesis inhibitors. In a further embodiment, the endogenous angiogenesis inhibitor is endostatin, a 20 kDa C-terminal fragment derived from type XVIII collagen, angiostatin (a 38 kDa fragment of plasmin), a member of the thrombospondin (TSP) family of proteins. In a further embodiment, the angiogenesis inhibitor is a TSP-1, TSP-2, TSP-3, TSP-4 and TSP-5. Methods for determining the likelihood of response to one or more of the following angiogenesis inhibitors are also provided a soluble VEGF receptor, e.g., soluble VEGFR-1 and neuropilin 1 (NPR1), angiopoietin-1, angiopoietin-2, vasostatin, calreticulin, platelet factor-4, a tissue inhibitor of metalloproteinase (TIMP) (e.g., TIMP1, TIMP2, TIMP3, TIMP4), cartilage-derived angiogenesis inhibitor (e.g., peptide troponin I and chrondomodulin I), a disintegrin and metalloproteinase with thrombospondin motif 1, an interferon (IFN), (e.g., IFN-α, IFN-β, IFN-γ), a chemokine, e.g., a chemokine having the C-X-C motif (e.g., CXCL10, also known as interferon gamma-induced protein 10 or small inducible cytokine B10), an interleukin cytokine (e.g., IL-4, IL-12, IL-18), prothrombin, antithrombin III fragment, prolactin, the protein encoded by the TNFSF15 gene, osteopontin, maspin, canstatin, proliferin-related protein.

In one embodiment, a method for determining the likelihood of response to one or more of the following angiogenesis inhibitors is provided is angiopoietin-1, angiopoietin-2, angiostatin, endostatin, vasostatin, thrombospondin, calreticulin, platelet factor-4, TIMP, CDAI, interferon α, interferon β, vascular endothelial growth factor inhibitor (VEGI) meth-1, meth-2, prolactin, VEGI, SPARC, osteopontin, maspin, canstatin, proliferin-related protein (PRP), restin, TSP-1, TSP-2, interferon gamma 1β, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with *salvia* and *Schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260, XV615 or a combination thereof.

In yet another embodiment, the angiogenesis inhibitor can include pazopanib (Votrient), sunitinib (Sutent), sorafenib (Nexavar), axitinib (Inlyta), ponatinib (Iclusig), vandetanib (Caprelsa), cabozantinib (Cometrig), ramucirumab (Cyramza), regorafenib (Stivarga), ziv-aflibercept (Zaltrap), motesanib, or a combination thereof. In another embodiment, the angiogenesis inhibitor is a VEGF inhibitor. In a further embodiment, the VEGF inhibitor is axitinib, cabozantinib, aflibercept, brivanib, tivozanib, ramucirumab or motesanib. In yet a further embodiment, the angiogenesis inhibitor is motesanib.

In one embodiment, the methods provided herein relate to determining a subject's likelihood of response to an antagonist of a member of the platelet derived growth factor (PDGF) family, for example, a drug that inhibits, reduces or modulates the signaling and/or activity of PDGF-receptors (PDGFR). For example, the PDGF antagonist, in one embodiment, is an anti-PDGF aptamer, an anti-PDGF antibody or fragment thereof, an anti-PDGFR antibody or fragment thereof, or a small molecule antagonist. In one embodiment, the PDGF antagonist is an antagonist of the PDGFR-α or PDGFR-β. In one embodiment, the PDGF antagonist is the anti-PDGF-β aptamer E10030, sunitinib, axitinib, sorefenib, imatinib, imatinib mesylate, nintedanib, pazopanib HCl, ponatinib, MK-2461, dovitinib, pazopanib, crenolanib, PP-121, telatinib, imatinib, KRN 633, CP 673451, TSU-68, Ki8751, amuvatinib, tivozanib, masitinib, motesanib diphosphate, dovitinib dilactic acid, linifanib (ABT-869).

Upon making a determination of whether a patient is likely to respond to angiogenesis inhibitor therapy, or selecting a patient for angiogenesis inhibitor therapy, in one embodiment, the patient is administered the angiogenesis inhibitor. The angiogenesis in inhibitor can be any of the angiogenesis inhibitors described herein.

Radiotherapy

In one embodiment, provided herein is a method for determining whether a patient is likely to respond to radiotherapy by determining the COCA subtype alone or in combination with other characterization methods as described herein (e.g., determining tissue of origin cancer subtype, proliferation signature or score, immune subtype and/or TMB status, etc.) of a sample obtained from the patient and, based on the COCA subtype alone or in combination with other characterization methods as described herein (e.g., tissue of origin cancer subtype, proliferation signature or score, immune subtype and/or TMB status, etc.), assessing whether the patient is likely to respond to or benefit from radiotherapy. In another embodiment, provided herein is a method of selecting a patient suffering from cancer for radiotherapy by determining a COCA subtype alone or in combination with other characterization methods as described herein (e.g., determining tissue of origin cancer subtype, proliferation signature or score, immune subtype and/or TMB status, etc.) of a sample from the patient and, based on the COCA subtype alone or in combination with other characterization methods as described herein (e.g., determining tissue of origin cancer subtype, proliferation signature or score, immune subtype and/or TMB status, etc.), selecting the patient for radiotherapy.

In some embodiments, the radiotherapy can include but are not limited to proton therapy and external-beam radiation therapy. In some embodiments, the radiotherapy can include any types or forms of treatment that is suitable for patients with specific types of cancer.

In some embodiments, a patient with a specific type of cancer can have or display resistance to radiotherapy. Radiotherapy resistance in any cancer or subtype thereof can be determined by measuring or detecting the expression levels of one or more genes known in the art and/or provided herein associated with or related to the presence of radiotherapy resistance. Genes associated with radiotherapy resistance can include NFE2L2, KEAP1 and CUL3. In some embodiments, radiotherapy resistance can be associated with the alterations of KEAP1 (Kelch-like ECH-associated protein 1)/NRF2 (nuclear factor E2-related factor 2) pathway. Association of a particular gene to radiotherapy resistance can be determined by examining expression of said gene in one or more patients known to be radiotherapy non-responders and comparing expression of said gene in one or more patients known to be radiotherapy responders.

Surgical Intervention

In one embodiment, provided herein is a method for determining whether a cancer patient is likely to respond to surgical intervention by determining the COCA subtype alone or in combination with other characterization methods as described herein (e.g., determining tissue of origin cancer subtype, proliferation signature or score, immune subtype and/or TMB status, etc.) of a sample obtained from the patient and, based on the COCA subtype alone or in combination with other characterization methods as described herein (e.g., determining tissue of origin cancer subtype, proliferation signature or score, immune subtype and/or TMB status, etc.), assessing whether the patient is likely to respond to or benefit from surgery. In another embodiment, provided herein is a method of selecting a patient suffering from cancer for surgery by determining a COCA subtype alone or in combination with other characterization methods as described herein (e.g., determining tissue of origin cancer subtype, proliferation signature or score, immune subtype and/or TMB status, etc.) of a sample from the patient and, based on the COCA subtype alone or in combination with other characterization methods as described herein (e.g., determining tissue of origin cancer subtype, proliferation signature or score, immune subtype and/or TMB status, etc.), selecting the patient for surgery. In some embodiments, the surgery can include laser technology, excision, dissection, and reconstructive surgery.

Prediction of Overall Survival Rate and Metastasis for Cancer Patients

The present disclosure provides methods for predicting overall survival rate for a cancer patient. In some embodiments, the prediction of overall survival rate can involve obtaining a tumor sample for a cancer patient. In some embodiments, the cancer patients can have various stages of cancers. In some embodiments, the overall survival rate can be determined by detecting the expression level of at least one subtype classifier of a publically available pan-cancer database or dataset. In some embodiments, an overall survival rate can be determined by detecting the expression level (e.g., protein and/or nucleic acid) of any subtype classifiers that are relevant across many types of cancer, for example, subtype classifiers relevant to cell of origin. In one embodiment, the subtype classifiers can be all or a subset of classifiers from Table 1. In some embodiments, the identification of the cell of origin (COCA) subtype is indicative of the overall survival in the patient. In some embodiments, the COCA subtype is selected from C1 ACC/PCPG, C2 GBM/LGG, C3 OV, C4 Squamous-like, C6 LUAD-Enriched, C8 PAAD/some STAD, C9 UCS, C10 BRCA/Basal, C12 UCEC, C14 PRAD, C15 CESC (subset of cervical), C16 BLCA, C17 TGCT, C19 COAD/READ, C20 SARC/MESO, C21 KIRK/KICH/KIRP, C22 Liver, C24 BRCA/Luminal, C25 THYM, C26 SKCM/UVM and C28 THCA.

The present disclosure provides methods for predicting nodal metastasis for a cancer patient. In some embodiments, the prediction of nodal metastasis can involve obtaining a tumor sample for a patient. In some embodiments, the patients can have various stages of cancers. In some embodiments, the nodal metastasis can be determined by detecting the expression level of at least one subtype classifier from a pan-cancer gene set. The pan-cancer gene set can be a publically available pan-cancer database or a gene set provided herein (e.g. Table 1) or a combination thereof. The publically available pan-cancer gene set can be a TCGA pan-cancer gene set. In one embodiment, nodal metastasis of cancer can be determined by detecting the expression level of all the subtype classifiers or subsets thereof of the classifiers found in Table 1.

In some embodiments, the C1 ACC/PCPG, C2 GBM/LGG, C3 OV, C4 Squamous-like, C6 LUAD-Enriched, C8 PAAD/some STAD, C9 UCS, C10 BRCA/Basal, C12 UCEC, C14 PRAD, C15 CESC (subset of cervical), C16 BLCA, C17 TGCT, C19 COAD/READ, C20 SARC/MESO, C21 KIRK/KICH/KIRP, C22 Liver, C24 BRCA/Luminal, C25 THYM, C26 SKCM/UVM or C28 THCA COCA subtype can be more likely to be associated with nodal metastasis compared with other subtypes. In some embodiments, the C1 ACC/PCPG, C2 GBM/LGG, C3 OV, C4 Squamous-like, C6 LUAD-Enriched, C8 PAAD/some STAD, C9 UCS, C10 BRCA/Basal, C12 UCEC, C14 PRAD, C15 CESC (subset of cervical), C16 BLCA, C17 TGCT, C19 COAD/READ, C20 SARC/MESO, C21 KIRK/KICH/KIRP, C22 Liver, C24 BRCA/Luminal, C25 THYM, C26 SKCM/UVM or C28 THCA COCA subtype can be most likely associated with positive lymph node metastasis compared with other subtypes. In some embodiments, the C1 ACC/PCPG, C2 GBM/LGG, C3 OV, C4 Squamous-like, C6 LUAD-Enriched, C8 PAAD/some STAD, C9 UCS, C10 BRCA/Basal, C12 UCEC, C14 PRAD, C15 CESC (subset of cervical), C16 BLCA, C17 TGCT, C19 COAD/READ, C20 SARC/MESO, C21 KIRK/KICH/KIRP, C22 Liver, C24 BRCA/Luminal, C25 THYM, C26 SKCM/UVM or C28 THCA COCA subtype can be at least about 0.1 times, at least about 0.2 times, at least about 0.3 times, at least about 0.4 times, at least about 0.5 times, at least about 0.6 times, at least about 0.7 times, at least about 0.8 times, at least about 0.9 times, at least about 1 time, at least about 1.2 times, at least about 1.5 times, at least about 1.7 times, at least about 2.0 times, at least about 2.2 times, at least about 2.5 times, at least about 2.7 times, at least about 3.0 times, at least about 3.2 times, at least about 3.5 times, at least about 3.7 times, at least about 4.0 times, at least about 4.2 times, at least about 4.5 times, at least about 4.7 times, at least about 5.0 times, inclusive of all ranges and subranges therebetween, more likely to have occult nodal metastasis compared to other COCA subtypes.

Detection Methods

In one embodiment, the methods and compositions provided herein allow for the detection of at least one biomarker in a tumor sample obtained from a subject. The at least one biomarker can be a classifier biomarker provided herein. The detection can be at the nucleic acid level or protein level. In one embodiment, the detection is at the nucleic acid level and the detection can be by using any amplification, hybridization and/or sequencing assay disclosed herein. In one embodiment, the at least one biomarker detected using the methods and compositions provided herein is selected from Table 1. Further to the above embodiment, the detection of the at least one biomarker selected from Table 1 is at the nucleic acid level. In one embodiment, the methods of detecting the biomarker(s) (e.g., classifier biomarkers) in the tumor sample obtained from the subject comprises, consists essentially of, or consists of measuring the expression level of at least one or a plurality of biomarkers using any of the methods provided herein. The biomarkers can be selected from Table 1. In one embodiment, the plurality of biomarker nucleic acids comprises, consists essentially of or consists of at least 4 biomarkers, at least 8 biomarkers, at least 12 biomarkers, at least 16 biomarkers, at least 20 biomarkers, at least 24 biomarkers, at least 28 biomarkers, at least 32 biomarkers, at least 36 biomarkers, at least 40 biomarkers, at least 44 biomarkers, at least 48 biomarkers, at least 52 biomarkers, at least 56 biomarkers, at least 60 biomarkers, at least 64 biomarkers, at least 68 biomarkers, at least 72 biomarkers, at least 76 biomarkers, at least 80 biomarkers or all 84 biomarkers of Table 1. In another embodiment, the plurality of biomarkers comprises, consists essentially of or consists of at least 8 biomarkers, at least 16 biomarkers, at least 24 biomarkers, at least 32 biomarkers, at least 40 biomarkers, at least 48 biomarkers, at least 56 biomarkers, at least 64 biomarkers, at least 72 biomarkers, at least 80 biomarkers or all 84 biomarkers of Table 1.

In another embodiment, the methods and compositions provided herein allow for the detection of at least one or a plurality of biomarkers selected from the biomarkers listed in Table 1 in combination with the detection of at least one or a plurality of biomarkers from one or more additional sets of biomarkers in a tumor sample obtained from a subject. The tumor sample can be any type of sample provided herein. The subject can be suffering from or suspected of suffering from cancer. The cancer can be any type of cancer provided herein. The detection can be at the nucleic acid level or protein level. In one embodiment, the detection is at the nucleic acid level and the detection can be by using any amplification, hybridization and/or sequencing assay disclosed herein. The one or more additional sets of biomarkers can be selected from a set of biomarkers whose presence, absence and/or level of expression is indicative of immune activation, proliferation, a tissue of origin cancer subtype, or any combination thereof. The additional set of biomarkers for indicating immune activation can be gene expression signatures of and/or Adaptive Immune Cells (AIC) and/or Innate immune Cells (IIC), individual immune biomarkers, interferon genes, major histocompatibility complex, class II (MHC H) genes or a combination thereof. The gene expression signatures of both IIC and AIC can be any gene signatures known in the art such as, for example, the gene signatures listed in Thorsson, V. et al., 2018, The immune landscape of cancer. *Immunity,* 48(4), pp. 812-830, Bindea et al. (Immunity 2013; 39(4); 782-795), Faruki H. et al., JTO, 12(6): 943-953 (2017), Charoentong P. et al., Cell reports, 18, 248-262 (2017) or WO2017/201165 and WO2017/201164, each of which is herein incorporated by reference in their entirety. The additional set of biomarkers for indicating proliferation can be gene expression signatures that include the 11 gene signature comprising BIRC5, CCNB1, CDC20, CDCA1, CEP55, KNTC2, MKI67, PTTG1, RRM2, TYMS, and UBE2C found in Martin M. et al., Breast Cancer Res Treat, 138: 457-466 (2013), the 18 gene signature found in US 20160115551 and/or the 26 gene signature found in 62/789,668 filed Jan. 8, 2019. The additional set of biomarkers for determining tissue of origin cancer subtypes can be any gene signature found in the art for subtyping specific tissue of origin cancers. In one embodiment, the additional set of biomarkers for determining tissue of origin cancer subtypes is the adenocarcinoma lung cancer subtyping gene expression signatures found in WO2017/201165, US20170114416 or U.S. Pat. No. 8,822,153. In one embodiment, the additional set of biomarkers for determining tissue of origin cancer subtypes is the squamous cell carcinoma lung cancer subtyping gene expression signatures found in WO2017/201164, US20170114416 or U.S. Pat. No. 8,822,153. In one embodiment, the additional set of biomarkers for determining tissue of origin cancer subtypes is the breast cancer subtyping gene expression signatures found in Parker J S et al., (2009) Supervised risk predictor of breast cancer based on intrinsic subtypes. J Clin Oncol 27:1160-1167, which is herein incorporated by reference in its entirety. In one embodiment, the additional set of biomarkers for determining tissue of origin cancer subtypes is the bladder cancer subtyping gene expression signatures found in 62/629,975 filed Feb. 13, 2018. In one embodiment, the additional set of biomarkers for determining tissue of origin cancer subtypes is the bladder cancer subtyping gene expression signatures found in The Cancer Genome Atlas Research Network. Comprehensive molecular characterization of urothelial bladder carcinoma. Nature volume 507, pages 315-322 (2014), or Robertson, A G, et al., Cell, 171(3): 540-556 (2017), each of which is herein incorporated by reference. In one embodiment, the additional set of biomarkers for determining tissue of origin cancer subtypes is a head and neck squamous cell carcinoma (HNSCC) subtyping gene expression signatures selected from PCT/US18/45522 or PCT/US18/48862. Further to any of the above embodiments, the methods and compositions provided herein further comprise determining tumor mutation burden (TMB) and/or TMB rate of the tumor sample. The TMB and/or TMB rate can be determined or calculated using any method known in the art. In one embodiment, the TMB and/or TMB rate is determined from RNA as described in 62/743,257 filed on Oct. 9, 2018 and 62/771,702 filed on Nov. 27, 2018.

Kits

Kits for practicing the methods provided herein can be further provided. By "kit" can encompass any manufacture (e.g., a package or a container) comprising at least one reagent, e.g., an antibody, a nucleic acid probe or primer, etc., for specifically detecting the expression of a biomarker provided herein. The kit may be promoted, distributed, or sold as a unit for performing the methods provided herein. Additionally, the kits may contain a package insert describing the kit and methods for its use.

In one embodiment, kits for practicing the methods provided herein are provided. Such kits are compatible with both manual and automated immunocytochemistry techniques (e.g., cell staining). These kits comprise at least one antibody directed to a biomarker of interest, chemicals for the detection of antibody binding to the biomarker, a counterstain, and, optionally, a bluing agent to facilitate identification of positive staining cells. Any chemicals that detect antigen-antibody binding may be used in the practice of the methods provided herein. The kits may comprise at least 2, at least 3, at least 4, at least 5, at least 6, at least 7, at least 8, at least 9, at least 10, or more antibodies for use in the methods provided herein.

In one embodiment, the kits for practicing the methods provided herein comprise at least one primer pair directed to a biomarker of interest, chemicals for the detection of amplification of the biomarker of interest, and, optionally, any agent necessary for quantifying the detection level of the biomarker of interest. Any chemicals that detect amplification products may be used in the practice of the methods provided herein. The kits may comprise at least 2, at least 3, at least 4, at least 5, at least 6, at least 7, at least 8, at least 9, at least 10, or more primer pairs for use in the methods provided herein.

In one embodiment, the kits for practicing the methods provided herein comprise at least one probe directed to a biomarker of interest, chemicals for the detection of hybridization of the probe to the biomarker of interest, and, optionally, any agent necessary for quantifying the level of the biomarker of interest. Any chemicals that detect hybridization products may be used in the practice of the methods provided herein. The kits may comprise at least 2, at least 3, at least 4, at least 5, at least 6, at least 7, at least 8, at least 9, at least 10, or more probes for use in the methods provided herein.

EXAMPLES

The present invention is further illustrated by reference to the following Examples. However, it should be noted that these Examples, like the embodiments described above, are illustrative and are not to be construed as restricting the scope of the invention in any way.

Example 1—Development and Validation of the 84-Gene Pan Cancer Subtyping Signature Background Recent genomic analyses of pathologically-defined tumor types has identified disease subtypes within a tissue. The extent to which genomic signatures are shared across tumorous tissues remains unclear.

Provided within this example is the development and validation of an 84-gene gene signature that can be used in a method for classifying a tumor sample obtained from a patient as one of 21 possible integrated, pan-cancer cluster of cluster assignment (COCA) subtypes, thereby providing valuable insight into tumor biology and potential therapeutic response. The 21 COCA subtypes that can be determined using the gene signature developed herein alone are listed in FIG. 1 and are designated as C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and C28 (THCA)).

Objective

This example was initiated to address the need for an efficient method for improved tumor classification based on cell-of-origin that could inform prognosis, drug response and patient management based on underlying genomic and biologic tumor characteristics. Using the data associated with the 2018 TCGA Pan-cancer publications (https://gdc-.cancer.gov/about-data/publications/pancanatlas) and comparing to the multi-platform cluster of cluster assignment (COCA) analysis performed in Hoadley et al, Cell. 2018 Apr. 5; 173(2):291-304 (hereinafter referred to as the "Gold Standard" for COCA subtyping) a pan-cancer COCA subtyping signature was developed. The gene signature developed in this example can be used in diagnostic methods that include evaluation of gene expression subtypes and application of an algorithm for categorization of a tumor sample obtained from a subject into one of 21 COCA subtypes C1 (ACC/PCPG), C2 (GBM/LGG), C3 (OV), C4 (Squamous-like), C6 (LUAD-Enriched), C8 (PAAD/some STAD), C9 (UCS), C10 (BRCA/Basal), C12 (UCEC), C14 (PRAD), C15 (CESC (subset of cervical)), C16 (BLCA), C17 (TGCT), C19 (COAD/READ), C20 (SARC/MESO), C21 (KIRK/KICH/KIRP), C22 (Liver), C24 (BRCA/Luminal), C25 (THYM), C26 (SKCM/UVM) and C28 (THCA))).

Methods/Results

To develop the aforementioned pan-cancer, COCA subtyper, data associated with the 2018 TCGA Pan-cancer publications (https://gdc.cancer.gov/about-data/publications/pancanatlas) was downloaded. In particular, the expression data from primary solid tumor samples (n=8545; primary solid tumor per TCGA barcode) that had expression data from the "EBPlusPlusAdjustPANCAN_IlluminaHiSeq_RNASeqV2" platform (i.e., EBPlusPlusAdjustPANCAN_IlluminaHiSeq_RNASeqV@-v2.geneExp.tsv) from the TCGA dataset was used, as were the merged sample quality annotations (i.e., merged_sample_quality_annotations.tsv). Data from "do_not_use=False" specified in the sample quality file (merged_sample_quality_annotations.tsv) as well as data from samples from the pilot study (designated tumor type="FFFP") were excluded. The 8545 samples were from 32 tumor types. The 32 tumor types were kidney renal papillary cell carcinoma (KIRP); breast invasive carcinoma (BRCA); thyroid cancer (THCA); bladder urothelial carcinoma (BLCA); prostate adenocarcinoma (PRAD); kidney chromophobe (KICH); cervical squamous cell carcinoma and endocervical adenocarcinoma (CESC); kidney renal clear cell carcinoma (KIRC); liver hepatocellular carcinoma (LTHC); low grade glioma (LGG); sarcoma (SARC); lung adenocarcinoma (LUAD); colon adenocarcinoma (COAD); head and neck squamous cell carcinoma (HNSC); uterine corpus endometrial carcinoma (UCEC); glioblastoma multiforme (GBM); esophageal carcinoma (ESCA); stomach adenocarcinoma (STAD); ovarian serous cystadenocarcinoma (OV); rectum adenocarcinoma (READ); adrenocortical carcinoma (ACC); uveal melanoma (UVM); mesothelioma (MESO); pheochromocytoma and paraganglioma (PCPG); skin cutaneous melanoma (SKCM); uterine carcinosarcoma (UCS); lung squamous cell carcinoma (LUSC); testicular germ cell tumors (TGCT); cholangiocarcinoma (CHOL); pancreatic adenocarcinoma (PAAD); thymoma (THYM); and Lymphoid Neoplasm Diffuse Large B-cell Lymphoma (DLBC).

The COCA subtypes (i.e., COCA_Sample_Assignment_n9759.csv) from Hoadley et al, (Cell. 2018 Apr. 5; 173(2):291-304) were then assigned to the 8545 samples from the TCGA data described above, excluding COCA subtypes with 30 or fewer samples. FIG. 1 shows the cross-tabulation of the TCGA tumor type and COCA subtype from the Hoadley et al, 2018 paper for samples with qualifying expression data as described herein. FIG. 1 also provides the integrated COCA subtypes and their designations as provided herein.

To develop the reduced and clinically applicable pan cancer COCA subtyper, the 8545 samples from the TCGA dataset described above (and the RNA-seq expression data associated therewith) were divided into a training set (⅔ of the data set; n=5696) and a test set (⅓ of the data set; n=2849), balancing for uniform tumor type of origin distributions (see the Table in FIG. 2). Gene expression values were log 2 transformed and genes with low variance and/or low mean were filtered out, while genes with mean variance and mean expression values greater than 4 were kept resulting in gene expression data for 2190 genes (see graph in FIG. 2). It should be noted that samples that were found to have a COCA subtype 5 (C5; n=41) using the gold standard COCA subtyper described in Hoadley et al, 2018 were excluded from the training set due to the presence of a small number of samples that were not well differentiated by gene expression. As a result, the training set subsequently used to generate the COCA subtyper via cross-validation and classification to the nearest centroid (ClaNC (Dabney, 2006)) had an n of 5655 samples.

As mentioned, a Classification to Nearest Centroid (CLaNC) algorithm (see Alan R. Dabney; ClaNC: point-and-click software for classifying microarrays to nearest centroids, Bioinformatics, Volume 22, Issue 1, 1 Jan. 2006, Pages 122-123) was applied to the gene expression data from the training set (n=5655) in order to choose different numbers of genes per subtype (see. FIG. 3) that were subsequently tested using 5-fold cross-validation (CV) to find the minimum number of genes that would be required to provide differentiation of the aforementioned COCA subtypes with sufficient agreement with the previously developed gold standard (i.e., COCA analysis on multiplatform 'omic' data as described in Hoadley et al, 2018). As shown in FIG. 3, said 5-fold cross validation suggested that 4 genes per subtype for a total of 84 genes (i.e., for the 21 COCA subtypes described herein) would achieve sufficient agreement between the classifier prediction and COCA subtype as determined using the gold standard method from Hoadley et al. 2018.

Regarding selection of the final 84 genes (i.e., 4 genes/COCA subtype) to be included in the 21 class COCA subtyper, the ClaNC software package (see Dabney, 2006) used on the entire training set calculated t-statistics and 84 genes were selected based on the ranks of the strongest t-statistics (i.e., both negatively and positively correlated genes for each COCA subtype can be and were selected) (see Table 1). Then an ordinary nearest centroid classifier was fit using the 21 COCA classes and 84 genes.

Validation of the reduced gene signature was performed by applying the 84-gene nearest centroid classifier of Table 1 to the test set (n=2849) and comparing the COCA subtypes as determined by the gold standard vs. the 84-gene classifier or signature (i.e., Table 1). As shown in FIG. 4, the test set showed an overall agreement of 90%, which was similar to the agreement with COCA GS subtyping of 91% for the training set. FIG. 5 showed that the 84 gene nearest centroid classifier called a vast majority of the COCA subtypes in the test set correctly.

Conclusion

Development and validation of an 84-gene signature for COCA subtyping was described. The resulting 84 gene signature maintains high concordance rates with the gold standard COCA subtyper as described in the art.

Subtypes provide potential biomarkers for targeted and immunotherapy response. The data demonstrate that differences in prognosis that may be meaningful to therapeutic management.

Example 2— Examination Use of COCA Subtype Signature as a Prognostic Indicator Objective This example describes the examination of the 84 gene COCA subtyper developed in Example 1 and found in Table 1 as a prognostic indicator for overall survival. Overall, the goal of the studies in this example was to determine if the 84-gene COCA signature has prognostic value across a myriad of tumor types.

Methods and Results

In order to determine if the 84 gene signature of Table 1 has prognostic utility, associations between overall survival and the 84 gene COCA signature were examined within specific tumor types (i.e., BLCA, BRCA and STAD). Associations between overall survival and the 84 gene signature were examined separately within tumor type by fitting cox models adjusted for age at diagnosis and stage with overall survival the outcome and classifier subtype as the predictor, reporting hazard ratios for classifier subtype, and testing (Wald's test) whether the coefficient for classifier subtype was different from zero. It should be noted that the association tests used only subtype categories having many samples. For example, BLCA tumors were classified into 8 predicted subtype categories (C10, C15, C16, C20, C25, C4, C8, C9; see FIG. 6) but 92% (345/375) were in two of them (C16 and C4), and only these categories were analyzed.

As shown in FIGS. 6-8, specific COCA subtypes can be associated with overall survival. For example, as shown in FIG. 6, the C4 COCA subtype was significantly associated with worse overall survival in BLCA (association test p-value for C4 subtype as determined using Table 1 gene signature was 0.0204, while the Hazard ratio was 1.53 (i.e., second column); FIG. 6), while the C8 COCA subtype in STAD (association test p-value for C8 subtype as determined using Table 1 gene signature was 0.00689, while the Hazard ratio was 1.67; FIG. 8) samples was also associated with worse overall survival. In contrast, the C24 COCA subtype in the BRCA sample had better overall survival (association test p-value was 0.00013, while the Hazard ratio was 0.37; FIG. 7).

INCORPORATION BY REFERENCE

The following references are incorporated by reference in their entireties for all purposes.

Hoadley, Katherine A., Christina Yau, Toshinori Hinoue, Denise M. Wolf, Alexander J. Lazar, Esther Drill, Ronglai Shen et al. "Cell-of-origin patterns dominate the molecular classification of 10,000 tumors from 33 types of cancer." Cell173, no. 2 (2018): 291-304.

Hoadley, Katherine A., Christina Yau, Denise M. Wolf, Andrew D. Cherniack, David Tamborero, Sam Ng, Max D M Leiserson et al. "Multiplatform analysis of 12 cancer types reveals molecular classification within and across tissues of origin." Cell 158, no. 4 (2014): 929-944.

Alan R. Dabney; ClaNC: point-and-click software for classifying microarrays to nearest centroids, Bioinformatics, Volume 22, Issue 1, 1 Jan. 2006, Pages 122-123.

Alan R. Dabney; Classification of microarrays to nearest centroids, Bioinformatics, Volume 21, Issue 22, 15 Nov. 2005, Pages 4148-4154.

FURTHER NUMBERED EMBODIMENTS OF THE DISCLOSURE

Other subject matter contemplated by the present disclosure is set out in the following numbered embodiments:

1. A method for determining a clustering of cluster assignments (COCA) subtype of a tumor cancer sample obtained from a patient, the method comprising detecting an expression level of at least one classifier biomarker of Table 1, wherein the detection of the expression level of the classifier biomarker specifically identifies a C1, C2, C3, C4, C6, C8, C9, C10, C12, C14, C15, C16, C17, C19, C20, C21, C22, C24, C25, C26 or C28 COCA subtype.

2. The method of embodiment 1, wherein the method further comprises comparing the detected levels of expression of the at least one classifier biomarker of Table 1 to the expression of the at least one classifier biomarker of Table 1 in at least one sample training set(s), wherein the at least one sample training set(s) comprises expression data of the at least one classifier biomarker of Table 1 from a reference C1 sample, expression data of the at least one classifier biomarker of Table 1 from a reference C2 sample, expression data of the at least one classifier biomarker of Table 1 from a reference C3 sample, expression data of the at least one classifier biomarker of Table 1 from a reference C4 sample, expression data of the at least one classifier biomarker of Table 1 from a reference C6 sample, expression data of the at least one classifier biomarker of Table 1 from a reference C8 sample, expression data of the at least one classifier biomarker of Table 1 from a reference C9 sample, expression data of the at least one classifier biomarker of Table 1 from a reference C10 sample, expression data of the at least one classifier biomarker of Table 1 from a reference C12 sample, expression data of the at least one classifier biomarker of Table 1 from a reference C14 sample, expression data of the at least one classifier biomarker of Table 1 from a reference C15 sample, expression data of the at least one classifier biomarker of Table 1 from a reference C16 sample, expression data of the at least one classifier biomarker of Table 1 from a reference C17 sample, expression data of the at least one classifier biomarker of Table 1 from a reference C19 sample, expression data of the at least one classifier biomarker of Table 1 from a reference C20 sample, expression data of the at least one classifier biomarker of Table 1 from a reference C21 sample, expression data of the at least one classifier biomarker of Table 1 from a reference C22 sample, expression data of the at least one classifier biomarker of Table 1 from a reference C24 sample, expression data of the at least one classifier biomarker of Table 1 from a reference C25 sample, expression data of the at least one classifier biomarker of Table 1 from a reference C26 sample, expression data of the at least one classifier biomarker of Table 1 from a reference C28 sample or a combination thereof; and classifying the sample as the C1, C2, C3, C4, C6, C8, C9, C10, C12, C14, C15, C16, C17, C19, C20, C21, C22, C24, C25, C26 or C28 COCA subtype based on the results of the comparing step.

3. The method of embodiment 2, wherein the comparing step comprises applying a statistical algorithm which comprises determining a correlation between the expression data obtained from the sample and the expression data from the at least one training set(s); and classifying the sample as a C1, C2, C3, C4, C6, C8, C9, C10, C12, C14, C15, C16, C17, C19, C20, C21, C22, C24, C25, C26 or C28 COCA subtype based on the results of the statistical algorithm.

4. The method of any one of embodiments 1-3, wherein the C1 COCA subtype indicates that a tumor sample is substantially similar to or is adrenocortical carcinoma; the C2 COCA subtype indicates that a tumor sample is substantially similar to or is glioblastoma; the C3 COCA subtype indicates that a tumor sample is substantially similar to or is an ovarian serous cystadenocarcinoma (epithelial ovarian cancer); the C4 COCA subtype indicates that a tumor sample is substantially similar to or is squamous cell carcinoma of the lung, the head and neck or the bladder; the C6 COCA subtype indicates that a tumor sample is substantially similar to or is lung adenocarcinoma; the C8 COCA subtype indicates that a tumor sample is substantially similar to or is pancreatic adenocarcinoma; the C9 COCA subtype indicates that a tumor sample is substantially similar to or is uterine carcinosarcoma; the C10 COCA subtype indicates that a tumor sample is substantially similar to or is the basal subtype of breast cancer; the C12 COCA subtype indicates that a tumor sample is substantially similar to or is uterine corpus endometrial cancer; the C14 COCA subtype indicates that a tumor sample is substantially similar to or is prostate cancer; the C15 COCA subtype can indicate that a tumor sample is substantially similar to or is non-squamous cervical cancer; the C16 COCA subtype indicates that a tumor sample is substantially similar to or is a bladder urothelial carcinoma; the C17 COCA subtype indicates that a tumor sample is substantially similar to or is a testicular germ cell tumor; the C19 COCA subtype indicates that a tumor sample is substantially similar to or is a colon, rectal, esophageal or stomach adenocarcinoma; the C20 COCA subtype indicates that a tumor sample is substantially similar to or is a sarcoma; the C21 COCA subtype indicates that a tumor sample is substantially similar to or is a kidney chromophobe, kidney renal papillary cell carcinoma or kidney renal clear cell carcinoma; the C22 COCA subtype indicates that a tumor sample is substantially similar to or is liver hepatocellular carcinoma; the C24 COCA subtype indicates that a tumor sample is substantially similar to or is the luminal subtype of breast cancer; the C25 COCA subtype indicates that a tumor sample is substantially similar to or is thymoma; the C26 COCA subtype indicates that a tumor sample is substantially similar to or is melanoma; or the C28 COCA subtype indicates that a tumor sample is substantially similar to or is thyroid cancer.

5. The method of any one of embodiments 1-4, wherein the expression level of the classifier biomarker is detected at the nucleic acid level.

6. The method of embodiment 5, wherein the nucleic acid level is RNA or cDNA.

7. The method embodiment 5 or 6, wherein the detecting an expression level comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques.

8. The method of embodiment 7, wherein the expression level is detected by performing RNAseq.

9. The method of embodiment 8, wherein the detection of the expression level comprises using at least one pair of oligonucleotide primers specific for at least one classifier biomarker of Table 1.

10. The method of any one of embodiments 1-9, wherein the sample is a formalin-fixed, paraffin-embedded (FFPE) tissue sample, a fresh or a frozen tissue sample, an exosome, wash fluids, cell pellets, or a bodily fluid obtained from the patient.

11. The method of embodiment 10, wherein the bodily fluid is blood or fractions thereof, urine, saliva, or sputum.

12. The method of any one embodiments 1-11, wherein the at least one classifier biomarker comprises a plurality of classifier biomarkers.

13. The method of embodiment 12, wherein the plurality of classifier biomarkers comprises, consists essentially of or consists of at least 2 classifier biomarkers, at least 4 classifier biomarkers, at least 6 classifier biomarkers, at least 8 classifier biomarkers, at least 10 classifier biomarkers, at least 12 classifier biomarkers, at least 14 classifier biomarkers, at least 16 classifier biomarkers, at least 18 classifier biomarkers, at least 20 classifier biomarkers, at least 30 classifier biomarkers, at least 40 classifier biomarkers, at least 50 classifier biomarkers, at least 60 classifier biomarkers, at least 70 classifier biomarkers or at least 80 classifier biomarkers of Table 1.

14. The method of any one of embodiments 1-13, wherein the at least one classifier biomarker comprises, consists essentially of or consists of all the classifier biomarkers of Table 1.

15. A method of detecting a biomarker in a tumor sample obtained from a patient, the method comprising measuring the expression level of a plurality of classifier biomarker nucleic acids selected from Table 1 using an amplification, hybridization and/or sequencing assay.

16. The method of embodiment 15, wherein the patient is suffering from or is suspected of suffering from kidney renal papillary cell carcinoma (KIRP); breast invasive carcinoma (BRCA); thyroid cancer (THCA); bladder urothelial carcinoma (BLCA); prostate adenocarcinoma (PRAD); kidney chromophobe (KICH); cervical squamous cell carcinoma and endocervical adenocarcinoma (CESC); kidney renal clear cell carcinoma (KIRC); liver hepatocellular carcinoma (LIHC); low grade glioma (LGG); sarcoma (SARC); lung adenocarcinoma (LUAD); colon adenocarcinoma (COAD); head and neck squamous cell carcinoma (HNSC); uterine corpus endometrial carcinoma (UCEC); glioblastoma multiforme (GBM); esophageal carcinoma (ESCA); stomach adenocarcinoma (STAD); ovarian serous cystadenocarcinoma (OV); rectum adenocarcinoma (READ); adrenocortical carcinoma (ACC); uveal melanoma (UVM); mesothelioma (MESO); pheochromocytoma and paraganglioma (PCPG); skin cutaneous melanoma (SKCM); uterine carcinosarcoma (UCS); lung squamous cell carcinoma (LUSC); testicular germ cell tumors (TGCT); cholangiocarcinoma (CHOL); pancreatic adenocarcinoma (PAAD); thymoma (THYM); or Lymphoid Neoplasm Diffuse Large B-cell Lymphoma (DLBC).

17. The method of embodiment 15 or 16, wherein the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques.

18. The method of embodiment 17, wherein the expression level is detected by performing RNAseq.

19. The method of embodiment 18, wherein the detection of the expression level comprises using at least one pair of oligonucleotide primers per each of the plurality of biomarker nucleic acids selected from Table 1.

20. The method of any one of embodiments 15-19, wherein the sample is a formalin-fixed, paraffin-embedded (FFPE) tissue sample, fresh or a frozen tissue sample, an exosome, wash fluids, cell pellets, or a bodily fluid obtained from the patient.

21. The method of embodiment 20, wherein the bodily fluid is blood or fractions thereof, urine, saliva, or sputum.

22. The method of any one of embodiments 15-21, wherein the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, at least 60 classifier biomarkers, at least 70 classifier biomarkers or at least 80 classifier biomarkers of Table 1.

23. The method of any one of embodiments 15-22, wherein the plurality of biomarker nucleic acids comprises, consists essentially of or consists of all the classifier biomarker nucleic acids of Table 1.

24. A method of treating cancer in a subject, the method comprising:

measuring the expression level of at least one biomarker nucleic acid in a tumor sample obtained from the subject, wherein the at least one biomarker nucleic acid is selected from a set of biomarkers listed in Table 1, wherein the presence, absence and/or level of the at least one biomarker indicates a COCA subtype of the cancer; and administering a therapeutic agent based on the COCA subtype of the cancer.

25. The method of embodiment 24, wherein the at least one biomarker nucleic acid selected from the set of biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, at least 60 classifier biomarkers, at least 70 classifier biomarkers or at least 80 classifier biomarkers of Table 1.

26. The method of embodiment 24 or 25, further comprising measuring the expression of at least one biomarker from an additional set of biomarkers.

27. The method of embodiment 26, wherein the additional set of biomarkers comprises at least an immune cell signature, a cell proliferation signature, or drug target genes.

28. The method of any one of embodiments 24-27, wherein the measuring the expression level is conducted using an amplification, hybridization and/or sequencing assay.

29. The method of embodiment 28, wherein the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques.

30. The method of embodiment 29, wherein the expression level is detected by performing RNAseq.

31. The method of any one of embodiments 24-30, wherein the sample is a formalin-fixed, paraffin-embedded (FFPE) tissue sample, fresh or a frozen tissue sample, an exosome, wash fluids, cell pellets, or a bodily fluid obtained from the patient.

32. The method of embodiment 31, wherein the bodily fluid is blood or fractions thereof, urine, saliva, or sputum.

33. The method of any one of embodiments 24-32, wherein the subject's COCA subtype is selected from C1, C2, C3, C4, C6, C8, C9, C10, C12, C14, C15, C16, C17, C19, C20, C21, C22, C24, C25, C26 or C28.

34. The method of embodiment 33, wherein the C1 COCA subtype indicates that a tumor sample is substantially similar to or is adrenocortical carcinoma; the C2 COCA subtype indicates that a tumor sample is substantially similar to or is glioblastoma; the C3 COCA subtype indicates that a tumor sample is substantially similar to or is an ovarian serous cystadenocarcinoma (epithelial ovarian cancer); the C4 COCA subtype indicates that a tumor sample is substantially similar to or is squamous cell carcinoma of the lung, the head and neck or the bladder; the C6 COCA subtype indicates that a tumor sample is substantially similar to or is lung adenocarcinoma; the C8 COCA subtype indicates that a tumor sample is substantially similar to or is pancreatic adenocarcinoma; the C9 COCA subtype indicates that a tumor sample is substantially similar to or is uterine carcinosarcoma; the C10 COCA subtype indicates that a tumor sample is substantially similar to or is the basal subtype of breast cancer; the C12 COCA subtype indicates that a tumor sample is substantially similar to or is uterine corpus endometrial cancer; the C14 COCA subtype indicates that a tumor sample is substantially similar to or is prostate cancer; the C15 COCA subtype can indicate that a tumor sample is substantially similar to or is non-squamous cervical cancer; the C16 COCA subtype indicates that a tumor sample is substantially similar to or is a bladder urothelial carcinoma; the C17 COCA subtype indicates that a tumor sample is substantially similar to or is a testicular germ cell tumor; the C19 COCA subtype indicates that a tumor sample is substantially similar to or is a colon, rectal, esophageal or stomach adenocarcinoma; the C20 COCA subtype indicates that a tumor sample is substantially similar to or is a sarcoma; the C21 COCA subtype indicates that a tumor sample is substantially similar to or is a kidney chromophobe, kidney renal papillary cell carcinoma or kidney renal clear cell carcinoma; the C22 COCA subtype indicates that a tumor sample is substantially similar to or is liver hepatocellular carcinoma; the C24 COCA subtype indicates that a tumor sample is substantially similar to or is the luminal subtype of breast cancer; the C25 COCA subtype indicates that a tumor sample is substantially similar to or is thymoma; the C26 COCA subtype indicates that a tumor sample is substantially similar to or is melanoma; or the C28 COCA subtype indicates that a tumor sample is substantially similar to or is thyroid cancer.

35. A method of predicting overall survival in a cancer patient, the method comprising detecting an expression level of at least one classifier biomarker of Table 1 in a tumor sample obtained from a patient, wherein the detection of the expression level of the at least one classifier biomarker specifically identifies a COCA subtype, and wherein identification of the COCA subtype is predictive of the overall survival in the patient.

36. The method of embodiment 35, wherein the method further comprises comparing the detected levels of expression of the at least one classifier biomarker of Table 1 to the expression of the at least one classifier biomarker of Table 1 in at least one sample training set(s), wherein the at least one sample training set(s) comprises expression data of the at least one classifier biomarker of Table 1 from a reference C1 sample, expression data of the at least one classifier biomarker of Table 1 from a reference C2 sample, expression data of the at least one classifier biomarker of Table 1 from a reference C3 sample, expression data of the at least one classifier biomarker of Table 1 from a reference C4 sample, expression data of the at least one classifier biomarker of Table 1 from a reference C6 sample, expression data of the at least one classifier biomarker of Table 1 from a reference C8 sample, expression data of the at least one classifier biomarker of Table 1 from a reference C9 sample, expression data of the at least one classifier biomarker of Table 1 from a reference C10 sample, expression data of the at least one classifier biomarker of Table 1 from a reference C12 sample, expression data of the at least one classifier biomarker of Table 1 from a reference C14 sample, expression data of the at least one classifier biomarker of Table 1 from a reference C15 sample, expression data of the at least one classifier biomarker of Table 1 from a reference C16 sample, expression data of the at least one classifier biomarker of Table 1 from a reference C17 sample, expression data of the at least one classifier biomarker of Table 1 from a reference C19 sample, expression data of the at least one classifier biomarker of Table 1 from a reference C20 sample, expression data of the at least one classifier biomarker of Table 1 from a reference C21 sample, expression data of the at least one classifier biomarker of Table 1 from a reference C22 sample, expression data of the at least one classifier biomarker of Table 1 from a reference C24 sample, expression data of the at least one classifier biomarker of Table 1 from a reference C25 sample, expression data of the at least one classifier biomarker of Table 1 from a reference C26 sample, expression data of the at least one classifier biomarker of Table 1 from a reference C28 sample or a combination thereof; and classifying the sample as the C1, C2, C3, C4, C6, C8, C9, C10, C12, C14, C15, C16, C17, C19, C20, C21, C22, C24, C25, C26 or C28 COCA subtype based on the results of the comparing step.

37. The method of embodiment 36, wherein the comparing step comprises applying a statistical algorithm which comprises determining a correlation between the expression data obtained from the sample and the expression data from the at least one training set(s); and classifying the sample as a C1, C2, C3, C4, C6, C8, C9, C10, C12, C14, C15, C16, C17, C19, C20, C21, C22, C24, C25, C26 or C28 COCA subtype based on the results of the statistical algorithm.

38. The method of any one of the embodiments 35-37, wherein the expression level of the classifier biomarker is detected at the nucleic acid level.

39. The method of embodiment 38, wherein the nucleic acid level is RNA or cDNA.

40. The method of any one of embodiments 35-39, wherein the detecting an expression level comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques.

41. The method of embodiment 40, wherein the expression level is detected by performing RNAseq.

42. The method of embodiment 35, wherein the detection of the expression level comprises using at least one pair of oligonucleotide primers specific for at least one classifier biomarker of Table 1.

43. The method of any one of embodiments 35-42, wherein the sample is a formalin-fixed, paraffin-embedded (FFPE) tissue sample, fresh or a frozen tissue sample, an exosome, wash fluids, cell pellets, or a bodily fluid obtained from the patient.

44. The method of embodiment 43, wherein the bodily fluid is blood or fractions thereof, urine, saliva, or sputum.

45. The method of any one of embodiments 35-44, wherein the at least one classifier biomarker comprises a plurality of classifier biomarkers.

46. The method of embodiment 45, wherein the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, at least 60 classifier biomarkers, at least 70 classifier biomarkers or at least 80 classifier biomarkers of Table 1.

47. The method of any one of embodiments 35-46, wherein the at least one classifier biomarker comprises, consists essentially of or consists of all the classifier biomarkers of Table 1.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of detecting a biomarker in a tumor sample obtained from a patient suffering from or suspected of suffering from a cancer, the method comprising measuring in the tumor sample the nucleic acid expression level of each and every biomarker from a plurality of biomarkers consisting of only Alpha-1-B glycoprotein (A1BG); Acid Phosphatase, Prostate (ACPP); APC2, WNT Signaling Pathway Regulator (APC2); Aquaporin 5 (AQP5); asialoglycoprotein receptor 1 (ASGR1); brevican (BCAN); BCL2 like 15 (BCL2L15); keratinocyte differentiation factor 1 (C1orf172); calcyphosine (CAPS); Cbl proto-oncogene C (CBLC); cadherin 1 (CDH1); carcinoembryonic antigen related cell adhesion molecule 5 (CEACAM5), carcinoembryonic antigen related cell adhesion molecule 6 (CEACAM6); multivesicular body protein 4C (CHMP4C); chloride channel accessory 2 (CLCA2); claudin 4 (CLDN4); collagen type XI alpha 2 chain (COL11A2); crumbs cell polarity complex component 3 (CRB3); cathepsin E (CTSE); cubilin (CUBN); cytochrome P450 family 2 subfamily B member 7, pseudogene (CYP2B7P1); distal-less homeobox 5 (DLX5); dimethylglycine dehydrogenase (DMGDH); E74 like ETS transcription factor 3 (ELF3); empty spiracles homeobox 2 (EMX2); EMX2 opposite strand/antisense RNA (EMX2OS); epithelial cell adhesion molecule (EPCAM); erb-b2 receptor tyrosine kinase 3 (ERBB3); estrogen receptor 1 (ESR1); family with sequence similarity 171 member A2 (FAM171A2); folate hydrolase 1 (FOLH1); gamma-aminobutyric acid type A receptor pi subunit (GABRP); GATA binding protein 3 (GATA3); glucosaminyl (N-acetyl) transferase 3, mucin type (GCNT3); glypican 2 (GPC2); G protein-coupled receptor 35 (GPR35); G protein-coupled receptor class C group 5 member A (GPRC5A); grainyhead like transcription factor 2 (GRHL2); HNF 1 homeobox A (HNF1A); hemopexin (HPX); iodotyrosine deiodinase (IYD); keratin 18 (KRT18); keratin 6A (KRT6A); keratin 6B (KRT6B); keratin 81 (KRT81); keratin 8 (KRT8); ladinin 1 (LAD 1); LCK proto-oncogene, Src family tyrosine kinase (LCK); galectin 4 (LGALS4); LY6/PLAUR domain containing 1 (LYPD1); MARVEL domain containing 3 (MARVELD3); maternally expressed 3 (MEG3); mucin 13, cell surface associated (MUC13); mucin 16, cell surface associated (MUC16); mucin 4, cell surface associated (MUC4); MYCN proto-oncogene, bHLH transcription factor (MYCN); napsin A aspartic peptidase (NAPSA); NK3 homeobox 1 (NKX3-1); natriuretic peptide receptor 1 (NPR1); paired box 8 (PAX8); preferentially expressed antigen in melanoma (PRAME); prostate stem cell antigen (PSCA); nectin cell adhesion molecule 4 (PVRL4); calcium binding protein P (S100P); spalt like transcription factor 4 (SALL4); surfactant protein D (SFTPD); premelanosome protein (SILV); signaling threshold regulating transmembrane adaptor 1 (SIT1); solute carrier family 26 member 4 (SLC26A4); solute carrier family 3 member 1 (SLC3A1); solute carrier family 45 member 3 (SLC45A3); SRY-box 17 (SOX17); SAM pointed domain containing ETS transcription factor (SPDEF); serine peptidase inhibitor, Kunitz type 2 (SPINT2); transcription elongation factor A like 5 (TCEAL5); thyroglobulin (TG); collectrin, amino acid transport regulator (TMEM27); tumor protein p63 (TP63); transcriptional repressor GATA binding 1 (TRPS 1); tetraspanin 8 (TSPAN8); uroplakin 3B (UPK3B); vitronectin (VTN); zinc finger protein 578 (ZNF578); and zinc finger protein 695 (ZNF695) using an amplification, hybridization and/or sequencing assay.

2. The method of claim 1, wherein the patient is suffering from or is suspected of suffering from kidney renal papillary cell carcinoma (KIRP); breast invasive carcinoma (BRCA); thyroid cancer (THCA); bladder urothelial carcinoma (BLCA); prostate adenocarcinoma (PRAD); kidney chromophobe (KICH); cervical squamous cell carcinoma and endocervical adenocarcinoma (CESC); kidney renal clear cell carcinoma (KIRC); liver hepatocellular carcinoma (LIHC); low grade glioma (LGG); sarcoma (SARC); lung adenocarcinoma (LUAD); colon adenocarcinoma (COAD); head and neck squamous cell carcinoma (HNSC); uterine corpus endometrial carcinoma (UCEC); glioblastoma multiforme (GBM); esophageal carcinoma (ESCA); stomach adenocarcinoma (STAD); ovarian serous cystadenocarcinoma (OV); rectum adenocarcinoma (READ); adrenocortical carcinoma (ACC); uveal melanoma (UVM); mesothelioma (MESO); pheochromocytoma and paraganglioma (PCPG); skin cutaneous melanoma (SKCM); uterine carcinosarcoma (UCS); lung squamous cell carcinoma (LUSC); testicular germ cell tumors (TGCT); cholangiocarcinoma (CHOL); pancreatic adenocarcinoma (PAAD); thymoma (THYM); or Lymphoid Neoplasm Diffuse Large B-cell Lymphoma (DLBC).

3. The method of claim 1, wherein the amplification, hybridization and/or sequencing assay comprises performing quantitative real time reverse transcriptase polymerase chain reaction (qRT-PCR), RNAseq, Serial Analysis of Gene Expression (SAGE), Rapid Analysis of Gene Expression (RAGE), nuclease protection assays or Northern blotting.

4. The method of claim 3, wherein the nucleic acid expression level is detected by performing RNAseq.

5. The method of claim 4, wherein the detection of the nucleic acid expression level comprises using at least one pair of oligonucleotide primers per each biomarker from the plurality of biomarkers consisting of only A1BG, ACPP, APC2, AQP5, ASGR1, BCAN, BCL2L15, C1orf172, CAPS, CBLC, CDH1, CEACAM5, CEACAM6, CHMP4C, CLCA2, CLDN4, COL11A2, CRB3, CTSE, CUBN, CYP2B7P1, DLX5, DMGDH, ELF3, EMX2, EMX2OS, EPCAM, ERBB3, ESR1, FAM171A2, FOLH1, GABRP, GATA3, GCNT3, GPC2, GPR35, GPRC5A, GRHL2, HNF1A, HPX, IYD, KRT18, KRT6A, KRT6B, KRT81, KRT8, LAD1, LCK, LGALS4, LYPD1, MARVELD3, MEG3, MUC13, MUC16, MUC4, MYCN, NAPSA, NKX3-1, NPR1, PAX8, PRAME, PSCA, PVRL4, S100P, SALL4, SFTPD, SILV, SIT1, SLC26A4, SLC3A1, SLC45A3, SOX17, SPDEF, SPINT2, TCEAL5, TG, TMEM27, TP63, TRPS1, TSPAN8, UPK3B, VTN, ZNF578 and ZNF695.

6. The method of claim 1, wherein the tumor sample is a formalin-fixed, paraffin-embedded (FFPE) tissue sample, fresh or a frozen tissue sample, an exosome, wash fluids, cell pellets, or a bodily fluid obtained from the patient.

7. The method of claim 6, wherein the bodily fluid is blood or fractions thereof, urine, saliva, or sputum.

* * * * *